United States Patent
Vyskocil et al.

(10) Patent No.: US 12,054,512 B2
(45) Date of Patent: *Aug. 6, 2024

(54) STING MODULATOR COMPOUNDS, AND METHODS OF MAKING AND USING

(71) Applicant: Takeda Pharmaceutical Company Limited, Osaka (JP)

(72) Inventors: Stepan Vyskocil, Arlington, MA (US); Jeffrey Ciavarri, Cambridge, MA (US); Courtney Cullis, Cambridge, MA (US); Dylan Bradley England, Cambridge, MA (US); Alexandra E. Gould, Cambridge, MA (US); Paul Greenspan, Cambridge, MA (US); Yongbo Hu, Cambridge, MA (US); Steven Langston, Cambridge, MA (US); Gang Li, Cambridge, MA (US); Hirotake Mizutani, Cambridge, MA (US); Masanori Okaniwa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,083

(22) Filed: Nov. 2, 2022

(65) Prior Publication Data
US 2024/0209017 A1    Jun. 27, 2024

Related U.S. Application Data

(63) Continuation of application No. 16/762,710, filed as application No. PCT/IB2018/058846 on Nov. 9, 2018, now Pat. No. 11,542,293.

(60) Provisional application No. 62/754,623, filed on Nov. 2, 2018, provisional application No. 62/718,613, filed on Aug. 14, 2018, provisional application No. 62/584,559, filed on Nov. 10, 2017.

(51) Int. Cl.
C07H 19/207    (2006.01)

(52) U.S. Cl.
CPC .................................. *C07H 19/207* (2013.01)

(58) Field of Classification Search
None
See application file for complete search history.

(56) References Cited

U.S. PATENT DOCUMENTS

| | | |
|---|---|---|
| 5,547,941 A | 8/1996 | Battisttnl et al. |
| 7,569,555 B2 | 8/2009 | Karaolis |
| 7,592,326 B2 | 9/2009 | Karaolis |
| 7,709,458 B2 | 5/2010 | Karaolis |
| 8,367,716 B2 | 2/2013 | Karaolis |
| 8,450,293 B2 | 5/2013 | Jones et al. |
| 9,090,646 B2 | 7/2015 | Jones et al. |
| 9,549,944 B2 | 1/2017 | Dubensky et al. |
| 9,597,391 B2 | 3/2017 | Ebenson et al. |
| 9,695,212 B2 | 7/2017 | Dubensky et al. |
| 9,718,848 B2 | 8/2017 | Adaais et al. |
| 9,724,408 B2 | 8/2017 | Dubensky et al. |
| 9,770,467 B2 | 9/2017 | Dubensky et al. |
| 9,840,533 B2 | 12/2017 | Patel et al. |
| 10,980,825 B2 | 4/2021 | Yoshikawa et al. |
| 11,542,293 B2 | 1/2023 | Vyskocil et al. |
| 11,666,594 B2 | 6/2023 | Yoshikawa et al. |
| 11,725,024 B2 | 8/2023 | Xu et al. |
| 2006/0167241 A1 | 7/2006 | Hayakawa et al. |
| 2014/0341976 A1 | 11/2014 | Dubensky et al. |
| 2015/0056224 A1 | 2/2015 | Dubensky et al. |
| 2017/0044206 A1 | 2/2017 | Altman |
| 2017/0146519 A1 | 5/2017 | Defilippis et al. |
| 2018/0093964 A1 | 4/2018 | Altman et al. |

(Continued)

FOREIGN PATENT DOCUMENTS

| | | |
|---|---|---|
| CN | 106459131 A | 2/2017 |
| CN | 106667914 A | 5/2017 |

(Continued)

OTHER PUBLICATIONS

Clivio, P., et al., "(3'-5')-Cyclic Dinucleotides: Synthetic Strategies and Biological Potential," Chemical Reviews 113:7354-7401, American Chemical Society, United States (2013).

(Continued)

*Primary Examiner* — Layla D Berry
(74) *Attorney, Agent, or Firm* — Sterne, Kessler, Goldstein & Fox P.L.L.C.

(57) ABSTRACT

The present disclosure provides STING modulators/agonists, and methods of synthesis and methods for using for the prophylaxis or treatment of cancer and other STING-related diseases.

The present disclosure relates to a compound represented by the Formula (I):

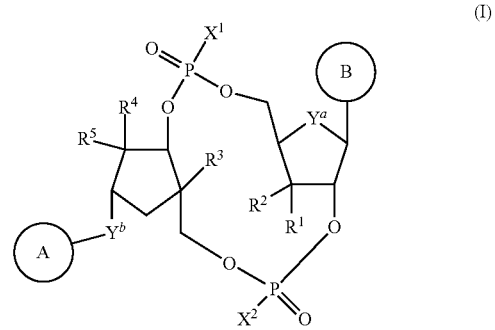

wherein each symbol is as defined in the description, or a pharmaceutically acceptable salt thereof.

23 Claims, No Drawings

(56) References Cited

U.S. PATENT DOCUMENTS

| | | |
|---|---|---|
| 2021/0015915 A1 | 1/2021 | Ciavarri et al. |
| 2022/0168330 A1 | 6/2022 | Xu et al. |
| 2022/0257630 A1 | 8/2022 | Lightcap et al. |
| 2022/0409734 A1 | 12/2022 | England et al. |
| 2023/0399356 A1 | 12/2023 | Xu et al. |

FOREIGN PATENT DOCUMENTS

| | | |
|---|---|---|
| EP | 1740192 B1 | 6/2012 |
| EP | 1729781 B1 | 10/2012 |
| EP | 3512861 B1 | 2/2021 |
| JP | 2017518302 A | 7/2017 |
| JP | 2020505405 A | 2/2020 |
| TW | 201639866 A | 11/2016 |
| TW | 201726700 A | 8/2017 |
| WO | WO-2005089777 A1 | 9/2005 |
| WO | WO-2006045041 A2 | 4/2006 |
| WO | WO-2007054279 A2 | 5/2007 |
| WO | WO-2009133560 A1 | 11/2009 |
| WO | WO-2011003025 A1 | 1/2011 |
| WO | WO-2013185052 A1 | 12/2013 |
| WO | WO-2014093936 A1 | 6/2014 |
| WO | WO-2014099824 A1 | 6/2014 |
| WO | WO-2014109256 A1 | 7/2014 |
| WO | WO-2014179335 A1 | 11/2014 |
| WO | WO-2014179760 A1 | 11/2014 |
| WO | WO-2014189805 A1 | 11/2014 |
| WO | WO-2014189806 A1 | 11/2014 |
| WO | WO-2015017652 A1 | 2/2015 |
| WO | WO-2015074145 A1 | 5/2015 |
| WO | WO-2015077354 A1 | 5/2015 |
| WO | WO-2015185565 A1 | 12/2015 |
| WO | WO-2016096174 A1 | 6/2016 |
| WO | WO-2016096577 A1 | 6/2016 |
| WO | WO-2017123657 A1 | 7/2016 |
| WO | WO-2016120305 A1 | 8/2016 |
| WO | WO-2016145102 A1 | 9/2016 |
| WO | WO-2017011444 A1 | 1/2017 |
| WO | WO-2017011622 A1 | 1/2017 |
| WO | WO-2017019896 A1 | 2/2017 |
| WO | WO-2017027645 A1 | 2/2017 |
| WO | WO-2017027646 A1 | 2/2017 |
| WO | WO-2017075477 A1 | 5/2017 |
| WO | WO-2017093933 A1 | 6/2017 |
| WO | WO-2017100305 A2 | 6/2017 |
| WO | WO-2017106740 A1 | 6/2017 |
| WO | WO-2017123669 A1 | 7/2017 |
| WO | WO-2017161349 A1 | 9/2017 |
| WO | WO-2017165506 A1 | 9/2017 |
| WO | WO-2018172206 A1 | 9/2017 |
| WO | WO-2017175147 A1 | 10/2017 |
| WO | WO-2017175156 A | 10/2017 |
| WO | WO-2017186711 A1 | 11/2017 |
| WO | WO-2018009466 A1 | 1/2018 |
| WO | WO-2018009648 A1 | 1/2018 |
| WO | WO-2018009652 A1 | 1/2018 |
| WO | WO-2018013887 A1 | 1/2018 |
| WO | WO-2018013908 A1 | 1/2018 |
| WO | WO-2018198076 A1 | 1/2018 |
| WO | WO-2018198084 A1 | 1/2018 |
| WO | WO-2018045204 A1 | 3/2018 |
| WO | WO-2018060323 A1 | 4/2018 |
| WO | WO-2018065360 A1 | 4/2018 |
| WO | WO-2018098203 A1 | 5/2018 |
| WO | WO-2018100558 A1 | 6/2018 |
| WO | WO-2018118664 A1 | 6/2018 |
| WO | WO-2018118665 A1 | 6/2018 |
| WO | WO-2018119117 A1 | 6/2018 |
| WO | WO-2018138684 A1 | 8/2018 |
| WO | WO-2018138685 A2 | 8/2018 |
| WO | WO-2018140831 A1 | 8/2018 |
| WO | WO-2018152450 A1 | 8/2018 |
| WO | WO-2018152453 A1 | 8/2018 |
| WO | WO-2018156625 A1 | 8/2018 |
| WO | WO-2018200812 A1 | 11/2018 |
| WO | WO-2019043634 A2 | 3/2019 |
| WO | WO-2019046496 A1 | 3/2019 |
| WO | WO-2019046500 A1 | 3/2019 |
| WO | WO-2019055750 A1 | 3/2019 |
| WO | WO-2019180683 A1 | 9/2019 |
| WO | WO-2020229982 A1 | 11/2020 |

OTHER PUBLICATIONS

Corrales, L., et al., "Direct Activation of STING in the Tumor Microenvironment leads to potent and systemic tumor regression and immunity," Cell Reports 11:1018-30, Cell Press, United States (2015).

Danilchanka, O., et al., "Cyclic Dinucleotides and the Innate Immune Response," Cell 154:962-970, Elsevier, Netherlands (2013).

Ertem, G., et al., "Synthesis of RNA oligomers on heterogeneous templates," Nature 379:238-40, Nature Publishing Group, United Kingdom (1996).

Fu, J., et al., "STING agonist formulated cancer vaccines can cure established tumors resistant to PD-1 blockade," Science Translational Medicine 283(7):1-11, American Association for the Advancement of Science, United States (2015).

Gaffney, B.L, et al., "One-Flask Syntheses of c-di-GMP and the [Rp,Rp] and [Rp,Sp] Thiophosphate Analogues," Organic Letters 12(14):3269-3271, American Chemical Society, Unites States (2010).

Ishikawa, H., et al.. "STING is an endoplasmic reticulum adaptor that facilitates innate immune signaling," Nature 455:674-78, Macmillan Publishers, United Kingdom (2008).

International Search Report and Written Opinion for International Application No. PCT/US2018/029570, European Patent Office, Netherlands, mailed on Aug. 17, 2018, 12 pages.

Karaolis, D., et al., "30,50-Cyclic diguanylic acid (c-di-GMP) inhibits basal and grmvth factor-stimulated human colon cancer cell proliferation," Biochemical and Biophysical Research Communications 329:40-45, Elsevier, Netherlands (2005).

Lioux, T., et al., "Design, Synthesis, and Biological Evaluation of Novel Cyclic Adenosine-Inosine Monophosphate (cAIMP) analogs that activate Stimulator of interferon genes," Journal of Medicinal Chemistry 59:10253-67, American Chemical Society, United States (2016).

Sawai, H., et al., "Synthesis of 2'-5' linked Oligouridylates in aqueous medium using the Pd2 + Ion," Chem Pharm Bull 29(8):2237-2245, Pharmaceutical Society of Japan, Japan (1981).

Sawai, H., et al., "Preparation and properties of Oligocytidylates with 2 '-5' Internucleotide linkage," Bull Chem Soc Japan 58:361-66, The Chemical Society of Japan, Japan (1985).

Schwede, F., et al., "The Chemistry of the Noncanonical Cyclic Dinucleotide 2'3 -cGAMP and its analogs," in the Handbook of Experimental Pharmacology, pp. 359-384, Springer International Publishing, Switzerland (2015).

Shanahan, C.A., et al., "Differential Analogue Binding by two classes of c-di-GMP riboswitches." J. Am. Chem. Soc. 133: 1 5578-92, American Chemical Society. United States (2011).

Shi, H., et al., "Molecular basis for the specific recognition of the metazoan cyclic GMP-AMP by the innate immune adaptor protein STING," PNAS 112(29)8947-52, National Academy of Sciences, United States (2015).

Steinberger, O., et al., "Elevated expression of the CD4 receptor and cell cycle arrest are induced in Jurkat cells by treatment with the novel cyclic dinucleotide 3',5'-Cyclic diguanylic acid," FEBS Letters 44(1):125-29, Elsevier, Netherlands (1999).

Zhao, J., et al., "Thiophosphate analogs of c-di-GMP: Impact on polymorphism," Nucleosides Nucleotides Nucleic Acids 28(5):352-378, Taylor and Francis, United Kingdom (2010).

Yan, H., et al., "Synthesis and immunostimulatory properties of the phosphorothioate analogues of cdiGMP," Bioorganic & Medicinal Chem Lett 18:5631-34, Elsevier, Netherlands (2008).

International Search Report and Written Opinion for International Application No. PCT/IB2017/057588, European Patent Office, Netherlands, mailed on Jun. 6, 2018, 22 pages.

Baird, J.R, et al., "Radiotherapy combined with Novel STING-targeting Oligonucleotides Results in Regression of Established

(56) References Cited

OTHER PUBLICATIONS

Tumors," Cancer Res 76( 1):50-61, American Association for Cancer Research, United States (2016).
Cheng, N., et al., "A nanoparticle-incorporated STING activator enhances antitumor immunity in PD-LI-insensitive models of triple-negative breast cancer." JCI insight 3(22): 20 pages, American Society for Clinical Investigation, United States (2018).
Dialer, C.R., et al., "A Click-Chemistry Linked 2'3 '-cGAMP Analog," Chem. Eur. J. 10.1002/chem.201805409, Wiley-VCH, Germany (2019).
Hanson, M.C., et al., "Nanoparticulate STING agonists are potent lymph node-targeted vaccine adjuvants," J Clin Invest 125(6): 2532-46, American Society for Clinical Investigation, United States (2015).
Koshy, S.T., et al., "Liposomal Delivery Enhances Immune Activation by STING Agonist for Cancer Immunotherapy," Adv. Biosyt: 24 pages, Wiley-Liss, United States (2017).
Leach, D.G., et al., "STINGel: Controlled release of a cyclic dinuckotide for enhanced cancer immunotherapy," Biomaterials 163:67-75, Elsevier, Netherlands (2018).
Miyabe, H., et al., "A new adjuvant delivery system 'cyclic di-GMP/YSK05 liposome' for cancer immunotherapy," Journal of Controlled Release 184:20-27, Elsevier, Netherlands (2014).
Nakamura, T., et al.. "Liposomes loaded with a STING pathway ligand, cyclic di-GMP, enhance cancer immunotherapy against metastatic melanoma," Journal of Controlled Release 216:149-157. Elsevier, Netherlands (2015).
Ramanjulu, J.M., et al., "Design of amidobenzimidazole STING receptor agonists with systemic activity," Nature 564:439-443, Springer Nature Limited, Germany (2018).
Sato, Y., et al., "A pH-sensitive cationic lipid facilitates the delivery of liposomal siRNA and gene silencing activity in vitro and in vivo," Journal of Controlled Release, 163:267-276, Elsevier, Netherlands (2012).
Schwede, F., et al., "The Chemistry of the Noncanonical Cyclic Dinucleotide 2'3 '-cGAMP and its analogs," Handbook of Exp Pharrn 238:359-84, Springer International Publishing, Switzerland (2015).
Seela, F., et al., "7-functionalized 7-deazapurine beta-D and beta-L-ribonucleosides related to tubercidin and 7-deazainosine: glycosylation of pyrrolo [2,3-d]pyrimidines with 1-O-acetyl-2,3,5-tri-O-benzoyl-beta-D or beta-L-libofuranose," Tetrahedron 63:9850-61, Elsevier, Netherlands (2007).
Sercombe, L. et al., "Advances and Challenges of Liposome Assisted Dmg Delivery," Frontiers in Pharmacology 6:286, Frontiers Media, Switzerland (2015).
Third Party Observation in International Application No. PCT/IB2017/057588 filed Dec. 1, 2017, Takeda Pharmaceutical Company Limited, Date of Submission Mar. 29, 2019.

Wilson, D.R., et al., "Biodegradable STING agonist nanoparticles for enhanced cancer imrnunotherapy." Nanomedicine, Nanotechnology, Biology, and Medicine 14:237-46, Elsevier, Netherlands (2018).
Yang, J., et al., "Preclinical characterization of GSK532, a novel STING agonist with potent anti-tumor activity," Cancer Research 78(13) Abstract 5554, Proceedings of AACR Annual Meeting Apr. 14-18, 2018.
Seela, F., et al., "7-Halogenated 7-Deazapurine 2'-C-Methylribonucleosides," Collect. Czech. Chem. Commun. 76(12):1413-1431, Wiley, United States (2011).
Miles, D.L., et al., "Interferon induction: A conformational hypothesis," Proc. Natl. Acad. Sci. USA 76(3):1018-1021, National Academy of Sciences, United States (1979).
International Preliminary Report on Patentability for International Application No. PCT/IB2017/057588, The International Bureau of WIPO, mailed on Jun. 4, 2019, 16 pages.
International Search Report and Written Opinion for International Application No. PCT/IB2017/057588, European Patent Office, Netherlands, mailed on Jun. 6, 2018, 20 pages.
International Preliminary Report on Patentability for International Application No. PCT/IB2018/058846, The International Bureau of WIPO, mailed on May 12, 2020, 7 pages.
International Search Report and Written Opinion for International Application No. PCT/IB2018/058846, European Patent Office, Netherlands, mailed on Jan. 1, 2019, 9 pages.
International Preliminary Report on Patentability for International Application No. PCT/IB2019/052364. The International Bureau of WIPO, mailed on Sep. 29, 2020, 6 pages.
International Search Report and Written Opinion for International Application No. PCT/IB2019/052364, European Patent Office, Netherlands, mailed on Jun. 21, 2019, 9 pages.
Office Action mailed on Apr. 9, 2020, in U.S. Appl. No. 16/185,258, Yoshikawa, M. et al., filed Nov. 9, 2018, 12 pages.
Office Action mailed on Dec. 4, 2019, in U.S. Appl. No. 16/185,258, Yoshikawa, M. et al., filed Nov. 9, 2018, 13 pages.
Office Action mailed on Jul. 8, 2019, in U.S. Appl. No. 16/185,258, Yoshikawa, M. et al., filed Nov. 9, 2018, 13 pages.
Su, T., et al., "STING activation in cancer immunotherapy," Theranostics 9(25):7759-7771, Ivyspring International Publisher, Australia (2019).
Co-pending U.S. Appl. No. 18/310,467, inventors Yoshikawa, M., et al., filed on May 1, 2023 (Not yet Published).
Co-pending U.S. Appl. No. 18/253,425, inventors Shaw, M., et al., filed on May 18, 2023 (Not yet Published).
Notice of Allowance mailed on Jul. 15, 2020, in U.S. Appl. No. 16/185,258, Yoshikawa, M. et al., filed Nov. 9, 2018, 16 pages.
Office Action mailed on Jul. 14, 2022, in U.S. Appl. No. 17/065,242, Yoshikawa, M. et al., filed Oct. 7, 2020, 17 pages.
Notice of Allowance mailed on Jan. 24, 2023, in U.S. Appl. No. 17/065,242, Yoshikawa, M. et al., filed Oct. 7, 2020, 17 pages.

STING MODULATOR COMPOUNDS, AND METHODS OF MAKING AND USING

TECHNICAL FIELD

The present disclosure relates to compounds that may be useful as STING (stimulator of interferon genes) modulators/agonists, methods of synthesis and methods of using for the prophylaxis or treatment of cancer and other diseases.

BACKGROUND

STING is a transmembrane receptor localized to the ER that recognizes and binds cyclic dinucleotides. The natural ligands recognized by STING include bacteria/protozoa-derived cyclic dinucleotides (CDNs), 2',3'-cGAMP synthesized by the upstream cGAS (cyclic GMP-AMP synthase), and the like. See Trends in Immunology 35, 88-93 (2014). It is reported that the natural ligand 2',3'-cGAMP is decomposed by ENPP1 (ecto-nucleotide pyrophosphatase/phosphodiesterase), a pyrophosphatase/phosphodiesterase, and that the other CDNs are decomposed by other phosphodiesterases. See Nat Chem Biol 10, 1043-1048 (2014); Cell Res 25, 539-550 (2015); and Biochemistry 55, 837-849 (2016). STING activation by these natural ligands induces the phosphorylation of TBK1 (TANK binding kinase 1) and IRF3 (Interferon regulatory factor 3), leading to the activation of the NFkB and type-I-interferon (IFN) response, respectively. See Trends in Immunology 35, 88-93 (2014).

The effects of STING on cancer cell growth control were demonstrated in a test using genetically modified mice. It was reported that STING-deficient and IRF3-deficient mice show uncontrolled tumor growth, compared to wild-type mice. See Immunity 41, 830-842 (2014). In addition, it was also reported that cancer cell growth in a tumor-allografted mouse was suppressed by radiation therapy, but in mice genetically deficient for STING and IFNAR1 (interferon (alpha and beta) receptor 1, receptor of I-type IFN produced by the downstream signal), the effect by the radiation therapy was reduced. See Immunity 41, 843-852 (2014). Taking the above mentioned evidence together, STING is considered to play a critical role in suppressing cancer cell growth. Therefore, STING agonists can be used as an anticancer agent. See e.g. WO 2015/074145, WO 2015/077354, WO 2015/185565, WO 2016/096174, WO 2016/096577, WO 2016/120305, WO 2016/145102, WO 2017/027645, WO 2017/027646, WO 2017/075477, WO 2017/093933, WO 2017/106740, WO 2017/123657, WO 2017/123669, and WO 2017/161349. In addition, the activation of STING can potentiate the immune effect of traditional vaccines, due to STING's ability to activate both innate and adaptive immunity. See Ther Adv Vaccines 1, 131-143 (2013). As such, STING agonists can also be used as an adjuvant for various vaccines.

SUMMARY OF THE DISCLOSURE

The present disclosure provides a novel compound of Formula (I) having a STING agonistic activity, which can be useful as an agent for the prophylaxis or treatment of cancer and other diseases.

The present disclosure provides a compound of Formula (I)

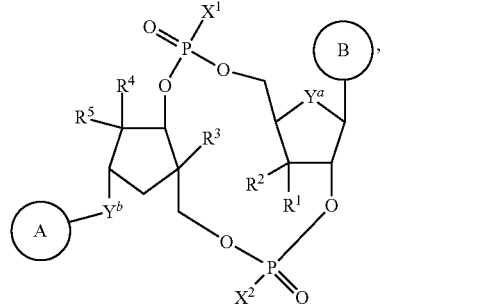

or a pharmaceutically acceptable salt thereof, wherein:
$X^1$ is —SH or —OH;
$X^2$ is —SH or —OH;
$Y^a$ is —O—, —S—, or —CH$_2$—;
$Y^b$ is —O—, —S—, —NH—, or —NR$^a$—, wherein R$^a$ is C$_1$-C$_4$alkyl;
$R^1$ is hydrogen, fluoro, —OH, —NH$_2$, —OR$^b$, or —NHR$^b$;
$R^2$ is hydrogen or fluoro;
$R^3$ is hydrogen; $R^4$ is hydrogen, fluoro, —OH, —NH$_2$, —OR$^b$, or —NHR$^b$; or $R^3$ and $R^4$ are taken together to form —CH$_2$O—;
$R^5$ is hydrogen or fluoro;
$R^b$ is C$_1$-C$_6$alkyl, halo(C$_1$-C$_6$)alkyl, or C$_3$-C$_6$cycloalkyl;
Ring A is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein Ring A comprises at least one N atom in the ring, and wherein $Y^b$ is attached to a carbon atom of Ring A; and
Ring B is an optionally substituted 9- or 10-membered bicyclic heteroaryl ring containing 2-5 heteroatoms selected from N, O, or S; wherein Ring B comprises at least two N atoms in the ring.

The present disclosure also provides a pharmaceutical composition comprising (a) a compound of Formula (I) or a pharmaceutically acceptable salt thereof, and (b) a pharmaceutically acceptable carrier.

The present disclosure further provides a method of inducing an immune response in a subject, comprising administering to the subject in need thereof a therapeutically effective amount of a compound of Formula (I) or a pharmaceutically acceptable salt thereof.

The present disclosure provides a method of inducing a STING-dependent type I interferon production in a subject, comprising administering to the subject in need thereof a therapeutically effective amount of a compound of Formula (I) or a pharmaceutically acceptable salt thereof.

The present disclosure provides a method of treating a cell proliferation disorder in a subject, comprising administering to the subject in need thereof a therapeutically effective amount of a compound of Formula (I) or a pharmaceutically acceptable salt thereof.

The present disclosure also provides a vaccine composition comprising an antigen and a compound of Formula (I) or a pharmaceutically acceptable salt thereof. The present disclosure further provides method of treating a disease in a subject, comprising administering to the subject in need thereof a therapeutically effective amount of the vaccine composition.

DETAILED DESCRIPTION OF THE DISCLOSURE

Definitions

In the present specification, examples of the "halogen atom" include fluorine, chlorine, bromine and iodine.

As used herein, the term "aromatic" includes aryl and heteroaryl groups as described generally below and herein.

The term "aliphatic" or "aliphatic group," as used herein, means a straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle," "cycloaliphatic," "cycloalkyl," or "cycloalkenyl"). For example, suitable aliphatic groups include linear, branched or cyclic alkyl, alkenyl, alkynyl groups and hybrids thereof, such as (cycloalkyl)alkyl, (cycloalkenyl)alkyl, or (cycloalkyl)alkenyl. In various embodiments, aliphatic groups have 1-12, 1-10, 1-8, 1-6, 1-5, 1-4, 1-3, or 1-2 carbon atoms.

The terms "cycloaliphatic," "carbocycle," "carbocyclyl," "carbocyclo," or "carbocyclic," used alone or as part of a larger moiety, refer to a saturated or partially unsaturated cyclic aliphatic ring system having from 3 to about 14 ring carbon atoms.

The term "alkyl," used alone or as part of a larger moiety, refers to a straight or branched chain saturated $C_1$-$C_{12}$ hydrocarbon group. In various embodiments, alkyl groups can have 1-12, 1-10, 1-8, 1-6, 1-5, 1-4, 1-3, or 1-2 carbon atoms. Examples of the "$C_1$-$C_6$alkyl" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

The term "cycloalkyl" refers to a saturated ring system of about 3 to about 10 ring carbon atoms. In various embodiments, alkyl groups can have 3-8, 3-7, or 3-6, 3-5 carbon atoms. Examples of the "$C_3$-$C_6$cycloalkyl" include cyclopropyl, cyclobutyl, cyclopentyl, and cyclohexyl.

The term "haloalkyl" refers to an alkyl group, as the case may be, which is substituted with one or more halogen atoms. As used herein, the term "halogen" or "halo" means F, Cl, Br, or I. In the present specification, examples of the "halo($C_1$-$C_6$)alkyl" include a $C_1$-6 alkyl group having 1 to 7, typically 1 to 5, halogen atoms. Specific examples thereof include chloromethyl, difluoromethyl, trichloromethyl, trifluoromethyl, 2-bromoethyl, 2,2,2-trifluoroethyl, tetrafluoroethyl, pentafluoroethyl, 2,2-difluoropropyl, 3,3,3-trifluoropropyl, 4,4,4-trifluorobutyl, 5,5,5-trifluoropentyl, and 6,6,6-trifluorohexyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" refers to a $C_6$-14 aromatic hydrocarbon moiety comprising one to three aromatic rings. In at least one embodiment, the aryl group is a $C_{6-10}$ aryl group. Aryl groups include, without limitation, optionally substituted phenyl, naphthyl, or anthracenyl. In certain embodiments, aryl groups can be optionally substituted as described herein. The term "aryl" as used herein, also includes groups in which an aryl ring is fused to one or more cycloaliphatic or heterocyclic rings to form an optionally substituted cyclic structure such as a tetrahydronaphthyl, indenyl, indanyl, or indolinyl ring. The term "aryl" may be used interchangeably with the terms "aryl group," "aryl ring," and "aromatic ring."

The terms "heteroaryl" and "heteroar-" refer to groups having 5 to 14 ring atoms, such as 5, 6, 9, or 10 ring atoms; having 6, 10, or 14 pi electrons shared in a cyclic array; and having, in addition to carbon atoms, from one to five heteroatoms. A heteroaryl group may be mono-, bi-, tri-, or polycyclic, for instance mono-, bi-, or tricyclic, such as mono- or bicyclic. In the context of "heteroar-" entities, the term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-," as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring," "heteroaryl group," or "heteroaromatic." In certain embodiments, heteroaryl groups can be optionally substituted as described herein.

As used herein, the terms "heterocycle," "heterocyclyl," "heterocyclic radical," and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, for instance one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, for instance mono-, bi-, or tricyclic, and such as mono- or bicyclic. The term "heterocyclylalkyl" refers to an alkyl group substituted by a heterocyclyl, and the alkyl and heterocyclyl portions can independently be optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined. The term "partially unsaturated" is intended to encompass rings having a tautomer that includes at least one double bond or triple bond between ring atoms. For example, a ring including a carbonyl group exists as an enol tautomer and thus is also considered as "partially unsaturated."

An aryl (including aralkyl, aralkoxy, aryloxyalkyl and the like) or heteroaryl (including heteroaralkyl and heteroarylalkoxy and the like) group can contain one or more substituents and thus can be "optionally substituted." In addition to the substituents defined above and herein, suitable substituents on the unsaturated carbon atom of an aryl or heteroaryl group also include and are generally selected from -halo, —$NO_2$, —CN, —$R^+$, —$C(R^+)$=$C(R^+)_2$, —C≡C—$R^+$, —$OR^+$, —$SR°$, —$S(O)R°$, —$SO_2R°$, —$SO_3R^+$, —$SO_2N(R^+)_2$, —$N(R^+)_2$, —$NR^+C(O)R^+$, —$NR^+C(S)R^+$, —$NR^+C(O)N(R^+)_2$, —$NR^+C(S)N(R^+)_2$, —$N(R^+)C(=NR^+)$—$N(R^+)_2$, —$N(R^+)C(=NR^+)$—$R°$, —$NR^+CO_2R^+$, —$NR^+SO_2R°$, —$NR^+SO_2N(R^+)_2$, —O—$C(O)R^+$, —O—$CO_2R^+$, —$OC(O)N(R^+)_2$, —$C(O)R^+$, —$C(S)R°$, —$CO_2R^+$, —C(O)—$C(O)R^+$, —$C(O)N(R^+)_2$, —$C(S)N(R^+)_2$, —$C(O)N(R^+)$—$OR^+$, —$C(O)N(R^+)C(=NR^+)$—$N(R^+)_2$, —$N(R^+)C(=NR^+)$—$N(R^+)$—$C(O)R^+$, —$C(=NR^+)$—$N(R^+)_2$, —$C(=NR^+)$—$OR^+$, —$N(R^+)$—$N(R^+)_2$, —$C(=NR^+)$—$N(R^+)$—$OR^+$, —$C(R°)$=N—$OR^+$, —$P(O)(R^+)_2$, —$P(O)(OR^+)_2$, —O—P(O)—$OR^+$, and —P(O)($NR^+$)—$N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl. In some embodiments, $R^+$, independently, is hydrogen, $C_{1-6}$ aliphatic, or $C_{3-6}$ cycloaliphatic. Each R° is, independently, an optionally substituted aliphatic, aryl, heteroaryl, cycloaliphatic, or heterocyclyl group.

An aliphatic or heteroaliphatic group, or a non-aromatic carbocyclic or heterocyclic ring can contain one or more substituents and thus can be "optionally substituted." Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C($R^*$)$_2$, =N—N($R^*$)$_2$, =N—OR*, =N—NHC(O)R*, =N—$NHCO_2R°$=N—$NHSO_2R°$ or =N—R* where R° is defined above, and each R* is independently selected from hydrogen or an optionally substituted $C_1$-6 aliphatic group.

In addition to the substituents defined above and herein, optional substituents on the nitrogen of a non-aromatic heterocyclic ring also include and are generally selected from —$R^+$, —$N(R^+)_2$, —$C(O)R^+$, —$C(O)OR^+$, —C(O)C(O)$R^+$, —C(O)$CH_2$C(O)$R^+$, —$S(O)_2R^+$, —$S(O)_2N(R^+)_2$, —$C(S)N(R^+)_2$, —C(=NH)—$N(R^+)_2$, or —$N(R^+)S(O)_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

For purposes of clarity, all bivalent groups described herein are intended to be read from left to right, with a corresponding left-to-right reading of the formula or structure in which the variable appears.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of $OR^+$

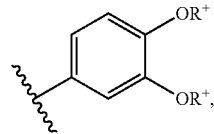

these two occurrences of $R^+$ are taken together with the oxygen atoms to which they are bound to form a fused 6-membered oxygen containing ring

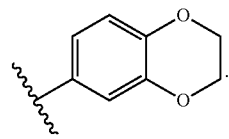

It will be appreciated that a variety of other rings (e.g., spiro and bridged rings) can be formed when two independent occurrences of $R^+$ (or any other variable similarly defined in the specification and claims herein) are taken together with their intervening atom(s) and that the examples detailed above are not intended to be limiting.

Unless otherwise stated, structures depicted herein are also meant to include all stereoisomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds disclosed herein are within the scope of the present disclosure. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this disclosure. Such compounds are useful, as a nonlimiting example, as analytical tools or probes in biological assays.

It is to be understood that, when a disclosed compound has at least one chiral center, the present disclosure encompasses one enantiomer free or substantially free from the corresponding optical isomer, a racemic mixture of the inhibitor, and mixtures enriched in one enantiomer relative to its corresponding optical isomer. When a mixture is enriched in one enantiomer relative to its optical isomers, the mixture contains, for example, an enantiomeric excess of at least 50%, 75%, 80%, 85%, 90%, 95%, 99%, or 99.5%.

The enantiomers of the present disclosure may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another compound by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present disclosure encompasses a diastereomer free or substantially free of other diastereomers, a pair of diastereomers free or substantially free from other diastereomeric pairs, mixtures of diasteromers, mixtures of diastereomeric pairs, mixtures of diasteromers in which one diastereomer is enriched relative to the other diastereomer(s) and mixtures of diastereomeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 80%, 85%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

Compounds of Formula (I)

The present disclosure provides a compound of Formula (I):

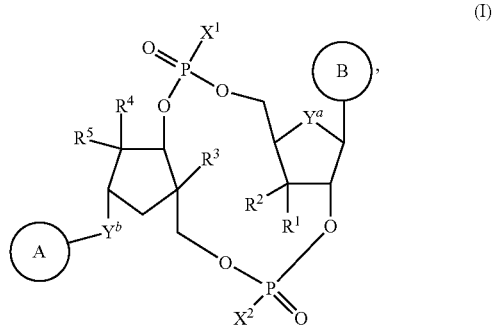

(I)

or a pharmaceutically acceptable salt thereof, wherein:

$X^1$ is —SH or —OH;

$X^2$ is —SH or —OH;

$Y^a$ is —O—, —S—, or —CH$_2$—;

$Y^b$ is —O—, —S—, —NH—, or —NR$^a$—, wherein R$^a$ is C$_1$-C$_4$alkyl;

$R^1$ is hydrogen, fluoro, —OH, —NH$_2$, —OR$^b$, or —NHR$^b$;

$R^2$ is hydrogen or fluoro;

$R^3$ is hydrogen; $R^4$ is hydrogen, fluoro, —OH, —NH$_2$, —OR$^b$, or —NHR$^b$; or $R^3$ and $R^4$ are taken together to form —CH$_2$O—;

$R^5$ is hydrogen or fluoro;

$R^b$ is C$_1$-C$_6$alkyl, halo(C$_1$-C$_6$)alkyl, or C$_3$-C$_6$cycloalkyl;

Ring A is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein Ring A comprises at least one N atom in the ring, and wherein $Y^b$ is attached to a carbon atom of Ring A; and Ring B is an optionally substituted 9- or 10-membered bicyclic heteroaryl ring containing 2-5 heteroatoms selected from N, O, or S; wherein Ring B comprises at least two N atoms in the ring.

In some embodiments, the compound of Formula (I) is represented by Formula (I-A), (I-B), (I-C), or (I-D):

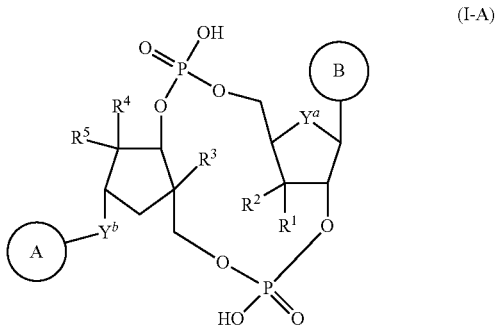

(I-A)

(I-B)
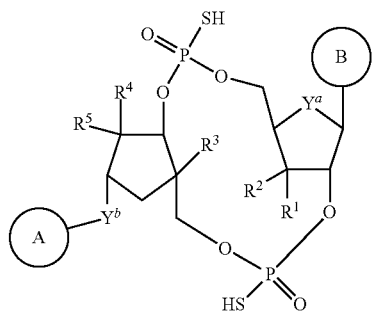

(I-C)
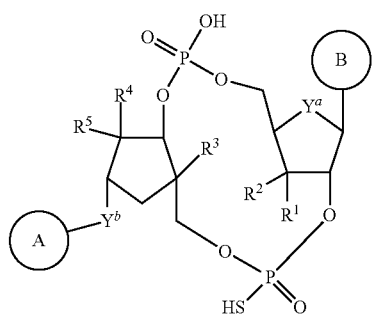

(I-D)
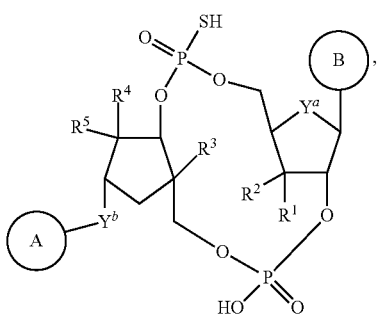

wherein $Y^a$, $Y^b$, $R^1$, $R^2$, $R^3$, $R^4$, $R^5$, Ring A, and Ring B have the values described herein.

In some embodiments, the compound of Formula (I) is represented by Formula (I-E) or (I-F):

(I-E)
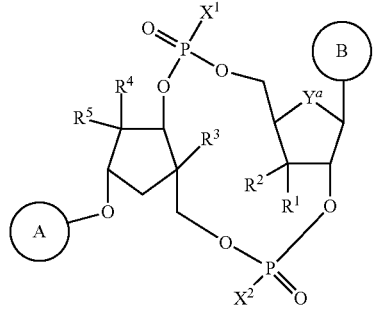

(I-F)
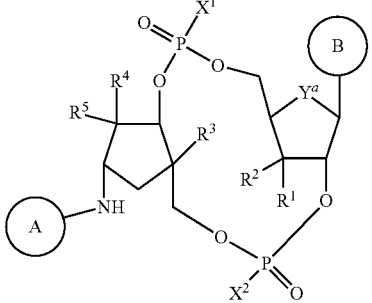

wherein $X^1$, $X^2$, $Y^a$, $R^1$, $R^2$, $R^3$, $R^4$, $R^5$, Ring A, and Ring B have the values described herein.

In some embodiments, the compound of Formula (I) is represented by Formula (II):

(II)
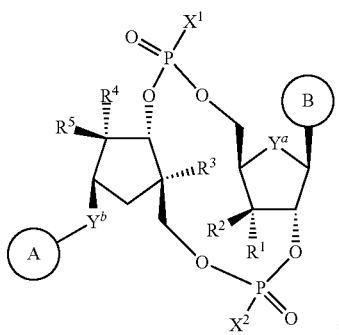

or a pharmaceutically acceptable salt thereof, wherein $X^1$ is —SH or —OH;

$X^2$ is —SH or —OH;

$Y^a$ is —O—, —S—, or —CH$_2$—;

$Y^b$ is —O—, —S—, —NH—, or —NR$^a$—, wherein R$^a$ is C$_1$-C$_4$alkyl;

$R^1$ is hydrogen, fluoro, —OH, —NH$_2$, —OR$^b$, or —NHR$^b$;

$R^2$ is hydrogen or fluoro;

$R^3$ is hydrogen; $R^4$ is hydrogen, fluoro, —OH, —NH$_2$, —OR$^b$, or —NHR$^b$; or $R^3$ and $R^4$ are taken together to form —CH$_2$O—;

$R^5$ is hydrogen or fluoro;

$R^b$ is C$_1$-C$_6$alkyl, halo(C$_1$-C$_6$)alkyl, or C$_3$-C$_6$cycloalkyl;

Ring A is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein Ring A comprises at least one N atom in the ring, and wherein $Y^b$ is attached to a carbon atom of Ring A; and Ring B is an optionally substituted 9- or 10-membered bicyclic heteroaryl ring containing 2-5 heteroatoms selected from N, O, or S; wherein Ring B comprises at least two N atoms in the ring.

In some embodiments, the compound of Formula (I) is represented by Formula (II-A) or (II-B):

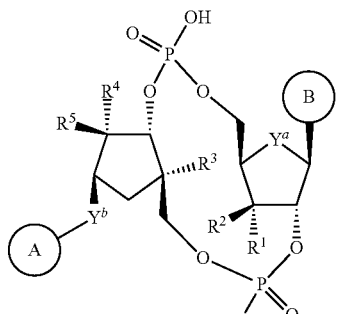
(II-A)

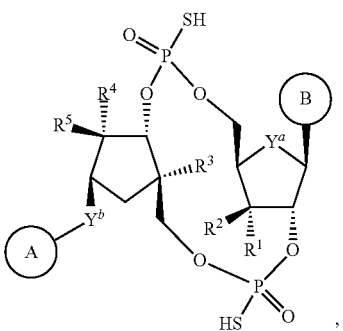
(II-B)

wherein $Y^a$, $Y^b$, $R^1$, $R^2$, $R^3$, $R^4$, $R^5$, Ring A, and Ring B have the values described herein.

In some embodiments, the compound of Formula (I) is represented by Formula (II-AA) or (II-BB):

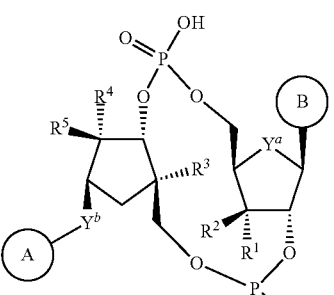
(II-AA)

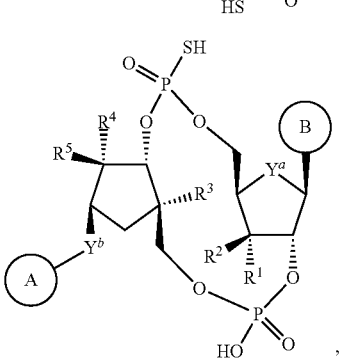
(II-BB)

wherein $Y^a$, $Y^b$, $R^1$, $R^2$, $R^3$, $R^4$, $R^5$, Ring A, and Ring B have the values described herein.

In some embodiments, the compound of Formula (I) is represented by Formula (II-C) or (II-D):

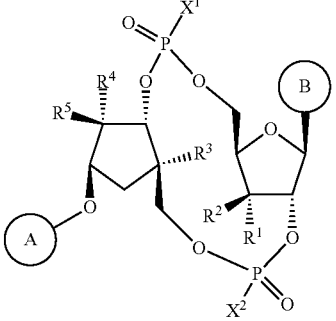
(II-C)

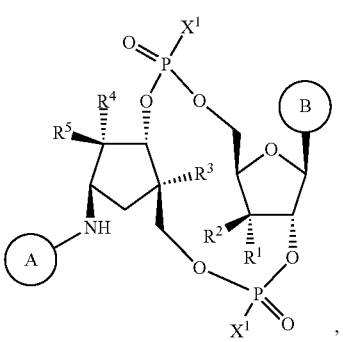
(II-D)

wherein $X^1$, $X^2$, $R^1$, $R^2$, $R^3$, $R^4$, $R^5$, Ring A, and Ring B have the values described herein. In some embodiments, both $X^1$ and $X^2$ are —OH. In some embodiments, both $X^1$ and $X^2$ are —SH. In some embodiments, $X^1$ is —OH and $X^2$ is —SH. In some embodiments, $X^1$ is —SH and $X^2$ is —OH.

In some embodiments, the compound of Formula (I) is represented by Formula (II-E) or (II-F):

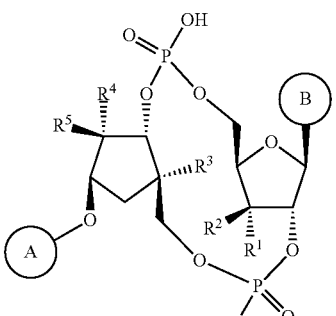
(II-E)

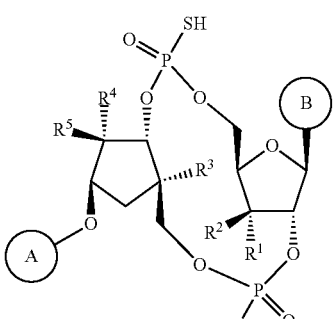
(II-F)

wherein $R^1$, $R^2$, $R^3$, $R^4$, $R^5$, Ring A, and Ring B have the values described herein.

In some embodiments, the compound of Formula (I) is represented by Formula (II-EE) or (II-FF):

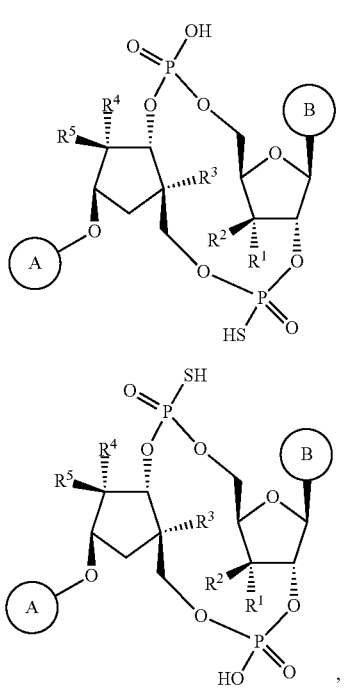

(II-EE)

(II-FF)

wherein $R^1$, $R^2$, $R^3$, $R^4$, $R^5$, Ring A, and Ring B have the values described herein.

In some embodiments, the compound of Formula (I) is represented by Formula (II-G) or (II-H):

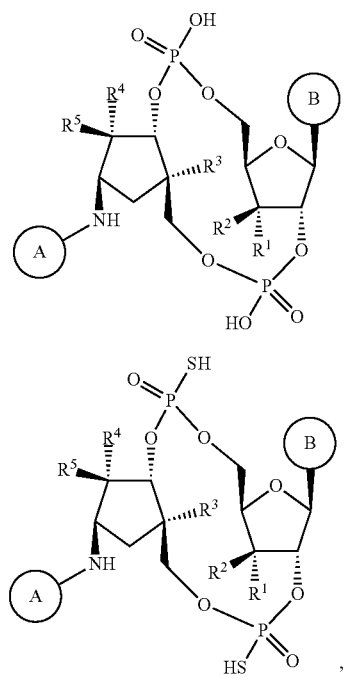

(II-G)

(II-H)

wherein $R^1$, $R^2$, $R^3$, $R^4$, $R^5$, Ring A, and Ring B have the values described herein.

In some embodiments, the compound of Formula (I) is represented by Formula (II-GG) or (II-HH):

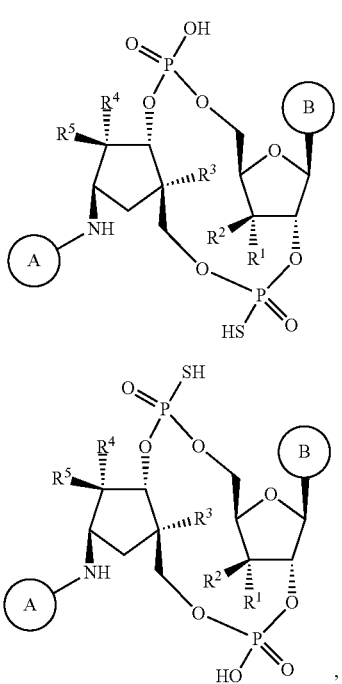

(II-GG)

(II-HH)

wherein $R^1$, $R^2$, $R^3$, $R^4$, $R^5$, Ring A, and Ring B have the values described herein.

In some embodiments, the compound of Formula (I) is represented by Formula (II-J) or (II-K):

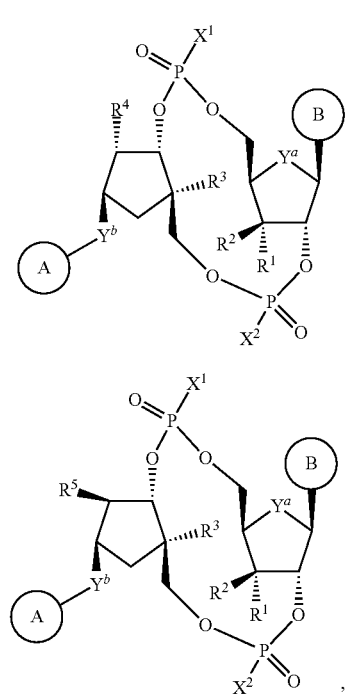

(II-J)

(II-K)

wherein $X^1$, $X^2$, $Y^a$, $Y^b$, $R^1$, $R^2$, $R^3$, $R^4$, $R^5$, Ring A, and Ring B have the values described herein. In some embodiments, both $X^1$ and $X^2$ are —OH. In some embodiments, both $X^1$ and $X^2$ are —SH. In some embodiments, $X^1$ is —OH and $X^2$ is —SH. In some embodiments, $X^1$ is —SH and $X^2$ is —OH.

In some embodiments, the compound of Formula (I) is represented by Formula (II-L) or (II-M):

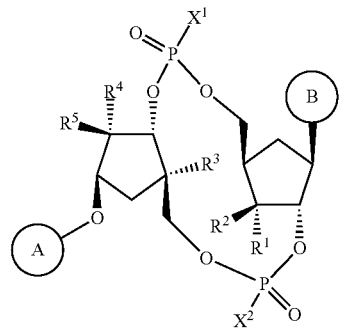

(II-L)

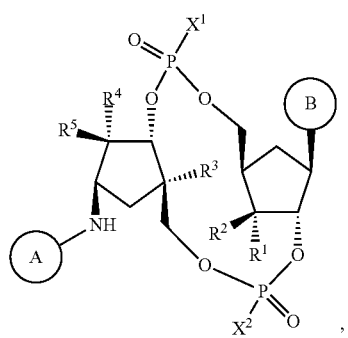

(II-M)

wherein $R^1$, $R^2$, $R^3$, $R^4$, $R^5$, Ring A, and Ring B have the values described herein. In some embodiments, both $X^1$ and $X^2$ are —OH. In some embodiments, both $X^1$ and $X^2$ are —SH. In some embodiments, $X^1$ is —OH and $X^2$ is —SH. In some embodiments, $X^1$ is —SH and $X^2$ is —OH. In some embodiments, $R^2$, $R^3$, and $R^5$ are hydrogen; $R^1$ and $R^4$ are each independently hydrogen, fluoro, —OH, or —OCH$_2$CF$_3$. In some embodiments, $R^2$, $R^3$, and $R^5$ are hydrogen; $R^1$ is hydrogen, fluoro, —OH, or —OCH$_2$CF$_3$; and $R^4$ is hydrogen, fluoro, or —OH. In some embodiments, $R^2$, $R^3$, and $R^5$ are hydrogen; $R^1$ is hydrogen or —OH; and $R^4$ is hydrogen or fluoro.

In some embodiments, the compound of Formula (I) is represented by Formula (III):

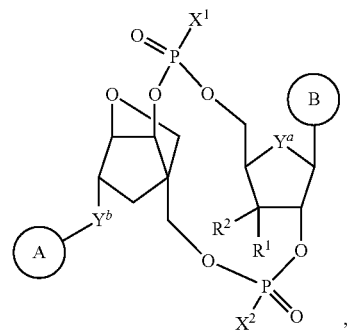

(III)

or a pharmaceutically acceptable salt thereof, wherein
$X^1$ is —SH or —OH;
$X^2$ is —SH or —OH;
$Y^a$ is —O—, —S—, or —CH$_2$—;
$Y^b$ is —O—, —S—, —NH—, or —NR$^a$—, wherein R$^a$ is C$_1$-C$_4$alkyl;
$R^1$ is hydrogen, fluoro, —OH, —NH$_2$, —OR$^b$, or —NHR$^b$;
$R^2$ is hydrogen or fluoro;
$R^b$ is C$_1$-C$_6$alkyl, halo(C$_1$-C$_6$)alkyl, or C$_3$-C$_6$cycloalkyl;
Ring A is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein Ring A comprises at least one N atom in the ring, and wherein $Y^b$ is attached to a carbon atom of Ring A; and
Ring B is an optionally substituted 9- or 10-membered bicyclic heteroaryl ring containing 2-5 heteroatoms selected from N, O, or S; wherein Ring B comprises at least two N atoms in the ring.

In some embodiments, the compound of Formula (I) is represented by Formula (III-A):

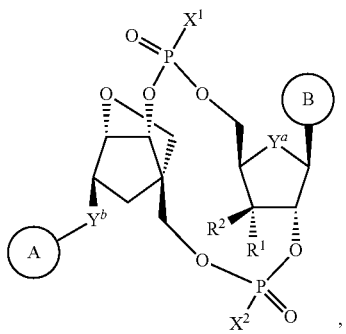

(III-A)

wherein $X^1$, $X^2$, $Y^a$, $Y^b$, $R^1$, $R^2$, Ring A, and Ring B have the values described herein.

In some embodiments, the compound of Formula (I) is represented by Formula (IV):

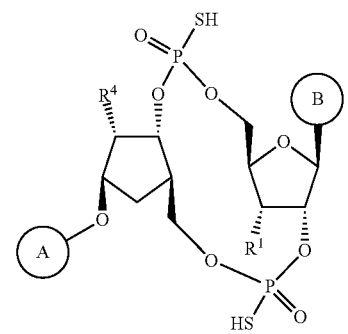

(IV)

or a pharmaceutically acceptable salt thereof, wherein $R^1$, $R^4$, Ring A, and Ring B have the values described herein. In some embodiments, $R^1$ and $R^4$ are each independently hydrogen, fluoro, —OH, or —OCH$_2$CF$_3$. In some embodiments, $R^1$ is hydrogen, fluoro, —OH, or —OCH$_2$CF$_3$, and $R^4$ is hydrogen, fluoro, or —OH. In some embodiments, $R^1$ is —OCH$_2$CF$_3$, and $R^4$ is hydrogen, fluoro, or —OH. In some embodiments, $R^1$ is —OH and $R^4$ is hydrogen. In some embodiments, $R^1$ is fluoro and $R^4$ is hydrogen. In some embodiments, $R^1$ is —OH and $R^4$ is fluoro. In some embodiments, both $R^1$ and $R^4$ are hydrogen. In some embodiments, both $R^1$ and $R^4$ are fluoro.

In some embodiments, the compound of Formula (I) is represented by Formula (IV-A) or (IV-B):

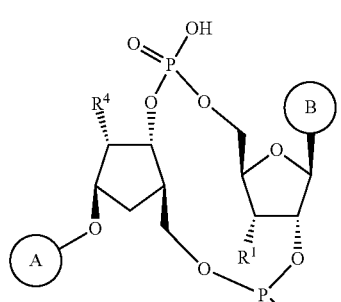
(IV-A)

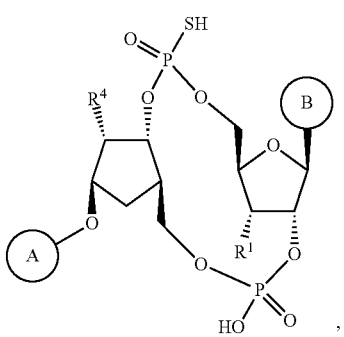
(IV-B)

or a pharmaceutically acceptable salt thereof, wherein $R^1$, $R^4$, Ring A, and Ring B have the values described herein. In some embodiments, $R^1$ and $R^4$ are each independently hydrogen, fluoro, —OH, or —OCH$_2$CF$_3$. In some embodiments, $R^1$ is hydrogen, fluoro, —OH, or —OCH$_2$CF$_3$, and $R^4$ is hydrogen, fluoro, or —OH. In some embodiments, $R^1$ is —OCH$_2$CF$_3$, and $R^4$ is hydrogen, fluoro, or —OH. In some embodiments, $R^1$ is —OH and $R^4$ is hydrogen. In some embodiments, $R^1$ is fluoro and $R^4$ is hydrogen. In some embodiments, $R^1$ is —OH and $R^4$ is fluoro. In some embodiments, both $R^1$ and $R^4$ are hydrogen. In some embodiments, both $R^1$ and $R^4$ are fluoro.

In some embodiments, the compound of Formula (I) is represented by Formula (IV-C):

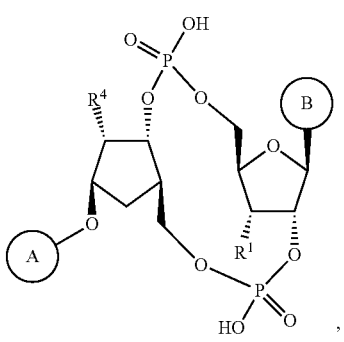
(IV-C)

or a pharmaceutically acceptable salt thereof, wherein $R^1$, $R^4$, Ring A, and Ring B have the values described herein. In some embodiments, $R^1$ and $R^4$ are each independently hydrogen, fluoro, —OH, or —OCH$_2$CF$_3$. In some embodiments, $R^1$ is hydrogen, fluoro, —OH, or —OCH$_2$CF$_3$, and $R^4$ is hydrogen, fluoro, or —OH. In some embodiments, $R^1$ is —OCH$_2$CF$_3$, and $R^4$ is hydrogen, fluoro, or —OH. In some embodiments, $R^1$ is —OH and $R^4$ is hydrogen. In some embodiments, $R^1$ is fluoro and $R^4$ is hydrogen. In some embodiments, $R^1$ is —OH and $R^4$ is fluoro. In some embodiments, both $R^1$ and $R^4$ are hydrogen. In some embodiments, both $R^1$ and $R^4$ are fluoro.

In some embodiments, the compound of Formula (I) is represented by Formula (V):

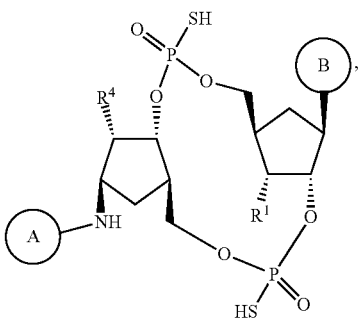
(V)

or a pharmaceutically acceptable salt thereof, wherein $R^1$, $R^4$, Ring A, and Ring B have the values described herein. In some embodiments, $R^1$ and $R^4$ are each independently hydrogen, fluoro, —OH, or —OCH$_2$CF$_3$. In some embodiments, $R^1$ is hydrogen, fluoro, —OH, or —OCH$_2$CF$_3$, and $R^4$ is hydrogen, fluoro, or —OH. In some embodiments, $R^1$ is —OCH$_2$CF$_3$, and $R^4$ is hydrogen, fluoro, or —OH. In some embodiments, $R^1$ is —OH and $R^4$ is hydrogen. In some embodiments, $R^1$ is fluoro and $R^4$ is hydrogen. In some embodiments, $R^1$ is —OH and $R^4$ is fluoro. In some embodiments, both $R^1$ and $R^4$ are hydrogen. In some embodiments, both $R^1$ and $R^4$ are fluoro.

In some embodiments, the compound of Formula (I) is represented by Formula (V-A) or (V-B):

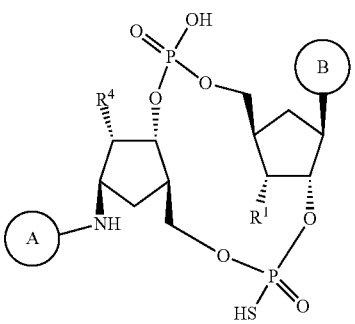
(V-A)

-continued

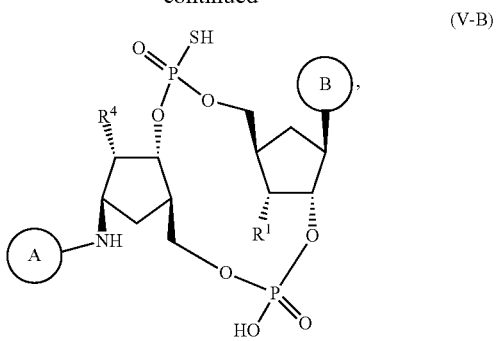

(V-B)

or a pharmaceutically acceptable salt thereof, wherein $R^1$, $R^4$, Ring A, and Ring B have the values described herein. In some embodiments, $R^1$ and $R^4$ are each independently hydrogen, fluoro, —OH, or —OCH$_2$CF$_3$. In some embodiments, $R^1$ is hydrogen, fluoro, —OH, or —OCH$_2$CF$_3$, and $R^4$ is hydrogen, fluoro, or —OH. In some embodiments, $R^1$ is —OCH$_2$CF$_3$, and $R^4$ is hydrogen, fluoro, or —OH. In some embodiments, $R^1$ is —OH and $R^4$ is hydrogen. In some embodiments, $R^1$ is fluoro and $R^4$ is hydrogen. In some embodiments, $R^1$ is —OH and $R^4$ is fluoro. In some embodiments, both $R^1$ and $R^4$ are hydrogen. In some embodiments, both $R^1$ and $R^4$ are fluoro.

In some embodiments, the compound of Formula (I) is represented by Formula (V-C):

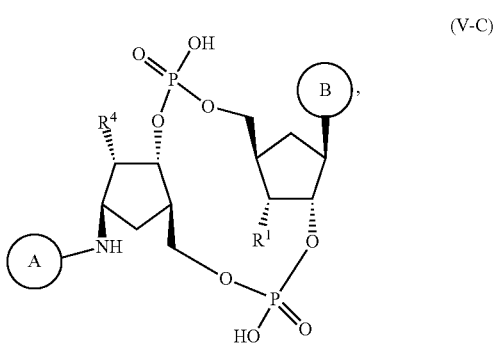

(V-C)

or a pharmaceutically acceptable salt thereof, wherein $R^1$, $R^4$, Ring A, and Ring B have the values described herein. In some embodiments, $R^1$ and $R^4$ are each independently hydrogen, fluoro, —OH, or —OCH$_2$CF$_3$. In some embodiments, $R^1$ is hydrogen, fluoro, —OH, or —OCH$_2$CF$_3$, and $R^4$ is hydrogen, fluoro, or —OH. In some embodiments, $R^1$ is —OCH$_2$CF$_3$, and $R^4$ is hydrogen, fluoro, or —OH. In some embodiments, $R^1$ is —OH and $R^4$ is hydrogen. In some embodiments, $R^1$ is fluoro and $R^4$ is hydrogen. In some embodiments, $R^1$ is —OH and $R^4$ is fluoro. In some embodiments, both $R^1$ and $R^4$ are hydrogen. In some embodiments, both $R^1$ and $R^4$ are fluoro.

The following values are described for any of formulas (I), (I-A), (I-B), (I-C), (I-D), (I-E), (I-F), (II), (II-A), (II-B), (II-AA), (II-BB), (II-C), (II-D), (II-E), (II-F), (II-EE), (II-FF), (II-G), (II-H), (II-GG), (II-HH), (II-J), (II-K), (II-L), (II-M), (III), (III-A), (IV), (IV-A), (IV-B), (IV-C), (V), (V-A), (V-B), and (V-C). The following values also apply to any of the formulas (VI), (VI-A), (VI-B), (VI-C), (VI-D), (VI-E), (VI-F), (VI-G), (VI-H), (VII), (VII-A), (VII-B), (VII-C), and (VII-D), described herein below.

In some embodiments, $X^1$ and $X^2$ are —SH, and the phosphorus atom of each phosphorothioate linkage is chiral and is independently $R_p$ or $S_p$.

In some embodiments, $X^1$ and $X^2$ are —SH, and the phosphorus atom of each phosphorothioate linkage is $R_p$.

In some embodiments, $X^1$ and $X^2$ are —OH.

In some embodiments, one of $X^1$ and $X^2$ is —OH, and the other is —SH, and the phosphorus atom of the phosphorothioate linkage is chiral and is $R_p$ or $S_p$.

In some embodiments, $Y^a$ is —O—, —S—, or —CH$_2$—. In some embodiments, $Y^a$ is —O—, or —S—. In some embodiments, $Y^a$ is —O—. In some embodiments, $Y^a$ is —S—. In some embodiments, $Y^a$ is —CH$_2$—.

In some embodiments, $Y^b$ is —O—, —S—, —NH—, or —NR$^a$—, wherein $R^a$ is $C_1$-$C_4$alkyl. In some embodiments, $Y^b$ is —O—. In some embodiments, $Y^b$ is —NH—. In some embodiments, $Y^b$ is —NMe-.

In some embodiments, $R^1$ is hydrogen, fluoro, —OH, —NH$_2$, —OR$^b$, or —NHR$^b$, wherein $R^b$ is $C_1$-$C_6$alkyl, halo($C_1$-$C_6$)alkyl, or $C_3$-$C_6$cycloalkyl. In some embodiments, $R^1$ is hydrogen, fluoro, —OH, or —OCH$_2$CF$_3$. In some embodiments, $R^1$ is fluoro or —OH. In some embodiments, $R^1$ is hydrogen. In some embodiments, $R^1$ is fluoro. In some embodiments, $R^1$ is —OH. In some embodiments, $R^1$ is —OCH$_2$CF$_3$.

In some embodiments, $R^2$ is hydrogen, or fluoro. In some embodiments, $R^2$ is hydrogen. In some embodiments, $R^2$ is fluoro.

In some embodiments, $R^1$ and $R^2$ are both hydrogen. In some embodiments, $R^1$ and $R^2$ are both fluoro. In some embodiments, $R^1$ is —OH and $R^2$ is hydrogen. In some embodiments, $R^1$ is fluoro and $R^2$ is hydrogen.

In some embodiments, $R^3$ is hydrogen; $R^4$ is hydrogen, fluoro, —OH, —NH$_2$, —OR$^b$, or —NHR$^b$, wherein $R^b$ is $C_1$-$C_6$alkyl, halo($C_1$-$C_6$)alkyl, or $C_3$-$C_6$cycloalkyl. In some embodiments, $R^3$ and $R^4$ are taken together to form —CH$_2$O—. In some embodiments, $R^3$ and $R^4$ are taken together to form —CH$_2$O—, wherein the carbon atom of —CH$_2$O— is directly connected to the carbon atom to which $R^3$ is directly connected.

In some embodiments, $R^3$ and $R^4$ are both hydrogen. In some embodiments, $R^3$ is hydrogen and $R^4$ is fluoro. In some embodiments, $R^3$ is hydrogen and $R^4$ is —OH.

In some embodiments, $R^5$ is hydrogen or fluoro. In some embodiments, $R^5$ is hydrogen. In some embodiments, $R^5$ is fluoro.

In some embodiments, $R^3$, $R^4$, $R^5$ are all hydrogen. In some embodiments, $R^3$ is hydrogen, $R^4$ is fluoro, and $R^5$ is hydrogen. In some embodiments, $R^3$ is hydrogen, $R^4$ is hydrogen, and $R^5$ is fluoro. In some embodiments, $R^3$ is hydrogen, and both $R^4$ and $R^5$ are fluoro.

In some embodiments, Ring A is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein Ring A comprises at least one N atom in the ring, and wherein $Y^b$ is attached to a carbon atom of Ring A.

In some embodiments, Ring A is an optionally substituted 6-membered monocyclic heteroaryl ring containing 1-3 N atoms. In some embodiments, Ring A is an optionally substituted 6-membered monocyclic heteroaryl ring containing one N atom, such as pyridinyl. In some embodiments, Ring A is an optionally substituted 6-membered monocyclic heteroaryl ring containing two N atoms, such as pyridazinyl, pyrimidinyl, and pyrazinyl. In some embodiments, Ring A is an optionally substituted 6-membered monocyclic heteroaryl ring containing three N atoms, such as 1,2,4-triazinyl, 1,3,5-triazinyl, thyminyl, and uracilyl.

In some embodiments, Ring A is

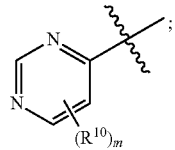

wherein:
each $R^{10}$ is independently hydrogen, halogen, —OH, —NH$_2$, C$_1$-C$_6$alkyl, halo(C$_1$-C$_6$)alkyl, C$_3$-C$_6$cycloalkyl, —OR$^{11}$, —NHR$^{11}$, —CN, —NO$_2$, or —C(O)NHR$^{12}$;
$R^{11}$ is C$_1$-C$_6$alkyl, halo(C$_1$-C$_6$)alkyl, or C$_3$-C$_6$cycloalkyl;
$R^{12}$ is hydrogen, C$_1$-C$_6$alkyl, halo(C$_1$-C$_6$)alkyl, or C$_3$-C$_6$cycloalkyl; and
m is 0, 1, or 2.

In some embodiments, m is 0.

In some embodiments, each $R^{10}$ is independently hydrogen, fluoro, chloro, —OH, —NH$_2$, —CH$_3$, —CF$_3$, —OCH$_3$, —CN, —NO$_2$, or —C(O)NH$_2$.

In some embodiments, each $R^{10}$ is independently hydrogen, fluoro, chloro, —CN, or C$_1$-C$_3$alkyl.

In some embodiments, $R^{10}$ is fluoro. In some embodiments, $R^{10}$ is chloro. In some embodiments, $R^{10}$ is —CN. In some embodiments, $R^{10}$ is —CH$_3$. In some embodiments, $R^{10}$ is —C(O)NH$_2$.

In some embodiments, Ring A is

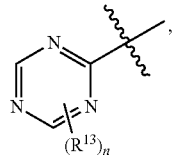

wherein:
each $R^{13}$ is independently hydrogen, halogen, —OH, —NH$_2$, C$_1$-C$_6$alkyl, halo(C$_1$-C$_6$)alkyl, C$_3$-C$_6$cycloalkyl, —OR$^{11}$, —NHR$^{11}$, —CN, —NO$_2$, or —C(O)NHR$^{12}$;
$R^{11}$ is C$_1$-C$_6$alkyl, halo(C$_1$-C$_6$)alkyl, or C$_3$-C$_6$cycloalkyl;
$R^{12}$ is hydrogen, C$_1$-C$_6$alkyl, halo(C$_1$-C$_6$)alkyl, or C$_3$-C$_6$cycloalkyl; and
n is 0, 1, or 2.

In some embodiments, n is 0.

In some embodiments, each $R^{13}$ is independently hydrogen, fluoro, chloro, —OH, —NH$_2$, —CH$_3$, —CF$_3$, —OCH$_3$, —CN, —NO$_2$, or —C(O)NH$_2$.

Examples of optionally substituted 6-membered monocyclic heteroaryl ring include, but are not limited to the following:

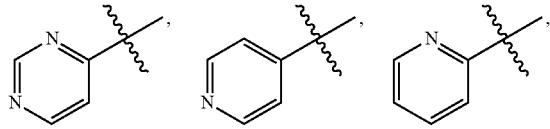

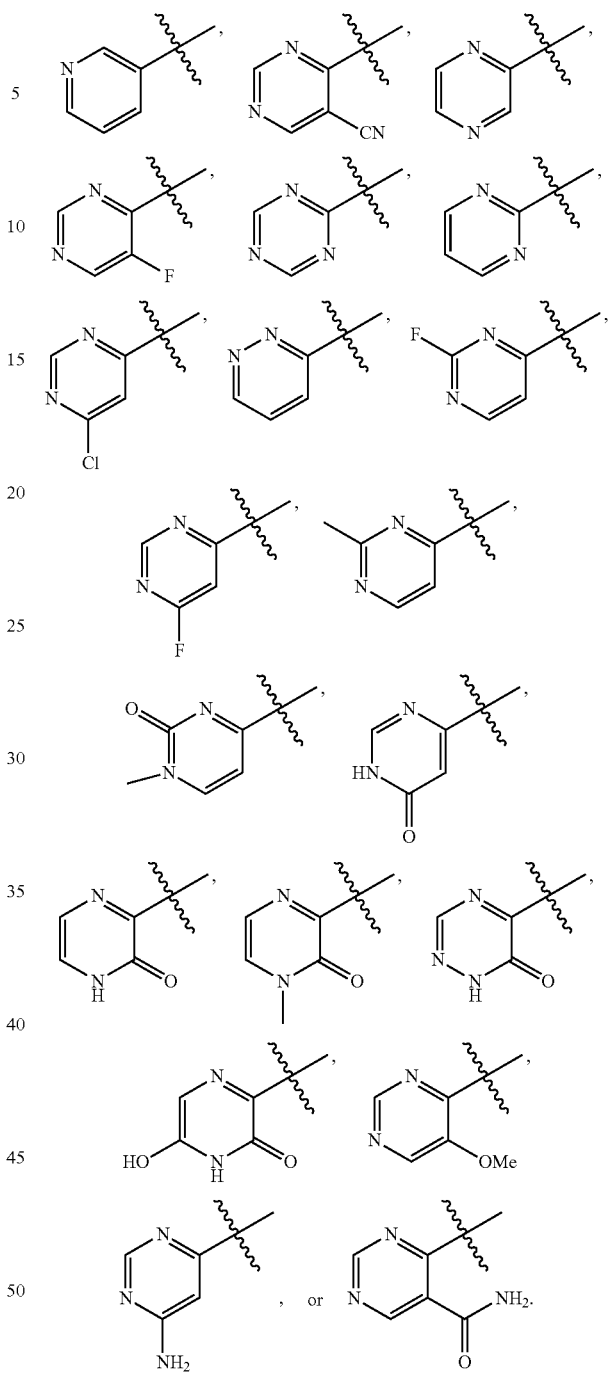

In some embodiments, Ring A is an optionally substituted 5-membered monocyclic heteroaryl ring containing 1-4 heteroatoms selected from N, O, or S. Examples of 5-membered monocyclic heteroaryl rings include but not limited to pyrrolyl, furanyl, thiophenyl, oxazolyl, pyrazolyl, isoxazolyl, thiazolyl, isothiazolyl, imidazolyl, 1,2,3-triazolyl, 1,2,4-triazolyl, tetrazolyl, 1,2,5-oxadizaolyl, 1,2,3,-oxadizaolyl, 1,3,4-thiadiazolyl, and 1,2,5-thiadizaolyl.

Examples of optionally substituted 5-membered monocyclic heteroaryl rings can also include the following:

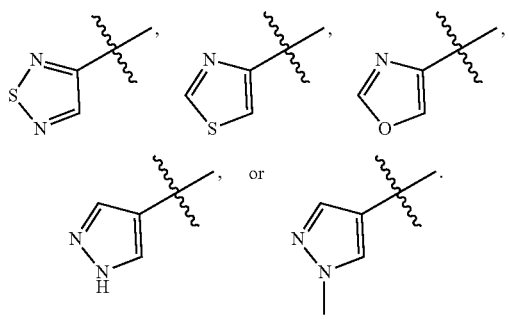

In some embodiments, Ring A is an optionally substituted 9- or 10-membered bicyclic heteroaryl ring containing 1-5 heteroatoms selected from N, O, or S. In some embodiments, Ring A is an optionally substituted 9-membered bicyclic heteroaryl ring containing at least 2 N atoms. In some embodiments, Ring A is an optionally substituted 9-membered bicyclic heteroaryl ring that comprises a pyrimidine ring.

Examples of optionally substituted 9-membered bicyclic heteroaryl rings include, but are not limited to the following:

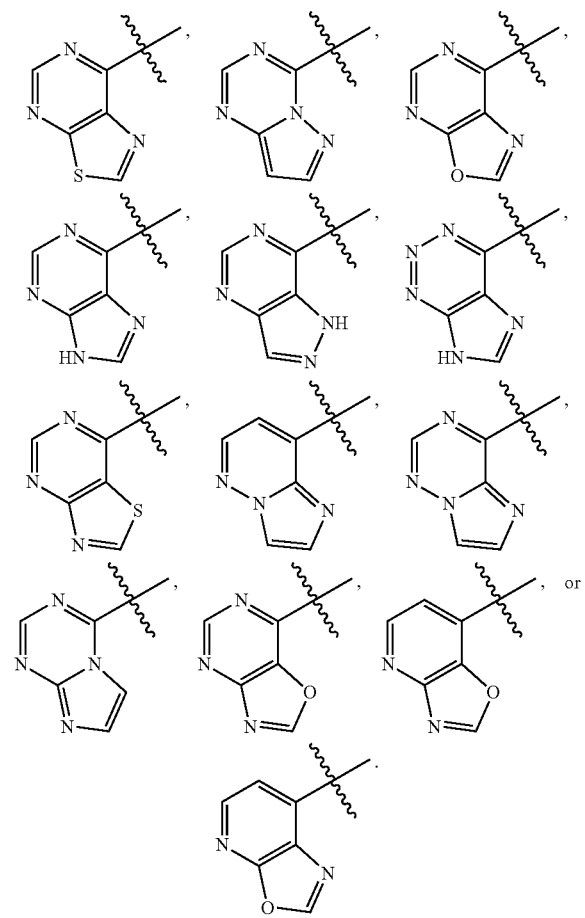

In some embodiments, Ring A can comprise a 6-membered monocyclic heteroaryl ring (e.g., a pyrimidine ring) fused to a non-aromatic ring, such as:

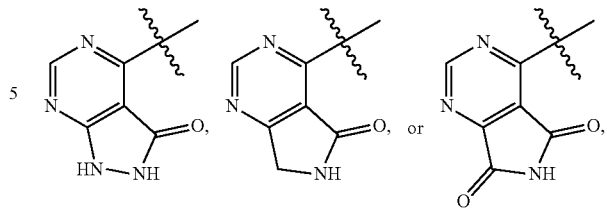

In some embodiments, Ring B is an optionally substituted 9- or 10-membered bicyclic heteroaryl ring containing 2-5 heteroatoms selected from N, O, or S. In some embodiments, Ring B comprises at least two N atoms in the ring. For example, WO2017/027645 and WO2017/027646 describe various 9-membered bicyclic heteroaryl rings. WO2017/027645 and WO2017/027646 are incorporated herein by reference in their entirety.

In some embodiments, Ring B is an optionally substituted 9-membered bicyclic heteroaryl ring containing 3-5 N atoms; and the $Y^a$-containing 5-membered ring is attached to a nitrogen atom of Ring B.

In some embodiments, Ring B is:

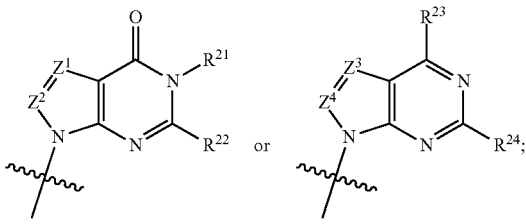

$Z^1$, $Z^2$, $Z^3$, and $Z^4$ are each independently N or $CR^{20}$;
$R^{21}$ is hydrogen or $C_1$-$C_6$alkyl, halo($C_1$-$C_6$)alkyl, or $C_3$-$C_6$cycloalkyl;
$R^{23}$ is hydrogen or —$NH_2$; and
$R^{20}$, $R^{22}$, and $R^{24}$ are each independently hydrogen, halogen, —OH, —$NH_2$, —CN, $C_1$-$C_6$alkyl, halo($C_1$-$C_6$)alkyl, or $C_3$-$C_6$cycloalkyl.
In some embodiments, $Z^1$, $Z^2$, $Z^3$, and $Z^4$ are each independently N, CH, or CF;
$R^{21}$ is hydrogen or —$CH_3$; and $R^{22}$ and $R^{24}$ are each independently hydrogen, —$NH_2$, or —$CH_3$.

In some embodiments, Ring B is a 9-membered bicyclic heteroaryl ring having the following structures:

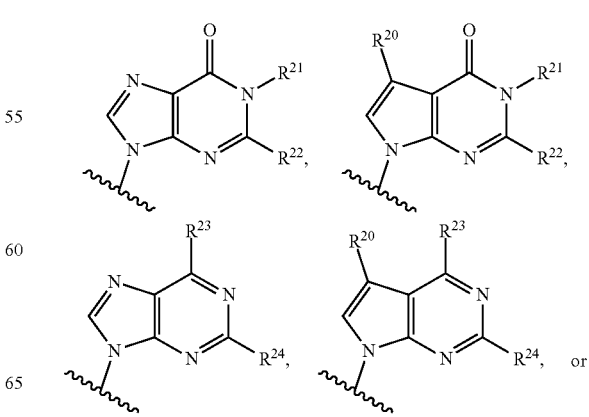

-continued

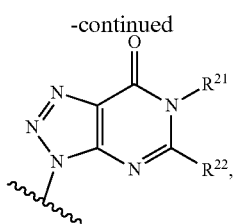

wherein $R^{20}$, $R^{21}$, $R^{22}$, $R^{23}$, and $R^{24}$ have the values described herein.

In some embodiments, $R^{20}$ is hydrogen or fluoro. In some embodiments, $R^{21}$ is hydrogen or —$CH_3$, and $R^{22}$ is hydrogen, —$NH_2$, or —$CH_3$. In some embodiments, $R^{23}$ is hydrogen or —$NH_2$, and $R^{24}$ is hydrogen, —$NH_2$, or —$CH_3$.

In some embodiments, Ring B is selected from:

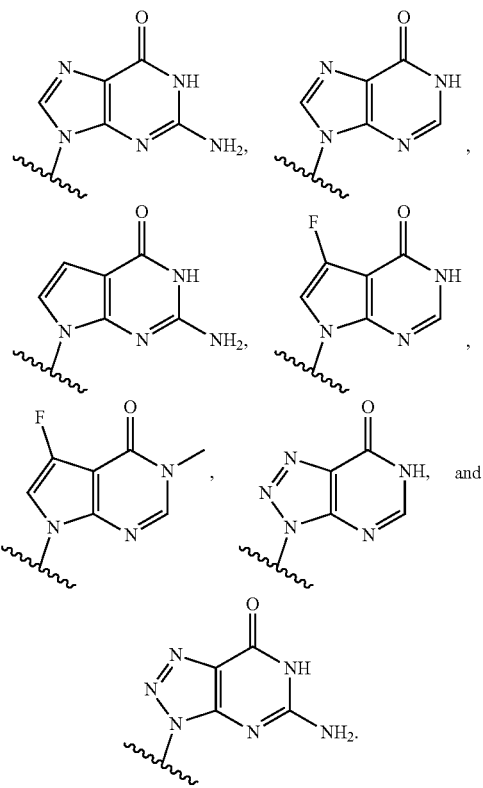

In some embodiments, Ring B is:

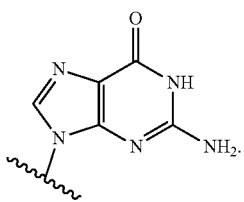 [SMILES: *n1cnc2c(=O)[nH]c(N)nc21]

Ring A and Ring B in the compounds disclosed herein can be optionally substituted. When Ring A or Ring B is substituted, the substituent is one or more substituents independently selected from the group consisting of halogen, —OH, —CN, —$NO_2$, $C_1$-$C_6$alkyl, halo($C_1$-$C_6$)alkyl, $C_3$-$C_6$cycloalkyl, —$OR^{11}$, —$SR^{12}$, —$N(R^{12})_2$, —$NR^{12}C(O)R^{12}$, —$C(O)R^{12}$, —$C(O)OR^{12}$, —$C(O)N(R^{12})_2$, and —$SO_2N(R^{12})_2$; or two adjacent substituents, taken together with the intervening ring atoms, form a 4- to 8-membered ring; wherein $R^{11}$ is $C_1$-$C_6$alkyl, halo($C_1$-$C_6$)alkyl, or $C_3$-$C_6$cycloalkyl; and $R^{12}$ is hydrogen, $C_1$-$C_6$alkyl, halo($C_1$-$C_6$)alkyl, or $C_3$-$C_6$cycloalkyl.

In some embodiments, Ring A and Ring B can be optionally substituted by one or more substitutents independently selected from fluoro, chloro, —OH, —CN, —$NO_2$, —$CH_3$, —$OCH_3$, —$NH_2$, —NHMe, —$NMe_2$, or —$C(O)NH_2$.

In some embodiments, two adjacent substituents on Ring A or Ring B, taken together with the intervening ring atoms, form a 4- to 8-membered ring, where the 4- to 8-membered ring can be saturated or partially unsaturated, cycloaliphatic or heterocyclic rings.

In some embodiments, the compound of Formula (I) is represented by Formula (VI):

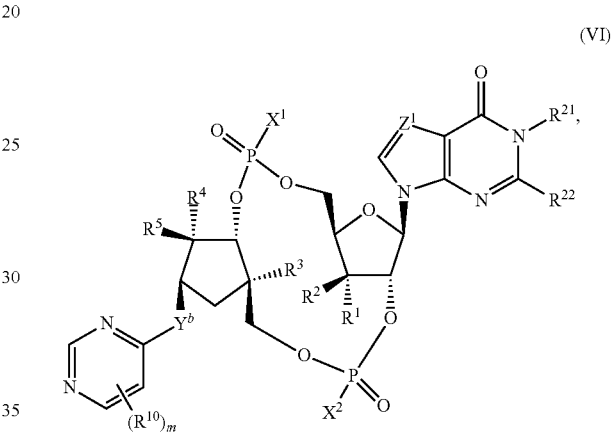

or a pharmaceutically acceptable salt thereof, wherein:
$X^1$ is —SH or —OH;
$X^2$ is —SH or —OH;
$Y^b$ is —O—, —S—, —NH—, or —NMe—;
$R^1$ is hydrogen, fluoro, —OH, or —$OR^b$;
$R^2$ is hydrogen or fluoro;
$R^3$ is hydrogen; $R^4$ is hydrogen, fluoro, or —OH; or $R^3$ and $R^4$ are taken together to form —$CH_2O$—;
$R^5$ is hydrogen or fluoro;
$R^b$ is $C_1$-$C_6$alkyl, halo($C_1$-$C_6$)alkyl, or $C_3$-$C_6$cycloalkyl;
each $R^{10}$ is independently hydrogen, halogen, —OH, —$NH_2$, $C_1$-$C_6$alkyl, halo($C_1$-$C_6$)alkyl, $C_3$-$C_6$cycloalkyl, —$OR^{11}$, —$NHR^{11}$, —CN, —$NO_2$, or —$C(O)NHR^{12}$;
$R^{11}$ is $C_1$-$C_6$alkyl, halo($C_1$-$C_6$)alkyl, or $C_3$-$C_6$cycloalkyl;
$R^{12}$ is hydrogen, $C_1$-$C_6$alkyl, halo($C_1$-$C_6$)alkyl, or $C_3$-$C_6$cycloalkyl;
m is 0, 1, or 2;
$Z^1$ is N, CH, or CF;
$R^{21}$ is hydrogen or —$CH_3$; and
$R^{22}$ is hydrogen, —$NH_2$, or —$CH_3$.

In some embodiments, $X^1$ and $X^2$ are —SH; and the phosphorus atom of each phosphorothioate linkage is chiral and is independently $R_p$ or $S_p$.

In some embodiments, $X^1$ and $X^2$ are —SH; and the phosphorus atom of each phosphorothioate linkage is $R_p$.

In some embodiments, $X^1$ and $X^2$ are —OH.

In some embodiments, one of $X^1$ and $X^2$ is —OH, and the other is —SH; and the phosphorus atom of the phosphorothioate linkage is chiral and is $R_p$ or $S_p$.

In some embodiments, $Y^b$ is —O—. In some embodiments, $Y^b$ is —NH— or —NMe-.

In some embodiments, $Z^1$ is N.

In some embodiments, $R^1$ is hydrogen, fluoro, —OH, or —OCH$_2$CF$_3$, and $R^2$ is hydrogen or fluoro.

In some embodiments, $R^3$ is hydrogen; $R^4$ is hydrogen, fluoro, or —OH; and $R^5$ is hydrogen or fluoro.

In some embodiments, $R^3$ and $R^4$ are taken together to form —CH$_2$O—; and $R^5$ is hydrogen.

In some embodiments, $R^2$, $R^3$, and $R^5$ are hydrogen.

In some embodiments, $R^1$ is hydrogen, fluoro, —OH, or —OCH$_2$CF$_3$. In some embodiments, $R^1$ is hydrogen, fluoro, or —OH. In some embodiments, $R^1$ is fluoro or —OH.

In some embodiments, $R^4$ is hydrogen, fluoro, or —OH. In some embodiments, $R^4$ is hydrogen or fluoro.

In some embodiments, m is 0.

In some embodiments, $R^{21}$ is hydrogen.

In some embodiments, $R^{22}$ is —NH$_2$.

In some embodiments, the compound of Formula (I) is represented by Formulae (VI-A) to (VI-D):

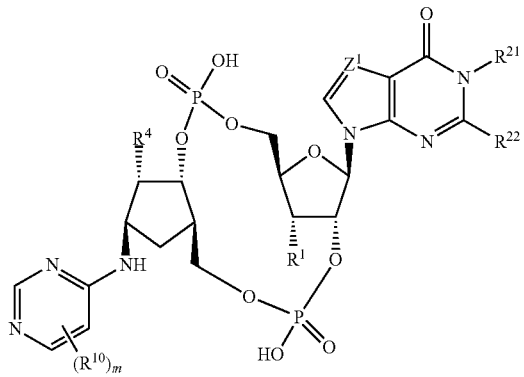

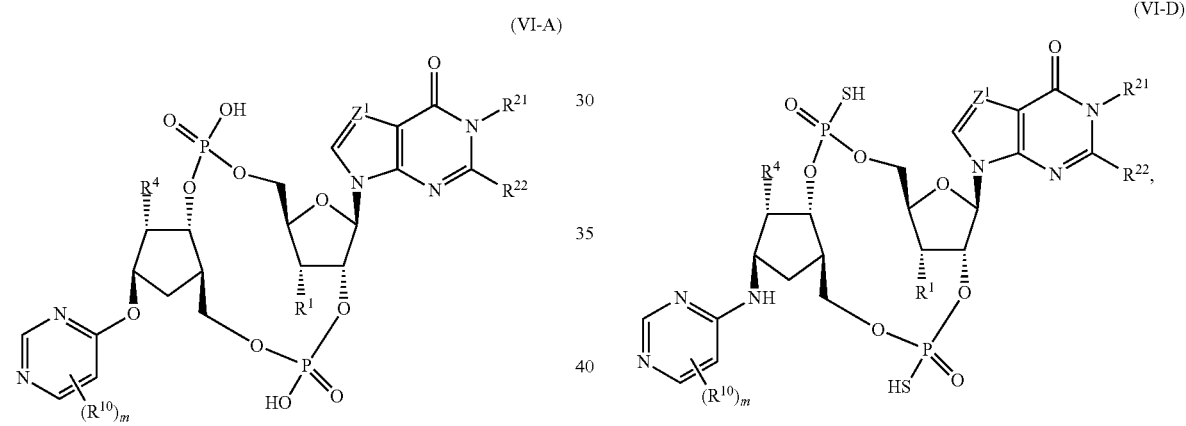

or a pharmaceutically acceptable salt thereof, wherein $R^1$, $R^4$, $R^{10}$, $R^{21}$, $R^{22}$, $Z^1$, and m have the values described herein.

In some embodiments, the compound of Formula (I) is represented by Formulae (VI-E) to (VI-H):

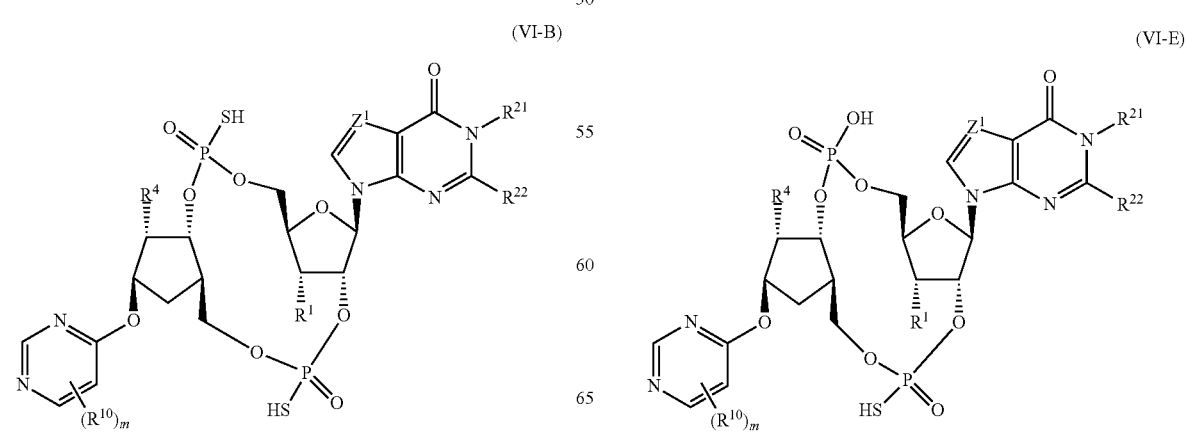

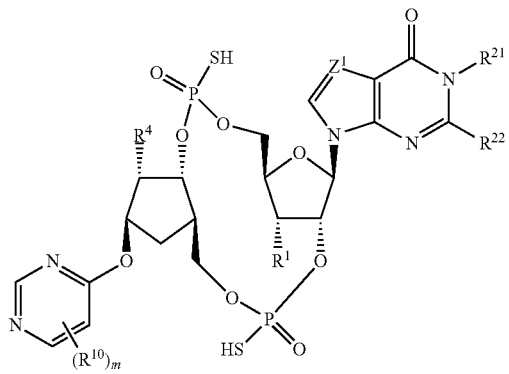
(VI-F)

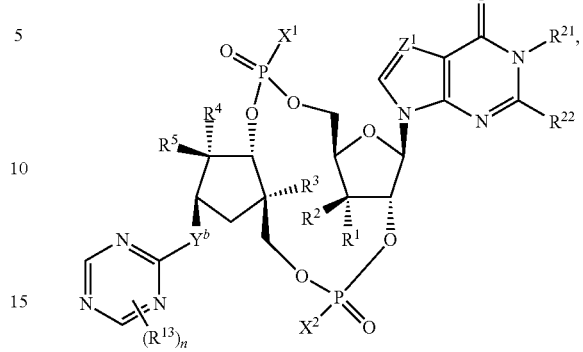
(VII)

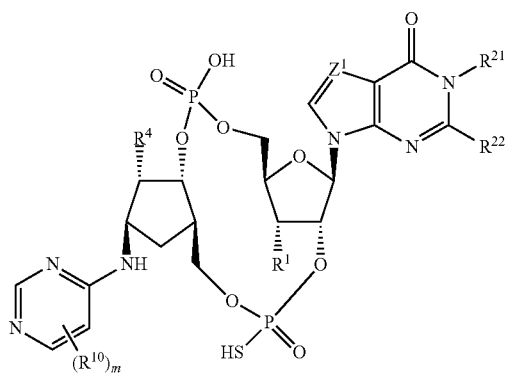
(VI-G)

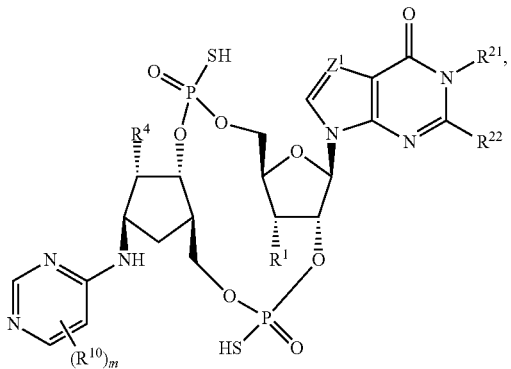
(VI-H)

or a pharmaceutically acceptable salt thereof, wherein $R^1$, $R^4$, $R^{10}$, $R^{21}$, $R^{22}$, $Z^1$, and m have the values described herein.

In some embodiments, the compound of Formula (I) is represented by Formula (VII):

or a pharmaceutically acceptable salt thereof, wherein:
$X^1$ is —SH or —OH;
$X^2$ is —SH or —OH;
$Y^b$ is —NH— or —NMe-;
$R^1$ is hydrogen, fluoro, —OH, or —$OR^b$;
$R^2$ is hydrogen or fluoro;
$R^3$ is hydrogen; $R^4$ is hydrogen, fluoro, or —OH; or $R^3$ and $R^4$ are taken together to form —$CH_2O$—;
$R^5$ is hydrogen or fluoro;
$R^b$ is $C_1$-$C_6$alkyl, halo($C_1$-$C_6$)alkyl, or $C_3$-$C_6$cycloalkyl;
each $R^{13}$ is independently hydrogen, halogen, —OH, —$NH_2$, $C_1$-$C_6$alkyl, halo($C_1$-$C_6$)alkyl, $C_3$-$C_6$cycloalkyl, —$OR^{11}$, —$NHR^{11}$, —CN, —$NO_2$, or —C(O)$NHR^{12}$;
$R^{11}$ is $C_1$-$C_6$alkyl, halo($C_1$-$C_6$)alkyl, or $C_3$-$C_6$cycloalkyl;
$R^{12}$ is hydrogen, $C_1$-$C_6$alkyl, halo($C_1$-$C_6$)alkyl, or $C_3$-$C_6$cycloalkyl;
n is 0, 1, or 2;
$Z^1$ is N, CH, or CF;
$R^{21}$ is hydrogen or —$CH_3$; and
$R^{22}$ is hydrogen, —$NH_2$, or —$CH_3$.

In some embodiments, $X^1$ and $X^2$ are —SH; and the phosphorus atom of each phosphorothioate linkage is chiral and is independently $R_p$ or $S_p$.

In some embodiments, $X^1$ and $X^2$ are —SH; and the phosphorus atom of each phosphorothioate linkage is $R_p$.

In some embodiments, $X^1$ and $X^2$ are —OH.

In some embodiments, one of $X^1$ and $X^2$ is —OH, and the other is —SH; and the phosphorus atom of the phosphorothioate linkage is chiral and is $R_p$ or $S_p$.

In some embodiments, $Y^b$ is —NH—.
In some embodiments, $Z^1$ is N.
In some embodiments, $R^1$ is hydrogen, fluoro, —OH, or —$OCH_2CF_3$, and $R^2$ is hydrogen or fluoro.
In some embodiments, $R^3$ is hydrogen; $R^4$ is hydrogen, fluoro, or —OH; and $R^5$ is hydrogen or fluoro.
In some embodiments, $R^3$ and $R^4$ are taken together to form —$CH_2O$—; and $R^5$ is hydrogen.
In some embodiments, $R^2$, $R^3$, and $R^5$ are hydrogen.
In some embodiments, $R^1$ is hydrogen, fluoro, —OH, or —$OCH_2CF_3$. In some embodiments, $R^1$ is hydrogen, fluoro, or —OH. In some embodiments, $R^1$ is fluoro or —OH.
In some embodiments, $R^4$ is hydrogen, fluoro, or —OH. In some embodiments, $R^4$ is hydrogen or fluoro.
In some embodiments, n is 0.
In some embodiments, $R^{21}$ is hydrogen.
In some embodiments, $R^{22}$ is —$NH_2$.
In some embodiments, the compound of Formula (I) is represented by Formulae (VII-A) to (VII-D):

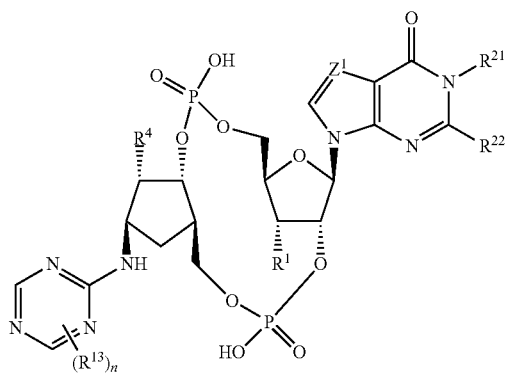
(VII-A)
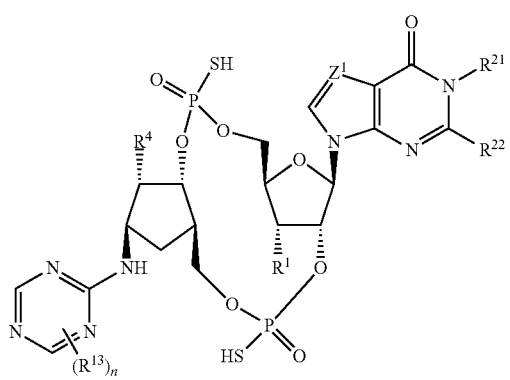
(VII-B)
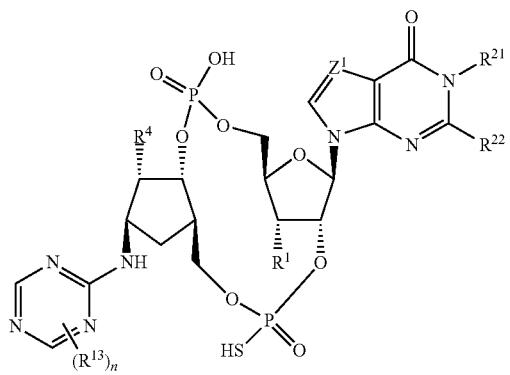
(VII-C)
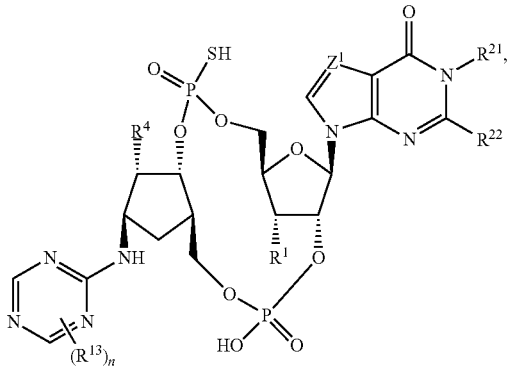
(VII-D)
or a pharmaceutically acceptable salt thereof, wherein $R^1$, $R^4$, $R^{13}$, $R^{21}$, $R^{22}$, $Z^1$, and n have the values described herein.
Representative examples of compounds of Formula (I) are shown in Table 1. Table 1
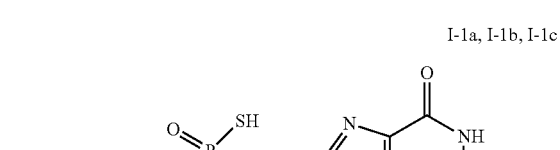
I-1a, I-1b, I-1c

I-2a, I-2b
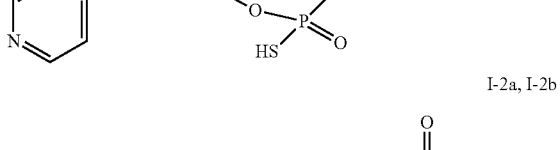
I-3a, I-3b
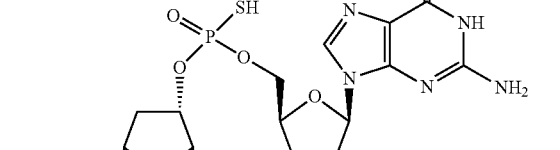
I-4a, I-4b I-5a, I-5b, I-5c, I-5d
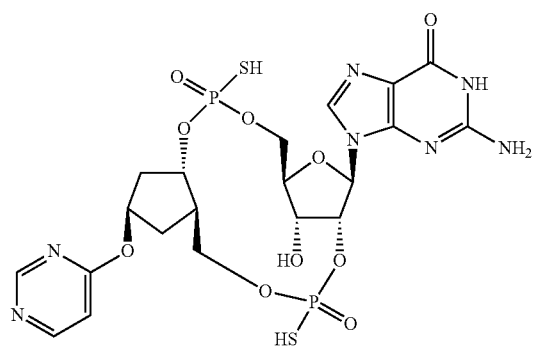
I-6
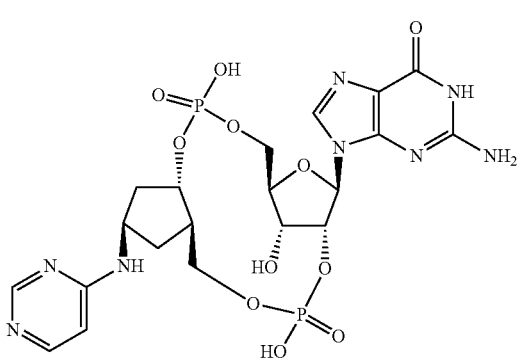
I-7
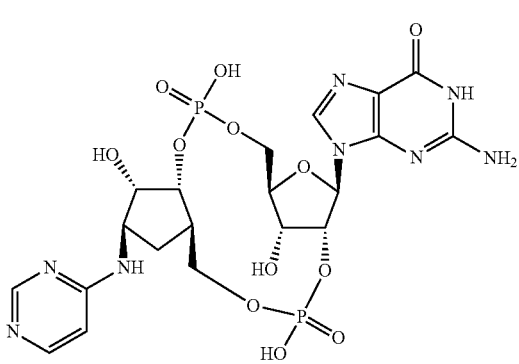
I-8
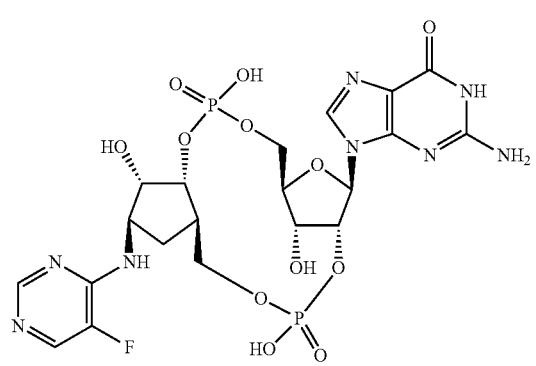
I-9a, I-9b, I-9c, I-9d
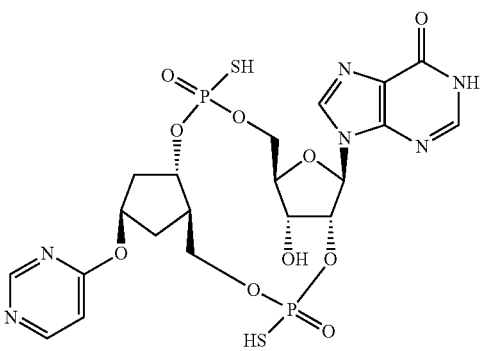
I-10
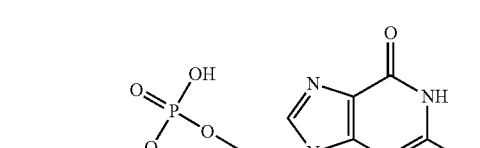
I-11
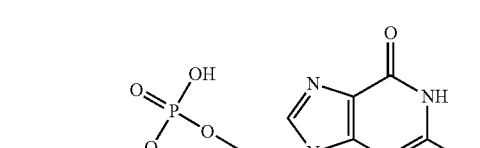
I-12a, I-12b
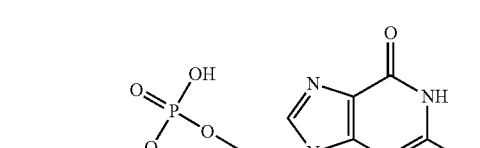

-continued
I-13
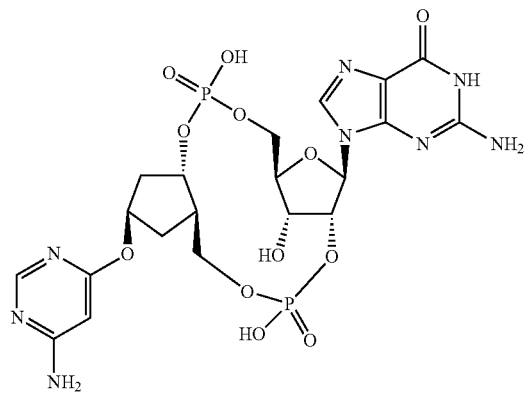
I-14
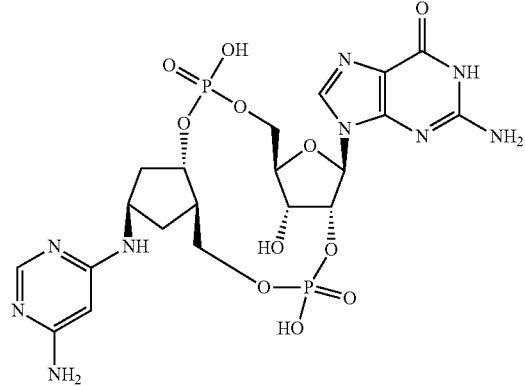
I-15
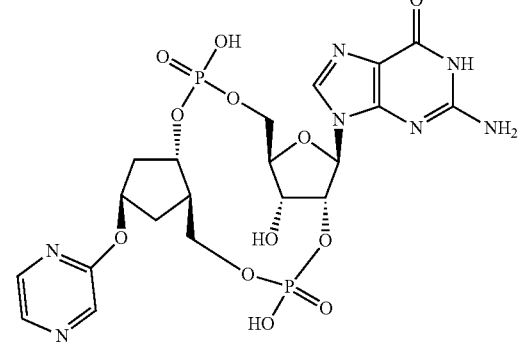
I-16
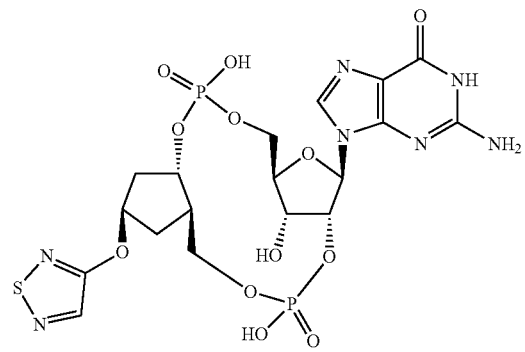
I-17
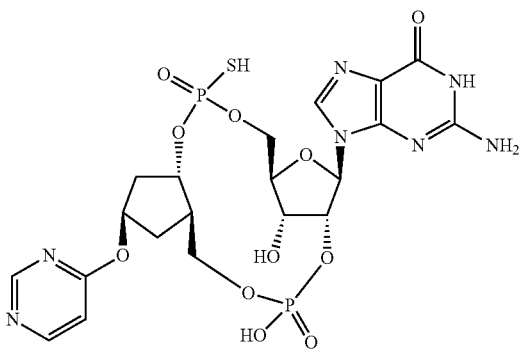
I-18
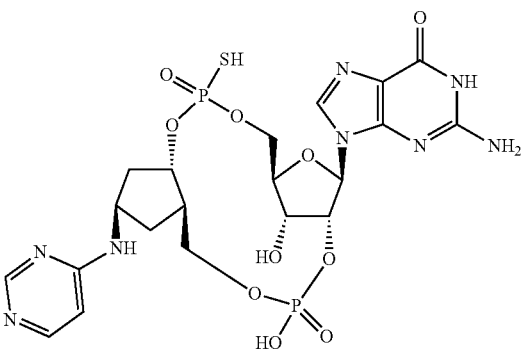
I-19a, I-19b
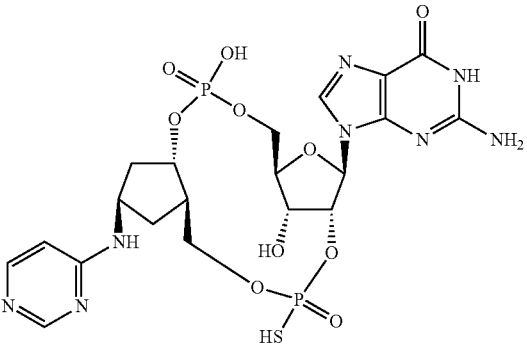
I-20a, I-20b
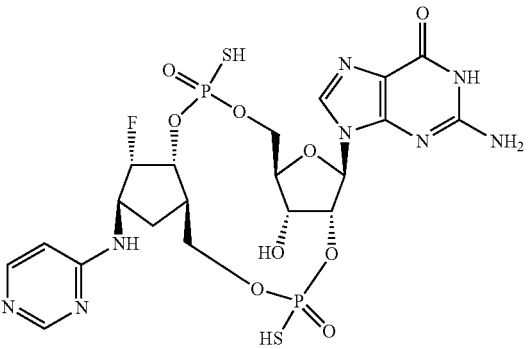

I-21
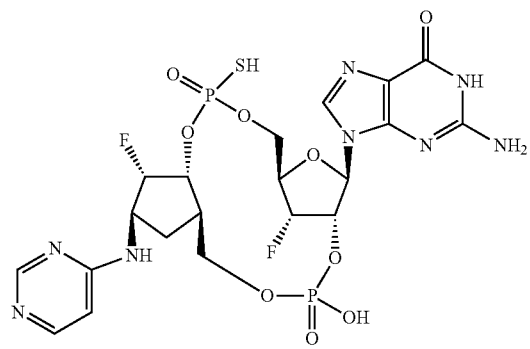
I-25a, I-25b
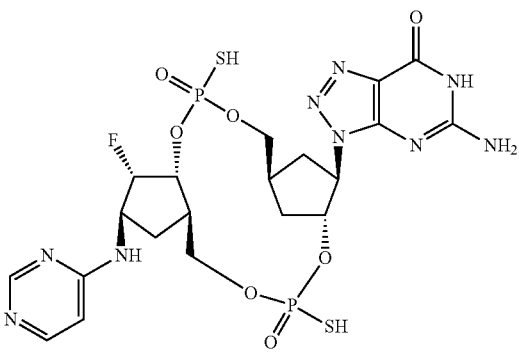
I-22a, I-22b
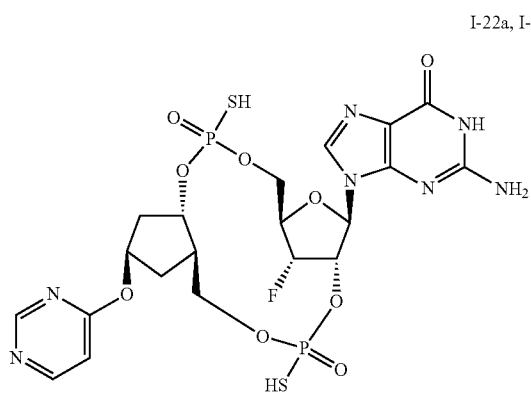
I-26
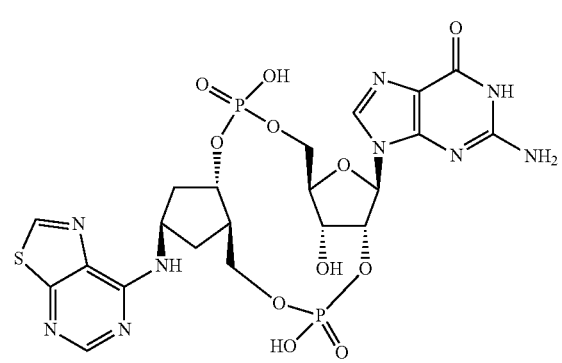
I-23a, I-23b
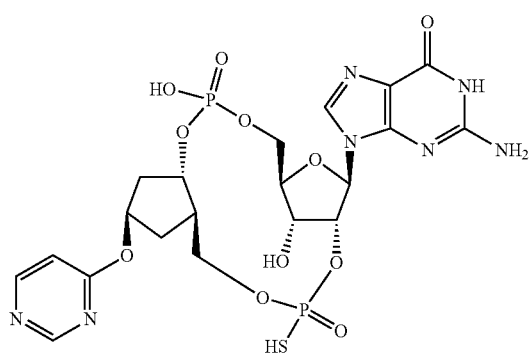
I-27
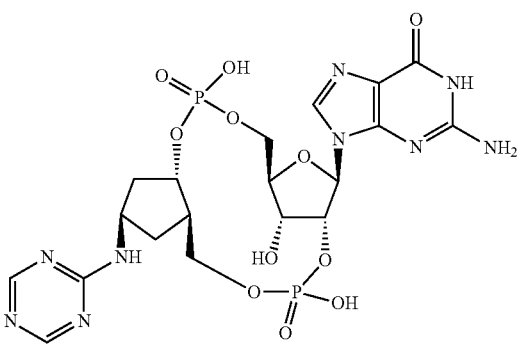
I-24a, I-24b
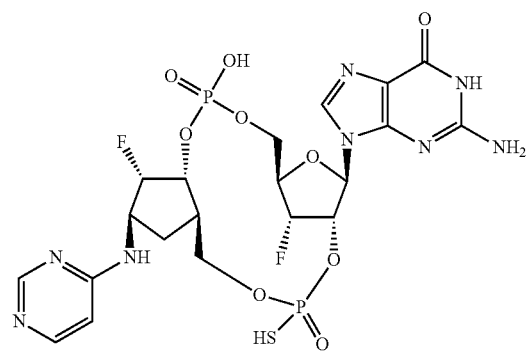
I-28
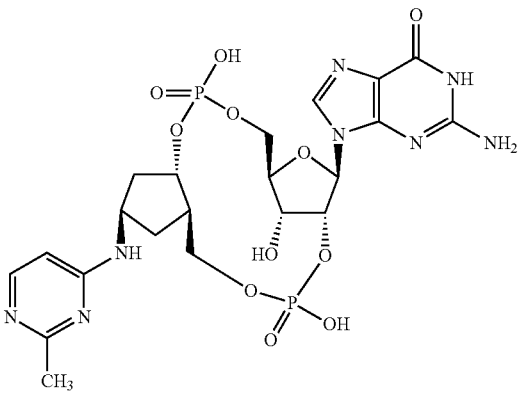

I-29
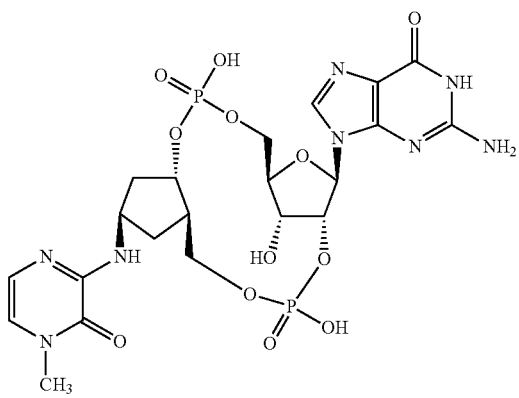
I-30a, I-30b, I-30c, I-30d
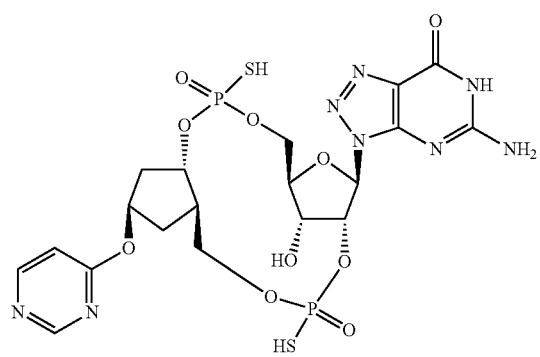
I-31a, I-31b
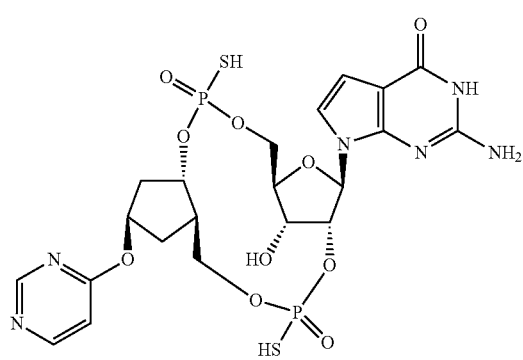
I-32a, I-32b
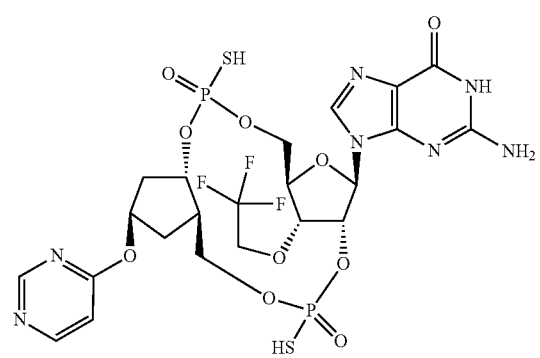
I-33
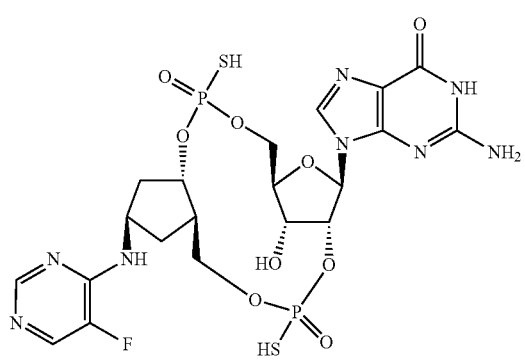
I-34a, I-34b
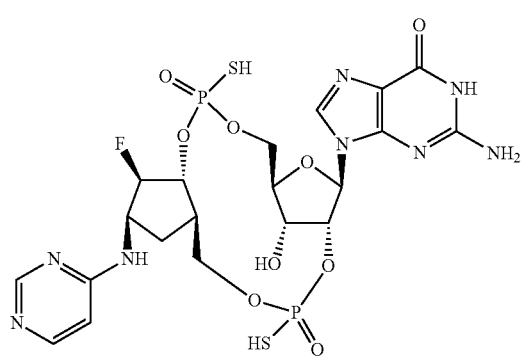
I-35a, I-35b, I-35c, I-35d
I-36
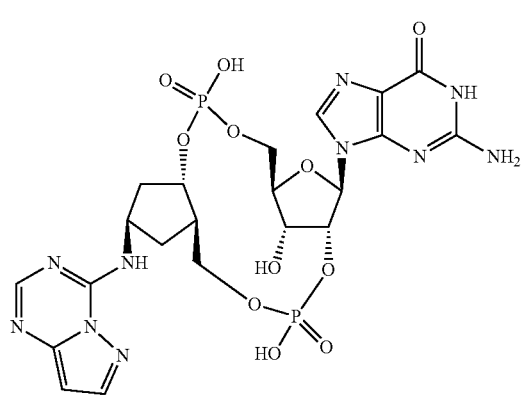

I-37a, I-37b, I-37c
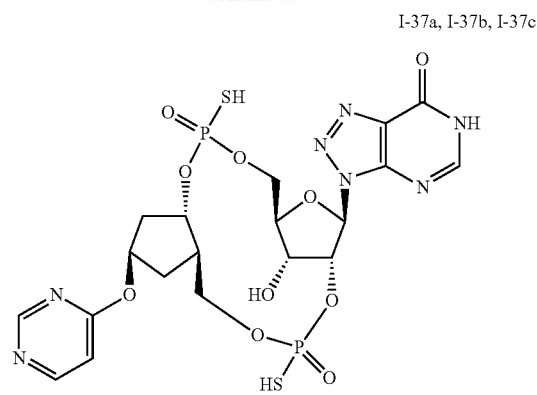
I-38a, I-38b
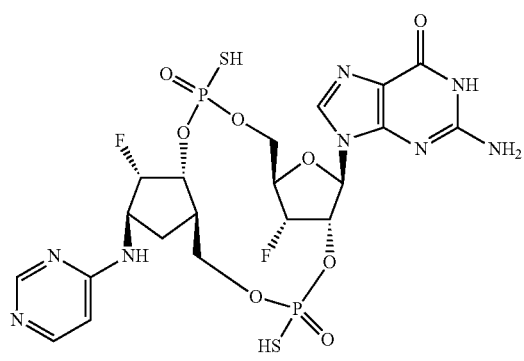
I-39a, I-39b
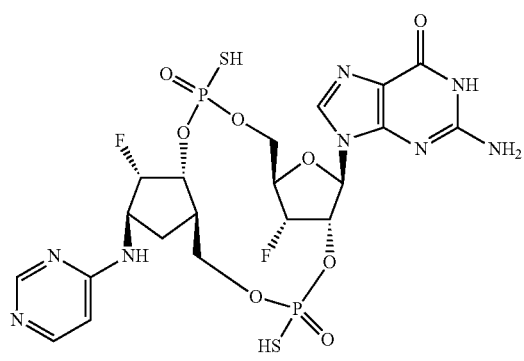
I-40
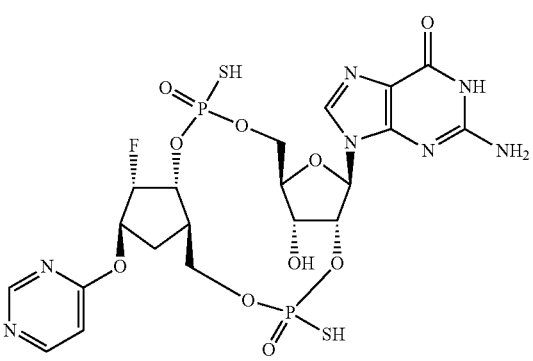
I-41a, I-41b
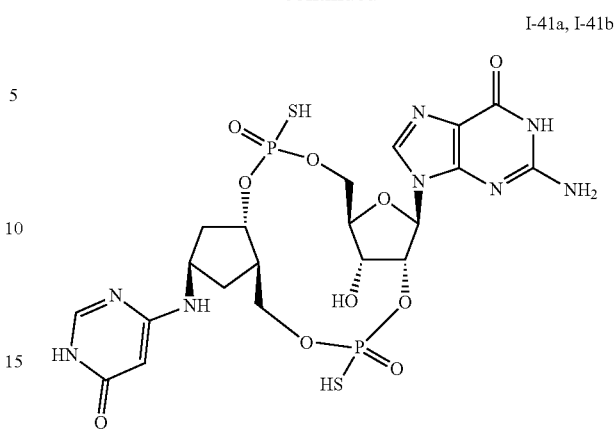
I-42
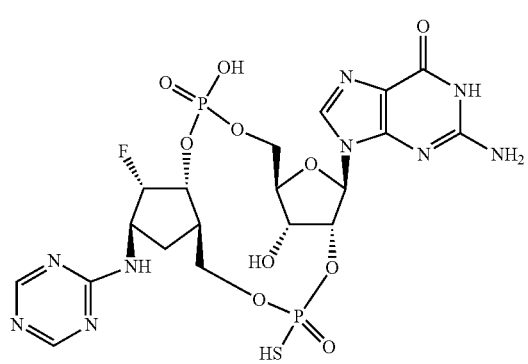
I-43
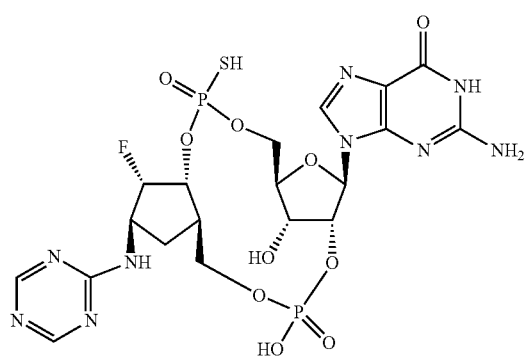
I-44a, I-44b
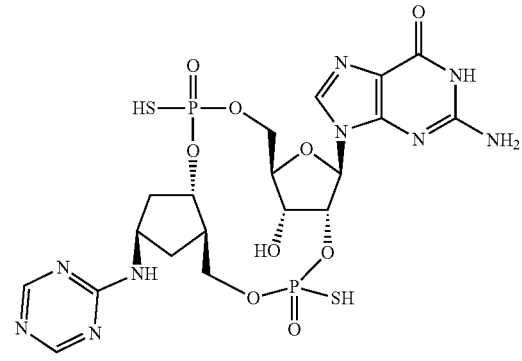

I-45

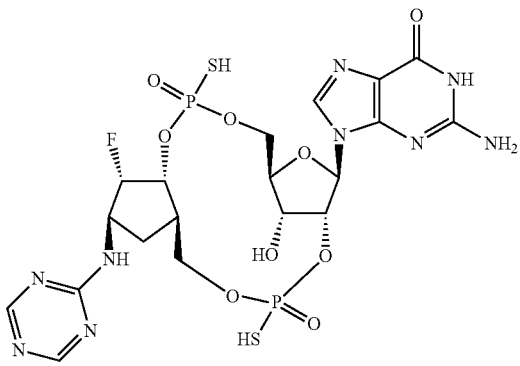

I-46

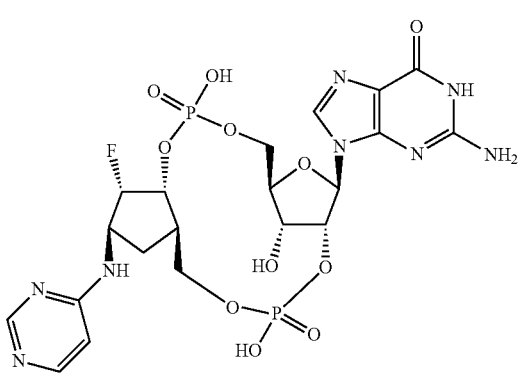

In Table 1, some structures correspond to more than one compound. In these cases, the compounds are diastereoisomers of each other.

The compounds in Table 1 may also be identified by the following chemical names:

| Compound | Name |
|---|---|
| I-1a | 2-amino-9-[(2S,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5S,7R,8R,10R,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5S,7R,8R,10R,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-1b | 2-amino-9-[(2S,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5S,7R,8R,10R,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5S,7R,8R,10R,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-1c | 2-amino-9-[(2S,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5S,7R,8R,10R,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5S,7R,8R,10R,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-2a | 2-amino-9-[(2S,5R,7R,8R,10S,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-2b | 2-amino-9-[(2S,5R,7R,8R,10S,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or |

| Compound | Name |
|---|---|
| | 2-amino-9-[(2R,5R,7R,8R,10S,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-3a | 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 5-fluoro-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 5-fluoro-7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 5-fluoro-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one |
| I-3b | 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 5-fluoro-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 5-fluoro-7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 5-fluoro-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one |
| I-4a | 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile |
| I-4b | 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile |
| I-5a | 2-amino-9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-5b | 2-amino-9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or |

| Compound | Name |
|---|---|
| | 2-amino-9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-5c | 2-amino-9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-5d | 2-amino-9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-6 | 2-amino-9-[(5R,7R,8R,12aR,14R,15aS,16R)-2,10,16-trihydroxy-2,10-dioxido-14-(pyrimidin-4-ylamino)decahydro-5,8-methanocyclopenta[l][1,3,6,9,11,2,10]pentaoxadiphosphacyclotetradecin-7-yl]-1,9-dihydro-6H-purin-6-one |
| I-7 | 2-amino-9-[(5R,7R,8R,12aR,14R,15S,15aR,16R)-2,10,15,16-tetrahydroxy-2,10-dioxido-14-(pyrimidin-4-ylamino)decahydro-5,8-methanocyclopenta[l][1,3,6,9,11,2,10]pentaoxadiphosphacyclotetradecin-7-yl]-1,9-dihydro-6H-purin-6-one |
| I-8 | 2-amino-9-{(5R,7R,8R,12aR,14R,15S,15aR,16R)-14-[(5-fluoropyrimidin-4-yl)amino]-2,10,15,16-tetrahydroxy-2,10-dioxidodecahydro-5,8-methanocyclopenta[l][1,3,6,9,11,2,10]pentaoxadiphosphacyclotetradecin-7-yl}-1,9-dihydro-6H-purin-6-one |
| I-9a | 9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-9b | 9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-9c | 9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or |

| Compound | Name |
|---|---|
| I-9d | 9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one 9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-10 | 2-amino-9-[(5R,7R,8R,12aR,14R,15aS,16R)-2,10,16-trihydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-1,9-dihydro-6H-purin-6-one |
| I-11 | 2-amino-9-[(5R,7R,8R,12aR,14R,15aS,16R)-2,10,16-trihydroxy-2,10-dioxido-14-(pyridin-2-yloxy)decahydro-5,8-methanocyclopenta[l][1,3,6,9,11,2,10]pentaoxadiphosphacyclotetradecin-7-yl]-1,9-dihydro-6H-purin-6-one |
| I-12a | 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one or 5-fluoro-7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one or 5-fluoro-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one or 5-fluoro-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one |
| I-12b | 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one or 5-fluoro- 7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one or 5-fluoro-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one or 5-fluoro-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one |
| I-13 | 2-amino-9-{(5R,7R,8R,12aR,14R,15aS,16R)-14-[(6-aminopyrimidin-4-yl)oxy]-2,10,16-trihydroxy-2,10-dioxidodecahydro-5,8-methanocyclopenta[l][1,3,6,9,11,2,10]pentaoxadiphosphacyclotetradecin-7-yl}-1,9-dihydro-6H-purin-6-one |
| I-14 | 2-amino-9-{(5R,7R,8R,12aR,14R,15aS,16R)-14-[(6-aminopyrimidin-4-yl)amino]-2,10,16-trihydroxy-2,10-dioxidodecahydro-5,8-methanocyclopenta[l][1,3,6,9,11,2,10]pentaoxadiphosphacyclotetradecin-7-yl}-1,9-dihydro-6H-purin-6-one |
| I-15 | 2-amino-9-[(5R,7R,8R,12aR,14R,15aS,16R)-2,10,16-trihydroxy-2,10-dioxido-14-(pyrazin-2-yloxy)decahydro-5,8-methanocyclopenta[l][1,3,6,9,11,2,10]pentaoxadiphosphacyclotetradecin-7-yl]-1,9-dihydro-6H-purin-6-one |
| I-16 | 2-amino-9-[(5R,7R,8R,12aR,14R,15aS,16R)-2,10,16-trihydroxy-2,10-dioxido-14-(1,2,5-thiadiazol-3-yloxy)decahydro-5,8-methanocyclopenta[l][1,3,6,9,11,2,10]pentaoxadiphosphacyclotetradecin-7-yl]-1,9-dihydro-6H-purin-6-one |
| I-17 | 2-amino-9-[(2S,5R,7R,8R,12aR,14R,15aS,16R)-10,16-dihydroxy-2,10-dioxido-14-(pyrimidin-4-yloxy)-2-sulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,12aR,14R,15aS,16R)-10,16-dihydroxy-2,10-dioxido-14-(pyrimidin-4-yloxy)-2-sulfanyldecahydro-5,8-methanocyclopenta[l][1,3,6,9,11,2,10]pentaoxadiphosphacyclotetradecin-7-yl]-1,9-dihydro-6H-purin-6-one |
| I-18 | 2-amino-9-[(2S,5R,7R,8R,12aR,14R,15aS,16R)-10,16-dihydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,12aR,14R,15aS,16R)-10,16-dihydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one |
| I-19a | 2-amino-9-[(5R,7R,8R,10S,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one or |

| Compound | Name |
|---|---|
| I-19b | 2-amino-9-[(5R,7R,8R,10R,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one 2-amino-9-[(5R,7R,8R,10S,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(5R,7R,8R,10R,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one |
| I-20a | 2-amino-9-[(2S,5R,7R,8R,10S,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-20b | 2-amino-9-[(2S,5R,7R,8R,10S,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-21 | 2-amino-9-[(2R,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]penta-oxadiphosphacyclotetradecin-7-yl]-1,9-dihydro-6H-purin-6-one |
| I-22a | 2-amino-9-[(2S,5R,7R,8S,10S,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10R,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8S,10R,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10S,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-22b | 2-amino-9-[(2S,5R,7R,8S,10S,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8S,10R,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10R,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10S,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-23a | 2-amino-9-[(5R,7R,8R,10S,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(5R,7R,8R,10R,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]penta-oxadiphosphacyclotetradecin-7-yl]-1,9-dihydro-6H-purin-6-one |

-continued

| Compound | Name |
|---|---|
| I-23b | 2-amino-9-[(5R,7R,8R,10S,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(5R,7R,8R,10R,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]penta-oxadiphosphacyclotetradecin-7-yl]-1,9-dihydro-6H-purin-6-one |
| I-24a | 2-amino-9-[(5R,7R,8S,10S,12aR,14R,15S,15aR,16R)-15,16-difluoro-2-hydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(5R,7R,8S,10R,12aR,14R,15S,15aR,16R)-15,16-difluoro-2-hydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one |
| I-24b | 2-amino-9-[(5R,7R,8S,10S,12aR,14R,15S,15aR,16R)-15,16-difluoro-2-hydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(5R,7R,8S,10R,12aR,14R,15S,15aR,16R)-15,16-difluoro-2-hydroxy-2,10-dioxido-14-(pyrimidin-4-ylamino)-10-sulfanyldecahydro-5,8-methanocyclopenta[l][1,3,6,9,11,2,10]penta-oxadiphosphacyclotetradecin-7-yl]-1,9-dihydro-6H-purin-6-one |
| I-25a | 5-amino-3-[(2S,5S,7R,8R,10S,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetra-oxadiphosphacyclotetradecin-7-yl]-3,6-dihydro-7H-[1,2,3]triazolo[4,5-d]pyrimidin-7-one or 5-amino-3-[(2S,5S,7R,8R,10R,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetra-oxadiphosphacyclotetradecin-7-yl]-3,6-dihydro-7H-[1,2,3]triazolo[4,5-d]pyrimidin-7-one or 5-amino-3-[(2R,5S,7R,8R,10R,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetra-oxadiphosphacyclotetradecin-7-yl]-3,6-dihydro-7H-[1,2,3]triazolo[4,5-d]pyrimidin-7-one |
| I-25b | 5-amino-3-[(2S,5S,7R,8R,10S,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetra-oxadiphosphacyclotetradecin-7-yl]-3,6-dihydro-7H-[1,2,3]triazolo[4,5-d]pyrimidin-7-one or 5-amino-3-[(2R,5S,7R,8R,10S,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetra-oxadiphosphacyclotetradecin-7-yl]-3,6-dihydro-7H-[1,2,3]triazolo[4,5-d]pyrimidin-7-one or 5-amino-3-[(2R,5S,7R,8R,10R,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetra-oxadiphosphacyclotetradecin-7-yl]-3,6-dihydro-7H-[1,2,3]triazolo[4,5-d]pyrimidin-7-one |
| I-26 | 2-amino-9-[(5R,7R,8R,12aR,14R,15aS,16R)-2,10,16-trihydroxy-2,10-dioxido-14-([1,3]thiazolo[5,4-d]pyrimidin-7-ylamino)decahydro-5,8-methanocyclopenta[l][1,3,6,9,11,2,10]penta-oxadiphosphacyclotetradecin-7-yl]-1,9-dihydro-6H-purin-6-one |
| I-27 | 2-amino-9-[(5R,7R,8R,12aR,14R,15aS,16R)-2,10,16-trihydroxy-2,10-dioxido-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |
| I-28 | 2-amino-9-{(5R,7R,8R,12aR,14R,15aS,16R)-2,10,16-trihydroxy-14-[(2-methylpyrimidin-4-yl)amino]-2,10-dioxidodecahydro-5,8-methanocyclopenta[l][1,3,6,9,11,2,10]penta-oxadiphosphacyclotetradecin-7-yl}-1,9-dihydro-6H-purin-6-one |
| I-29 | 2-amino-9-{(5R,7R,8R,12aR,14R,15aS,16R)-2,10,16-trihydroxy-14-[(4-methyl-3-oxo-3,4-dihydropyrazin-2-yl)amino]-2,10-dioxidodecahydro-5,8-methanocyclopenta[l][1,3,6,9,11,2,10]penta-oxadiphosphacyclotetradecin-7-yl}-1,9-dihydro-6H-purin-6-one |
| I-30a | 5-amino-3-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-3,6-dihydro-7H-[1,2,3]triazolo[4,5-d]pyrimidin-7-one or 5-amino-3-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-3,6-dihydro-7H-[1,2,3]triazolo[4,5-d]pyrimidin-7-one or 5-amino-3-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]penta- |

| Compound | Name |
|---|---|
| | oxadiphosphacyclotetradecin-7-yl]-3,6-dihydro-7H-[1,2,3]triazolo[4,5-d]pyrimidin-7-one |
| I-30b | 5-amino-3-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3 ]triazolo[4,5-d]pyrimidin-7-one or 5-amino-3-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one |
| I-30c | 5-amino-3-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3 ]triazolo[4,5-d]pyrimidin-7-one or 5-amino-3-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3 ]triazolo[4,5-d]pyrimidin-7-one or 5-amino-3-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one |
| I-30d | 5-amino-3-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one |
| I-31a | 2-amino-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one |
| I-31b | 2-amino-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one |
| I-32a | 2-amino-9-[(2S,5R,7R,8R,10S,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]penta- |

| Compound | Name |
|---|---|
| | oxadiphosphacyclotetradecin-7-yl]-1,9-dihydro-6H-purin-6-one |
| I-32b | 2-amino-9-[(2S,5R,7R,8R,10S,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10S,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15aS,16R)-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]penta-oxadiphosphacyclotetradecin-7-yl]-1,9-dihydro-6H-purin-6-one |
| I-33 | 2-amino-9-{(5R,7R,8R,12aR,14R,15aS,16R)-2,10,16-trihydroxy-14-[methyl(1,3,5-triazin-2-yl)amino]-2,10-dioxidodecahydro-5,8-methanocyclopenta[l][1,3,6,9,11,2,10]penta-oxadiphosphacyclotetradecin-7-yl}-1,9-dihydro-6H-purin-6-one |
| I-34a | 2-amino-9-{(2S,5R,7R,8R,10S,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10S,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2S,5R,7R,8R,10R,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10R,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one |
| I-34b | 2-amino-9-{(2S,5R,7R,8R,10S,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10S,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2S,5R,7R,8R,10R,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10R,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]penta-oxadiphosphacyclotetradecin-7-yl}-1,9-dihydro-6H-purin-6-one |
| I-35a | 2-amino-9-[(2S,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-35b | 2-amino-9-[(2S,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentao-xadiphosphacyclotetradecin-7-yl]-1,9-dihydro-6H-purin-6-one |
| I-35c | 2-amino-9-[(2S,5R,7R,8R,10S,12aR,14R,15R,15aR,16R)-15-fluoro-16-hydroxy-2,10-dioxido-14-(pyrimidin-4-ylamino)- |

| Compound | Name |
|---|---|
| | 2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-35d | 2-amino-9-[(2S,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one |
| I-36 | 2-amino-9-[(5R,7R,8R,12aR,14R,15aR,16R)-2,10,16-trihydroxy-2,10-dioxido-14-(pyrazolo[1,5-a][1,3,5]triazin-4-ylamino)decahydro-5,8-methanocyclopenta[l][1,3,6,9,11,2,10]pentaoxadiphosphacyclotetradecin-7-yl]-1,9-dihydro-6H-purin-6-one |
| I-37a | 3-[(2S,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one |
| I-37b | 3-[(2S,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one |
| I-37c | 3-[(2S,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one |
| I-38a | 2-amino-9-[(2S,5R,7R,8S,10S,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8S,10S,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8S,10R,12aR,14R,15S,15aR,16R)-15,16-difluoro-2,10-dioxido-14-(pyrimidin-4-ylamino)- |

| Compound | Name |
|---|---|
| | 2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10R,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-38b | 2-amino-9-[(2S,5R,7R,8S,10S,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10S,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8S,10R,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8S,10R,12aR,14R,15S,15aR,16R)-15,16-difluoro-2,10-dioxido-14-(pyrimidin-4-ylamino)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-39a | 2-amino-9-[(2S,5R,7R,8R,10S,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-39b | 2-amino-9-[(2S,5R,7R,8R,10S,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10S,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-16-hydroxy-2,10-dioxido-14-(pyrimidin-4-yloxy)-2,10-disulfanyldecahydro-5,8-methanocyclopenta[l][1,3,6,9,11,2,10]penta-oxadiphosphacyclotetradecin-7-yl]-1,9-dihydro-6H-purin-6-one |
| I-40 | 2-amino-9-[(5R,7R,8R,12aR,14R,15S,15aR,16R)-15-fluoro-2,10,16-trihydroxy-2,10-dioxido-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |
| I-41a | 2-amino-9-{(2S,5R,7R,8R,10S,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10R,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2S,5R,7R,8R,10R,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10S,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one |
| I-41b | 2-amino-9-{(2S,5R,7R,8R,10S,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2R,5R,7R,8R,10R,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one or 2-amino-9-{(2S,5R,7R,8R,10R,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}- |

| Compound | Name |
|---|---|
| | 1,9-dihydro-6H-purin-6-one or 2-amino-9-{(2R,5R,7R,8R,10S,12aR,14R,15aS,16R)-16-hydroxy-2,10-dioxido-14-[(6-oxo-1,6-dihydropyrimidin-4-yl)amino]-2,10-disulfanyldecahydro-5,8-methanocyclopenta[l][1,3,6,9,11,2,10]penta-oxadiphosphacyclotetradecin-7-yl}-1,9-dihydro-6H-purin-6-one |
| I-42 | 2-amino-9-[(5R,7R,8R,10S,12aR,14R,15S,15aR,16R)-15-fluoro-2,16-dihydroxy-2,10-dioxido-10-sulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(5R,7R,8R,10R,12aR,14R,15S,15aR,16R)-15-fluoro-2,16-dihydroxy-2,10-dioxido-10-sulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |
| I-43 | 2-amino-9-[(2R,5R,7R,8R,12aR,14R,15S,15aR,16R)-15-fluoro-10,16-dihydroxy-2,10-dioxido-2-sulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,12aR,14R,15S,15aR,16R)-15-fluoro-10,16-dihydroxy-2,10-dioxido-2-sulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |
| I-44a | 2-amino-9-[(2S,5R,7R,8R,10S,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |
| I-44b | 2-amino-9-[(2S,5R,7R,8R,10S,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15aS,16R)-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |
| I-45 | 2-amino-9-[(2S,5R,7R,8R,10S,12aR,14R,15S,15aR,16R)-15-fluoro-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one or 2-amino-9-[(2S,5R,7R,8R,10R,12aR,14R,15S,15aR,16R)-15-fluoro-16-hydroxy-2,10-dioxido-2,10-disulfanyl-14-(1,3,5-triazin-2-ylamino)decahydro-5,8-methanocyclopenta[l][1,3,6,9,11,2,10]penta-oxadiphosphacyclotetradecin-7-yl]-1,9-dihydro-6H-purin-6-one |

-continued

| Compound | Name |
|---|---|
| I-46 | 2-amino-9-[(5R,7R,8R,12aR,14R,15S,15aR,16R)-15-fluoro-2,10,16-trihydroxy-2,10-dioxido-14-(pyrimidin-4-ylamino)decahydro-5,8-methanocyclopenta[l][1,3,6,9,11,2,10]pentaoxadiphosphacyclotetradecin-7-yl]-1,9-dihydro-6H-purin-6-one |

When a compound of Formula (I) includes two phosphorothioate linkages, each phosphorus atom can be $R_p$ or $S_p$. As such, there are four diastereomers for the compound with respect to the chiral phosphorus atoms, $R_pS_p$, $R_pR_p$, $S_pS_p$, and $S_pR_p$. Each compound number listed in Table 1 (e.g., I-1a, I-1b, or I-1c) refers to a single diastereomer. The absolute stereochemistry of the phosphorothioate linkages in the compounds have not been determined, and the compound number refers to one of the four possible diastereomers.

When compound (I) is in a form of a salt, the salt is typically a pharmacologically acceptable salt. Examples include salts with inorganic base, salts with organic base, salts with inorganic acid, salts with organic acid, and salts with basic or acidic amino acid.

Useful examples of the salt with inorganic base include alkali metal salts such as sodium salt, potassium salt and the like; alkaline-earth metal salts such as calcium salt, magnesium salt and the like; aluminium salt and ammonium salt.

Useful examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine and N,N-dibenzyl ethylene diamine.

Useful examples of the salt with inorganic acid include salts with hydrochloric acid, hydrobromic acid, nitric acid, sulfuric acid and phosphoric acid.

Useful examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.

Useful examples of the salt with basic amino acid include salts with arginine, lysine and ornithine.

Useful examples of the salt with acidic amino acid include salts with aspartic acid and glutamic acid.

When a compound of Formula (I) is in a form of a salt, in one embodiment, the salt is a salt with triethylamine or sodium. In some embodiments, the salt is a salt with sodium. In some embodiments, the salt is a salt with triethylamine.

General Synthetic Methods and Intermediates

The compounds of the present disclosure can be prepared by methods known to one of ordinary skill in the art and/or by reference to the schemes shown below and the synthetic examples. See e.g., Org. Lett., 2010, 12 (14), pp 3269-3271; WO 2017/075477 (A1). Starting materials and intermediates are purchased from commercial sources, prepared via published procedures or are illustrated below. Exemplary synthetic routes are set forth in Schemes below, and in the Examples.

Scheme 1: General route for preparing cyclic diphosphates

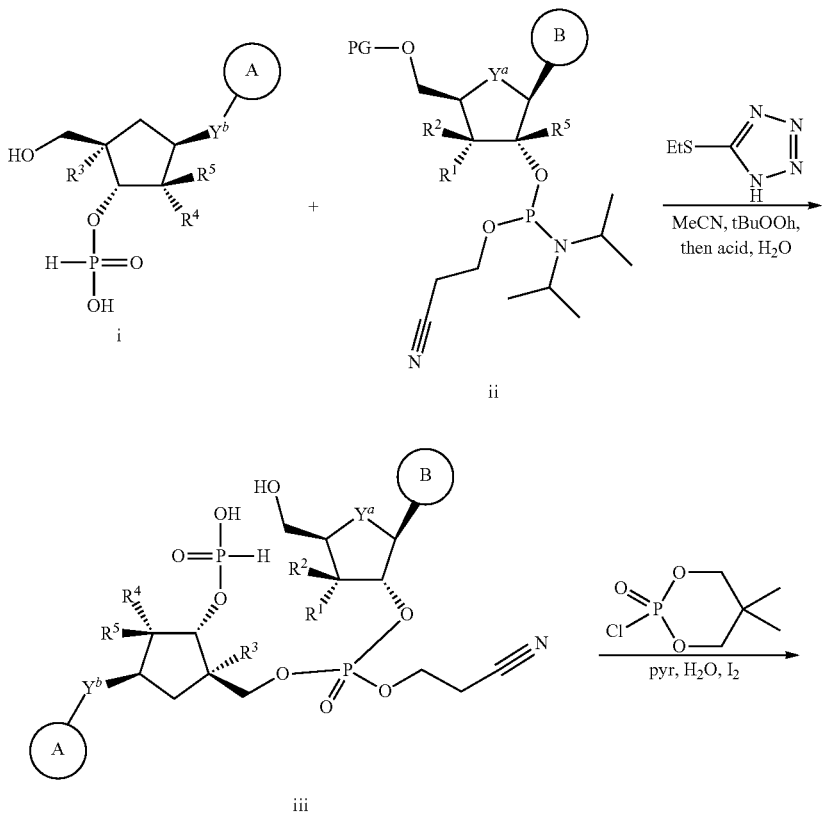

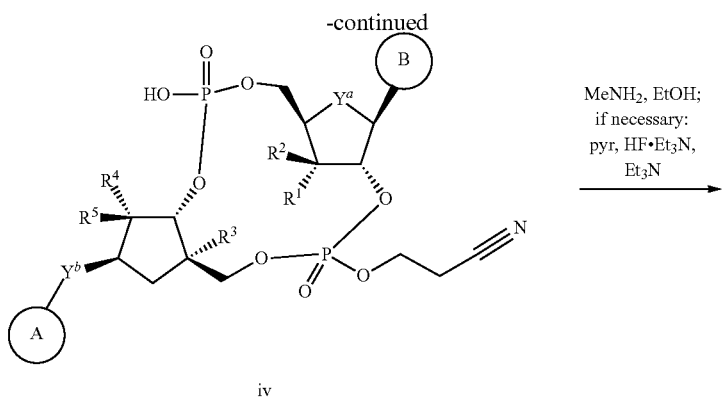

iv

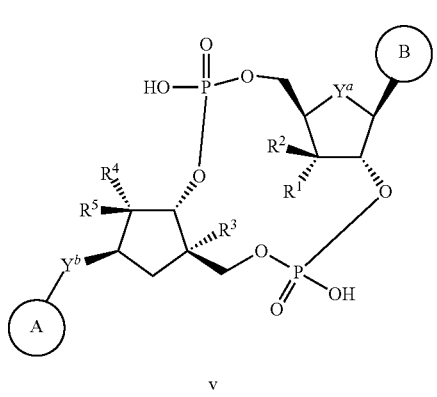

v

Scheme 1 shows a general route for the preparation of compounds of formula v from a cyclopentane-derived and appropriately protected H-phosphonate i (where $R^4$ is a silyl protected hydroxyl, hydrogen, fluoro or is taken together with $R^3$ to form $OCH_2$, $R_3$ is H, and $R^5$ is hydrogen or fluoro) that is coupled to an appropriately protected compound ii with a phosphoramidite functionality at the 2' position in the presence of a mild acid like ethylthio-tetrazole. The resulting phosphite ester is oxidized with t-butyl hydrogen peroxide or other oxidant. Removal of the protecting group on the 5' oxygen with AcOH/water if the protecting group is a dimethoxytrityl ether or with TFA/water if the protecting group is silyl-based (where $R^1$ and OPG are connected via OSi $(iPr)_2OSi(iPr)_2O$) provides phosphate ester iii. Treatment of compound iii with 2-chloro-5,5-dimethyl-1,3,2-dioxaphosphorinane 2-oxide or other coupling agent, followed by oxidation with iodine or other mild oxidant, provides the protected cyclic diphosphate iv. Removal of protecting groups from the phosphate and Rings A and B is accomplished by treatment with methyl amine in ethanol. Removal of any silyl-based protecting groups is accomplished with hydrogen fluoride-triethyl amine and results in the fully deprotected cyclic diphosphate compound v.

Scheme 2: General route for preparing cyclic diphosphorothioates

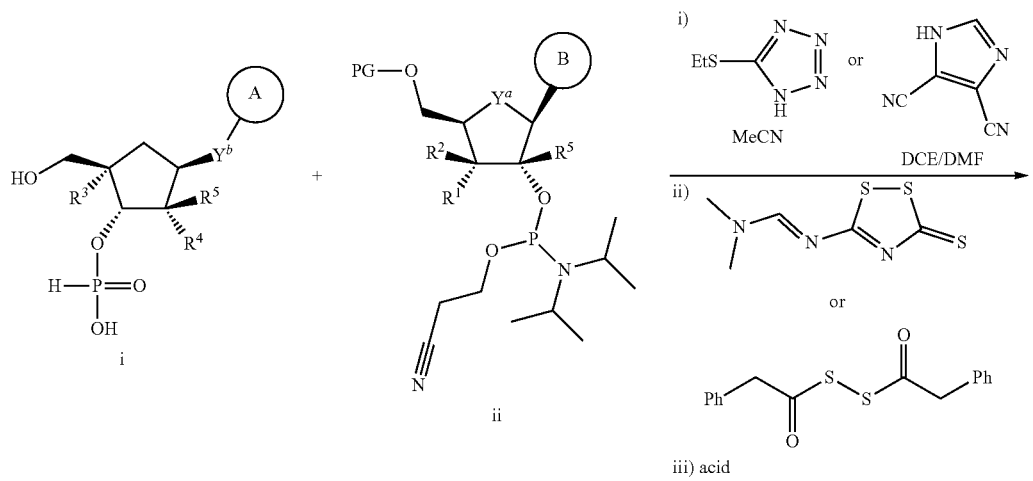

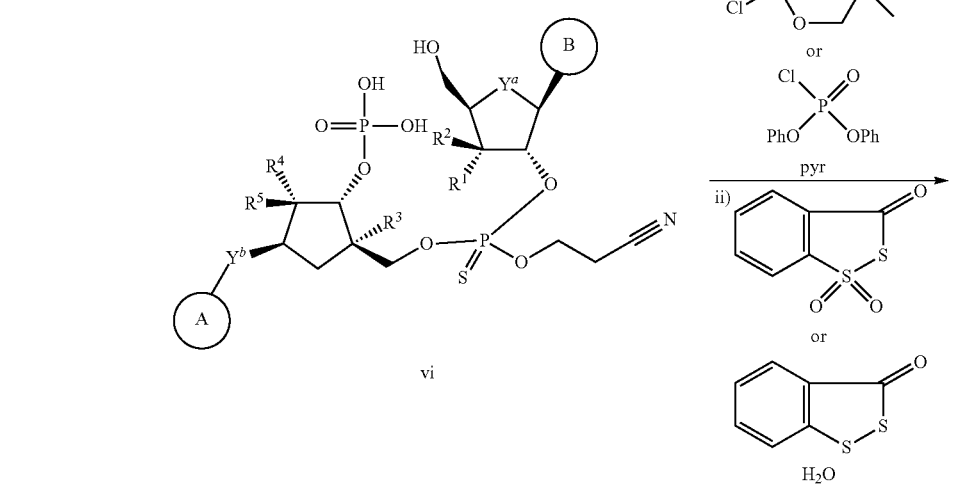

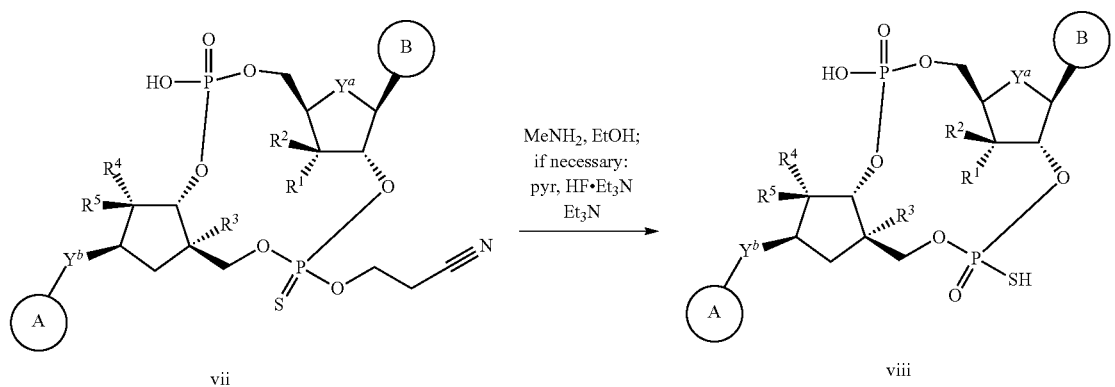

Scheme 2 shows a general route for the preparation of diphosphorothioate compounds of formula viii from a cyclopentane-derived and appropriately protected H-phosphonate i (where $R^4$ is a silyl protected hydroxyl, hydrogen or fluoro or is taken together with $R^3$ to form $OCH_2$, $R^3$ is H, and $R^5$ is hydrogen or fluoro) that is coupled to an appropriately protected compound ii with a phosphoramidite functionality at the 2' position in the presence of a mild acid like ethylthio-tetrazole, or with 4,5-dicyanoimidazole The resulting phosphite ester is oxidized to the phosphorothioate using a sulfur transfer reagent (such as ((dimethylamino-methylidene)amino)-3H-1,2,4-dithiazoline-3-thione) or bis(phenylacetyl)disulfide. Removal of the protecting group on the 5' oxygen with AcOH/water if the protecting group is a dimethoxytrityl ether or with TFA/water if the protecting group is silyl-based (where $R^1$ and OPG are connected via OSi $(iPr)_2OSi(iPr)_2O$) provides phosphorothioate vi. Treatment of compound vi with 2-chloro-5,5-dimethyl-1,3,2-dioxaphosphorinane 2-oxide or diphenyl chlorophosphate, followed by treatment with a sulfur transfer reagent (such as 3H-1,2-benzodithiol-3-one 1,1-dioxide or 3H-1,2-benzodithiol-3-one) provides the cyclic diphosphorothioate vii. Removal of protecting groups from the thiophosphate and Rings A and B is accomplished by treatment with methyl amine in ethanol. Removal of any silyl-based protecting groups is accomplished with hydrogen fluoride-triethyl amine and results in the fully deprotected cyclic diphosphorothioate compound viii.

Scheme 3: Alternate route for preparing cyclic diphosphates or cyclic diphosphorothioates

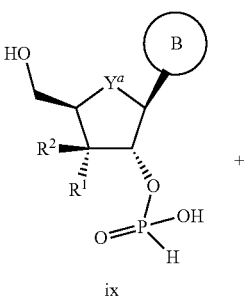

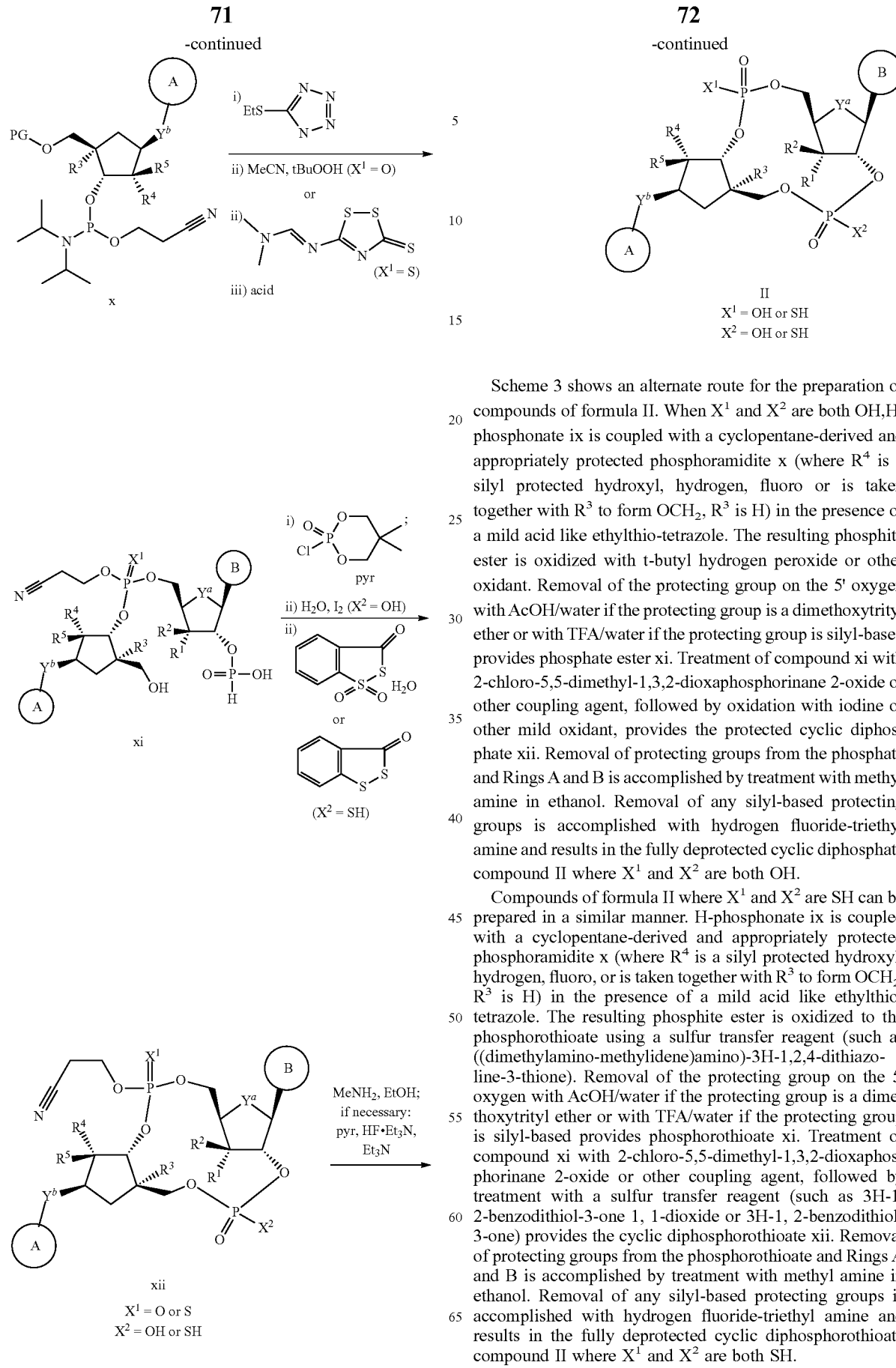

Scheme 3 shows an alternate route for the preparation of compounds of formula II. When $X^1$ and $X^2$ are both OH, H-phosphonate ix is coupled with a cyclopentane-derived and appropriately protected phosphoramidite x (where $R^4$ is a silyl protected hydroxyl, hydrogen, fluoro or is taken together with $R^3$ to form $OCH_2$, $R^3$ is H) in the presence of a mild acid like ethylthio-tetrazole. The resulting phosphite ester is oxidized with t-butyl hydrogen peroxide or other oxidant. Removal of the protecting group on the 5' oxygen with AcOH/water if the protecting group is a dimethoxytrityl ether or with TFA/water if the protecting group is silyl-based provides phosphate ester xi. Treatment of compound xi with 2-chloro-5,5-dimethyl-1,3,2-dioxaphosphorinane 2-oxide or other coupling agent, followed by oxidation with iodine or other mild oxidant, provides the protected cyclic diphosphate xii. Removal of protecting groups from the phosphate and Rings A and B is accomplished by treatment with methyl amine in ethanol. Removal of any silyl-based protecting groups is accomplished with hydrogen fluoride-triethyl amine and results in the fully deprotected cyclic diphosphate compound II where $X^1$ and $X^2$ are both OH.

Compounds of formula II where $X^1$ and $X^2$ are SH can be prepared in a similar manner. H-phosphonate ix is coupled with a cyclopentane-derived and appropriately protected phosphoramidite x (where $R^4$ is a silyl protected hydroxyl, hydrogen, fluoro, or is taken together with $R^3$ to form $OCH_2$, $R^3$ is H) in the presence of a mild acid like ethylthio-tetrazole. The resulting phosphite ester is oxidized to the phosphorothioate using a sulfur transfer reagent (such as ((dimethylamino-methylidene)amino)-3H-1,2,4-dithiazoline-3-thione). Removal of the protecting group on the 5' oxygen with AcOH/water if the protecting group is a dimethoxytrityl ether or with TFA/water if the protecting group is silyl-based provides phosphorothioate xi. Treatment of compound xi with 2-chloro-5,5-dimethyl-1,3,2-dioxaphosphorinane 2-oxide or other coupling agent, followed by treatment with a sulfur transfer reagent (such as 3H-1, 2-benzodithiol-3-one 1, 1-dioxide or 3H-1, 2-benzodithiol-3-one) provides the cyclic diphosphorothioate xii. Removal of protecting groups from the phosphorothioate and Rings A and B is accomplished by treatment with methyl amine in ethanol. Removal of any silyl-based protecting groups is accomplished with hydrogen fluoride-triethyl amine and results in the fully deprotected cyclic diphosphorothioate compound II where $X^1$ and $X^2$ are both SH.

Scheme 4: Route for preparing cyclic monophosphorothioates

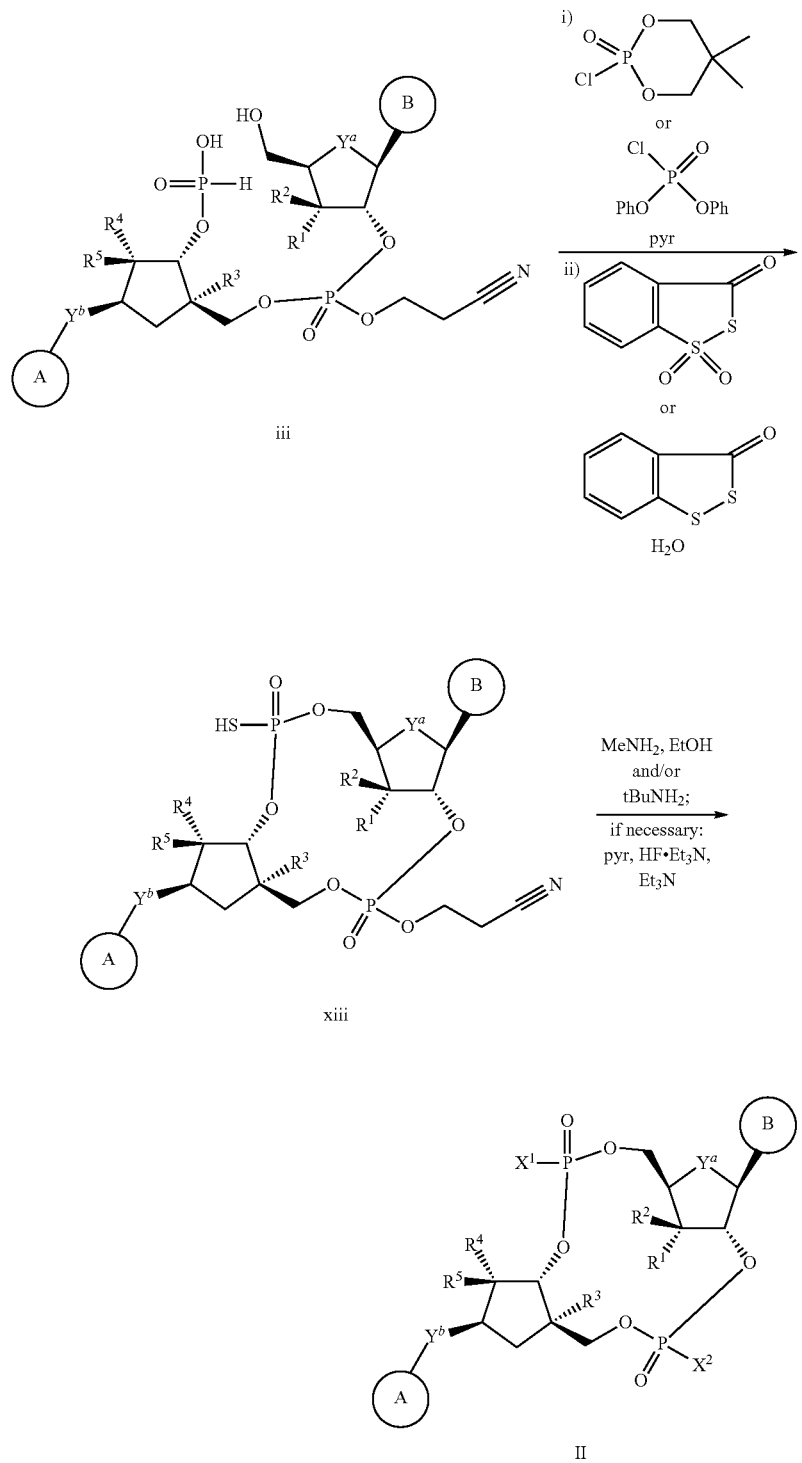

Scheme 4 shows the synthesis of a monophosphorothioate (compound II where $X^1$ is SH and $X^2$ is OH). Treatment of compound iii with 2-chloro-5,5-dimethyl-1,3,2-dioxaphosphorinane 2-oxide or diphenyl chlorophosphosphate, followed by treatment with a sulfur transfer reagent (such as 3H-1,2-benzodithiol-3-one 1,1-dioxide or 3H-1,2-benzodithiol-3-one) provides the cyclic monophosphorothioate xiii. Removal of protecting groups from the phosphate and Rings A and B is accomplished by treatment with methyl amine in ethanol and/or tert-butyl amine. Removal of any silyl-based protecting groups is accomplished with hydrogen fluoride-triethyl amine and results in the fully deprotected cyclic monophosphorothioate compound 1U where $X^1$ is SH and $X^2$ is OH.

Scheme 5: Alternate route for preparing cyclic monophosphorothioates

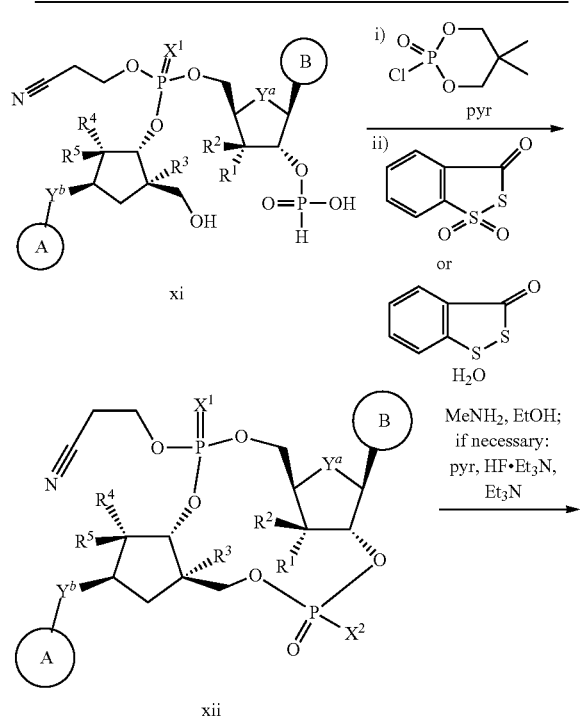

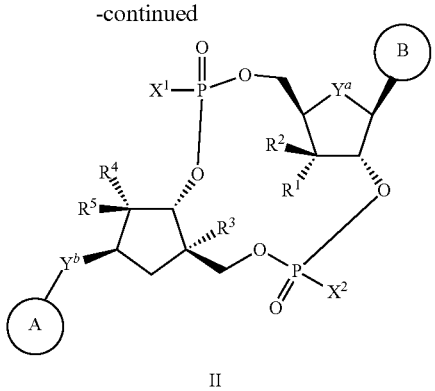

Scheme 5 shows the synthesis of a monophosphorothioate (compound II where $X^1$ is OH and $X^2$ is SH). Treatment of compound xi where $X^1$ is O with 2-chloro-5,5-dimethyl-1,3,2-dioxaphosphorinane 2-oxide or other coupling agent, followed by treatment with a sulfur transfer reagent (such as 3H-1,2-benzodithiol-3-one 1,1-dioxide or 3H-1,2-benzodithiol-3-one) provides the cyclic monophosphorothioate xii ($X^2$ is SH). Removal of protecting groups from the phosphate and Rings A and B is accomplished by treatment with methyl amine in ethanol. Removal of any silyl-based protecting groups is accomplished with hydrogen fluoride-triethyl amine and results in the fully deprotected cyclic monophosphorothioate compound 1U where $X^1$ is OH and $X^2$ is SH.

Scheme 6: Another method for preparing cyclic monophosphorothioates

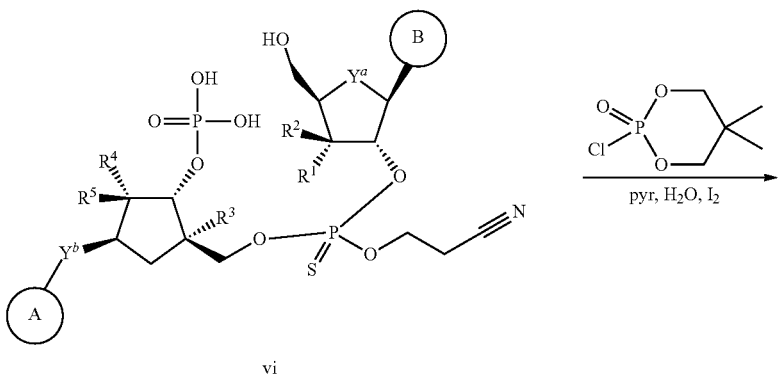

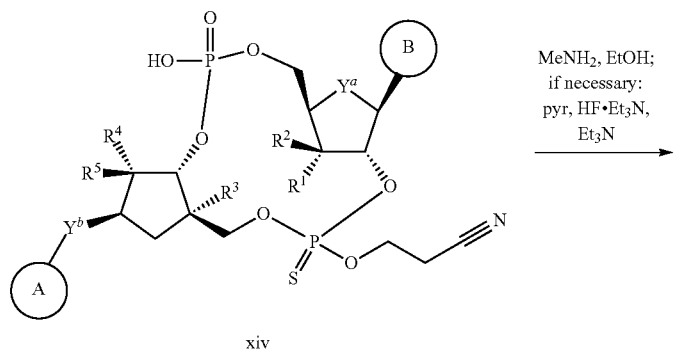

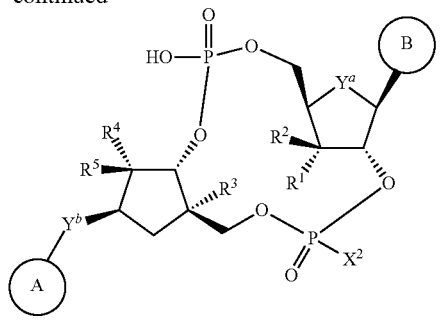

II

Scheme 6 shows the synthesis of a monophosphorothioate (compound II where $X^1$ is OH and $X^2$ is SH). Treatment of compound vi with 2-chloro-5,5-dimethyl-1,3,2-dioxaphosphorinane 2-oxide or other coupling agent, followed by oxidation with iodine or other mild oxidant, provides the cyclic monophosphorothioate xiv. Removal of protecting groups from the thiophosphate and Rings A and B is accomplished by treatment with methyl amine in ethanol. Removal of any silyl-based protecting groups is accomplished with hydrogen fluoride-triethyl amine and results in the fully deprotected cyclic monophosphorothioate compound 1U where $X^1$ is OH and $X^2$ is SH.

Scheme 7: Synthesis of heteroaryl N- and O-linked cyclopentane H-phosphonates

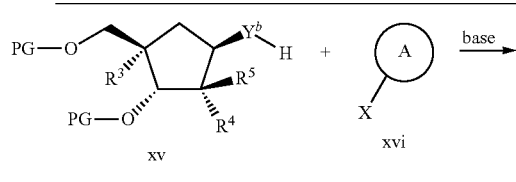

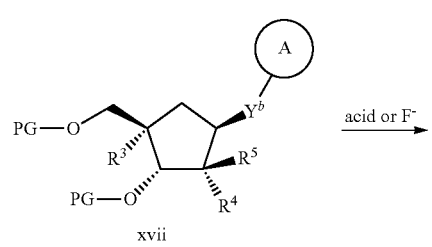

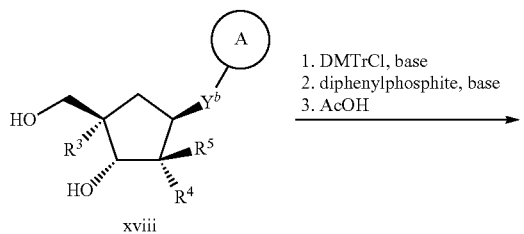

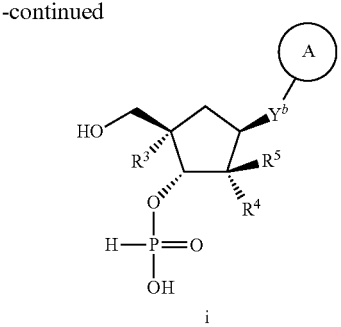

i

Scheme 7 shows a general route for the preparation of cyclopentane H-phosphonate intermediate i (where $R^4$ is a silyl protected hydroxyl, hydrogen, fluoro or is taken together with $R^3$ to form $OCH_2$, $R^3$ is H, and $R^5$ is hydrogen or fluoro). Cyclopentane xv (where PG is an appropriate protecting group, such as a trityl, benzyl, or silyl derivative) is reacted with a heterocyclic halide xvi under basic conditions (using a base such as LDA, DIPEA, $K_2CO_3$, or KOtBu) to provide intermediate xvii. In some examples the heterocycle A in intermediate xvii may be substituted with chlorine which is reduced using hydrogenation with palladium on carbon or $Pd(OH)_2$. In some examples where $Y^b$ is NH, $Y^b$ may be alkylated using an alkyl halide such as MeI and a base such as NaH. The alcohol protecting groups are then removed using an acid (such as TFA or HCl) or a fluoride source (such as TBAF) to provide diol xviii. The primary alcohol is then temporarily protected with the dimethoxytrityl group in the presence of a base (such as DBU, $NEt_3$, or pyr), the H-phosphonate is installed using diphenylphosphite and base (such as $Et_3N$ or pyr), and the dimethoxytrityl group is removed using a mild acid (such as AcOH or DCA) to provide compound i. In examples where the primary alcohol is protected with a benzyl group deprotection is performed using boron trichloride to yield compound i.

Scheme 8: Alternate synthesis of heteroaryl O-linked cyclopentane intermediates

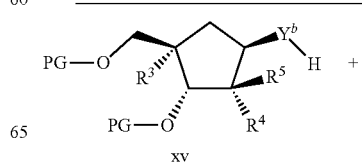

79
-continued

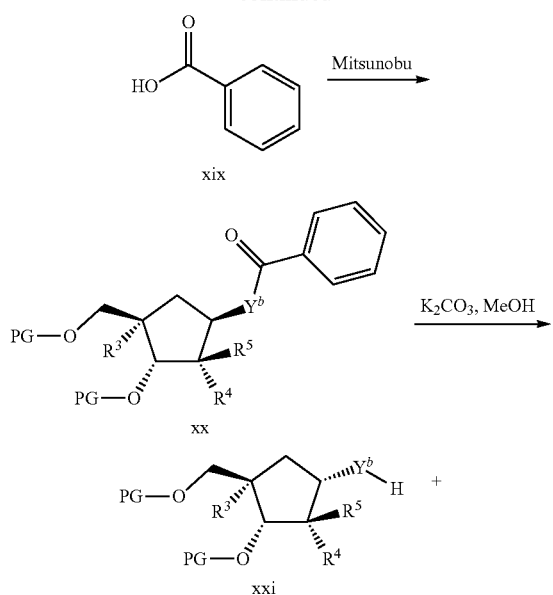

Scheme 8 shows an alternate general method for the preparation of xvii when $Y^b$ is O. Cyclopentane xv where $Y^b$ is O is treated under Mitsunobu inversion conditions such as benzoic acid, triphenylphosphine and DIAD. The benzoate group is removed under mild basic conditions such as potassium carbonate to provide the inverted alcohol xxi. A subsequent Mitsunobu reaction with a heteroaromatic alcohol xxii under standard conditions using triphenylphosphine and a diazodicarboxylate reagent (such as DEAD, DIAD or DBAD) provides compound xvii.

Scheme 9: Synthesis of cyclopentane phosphoramidites

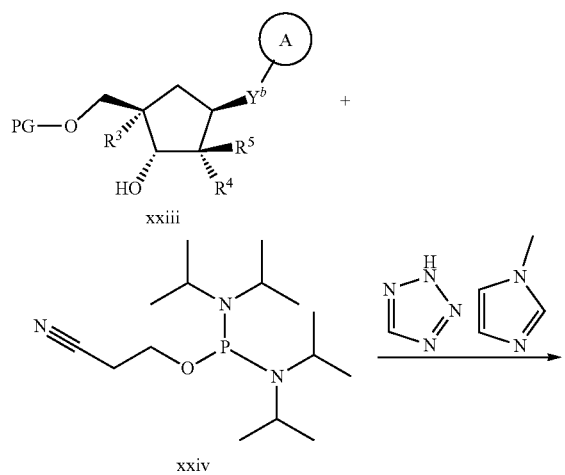

80
-continued

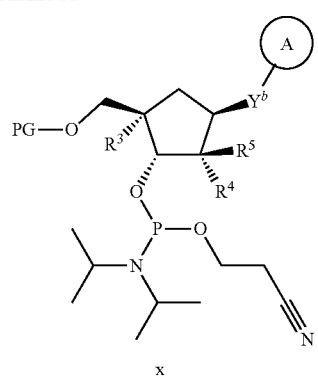

Scheme 9 depicts a general scheme to prepare cyclopentane phosphoramidites x. Cyclopentane xxiii and 2-cyanoethyl N, N, N', N'-tetraisopropylphosphorodiamidite xxiv are combined under conditions such as tetrazole and N-methylimidazole.

Scheme 10: Synthetic route for the preparation of H-phosphonates

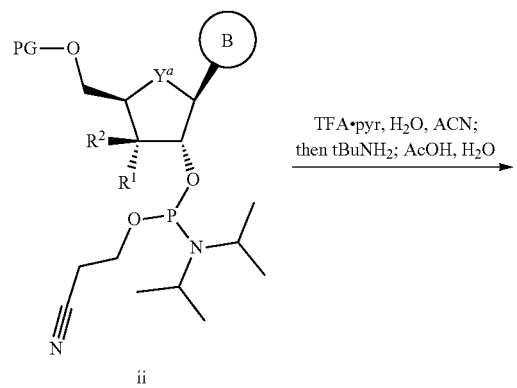

Scheme 10 shows a route for the preparation of compounds of formula ix from compound ii with a phosphoramidite functionality at the 2' position that is converted to an H-phosphonate in the presence of aqueous TFA/pyridine followed by treatment with a base such as tert-butylamine. The primary alcohol is then deprotected using mildly acidic conditions such as AcOH.

Scheme 11: General route for the preparation of phosphoamidites

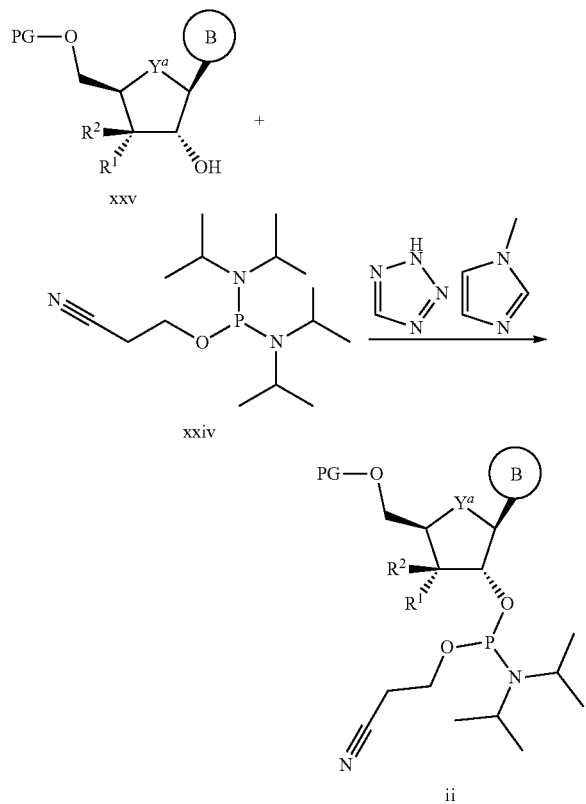

Scheme 11 shows a general route for the preparation of phosphoramidite intermediate ii (where PG is an appropriate protecting group, such as trityl or where $R^1$ and OPG are connected via $OSi(iPr)_2OSi(iPr)_2O$). Alcohol xxv and 2-cyanoethyl N, N, N', N'-tetraisopropylphosph orodiamidite xxiv are combined under conditions such as tetrazole and N-methylimidazole.

Method of Use of Compounds of Formula (I)

Compound of the present disclosure show STING modulating/agonistic activity. Certain compounds of the present disclosure can be superior in terms of efficacy expression, pharmacokinetics (e.g., absorption, distribution, metabolism, excretion), solubility (e.g., water solubility), interaction with other medicaments (e.g., drug-metabolizing enzyme inhibitory action), safety (e.g., acute toxicity, chronic toxicity, genetic toxicity, reproductive toxicity, cardiotoxicity, carcinogenicity, central toxicity) and/or stability (e.g., chemical stability, stability to an enzyme), and can be useful as a medicament.

A compound of the present disclosure can be used for increasing STING activity in a mammal (e.g., mouse, rat, hamster, rabbit, cat, dog, cow, sheep, monkey, human).

A compound of the present disclosure can be used as a medicament such as an agent for the prophylaxis or treatment of diseases that can be influenced by STING (in the present specification, sometimes to be abbreviated as "STING-related diseases"), for example, cancers—e.g., colorectal cancers (e.g., colorectal cancer, rectal cancer, anus cancer, familial colorectal cancer, hereditary nonpolyposis colorectal cancer, gastrointestinal stromal tumor), lung cancers (e.g., non-small-cell lung cancer, small-cell lung cancer, malignant mesothelioma), mesothelioma, pancreatic cancers (e.g., pancreatic ductal carcinoma, pancreatic endocrine tumor), pharynx cancer, larynx cancer, esophageal cancer, stomach cancers (e.g., papillary adenocarcinoma, mucinous adenocarcinoma, adenosquamous carcinoma), duodenal cancer, small intestinal cancer, breast cancers (e.g., invasive ductal carcinoma, non-invasive ductal carcinoma, inflammatory breast cancer), ovarian cancers (e.g., ovarian epithelial cancer, extragonadal germ cell tumor, ovarian germ cell tumor, ovarian low-malignant potential tumor), testis tumor, prostate cancers (e.g., hormone-dependent prostate cancer, non-hormone dependent prostate cancer, castration-resistant prostate cancer), liver cancers (e.g., hepatocellular cancer, primary liver cancer, extrahepatic bile duct cancer), thyroid cancers (e.g., medullary thyroid carcinoma), renal cancers (e.g., renal cell cancers (e.g., clear cell renal cell cancer), transitional cell cancer of renal pelvis and ureter), uterine cancers (e.g., cervical cancer, uterine body cancer, uterus sarcoma), gestational choriocarcinoma, brain tumors (e.g., medulloblastoma, glioma, pineal astrocytic tumors, pilocytic astrocytoma, diffuse astrocytoma, anaplastic astrocytoma, pituitary adenoma), retinoblastoma, skin cancers (e.g., basalioma, malignant melanoma), sarcomas (e.g., rhabdomyosarcoma, leiomyosarcoma, soft tissue sarcoma, spindle cell sarcoma), malignant bone tumor, bladder cancer, blood cancers (e.g., multiple myeloma, leukemias (e.g., acute myelogenous leukemia), malignant lymphoma, Hodgkin's disease, chronic myeloproliferative disease), cancer of unknown primary; a cancer growth inhibitor; a cancer metastasis inhibitor; an apoptosis promoter; an agent for the treatment of precancerous lesions (e.g., myelodysplastic syndromes); and the like.

In certain embodiments, a compound of the present disclosure can be used as a medicament for colorectal cancer, breast cancer, skin cancer, malignant lymphoma or lung cancer.

A compound of the present disclosure can be administered orally or parenterally as is or in a mixture with a pharmacologically acceptable carrier as a medicament, to a mammal (typically a human).

The medicament containing a compound of the present disclosure (hereinafter sometimes to be abbreviated as "the medicament of the present disclosure") is explained in detail below. Examples of the dosage form of the medicament of the present disclosure include oral preparations such as tablet (e.g., sugar-coated tablet, film-coated tablet, sublingual tablet, buccal, orally disintegrating tablet), pill, granule, powder, capsule (e.g., soft capsule, microcapsule), syrup, emulsion, suspension, films (e.g., orally disintegrable films, oral mucosa-adhesive film) and the like. In addition, examples of the dosage form of the medicament of the present disclosure include parenteral preparations such as injection, drip infusion, transdermal absorption type preparation (e.g., iontophoresis transdermal absorption type preparation), suppository, ointment, nasal preparation, pulmonary preparation, eye drop and the like. Moreover, the medicament of the present disclosure may be a release control preparation such as an immediate-release preparation, a sustained-release preparation (e.g., a sustained-release microcapsule) and the like.

As the dosage form of the medicament of the present disclosure, a nanoparticle preparation and a preparation using a bacteria-derived membrane can also be used.

The medicament of the present disclosure may be prepared according to a method known per se (e.g., the method described in the US Pharmacopoeia etc.) generally used in the field of preparation. In addition, the medicament of the present disclosure may contain a suitable amount of an additive such as a excipient, a binder, a disintegrant, a lubricant, a sweetening agent, a surfactant, a suspending agent, an emulsifier, a colorant, a preservative, an aromatic, a corrigent, a stabilizer, a thickening agent and the like generally used in the field of preparation as necessary. Examples of the pharmacologically acceptable carrier include these additives.

For example, tablet may be prepared using an excipient, a binder, a disintegrant, a lubricant and the like, and pill or granule may be prepared using an excipient, a binder and a disintegrant. Powder or capsule may be prepared using an excipient and the like, syrup may be prepared using a sweetening agent and the like, and emulsion or suspension may be prepared using a suspending agent, a surfactant, an emulsifier and the like.

Examples of useful excipients include lactose, sucrose, glucose, starch, sucrose, crystalline cellulose, powdered *Glycyrrhiza*, mannitol, sodium hydrogencarbonate, calcium phosphate and calcium sulfate.

Examples of useful binders include 5 to 10 wt % starch liquid paste, 10 to 20 wt % gum arabic solution or gelatin solution, 1 to 5 wt % tragacanth solution, carboxymethyl cellulose solution, sodium alginate solution and glycerin.

Examples of useful disintegrants include starch and calcium carbonate.

Examples of useful lubricants include magnesium stearate, stearic acid, calcium stearate and purified talc.

Examples of useful sweeteners include glucose, fructose, invert sugar, sorbitol, xylitol, glycerin and simple syrup.

Examples of useful surfactants include sodium lauryl sulfate, polysorbate 80, sorbitan monofatty acid ester and polyoxyl 40 stearate.

Examples of useful suspending agents include gum arabic, sodium alginate, sodium carboxymethyl cellulose, methyl cellulose and bentonite.

Examples of useful emulsifiers include gum arabic, tragacanth, gelatin and Polysorbate 80.

For example, when the medicament of present disclosure is a tablet, for example, an excipient (e.g., lactose, sucrose, starch), a disintegrant (e.g., starch, calcium carbonate), a binder (e.g., starch, gum arabic, carboxymethyl cellulose, polyvinyl pyrrolidone, hydroxypropyl cellulose) or a lubricant (e.g., talc, magnesium stearate, polyethylene glycol 6000) is added to a compound of the present disclosure, and the mixture is compression-molded, according to a method known per se, and then where necessary, the molded product is coated according to a method known per se for the purpose of masking of taste, enteric property or durability, to give a tablet. As the coating agent for the coating, for example, hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (methacrylic acid-acrylic acid copolymer, manufactured by Rohm, DE) and pigment (e.g., iron oxide red, titanium dioxide) may be used.

Examples of the injection include intravenous injection as well as subcutaneous injection, intracutaneous injection, intramuscular injection, intraperitoneal injection, drip injection, intratumoral injection and the like.

Such injections are prepared according to a method known per se, or by dissolving, suspending or emulsifying a compound of the present disclosure in a sterilized aqueous or oily liquid. Examples of the aqueous liquid include physiological saline, isotonic solutions containing glucose or other auxiliary drugs (e.g., D-sorbitol, D-mannitol, sodium chloride) and the like. The aqueous liquid may contain a suitable solubilizing agent such as an alcohol (e.g., ethanol), a polyalcohol (e.g., propylene glycol, polyethylene glycol), a nonionic surfactant (e.g., polysorbate 80, HCO-50) and the like. Examples of the oily liquid include sesame oil, soybean oil and the like. The oily liquid may contain a solubilizing agent. Examples of the solubilizing agent include benzyl benzoate, benzyl alcohol and the like. In addition, the injection may be blended with a buffer (e.g., phosphate buffer, sodium acetate buffer), a soothing agent (e.g., benzalkonium chloride, procaine hydrochloride), a stabilizer (e.g., human serum albumin, polyethylene glycol), a preservative (e.g., benzyl alcohol, phenol) and the like. A prepared injection may be generally filled in an ampoule.

While the content of a compound of the present disclosure in the medicament of the present disclosure varies depending on the form of the pharmaceutical preparation, it is generally about 0.01 to about 100 wt %, typically about 2 to about 85 wt %, or about 5 to about 70 wt %, relative to the entire preparation.

While the content of the additive in the medicament of the present disclosure varies depending on the form of the pharmaceutical preparation, it is generally about 1 to about 99.9 wt %, typically about 10 to about 90 wt %, relative to the entire preparation.

While the daily dose of a compound of the present disclosure varies depending on the condition and body weight of patients, the kind of compound, administration route and the like, in the case of, for example, oral administration to patients for the treatment of cancer, the daily dose to an adult (body weight about 60 kg) is about 1 to about 1000 mg, typically about 3 to about 300 mg, or about 10 to about 200 mg, as a compound of the present disclosure, which may be given in a single administration or administered in 2 or 3 portions a day.

When a compound of the present disclosure is administered parenterally, it is generally administered in the form of a liquid (e.g., injection). While the dose of a compound of the present disclosure varies depending on the subject of administration, target organ, symptom, administration method and the like, it is, for example, about 0.01 mg to about 100 mg, typically about 0.01 to about 50 mg, or about 0.01 to about 20 mg, relative to 1 kg body weight, which is typically given by intravenous injection.

The present disclosure also includes a compound of the present disclosure for use (i) in, (ii) as a medicament for, or (iii) in the preparation of a medicament for: (a) inducing an immune response in a patient, or (b) inducing a STING-dependent cytokine production in a patient. In these uses, the compounds of the present disclosure can optionally be employed in combination with one or more second therapeutic agents.

As used herein, the term "immune response" relates to any one or more of the following: specific immune response, non-specific immune response, both specific and non-specific response, innate response, primary immune response, adaptive immune response, secondary immune response, memory immune response, immune cell activation, immune cell proliferation, immune cell differentiation, and cytokine expression.

In one embodiment, the compound of Formula (I) disclosed herein can be used for inducing a STING-dependent type I interferon production in a subject. The compound of Formula (I) or a pharmaceutically acceptable salt thereof can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

The compounds of the present disclosure may also be used as adjuvants to improve the immune response raised to any given antigen and/or reduce reactogenicity/toxicity in a patient, particularly a human, in need thereof. As such, a compound of the present disclosure may be used in combination with vaccine compositions to modify, especially to enhance, the immune response for example by increasing the level or duration of protection and/or allowing a reduction in the antigenic dose. The compounds of Formula (I) and pharmaceutically acceptable salts thereof may be used in combination with one or more vaccines or immunogenic antigens useful in the prevention or treatment of viral infections.

The present disclosure also provides a vaccine composition comprising an antigen and the compounds of Formula (I) or a pharmaceutically acceptable salt thereof.

A compound of the present disclosure can be used concurrently with other drugs. To be specific, a compound of the present disclosure can be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with a compound of the present disclosure are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin, leuprorelin acetate), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide, enzalutamide), 5α-reductase inhibitors (e.g., finasteride, epristeride, dutasteride), aderenal cortex hormone drugs (e.g., dexamethasone, prednisolone, betamethasone, triamcinolone), androgen synthesis inhibitors (e.g., abiraterone), retinoid and drugs that retard retinoid metabolism (e.g., liarozole), thyroid hormone, and DDS (Drug Delivery System) preparations thereof.

Examples of the "chemotherapeutic agents" include alkylating agents, antimetabolites, anticancer antibiotics and plant-derived anticancer agents.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, and DDS preparations thereof.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and DDS preparations thereof (e.g., doxorubicin-including PEG liposome).

Examples of the "plant-derived anticancer agents" include etoposide, etoposide phosphate, vinblastine sulfate, vincristine sulfate, vindesine sulfate, teniposide, paclitaxel, docetaxel, cabazitaxel, vinorelbine, and DDS preparations thereof.

Examples of the "immunotherapeutic agents (BRM)" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibodies (e.g., ipilimumab, tremelimumab), anti-PD-1 antibodies (e.g., nivolumab, pembrolizumab), and anti-PD-L1 antibody.

Example of the "cell growth factors" in the "medicaments inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα], (2) insulin or substances possessing substantially the same activity as insulin [e.g., insulin, IGF (insulin-like growth factor)-1, IGF-2], (3) FGF (fibroblast growth factor) or substances possessing substantially the same activity as FGF [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin].

Examples of the "cell growth factor receptors" include any receptors capable of binding to the aforementioned cell growth factors, including EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor and the like.

Examples of the "medicaments inhibiting the action of cell growth factors or cell growth factor receptors" include EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, ROR1 inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor, PI3K inhibitor and the like. More specifically, anti-VEGF antibody (e.g., Bevacizumab, Ramucurumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2(R),3-dihydroxypropoxy]-3,4-difluoro-2-(2-fluoro-4-iodophenylamino)benzamide (PD-0325901), Bosutinib, Regorafenib, Afatinib, Idelalisib, Ceritinib, Dabrafenib and the like may be used.

In addition to the aforementioned drugs, L-asparaginase, L-arginase, arginine deiminase, aceglatone, procarbazine hydrochloride, protoporphyrin-cobalt complex salt, mercuric hematoporphyrin-sodium, topoisomerase I inhibitors (e.g., irinotecan, topotecan, indotecan, Indimitecan), topoisomerase II inhibitors (e.g., sobuzoxane), differentiation inducers (e.g., retinoid, vitamin D), other angiogenesis inhibitors (e.g., humagillin, shark extract, COX-2 inhibitor), α-blockers (e.g., tamsulosin hydrochloride), bisphosphonic acids (e.g., pamidronate, zoledronate), thalidomide, lenalidomide, pomalidomide, azacytidine, decitabine, proteasome inhibitors (e.g., bortezomib, carfilzomib, ixazomib), NEDD8 inhibitors (e.g., Pevonedistat), UAE inhibitors, PARP inhibitors (e.g., Olaparib, Niraparib, Veliparib), antitumor antibodies such as anti-CD20 antibodies (e.g., Rituximab, Obinutuzumab), anti-CCR4 antibodies (e.g., Mogamulizumab) and the like, antibody-drug conjugates (e.g., trastuzumab emtansine, Brentuximab vedotin) and the like may also be used as a concomitant drug.

By combining a compound of the present disclosure and a concomitant drug, a superior effect such as (1) the dose may be reduced as compared to single administration of a compound of the present disclosure or a concomitant drug, (2) the drug to be combined with a compound of the present disclosure may be selected according to the condition of patients (mild case, severe case and the like), (3) the period of treatment may be set longer, (4) a sustained treatment effect may be designed, (5) a synergistic effect may be afforded by a combined use of a compound of the present disclosure and a concomitant drug, and the like, may be achieved.

In the present specification, a compound of the present disclosure and a concomitant drug used in combination are referred to as the "combination agent of the present disclosure".

For use of the combination agent of the present disclosure, the administration time of a compound of the present disclosure and the concomitant drug is not restricted, and a compound of the present disclosure and the concomitant drug can be administered to an administration subject simultaneously, or may be administered at different times. When administered at a time interval, the interval differs depending on the effective ingredient to be administered, dosage form and administration method, and for example, when the concomitant drug is administered first, a compound of the present disclosure may be administered within time range of from 1 min to 3 days, typically from 10 min to 1 day, or from 15 min to 1 hr after administration of the concomitant drug. When a compound of the present disclosure is administered first, the concomitant drug is administered within time range of from 1 min to 1 day, typically from 10 min to 6 hrs, or from 15 min to 1 hr after administration of a compound of the present disclosure. The dosage of the concomitant drug may be determined according to the dose clinically set, and may be appropriately selected depending on the administration subject, administration route, disease, combination and the like.

Examples of the administration mode of the combined use of a compound of the present disclosure and the concomitant drug include the following methods: (1) A compound of the present disclosure and the concomitant drug are simultaneously produced to give a single preparation, which is then administered. (2) A compound of the present disclosure and the concomitant drug are separately produced to give two kinds of preparations which are administered simultaneously by the same administration route. (3) A compound of the present disclosure and the concomitant drug are separately produced to give two kinds of preparations which are administered by the same administration route at different times. (4) A compound of the present disclosure and the concomitant drug are separately produced to give two kinds of preparations which are administered simultaneously by different administration routes. (5) A compound of the present disclosure and the concomitant drug are separately produced to give two kinds of preparations which are administered by different administration routes at different times (e.g., a compound of the present disclosure and the concomitant drug are administered in this order, or in the reverse order).

The dose of the concomitant drug may be appropriately determined in accordance with its clinical dose, and the ratio of a compound of the present disclosure and the concomitant drug may be appropriately determined depending on the administration subject, administration route, target disease, symptom, combination, and the like. For example, when the administration subject is human, the concomitant drug is used in 0.01 to 100 (parts by weight), relative to 1 part by weight of a compound of the present disclosure.

Furthermore, a compound of the present disclosure or the combination agent of the present disclosure may be used concurrently with a non-drug therapy. To be precise, a compound of the present disclosure or the combination agent of the present disclosure may be combined with a non-drug therapy such as (1) surgery, (2) hypertensive chemotherapy using angiotensin II etc., (3) gene therapy, (4) thermotherapy, (5) cryotherapy, (6) laser cauterization and (7) radiotherapy.

For example, by using a compound of the present disclosure or the combination agent of the present disclosure before or after the above-mentioned surgery and the like, or before or after a combined treatment of two or three kinds thereof, effects such as prevention of emergence of resistance, prolongation of Disease-Free Survival, suppression of cancer metastasis or recurrence, prolongation of life and the like may be afforded.

In addition, it is possible to combine a treatment with a compound of the present disclosure or the combination agent of the present disclosure with a supportive therapy: (i) administration of antibiotic (e.g., β-lactam type such as pansporin and the like, macrolide type such as clarithromycin and the like) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like.

In one embodiment, the disclosure provides a kit comprising two or more separate pharmaceutical compositions, at least one of which contains a compound of Formula (I) or pharmaceutically acceptable salt thereof. A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

EXAMPLES

Exemplification

As depicted in the Examples below, in certain exemplary embodiments, compounds are prepared according to the following general procedures. It will be appreciated that, although the general methods depict the synthesis of certain compounds of the present disclosure, the following general methods, and other methods known to one of ordinary skill in the art, can be applied to all compounds and subclasses and species of each of these compounds, as described herein.

| | Definitions |
|---|---|
| AA | LCMS method using ammonium acetate |
| Ac | acetate |
| ACN | acetonitrile |
| atm | atmosphere |
| aq | aqueous |
| BBN | borabicyclo(3.3.1)nonane |
| Bn | benzyl |
| Boc | tert-butoxycarbonyl |
| (Bpin)$_2$ | bis(pinacolato)diboron |
| tBu | tert-butyl |
| Bz | benzoyl |
| C. | Celsius |
| DBAD | di-tert-butyl azodicarboxylate |
| DBU | 1,8-diazabicyclo[5.4.0]undec-7-enedichloroacetic acid |
| DCA | dichloroacetic acid |
| DCE | dichloroethane |
| DCM | dichloromethane |
| DEAD | diethyl azodicarboxylate |
| DIAD | diisopropyl azodicarboxylate |

| | Definitions |
|---|---|
| DIPEA | N,N-diisopropylethylamine |
| DMAP | 4-dimethylaminopyridine |
| DMF | N,N-dimethylformamide |
| DMSO | dimethylsulfoxide |
| DMTr | 4,4'-dimethoxytrityl |
| Et | ethyl |
| EtOH | ethanol |
| EtOAc | ethyl acetate |
| FA | LCMS method using formic acid |
| h | hours |
| Int | Intermediate |
| HPLC | high pressure liquid chromatography |
| HRMS | high resolution mass spectrometry |
| IC$_{50}$ | inhibitory concentration 50% |
| IPA | isopropyl alcohol |
| IPC | diisopinocampheyl |
| LCMS | liquid chromatography mass spectrometry |
| LDA | lithium diisopropylamide |
| LHMDS | lithium bis(trimethylsilyl)amide |
| m/z | mass to charge |
| MHz | mega hertz |
| Me | methyl |
| MeOH | methanol |
| min | minutes |
| mL | milliliters |
| MS | mass spectrum |
| nBu | n-butane |
| NMP | 1-methyl-2-pyrrolidinone |
| NMR | nuclear magnetic resonance |
| PE | petroleum ether |
| Ph | phenyl |
| psi | pounds per square inch |
| pyr | pyridine |
| rt | room temperature |
| SFC | supercritical fluid chromatography |
| T3P | 2,4,6-tripropyl-1,3,5,2,4,6-trioxatriphosphorinane-2,4,6-trioxide |
| TDA-1 | tris[2-(2-methoxyethoxy)ethyl]amine |
| TBAF | tetrabutylammonium fluoride |
| TBS | tert-butyldimethylsilyl |
| TBTU | O-(benzotriazol-1-yl)-N,N,N',N'-tetramethyluronium tetrafluoroborate |
| TEA | triethylamine |
| TFA | trifluoroacetic acid |
| TIDPSi | 1,1,3,3-tetraisopropyldisiloxane |
| TIPS | triisopropylsilyl |
| THF | tetrahydrofuran |
| UPLC | ultra performance liquid chromatography |
| Xantphos | 4,5-bis(diphenylphosphino)-9,9-dimethylxanthene |

Analytical Methods

NMR Conditions:

$^1$H NMR spectra were run on a 400 MHz Bruker spectrometer unless otherwise stated. $^{31}$P NMR spectra were run on a 400 MHz Bruker spectrometer and acquired with $^1$H decoupling unless otherwise stated.

LCMS Conditions:

LCMS spectra were recorded on a Hewlett-Packard HP1100 or Agilent 1100 Series LC system connected to a Micromass mass spectrometer using reverse phase C$_{18}$ columns. Various gradients and run times were selected in order to best characterize the compounds. Mobile phases were based on ACN/water or MeOH/water gradients and contained either 0.1% formic acid (methods indicated as FA) or 10 mM ammonium acetate (methods indicated as AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run.

In some cases, LCMS spectra were recorded on an Agilent 1290 Infinity UPLC system connected to an Agilent 6130 mass spectrometer, a Waters Acquity UPLC system connected to a Waters Acquity SQ mass spectrometer, or an Agilent 1100 Series HPLC system connected to a Waters Micromass ZQ mass spectrometer using reverse phase $C_{18}$ columns. Various gradients and run times were selected in order to best characterize the compounds. Mobile phases were based on ACN/water or MeOH/water gradients and contained either 0.1% formic acid (methods indicated as FA) or 10 mM ammonium acetate (methods indicated as AA). One example of a solvent gradient that was used was 95% mobile phase A (mobile phase A=99% water+1% ACN+ 0.1% formic acid) to 100% mobile phase B (mobile phase B=95% ACN+5% water+0.1% formic acid) at a flow rate of 0.5 mL/min for a 5 min run.

Preparative HPLC:

Preparative HPLC are conducted using 18×150 mm Sunfire C-18 columns eluting with water-ACN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

One of ordinary skill in the art will recognize that modifications of the gradient, column length, and flow rate are possible and that some conditions may be more suitable for compound characterization than others, depending on the chemical species being analyzed.

Preparative SFC:

Preparative SFC is conducted using 10, 20 or 30 mm×250 mm ChiralPak columns (typically IA, IB, IC, ID, IE and IF), 10 or 20 mm×250 mm Phenomenex Lux Cellulose-4, or 2-ethylpyridine columns eluting with appropriate percentages of supercritical carbon dioxide and alcohol containing 0.3% diethyl amine or 0.3% TEA or 0.3% formic acid or without any acid or base additives. Isocratic conditions with flow rates in the range of 10-100 mL/min and a column temperature of 40° C. are typical. Preparative SFC is conducted on A Jasco SFC prep purification system with UV/visible triggered fraction collection set to between 200 nm and 400 nm and back pressure regulation set to 10 MPa.

One of ordinary skill in the art will recognize that modifications of the gradient, column length, and flow rate are possible and that some conditions may be more suitable for compound characterization than others, depending on the chemical species being analyzed.

Example 1

(1R,3R,4S)-3-[[tert-butyl(dimethyl)silyl]oxymethyl]-4-triisopropylsilyloxy-cyclopentanol, Intermediate 2

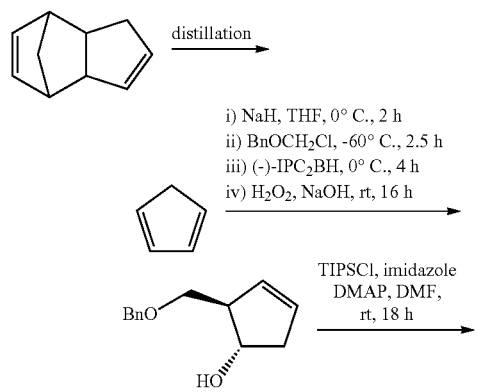

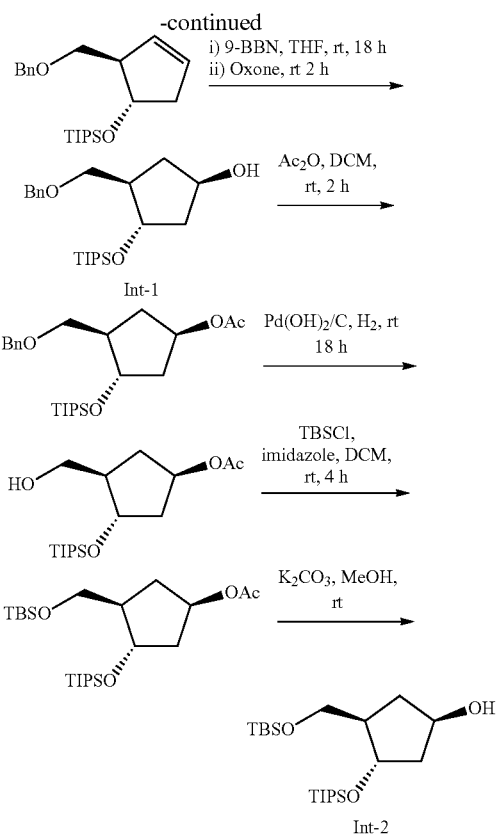

Step 1: cyclopenta-1,3-diene 3a,4,7,7a-Tetrahydro-1H-4,7-methanoindene (800 g, 6.05 mmol) was distilled at 180° C. to give cyclopenta-1,3-diene (300 g, 75%) as white liquid, which was used for next step without further purification. $^{1}$H NMR (chloroform-d) δ 6.58 (d, J=4.4 Hz, 2H), 6.47 (d, J=4.4 Hz, 2H), 2.99 (s, 2H).

Step 2: (1S,2R)-2-((benzyloxy)methyl)cyclopent-3-enol

A solution of cyclopenta-1,3-diene (100 g, 1.51 mol) in THF (2.00 L) was cooled to −5° C. NaH (60% in mineral oil, 50.3 g, 1.26 mol) was added in portions and the resulting mixture was allowed to stir at −5° C. for 2 h. The reaction mixture was cooled to −60° C. and ((chloromethoxy)methyl)benzene (236 g, 1.51 mol) was added drop-wise under nitrogen atmosphere. After stirring at −60° C. for 2.5 h, bis((1R,2S,3R,5R)-2,6,6-trimethylbicyclo[3.1.1]heptan-3-yl)borane (229 g, 799 mmol) in THF (500 mL) was added drop-wise. The reaction mixture was allowed to warm to 0° C. and stirred for 3.5 h. Then NaOH (3.00 M in water, 500 mL, 1.51 mol) was added, followed by $H_2O_2$ (30% in water, 400 mL, 3.93 mol) drop-wise at 0° C. The reaction mixture was allowed to stir for 16 h at 20° C. The reaction mixture was quenched with saturated $Na_2SO_3$ (1.00 L). The organic phase was separated and the aqueous phase was extracted with EtOAc (2×1.00 L). The combined organic phases were concentrated in vacuum. The residue was purified by silica gel chromatography (3-10% EtOAc in PE) to give the desired product (1S,2R)-2-((benzyloxy)methyl)cyclopent-3-enol (40.0 g, 13%) as a yellow oil. $^{1}$H NMR (CDCl$_3$) δ 7.26-7.39 (m, 5H), 5.74 (dq, J=6.2, 2.3 Hz, 1H), 5.56 (dq, J=6.2, 2.1 Hz, 1H), 4.54 (s, 2H), 4.32 (dt, J=7.0, 4.1 Hz, 1H), 3.57 (dd, J=9.1, 5.3 Hz, 1H), 3.30 (t, J=8.8 Hz, 1H), 2.80-2.95 (m, 1H), 2.64-2.76 (m, 1H), 2.25-2.35 (m, 1H), 1.87-1.98 (br, 1H).

Step 3: (((1S,2R)-2-((benzyloxy)methyl)cyclopent-3-en-1-yl)oxy)triisopropylsilane To a solution of (1S,2R)-2-((benzyloxy)methyl)cyclopent-3-enol (60.0 g, 293 mmol) in DMF (600 mL) was added with TIPSCl (84.6 g, 439 mmol), imidazole (79.6 g, 1.17 mol) and DMAP (1.78 g, 14.6 mmol) in sequence. The resulting mixture was allowed to stir at 20° C. for 16 h under a nitrogen atmosphere. The reaction mixture was quenched with saturated NaHCO$_3$(500 mL), extracted with EtOAc (3×250 mL). The combined organic phases were washed with brine (2×250 mL), dried over anhydrous Na$_2$SO$_4$, filtered, and concentrated in vacuum to give a residue, which was purified by silica gel chromatography (100% PE) to give the desired product (((1S,2R)-2-((benzyloxy)methyl) cyclopent-3-en-1-yl)oxy)triisopropylsilane (70.0 g, 66%) as colorless liquid. $^1$H NMR (CDCl$_3$) δ 7.29-7.38 (m, 5H), 5.68-5.77 (m, 2H), 4.54 (s, 2H), 4.40 (dt, J=6.7, 3.3 Hz, 1H), 3.43 (ddd, J=16.8, 9.2, 6.0 Hz, 2H), 2.86-2.93 (m, 1H), 2.69 (ddq, J=16.7, 6.4, 1.9 Hz, 1H), 2.33 (dsxt, J=16.7, 1.9 Hz, 1H), 1.05-1.08 (m, 21H).

Step 4: (1R,3R,4S)-3-((benzyloxy)methyl)-4-((triisopropylsilyl)oxy)cyclopentan-1-ol, Intermediate 1

A solution of 9-BBN (0.500 M in THF, 440 mL, 220 mmol) was added dropwise at −10° C. under a nitrogen atmosphere to a solution of (((1S,2R)-2-((benzyloxy) methyl) cyclopent-3-en-1-yl)oxy)triisopropylsilane (40.0 g, 110 mmol) in THE (800 mL). The reaction mixture was allowed to warm slowly to rt and stir for 18 h. The reaction mixture was cooled to 0° C., treated with a solution of Oxone (338 g, 550 mmol) in water (3.50 L) and allowed to stir for 2 h. The aqueous phase was extracted with EtOAc (3×1.0 L) and the combined organic phases were washed with saturated NaHCO$_3$(1.0 L), dried over Na$_2$SO$_4$, filtered and concentrated in vacuo. The residue was purified by silica gel chromatography (50/1/0.1 to 10/1/0.1 PE/EtOAc/NH$_3$·H$_2$O) to afford (1R,3R,4S)-3-((benzyloxy)methyl)-4-((triisopropylsilyl)oxy)cyclopentan-1-ol (Intermediate 1) (14.6 g, 35%) as a colorless oil. $^1$H NMR (CDCl$_3$) δ 7.29-7.39 (m, 5H), 4.51-4.62 (m, 2H), 4.42 (ddd, J=6.4, 4.4 Hz, 1H), 4.33 (spt, J=3.0 Hz, 1H), 3.59 (dd, J=8.9, 4.3 Hz, 1H), 3.51 (dd, J=8.9, 4.1 Hz, 1H), 2.36 (ddd, J=13.8, 10.0, 6.0 Hz, 1H), 2.13-2.24 (m, 1H), 1.97-2.06 (m, 1H), 1.79-1.90 (m, 1H), 1.64-1.77 (m, 1H), 1.41-1.62 (m, 1H), 1.02-1.08 (m, 21H).

Step 5: (1R,3R,4S)-3-((benzyloxy)methyl)-4-((triisopropylsilyl)oxy)cyclopentyl acetate To a mixture of (1R,3R,4S)-3-((benzyloxy)methyl)-4-(triisopropylsilyl)oxy) cyclopentanol (18.0 g, 5.28 mmol), TEA (7.92 mL, 56.9 mmol) and DMAP (289 mg, 2.37 mmol) in DCM (280 mL) was added Ac$_2$O (5.37 mL, 56.9 mmol) drop-wise at 0° C. The reaction mixture was allowed to warm rt and stir for 20 h and then diluted with DCM (500 mL) and washed with 1 M HCl (50 mL). The organic phase was dried over Na$_2$SO$_4$ and concentrated. The crude compound was purified by silica gel chromatography (1-5% EtOAc in PE) to provide (1R,3R,4S)-3-((benzyloxy) methyl)-4-((triisopropylsilyl)oxy)cyclopentyl acetate (17.1 g, 86%) as a colorless oil. $^1$H NMR (CDCl$_3$) δ 7.28-7.37 (m, 5H), 5.19-5.27 (m, 1H), 4.47-4.55 (m, J=2.4 Hz, 2H), 4.29 (q, J=5.2 Hz, 1H), 3.50 (dd, J=9.3, 5.6 Hz, 1H), 3.42 (dd, J=9.2, 6.7 Hz, 1H), 2.39 (dt, J=15.9, 8.2 Hz, 1H), 2.12-2.24 (m, 1H), 2.00-2.06 (m, 1H), 1.99 (s, 3H), 1.89-1.96 (m, 1H), 1.48-1.60 (m, 1H), 1.04 (s, 21H).

Step 6: (1R,3R,4S)-3-(hydroxymethyl)-4-((triisopropylsilyl)oxy)cyclopentyl acetate A mixture of (1R,3R,4S)-3-((benzyloxy)methyl)-4-((triisopropylsilyl)oxy) cyclopentyl acetate (17.1 g, 40.6 mmol) and Pd(OH)$_2$ (10 wt % on carbon, 6.27 g, 4.06 mmol) in MeOH (400 mL) was allowed to stir at 25° C. under 40 psi of hydrogen for 18 h. The reaction mixture was filtered through Celite and the filtrate was concentrated to give (1R,3R,4S)-3-(hydroxymethyl)-4-((triisopropylsilyl)oxy) cyclopentyl acetate (13.1 g, 98%) as a colorless oil, which was used without further purification. $^1$H NMR (CDCl$_3$) δ 5.25 (dddd, J=7.2, 4.8 Hz, 1H), 4.31 (q, J=6.2 Hz, 1H), 3.64-3.75 (m, 2H), 2.39 (dt, J=14.3, 8.3 Hz, 1H), 1.98 (s, 3H), 1.94-2.16 (m, 2H), 1.71 (m, 1H), 1.63 (m, 1H), 1.42 (ddd, J=13.7, 7.8, 4.8 Hz, 1H), 1.09 (s, 21H).

Step 7: (1R,3R,4S)-3-(((tert-butyldimethylsilyl)oxy) methyl)-4-((triisopropylsilyl)oxy) cyclopentyl acetate To a solution of (1R,3R,4S)-3-(hydroxymethyl)-4-((triisopropylsilyl)oxy) cyclopentyl acetate (12.7 g, 38.4 mmol) in DCM (200 mL) was added TBSCl (7.52 g, 49.9 mmol) and imidazole (3.91 g, 57.5 mmol) in sequence. The resulting mixture was allowed to stir at 25° C. for 18 h. The reaction mixture was quenched with water (50 mL) and extracted with DCM (150 mL×3). The combined organic phases were washed with brine (100 mL), dried over anhydrous Na$_2$SO$_4$, filtered and concentrated. The residue was purified by silica gel chromatography (5% EtOAc in PE) to give (1R,3R,4S)-3-(((tert-butyldimethylsilyl)oxy)methyl)-4-((triisopropylsilyl)oxy)cyclopentyl acetate (15.6 g, 93%) as colorless oil. $^1$H NMR (CDCl$_3$) δ 5.14-5.22 (m, 1H), 4.25 (q, J=5.2 Hz, 1H), 3.49-3.58 (m, 2H), 2.27 (dt, J=14.2, 8.3 Hz, 1H), 1.97-2.01 (m. 1H), 1.99 (s, 3H), 1.78-1.91 (m, 1H), 1.39-1.53 (m, 1H), 1.34-1.48 (m, 1H), 1.01 (s, 21H), 0.86 (s, 9H), 0.00 (s, 6H).

Step 8: (1R,3R,4S)-3-(((tert-butyldimethylsilyl)oxy) methyl)-4-((triisopropylsilyl)oxy) cyclopentanol, Intermediate 2

To a solution of (1R,3R,4S)-3-(((tert-butyldimethylsilyl)oxy)methyl)-4-((triisopropylsilyl)oxy)cyclopentyl acetate (16.0 g, 35.9 mmol), was added K$_2$CO$_3$ (9.92 g, 71.8 mmol) in MeOH (200 mL) and the reaction mixture was allowed to stir at 25° C. for 16 h. The mixture was concentrated and water was added (200 mL), and then extracted with DCM (3×200 mL). The combined organic phases were dried over Na$_2$SO$_4$, filtered and concentrated. The residue was purified by silica gel chromatography (2.5-5% EtOAc in PE) to provide (1R,3R,4S)-3-(((tert-butyldimethylsilyl)oxy) methyl)-4-((triisopropylsilyl)oxy)cyclopentanol (Intermediate 2) (10.9 g, 67%) as colorless oil. $^1$H NMR (CDCl$_3$) δ 4.31-4.37 (m, 1H), 4.17 (spt, J=3.0 Hz, 1H), 3.68 (dd, J=9.8, 3.8 Hz, 1H), 3.53 (dd, J=9.8, 3.8 Hz, 1H), 2.16-2.27 (m, 1H), 1.99-2.07 (m, 1H), 1.89-1.98 (m, 1H), 1.65-1.75 (m, 1H), 1.37 (dquin, J=13.8, 2.0 Hz, 1H), 0.97 (s, 21H), 0.82 (s, 9H), 0.00 (s, 6H).

Example 2

[(1S,2R,4R)-2-(hydroxymethyl)-4-pyrimidin-4-yloxy-cyclopentoxy]phosphinic acid, Intermediate 6

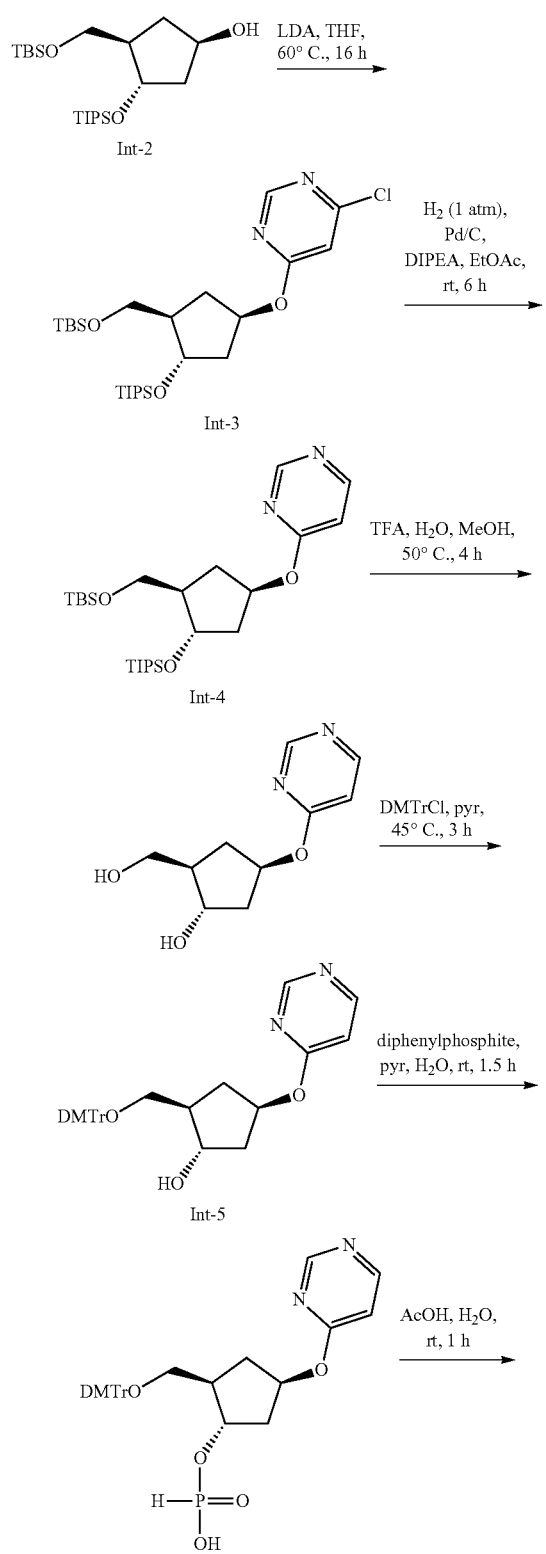

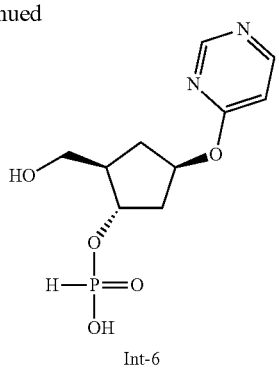

Int-6

Step 1: tert-butyl-[[(1R,2S,4R)-4-(6-chloropyrimidin-4-yl)oxy-2-triisopropylsilyloxy-cyclopentyl]methoxy]-dimethyl-silane, Intermediate 3

Intermediate 2 (3.55 g, 8.81 mmol) was dissolved in THF (80.0 mL, 983 mmol), then LDA (1.00 M in THF/hexanes, 12.3 mL, 12.3 mmol) was added to the solution with stirring. 4,6-Dichloropyrimidine (1.51 g, 10.1 mmol) was added under an atmosphere of argon. The reaction mixture was allowed to stir for 1 h, and then heated at 60° C. overnight. The solution was poured into saturated, aqueous $NH_4C_1$ (40 mL). This mixture was extracted with EtOAc (3×50 mL). The combined organic phases were concentrated. The residue was purified by silica gel chromatography (0-25% EtOAc in hexanes) to provide tert-butyl-[[(1R,2S,4R)-4-(6-chloropyrimidin-4-yl)oxy-2-triisopropylsilyloxy-cyclopentyl]methoxy]-dimethyl-silane (3.25 g, 72%) as a colorless sticky solid. $^1$H NMR (CDCl$_3$) δ 8.53 (s, 1H), 6.66 (s, 1H), 5.44-5.58 (m, 1H), 4.33 (q, J=5.1 Hz, 1H), 3.46-3.63 (m, 2H), 2.40 (dt, J=14.9, 7.9 Hz, 1H), 2.04-2.17 (m, 2H), 1.94-2.02 (m, 1H), 1.53 (dt, J=12.2, 5.5 Hz, 1H), 1.03 (s, 21H), 0.85 (s, 9H), −0.03-0.04 (m, 6H).

Step 2: tert-butyl-dimethyl-[[(1R,2S,4R)-4-pyrimidin-4-yloxy-2-triisopropylsilyloxy-cyclopentyl]methoxy]silane, Intermediate 4

Intermediate 3 (3.25 g, 6.31 mmol) was dissolved in DIPEA (2.25 mL, 12.6 mmol) and ethyl acetate (40.0 mL). Palladium (10 wt % on carbon, 335 mg, 0.316 mmol) was added to the reaction mixture. A balloon of hydrogen was attached and the reaction mixture was allowed to stir at rt for 6 h. The reaction mixture was filtered and the solid was washed with methanol. The filtrate was concentrated. The residue was dissolved in EtOAc (60 mL), and washed with water (2×10 mL). The organic phase was concentrated to give tert-butyl-dimethyl-[[(1R,2S,4R)-4-pyrimidin-4-yloxy-2-triisopropylsilyloxy-cyclopentyl]methoxy]silane (Intermediate 4) (2.93 g, 96%) that was used without further purification. $^1$H NMR (CDCl$_3$) δ 8.73 (s, 1H), 8.36 (d, J=5.8 Hz, 1H), 6.63 (d, J=5.9 Hz, 1H), 5.49-5.56 (m, 1H), 4.34 (q, J=5.0 Hz, 1H), 3.58 (d, J=5.8 Hz, 2H), 2.42 (dt, J=14.3, 8.0

Hz, 1H), 2.04-2.18 (m, 2H), 2.00 (dt, J=13.4, 5.5 Hz, 1H), 1.49-1.59 (m, 1H), 1.04 (s, 21H), 0.85 (s, 9H), −0.03-0.03 (m, 6H).

Step 3: (1S,2R,4R)-2-(hydroxymethyl)-4-pyrimidin-4-yloxy-cyclopentanol

Intermediate 4 (2.92 g, 6.07 mmol) was dissolved in a mixture of water (10.0 mL) and methanol (10.0 mL). TFA (20.0 mL, 261 mmol) was added slowly to the solution with stirring at rt. The reaction mixture was heated at 50° C. for 4 h. The reaction mixture was concentrated and the residue was purified by reverse phase flash column chromatography (0-100% ACN in water with 0.1% formic acid) to provide (1S,2R,4R)-2-(hydroxymethyl)-4-pyrimidin-4-yloxy-cyclopentanol (1.00 g, 78%) as a sticky oil. LCMS (FA): m/z=211.1 (M+H).

Step 4: (1S,2R,4R)-2-[[bis(4-methoxyphenyl)-phenyl-methoxy]methyl]-4-pyrimidin-4-yloxy-cyclopentanol, Intermediate 5

(1S,2R,4R)-2-(hydroxymethyl)-4-pyrimidin-4-yloxy-cyclopentanol (779 mg, 3.71 mmol) was dissolved in pyridine (20.6 mL, 254 mmol), then DMTrCl (1.40 g, 4.08 mmol) was added and the reaction mixture was allowed to stir at 45° C. for 1 h. Additional DMTrCl (634 mg, 1.85 mmol) was added and the mixture was heated for 3 h. MeOH (5 mL) was added and the mixture was allowed to stir for 10 min. The mixture was poured into water (30 mL), and extracted with EtOAc (2×30 mL). The combined organic phases were concentrated. The residue was purified by silica gel chromatography (20-100% EtOAc in hexanes) to provide (1S,2R,4R)-2-[[bis(4-methoxyphenyl)-phenyl-methoxy]methyl]-4-pyrimidin-4-yloxy-cyclopentanol (Intermediate 5) (1.37 g, 72%) as a yellow solid. LCMS (FA): m/z=531.3 (M+H).

Step 5: [(1S,2R,4R)-2-(hydroxymethyl)-4-pyrimidin-4-yloxy-cyclopentoxy]phosphinic acid To a solution of Intermediate 5 (1.70 g, 3.31 mmol) in pyridine (20.0 mL, 247 mmol) was added diphenyl phosphite (1.27 mL, 6.62 mmol). The reaction mixture was allowed to stir at rt under argon for 1.5 h. Water (40.0 mL, 2.22 mol) was then added. The clear solution quickly turned milky and was allowed to stir at rt for 1 h, resulting in a clear solution. The reaction mixture was diluted with EtOAc and brine, then extracted with EtOAc. The combined organic phases were washed with water, brine, dried using $Na_2SO_4$, filtered and concentrated to dryness. The residue was concentrated from toluene to give [(1S,2R,4R)-2-[[bis(4-methoxyphenyl)-phenyl-methoxy]methyl]-4-pyrimidin-4-yloxy-cyclopentoxy]phosphinic acid (1.91 g, 100%), which was used without further purification.

Step 6: [(1S,2R,4R)-2-(hydroxymethyl)-4-pyrimidin-4-yloxy-cyclopentoxy]phosphinic acid, Intermediate 6

To [(1S,2R,4R)-2-[[bis(4-methoxyphenyl)-phenyl-methoxy]methyl]-4-pyrimidin-4-yloxy-cyclopentoxy]phosphinic acid (1.91 g, 3.31 mmol) was added water (2.0 mL, 110 mmol) and acetic acid (7.6 mL, 130 mmol). The mixture was sonicated and the resulting bright orange reaction mixture was allowed to stir at rt for 1 h. The reaction mixture was then concentrated from toluene. The crude material was purified by silica gel chromatography (0-100% MeOH in DCM) to give [(1S,2R,4R)-2-(hydroxymethyl)-4-pyrimidin-4-yloxy-cyclopentoxy]phosphinic acid (Intermediate 6) (908 mg, 76%). LCMS (FA): m/z=275.0 (M+H), $^1$H NMR (MeOD) δ 8.84 (s, 1H), 8.49 (dd, J=6.2, 0.7 Hz, 1H), 7.62 (s, 0.5H) 6.98 (dd, J=6.2, 1.0 Hz, 1H,) 5.99 (s, 0.5H), 5.65 (ddd, J=6.7, 4.8, 2.0 Hz, 1H), 4.72 (dd, J=9.4, 6.2 Hz, 1H), 3.58-3.69 (m, 2H), 2.44-2.59 (m, 1H), 2.23-2.37 (m, 3H.) 1.63-1.76 (m, 1H). $^{31}$P NMR (MeOD) δ 4.37 (s, 1P).

Example 3

The compound listed below (Intermediate 7) was prepared as described in Example 2 starting with Step 3, substituting the starting material shown in the table (Intermediate 9 which was prepared as described in Example 5) for Intermediate 4.

| Starting material | Intermediate | LCMS data |
| --- | --- | --- |
| Int-9 | Int-7 | LCMS (FA): m/z = 274.1 (M + H) |

Example 4

Alternate preparation of tert-butyl-dimethyl-[[(1R,2S,4R)-4-pyrimidin-4-yloxy-2-triisopropylsilyloxy-cyclopentyl]methoxy]silane, Intermediate 4

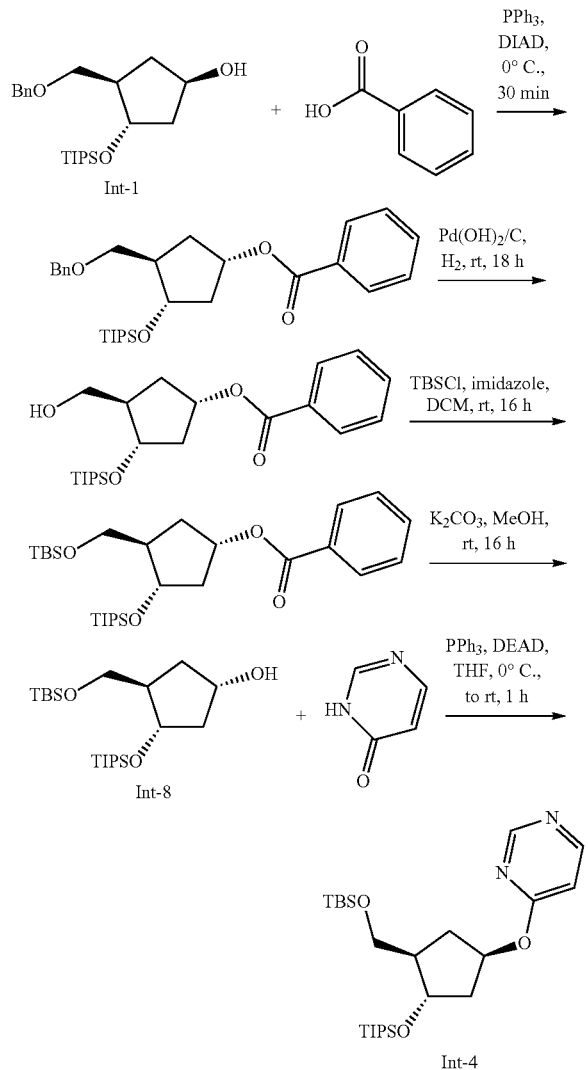

Step 1: (1S,3R,4S)-3-[(benzyloxy)methyl]-4-[(triisopropylsilyl)oxy]cyclopentyl benzoate To a mixture of Intermediate 1 (25.0 g, 66.0 mmol), benzoic acid (9.70 g, 79.2 mmol) and $PPh_3$ (20.7 g, 79.2 mmol) in THF (250 mL) was added DIAD (16.0 g, 79.2 mmol) drop-wise at 0° C. under an atmosphere of nitrogen. The reaction mixture was allowed to stir at 0° C. for 30 min. The solvent was removed under reduced pressure. The residue was diluted with EtOAc (350 mL), and washed with brine (2×150 mL). The organic phase was dried over anhydrous $Na_2SO_4$, filtered and concentrated in vacuum to give a residue. The crude compound was purified by silica gel chromatography (1-10% EtOAc in PE) to give (1S,3R,4S)-3-[(benzyloxy)methyl]-4-[(triisopropylsilyl)oxy]cyclopentyl benzoate (28 g, 88%) as a light yellow oil. $^1H$ NMR (CDCl$_3$) δ 8.05 (d, J=7.2 Hz, 2H), 7.53 (t, J=7.6 Hz, 1H), 7.40 (t, J=7.6 Hz, 2H), 7.35-7.20 (m, 5H), 5.34 (sept, J=3.6 Hz, 1H), 4.51 (d, J=2.0 Hz, 2H), 4.22 (q, J=6.4 Hz, 1H), 3.50 (ddd, J=5.2, 9.6, 26.4 Hz, 2H), 2.42 (m, 2H), 2.15 (m, 1H), 1.95 (m, 2H), 1.00 (m, 21H).

Step 2: (1S,3R,4S)-3-(hydroxymethyl)-4-[(triisopropylsilyl)oxy]cyclopentyl benzoate To a solution of (1S,3R,4S)-3-[(benzyloxy)methyl]-4-[(triisopropylsilyl)oxy]cyclopentyl benzoate (28.0 g, 58.0 mmol) in MeOH (560 mL) was added Pd(OH)$_2$/C (20% w/w, 4.10 g, 5.80 mmol). The resulting mixture was allowed to stir at rt under 40 psi of hydrogen for 18 h. The reaction mixture was filtered through Celite and washed with MeOH (3×150 mL). The filtrate was concentrated in vacuum to give the desired product (1S,3R,4S)-3-(hydroxymethyl)-4-[(triisopropylsilyl)oxy]cyclopentyl benzoate (22.0 g, 97%) as a colorless oil, which was taken on directly without further purification.

Step 3: (1S,3R,4S)-3-({[tert-butyl(dimethyl)silyl]oxy}methyl)-4-[(triisopropylsilyl) oxy]cyclopentyl benzoate To a solution of (1S,3R,4S)-3-(hydroxymethyl)-4-[(triisopropylsilyl)oxy]cyclopentyl benzoate (44.0 g, 112 mmol) in DCM (600 mL) was added TBSCl (21.8 g, 145 mmol) and imidazole (11.4 g, 168 mmol). The reaction mixture was allowed to stir at rt for 4 h. The reaction mixture was quenched with water (500 mL) and extracted with DCM (2×600 mL). The combined organic phases were washed with brine (800 mL), dried over anhydrous $Na_2SO_4$, filtered and concentrated in vacuum. The residue was purified by silica gel chromatography (1-30% EtOAc in PE) to give (1S,3R,4S)-3-({[tert-butyl(dimethyl)silyl]oxy}methyl)-4-[(triisopropylsilyl)oxy]cyclopentyl benzoate (50 g, 88%) as a colorless oil. $^1H$ NMR (CDCl$_3$) δ 8.00-7.94 (m, 2H), 7.48-7.42 (m, 1H), 7.36-7.31 (m, 2H), 5.26 (tt, J=7.0, 3.7 Hz, 1H), 4.23-4.14 (m, 1H), 3.62-3.46 (m, 2H), 2.35 (dt, J=13.9, 6.8 Hz, 1H), 2.21 (tt, J=9.8, 4.9 Hz, 1H), 2.04-1.93 (m, 1H), 1.91-1.76 (m, 2H), 0.97 (d, J=1.9 Hz, 21H), 0.81 (s, 9H), −0.04 (d, J=1.0 Hz, 6H).

Step 4: (1S,3R,4S)-3-({[tert-butyl(dimethyl)silyl]oxy}methyl)-4-[(triisopropylsilyl) oxy]cyclopentanol, Intermediate 8

To a solution of (1S,3R,4S)-3-({[tert-butyl(dimethyl)silyl]oxy}methyl)-4-[(triisopropylsilyl)oxy]cyclopentyl benzoate (50.0 g, 98.6 mmol) in MeOH (650 mL) was added $K_2CO_3$ (20.3 g, 147 mmol). The reaction mixture was allowed to stir at 20° C. for 16 h. The reaction mixture was quenched with water (600 mL). The mixture was extracted with DCM (3×600 mL) and the combined organic phases were dried over $Na_2SO_4$, filtered and concentrated. The residue was purified by silica gel chromatography (1-5% EtOAc in PE) to provide (1S,3R,4S)-3-({[tert-butyl(dimethyl)silyl]oxy}methyl)-4-[(triisopropylsilyl)oxy]cyclopentanol (Intermediate 8) (25.2 g, 63%) as a light yellow oil. LCMS (FA): m/z=403.5 (M+H).

Step 5: tert-butyl-dimethyl-[[(1R,2S,4R)-4-pyrimidin-4-yloxy-2-triisopropylsilyloxy-cyclopentyl]methoxy]silane, Intermediate 4

Intermediate 8 (5.00 g, 12.4 mmol), $PPh_3$ (3.74 g, 14.3 mmol) and 4(3H)-pyrimidone (1.46 g, 14.9 mmol) were dissolved in THF (100 mL) under an atmosphere of argon. The solution was cooled to 0° C. DEAD (2.15 mL, 13.7 mmol) was added and the reaction mixture was allowed to stir at rt for 1 h. The reaction mixture was concentrated to dryness and adsorbed onto Celite. The crude compound was purified by silica gel chromatography (0-15% EtOAc in hexanes) to provide tert-butyl-dimethyl-[[(1R,2S,4R)-4-pyrimidin-4-yloxy-2-triisopropylsilyloxy-cyclopentyl]methoxy]silane (Intermediate 4) (5.18 g, 83%). LCMS (FA): m/z=481.3 (M+H), $^1$H NMR (DMSO-$d_6$) δ 8.75 (s, 1H,) 8.48 (d, J=5.8 Hz, 1H,) 6.85 (d, J=5.9 Hz, 1H), 5.46 (m, 1H), 4.34 (m, 1H), 3.58 (m, 2H), 2.31-2.44 (m, 1H), 1.94-2.11 (m, 3H,) 1.44-1.53 (m, 1H), 1.04 (s, 21H) 0.84 (s, 9H,) 0.00 (d, J=3.1 Hz, 6H).

Example 5

The compound listed below (Intermediate 9) was prepared as described in Example 4 starting with Step 5, substituting the starting material shown in the table for 4(3H)-pyrimidone.

| Starting material | Intermediate | LCMS data |
|---|---|---|
| HN, O (structure) | Int-9 (structure) | LCMS (FA): m/z = 480.4 (M + H) |

Example 6

Alternate preparation of [(1S,2R,4R)-2-(hydroxymethyl)-4-pyrimidin-4-yloxy-cyclopentoxy]phosphinic acid, Intermediate 6

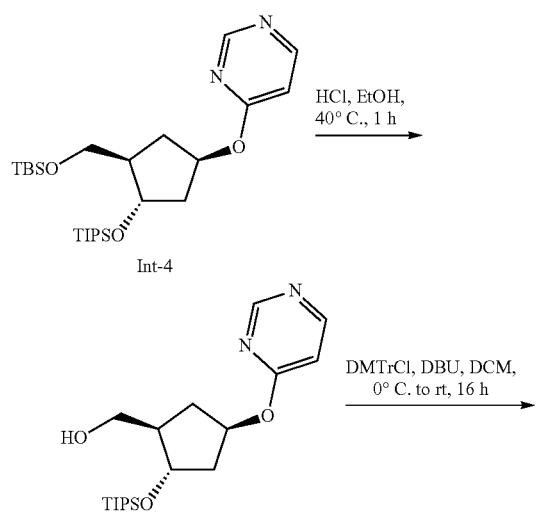

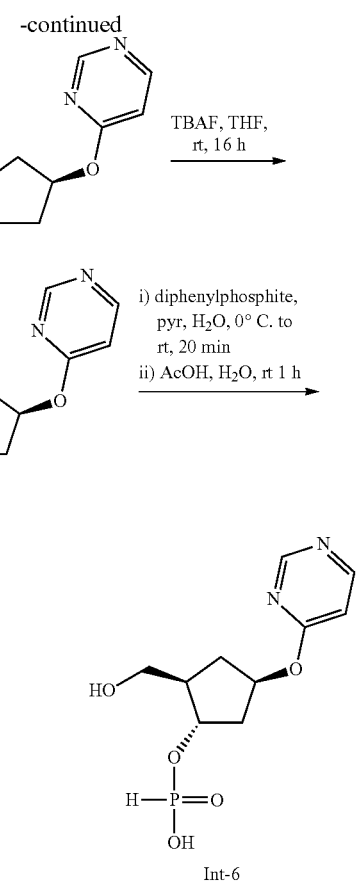

Step 1: {(1R,2S,4R)-4-(pyrimidin-4-yloxy)-2-[(triisopropylsilyl)oxy]cyclopentyl}methanol Intermediate 4 (5.98 g, 12.4 mmol) was taken up in EtOH (50.0 mL). A solution of HCl (12.0 mol/L, 2.07 mL, 24.9 mmol) in EtOH (50.0 mL) was added. The reaction mixture was allowed to stir at 40° C. for 1 h. The reaction mixture was diluted with saturated aqueous sodium bicarbonate and concentrated to remove the EtOH. The aqueous residue was extracted with EtOAc and the combined organic phases were washed with water and brine, dried with $Na_2SO_4$ and concentrated. The crude compound was purified by silica gel chromatography (0-60% EtOAc in hexanes) to provide {(1R,2S,4R)-4-(pyrimidin-4-yloxy)-2-[(triisopropylsilyl)oxy]cyclopentyl}methanol (3.03 g, 66%). LCMS (FA): m/z=367.2 (M+H).

Step 2: 4-({(1R,3R,4S)-3-{[bis(4-methoxyphenyl)(phenyl)methoxy]methyl}-4-[(triisopropylsilyl)oxy]cyclopentyl}oxy)pyrimidine To a solution of {(1R,2S,4R)-4-(pyrimidin-4-yloxy)-2-[(triisopropylsilyl)oxy]cyclopentyl}methanol (3.03 g, 8.26 mmol) in DCM (100 mL) was added DBU (3.70 mL, 24.8 mmol). The reaction mixture was cooled to 0° C. and DMTrCl (5.60 g, 16.5 mmol) was added. The reaction mixture was then warmed to rt and allowed to stir overnight. Water was added and the mixture was extracted with DCM. The combined organic phases were washed with water and brine, dried with $Na_2SO_4$ and concentrated. The crude compound was purified by silica gel chromatography (0-50%

EtOAc in hexanes) to provide 4-({(1R,3R,4S)-3-{[bis(4-methoxyphenyl)(phenyl)methoxy]methyl}-4-[(triisopropylsilyl)oxy]cyclopentyl}oxy)pyrimidine (5.30 g, 96%). LCMS (FA): m/z=669.4 (M+H).

Step 3: (1S,2R,4R)-2-{[bis(4-methoxyphenyl)(phenyl)methoxy]methyl}-4-(pyrimidin-4-yloxy)cyclopentanol Intermediate 5

To a solution of 4-({(1R,3R,4S)-3-{[bis(4-methoxyphenyl)(phenyl)methoxy]methyl}-4-[(triisopropylsilyl)oxy]cyclopentyl}oxy)pyrimidine (5.30 g, 7.90 mmol) in THF (25 mL) was added TBAF (1.00 mol/L, 9.50 mL, 9.50 mmol) at rt, The reaction mixture was allowed to stir at rt overnight. Brine was added and the mixture was extracted with EtOAc. The combined organic phases were dried with $Na_2SO_4$ and concentrated. The crude compound was purified by silica gel chromatography (0-70% EtOAc in hexanes) to provide (1S,2R,4R)-2-{[bis(4-methoxyphenyl)(phenyl)methoxy]methyl}-4-(pyrimidin-4-yloxy)cyclopentanol (2.80 g, 69%). LCMS (FA): m/z=513.3 (M+H).

Step 4 [(1S,2R,4R)-2-(hydroxymethyl)-4-pyrimidin-4-yloxy-cyclopentoxy]phosphinic acid, Intermediate 6

Intermediate 5 (1.44 g, 2.81 mmol) was dissolved in pyridine (12.0 mL). The solution was cooled to 0° C. and diphenyl phosphite (1.08 mL, 5.62 mmol) was slowly added over 1 min. The reaction mixture was warmed to rt and allowed to stir for 20 min. The reaction mixture was cooled back to 0° C. and water (2.77 mL, 154 mmol) was added. The reaction mixture was warmed to rt and allowed to stir for 30 min. The reaction mixture was concentrated and concentrated from toluene (2×50 mL). The residue was taken up in acetic acid (6.45 mL, 112 mmol) and water (1.70 mL) and the reaction mixture was allowed to stir at rt for 1 h. The reaction mixture was concentrated. The crude compound was purified by silica gel chromatography (0-100% MeOH in DCM) to provide [(1S,2R,4R)-2-(hydroxymethyl)-4-pyrimidin-4-yloxy-cyclopentoxy]phosphinic acid (Intermediate 6) (600 mg, 78%). LCMS (FA): m/z=275.2 (M+H), $^1$H NMR (400 MHz, MeOD) δ 8.84 (s, H), 8.49 (dd, J=6.24, 0.7 Hz, 1H), 7.62 (s, 0.5H), 6.98 (dd, J=6.2, 1.0 Hz, 1H), 5.99 (s, 0.5H), 5.65 (ddd, J=6.7, 4.8, 2.0 Hz, 1H,) 4.72 (dd, J=9.4, 6.2 Hz, 1H), 3.58-3.69 (m, 2H), 2.44-2.59 (m, 1H), 2.23-2.37 (m, 3H), 1.63-1.76 (m, 1H). $^{31}$P NMR (MeOD) δ 4.37 (s, 1P).

Example 6A

Alternate preparation of [(1S,2R,4R)-2-(hydroxymethyl)-4-pyrimidin-4-yloxy-cyclopentoxy]phosphinic acid; N,N-diethylethanamine, Intermediate 6

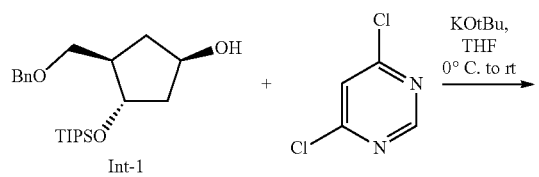

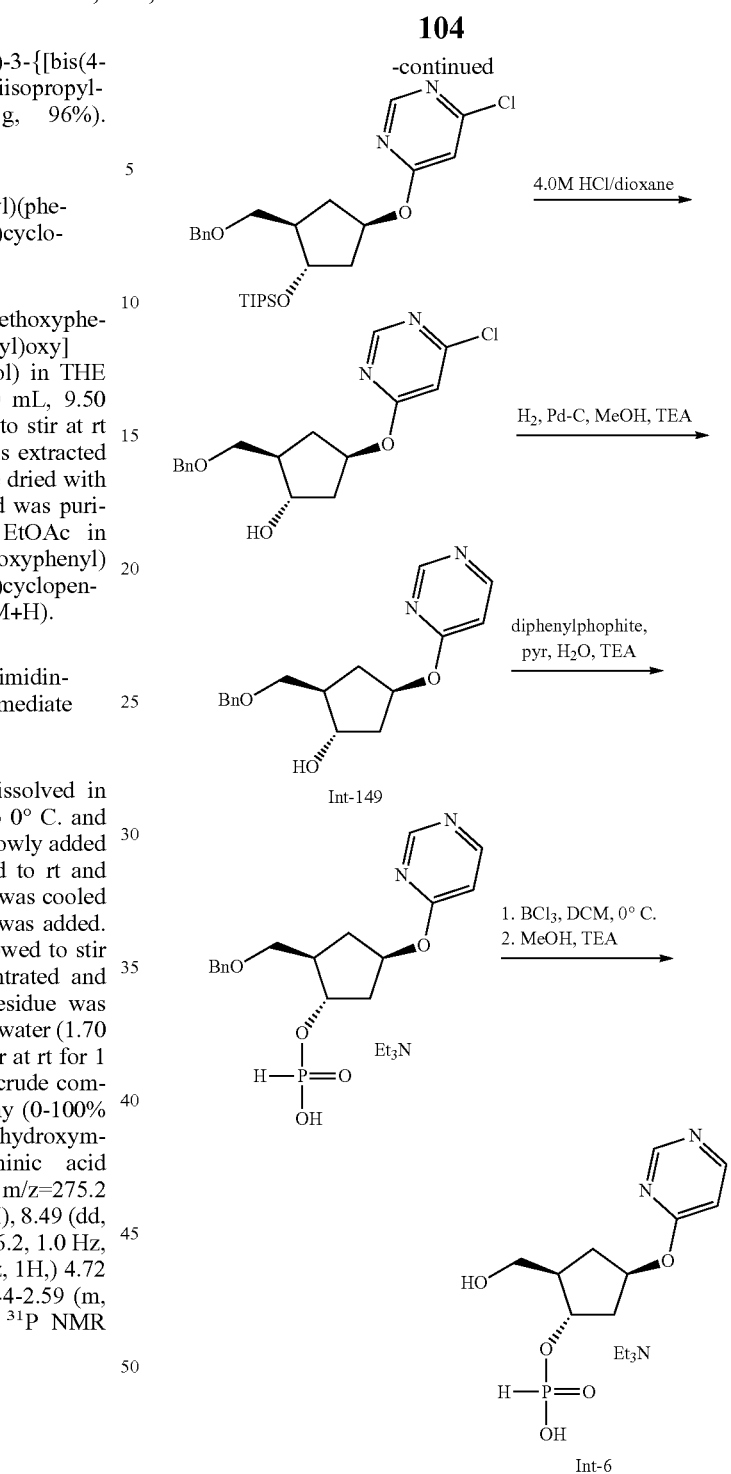

Step 1: 4-(((1R,3R,4S)-3-((benzyloxy)methyl)-4-((triisopropylsilyl)oxy)cyclopentyl)oxy)-6-chloropyrimidine Intermediate 1 (4.00 g, 10.6 mmol) was dissolved in THF (80.0 mL) and the reaction mixture was cooled to 0° C. Potassium tert-butoxide (2.25 g, 19.0 mmol) was added and the reaction mixture was allowed to stir at 0° C. for 10 min. 4,6-Dichloropyrimidine (2.52 g, 16.9 mmol) was added to the solution and the reaction mixture was allowed to stir at 0° C. for 10 min, then allowed to warm to rt and stirred for 2 h. The reaction mixture was quenched with HCl (0.2M, 80 mL) and extracted with EtOAc (2×100 mL). The combined organic phases were washed with brine, dried over MgSO₄, filtered, and concentrated to give crude 4-(((1R,3R,4S)-3-((benzyloxy)methyl)-4-((triisopropylsilyl)oxy)cyclopentyl)oxy)-6-chloropyrimidine as a yellow oil which was used without further purification in the next step.

Step 2: (1S,2R,4R)-2-((benzyloxy)methyl)-4-((6-chloropyrimidin-4-yl)oxy)cyclopentan-1-ol To crude 4-(((1R,3R,4S)-3-((benzyloxy)methyl)-4-((triisopropylsilyl)oxy)cyclopentyl)oxy)-6-chloropyrimidine was added a solution of HCl (4.0M in dioxane, 30.0 mL, 120 mmol). The reaction mixture was allowed to stir at rt for 2 h. The solvents were completely evaporated and the residue was purified by silica gel chromatography (20 to 83.3% EtOAc:hexanes) to provide the title compound as a colorless oil (2.32 g, 66%). LCMS (FA): m/z=335.1 (M+H).

Step 3: (1S,2R,4R)-2-((benzyloxy)methyl)-4-(pyrimidin-4-yloxy)cyclopentan-1-ol, Intermediate 149

(1S,2R,4R)-2-((benzyloxy)methyl)-4-((6-chloropyrimidin-4-yl)oxy)cyclopentan-1-ol (1.21 g, 3.62 mmol,) and TEA (1.47 g, 14.5 mmol) were dissolved in MeOH (40.0 mL). Palladium (10% on carbon, 192 mg amount?) was added and the mixture was stirred under an atmosphere of H₂ at rt for 3 h. The reaction mixture was filtered and washed with methanol. The filtrate was concentrated, dissolved in EtOAc and washed with water (2×10 mL). The organic phase was dried and concentrated to provide the title compound (1.04 g, 96%). LCMS (AA): m/z=301.2 (M+H).

Step 4: [(1S,2R,4R)-2-(benzyloxymethyl)-4-pyrimidin-4-yloxy-cyclopentoxy]phosphinic acid;N,N-diethylethanamine (1S,2R,4R)-2-((benzyloxy)methyl)-4-(pyrimidin-4-yloxy)cyclopentan-1-ol (1.03 g, 3.42 mmol) was dissolved in pyridine (15.0 mL), and diphenyl phosphite (1.31 mL, 6.85 mmol) was added. The reaction mixture was allowed to stir at rt for 30 min. Water (5.00 mL) was added and the reaction mixture was allowed to stir at rt for 30 min. The solvents were evaporated and the residue was dissolved a mixture of methanol (20 mL) and TEA (5 mL). The solvents were evaporated and the residue was dried under vacuum. The residue was purified by silica gel chromatography (O % to 60% MeOH/DCM) to provide [(1 S,2R,4R)-2-(benzyloxymethyl)-4-pyrimidin-4-yloxy-cyclopentoxy]phosphinic acid;N,N-diethylethanamine (1.63 g, 84%). LCMS (FA): m/z=165.2 (M+H).

Step 5: [(1S,2R,4R)-2-(hydroxymethyl)-4-pyrimidin-4-yloxy-cyclopentoxy]phosphinic acid;N,N-diethylethanamine, Intermediate 6

[(1S,2R,4R)-2-(benzyloxymethyl)-4-pyrimidin-4-yloxy-cyclopentoxy]phosphinic acid;N,N-diethylethanamine (1.50 g, 3.22 mmol) was dissolved in DCM (20 mL) and the mixture was cooled to 0° C. Boron trichloride (1.0 M in DCM, 12.9 mL, 12.9 mmol) was added dropwise via a syringe pump at 0° C. The mixture was allowed to stir at 0° C. for 30 min, and then quenched with MeOH (10 mL) at 0° C. The solvents were evaporated and the residue was concentrated from toluene. MeOH (15 mL) and TEA (5 mL) were added to the residue and after stirring for 5 min, the solvents were completely evaporated. The residue was purified by silica gel chromatography (10 to 50% MeOH/DCM) to provide Intermediate 6 as the N,N-diethylethanamine salt. (699 mg, 58%). ¹H NMR (MeOD) δ 8.72 (s, 1H), 8.42 (d, J=6.0 Hz, 1H), 7.56 (s, 0.5H), 6.86 (dd, J=6.0, 1.0 Hz, 1H), 6.01 (s, 0.5H), 5.54-5.62 (m, 1H), 4.49-4.68 (m, 1H), 3.63-3.72 (m, 1H), 3.55-3.63 (m, 1H), 3.20 (d, J=7.4 Hz, 6H), 2.42-2.58 (m, 1H), 2.16-2.33 (m, 3H), 1.59-1.74 (m, 1H), 1.31 (t, J=7.34 Hz, 9H). ³¹P NMR (MeOD) δ 3.52 (s, 1 P).

Example 6B

Alternate Synthesis of [(1S,2R,4R)-2-(hydroxymethyl)-4-pyrimidin-4-yloxy-cyclopentoxy]phosphinic acid;ammoniate, Intermediate 6

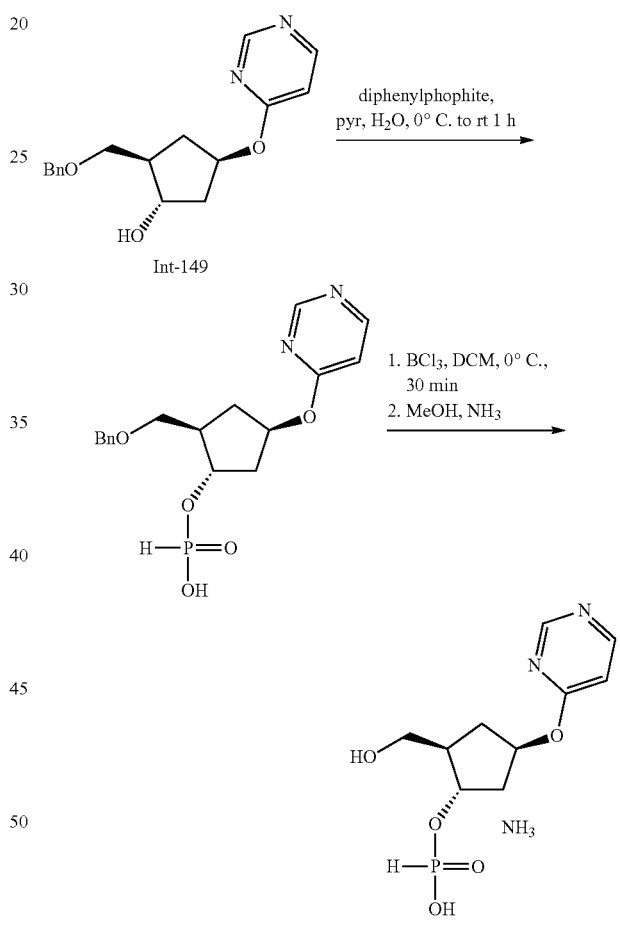

Step 1: [(1S,2R,4R)-2-(benzyloxymethyl)-4-pyrimidin-4-yloxy-cyclopentoxy]phosphinic acid (1S,2R,4R)-2-((benzyloxy)methyl)-4-(pyrimidin-4-yloxy)cyclopentan-1-ol, (Intermediate 149) (5.14 g, 17.1 mmol) was dissolved in dry acetonitrile and concentrated to dryness (3×~50 mL). Pyridine (70.0 mL) was added and the reaction mixture was cooled to 0° C. under an atmosphere of nitrogen. Diphenyl phosphite (4.91 mL, 25.7 mmol) was added dropwise and the reaction mixture was allowed to warm to rt and allowed to stir for 40 min. Water (8.0 mL) was added and the reaction mixture was allowed to stir at rt for 1 h. The solvents were evaporated and the residue was concentrated from toluene (2×~10 mL). The residue was purified by silica gel chromatography (0 to 60% MeOH/DCM) to provide [(1S,2R,4R)-2-(benzyloxymethyl)-4-pyrimidin-4-yloxy-cyclopentoxy]phosphinic acid (5.26 g, 71%). LCMS (FA): m/z=365.2 (M+H).

Step 2: [(1S,2R,4R)-2-(hydroxymethyl)-4-pyrimidin-4-yloxy-cyclopentoxy]phosphinic acid;ammoniate, Intermediate 6

A solution of [(1S,2R,4R)-2-(benzyloxymethyl)-4-pyrimidin-4-yloxy-cyclopentoxy]phosphinic acid (5.21 g, 13.0 mmol) in DCM (80.0 mL) was cooled to 0° C. Boron trichloride (1.0 M in DCM, 52.0 mL, 52.0 mmol) was added slowly and reaction was allowed to stir at 0° C. for 30 min. Ethanol (18.9 mL 325 mmol) was added and the reaction mixture was allowed to stir at 0° C. for 5 min, The solvents were evaporated and the residue was dissolved in methanol (10 mL). Ammonia (7.0 M in methanol, 22.0 mL, 156 mmol) was added and the solvents were evaporated. The residue was purified by silica gel chromatography (0 to 75% MeOH/DCM) followed by further purification by silica gel chromatography (0 to 100% EtOAc/DCM) to provide [(1S,2R,4R)-2-(hydroxymethyl)-4-pyrimidin-4-yloxy-cyclopentoxy]phosphinic acid;ammoniate, Intermediate 6 ammonium salt (2.60 g, 62%). $^1$H NMR (DMSO-$d_6$) δ 8.75 (s, 1H), 8.48 (d, J=5.9 Hz, 1H), 7.32 (br s, 4.5H), 6.89 (dd, J=1.1, 5.9 Hz, 1H), 5.87 (s, 0.5H), 5.44-5.36 (m, 1H), 4.38 (qd, J=6.8, 10.5 Hz, 1H), 4.12 (br s, 1H), 3.44-3.36 (m, 2H), 2.32 (ddd, J=7.2, 8.4, 13.8 Hz, 1H), 2.10-1.95 (m, 3H), 1.38 (ddd, J=5.1, 8.7, 13.8 Hz, 1H).

Example 7

N-(6-{[(1R,3S,4R)-3-hydroxy-4-(hydroxymethyl)cyclopentyl]amino}pyrimidin-4-yl) benzamide, Intermediate 12

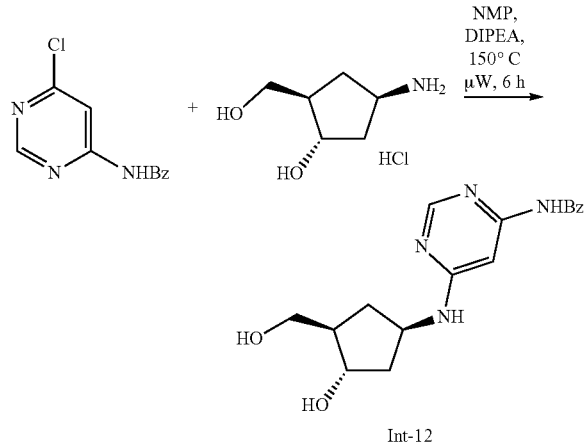

N-(6-chloro-4-pyrimidinyl)-benzamide (2.10 g, 9.01 mmol) was dissolved in NMP (10 mL). DIPEA (6.75 mL, 38.7 mmol) was added, followed by (1S,2R,4R)-4-amino-2-(hydroxymethyl)cyclopentanolhydrochloride (1.30 g, 7.76 mmol). The reaction mixture was heated under microwave irradiation at 150° C. for 6 h. The reaction mixture was diluted with EtOAc and concentrated to give N-(6-{[(1R,3S,4R)-3-hydroxy-4-(hydroxymethyl) cyclopentyl] amino}pyrimidin-4-yl)benzamide (Intermediate 12, 2.50 g, 98%) which was used without further purification.

Example 8

(1R,2S,3R,5R)-5-{[bis(4-methoxyphenyl)(phenyl)methoxy]methyl}-2-{[tert-butyl (dimethyl)silyl]oxy}-3-(pyrimidin-4-ylamino)cyclopentanol, Intermediate 14

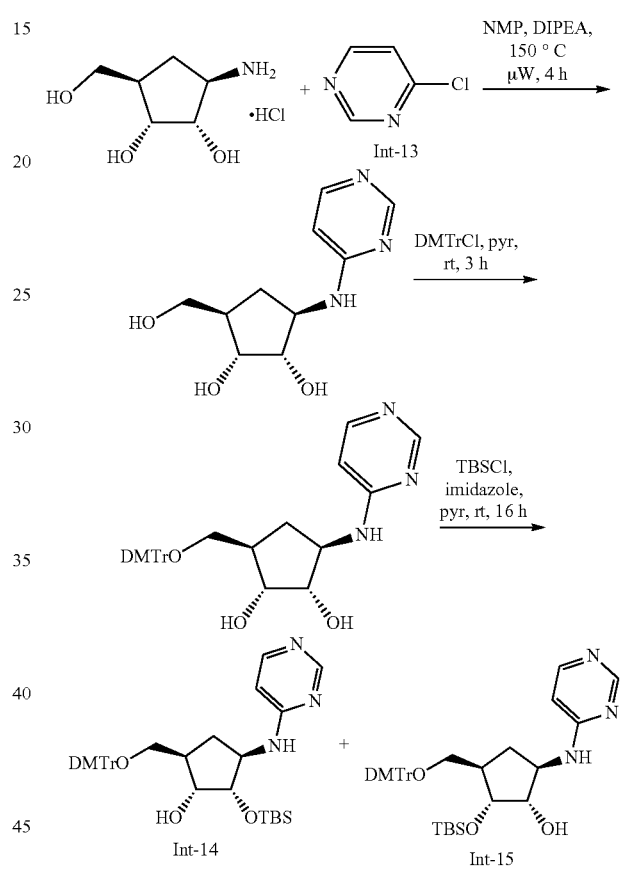

Step 1: (1S,2R,3R,5R)-3-(hydroxymethyl)-5-(pyrimidin-4-ylamino)cyclopentane-1,2-diol 4-Chloropyrimidine (572 mg, 4.79 mmol) was dissolved in a mixture of NMP (10 mL) and DIPEA (3.04 mL, 17.4 mmol). (1R,2S,3R,4R)-2,3-Dihydroxy-4-(hydroxymethyl)-1-aminocyclopentane hydrochloride (800 mg, 4.36 mmol) was added. The reaction mixture was heated at 150° C. under microwave irradiation for 4 h. The reaction mixture was diluted with EtOAc and concentrated to provide (1S,2R,3R,5R)-3-(hydroxymethyl)-5-(pyrimidin-4-ylamino) cyclopentane-1,2-diol which was used without further purification.

Step 2: (1S,2R,3R,5R)-3-{[bis(4-methoxyphenyl)(phenyl)methoxy]methyl}-5-(pyrimidin-4-ylamino)cyclopentane-1,2-diol (1S,2R,3R,5R)-3-(hydroxymethyl)-5-(pyrimidin-4-ylamino)cyclopentane-1,2-diol (1.96 g, 8.70 mmol) was concentrated from dry pyridine (~20 mL), then dissolved in pyridine (30.0 mL). DMTrCl (4.47 g, 13.1 mmol) was added and the reaction mixture was allowed to stir at rt for 3 h. The reaction mixture was concentrated and diluted with water. The mixture was extracted with EtOAc and then the organic phase was washed with brine, dried with $Na_2SO_4$ and concentrated. The crude compound was purified by silica gel chromatography (0-100% EtOAc in hexanes, followed by 0-20% MeOH in EtOAc) to provide (1S,2R,3R,5R)-3-{[bis(4-methoxyphenyl)(phenyl)methoxy]methyl}-5-(pyrimidin-4-ylamino)cyclopentane-1,2-diol (1.10 g, 24%). LCMS (FA): m/z=528.3 (M+H).

Step 3: (1R,2S,3R,5R)-5-{[bis(4-methoxyphenyl)(phenyl)methoxy]methyl}-2-{[tert-butyl(dimethyl)silyl]oxy}-3-(pyrimidin-4-ylamino)cyclopentanol and (1S,2R,3R,5R)-3-((bis(4-methoxyphenyl)(phenyl)methoxy)methyl)-2-((tert-butyldimethylsilyl)oxy)-5-(pyrimidin-4-ylamino)cyclopentan-1-ol, Intermediate 14

(1S,2R,3R,5R)-3-{[bis(4-methoxyphenyl)(phenyl)methoxy]methyl}-5-(pyrimidin-4-ylamino)cyclopentane-1,2-diol (1.11 g, 2.10 mmol) was concentrated from toluene (3×50 mL) and then taken up in pyridine (50.0 mL) at rt. TBSCl (1.60 g, 10.5 mmol) and imidazole (578 mg, 8.40 mmol) were added. The reaction mixture was allowed to stir at rt for 4 h. The reaction mixture was diluted with water and extracted with EtOAc. The combined organic phases were washed with brine, dried with $Na_2SO_4$ and concentrated. The crude mixture was purified by silica gel chromatography (40-80% EtOAc in hexanes) to provide Intermediate 14 (339 mg, 25%). $^1$H NMR (DMSO-$d_6$) δ 8.32 (s, 1H), 7.97 (br d, J=5.4 Hz, 1H), 7.34-7.42 (m, 2H), 7.26-7.32 (m, 3H), 7.17-7.26 (m, 6H), 6.87 (d, J=8.7 Hz, 4H), 6.40 (br d, J=4.6 Hz, 1H), 4.11 (br d, J=4.8 Hz, 1H), 3.76 (t, J=5.0 Hz, 1H), 3.72 (s, 6H), 3.64 (q, J=5.0 Hz, 1H), 3.03 (dd, J=8.8, 5.1 Hz, 1H), 2.93 (dd, J=8.9, 6.0 Hz, 1H), 2.03-2.21 (m, 2H), 1.22 (m, 1H), 0.79 (s, 9H), 0.00 (s, 3H), −0.05 (s, 3H) as the first eluting peak and regio-isomer Intermediate 15 (422 mg, 31%)$^1$H NMR (DMSO-$d_6$) δ 8.37 (s, 1H), 8.01 (br s, 1H,) 7.19-7.40 (m, 10H), 6.85-6.91 (m, 4H), 6.45 (br d, J=5.6 Hz, 1H), 4.42 (br d, J=5.8 Hz, 1H), 3.97-4.23 (br s, 1H), 3.79 (t, J=5.1 Hz, 1H), 3.73 (s, 6H,) 3.61 (q, J=5.9 Hz, 1H), 3.06 (dd, J=8.9, 5.3 Hz, 1H), 2.90 (dd, J=8.8, 7.1 Hz, 1H), 2.28-2.40 (m, 1H), 2.14 (m, 1H), 1.02-1.21 (m, 1H), 0.78 (s, 9H), −0.02 (s, 3H), −0.07 (s, 3H) as the second eluting peak.

Example 9

The compound listed below (Intermediate 16) was prepared as described in Example 8 starting with Step 1, substituting the starting material shown in the table for Intermediate 13.

| Starting material | Intermediate | NMR data |
|---|---|---|
| ![F-pyrimidine-Cl] | Int-16 | $^1$H NMR (MeOD) δ 8.24 (d, J = 2.4 Hz, 1H), 7.98 (br d, J = 3.5 Hz, 1H), 7.39-7.48 (m, 2H), 7.13-7.36 (m, 7H), 6.84 (d, J = 8.8 Hz, 4H), 4.61 (s, 1H), 4.46 (q, J = 8 .1 Hz, 1H), 3.94-4.02 (m, 1H), 3.86 (dd, J = 7.2, 5.4 Hz, 1H), 3.77 (s, 6H,) 3.22 (dd, J = 9.0, 5.5 Hz, 1H), 3.07 (dd, J = 9.0, 6.4 Hz, 1H), 2.42 (dt, J = 13.0, 8.4 Hz, 1H), 2.19-2.32 (m, 1H,) 1.38 (dt, J = 13.0, 9.0 Hz, 1H), 0.87 (s, 9H), 0.05 (s, 3H), 0.00 (s, 3H). |

Example 10

(1S,2R,4R)-4-{[6-(benzoylamino)pyrimidin-4-yl]oxy}-2-(hydroxymethyl)cyclopentyl hydrogen phosphonate, Intermediate 20

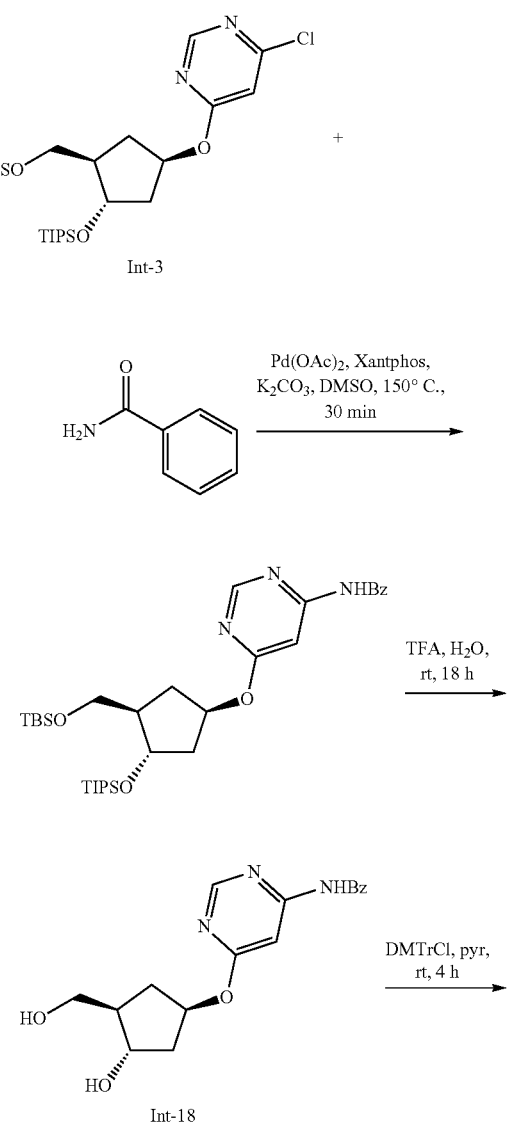

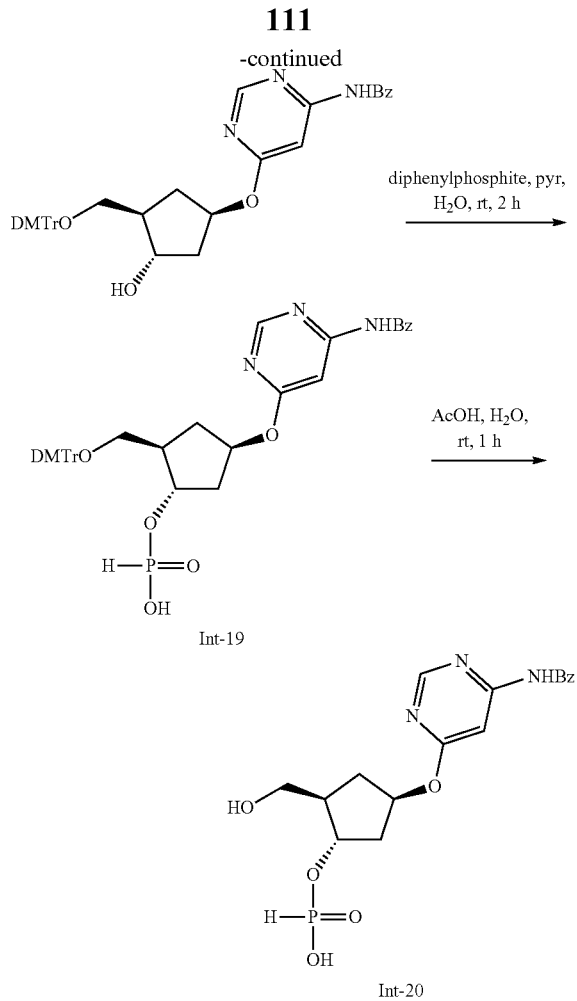

Step 1: N-[6-[(1R,3R,4S)-3-[[tert-butyl(dimethyl) silyl]oxymethyl]-4-triisopropylsilyloxy-cyclopentoxy]pyrimidin-4-yl]benzamide Intermediate 3 (2.90 g, 5.23 mmol), benzamide (1.58 g, 13.07 mmol), palladium(II) acetate (58.7 mg, 0.261 mmol) and Xantphos (302 mg, 0.523 mmol) were dissolved in DMSO (30.0 mL), then potassium carbonate (1.63 g, 10.5 mmol) was added. The reaction mixture was sealed under an atmosphere of argon and heated at 150° C. for 30 min. The cooled reaction mixture was poured into water (300 mL) and extracted with EtOAc (3×120 mL). The combined organic phases were concentrated. The crude compound was purified by silica gel chromatography (0-35% EtOAc in hexane) to provide N-[6-[(1R,3R,4S)-3-[[tert-butyl (dimethyl)silyl] oxymethyl]-4-triisopropylsilyloxy-cyclopentoxy]pyrimidin-4-yl]benzamide (2.62 g, 83%). $^1$H NMR (CDCl$_3$) δ 8.47 (br s, 1H), 8.43 (d, J=0.8 Hz, 1H), 7.84-7.89 (m, 2H), 7.61-7.65 (m, 1H), 7.56 (tt, J=7.4, 2.1 Hz, 1H), 7.45-7.52 (m, 2H), 5.50 (dddd, J=7.2, 5.2 Hz, 1H), 4.33 (q, J=5.1 Hz, 1H), 3.52-3.64 (m, 2H), 2.42 (dt, J=14.6, 8.0 Hz, 1H), 2.02-2.18 (m, 3H), 1.58-1.51 (m, 1H), 1.03 (s, 21H), 0.85 (s, 9H), 0.00 (s, 6H).

Step 2: N-[6-[(1R,3S,4R)-3-hydroxy-4-(hydroxymethyl)cyclopentoxy]pyrimidin-4-yl]benzamide N-[6-[(1R,3R,4S)-3-[[tert-butyl(dimethyl)silyl]oxymethyl]-4-triisopropylsilyloxy-cyclopentoxy]pyrimidin-4-yl]benzamide (2.92 g, 4.87 mmol) was dissolved in water (10.0 mL) and TFA (20.0 mL). The reaction mixture was allowed to stir at rt overnight and then concentrated. The crude compound was purified by reverse phase flash column chromatography (10-100% ACN in aq. formic acid (0.1%)) to provide N-[6-[(1R,3S,4R)-3-hydroxy-4-(hydroxymethyl) cyclopentoxy]pyrimidin-4-yl]benzamide (1.28 g, 80%). LCMS (FA): m/z=330.2 (M+H).

Step 3: N-[6-[(1R,3R,4S)-3-[[bis(4-methoxyphenyl)-phenyl-methoxy]methyl]-4-hydroxy-cyclopentoxy]pyrimidin-4-yl]benzamide N-[6-[(1R,3S,4R)-3-hydroxy-4-(hydroxymethyl)cyclopentoxy]pyrimidin-4-yl]benzamide (1.28 g, 3.89 mmol) was dissolved in dry acetonitrile and concentrated to dryness, and then taken up in pyridine (25 mL). DMTrCl (1.33 g, 3.89 mmol) was added and the reaction mixture was allowed to stir at rt for 1 h. Additional DMTrCl (666 mg, 1.95 mmol) was added to the reaction mixture and stirring was continued for 3 h. MeOH (5 mL) was added and the mixture was allowed to stir for 10 min, and then poured into water (80 mL). The mixture was extracted with EtOAc (3×80 mL). The combined organic phases were concentrated. The crude compound was purified by silica gel chromatography (30-100% EtOAc in hexanes) to provide N-[6-[(1R,3R,4S)-3-[[bis(4-methoxyphenyl)-phenyl-methoxy]methyl]-4-hydroxy-cyclopentoxy]pyrimidin-4-yl]benzamide (1.73 g, 70%). LCMS (FA): m/z=632.4 (M+H).

Step 4: [(1S,2R,4R)-4-(6-benzamidopyrimidin-4-yl) oxy-2-[[bis(4-methoxyphenyl)-phenyl-methoxy] methyl]cyclopentoxy]phosphinic acid, Intermediate 19

To a solution of N-[6-[(1R,3R,4S)-3-[[bis(4-methoxyphenyl)-phenyl-methoxy]methyl]-4-hydroxy-cyclopentoxy]pyrimidin-4-yl]benzamide (1.00 g, 1.58 mmol) in pyridine (14.9 mL) was added diphenyl phosphite (0.609 mL, 3.17 mmol). The reaction mixture was allowed to stir at rt under an atmosphere of argon for 2 h. Water (29.9 mL) was added, and the yellow reaction mixture was allowed to stir at rt for 1 h. ACN (15 mL) was added to dissolve fine particulates and stirring continued for 5 min. Brine (30 mL) was added and the mixture was extracted with EtOAc (2×60 mL). The combined organic phases were washed with water and brine, dried over Na$_2$SO$_4$ and concentrated. The residue was concentrated from toluene (3×10 mL) and taken on directly to the next step without further purification.

Step 5: (1S,2R,4R)-4-{[6-(benzoylamino)pyrimidin-4-yl]oxy}-2-(hydroxymethyl) cyclopentyl hydrogen phosphonate, Intermediate 20

[(1S,2R,4R)-4-(6-benzamidopyrimidin-4-yl)oxy-2-[[bis (4-methoxyphenyl)-phenyl-methoxy]methyl]cyclopentoxy] phosphinic acid (1.06 g, 1.52 mmol) was taken up in water (1.42 mL) and acetic acid (5.70 mL, 99.40 mmol). The reaction mixture was sonicated for 1 min, and the resulting bright orange solution was allowed to stir at rt for 1 h. The reaction mixture was concentrated from toluene (2×10 mL). The residue was then adsorbed onto Celite and purified by silica gel chromatography (0-60% MeOH in DCM) to provide (1S,2R,4R)-4-{[6-(benzoylamino)pyrimidin-4-yl] oxy}-2-(hydroxymethyl)cyclopentyl hydrogen phosphonate (Intermediate 20, 630 mg, 71%). LCMS (FA): m/z=394.1 (M+H), $^1$H NMR (DMSO-d$_6$) δ 11.07 (br s, 1H), 8.58 (d, J=1.0 Hz, 1H), 8.03-7.97 (m, 2H), 7.65-7.58 (m, 1H), 7.56-7.48 (m, 3H), 7.31 (s, 0.5H), 5.92-5.85 (m, 1.5H), 5.43-5.34 (m, 1H), 4.43-4.33 (m, 1H), 3.46-3.35 (m, 2H), 2.36-2.25 (m, 1H), 2.09-1.95 (m, 3H), 1.42-1.31 (m, 1H) $^{31}$P NMR (DMSO-d$_6$) δ 1.53 (s, 1P).

Example 11

The compounds listed below were prepared as described in Example 10 starting with Step 3, substituting the starting material shown in the table for Intermediate 18.

| Starting material | Intermediate | LCMS data |
|---|---|---|
| 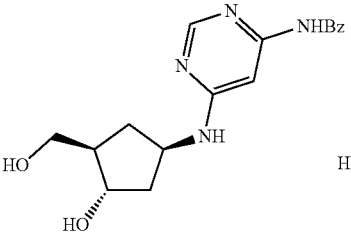 Int-12 | 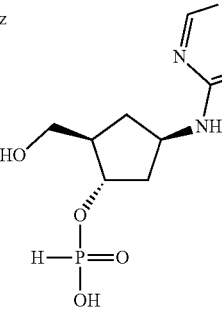 Int-21 | LCMS (FA): m/z = 393.1 (M + H). |
| 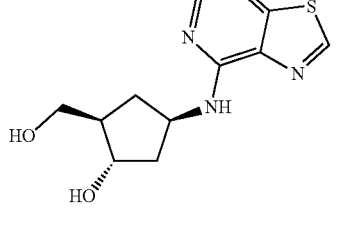 Int-65 | 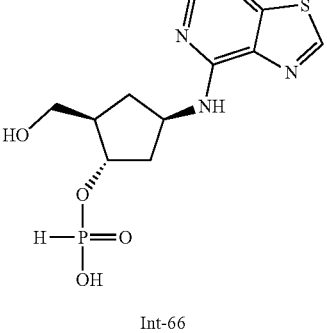 Int-66 | LCMS (AA): m/z = 331.1 (M + H). |
| 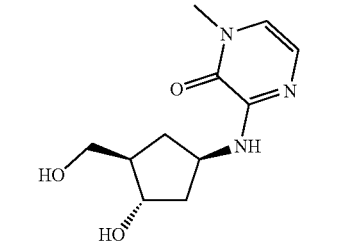 Int-67 | 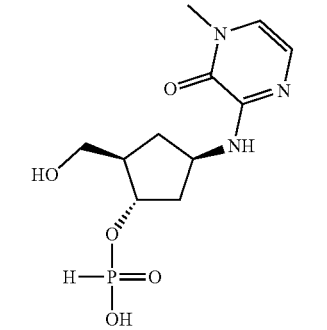 [SMILES: Cn1ccnc(N[C@@H]2C[C@H](CO)[C@@H](O[PH](=O)O)C2)c1=O] Int-68 | LCMS (AA): m/z = 304.1 (M + H). |

Example 12

The compounds listed below were prepared as described in Example 10 starting with Step 4, substituting the starting material shown in the table for N-[6-[(1R,3R,4S')-3-[[bis(4-methoxyphenyl)-phenyl-methoxy]methyl]-4-hydroxy-cyclopentoxy]pyrimidin-4-yl]benzamide.

| Starting material | Intermediate | LCMS data |
|---|---|---|
| Int-14 | Int-22 | LCMS (FA): m/z = 404.2 (M + H) |
| Int-30 | Int-23 | LCMS (AA): m/z = 274.1 (M + H) |
| Int-16 | Int-24 | LCMS (AA): m/z = 422.2 (M + H) |
Example 13
(1S,2R,4R)-2-(hydroxymethyl)-4-(pyrazin-2-yloxy)cyclopentyl hydrogen phosphonate, Intermediate 25
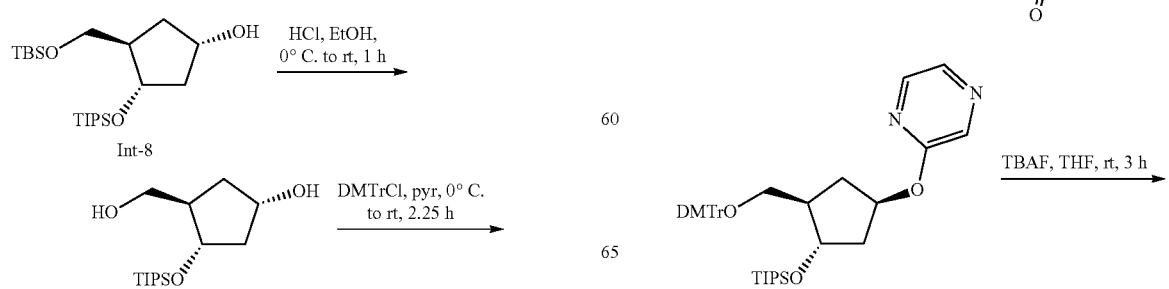

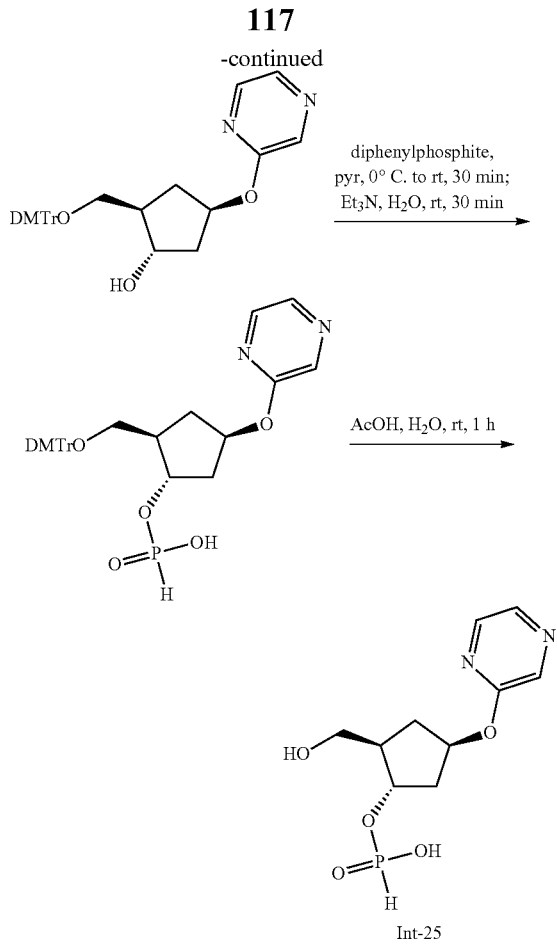

Step 1: (1S,3R,4S)-3-(hydroxymethyl)-4-[(triisopropylsilyl)oxy]cyclopentanol A solution of HCl (12.0 M in water, 0.750 mL, 9.00 mmol) in EtOH (70.0 mL) was cooled to 0° C. and a solution of Intermediate 8 (1.65 g, 4.10 mmol) in EtOH (70.0 mL) was added slowly. The reaction mixture was warmed to rt and allowed to stir for 1 h. Water (10.0 mL) and sodium bicarbonate (1.80 g, 21.4 mmol) were added and the reaction mixture was allowed to stir at rt for 5 min. The mixture was concentrated and concentrated from toluene. The crude compound was purified by silica gel chromatography (0-95% MeOH in DCM) to provide (1S,3R,4S)-3-(hydroxymethyl)-4-[(triisopropylsilyl)oxy]cyclopentanol (870 mg, 74%). LCMS (FA): m/z=289.2 (M+H).

Step 2: (1S,3R,4S)-3-{[bis(4-methoxyphenyl)(phenyl)methoxy]methyl}-4-[(triisopropylsilyl)oxy]cyclopentanol (1S,3R,4S)-3-(hydroxymethyl)-4-[(triisopropylsilyl)oxy] cyclopentanol (865 mg, 3.00 mmol) was taken up in pyridine (20.0 mL) and cooled to 0° C. A solution of DMTrCl (1.13 g, 3.17 mmol) in pyridine (10.0 mL) was added and the reaction mixture was allowed to stir at 0° C. for 2 h. An additional portion of DMTrCl (150 mg, 0.421 mmol) was added and the reaction mixture was allowed to warm to rt and stir for 15 min. MeOH (20.0 mL) was added and the reaction mixture was concentrated. The residue was concentrated from toluene (2×50 mL) and adsorbed onto Celite. The crude compound was purified by silica gel chromatography (0-15% EtOAc in hexanes) to provide (1S,3R,4S)-3-{[bis(4-methoxyphenyl)(phenyl)methoxy]methyl}-4-[(triisopropylsilyl)oxy]cyclopentanol (1.77 g, 61%). $^1$H NMR (DMSO-$d_6$) δ 7.36 (d, J=7.5 Hz, 2H), 7.30 (t, J=7.3 Hz, 2H), 7.21 (d, J=8.8 Hz, 5H), 6.88 (d, J=8.8 Hz, 4H), 4.52 (d, J=4.4 Hz, 1H), 4.03-4.08 (m, 1H), 3.87 (q, J=7.1 Hz, 1H), 3.73 (s, 6H), 3.14 (dd, J=8.7, 4.3 Hz, 1H), 2.83 (t, J=8.1 Hz, 1H), 2.20 (quin, J=7.0 Hz, 2H), 1.87 (ddd, J=12.1, 7.8, 3.2 Hz, 1H), 1.64 (ddd, J=13.3, 8.9, 6.6 Hz, 1H), 1.42 (quin, J=5.8 Hz, 1H), 0.82-0.96 (m, 21H).

Step 3: 2-({(1R,3R,4S)-3-{[bis(4-methoxyphenyl)(phenyl)methoxy]methyl}-4-[(triisopropylsilyl)oxy]cyclopentyl}oxy)pyrazine (1S,3R,4S)-3-{[bis(4-methoxyphenyl)(phenyl)methoxy]methyl}-4-[(triisopropylsilyl)oxy]cyclopentanol (1.35 g, 2.28 mmol), 2-hydroxypyrazine (330 mg, 3.43 mmol), and triphenylphosphine (752 mg, 2.87 mmol) were taken up in THF (22.8 mL). The reaction mixture was cooled to 0° C. and DBAD (660 mg, 2.87 mmol) was added. The reaction mixture was allowed to warm to rt and stir for 1 h. MeOH was added (10.0 mL) and the mixture was concentrated. The crude compound was purified by silica gel chromatography [0-90% EtOAc in hexanes (with 0.5% TEA)) to provide 2-({(1R,3R,4S)-3-{[bis(4-methoxyphenyl)(phenyl)methoxy]methyl}-4-[(triisopropylsilyl)oxy]cyclopentyl}oxy)pyrazine (1.53 g, 85%). LCMS (AA): m/z=669.4 (M+H).

Step 4: (1S,2R,4R)-2-{[bis(4-methoxyphenyl)(phenyl)methoxy]methyl}-4-(pyrazine-2-yloxy)cyclopentanol To a solution of 2-({(1R,3R,4S)-3-{[bis(4-methoxyphenyl)(phenyl)methoxy]methyl}-4-[(triisopropylsilyl)oxy]cyclopentyl}oxy)pyrazine (2.40 g, 3.59 mmol) in THF (29.0 mL) was added TBAF (1.00 M in THF, 4.50 mL, 4.50 mmol). The reaction mixture was allowed to stir at rt for 1.25 h. An additional portion of TBAF (1.00 M in THF, 4.00 mL, 4.00 mmol) was added and stirring was continued for 2 h. The reaction mixture was concentrated. The crude compound was purified by silica gel chromatography (0-5% MeOH in DCM (with 0.5% TEA)) to provide (1S,2R,4R)-2-{[bis(4-methoxyphenyl)(phenyl)methoxy]methyl}-4-(pyrazine-2-yloxy)cyclopentanol (1.68 g, 91%). LCMS (AA): m/z=513.3 (M+H).

Step 5: (1S,2R,4R)-2-{[bis(4-methoxyphenyl)(phenyl)methoxy]methyl}-4-(pyrazine-2-yloxy)cyclopentyl hydrogen phosphonate (1S,2R,4R)-2-{[bis(4-methoxyphenyl)(phenyl)methoxy]methyl}-4-(pyrazine-2-yloxy)cyclopentanol (1.04 g, 2.03 mmol) was taken up in pyridine (8.90 mL) and cooled to 0° C. Diphenyl phosphite (0.796 mL, 4.14 mmol) was slowly added over 1 min. The reaction mixture was allowed to warm to rt and stir for 30 min. The reaction mixture was cooled to 0° C. and TEA (2.00 mL, 14.2 mmol) was added followed by water (2.00 mL). The reaction mixture was allowed to warm to rt and stir for 30 min. The reaction mixture was concentrated. The residue was concentrated from toluene (2×50 mL). The crude compound was purified by silica gel chromatography [0-5% MeOH in DCM (with 0.5% TEA))] to provide (1S,2R,4R)-2-{[bis(4-methoxyphenyl)(phenyl)methoxy]methyl}-4-(pyrazin-2-yloxy)cyclopentyl hydrogen phosphonate (985 mg, 72%) as the N,N-diethylethanamine salt. LCMS (AA): m/z=575.2 (M–H).

Step 6: (1S,2R,4R)-2-(hydroxymethyl)-4-(pyrazin-2-yloxy)cyclopentyl hydrogen phosphonate, Intermediate 25

(1S,2R,4R)-2-{[bis(4-methoxyphenyl)(phenyl)methoxy]methyl}-4-(pyrazine-2-yloxy)cyclopentyl hydrogen phosphonate (988 mg, 1.46 mmol) was taken up in water (1.2 mL) and acetic acid (5.6 mL). The reaction mixture was sonicated for 2 min and then the reaction mixture was allowed to stir at rt for 1 h. The reaction mixture was concentrated and the residue with concentrated from toluene and dried under vacuum for 1 h. The crude compound was purified by silica gel chromatography (10-80% MeOH in DCM) to provide (1S,2R,4R)-2-(hydroxymethyl)-4-(pyrazin-2-yloxy)cyclopentyl hydrogen phosphonate (Intermediate 25,348 mg, 64%) as the N,N-diethylethanamine salt. LCMS (AA): m/z=275.1 (M+H), $^1$H NMR (DMSO-$d_6$) δ 10.52 (br s, 1H), 8.24 (d, J=1.1 Hz, 1H), 8.13-8.20 (m, 2H), 7.35 (s, 0.5H), 5.88 (s, 0.5H), 5.29-5.37 (m, 1H), 4.42 (dq, J=10.4, 6.7 Hz, 1H), 3.36-3.48 (m, 2H), 3.03 (q, J=7.2 Hz, 6H), 2.28-2.37 (m, 1H), 1.97-2.11 (m, 3H), 1.40 (m, 1H), 1.18 (t, J=7.27 Hz, 9H). $^{31}$P NMR (DMSO-$d_6$) δ 1.41 (s, 1P).

Example 13A

The compounds listed below were prepared as described in Example 13 starting with Step 5, substituting the starting material shown in the table for (1S,2R,4R)-2-{[bis(4-methoxyphenyl)(phenyl)methoxy]methyl}-4-(pyrazine-2-yloxy)cyclopentanol in Example 13.

| Starting material | Intermediate | LCMS data |
|---|---|---|
| Int-71 | Int-72 | LCMS (AA): m/z = 288.2 (M + H) |
| Int-73 | Int-74 | LCMS (FA): m/z = 314.1 (M + H) |
| Int-76 | Int-77 | LCMS (AA): m/z = 289.1 (M + H) |

-continued

| Starting material | Intermediate | LCMS data |
|---|---|---|
| Int-69 | Int-70 | LCMS (FA): m/z = 292.1 (M + H) |
| Int-78 | Int-79 | LCMS (AA): m/z = 275.1 (M + H) |
| Int-150 | Int-151 | LCMS (FA): m/z = 293.0 (M + H) |
| Int-157 | Int-158 | LCMS (FA): m/z = 289.9 (M + H) |

Example 14

2-amino-9-[(5R,7R,8R,12aR,14R,15aS,16R)-2,10,16-trihydroxy-2,10-dioxido-14-(pyrimidin-4-yloxy)decahydro-5,8-methanocyclopenta[l][1,3,6,9,11,2,10]pentaoxadiphosphacyclo tetradecin-7-yl]-1,9-dihydro-6H-purin-6-one, Compound I-10

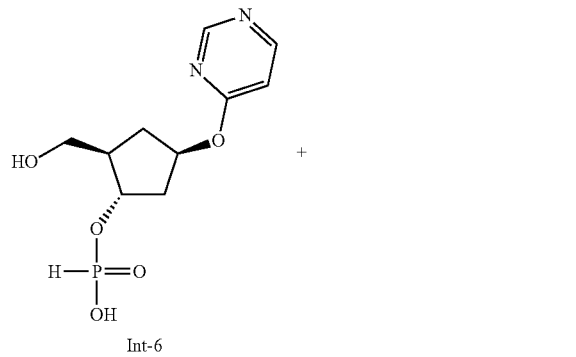

Int-6

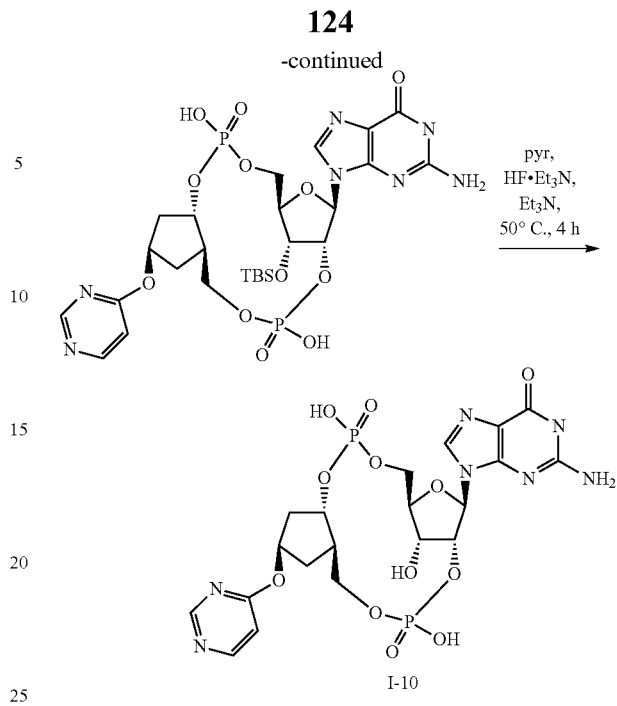

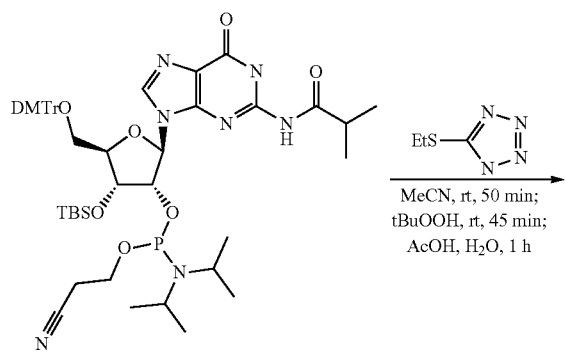

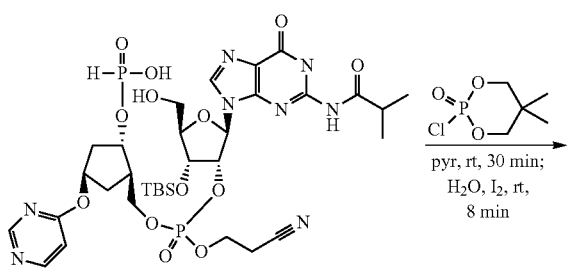

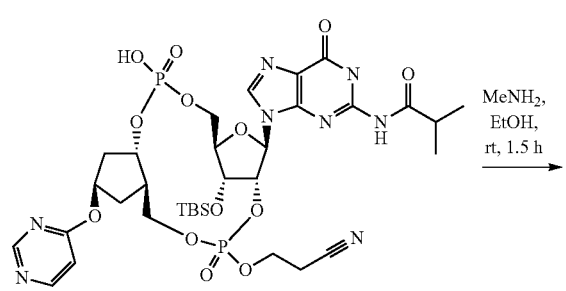

Step 1: [(1S,2R,4R)-2-[[[(2R,3R,4R,5R)-4-[tert-butyl(dimethyl)silyl]oxy-5-(hydroxymethyl)-2-[2-(2-methylpropanoylamino)-6-oxo-1H-purin-9-yl]tetrahydrofuran-3-yl]oxy-(2-cyanoethoxy)phosphoryl]oxymethyl]-4-pyrimidin-4-yloxy-cyclopentoxy] phosphinic acid A mixture of Intermediate 6 (175 mg, 0.638 mmol) and N-[9-[(2R,3R,4R,5R)-5-[[bis(4-methoxyphenyl)-phenyl-methoxy]methyl]-4-[tert-butyl(dimethyl) silyl]oxy-3-[2-cyanoethoxy-(diisopropylamino)phosphanyl]oxy-tetrahydrofuran-2-yl]-6-oxo-1H-purin-2-yl]-2-methyl-propanamide (743 mg, 0.766 mmol) were concentrated from dry ACN (3×15 mL). The residue was then suspended in ACN (2.34 mL) under argon. In a separate flask, 5-(ethyl-thio)-1H-tetrazole (249 mg, 1.91 mmol) was concentrated from dry ACN (3×10 mL), dissolved in ACN (1.06 mL) and added to the reaction mixture under an atmosphere of argon. The reaction mixture was allowed to stir at rt for 50 min. tert-Butyl hydroperoxide (5.5 M in nonane, 0.35 mL, 1.91 mmol) was added and the reaction mixture was allowed to stir at rt for 45 min. The reaction mixture was quenched by the addition of sodium thiosulfate (353 mg, 2.23 mmol) in water (0.353 mL). The solvents were evaporated and then placed under vacuum for 2 min. The residue was dissolved in a mixture of acetic acid (2.53 mL, 44.2 mmol) and water (0.63 mL). The reaction mixture was allowed to stir at rt for 1 h, then concentrated from toluene and concentrated. The residue was concentrated again with toluene and then purified by silica gel chromatography (0-50% MeOH in DCM) to give [(1S,2R,4R)-2-[[[(2R,3R,4R,5R)-4-[tert-butyl(dimethyl)silyl]oxy-5-(hydroxymethyl)-2-[2-(2-methylpropanoylamino)-6-oxo-1H-purin-9-yl]tetrahydrofuran-3-yl]oxy-(2-cyanoethoxy)phosphoryl]oxymethyl]-4-pyrimidin- 4-yloxy-cyclopentoxy]phosphinic acid (372 mg, 65%). LCMS (FA): m/z=857.3 (M+H).

Step 2: N-{9-[(5R,7R,8R,12aR,14R,15aS,16R)-16-{[tert-butyl(dimethyl)silyl]oxy}-10-(2-cyanoethoxy)-2-hydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide

[(1S,2R,4R)-2-[[[(2R,3R,4R,5R)-4-[tert-butyl(dimethyl)silyl]oxy-5-(hydroxymethyl)-2-[2-(2-methylpropanoylamino)-6-oxo-1H-purin-9-yl]tetrahydrofuran-3-yl]oxy-(2-cyanoethoxy)phosphoryl]oxymethyl]-4-pyrimidin-4-yloxy-cyclopentoxy]phosphinic acid (370 mg, 0.432 mmol) was concentrated from dry ACN (3×15 mL) then placed under vacuum for 15 min. The residue was dissolved in pyridine (8.64 mL) under an argon atmosphere. 2-Chloro-5,5-dimethyl-1,3,2-dioxaphosphorinane 2-oxide (291 mg, 1.51 mmol) was then added and the reaction mixture was allowed to stir at rt for 30 min. Water was added (0.272 mL) followed by iodine (143 mg, 0.561 mmol). The mixture was allowed to stir at rt under argon for 8 min. Sodium thiosulfate (91.5 mg, 0.561 mmol) in water (0.5 mL) were added. The reaction mixture was allowed to stir at rt for 10 min. Dry toluene was added (15 mL) and concentrated. The residue was concentrated from toluene (2×15 mL). The crude mixture was purified by silica gel chromatography (0-50% MeOH in DCM) to provide N-{9-[(5R,7R,8R,12aR,14R,15aS,16R)-16-{[tert-butyl(dimethyl)silyl]oxy}-10-(2-cyanoethoxy)-2-hydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide (366 mg, 99%). LCMS (FA): m/z=855.3 (M+H).

Step 3: 2-amino-9-[(5R,7R,8R,12aR,14R,15aS,16R)-16-{[tert-butyl(dimethyl)silyl]oxy}-2,10-dihydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-1,9-dihydro-6H-purin-6-one N-{9-[(5R,7R,8R,12aR,14R,15aS,16R)-16-{[tert-butyl(dimethyl)silyl]oxy}-10-(2-cyanoethoxy)-2-hydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide (366 mg, 0.428 mmol) was taken up in methylamine (33% in EtOH, 12.8 mL, 103 mmol) and the mixture was allowed to stir at rt for 90 min. The reaction mixture was concentrated. The residue was then dry loaded on silica gel and purified by silica gel chromatography (0-80% MeOH in DCM) to provide 2-amino-9-[(5R,7R,8R,12aR,14R,15aS,16R)-16-{[tert-butyl (dimethyl)silyl]oxy}-2,10-dihydroxy-2,10-dioxido-14-(pyrimidin-4-yloxy)decahydro-5,8-methanocyclopenta[l][1,3,6,9,11,2,10]pentaoxadiphosphacyclotetra-decin-7-yl]-1,9-dihydro-6H-purin-6-one (159 mg, 51%) as a white solid. LCMS (FA): m/z=732.3 (M+H).

Step 4: 2-amino-9-[(5R,7R,8R,12aR,14R,15aS,16R)-2,10,16-trihydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-1,9-dihydro-6H-purin-6-one-N,N-diethylethanamine (1:2), compound I-10

To a suspension of 2-amino-9-[(5R,7R,8R,12aR,14R,15aS,16R)-16-{[tert-butyl (dimethyl)silyl]oxy}-2,10-dihydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-1,9-dihydro-6H-purin-6-one (159 mg, 0.217 mmol) in pyridine (1.09 mL) was added triethylamine trihydrofluoride (0.175 mL, 1.09 mmol), then TEA (2.72 mL, 19.3 mmol). The reaction mixture was sealed in a propylene tube and vigorously stirred at 50° C. for 4 h. The reaction mixture was cooled to rt. The reaction mixture was diluted with water (6.4 mL) then $CaCl_2$) (0.339 M in water, 6.4 mL, 2.17 mmol) was added. The cloudy white mixture was allowed to stir at rt for 30 min. The suspension was filtered through Celite and the Celite was washed with water (5×5 mL). The clear aqueous filtrate was concentrated to a solid residue. No HF was observed by $^{19}$F NMR. The crude residue was suspended in can (25 mL) and then adsorbed on Celite. The crude compound was purified by reverse phase flash column chromatography (10% ACN in aqueous triethylammonium acetate (10 mM)) to provide 2-amino-9-[(5R,7R,8R,12aR,14R,15aS,16R)-2,10,16-trihydroxy-2,10-dioxido-14-(pyrimidin-4-yloxy)decahydro-5,8-methanocyclopenta[l][1,3,6,9,11,2,10]pentaoxadiphosphacyclotetradecin-7-yl]-1,9-dihydro-6H-purin-6-one-N,N-diethylethanamine (I-10) (70 mg, 39%). LCMS (FA): m/z=618.1 (M+H). $^1$H NMR ($D_2O$) δ 8.63 (s, 1H), 8.40 (d, J=6.0 Hz, 1H), 8.04 (s, 1H), 6.78 (dd, J=6.1, 1.1 Hz, 1H), 5.99 (d, J=8.4 Hz, 1H), 5.31-5.43 (m, 2H), 4.77-4.87 (m, 1H), 4.62 (d, J=4.2 Hz, 1H), 4.38 (q, J=2.3 Hz, 1H), 4.14-4.19 (m, 2H), 3.95 (dt, J=10.6, 3.4 Hz, 1H), 3.82 (dt, J=10.6, 6.5 Hz, 1H), 3.15 (q, J=7.3 Hz, 12H), 2.33-2.56 (m, 3H), 2.20-2.31 (m, 1H), 1.54-1.68 (m, 1H), 1.23 (t, J=7.3 Hz, 18H). $^{31}$P NMR ($D_2O$) δ −0.57 (s, 1P), −0.65 (s, 1P).

Example 15

The compounds listed below were prepared as described in Example 14 starting with Step 1, substituting the H-phosphonate shown in the table for Intermediate 6. Unless otherwise noted the compounds are N,N-diethylethanamine salts.

| Compound | Salt Form | H-phosphonate | Final compound/ LCMS data | NMR data |
|---|---|---|---|---|
| I-11 | Et₃N | 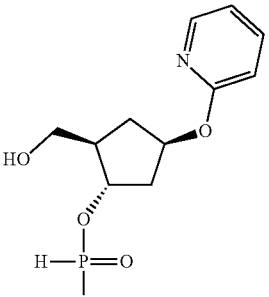 Int-7 | 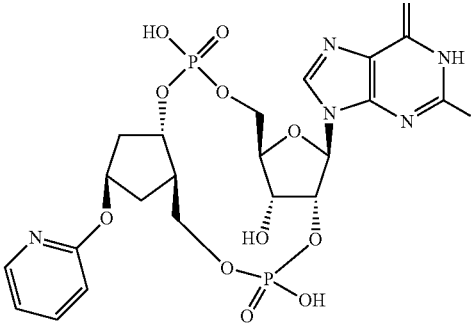 LCMS (AA): m/z = 617.2 (M + H) | ¹H NMR (MeOD) δ 8.03 (s, 1H), 7.98 (dd, J = 5.0, 1.1 Hz, 1H), 7.53 (ddd, J = 8.7, 7.2, 1.9 Hz, 1H), 6.79 (dd, J = 6.4, 5.5 Hz, 1H), 6.61 (d, J = 8.3 Hz, 1H), 5.94 (d, J = 8.3 Hz, 1H), 5.28-5.40 (m, 2H), 4.85 (quin, J = 4.3 Hz, 1H), 4.60 (d, J = 4.0 Hz, 1H), 4.17-4.23 (m, 2H), 4.00-4.10 (m, 1H), 3.92-4.00 (m, 1H), 3.64-3.78 (m, 1H), 3.03 (d, J = 7.4 Hz, 12H), 2.24-2.45 (m, 4H), 1.37-1.49 (m, 1H), 1.16 (t, J = 7.3 Hz, 18H); ³¹P NMR (MeOD) δ −0.42 (s, 1P), −0.56 (s, 1P). |
| I-13* | Et₃N | 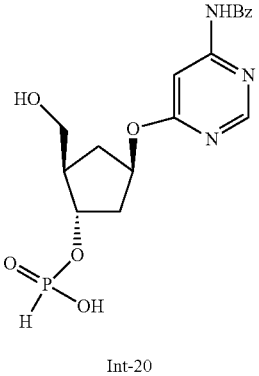 Int-20 | 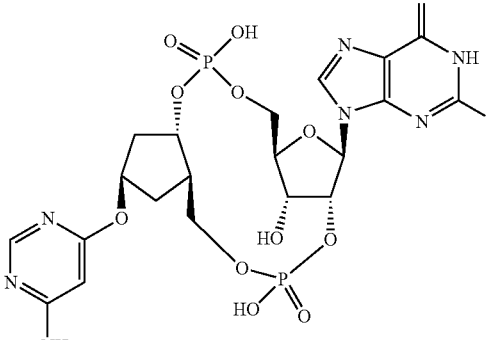 LCMS (AA): m/z = 633.2 (M + H) | ¹H NMR (D₂O) δ 8.14 (s, 1H), 8.08 (s, 1H), 6.03 (d, J = 8.3 Hz, 1H), 5.91-5.87 (m, 1H), 5.41 (dt, J = 4.1, 8.4 Hz, 1H), 5.24-5.16 (m, 1H), 4.84 (quin, J = 6.3 Hz, 1H), 4.66 (d, J = 4.2 Hz, 1H), 4.45-4.40 (m, 1H), 4.25-4.18 (m, 2H), 4.03-3.95 (m, 1H), 3.90-3.81 (m, 1H), 3.19 (q, J = 7.3 Hz, 10H), 2.55-2.36 (m, 3H), 2.30-2.19 (m, 1H), 1.69-1.59 (m, 1H), 1.27 (t, J = 7.3 Hz, 15H); ³¹P NMR (D₂O) δ −0.61 (s, 1P), −0.67 (s, 1P). |
| I-14** | Et₃N | 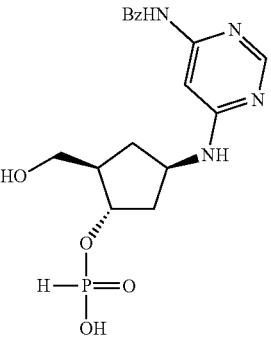 Int-21 | 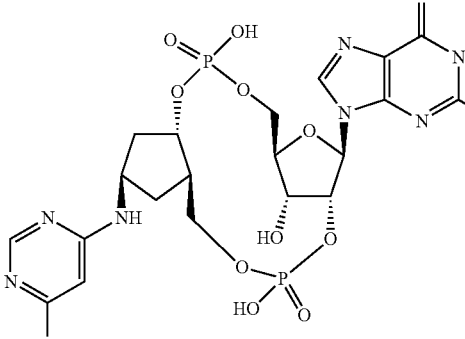 LCMS (AA): m/z = 632.2 (M + H) | ¹H NMR (D₂O) δ 7.99 (s, 1H), 7.96 (s, 1H), 5.97 (d, J = 8.4 Hz, 1H), 5.56 (s, 1H), 5.39 (td, J = 8.6, 4.2 Hz, 1H), 4.72-4.80 (m, 1H), 4.60 (d, J = 4.2 Hz, 1H), 4.38 (q, J = 2.6 Hz, 1H), 4.03-4.22 (m, 3H), 3.94 (dt, J = 10.4, 2.6 Hz, 1H), 3.74-3.83 (m, 1H), 3.15 (q, J = 7.3 Hz, 12H), 2.33-2.47 (m, 2H), 2.12-2.21 (m, 2H), 1.28-1.36 (m, 1H), 1.23 (t, J = 7.3 Hz, 18H); ³¹P NMR (D₂O) δ −0.77 (s, 1P), −0.83 (s, 1P). |

-continued

| Compound | Salt Form | H-phosphonate | Final compound/ LCMS data | NMR data |
|---|---|---|---|---|
| I-7*** | parent | 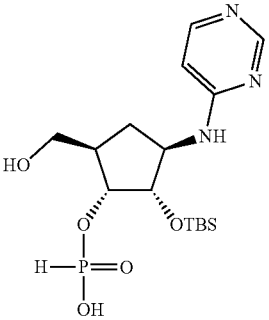 [SMILES: CC(C)(C)[Si](C)(C)O[C@@H]1[C@H](O[PH](=O)O)[C@@H](CO)C[C@H]1Nc1ccncn1] Int-22 | 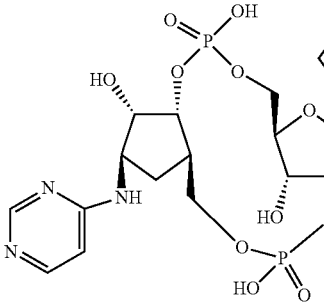 LCMS (AA): m/z = 633.0 (M + H) | $^1$H NMR (D$_2$O) δ 8.43-8.57 (m, 1 H), 7.95-8.01 (m, 1 H), 7.93 (s, 1 H), 6.45-6.58 (m, 1 H), 5.94 (d, J = 8.4 Hz, 1 H), 5.44 (td, J = 8.8, 4.2 Hz, 1 H), 4.62-4.67 (m, 1H), 4.58 (d, J = 4.2 Hz, 1H), 4.38 (br s, 1 H), 4.27-4.30 (m, 1 H), 4.21 (ddd, J = 11.7, 5.1, 2.8 Hz, 2H), 4.09-4.15 (m, 1 H), 3.86-3.97 (m, 2 H), 2.43-2.56 (m, 2 H), 1.41-1.54 (m, 1H); $^{31}$P NMR (D$_2$O) δ −0.86 (s, 1P), −1.10 (s, 1P). |
| I-8*** | Et$_3$N | 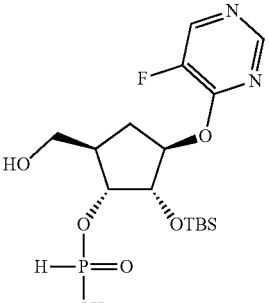 Int-24 | 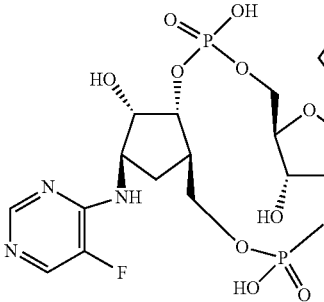 LCMS (AA): m/z = 651.0 (M + H) | $^1$H NMR (D$_2$O) δ 8.23 (d, J = 2.0 Hz, 1H), 7.96 (s, 1H), 7.87 (d, J = 3.5 Hz, 1H), 5.95 (d, J = 8.6 Hz, 1H), 5.43 (dt, J = 4.0, 7.9 Hz, 1H), 4.76-4.73 (m, 1H), 4.64 (d, J = 4.0 Hz, 1H), 4.43-4.40 (m, 1H), 4.30 (t, J = 3.4 Hz, 1H), 4.25-4.19 (m, 2H), 4.17-4.12 (m, 1H), 4.07-4.02 (m, 1H), 3.99-3.93 (m, 1H), 3.15 (q, J = 6.8 Hz, 6H), 2.60-2.47 (m, 2H), 1.54-1.47 (m, 1H), 1.23 (br t, J = 6.6 Hz, 9H). $^{31}$P NMR (D$_2$O) δ −0.84 (s, 1P), −1.31 (s, 1P). |
| I-15 | Et$_3$N | 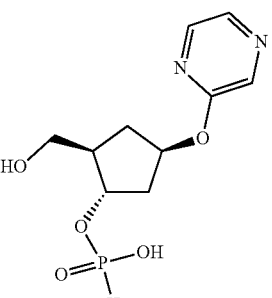 Int-25 | 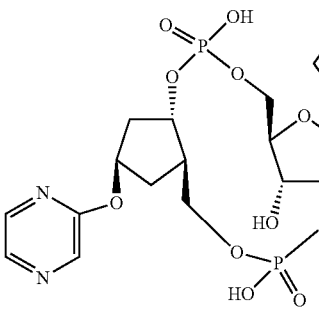 LCMS (AA): m/z = 618.2 (M + H) | $^1$H NMR (MeOD) δ 8.02 (dd, J = 2.8, 1.3 Hz, 1H), 7.99-8.01 (m, 2H), 7.95 (d, J = 2.8 Hz, 1H), 5.93 (d, J = 8.4 Hz, 1H), 5.37-5.46 (m, 1H), 5.33 (ddd, J = 8.8, 5.4, 4.5 Hz, 1H), 4.84 (quin, J = 5.8 Hz, 1H), 4.58 (d, J = 4.2 Hz, 1H), 4.11-4.21 (m, 2H), 4.03 (ddd, J = 11.2, 8.1, 2.2 Hz, 1H), 3.96 (ddd, J = 10.5, 5.9, 3.1 Hz, 1H), 3.71 (ddd, J = 10.8, 8.4 Hz, 1H), 3.02 (q, J = 7.3 Hz, 15H), 2.33-2.46 (m, 3H), 2.28 (dt, J = 14.4, 5.5 Hz, 1H), 1.44 (ddd, J = 17.6, 10.4, 4.8 Hz, 1H), 1.15 (t, J = 7.3 Hz, 23H); $^{31}$P NMR (MeOD) δ −0.42 (s, 1P), −0.58 (s, 1P) |

-continued

| Compound | Salt Form | H-phosphonate | Final compound/ LCMS data | NMR data |
|---|---|---|---|---|
| I-26**** | AcOH | 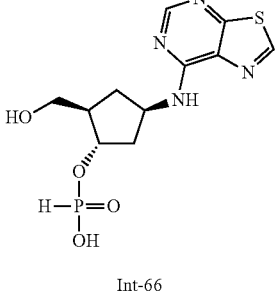<br>Int-66 | 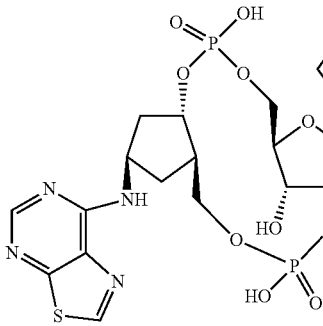<br>LCMS (AA): m/z = 674.1 (M + H) | $^1$H NMR (D$_2$O) δ 8.87-8.85 (m, 1H), 8.41-8.39 (m, 1H), 7.99-7.96 (m, 1H), 6.01-5.97 (m, 1H), 5.53-5.47 (m, 1H), 4.97-4.89 (m, 1H), 4.70 (d, J = 4.2 Hz, 1H), 4.60-4.52 (m, 1H), 4.45-4.40 (m, 1H), 4.26-4.17 (m, 2H), 4.16-4.10 (m, 1H), 4.01-3.95 (m, 1H), 2.62-2.44 (m, 3H), 2.27-2.16 (m, 1H), 1.92-1.90 (m, 6H), 1.65-1.55 (m, 1H); $^{31}$P NMR (D$_2$O) δ −0.75 (s, 1P), −0.78 (s, 1P) |
| I-28 | Et$_3$N | 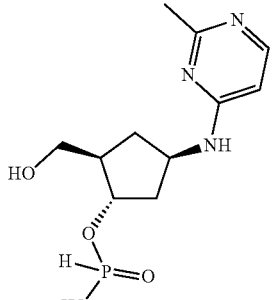<br>Int-72 | 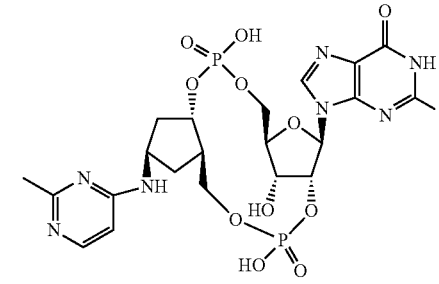<br>LCMS (AA): m/z = 631.1 (M + H) | $^1$H NMR (D$_2$O) δ 7.89 (s, 1H), 7.69 (br s, 1H), 6.33 (br s, 1H), 5.87 (d, J = 8.4 Hz, 1H), 5.22 (dt, J = 4.2, 8.7 Hz, 1H), 4.82-4.75 (m, 1H), 4.47 (d, J = 4.2 Hz, 2H), 4.27-4.24 (m, 1H), 4.09-3.98 (m, 2H), 3.85-3.79 (m, 1H), 3.70-3.62 (m, 1H), 3.03 (q, J = 7.3 Hz, 12H), 2.38 (br s, 3H), 2.34-2.22 (m, 2H), 2.18-2.02 (m, 2H), 1.29-1.19 (m, 1H), 1.10 (t, J = 7.3 Hz, 18H); $^{31}$P NMR (D$_2$O) δ −0.71 (s, 1P), −0.79 (s, 1P) |
| I-36 | Et$_3$N | 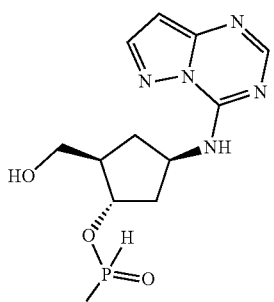<br>Int-74 | 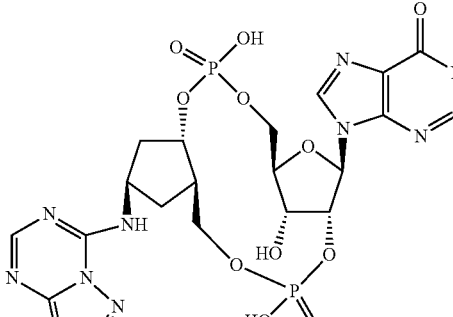<br>LCMS (AA): m/z = 657.2 (M + H) | $^1$H NMR (D$_2$O) δ 8.07 (s, 1H), 8.04 (s, 1H), 7.90 (d, J = 2.2 Hz, 1H), 6.37 (d, J = 2.2 Hz, 1H), 5.99 (d, J = 8.4 Hz, 1H), 5.43 (dt, J = 4.2, 7.8 Hz, 1H), 4.91-4.83 (m, 1H), 4.69 (d, J = 4.2 Hz, 1H), 4.63-4.55 (m, 1H), 4.43-4.40 (m, 1H), 4.25-4.15 (m, 2H), 4.13-4.07 (m, 1H), 3.97-3.89 (m, 1H), 3.16 (q, J = 7.3 Hz, 12H), 2.60-2.39 (m, 3H), 2.35-2.26 (m, 1H), 1.62-1.53 (m, 1H), 1.25 (t, J = 7.3 Hz, 18H); $^{31}$P NMR (D$_2$O) δ −0.73 (s, 1P), −0.77 (s, 1P) |

| Com- pound | Salt Form | H-phosphonate | Final compound/ LCMS data | NMR data |
|---|---|---|---|---|
| I-33 | Et$_3$N | 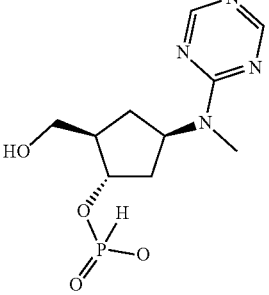<br>Int-77 | 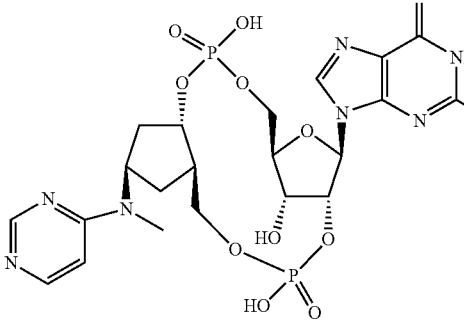<br>LCMS (AA): m/z = 632.2 (M + H) | $^1$H NMR (D$_2$O) δ 8.33 (s, 2H), 7.99 (s, 1H), 5.91 (d, J = 8.3 Hz, 1H), 5.25-5.10 (m, 2H), 4.63-4.60 (m, 1H), 4.53 (d, J = 4.3 Hz, 1H), 4.31-4.26 (m, 1H), 4.14-4.00 (m, 2H), 3.92-3.83 (m, 1H), 3.74-3.64 (m, 1H), 3.04 (q, J = 7.3 Hz, 12H), 2.85 (s, 3H), 2.34-2.22 (m, 1H), 2.18-2.03 (m, 2H), 2.02-1.91 (m, 1H), 1.40-1.25 (m, 1H), 1.12 (t, J = 7.3 Hz, 18H). $^{31}$P NMR (D$_2$O) δ −0.43 (s, 1P), −0.79 (s, 1P) |
| I-29 | Et$_3$N | 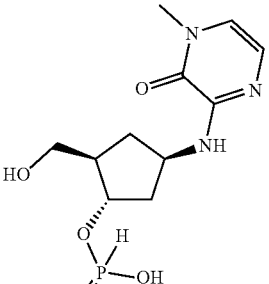<br>Int-68 | 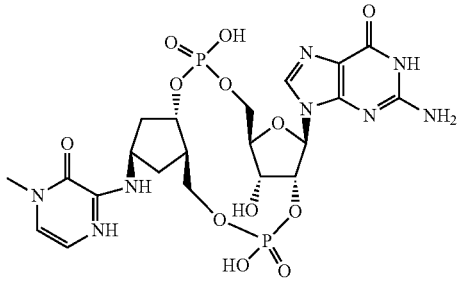 [SMILES: Cn1ccnc(N[C@@H]2C[C@@H]3COP(=O)(O)O[C@@H]4[C@H](O)[C@@H](COP(=O)(O)O[C@H]3C2)O[C@H]4n2cnc3c(=O)[nH]c(N)nc32)c1=O]<br>LCMS (FA): m/z = 647.2 (M + H) | $^1$H NMR (D$_2$O) δ 7.92 (s, 1H), 6.76 (d, J = 4.6 Hz, 1H), 6.63 (d, J = 4.9 Hz, 1H), 5.92 (d, J = 8.4 Hz, 1H), 5.39-5.32 (m, 1H), 4.82-4.75 (m, 1H), 4.62 (d, J = 4.1 Hz, 1H), 4.38-4.35 (m, 1H), 4.17-4.11 (m, 3H), 4.03-3.98 (m, 1H), 3.87-3.80 (m, 1H), 3.29 (s, 3H), 3.12 (q, J = 7.4 Hz, 16H), 2.45-2.32 (m, 2H), 2.30-2.22 (m, 1H), 2.07 (td, J = 6.8, 13.2 Hz, 1H), 1.40-1.33 (m, 1H), 1.20 (t, J = 7.3 Hz, 24H). $^{31}$P NMR (D$_2$O) δ −0.72 (s, 1P), −0.90 (s, 1P) |
| I-27 | Et$_3$N | 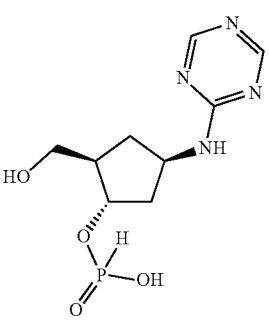 [SMILES: O=[PH](O)O[C@H]1C[C@H](Nc2ncncn2)C[C@@H]1CO]<br>Int-79 | 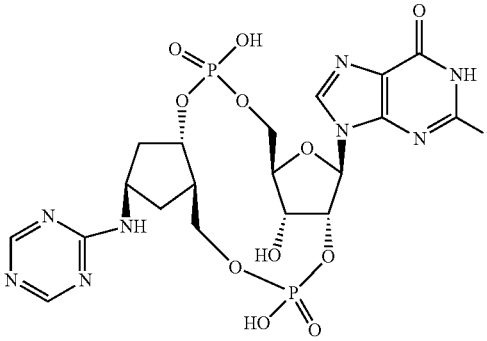<br>LCMS (FA): m/z = 618.0 (M + H) | $^1$H NMR (D$_2$O) δ 8.48 (s, 1H), 8.36 (s, 1H), 8.02 (s, 1H), 6.00 (d, J = 8.4 Hz, 1H), 5.33 (dt, J = 4.2, 8.5 Hz, 1H), 4.77-4.73 (m, 1H), 4.62 (d, J = 4.2 Hz, 1H), 4.43-4.35 (m, 2H), 4.22-4.08 (m, 2H), 3.98-3.91 (m, 1H), 3.81-3.73 (m, 1H), 3.14 (q, J = 7.3 Hz, 12H), 2.44-2.34 (m, 2H), 2.30-2.22 (m, 1H), 2.18-2.09 (m, 1H), 1.33-1.26 (m, 1H), 1.22 (t, J = 7.3 Hz, 18H). $^{31}$P NMR (D$_2$O) δ −0.50 (s, 1P), −0.78 (s, 1P) |

\* The benzoyl group in this compound was removed under the conditions used in example 14 step 3

\*\* The benzoyl group in this compound was removed using the following procedure: N-(6-{[(5R,7R,8R,12aR,14R,15aS,16R)-7-(2-amino-6-oxo-1,6-dihydro-9H-purin-9-yl)-16-{[tert-butyl(dimethyl)silyl]oxy}-2,10-dihydroxy-2,10-dioxidodecahydro-5,8-methanocyclopenta[l][1,3,6,9,11,2,10]pentaoxadiphosphacyclotetradecin-14-yl]amino}pyrimidin-4-yl)benzamide (210 mg, 0.247 mmol) was dissolved in ammonium hydroxide (10 mL) and the reaction mixture was heated in a sealed tube at 50° C. for 24 h. Further ammonium hydroxide (5 mL) was added and heating was continued for 24 h. The reaction mixture was concentrated and concentrated from toluene. The crude compound was purified by reverse phase flash column chromatography (10-100% ACN in aqueous ammonium acetate (10 mM)) to provide 2-amino-9-[(5R,7R,8R,12aR,14R,15aS,16R)-14-[(6-aminopyrimidin-4-yl)amino]-16-{[tert-butyl(dimethyl)silyl]oxy}-2,10-dihydroxy-2,10-dioxidodecahydro-5,8-methanocyclopenta[l][1,3,6,9,11,2,10]pentaoxadiphosphacyclotetradecin-7-yl]-1,9-dihydro-6H-purin-6-one (82 mg, 45%). LCMS (AA): m/z=746.3 (M+H).

\*\*\* Both TBS groups in this compound were removed under the conditions used in Example 14, Step 4.

\*\*\*\* Purified by preparative HPLC (AA)

Example 16

2-amino-9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one Diastereomer 1 (I-5a), Diastereomer 2 (I-5b), Diastereomer 3 (I-5c), Diastereomer 4 (I-5d)

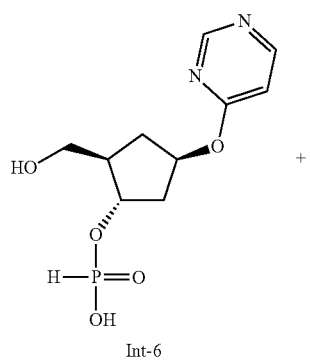

Int-6

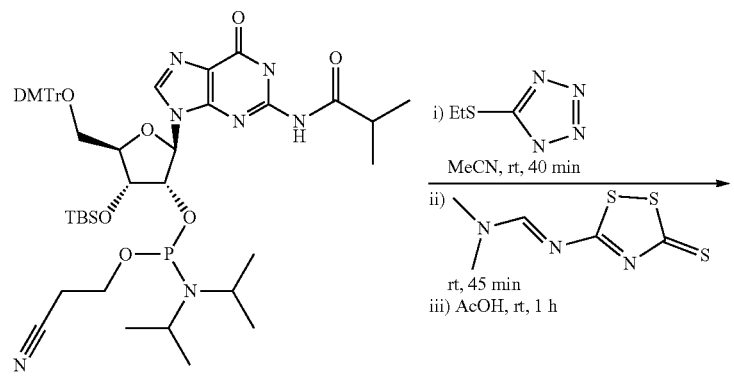

-continued
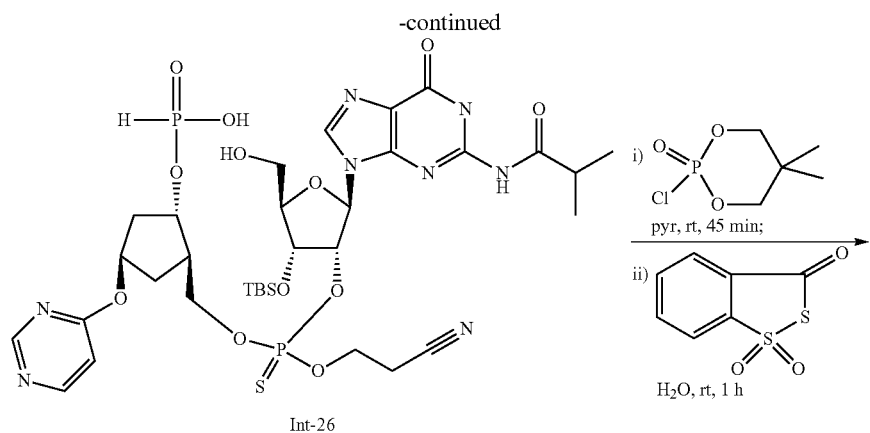
Int-26
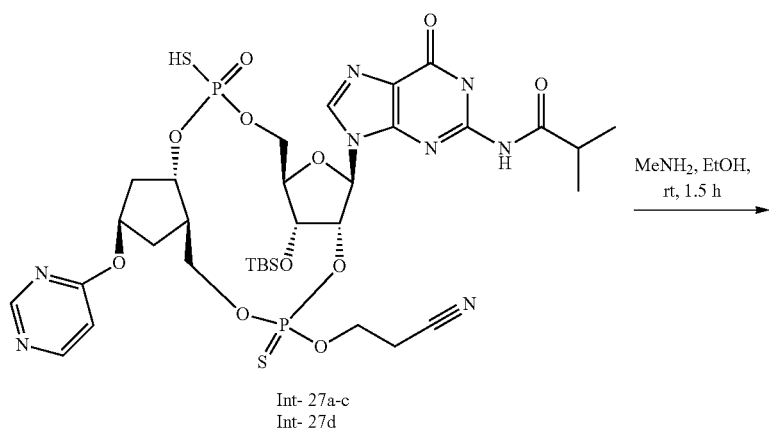
Int-27a-c
Int-27d
MeNH₂, EtOH,
rt, 1.5 h
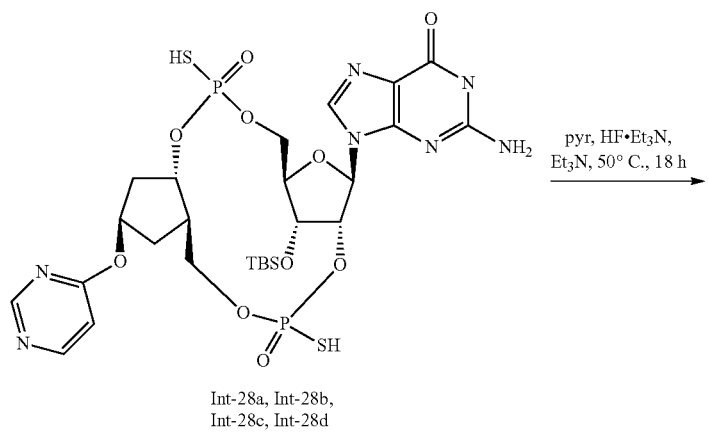
Int-28a, Int-28b,
Int-28c, Int-28d
pyr, HF·Et₃N,
Et₃N, 50° C., 18 h
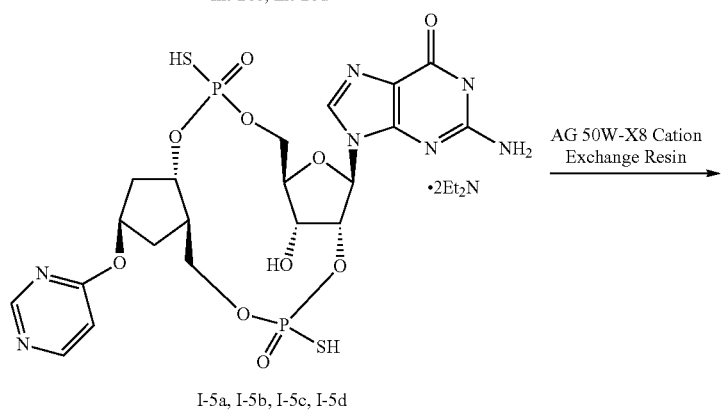
I-5a, I-5b, I-5c, I-5d
AG 50W-X8 Cation
Exchange Resin

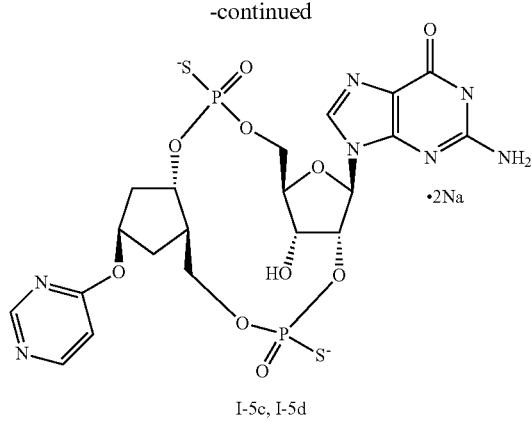

I-5c, I-5d

Step 1: (1S,2R,4R)-2-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-(pyrimidin-4-yloxy) cyclopentyl hydrogen phosphonate, and (1S,2R,4R)-2-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-(pyrimidin-4-yloxy) cyclopentyl hydrogen phosphonate, Intermediate 26

A mixture of Intermediate 6 (487 mg, 1.78 mmol) and N-[9-[(2R,3R,4R,5R)-5-[[bis(4-methoxyphenyl)-phenylmethoxy]methyl]-4-[tert-butyl(dimethyl)silyl]oxy-3-[2-cyanoethoxy-(diisopropylamino)phosphanyl]oxy-tetrahydrofuran-2-yl]-6-oxo-1H-purin-2-yl]-2-methyl-propanamide (2.24 g, 2.31 mmol) were dissolved in ACN and concentrated to dryness three times. The residue was then dissolved in ACN (6.51 mL) under argon. In a separate flask, 5-(ethylthio)-1H-tetrazole (694 mg, 5.33 mmol) was dissolved in ACN and concentrated (3×10 mL), dissolved in ACN (3 mL) and added to the reaction mixture. The resulting reaction mixture was allowed to stir at rt for 40 min. ((Dimethylamino-methylidene)amino)-3H-1,2,4-dithiazoline-3-thione (437 mg, 2.13 mmol) was added as a solid and the reaction mixture was allowed to stir at rt for 45 min. The solvent was evaporated, and then the residue was dried under vacuum for 10 min. The residue was dissolved in a mixture of acetic acid (7.0 mL) and water (1.8 mL), sonicated briefly and then allowed to stir at rt for 1 h. The reaction mixture was diluted with dry toluene and evaporated to dryness (3×15 mL) to give a yellow oil. The crude mixture was purified by silica gel chromatography (0-50% MeOH in DCM) to provide Intermediate 26 (971 mg, 63%) as a mixture of two diastereomers. LCMS (FA): m/z=873.3 (M+H).

Step 2: N-{9-[(2R,5R,7R,8R,10R,12aR,14R,15aS,16R)-16-{[tert-butyl(dimethyl)silyl]oxy}-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, and N-{9-[(2S,5R,7R,8R,10R,12aR,14R,15aS,16R)-16-{[tert-butyl(dimethyl)silyl]oxy}-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, and N-{9-[(2R,5R,7R,8R,10S,12aR,14R,15aS,16R)-16-{[tert-butyl(dimethyl)silyl]oxy}-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, and N-{9-[(2S,5R,7R,8R,10S,12aR,14R,15aS,16R)-16-{[tert-butyl(dimethyl)silyl]oxy}-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediates 27a-d Intermediate 26 (969 mg, 1.11 mmol) was dissolved in dry acetonitrile and concentrated to dryness (3×10 mL), dried under vacuum for 10 min, and then dissolved in pyridine (22 mL) under a nitrogen atmosphere. 2-chloro-5,5-dimethyl-1,3,2-dioxaphosphorinane 2-oxide (717 mg, 3.89 mmol) was added. The reaction mixture was allowed to stir at rt for 45 min. Water was added (0.70 mL, 38.9 mmol) followed by 3H-1,2-benzodithiol-3-one 1,1-dioxide (269 mg, 1.33 mmol), and the reaction mixture was allowed to stir at rt under nitrogen for 60 min. An additional portion of 3H-1,2-benzodithiol-3-one 1,1-dioxide (67.0 mg, 0.331 mmol) was added and stirring was continued for 10 min. Toluene was added and the mixture was concentrated, then concentrated from toluene (3×25 mL) to provide a mixture of four diastereomers, two major and two minor. The crude mixture was adsorbed onto silica gel and purified by silica gel chromatography (0-50% MeOH in DCM). Intermediates 27a-c eluted as a mixture (520 mg, 53%), and Intermediate 27d was cleanly obtained (230 mg, 23%). LCMS (FA): m/z=887.3 (M+H).

Step 3: 2-amino-9-[(2R,5R,7R,8R,10S,12aR,14R, 15aS,16R)-16-{[tert-butyl(dimethyl) silyl]oxy}-2, 10-dioxido-14-(pyrimidin-4-yloxy)-2,10-disulfanyl-decahydro-5,8-methanocyclopenta[l][1,3,6,9,11,2, 10]pentaoxadiphosphacyclotetradecin-7-yl]-1,9-dihydro-6H-purin-6-one, or 2-amino-9-[(2S,5R,7R,8R,10S,12aR,14R,15aS, 16R)-16-{[tert-butyl(dimethyl) silyl]oxy}-2,10-di-oxido-14-(pyrimidin-4-yloxy)-2,10-disulfanyldeca-hydro-5,8-methanocyclopenta[l][1,3,6,9,11,2,10] pentaoxadiphosphacyclotetradecin-7-yl]-1,9-dihydro-6H-purin-6-one, or 2-amino-9-[(2R,5R,7R,8R,10R,12aR,14R,15aS, 16R)-16-{[tert-butyl(dimethyl) silyl]oxy}-2,10-di-oxido-14-(pyrimidin-4-yloxy)-2,10-disulfanyldeca-hydro-5,8-methanocyclopenta[l][1,3,6,9,11,2,10] pentaoxadiphosphacyclotetradecin-7-yl]-1,9-dihydro-6H-purin-6-one, or 2-amino-9-[(2S,5R,7R,8R,10R,12aR,14R,15aS, 16R)-16-{[tert-butyl(dimethyl)silyl]oxy}-2,10-di-oxido-14-(pyrimidin-4-yloxy)-2,10-disulfanyldeca-hydro-5,8-methanocyclopenta[l][1,3,6,9,11,2,10] pentaoxadiphosphacyclotetradecin-7-yl]-1,9-dihydro-6H-purin-6-one, Intermediates 28a-c The mixture of Intermediates 27a-c (473 mg, 0.533 mmol) was dissolved in methylamine (33% in EtOH, 16 mL, 129 mmol) and the reaction mixture was allowed to stir under an atmosphere of nitrogen at rt for 90 min. The reaction mixture was concentrated and dried on vacuum for 10 min. The UPLC/MS of this crude mixture shows three peaks with desired product mass (one major peak). The crude mixture was purified by reverse phase flash column chromatography (10-100% ACN in aqueous ammonium acetate (10 mM)) to give Intermediate 28a (27 mg, 7%), Intermediate 28b (55 mg, 11%) and Intermediate 28c (131 mg, 32%). LCMS (AA): m/z=764.2 (M+H).

Intermediate 27d (227 mg, 0.256 mmol) from step 2 was treated in an analogous fashion to the above procedure to provide Intermediate 28d (150 mg, 77%)

Step 4: 2-amino-9-[(2R,5R,7R,8R,10S,12aR,14R, 15aS,16R)-16-hydroxy-2,10-dioxido-14-(pyrimidin-4-yloxy)-2,10-disulfanyldecahydro-5,8-methanocy-clopenta[l][1,3,6,9,11,2,10] pentaoxadiphosphacyclotetradecin-7-yl]-1,9-dihydro-6H-purin-6-one, or 2-amino-9-[(2S,5R,7R,8R,10S,12aR,14R,15aS, 16R)-16-hydroxy-2,10-dioxido-14-(pyrimidin-4-yloxy)-2,10-disulfanyldecahydro-5,8-methanocyclo-penta[l][1,3,6,9,11,2,10] pentaoxadiphosphacyclotetradecin-7-yl]-1,9-dihydro-6H-purin-6-one, or 2-amino-9-[(2R,5R,7R,8R,10R,12aR,14R,15aS, 16R)-16-hydroxy-2,10-dioxido-14-(pyrimidin-4-yloxy)-2,10-disulfanyldecahydro-5,8-methanocyclo-penta[l][1,3,6,9,11,2,10] pentaoxadiphosphacyclotetradecin-7-yl]-1,9-dihydro-6H-purin-6-one, or 2-amino-9-[(2S,5R,7R,8R,10R,12aR,14R,15aS, 16R)-16-hydroxy-2,10-dioxido-14-(pyrimidin-4-yloxy)-2,10-disulfanyldecahydro-5,8-methanocyclo-penta[l][1,3,6,9,11,2,10] pentaoxadiphosphacyclotetradecin-7-yl]-1,9-dihydro-6H-purin-6-one, I-5a-d Intermediate 28c (131 mg, 0.172 mmol) was taken up in pyridine (0.86 mL) to give a suspension. Triethylamine trihydrofluoride (0.14 mL, 0.86 mmol) was added, followed by TEA (2.1 mL). The reaction mixture was sealed in a propylene tube and allowed to stir at 50° C. overnight. The reaction mixture was diluted with water (3.21 mL), and then a solution of $CaCl_2$) in water (0.556 M in water, 3.2 mL, 1.72 mmol) was added. The cloudy white mixture was allowed to stir at rt for 60 min. The suspension was filtered through Celite, and the Celite was washed with water (5×5 mL). The clear aqueous filtrate was concentrated to a solid residue. No HF was observed by $^{19}F$ NMR. The crude compound was adsorbed onto Celite and purified by reverse phase flash column chromatography (10% ACN in aqueous triethylam-monium acetate (10 mM)) to provide clean I-5c as a N,N-diethylethanamine salt (78 mg, 53%). LCMS (AA) m/z=650.1 (M+H).

Step 5: (2S,5R,7R,8R,10S,12aR,14R,15aS,16R)-7-(2-amino-6-oxo-1,6-dihydro-9H-purin-9-yl)-16-hydroxy-14-(pyrimidin-4-yloxy)decahydro-5,8-methanocyclopenta[l][1,3,6,9,11,2,10]pentaoxadiphosphacyclotetradecine-2,10-bis(thiolate) 2,10-dioxide, or (2S,5R,7R,8R,10R,12aR,14R,15aS,16R)-7-(2-amino-6-oxo-1,6-dihydro-9H-purin-9-yl)-16-hydroxy-14-(pyrimidin-4-yloxy)decahydro-5,8-methanocyclopenta[l][1,3,6,9,11,2,10]pentaoxadiphosphacyclotetradecine-2,10-bis(thiolate) 2,10-dioxide, or (2R,5R,7R,8R,10S,12aR,14R,15aS,16R)-7-(2-amino-6-oxo-1,6-dihydro-9H-purin-9-yl)-16-hydroxy-14-(pyrimidin-4-yloxy)decahydro-5,8-methanocyclopenta[l][1,3,6,9,11,2,10]pentaoxadiphosphacyclotetradecine-2,10-bis(thiolate) 2,10-dioxide, or (2R,5R,7R,8R,10R,12aR,14R,15aS,16R)-7-(2-amino-6-oxo-1,6-dihydro-9H-purin-9-yl)-16-hydroxy-14-(pyrimidin-4-yloxy)decahydro-5,8-methanocyclopenta[l][1,3,6,9,11,2,10]pentaoxadiphosphacyclotetradecine-2,10-bis(thiolate) 2,10-dioxide, (I-5c)

800 mg Bio-Rad BT AG 50W-X8 resin, 100-200 mesh hydrogen form was slurried in water (8 mL) then loaded in a glass column (0.5"×6"), excess water was drained by gravity. NaOH (1 N in water, 8 mL) was passed through the column via gravity. The column was then rinsed with water (16 mL) via gravity. pH paper was used to confirmed the final portion of water was neutral. The bis-N,N-diethylethanamine salt of I-5c (40.5 mg, 0.0475 mmol) was dissolved in 1 mL water and loaded onto the column, and another 1 mL of water was used to rinse the vial onto the column. The column was eluted with 10 mL water, and collected in two fractions in scintillation vials, the first one ~8 mL and the second fraction ~4 mL. By UPLC/MS only the first fraction (~8 mL) contained product, so this fraction was lyophilized overnight to give I-5c disodium salt (31.0 mg, 94%). LCMS (AA): m/z=650.1 (M+H). $^1$H NMR (D$_2$O) δ 8.63 (s, 1H), 8.39 (d, J=6.0 Hz, 1H), 8.02 (s, 1H), 6.75 (dd, J=6.0, 0.9 Hz, 1H), 5.98 (d, J=8.4 Hz, 1H), 5.46 (td, J=9.3, 3.9 Hz, 1H), 5.35-5.42 (m, 1H), 4.98 (quin, J=6.7 Hz, 1H), 4.63-4.69 (m 1H), 4.43 (br d, J=1.5 Hz, 1H), 4.34 (ddd, J=11.6, 9.0, 2.4 Hz, 1H), 4.09 (dd, J=12.1, 2.2 Hz, 1H), 3.95-4.03 (m, 1H), 3.81-3.90 (m, 1H), 2.37-2.60 (m, 3H), 2.29 (dt, J=13.8, 6.6 Hz, 1H), 1.55-1.72 (m, 1H). $^{31}$P NMR (D$_2$O) δ 54.13 (s, 1P), 52.59 (s, 1P).

Example 16A

The compounds listed below were prepared as described in Example 16 starting with Step 4, substituting the starting material shown in the table for Intermediate 28c. In cases where the N,N-diethylethanamine salt was obtained, step 5 of Example 16 was not performed.

| ML number product | Salt form | Starting material | LCMS data | NMR data |
|---|---|---|---|---|
| I-5a | Et$_3$N | Intermediate 28a | LCMS (AA): m/z = 650.1 (M + H). | $^1$H NMR (D$_2$O) δ 8.64 (s, 1H), 8.47 (s, 1H), 8.40 (d, J = 6.1 Hz, 1H), 6.88 (d, J = 6.1 Hz, 1H), 6.02 (d, J = 8.4 Hz, 1H), 5.32-5.46 (m, 2H), 4.96-5.06 (m, 1H), 4.60 (d, J = 4.2 Hz, 1H), 4.40 (d, J = 2.0 Hz, 1H), 4.02-4.22 (m, 3H), 3.85 (dt, J = 11.1, 3.1 Hz, 1H), 3.15 (q, J = 7.3 Hz, 8H), 2.40-2.57 (m, 4H), 1.51-1.63 (m, 1H), 1.23 (t, J = 7.3 Hz, 12H); $^{31}$P NMR (D$_2$O) δ 58.98 (s, 1P), 53.96 (s, 1P). |
| I-5b | Et$_3$N | Intermediate 28b | LCMS (AA): m/z = 650.0 (M + H). | $^1$H NMR (D$_2$O) δ 8.64 (s, 1H), 8.40 (d, J = 6.0 Hz, 1H), 8.10 (s, 1H), 6.86 (d, J = 6.0 Hz, 1H), 5.99 (d, J = 8.4 Hz, 1H), 5.44 (spt, J = 4.4 Hz, 2H), 5.02-5.10 (m, 1H), 4.54 (d, J = 4.3 Hz, 1H), 4.41 (d, J = 2.3 Hz, 1H), 4.31 (ddd, J = 12.2, 10.1, 2.2 Hz, 1H), 3.98-4.13 (m, 2H), 3.83 (dt, J = 10.5, 2.9 Hz, 1H), 3.15 (q, J = 7.3 Hz, 12H), 2.37-2.55 (m, 4H), 1.54-1.66 (m, 1H), 1.23 (t, J = 7.2 Hz, 18H); $^{31}$P NMR (D$_2$O) δ 58.60 (s, 1P), 54.10 (s, 1P). |
| I-5d | 2•Na | Intermediate 28d | LCMS (AA): m/z = 650.1 (M + H). | $^1$H NMR (D$_2$O) δ 8.64 (s, 1H), 8.40 (br d, J = 6.0 Hz, 1H), 8.10 (s, 1H), 6.86 (br d, J = 5.4 Hz, 1H), 5.99 (br d, J = 8.3 Hz, 1H), 5.35-5.51 (m, 2H), 5.06 (br s, 1H), 4.55 (br d, J = 3.8 Hz, 1H), 4.41 (br s, 1H), 4.25-4.37 (m, 1H), 3.97-4.15 (m, 2H), 3.77-3.88 (m, 1H), 2.36-2.59 (m, 4H), 1.60 (br q, J = 7.6 Hz, 1H); $^{31}$P NMR (D$_2$O) δ 58.61 (s, 1P), 54.13 (s, 1P). |

Although compounds I-5b and I-5d were isolated separately, further analysis by NMR and MS showed that I-5b and I-5d are the same compound.

Example 16B

Alternative synthesis of 2-amino-9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, I-5c

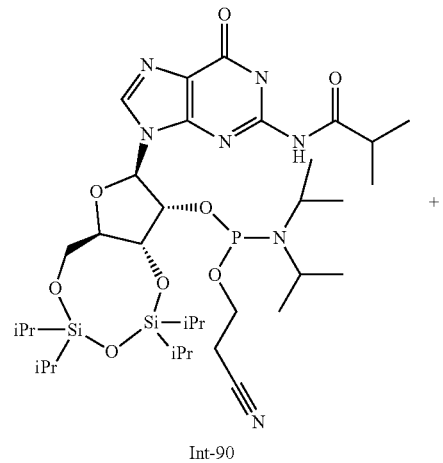
Int-90

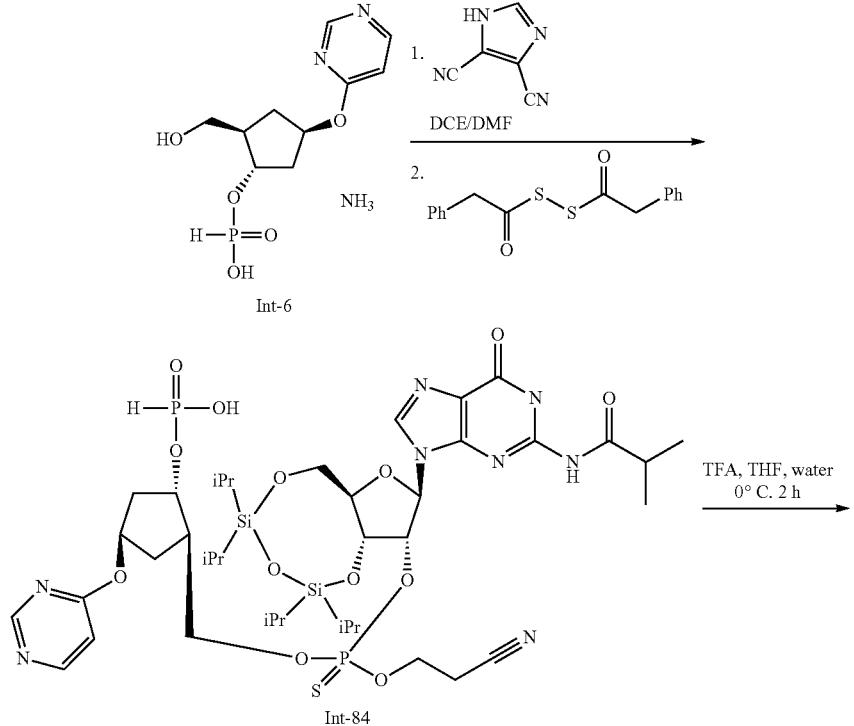
Int-84

-continued
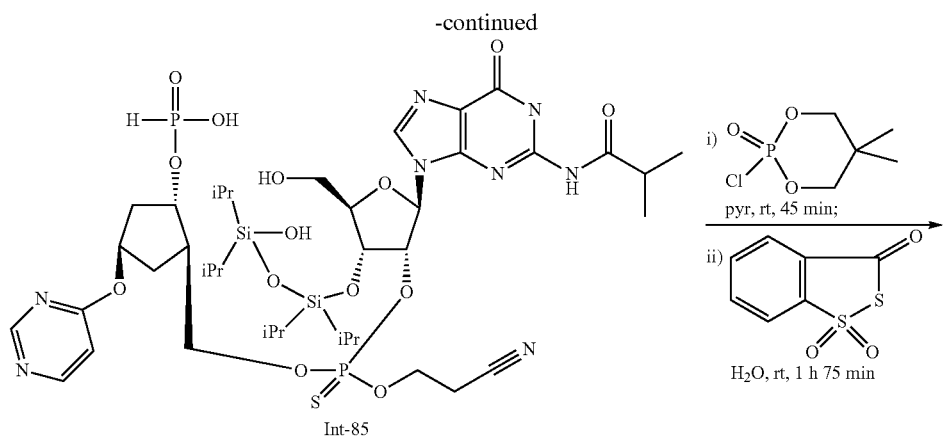
Int-85
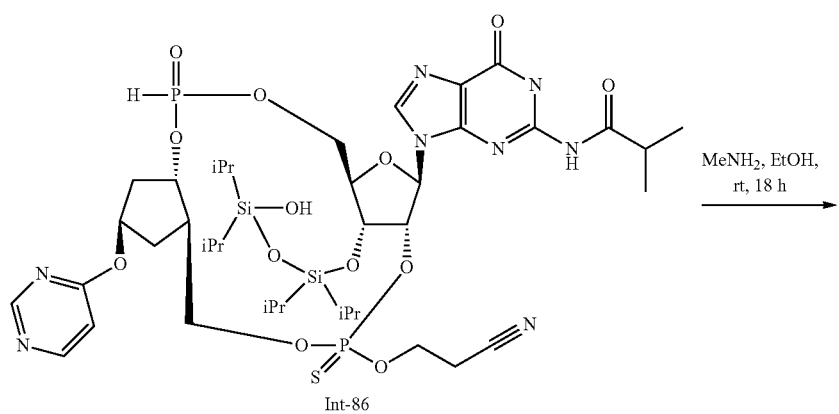
Int-86
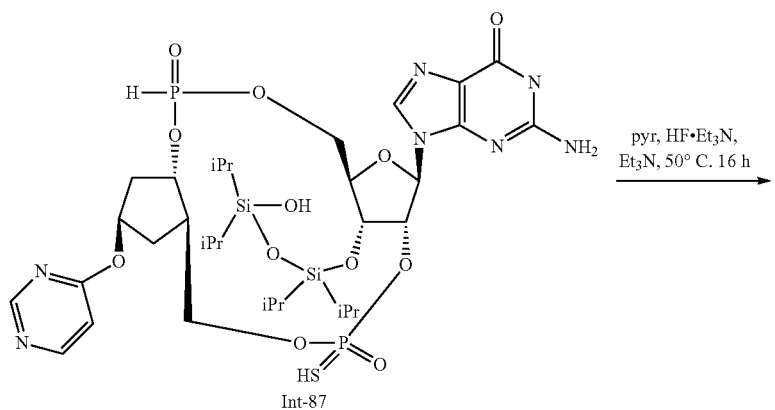
Int-87
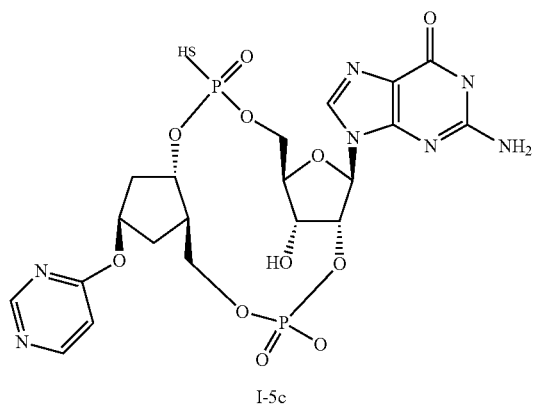
I-5c Step 1: (1S,2R,4R)-2-({[(R)-(2-cyanoethoxy)({(6aR,8R,9R,9aR)-8-[2-(isobutyrylamino)-6-oxo-1,6-dihydro-9H-purin-9-yl-2,2,4,4-tetraisopropyltetrahydro-6H-furo[3,2-f][1,3,5,2,4]trioxadisilocin-9-yl}oxy)phosphorothioyl]oxy}methyl)-4-(pyrimidin-4-yloxy)cyclopentyl hydrogen phosphonate or (1S,2R,4R)-2-({[(S)-(2-cyanoethoxy)({(6aR,8R,9R,9aR)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy)phosphorothioyl]oxy}methyl)-4-(pyrimidin-4-yloxy)cyclopentyl hydrogen phosphonate, Intermediate 84

A mixture of Intermediate 6 ammonium salt (3.40 g, 11.7 mmol) and Intermediate 90 (13.0 g, 16.4 mmol) were dissolved in dry ACN and concentrated (3×100 mL). This was repeated with dry toluene (100 mL) and the mixture was finally dried under vacuum for 30 min DMF (19 mL) and DCE (77 mL) were added to provide a suspension. In a separate flask 4,5-dicyanoimidazole (2.90 g, 24.5 mmol) was dissolved in dry ACN and concentrated to dryness (2×50 mL); this was repeated with dry toluene (50 mL) and the resulting mixture was then dissolved in DMF (4.4 mL) and DCE (17.6 mL) and added to the reaction mixture under an atmosphere of nitrogen. The reaction mixture was allowed to stir at rt for 3 h. Bis(phenylacetyl)disulfide (3.89 g, 12.9 mmol) was added as a solid and the reaction mixture was allowed to stir for 90 min. The DCE was evaporated and the mixture was diluted with EtOAc (240 mL), THE (120 mL) and 1:1 aq. sat. NaHCO₃ solution/water (120 mL). The organic phase was separated and to the aqueous phase was added EtOAc (240 mL), THE (120 mL), and brine (40 mL). The organic phase was separated and the aqueous phase was extracted with EtOAc (250 mL). The combined organic phases were washed with brine (60 mL), dried over Na₂SO₄ and concentrated. A mixture of methanol and DCM (10% MeOH, 100 mL) was added to the oily mixture and the precipitate was filtered and washed with DCM (5×5 mL). The filtrate was evaporated and the crude product was adsorbed onto celite and purified by silica gel chromatography in two portions (5-40% MeOH in DCM) to give Intermediate 84 as the first eluting peak (4.95, 40%) LCMS (AA): m/z=1001.1 (M+H).

Step 2: (1S,2R,4R)-2-({[(R)-(2-cyanoethoxy)({(2R,3R,4R,5R)-5-(hydroxymethyl)-4-[(3-hydroxy-1,1,3,3-tetraisopropyldisiloxanyl)oxy]-2-[2-(isobutyrylamino)-6-oxo-1,6-dihydro-9H-purin-9-yl]tetrahydrofuran-3-yl}oxy)phosphorothioyl]oxy}methyl)-4-(pyrimidin-4-yloxy)cyclopentyl hydrogen phosphonate or (1S,2R,4R)-2-({[(S)-(2-cyanoethoxy)({(2R,3R,4R,5R)-5-(hydroxymethyl)-4-[(3-hydroxy-1,1,3,3-tetraisopropyldisiloxanyl)oxy]-2-[2-(isobutyrylamino)-6-oxo-1,6-dihydro-9H-purin-9-yl]tetrahydrofuran-3-yl}oxy)phosphorothioyl]oxy}methyl)-4-(pyrimidin-4-yloxy)cyclopentyl hydrogen phosphonate, Intermediate 85

Intermediate 85 was prepared from Intermediate 84 following the procedure described in Example 49, Step 2. LCMS (AA): m/z=1019.2 (M+H).

Step 3: N-{9-[(2S,5R,7R,8R,10R,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10R,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2S,5R,7R,8R,10S,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10S,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide Intermediate 85 (5.36 g, 5.26 mmol) was dissolved in dry ACN and concentrated to dryness (3×30 mL), dried under vacuum for 10 min, and then dissolved in pyridine (105 mL) under a nitrogen atmosphere. 2-Chloro-5,5-dimethyl-1,3,2-dioxaphosphorinane 2-oxide (3.40 g, 18.4 mmol) was added. The reaction mixture was allowed to stir at rt for 45 min. Water was added (3.32 mL, 184 mmol) followed by 3H-1,2-benzodithiol-3-one 1,1-dioxide (1.60 g, 7.89 mmol), and the reaction mixture was allowed to stir at rt under nitrogen for 1 hr 15 min. The mixture was concentrated and diluted with EtOAc (240 mL) and 5% NaHCO₃ (80 mL) then extracted. The phases were separated and the aqueous phase was diluted with brine (25 mL) then extracted with EtOAc (240 mL then 200 mL). The combined organic phases were washed with brine (60 mL) then dried over Na₂SO₄ and evaporated to give the crude product as a single major diastereomer containing trace amount of a minor diastereomer. The crude material was adsorbed onto celite and purified by silica gel chromatography (0-10% MeOH in DCM) to give Intermediate 86 (2.01 g, 37%). LCMS (AA): m/z=1033.2 (M+H).

Step 4: 2-amino-9-[(2S,5R,7R,8R,10S,12aR,14R, 15aS,16R)-16-[(3-hydroxy-1,1,3,3-tetraisopropyld- isiloxanyl)oxy]-2,10-dioxido-14-(pyrimidin-4- yloxy)-2,10-disulfanyldecahydro-5,8- methanocyclopenta[l][1,3,6,9,11,2,10] pentaoxadiphosphacyclotetradecin-7-yl]-1,9- dihydro-6H-purin-6-one or 2-amino-9-[(2S,5R,7R,8R,10R,12aR,14R,15aS, 16R)-16-[(3-hydroxy-1,1,3,3-tetraisopropyldisiloxa- nyl)oxy]-2,10-dioxido-14-(pyrimidin-4-yloxy)-2,10- disulfanyldecahydro-5,8-methanocyclopenta[l][1,3, 6,9,11,2,10]pentaoxadiphosphacyclotetradecin-7-yl]- 1,9-dihydro-6H-purin-6-one or 2-amino-9-[(2R,5R,7R,8R,10S,12aR,14R,15aS, 16R)-16-[(3-hydroxy-1,1,3,3-tetraisopropyldisiloxa- nyl)oxy]-2,10-dioxido-14-(pyrimidin-4-yloxy)-2,10- disulfanyldecahydro-5,8-methanocyclopenta[l][1,3, 6,9,11,2,10]pentaoxadiphosphacyclotetradecin-7-yl]- 1,9-dihydro-6H-purin-6-one or 2-amino-9-[(2R,5R,7R,8R,10R,12aR,14R,15aS, 16R)-16-[(3-hydroxy-1,1,3,3-tetraisopropyldisiloxa- nyl)oxy]-2,10-dioxido-14-(pyrimidin-4-yloxy)-2,10- disulfanyldecahydro-5,8-methanocyclopenta[l][1,3, 6,9,11,2,10]pentaoxadiphosphacyclotetradecin-7-yl]- 1,9-dihydro-6H-purin-6-one, Intermediate 87

Intermediate 86 (2.01 g, 1.95 mmol) was dissolved in a solution of methylamine (33% in EtOH, 58.4 mL, 469 mmol) under an atmosphere of nitrogen and the reaction mixture was allowed to stir at rt for 3 h After this time, another portion of methylamine (33% in EtOH, 15.0 mL, 120 mmol) was added and the reaction mixture was allowed to stir at rt for 1 h. The reaction mixture was concentrated and starting material was seen by LCMS. More methylamine (33% in EtOH, 10.0 mL, 80.3 mmol) was added and the reaction mixture was allowed to stir at rt for 1 h when another portion of methylamine (33% in EtOH, 10.0 mL, 80.3 mmol) was added and the reaction mixture was allowed to stir for 18 h. The reaction mixture was concentrated then placed under vacuum for 10 minutes. The crude material was adsorbed onto celite and purified by silica gel chromatography (2-40% MeOH in DCM) to give Intermediate 87 (1.07 g, 60.4%). LCMS (AA): m/z=910.1 (M+H).

Step 5: 2-amino-9-[(2R,5R,7R,8R,10S,12aR,14R, 15aS,16R)-16-hydroxy-2,10-dioxido-14-(pyrimidin- 4-yloxy)-2,10-disulfanyldecahydro-5,8-methanocy- clopenta[l][1,3,6,9,11,2,10] pentaoxadiphosphacyclotetradecin-7-yl]-1,9- dihydro-6H-purin-6-one, or 2-amino-9-[(2S,5R,7R,8R,10S,12aR,14R,15aS, 16R)-16-hydroxy-2,10-dioxido-14-(pyrimidin-4- yloxy)-2,10-disulfanyldecahydro-5,8-methanocyclo- penta[l][1,3,6,9,11,2,10] pentaoxadiphosphacyclotetradecin-7-yl]-1,9- dihydro-6H-purin-6-one, or 2-amino-9-[(2R,5R,7R,8R,10R,12aR,14R,15aS, 16R)-16-hydroxy-2,10-dioxido-14-(pyrimidin-4- yloxy)-2,10-disulfanyldecahydro-5,8-methanocyclo- penta[l][1,3,6,9,11,2,10] pentaoxadiphosphacyclotetradecin-7-yl]-1,9- dihydro-6H-purin-6-one, or 2-amino-9-[(2S,5R,7R,8R,10R,12aR,14R,15aS, 16R)-16-hydroxy-2,10-dioxido-14-(pyrimidin-4- yloxy)-2,10-disulfanyldecahydro-5,8-methanocyclo- penta[l][1,3,6,9,11,2,10] pentaoxadiphosphacyclotetradecin-7-yl]-1,9- dihydro-6H-purin-6-one, I-5c Intermediate 87 (553 mg mg, 0.608 mmol) was taken up in pyridine (3.04 mL, 37.6 mmol) to give a suspension. Triethylamine trihydrofluoride (0.505 mL, 3.04 mmol) was added, followed by TEA (7.60 mL, 54.0 mmol). The reaction mixture was sealed in a propylene tube and allowed to stir at 50° C. overnight. The reaction mixture was diluted with water (11.4 mL, 632 mmol). Then a solution of CaCl$_2$) (1.05 g, 9.12 mmol) in water (11.4 mL) was added. The cloudy white mixture was allowed to stir at rt for 60 min. The suspension was filtered through Celite, and the Celite was washed with water (7×5 mL). The slightly cloudy aqueous filtrate was filtered through celite again then concentrated to a solid residue. No HF was observed by $^{19}$F NMR. The crude compound was adsorbed onto Celite and purified by reverse phase flash column chromatography (0-15% ACN in aqueous triethylammonium acetate (10 mM)) to provide clean I-5c as the bis-N,N-diethyl-ethanamine salt (430 mg, 83.1%). LCMS (AA): m/z=650.0 (M+H).

Example 17

(1S,2R,4R)-2-{[bis(4-methoxyphenyl)(phenyl) methoxy]methyl}-4-(pyrimidin-4-ylamino)cyclopentyl 2-cyanoethyl diisopropylphosphoramidoite, Intermediate 31

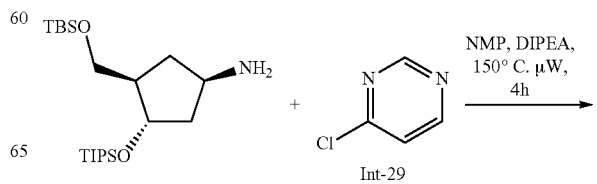

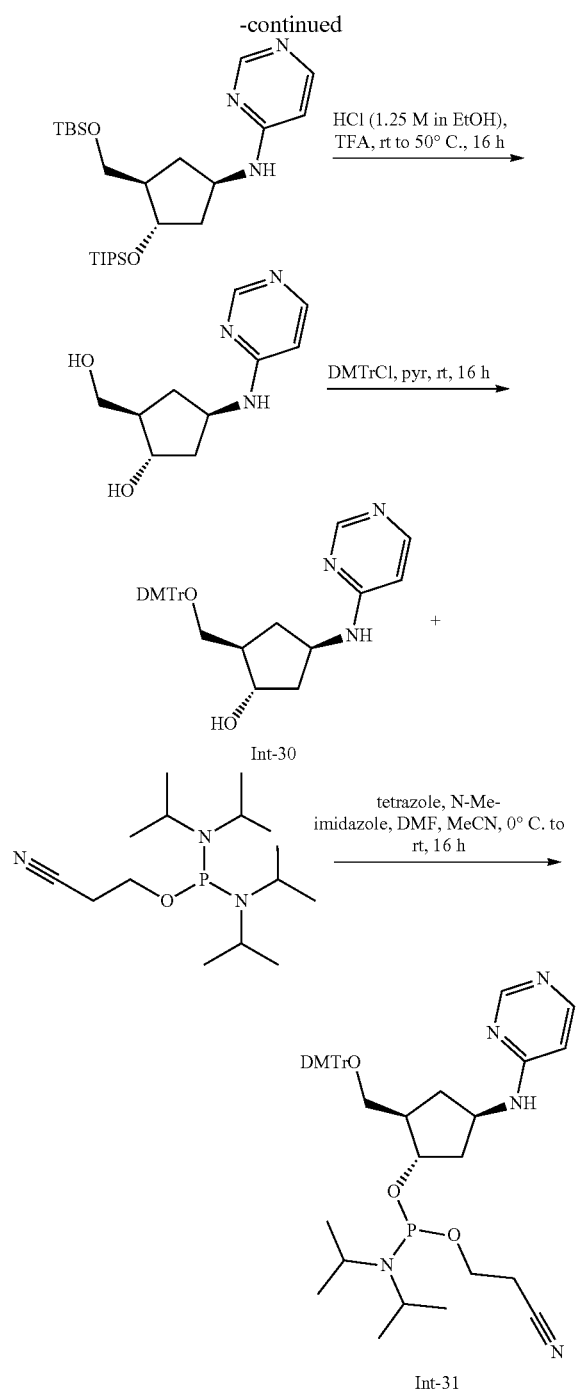

Int-30

Int-31

Step 1: N-{(1R,3R,4S)-3-({[tert-butyl(dimethyl) silyl]oxy}methyl)-4-[(triisopropylsilyl) oxy] cyclopentyl}pyrimidin-4-amine To a solution of 4-chloropyrimidine (916 mg, 7.68 mmol) in NMP (8.00 mL) was added DIPEA (3.35 mL, 19.2 mmol) at rt. Then (1R,3R,4S)-3-({[tert-butyl(dimethyl) silyl] oxy}methyl)-4-[(triisopropylsilyl)oxy]cyclopentanamine (2.57 g, 6.40 mmol) was added and the reaction mixture was allowed to stir for 5 min. The reaction mixture was heated under microwave irradiation at 150° C. for 4 h. The reaction mixture was cooled to rt and water was added then extracted with EtOAc. The combined organic phases were washed with brine, dried with $Na_2SO_4$ and concentrated. The crude compound was purified by silica gel chromatography (0-100% EtOAc in hexanes) to provide N-{(1R,3R,4S)-3-({[tert-butyl(dimethyl)silyl]oxy}methyl)-4-[(triisopropylsilyl)oxy]cyclopentyl}pyrimidin-4-amine (870 mg, 28%). LCMS (FA): m/z=480.4 (M+H).

Step 2: (1S,2R,4R)-2-(hydroxymethyl)-4-(pyrimidin-4-ylamino)cyclopentanol

N-{(1R,3R,4S)-3-({[tert-butyl(dimethyl)silyl]oxy}methyl)-4-[(triisopropylsilyl) oxy]cyclopentyl}pyrimidin-4-amine (860 mg, 1.79 mmol) was dissolved in HCl (1.25 M in EtOH, 2.00 mL, 2.50 mmol) and TFA (2.00 mL, 26.0 mmol). The reaction mixture was allowed to stir at rt overnight, then heated at 50° C. for 2 h. The reaction mixture was concentrated and the residue was concentrated from pyridine (3×15 mL). The crude compound was used directly in the next step without further purification.

Step 3: (1S,2R,4R)-2-{[bis(4-methoxyphenyl)(phenyl)methoxy]methyl}-4-(pyrimidin-4-ylamino)cyclopentanol, Intermediate 30

To a solution of (1S,2R,4R)-2-(hydroxymethyl)-4-(pyrimidin-4-ylamino) cyclopentanol (375 mg, 1.79 mmol) in pyridine (10.0 mL) was added DMTrCl (705 mg, 2.06 mmol). The reaction mixture was allowed to stir at rt overnight. The reaction mixture was concentrated and taken up in EtOAc. This solution was washed with brine, dried with $Na_2SO_4$ and concentrated. The crude compound was purified by silica gel chromatography (0-15% MeOH in EtOAc) to provide (1S,2R,4R)-2-{[bis(4-methoxyphenyl)(phenyl)methoxy]methyl}-4-(pyrimidin-4-ylamino)cyclopentanol (Intermediate 30, 490 mg, 53%). LCMS (FA): m/z=512.3 (M+H).

Step 4: (1S,2R,4R)-2-{[bis(4-methoxyphenyl)(phenyl)methoxy]methyl}-4-(pyrimidin-4-ylamino)cyclopentyl 2-cyanoethyl diisopropylphosphoramidite, Intermediate 31

Intermediate 30 (870 mg, 1.70 mmol) was dissolved in dry ACN and concentrated to dryness. The residue was taken up in DMF (2.2 mL). 1-Methylimidazole (83.7 mg, 1.07 mmol) and 1H-tetrazole (0.45 M in ACN, 4.50 mL, 2.04 mmol) were added. The reaction mixture was cooled to 0° C., then 2-cyanoethyl N,N,N',N'-tetraisopropylphosphorodiamidite (1.22 mL, 3.83 mmol) was added dropwise. The reaction mixture was then warmed to rt and allowed to stir for 16 h. The reaction mixture was diluted with EtOAc (100 mL) and washed with saturated aqueous $NaHCO_3$ solution (10 mL). The aqueous phase was extracted with EtOAc (2×60 mL). The combined organic phases were washed with brine, dried over $MgSO_4$ and concentrated. This crude compound was purified by silica gel chromatography (0-100% EtOAc in hexanes, with 0.5% TEA) to provide (1S,2R,4R)-2-{[bis(4-methoxyphenyl)(phenyl)methoxy]methyl}-4-(pyrimidin-4-ylamino) cyclopentyl 2-cyanoethyl diisopropylphosphoramidite (Intermediate 31, 880 mg, 73%) as a mixture of diastereomers. $^1$H NMR (DMSO-$d_6$) δ 8.38-8.41 (m, 1H), 7.99-8.03 (m, 1H), 7.36-7.43 (m, 3H), 7.28-7.34 (m, 2H), 7.20-7.28 (m, 5H), 6.85-6.92 (m, 4H), 6.39-6.43 (m, 1H), 4.10-4.26 (m, 1H), 3.73-3.76 (m, 6H), 3.62-3.72 (m, 1H), 3.46-3.59 (m, 4H), 3.09-3.15 (m, 1H), 2.86-3.02 (m, 1H), 2.72-2.77 (m, 1H), 2.61-2.66 (m, 1H), 2.29-2.42 (m, 1H), 2.16-2.27 (m, 1H), 2.00-2.15 (m, 1H), 1.64-1.75 (m, 1H), 1.25-1.38 (m, 1H), 1.00-1.22 (m, 12H). $^{31}$P NMR (DMSO-$d_6$) δ 146.69 (s, 0.5P), 146.39 (s, 0.5P).

Example 18

The compounds listed below were prepared as described in Example 17 starting with Step 4, substituting the starting material shown in the table for Intermediate 30.

| Starting material | Intermediate | NMR data |
|---|---|---|
| 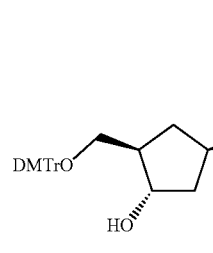 Int-5 | 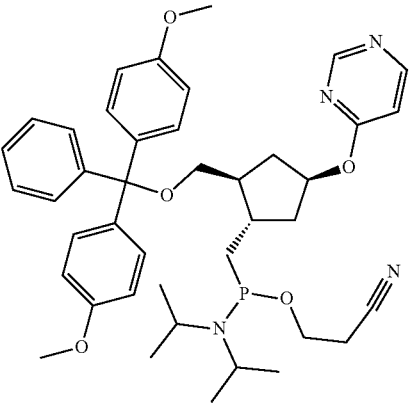 [SMILES: COc1ccc(C(OC[C@H]2C[C@@H](Oc3ccncn3)C[C@@H]2CP(OCCC#N)N(C(C)C)C(C)C)(c2ccccc2)c2ccc(OC)cc2)cc1] Int-32 | $^1$H NMR (DMSO-$d_6$) δ 8.76-8.78 (m, 1H), 8.48-8.51 (m, 1H), 7.34-7.40 (m, 2H), 7.18-7.33 (m, 7H), 6.79-6.89 (m, 5H), 5.41-5.50 (m, 1H), 4.19-4.35 (m, 1H), 3.72-3.76 (m, 6H), 3.62-3.71 (m, 1H), 3.46-3.61 (m, 3H), 3.10-3.16 (m, 1H), 2.96-3.09 (m, 1H), 2.62-2.75 (m, 2H), 2.41-2.48 (m, 1H), 2.20-2.31 (m, 1H), 2.05-2.19 (m, 1H), 1.94-2.04 (m, 1H), 1.52-1.65 (m, 1H), 1.01-1.24 (m, 12H). $^{31}$P NMR (DMSO-$d_6$) δ 146.88 (s, 0.5P), 146.49 (s, 0.5P). |
| 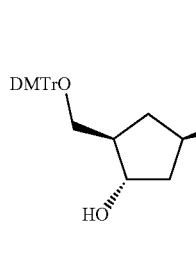 Int-95 | 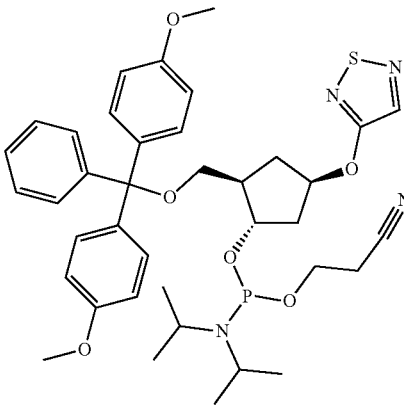 Int-96 | $^1$H NMR (DMSO-$d_6$) δ 8.29-8.26 (m, 1H), 7.37 (t, J = 7.0 Hz, 2H), 7.33-7.26 (m, 2H), 7.26-7.18 (m, 5H), 6.91-6.83 (m, 4H), 5.33-5.24 (m, 1H), 4.37-4.18 (m, 1H), 3.75-3.72 (m, 7H), 3.62-3.43 (m, 3H), 3.17-3.11 (m, 1H), 3.10-2.98 (m, 1H), 2.78-2.71 (m, 1H), 2.70-2.61 (m, 1H), 2.35-2.02 (m, 3H), 1.73-1.59 (m, 1H), 1.21-0.97 (m, 13H). $^{31}$P NMR (DMSO-$d_6$) δ 146.95 (s, 0.5P), 146.58 (s, 0.5P). |

Example 18A

The compounds listed below were prepared as described in Example 17 starting with Step 3, substituting the starting material shown in the table for (1S,2R,4R)-2-(hydroxymethyl)-4-(pyrimidin-4-ylamino)cyclopentanol

| Starting material | Intermediate | NMR data |
|---|---|---|
| 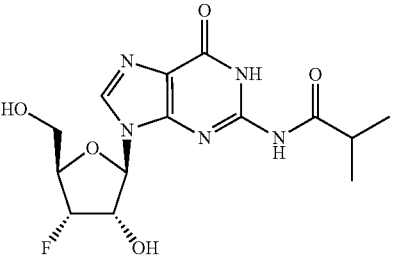 [SMILES: CC(C)C(=O)Nc1nc2c(ncn2[C@@H]2O[C@H](CO)[C@@H](F)[C@H]2O)c(=O)[nH]1] | 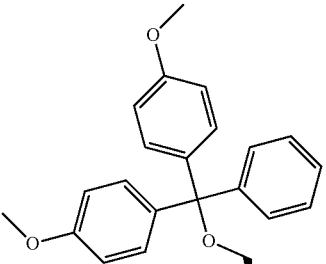
Int-99 | $^1$H NMR (DMSO-d$_6$) δ 12.09 (br s, 1H), 11.55 (br s, 1H), 8.07-8.10 (m, 1H), 7.19-7.38 (m, 9H), 6.81-6.88 (m, 4H), 5.98-6.03 (m, 1H), 5.05-5.43 (m, 2H), 4.27-4.47 (m, 1H), 3.71-3.78 (m, 7H), 3.34-3.63 (m, 5H), 2.66-2.84 (m, 2H), 2.53-2.62 (m, 1H), 0.96-1.18 (m, 15H), 0.76 (d, J = 6.7 Hz, 3H). $^{31}$P NMR (DMSO-d$_6$) δ 151.56 (br d, J = 7.8 Hz, 0.5 P), 151.36 (br d, J = 3.9 Hz, 0.5 P). |
| 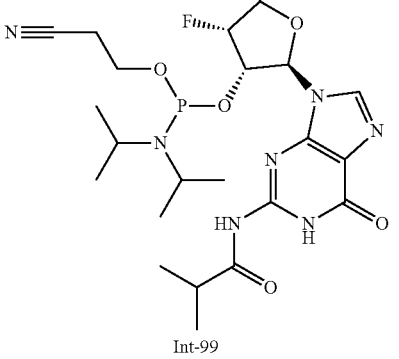 | 
Int-107 | $^1$H NMR (DMSO-d$_6$) δ 12.06 (br s, 1H), 11.61 (s, 1H), 8.14 (d, J = 3.4 Hz, 1H), 7.17-7.35 (m, 9H), 6.80-6.86 (m, 4H), 5.89-6.05 (m, 1H), 4.98-5.19 (m, 1H), 3.94-4.47 (m, 5H), 3.73 (d, J = 1.2 Hz, 7H), 3.39-3.57 (m, 4H), 2.87-2.91 (m, 1H) 2.70-2.79 (m, 2H), 0.99-1.25 (m, 15H), 0.80 (d, J = 6.7 Hz, 3H). $^{31}$P NMR (DMSO-d$_6$) δ 151.15 (s, 0.5P), 150.19 (s, 0.5P) |
| 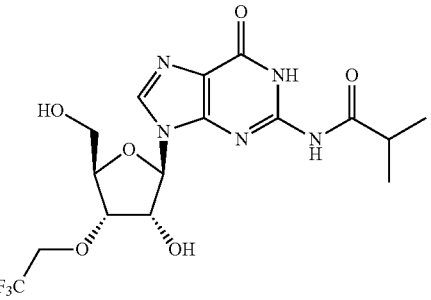
Int-97 | 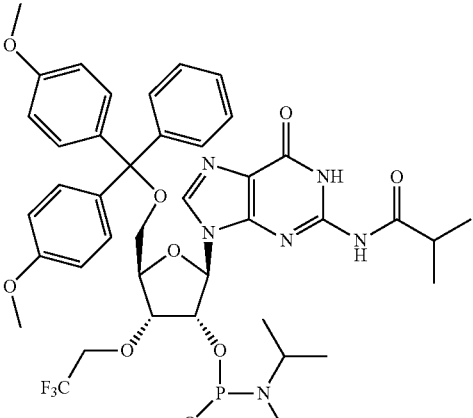
Int-98 | $^1$H NMR (CDCl$_3$) δ 12.05 (m, 1H), 8.72 (m, 1H), 7.48 (m, 2H), 7.33 (m, 7H), 6.85 (m, 4H), 5.09 (m, 1H), 4.86 (m, 1H), 3.81 (m, 7H), 3.61 (m, 2H), 3.45 (m, 1H), 3.16 (m, 2H), 2.63 (m, 3H), 2.42 (m, 3H), 2.04 (m, 2H), 1.14 (m, 15H), 0.88 (m, 3H). $^{31}$P NMR (CDCl$_3$) δ 149.09 (s, 0.5P), 147.58 (s, 0.5P). |

Example 19

The compound listed below was prepared as described in Example 17 starting with Step 1, substituting the starting material shown in the table for Intermediate 29.

| Starting material | Intermediate | NMR data |
|---|---|---|
| (5-chloropyrimidine-4-carbonitrile structure) | Int-33 (DMTrO cyclopentane phosphoramidite structure) | $^1$H NMR (DMSO-$d_6$) δ 8.62-8.64 (m, 1H), 8.59-8.60 (m, 1H), 8.03-8.08 (m, 1H), 7.37-7.42 (m, 2H), 7.22-7.35 (m, 7H), 6.86-6.92 (m, 4H), 4.66-4.77 (m, 1H), 4.14-4.29 (m, 1H), 3.74 (d, J = 1.7 Hz, 6H), 3.64-3.72 (m, 1H), 3.47-3.61 (m, 3H), 3.09-3.17 (m, 1H), 2.87-3.00 (m, 1H), 2.63-2.76 (m, 2H), 2.19-2.32 (m, 2H), 1.93-2.09 (m, 1H), 1.82-1.92 (m, 1H), 1.42-1.53 (m, 1H), 1.08-1.15 (m, 9H), 1.01 (d, J = 6.7 Hz, 3H). $^{31}$P NMR (DMSO-$d_6$) δ 146.75 (s, 0.5P), 146.54 (s, 0.5P). |

Example 20

(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl hydrogen phosphonate, Intermediate 34

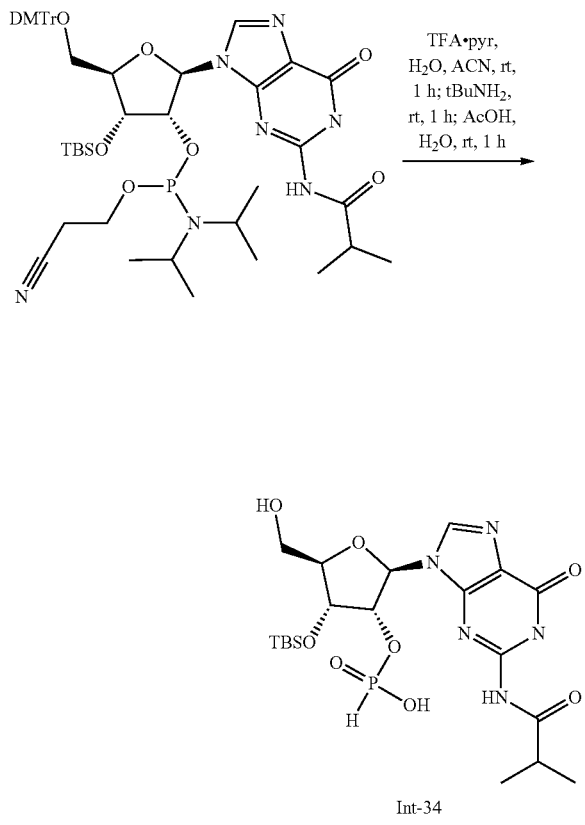

Int-34

To a solution of (2R,3R,4R,5R)-5-f{[bis(4-methoxyphenyl)(phenyl)methoxy]methyl}-4-{[tert-butyl(dimethyl)silyl]oxy}-2-[2-(isobutyrylamino)-6-oxo-1,6-dihydro-9H-purin-9-yl]tetrahydrofuran-3-yl 2-cyanoethyl diisopropylphosphoramidite (1.00 g, 1.03 mmol) in ACN (5 mL) was added water (40.0 μL, 2.22 mmol) and pyridine trifluoroacetate (235 mg, 1.22 mmol). The reaction mixture was allowed to stir at rt for 1 h. tert-Butylamine (5.00 mL, 47.6 mmol) was added and the reaction mixture was allowed to stir at rt for 1 h. The reaction mixture was concentrated and the residue was dissolved in acetic acid (3.81 mL, 66.6 mmol) and water (800 μL, 4.44 mmol). The resulting orange reaction mixture was allowed to stir at rt for 1 h. The reaction mixture was concentrated and concentrated from ACN (2×25 mL) and toluene (2×25 mL). The crude compound was purified by silica gel chromatography (0-40% MeOH/EtOH [1:1] in DCM) to provide (2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl hydrogen phosphonate (Intermediate 34) as the tert-butylamine salt (375 mg, 68%). LCMS (FA): m/z=532.2 (M+H). $^1$H NMR (DMSO-$d_6$) δ 8.29 (s, 1H), 7.25 (s, 1H), 5.86 (d, J=7.3 Hz, 1H), 5.80 (s, 1H), 5.17-5.09 (m, 1H), 5.06-4.96 (m, 1H), 4.34 (dd, J=1.4, 4.7 Hz, 1H), 3.92-3.87 (m, 1H), 3.61-3.46 (m, 2H), 3.17 (s, 1H), 2.81-2.72 (m, 1H), 1.23-1.19 (m, 9H), 1.12 (d, J=6.2 Hz, 6H), 0.90 (s, 9H), 0.14 (d, J=4.5 Hz, 6H). $^{31}$P NMR (DMSO-$d_6$) δ −0.95 (s, 1P).

Example 21

The compound listed below was prepared as described in Example 20 substituting the starting material shown in the table for the 2-cyanoethyl diisopropylphosphoramidite starting material.

| Starting material | Intermediate | LCMS data |
|---|---|---|
| 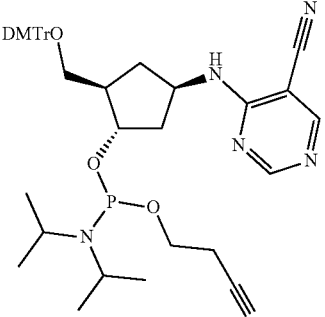 Int-33 | 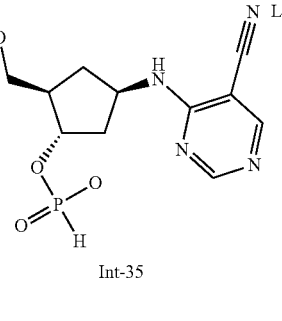 Int-35 | LCMS (FA): m/z = 299.1 (M + H). |
Example 22
2-amino-9-[(5R,7R,8R,12aR,14R,15aS,16R)-2,10,16-trihydroxy-2,10-dioxido-14-(pyrimidin-4-ylamino)decahydro-5,8-methanocyclopenta[l][1,3,6,9,11,2,10]pentaoxadiphosphacyclotetradecin-7-yl]-1,9-dihydro-6H-purin-6-one, Compound I-6
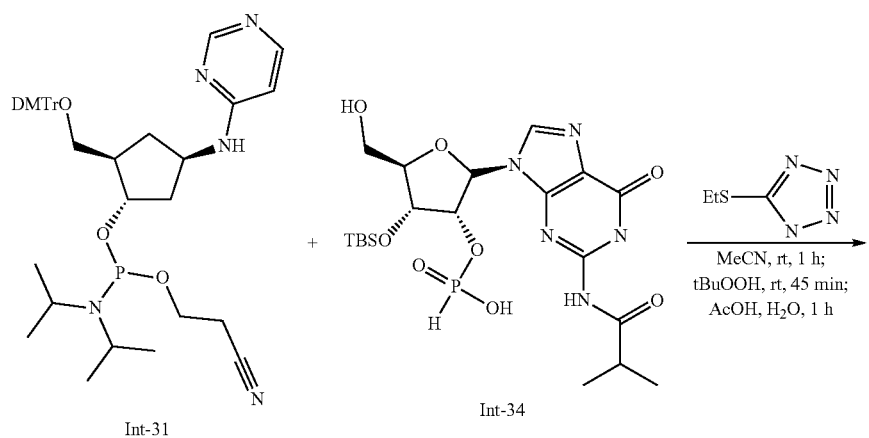
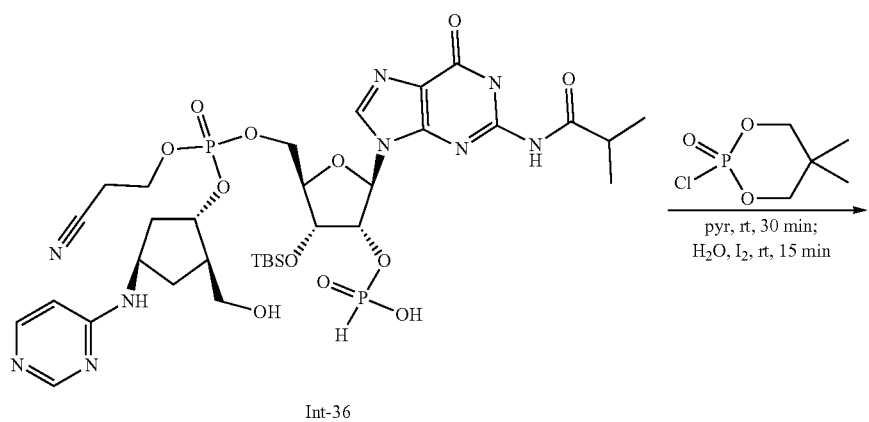

-continued

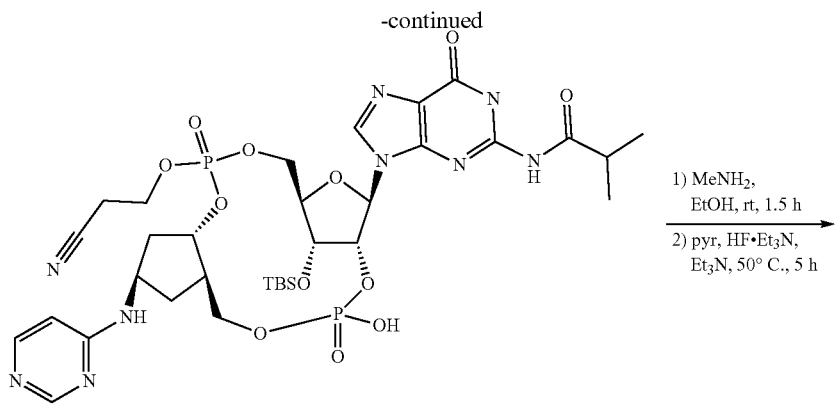

Int-37

1) MeNH₂, EtOH, rt, 1.5 h
2) pyr, HF·Et₃N, Et₃N, 50° C., 5 h

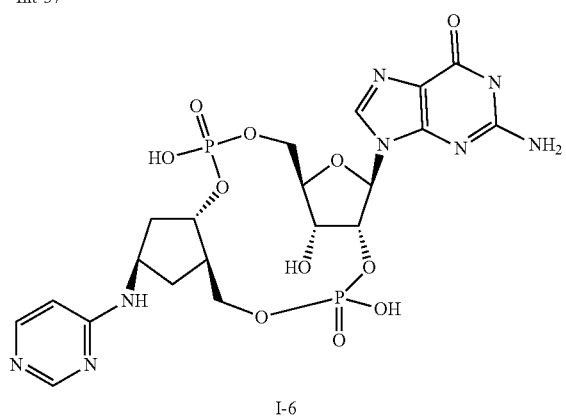

I-6

Step 1: (2R,3R,4R,5R)-4-{[tert-butyl(dimethyl)silyl]oxy}-5-({[(S)-(2-cyanoethoxy) {[(1S,2R,4R)-2-(hydroxymethyl)-4-(pyrimidin-4-ylamino)cyclopentyl]oxy}phosphoryl]oxy}methyl)-2-[2-(isobutyrylamino)-6-oxo-1,6-dihydro-9H-purin-9-yl]tetrahydrofuran-3-yl hydrogen phosphonate, and (2R,3R,4R,5R)-4-{[tert-butyl(dimethyl)silyl]oxy}-5-({[(R)-(2-cyanoethoxy) {[(1S,2R,4R)-2-(hydroxymethyl)-4-(pyrimidin-4-ylamino)cyclopentyl]oxy}phosphoryl]oxy}methyl)-2-[2-(isobutyrylamino)-6-oxo-1,6-dihydro-9H-purin-9-yl]tetrahydrofuran-3-yl hydrogen phosphonate, Intermediate 36

A mixture of Intermediate 31 (630 mg, 0.885 mmol) and Intermediate 34 (360 mg, 0.677 mmol) were dissolved in dry acetonitrile and concentrated to dryness (3×25 mL). The residue was then dissolved in ACN (2.63 mL) under an atmosphere of nitrogen. In a separate flask, 5-(ethylthio)-1H-tetrazole (265 mg, 2.03 mmol) was dissolved in dry acetonitrile and concentrated to dryness (3×10 mL), taken up in ACN (1.20 mL) and added to the reaction mixture. The reaction mixture was allowed to stir at rt for 1 h. tert-Butyl hydroperoxide (5.50 M in nonane, 0.370 mL, 2.03 mmol) was added, and the reaction mixture was allowed to stir at rt for 45 min. The reaction mixture was quenched by addition of sodium thiosulfate (375 mg, 2.37 mmol) in water (0.398 mL, 22.1 mmol). The reaction mixture was concentrated and dried on vacuum for 2 min. The residue was dissolved in a mixture of acetic acid (2.85 mL, 49.8 mmol) and water (0.713 mL, 39.6 mmol). The reaction mixture was sonicated for 2 min, and allowed to stir at rt for 1 h. The reaction mixture was diluted with toluene and concentrated. The residue was concentrated from toluene. The crude compound was purified by silica gel chromatography (0-70% MeOH in DCM) to provide Intermediate 36 (320 mg, 53%) as a mixture of diastereomers. LCMS (AA): m/z=856.4 (M+H).

Step 2: N-{9-[(2S,5R,7R,8R,12aR,14R,15aS,16R)-16-{[tert-butyl(dimethyl)silyl]oxy}-2-(2-cyanoethoxy)-10-hydroxy-2,10-dioxido-14-(pyrimidin-4-ylamino)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, and N-{9-[(2R,5R,7R,8R,12aR,14R,15aS,16R)-16-{[tert-butyl(dimethyl)silyl]oxy}-2-(2-cyanoethoxy)-10-hydroxy-2,10-dioxido-14-(pyrimidin-4-ylamino)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 37

Intermediate 36 (300 mg, 0.351 mmol) was dissolved in dry acetonitrile and concentrated to dryness (3×10 mL) then dried under vacuum for 15 min. The residue was dissolved in pyridine (7.99 mL, 98.7 mmol) under an argon atmosphere, then 2-chloro-5,5-dimethyl-1,3,2-dioxaphosphorinane 2-oxide (236 mg, 1.23 mmol) was added and the reaction mixture was allowed to stir at rt for 45 min. Water (0.221 mL, 12.3 mmol) and iodine (116 mg, 0.456 mmol)

were added and stirring was continued for 8 min. Sodium thiosulfate (74.3 mg, 0.456 mmol) in water (0.5 mL) was added. The reaction mixture was allowed to stir at rt for 15 min. Toluene (15 mL) was added and the reaction mixture was concentrated. The residue was concentrated from toluene (15 mL) and dried on vacuum for 15 min. The crude compound was purified by silica gel chromatography (0-100% MeOH in DCM) to provide Intermediate 37 (170 mg, 57%) as a mixture of diastereomers. LCMS (AA): m/z=854.3 (M+H).

Step 3: 2-amino-9-[(5R,7R,8R,12aR,14R,15aS, 16R)-16-{[tert-butyl(dimethyl)silyl]oxy}-2,10-dihydroxy-2,10-dioxido-14-(pyrimidin-4-ylamino)decahydro-5,8-methanocyclopenta[l][1,3,6,9,11,2,10] pentaoxadiphosphacyclotetradecin-7-yl]-1,9-dihydro-6H-purin-6-one Intermediate 37 was taken up in methylamine (33% in EtOH, 5.87 mL, 47.1 mmol) and the reaction mixture was allowed to stir at rt for 90 min. The reaction mixture was concentrated and dried on vacuum for 10 minutes. The crude compound was purified by silica gel chromatography (0-100% MeOH in DCM) to provide 2-amino-9-[(5R,7R, 8R,12aR, 14R,15aS,16R)-16-{[tert-butyl(dimethyl)silyl] oxy}-2,10-dihydroxy-2,10-dioxido-14-(pyrimidin-4-ylamino)decahydro-5,8-methanocyclopenta[l][1,3,6,9,11,2, 10]pentaoxadiphosphacyclotetradecin-7-yl]-1,9-dihydro-6H-purin-6-one (135 mg, 95%). LCMS (FA): m/z=731.3 (M+H).

Step 4: 2-amino-9-[(5R,7R,8R,12aR,14R,15aS, 16R)-2,10,16-trihydroxy-2,10-dioxido-14-(pyrimidin-4-ylamino)decahydro-5,8-methanocyclopenta[l] [1,3,6,9,11,2,10]pentaoxadiphosphacyclotetradecin-7-yl]-1,9-dihydro-6H-purin-6-one, I-6

To a suspension of 2-amino-9-[(5R,7R,8R,12aR,14R, 15aS,16R)-16-{[tert-butyl (dimethyl)silyl]oxy}-2,10-dihydroxy-2,10-dioxido-14-(pyrimidin-4-ylamino)decahydro-5, 8-methanocyclopenta[l][1,3,6,9,11,2,10]pentaoxadiphosphacyclotetradecin-7-yl]-1,9-dihydro-6H-purin-6-one (131 mg, 0.179 mmol) in pyridine (0.896 mL, 11.1 mmol) was added triethylamine trihydrofluoride (0.149 mL, 0.896 mmol), and then TEA (2.14 mL, 15.2 mmol). The reaction mixture was sealed in a propylene tube and allowed to stir at 50° C. for 5 h. The reaction mixture was cooled to rt. The reaction mixture was diluted with water (3.21 mL), then CaCl$_2$) (207 mg, 2.17 mmol) in water (3.21 mL) was added. The cloudy white mixture was allowed to stir at rt for 60 min. Then the suspension was filtered through Celite and the Celite was washed with water (5×5 mL). The clear aqueous filtrate was concentrated to a solid residue. No HF was observed by $^{19}$F NMR. The crude residue was suspended in ACN (25 mL) and adsorbed onto Celite. The crude mixture was purified by reverse phase flash column chromatography (10-100% ACN in aqueous triethylammonium acetate (10 mM)) to provide 2-amino-9-[(5R,7R,8R,12aR,14R,15aS, 16R)-2,10,16-trihydroxy-2,10-dioxido-14-(pyrimidin-4-ylamino)decahydro-5,8-methanocyclopenta[l][1,3,6,9,11,2, 10]pentaoxadiphosphacyclotetradecin-7-yl]-1,9-dihydro-6H-purin-6-one as an N,N-diethylethanamine (I-6, 73 mg, 50%). LCMS (AA): m/z=617.1 (M+H). $^1$H NMR (D$_2$O) δ 8.50 (br s, 1H), 8.02 (s, 1H), 7.95 (br s, 1H), 6.59 (br s, 1H), 5.99 (d, J=8.3 Hz, 1H), 5.37 (td, J=8.7, 4.2 Hz, 1H), 4.73-4.80 (m, 1H), 4.61 (d, J=4.2 Hz, 1H), 4.47 (br s, 1H), 4.39 (q, J=2.2 Hz, 1H), 4.11-4.23 (m, 2H), 3.95 (dt, J=10.6, 2.7 Hz, 1H), 3.75-3.84 (m, 1H), 3.16 (q, J=7.3 Hz, 8H), 2.35-2.48 (m, 2H), 2.23 (br d, J=6.2 Hz, 2H), 1.37 (s, 1H), 1.24 (t, J=7.3 Hz, 12H); $^{31}$P NMR (D$_2$O) δ −0.72 (s, 1P), −0.79 (s, 1P).

Example 22A

The compounds listed below were prepared as described in Example 22 starting with Step 1, substituting the starting material shown in the table for Intermediate 31. Unless otherwise noted the compounds are the N,N-diethylethanamine salts.

| Compound | Salt Form | Starting Material | Final compound/ LCMS data | NMR data |
|---|---|---|---|---|
| I-16 | Et$_3$N | 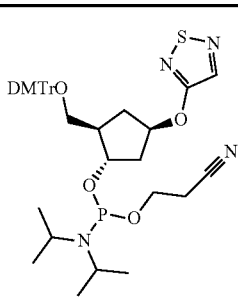 Int-96 | 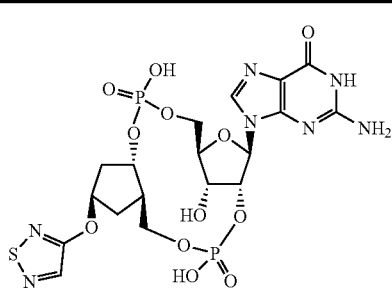 LCMS (AA): m/z = 624.0 (M + H) | $^1$H NMR (D$_2$O) δ 7.96 (s, 1H), 7.88 (s, 1H), 5.90 (d, J = 8.4 Hz, 1H), 5.29-5.19 (m, 2H), 4.74-4.68 (m, 1H), 4.53 (d, J = 4.1 Hz, 1H), 4.30-4.26 (m, 1H), 4.09-4.05 (m, 2H), 3.89-3.83 (m, 1H), 3.77-3.69 (m, 1H), 3.04 (q, J = 7.3 Hz, 12H), 2.47-2.34 (m, 2H), 2.34-2.25 (m, 1H), 2.22-2.13 (m, 1H), 1.57-1.50 (m, 1H), 1.12 (t, J = 7.3 Hz, 18H). $^{31}$P NMR (D$_2$O) δ −0.56 (s, 1P), −0.65 (s, 1P). |

Example 23

4-{[(2R,5R,7R,8R,10S,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2S,5R,7R,8R,10S,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2S,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, I-4a or I-4b

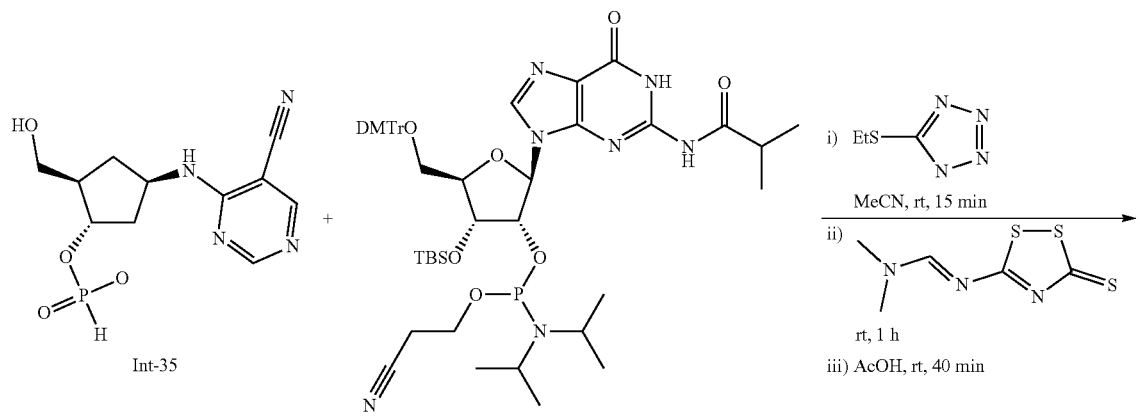

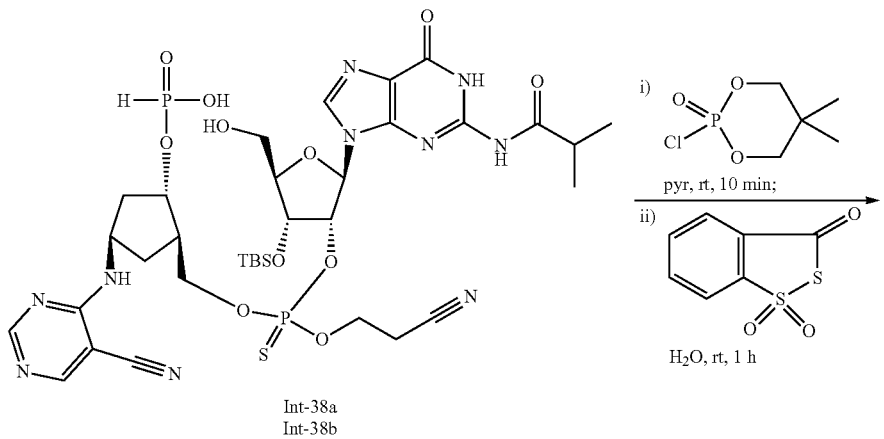

-continued

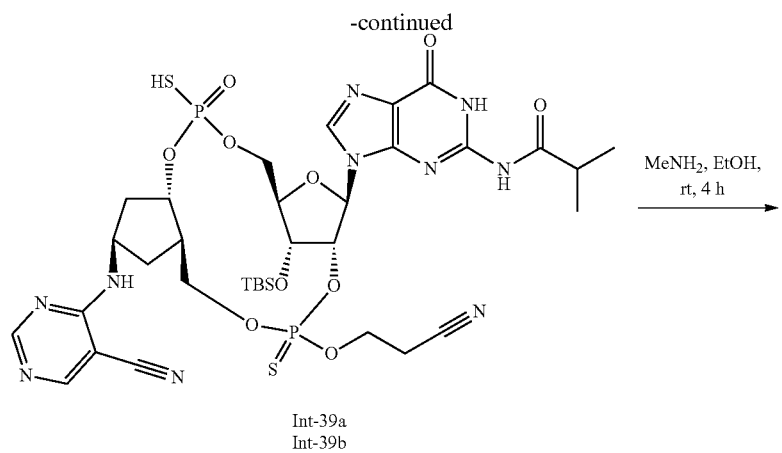

Int-39a
Int-39b

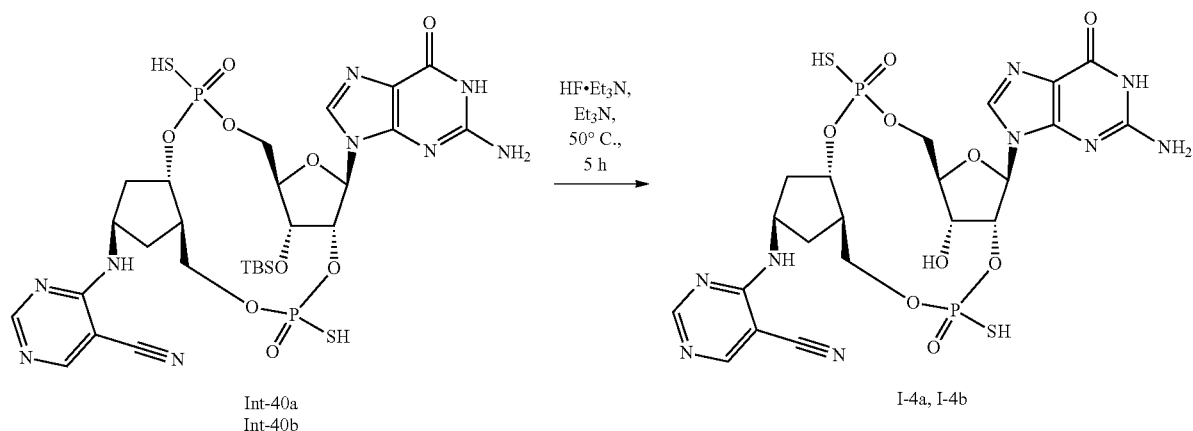

Int-40a
Int-40b

I-4a, I-4b

Step 1: (1S,2R,4R)-2-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-[(5-cyanopyrimidin-4-yl)amino]cyclopentyl hydrogen phosphonate, and (1S,2R,4R)-2-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-[(5-cyanopyrimidin-4-yl)amino]cyclopentyl hydrogen phosphonate, Intermediates 38a and 38b N-[9-[(2R,3R,4R,5R)-5-[[bis(4-methoxyphenyl)-phenyl-methoxy]methyl]-4-[tert-butyl(dimethyl)silyl]oxy-3-[2-cyanoethoxy-(diisopropylamino)phosphanyl]oxy-tetrahydrofuran-2-yl]-6-oxo-1H-purin-2-yl]-2-methyl-propanamide (1.57 g, 1.62 mmol) and Intermediate 35 (500 mg, 1.35 mmol) were dissolved in dry acetonitrile and concentrated to dryness (3×50 mL) and dried under vacuum for 1 h, then suspended in ACN (5.0 mL) under an atmosphere of argon. Separately, 5-(ethylthio)-1H-tetrazole (526 mg, 4.04 mmol) was concentrated from ACN (3×20 mL), dried under vacuum for 1 h, dissolved in ACN (3.0 mL) and added to the reaction mixture. The reaction mixture was allowed to stir at rt for 15 min. ((Dimethylamino-methylidene) amino)-3H-1,2,4-dithiazoline-3-thione (346 mg, 1.62 mmol) was added and the reaction mixture was allowed to stir at rt for 1 h. The reaction mixture was concentrated and the residue was dried under vacuum for 1 h. To the residue was added acetic acid (5.41 mL) and water (1.3 mL) and the reaction mixture was allowed to stir at rt for 40 min. The reaction mixture was concentrated and the residue was concentrated from toluene and dried under vacuum. The crude compound was purified by silica gel chromatography (20-50% MeOH in DCM) to provide Intermediate 38a (264 mg, 21%) as the first eluting peak and Intermediate 38b (670 mg, 52%) as an impure mixture in the second eluting peak. LCMS (FA): m/z=897.3 (M+H).

Step 2: N-(9-{(2R,5R,7R,8R,10R,12aR,14R,15aS, 16R)-16-{[tert-butyl(dimethyl)silyl]oxy}-10-(2-cyanoethoxy)-14-[(5-cyanopyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide, or N-(9-{(2S,5R,7R,8R,10R,12aR,14R,15aS,16R)-16-{[tert-butyl(dimethyl)silyl]oxy}-10-(2-cyanoethoxy)-14-[(5-cyanopyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide, or N-(9-{(2R,5R,7R,8R,10S,12aR,14R,15aS,16R)-16-{[tert-butyl(dimethyl)silyl]oxy}-10-(2-cyanoethoxy)-14-[(5-cyanopyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide, or N-(9-{(2S,5R,7R,8R,10S,12aR,14R,15aS,16R)-16-{[tert-butyl(dimethyl)silyl]oxy}-10-(2-cyanoethoxy)-14-[(5-cyanopyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide, Intermediate 39a Intermediate 38a (260 mg, 0.290 mmol) was dissolved in dry acetonitrile and concentrated to dryness (3×10 mL), dried under vacuum for 1 h and dissolved in pyridine (6.00 mL). 2-Chloro-5,5-dimethyl-1,3,2-dioxaphosphorinane 2-oxide (187 mg, 1.02 mmol) was added to the reaction mixture. The reaction mixture was allowed to stir at rt for 10 min. Water (0.18 mL, 10.2 mmol) and 3H-1,2-benzodithiol-3-one 1,1-dioxide (70.4 mg, 0.348 mmol) were added and the reaction mixture was allowed to stir at rt for 1 h. Toluene was added, the reaction mixture was concentrated and concentrated from toluene (2×20 mL) to dryness. The crude mixture of diastereomers was purified by silica gel chromatography (10-40% MeOH in DCM) to provide Intermediate 39a (180 mg, 68%) as the second eluting peak. LCMS (AA): m/z=911.2 (M+H).

Step 3: 4-{[(2R,5R,7R,8R,10S,12aR,14R,15aS, 16R)-7-(2-amino-6-oxo-1,6-dihydro-9H-purin-9-yl)-16-{[tert-butyl(dimethyl)silyl]oxy}-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2S,5R,7R,8R,10S,12aR,14R,15aS,16R)-7-(2-amino-6-oxo-1,6-dihydro-9H-purin-9-yl)-16-{[tert-butyl(dimethyl)silyl]oxy}-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2R,5R,7R,8R,10R,12aR,14R,15aS,16R)-7-(2-amino-6-oxo-1,6-dihydro-9H-purin-9-yl)-16-{[tert-butyl(dimethyl)silyl]oxy}-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2S,5R,7R,8R,10R,12aR,14R,15aS,16R)-7-(2-amino-6-oxo-1,6-dihydro-9H-purin-9-yl)-16-{[tert-butyl(dimethyl)silyl]oxy}-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, Intermediate 40a Intermediate 39a (207 mg, 0.2272 mmol) was dissolved in methylamine (33% in EtOH, 6.00 mL, 48.2 mmol) under an atmosphere of nitrogen and the reaction mixture was allowed to stir at rt for 4 h. The reaction mixture was concentrated. The crude compound was purified by reverse phase flash column chromatography (10-100% ACN in aqueous ammonium acetate (10 mM)) to provide impure product which was further purified by silica gel chromatography (30-70% MeOH in DCM) to provide Intermediate 40a (78 mg, 44%). LCMS (AA): m/z=788.1 (M+H).

Step 4: 4-{[(2R,5R,7R,8R,10S,12aR,14R,15aS, 16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2S,5R,7R,8R,10S,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, or 4-{[(2R,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1, 3,6,9,11,2,10]pentaoxadiphosphacyclotetradecin-14-yl]amino}pyrimidine-5-carbonitrile, or 4-{[(2S,5R,7R,8R,10R,12aR,14R,15aS,16R)-7-(2-amino-6-oxo-1,6-dihydro-9H-purin-9-yl)-16-hydroxy-2,10-dioxido-2,10-disulfanyldecahydro-5,8-methanocyclopenta[l][1,3,6,9,11,2,10]pentaoxadiphosphacyclotetradecin-14-yl]amino}pyrimidine-5-carbonitrile, I-4a Intermediate 40a (77 mg, 0.098 mmol) was suspended in TEA (0.300 mL, 2.96 mmol) in a polypropylene tube.

Triethylamine trihydrofluoride (0.080 mL, 0.489 mmol) was added and the reaction mixture was allowed to stir at 50° C. for 5 h. The reaction mixture was cooled to rt and $CaCl_2$) (109 mg, 0.977 mmol) in water (1.5 mL) was added and the reaction mixture was allowed to stir at rt for 1 h. An additional portion of calcium chloride (33.0 mg, 0.296 mmol) was added and stirring was continued for 1 hour. The suspension was filtered through Celite, and the Celite was washed with water. The clear aqueous filtrate was concentrated to a solid residue. No HF was observed by $^{19}$F NMR. The crude mixture was purified by reverse phase flash column chromatography (10-30% ACN in aqueous triethylammonium acetate (10 mM)) to provide I-4a as an N,N-diethylethanamine salt (27 mg, 32%). LCMS (AA): m/z=674.1 (M+H). $^1$H NMR ($D_2O$) δ 8.51 (s, 1H), 8.40 (s, 1H), 7.99 (s, 1H), 5.95 (d, J=8.4 Hz, 1H), 5.42 (td, J=8.8, 4.1 Hz, 1H), 4.88 (quin, J=5.5 Hz, 1H), 4.51-4.56 (m, 2H), 4.41 (br d, J=1.9 Hz, 1H), 4.31 (ddd, J=11.3, 8.5, 2.6 Hz, 1H), 3.95-4.10 (m, 2H), 3.75-3.86 (m, 1H), 3.12 (q, J=7.4 Hz, 9H), 2.25-2.46 (m, 3H), 2.13-2.24 (m, 1H), 1.31-1.43 (m, 1H), 1.20 (t, J=7.3 Hz, 14H). $^{31}$P NMR ($D_2O$) δ 54.02 (s, 1P), 52.63 (s, 1P).

Example 23A

The compound listed below was prepared as described in Example 23 starting with Step 2, substituting the starting material shown in the table for Intermediate 38a.

| Compound | Salt Form | Starting Material | Final compound/ LCMS data | NMR data |
|---|---|---|---|---|
| I-4b | Et$_3$N | Intermediate 38b | LCMS (AA): m/z = 674.0 (M + H) | $^1$H NMR ($D_2O$) δ 8.50 (s, 1H), 8.42 (s, 1H), 8.12 (d, J = 1.6 Hz, 1H), 5.98 (d, J = 8.5 Hz, 1H), 5.30-5.45 (m, 1H), 4.90-4.99 (m, 1H), 4.63 (quin, J = 8.0 Hz, 2H), 4.51 (d, J = 4.4 Hz, 1H), 4.39 (q, J = 2.3 Hz, 1H), 4.28 (ddd, J = 12.3, 10.2, 1.9 Hz, 1H), 4.05 (dt, J = 12.3, 2.0 Hz, 1H), 3.78-3.95 (m, 2H), 3.11 (q, J = 7.3 Hz, 12H), 2.34-2.49 (m, 3H), 2.03 (ddd, J = 14.7, 8.9, 5.9 Hz, 1H), 1.19 (t, J = 7.3 Hz, 19H); $^{31}$P NMR ($D_2O$) δ 58.55 (s, 1P), 53.99 (s, 1P). |

Example 23B

The compounds listed below were prepared as described in Example 23 starting with Step 1, substituting the H-phosphonate shown in the table for Intermediate 35.

| Compound | Salt Form | H-phosphonate | Final compound/ LCMS data | NMR data |
|---|---|---|---|---|
| I-41a | Et$_3$N | Int-158 | LCMS (AA): m/z = 665.1 (M + H) | $^1$H NMR (MeOD) δ 8.12 (s, 1H), 7.67 (s, 1H), 5.87 (d, J = 8.0 Hz, 1H), 5.36-5.30 (m, 1H), 5.11 (s, 1H), 4.96-4.94 (m, 1H), 4.38 (d, J = 4.0 Hz, 1H), 4.16-4.07 (m, 3H), 3.93-3.88 (m, 2H), 3.60-3.57 (m, 1H), 2.45-2.41 (m, 1H), 2.31-2.28 (m, 3H), 0.86-0.83 (m, 1H); $^{31}$P NMR (MeOD) δ 61.17 (s, 1P), 55.29 (s, 1P). |

| Compound | Salt Form | H-phosphonate | Final compound/ LCMS data | NMR data |
|---|---|---|---|---|
| I-41b | Et₃N | 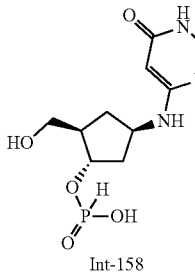<br>Int-158 | 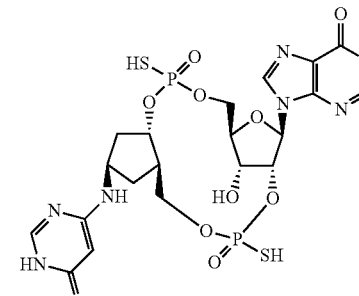<br>LCMS (AA): m/z = 665.2 (M + H) | ¹H NMR (D₂O) δ 7.87 (s, 1H), 7.77 (s, 1H), 5.86 (d, J = 8.0 Hz, 1H), 5.42-5.37 (m, 1H), 5.19 (s, 1H), 4.84-4.81 (m, 1H), 4.37 (d, J = 4.0 Hz, 1H), 4.32 (bs, 1H), 4.27-4.21 (m, 1H), 4.00-3.93 (m, 2H), 3.86-3.83 (m, 1H), 3.76-3.71 (m, 1H), 2.33-2.26 (m, 2H), 2.13-2.09 (m, 2H), 1.25-1.21 (m, 1H); ³¹P NMR (D₂O) δ 53.93 (s, 1P), 52.90 (s, 1P). |

Example 24

(2R,3R,4R,5R)-4-{[tert-butyl(dimethyl)silyl]oxy}-5-(hydroxymethyl)-2-(6-oxo-1,6-dihydro-9H-purin-9-yl)tetrahydrofuran-3-yl hydrogen phosphonate, Intermediate 43

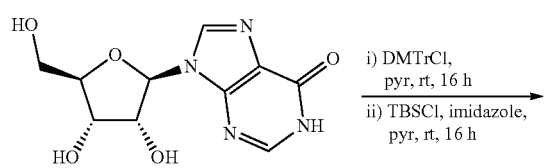

i) DMTrCl, pyr, rt, 16 h
ii) TBSCl, imidazole, pyr, rt, 16 h

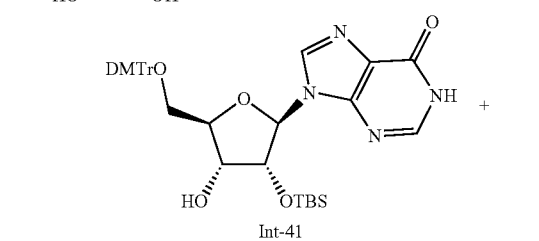
Int-41

+

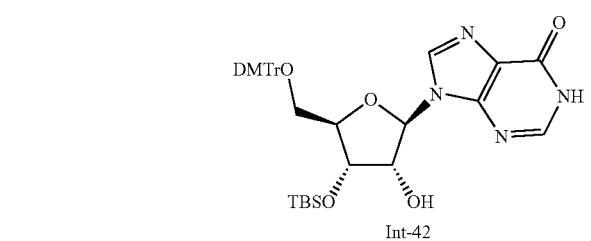
Int-42 diphenylphosphite
pyr, H₂O, rt, 2 h

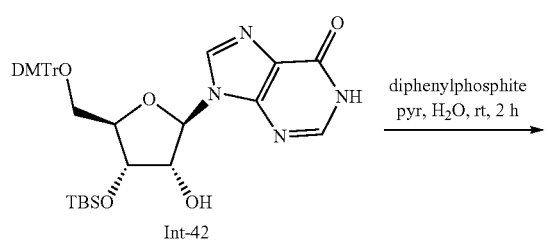
Int-42

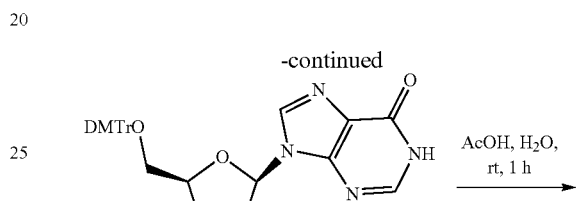

AcOH, H₂O, rt, 1 h

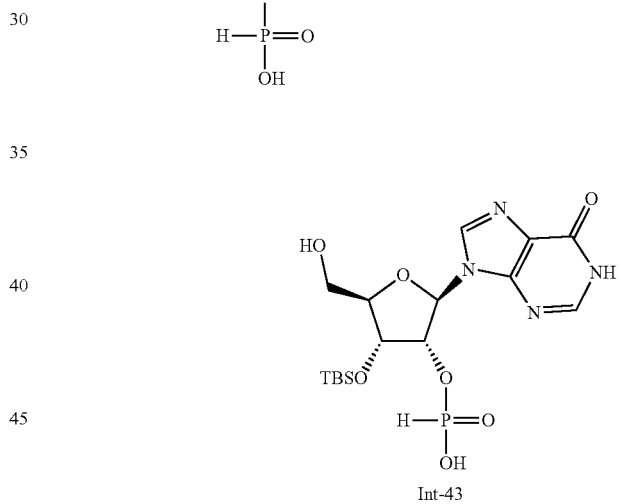
Int-43

Step 1: 9-[(2R,3R,4S,5R)-5-{[bis(4-methoxyphenyl)(phenyl)methoxy]methyl}-3,4-dihydroxytetrahydrofuran-2-yl]-1,9-dihydro-6H-purin-6-one Inosine (5.40 g, 20.1 mmol) was dried under vacuum for 5 h at 50° C., and then taken up in pyridine (104 mL) under an atmosphere of nitrogen. DMTrCl (4.10 g, 12.1 mmol) was added, and the reaction mixture was allowed to stir at rt for 10 min. Another portion of DMTrCl (4.10 g, 12.1 mmol) was added, and the reaction mixture was allowed to stir at rt overnight. MeOH (10 mL) was added, and the reaction mixture was concentrated. The residue was diluted with EtOAc and water. The phases were separated, and the aqueous phase was extracted with EtOAc. The combined organic phases were washed with water, dried with Na₂SO₄ and concentrated. The crude compound was purified by silica gel chromatography (0-10% MeOH in DCM) to provide 9-[(2R,3R,4S,5R)-5-{[bis(4-methoxyphenyl)(phenyl) methoxy]methyl}-3,4-dihydroxytetrahydrofuran-2-yl]-1,9-dihydro-6H-purin-6-one (7.02 g, 62%). LCMS (FA): m/z=571.2 (M+H).

Step 2: 9-[(2R,3R,4R,5R)-5-{[bis(4-methoxyphenyl)(phenyl)methoxy]methyl}-3-{[tert-butyl(dimethyl)silyl]oxy}-4-hydroxytetrahydrofuran-2-yl]-1,9-dihydro-6H-purin-6-one, Intermediate 41, and 9-[(2R,3R,4S,5R)-5-{[bis(4-methoxyphenyl)(phenyl)methoxy]methyl}-4-{[tert-butyl (dimethyl)silyl]oxy}-3-hydroxytetrahydrofuran-2-yl]-1,9-dihydro-6H-purin-6-one, Intermediate 42

9-[(2R,3R,4S,5R)-5-{[bis(4-methoxyphenyl)(phenyl)methoxy]methyl}-3,4-dihydroxytetrahydrofuran-2-yl]-1,9-dihydro-6H-purin-6-one (6.80 g, 11.9 mmol), TBSCl (2.81 g, 18.5 mmol), and imidazole (2.43 g, 35.3 mmol) were taken up in pyridine (152 mL) under an atmosphere of nitrogen. The reaction mixture was allowed to stir at rt overnight, then concentrated and diluted with EtOAc and water. The phases were separated and the aqueous phase was extracted with EtOAc. The combined organic phases were washed with water, dried with $Na_2SO_4$ and concentrated. The residue was concentrated from toluene, then purified by silica gel chromatography (0-70% EtOAc in DCM) to provide 9-[(2R,3R,4R,5R)-5-{[bis(4-methoxyphenyl)(phenyl)methoxy]methyl}-3-{[tert-butyl(dimethyl)silyl]oxy}-4-hydroxytetrahydrofuran-2-yl]-1,9-dihydro-6H-purin-6-one (Intermediate 41) (3.19 g, 39%) as the first eluting peak LCMS (FA): m/z=685.3 (M+H), $^1$H NMR (DMSO-$d_6$) δ 12.40 (s, 1H), 8.23 (s, 1H), 8.01 (s, 1H), 7.39-7.44 (m, 2H), 7.22-7.35 (m, J=8.9, 1.6 Hz, 7H), 6.88 (dd, J=9.0, 2.9 Hz, 4H), 5.95 (d, J=5.0 Hz, 1H), 5.17 (d, J=6.0 Hz, 1H), 4.72 (t, J=5.0 Hz, 1H), 4.20 (q, J=5.5 Hz, 1H), 4.12 (q, J=4.2 Hz, 1H), 3.76 (s, 6H), 3.29 (d, J=4.6 Hz, 2H), 0.79 (s, 9H), 0.00 (s, 3H), −0.09 (s, 3H) and 9-[(2R,3R,4S,5R)-5-{[bis(4-methoxyphenyl) (phenyl)methoxy]methyl}-4-{[tert-butyl (dimethyl)silyl]oxy}-3-hydroxytetrahydrofuran-2-yl]-1,9-dihydro-6H-purin-6-one (Intermediate 42) (1.77 g, 22%) as the second eluting peak LCMS (FA): m/z=685.4 (M+H), $^1$H NMR (DMSO-$d_6$) δ: 12.39 (br s, 1H), 8.26 (s, 1H), 7.98 (s, 1H), 7.32-7.38 (m, 2H), 7.19-7.29 (m, 7H), 6.81-6.86 (m, 4H), 5.86-5.89 (m, 1H), 5.42-5.45 (m, 1H), 4.65-4.70 (m, 1H), 4.36-4.40 (m, 1H), 3.99-4.03 (m, 1H), 3.73 (s, 6H), 3.25-3.28 (m, 1H), 3.09-3.16 (m, 1H), 0.82 (s, 9H), 0.06 (s, 3H), 0.02 (s, 3H).

Step 3: (2R,3R,4R,5R)-5-{[bis(4-methoxyphenyl)(phenyl)methoxy]methyl}-4-{[tert-butyl(dimethyl)silyl]oxy}-2-(6-oxo-1,6-dihydro-9H-purin-9-yl)tetrahydrofuran-3-yl hydrogen phosphonate To a solution of Intermediate 42 (3.08 g, 4.50 mmol) in pyridine (42.5 mL) was added diphenyl phosphite (1.73 mL, 9.01 mmol) under an atmosphere of argon. The reaction mixture was allowed to stir at rt for 2 h. Water (85.2 mL) was added, and the white reaction mixture was allowed to stir at rt for 1 h to give a colorless solution. The reaction mixture was concentrated and concentrated from toluene (3×10 mL) to give (2R,3R,4R,5R)-5-{[bis(4-methoxyphenyl)(phenyl)methoxy]methyl}-4-{[tert-butyl(dimethyl)silyl]oxy}-2-(6-oxo-1,6-dihydro-9H-purin-9-yl)tetrahydrofuran-3-yl hydrogen phosphonate (3.37 g, 99%), which was used directly in the next step without further purification.

Step 4: (2R,3R,4R,5R)-4-{[tert-butyl(dimethyl)silyl]oxy}-5-(hydroxymethyl)-2-(6-oxo-1,6-dihydro-9H-purin-9-yl)tetrahydrofuran-3-yl hydrogen phosphonate, Intermediate 43

To (2R,3R,4R,5R)-5-f{[bis(4-methoxyphenyl)(phenyl)methoxy]methyl}-4-{[tert-butyl(dimethyl)silyl]oxy}-2-(6-oxo-1,6-dihydro-9H-purin-9-yl)tetrahydrofuran-3-yl hydrogen phosphonate (3.37 g, 4.50 mmol) was added water (4.21 mL, 234 mmol) and acetic acid (16.8 mL, 294 mmol). The reaction mixture was sonicated, and the resulting bright orange solution was allowed to stir at rt for 1 h. The reaction mixture was concentrated from toluene (2×10 mL) and adsorbed onto Celite. The crude compound was purified by silica gel chromatography (0-70% MeOH in DCM) to provide (2R,3R,4R,5R)-4-{[tert-butyl(dimethyl)silyl]oxy}-5-(hydroxymethyl)-2-(6-oxo-1,6-dihydro-9H-purin-9-yl) tetrahydrofuran-3-yl hydrogen phosphonate (Intermediate 43) (1.85 g, 58%) as a white solid. LCMS (FA): m/z=447.2 (M+H). $^1$H NMR (DMSO-$d_6$) δ 12.30 (br s, 1H), 8.19 (s, 1H), 7.89 (s, 1H), 6.35 (d, J=580.1 Hz, 1H), 5.79 (d, J=6.8 Hz, 1H), 4.97 (t, J=5.5 Hz, 1H), 4.90 (ddd, J=11.0, 6.7, 5.0 Hz, 1H), 4.25 (dd, J=4.6, 2.2 Hz, 1H), 3.78 (q, J=2.1 Hz, 1H), 3.43-3.53 (m, 1H), 3.33-3.42 (m, 1H), 0.76 (s, 9H), 0.00 (s, 6H). $^{31}$P NMR (DMSO-$d_6$) δ −0.51 (s, 1P).

Example 25

9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, I-9a-d

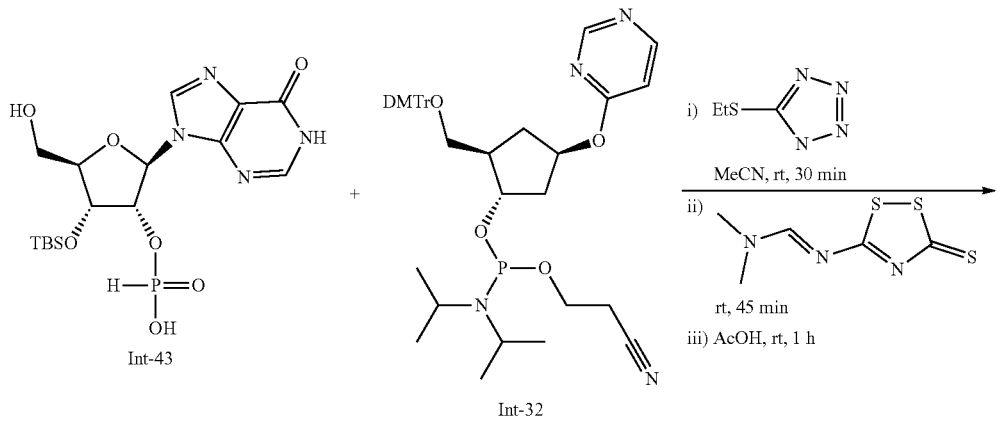

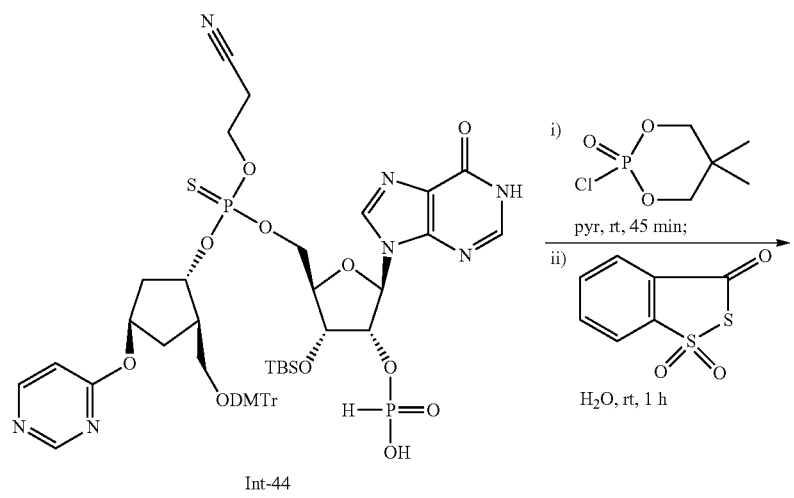

-continued

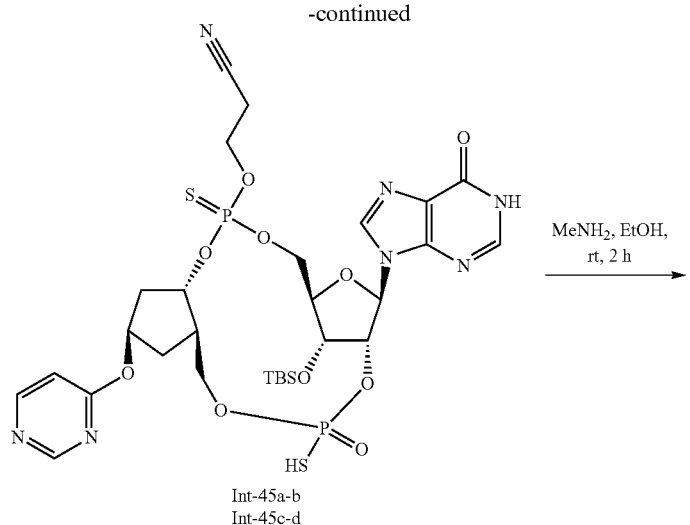

Int-45a-b
Int-45c-d

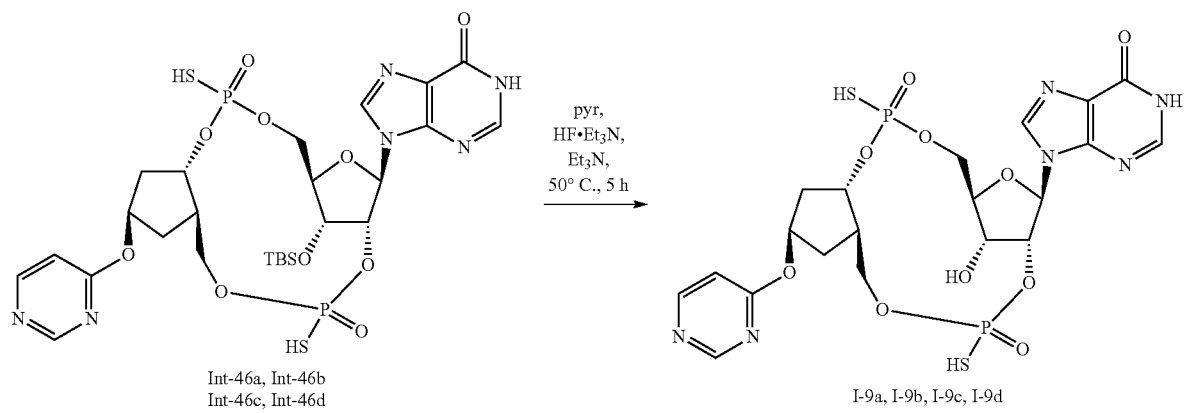

Int-46a, Int-46b
Int-46c, Int-46d

I-9a, I-9b, I-9c, I-9d

Step 1: (2R,3R,4R,5R)-5-({[(R)-{[(1S,2R,4R)-2-{[bis(4-methoxyphenyl)(phenyl) methoxy]methyl}-4-(pyrimidin-4-yloxy)cyclopentyl]oxy}(2-cyanoethoxy) phosphorothioyl]oxy}methyl)-4-{[tert-butyl(dimethyl)silyl]oxy}-2-(6-oxo-1,6-dihydro-9H-purin-9-yl)tetrahydrofuran-3-yl hydrogen phosphonate, and (2R,3R,4R,5R)-5-({[(S)-{[(1S,2R,4R)-2-{[bis(4-methoxyphenyl)(phenyl)methoxy]methyl}-4-(pyrimidin-4-yloxy)cyclopentyl]oxy}(2-cyanoethoxy) phosphorothioyl]oxy}methyl)-4-{[tert-butyl(dimethyl)silyl]oxy}-2-(6-oxo-1,6-dihydro-9H-purin-9-yl) tetrahydrofuran-3-yl hydrogen phosphonate, Intermediate 44

A mixture of Intermediate 43 (873 mg, 1.80 mmol) and Intermediate 32 (1.67 g, 2.34 mmol) was concentrated from ACN (3×10 mL), dried on vacuum for 1 h, and then suspended in ACN (6.59 mL) and THF (1.00 mL) under an atmosphere of argon. Separately, 5-(ethylthio)-1H-tetrazole (703 mg, 5.40 mmol) was concentrated from ACN (3×10 mL), dissolved in ACN (3.00 mL) and then added to the reaction mixture. The reaction mixture was allowed to stir at rt for 30 min. ((Dimethylamino-methylidene)amino)-3H-1,2,4-dithiazoline-3-thione (442 mg, 2.15 mmol) was added to the reaction mixture and stirring continued for 45 min at rt. The reaction mixture was concentrated and dried on vacuum for 10 min. The residue was taken up in acetic acid (7.13 mL) and water (1.78 mL). The reaction mixture was sonicated for 2 min, and then allowed to stir at rt for 1 h. The reaction mixture was concentrated from toluene (2×10 mL) and adsorbed onto Celite. The crude compound was purified by silica gel chromatography (0-60% MeOH in DCM) to provide Intermediate 44 (1.17 g, 70%) as a mixture of two diastereomers that was taken on without further purification. LCMS (FA): m/z=788.3 (M+H).

Step 2: 3-{[(2R,5R,7R,8R,10S,12aR,14R,15aS,16R)-16-{[tert-butyl(dimethyl)silyl]oxy}-10-oxido-7-(6-oxo-1,6-dihydro-9H-purin-9-yl)-14-(pyrimidin-4-yloxy)-10-sulfanyl-2-sulfidodecahydro-5,8-methanocyclopenta[l][1,3,6,9,11,2,10]pentaoxadiphosphacyclotetradecin-2-yl]oxy}propanenitrile, and 3-{[(2R,5R,7R,8R,10R,12aR,14R,15aS,16R)-16-{[tert-butyl(dimethyl)silyl]oxy}-10-oxido-7-(6-oxo-1,6-dihydro-9H-purin-9-yl)-14-(pyrimidin-4-yloxy)-10-sulfanyl-2-sulfidodecahydro-5,8-methanocyclopenta[l][1,3,6,9,11,2,10]pentaoxadiphosphacyclotetradecin-2-yl]oxy}propanenitrile, and 3-{[(2S,5R,7R,8R,10S,12aR,14R,15aS,16R)-16-{[tert-butyl(dimethyl)silyl]oxy}-10-oxido-7-(6-oxo-1,6-dihydro-9H-purin-9-yl)-14-(pyrimidin-4-yloxy)-10-sulfanyl-2-sulfidodecahydro-5,8-methanocyclopenta[l][1,3,6,9,11,2,10]pentaoxadiphosphacyclotetradecin-2-yl]oxy}propanenitrile, and 3-{[(2S,5R,7R,8R,10R,12aR,14R,15aS,16R)-16-{[tert-butyl(dimethyl)silyl]oxy}-10-oxido-7-(6-oxo-1,6-dihydro-9H-purin-9-yl)-14-(pyrimidin-4-yloxy)-10-sulfanyl-2-sulfidodecahydro-5,8-methanocyclopenta[l][1,3,6,9,11,2,10]pentaoxadiphosphacyclotetradecin-2-yl]oxy}propanenitrile, Intermediates 45 a-d Intermediate 44 (1.17 g, 1.26 mmol) was dissolved in dry pyridine and concentrated to dryness (3×10 mL), dried under vacuum for 10 min. and then dissolved in pyridine (25.3 mL) under an atmosphere of argon. 2-Chloro-5,5-dimethyl-1,3,2-dioxaphosphorinane 2-oxide (815 mg, 4.42 mmol) was added, and the reaction mixture was allowed to stir at rt for 1.5 h. An additional portion of 2-chloro-5,5-dimethyl-1,3,2-dioxaphosphorinane 2-oxide (100 mg, 0.542 mmol) was added and stirring was continued at rt for 15 min. Water was added (0.796 mL), followed by 3H-1,2-benzodithiol-3-one 1,1-dioxide (306 mg, 1.51 mmol). The reaction mixture was allowed to stir at rt for 1 h. An additional portion of 3H-1,2-benzodithiol-3-one 1,1-dioxide (77.0 mg, 0.380 mmol) was added and stirring was continued at rt for 20 min. The reaction mixture was concentrated, concentrated from toluene (2×10 mL) and adsorbed onto Celite. The crude compound was purified by silica gel chromatography (0-50% MeOH in DCM). Intermediates 45a-b eluted as a mixture (640 mg, 46%), followed by a mixture of Intermediates 45c-d (500 mg, 32%). LCMS (FA): m/z=802.2 (M+H).

Step 3: 9-[(2S,5R,7R,8R,10S,12aR,14R,15aS,16R)-16-{[tert-butyl(dimethyl)silyl]oxy}-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2S,5R,7R,8R,10R,12aR,14R,15aS,16R)-16-{[tert-butyl(dimethyl)silyl]oxy}-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2R,5R,7R,8R,10S,12aR,14R,15aS,16R)-16-{[tert-butyl(dimethyl)silyl]oxy}-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2R,5R,7R,8R,10R,12aR,14R,15aS,16R)-16-{[tert-butyl(dimethyl)silyl]oxy}-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, Intermediates 46 a-d The mixture of Intermediates 45a-b (640 mg, 0.583 mmol) was dissolved in methylamine (33% in EtOH, 29.0 mL, 233 mmol), and the reaction mixture was allowed to stir at rt for 2 h. The reaction mixture was concentrated and adsorbed onto Celite. The crude compound was purified by reverse phase flash column chromatography (10-100% ACN in aqueous ammonium acetate (10 mM)) to provide Intermediate 46a (92 mg, 20%) and Intermediate 46b (32 mg, 7%). LCMS (FA): m/z=749.2 (M+H).

The mixture of Intermediates 45c-d were treated in an analogous fashion to the above procedure to provide Intermediate 46c (74 mg, 24%) and Intermediate 46d (82 mg, 26%).

Step 4: 9-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 9-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, I-9b To a suspension of Intermediate 46b (137 mg, 0.183 mmol) in pyridine (0.915 mL) and TEA (2.29 mL) in a propylene tube was added triethylamine trihydrofluoride (0.152 mL, 0.915 mmol). The tube was capped and sealed and the reaction mixture was allowed to stir at 50° C. for 8 h and then at rt overnight. The reaction mixture was diluted with water (3.43 mL) and a solution of $CaCl_2$ (212 mg, 1.83 mmol) in water (3.43 mL) was added. The cloudy white reaction mixture was sonicated for 2 minutes and allowed to stir at rt for 1 h. The reaction mixture was filtered through Celite, and the Celite was washed with water (5×3 mL). The filtrate was concentrated to give an off-white solid. No HF was observed by $^{19}F$ NMR. The residue was concentrated from toluene (3×5 mL) and adsorbed onto Celite. The crude compound was purified by reverse phase flash column chromatography (0-20% ACN in aqueous triethylammonium acetate (10 mM)) to provide I-9b (99 mg, 61%) as an N,N-diethylethanamine salt. LCMS (AA): m/z=635.2 (M+H). $^1H$ NMR ($D_2O$) $^1H$ NMR ($D_2O$) δ: 8.68 (s, 1H), 8.56 (s, 1H), 8.44 (d, J=6.0 Hz, 1H), 8.22 (s, 1H), 6.88 (dd, J=6.1, 1.0 Hz, 1H), 6.29 (d, J=8.3 Hz, 1H), 5.44-5.51 (m, 1H), 5.33 (ddd, J=10.0, 8.4, 4.2 Hz, 1H), 4.87-4.94 (m, 2H), 4.51-4.54 (m, J=2.4 Hz, 1H), 4.40 (ddd, J=12.0, 10.0, 1.7 Hz, 1H), 4.02-4.15 (m, 2H), 3.83 (dt, J=10.5, 7.9 Hz, 1H), 3.20 (q, J=7.3 Hz, 12H), 2.47-2.57 (m, 3H), 2.36-2.47 (m, 1H), 1.53-1.64 (m, 1H), 1.28 (t, J=7.3 Hz, 18H). $^{31}P$ NMR ($D_2O$) δ 54.31 (s, 1P), 53.13 (s, 1P).

Example 25A

The compounds listed below were prepared as described in Example 25 starting with Step 4, substituting the starting material shown in the table for Intermediate 46b.

| Compound | Salt form | Starting material | LCMS data | NMR data |
|---|---|---|---|---|
| I-9a | Et₃N | Intermediate 46a | LCMS (AA): m/z = 635.0 (M + H) | $^1H$ NMR ($D_2O$) δ 8.86 (s, 1H), 8.68-8.67 (m, 1H), 8.44 (d, J = 6.0 Hz, 1H), 8.22 (s, 1H), 6.86 (d, J = 6.0 Hz, 1H), 6.29 (d, J = 8.3 Hz, 1H), 5.48-5.42 (m, 1H), 5.34 (ddd, J = 4.2, 8.3, 9.9 Hz, 1H), 4.91-4.85 (m, 1H), 4.83 (d, J = 4.0 Hz, 2H), 4.53-4.51 (m, 1H), 4.30-4.16 (m, 2H), 4.12-4.06 (m, 1H), 3.91-3.83 (m, 1H), 3.20 (q, J = 7.3 Hz, 12H), 2.63-2.46 (m, 3H), 2.40-2.31 (m, 1H), 1.27 (t, J = 7.3 Hz, 18H); $^{31}P$ NMR ($D_2O$) δ 54.09 (s, 1P), 52.79 (s, 1P). |
| I-9c | Et₃N | Intermediate 46c | LCMS (AA): m/z = 635.0 (M + H) | $^1H$ NMR ($D_2O$) δ 8.90 (s, 1H), 8.62 (s, 1H), 8.39 (d, J = 6.1 Hz, 1H), 8.16 (s, 1H), 6.87 (dd, J = 6.0, 1.0 Hz, 1H), 6.23 (d, J = 8.3 Hz, 1H), 5.41 (m, 1H), 5.32 (ddd, J = 12.7, 8.3, 4.3 Hz, 1H), 4.95-5.05 (m, 1H), 4.59 (d, J = 4.3 Hz, 1H), 4.43 (d, J = 1.8 Hz, 1H), 4.20 (ddd, J = 11.9, 7.5, 1.3 Hz, 1H), 4.00-4.13 (m, 2H), 3.82 (dt, J = 10.5, 3.1 Hz, 1H), 3.13 (q, J = 7.3 Hz, 12H), 2.39-2.56 (m, 4H), 1.55 (qd, J = 9.4, 3.2 Hz, 1H), 1.21 (t, J = 7.3 Hz, 18H); $^{31}P$ NMR ($D_2O$) δ 59.23 (s, 1P), 54.26 (s, 1P). |
| I-9d | Et₃N | Intermediate 46d | LCMS (AA): m/z = 635.2 (M + H) | $^1H$ NMR ($D_2O$) δ 8.62 (s, 1H), 8.57 (s, 1H), 8.39 (d, J = 6.1 Hz, 1H), 8.16 (s, 1H), 6.88 (dd, J = 6.0, 1.1 Hz, 1H), 6.23 (d, J = 8.3 Hz, 1H), 5.40-5.47 (m, 1H), 5.25 (ddd, J = 12.8, 8.3, 4.4 Hz, 1H), 4.96-5.05 (m, 1H), 4.55 (d, J = 4.4 Hz, 1H), 4.45 (d, J = 2.2 Hz, 1H), 4.26-4.36 (m, 1H), 3.96-4.10 (m, 2H), 3.80 (dt, J = 10.6, 3.4 Hz, 1H), 3.13 (q, J = 7.3 Hz, 12H), 2.39-2.53 (m, 4H), 1.48-1.60 (m, 1H), 1.21 (t, J = 7.3 Hz, 18H); $^{31}P$ NMR ($D_2O$) δ 59.17 (s, 1P), 54.35 (s, 1P). |

Example 26

2-amino-9-[(2R,5S,7R,8R,10S,12aR,14R,15aS)-2,
10-dioxido-14-(pyrimidin-4-yloxy)-2,10-disulfanyl-
decahydro-5,8-methanocyclopenta[l][1,3,6,9,11,2,
10]pentaoxadiphosphacyclotetradecin-7-yl]-1,9-
dihydro-6H-purin-6-one, or 2-amino-9-[(2S,5S,7R,8R,10S,12aR,14R,15aS)-2,
10-dioxido-14-(pyrimidin-4-yloxy)-2,10-disulfanyl-
decahydro-5,8-methanocyclopenta[l][1,3,6,9,11,2,
10]pentaoxadiphosphacyclotetradecin-7-yl]-1,9-
dihydro-6H-purin-6-one, or 2-amino-9-[(2R,5S,7R,8R,10R,12aR,14R,15aS)-2,
10-dioxido-14-(pyrimidin-4-yloxy)-2,10-disulfanyl-
decahydro-5,8-methanocyclopenta[l][1,3,6,9,11,2,
10]pentaoxadiphosphacyclotetradecin-7-yl]-1,9-
dihydro-6H-purin-6-one, or 2-amino-9-[(2S,5S,7R,8R,10R,12aR,14R,15aS)-2,
10-dioxido-14-(pyrimidin-4-yloxy)-2,10-disulfanyl-
decahydro-5,8-methanocyclopenta[l][1,3,6,9,11,2,
10]pentaoxadiphosphacyclotetradecin-7-yl]-1,9-
dihydro-6H-purin-6-one, I-1a-c

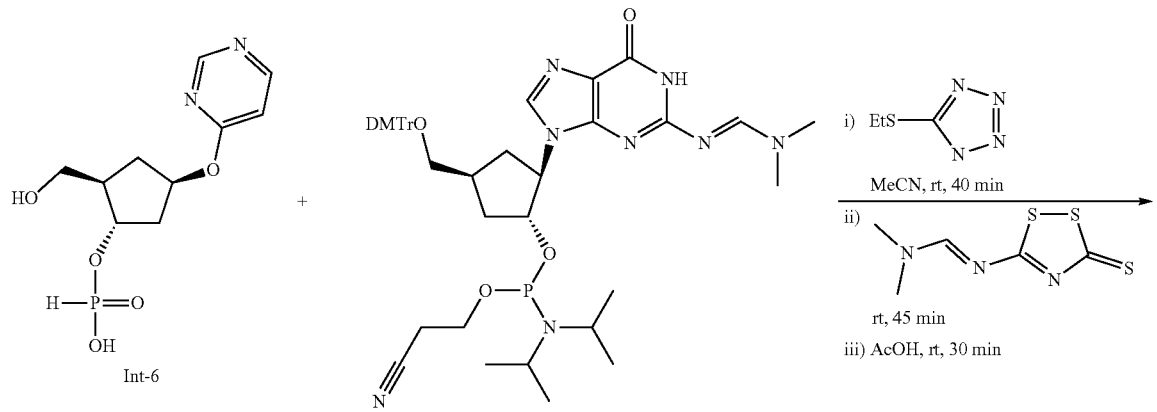

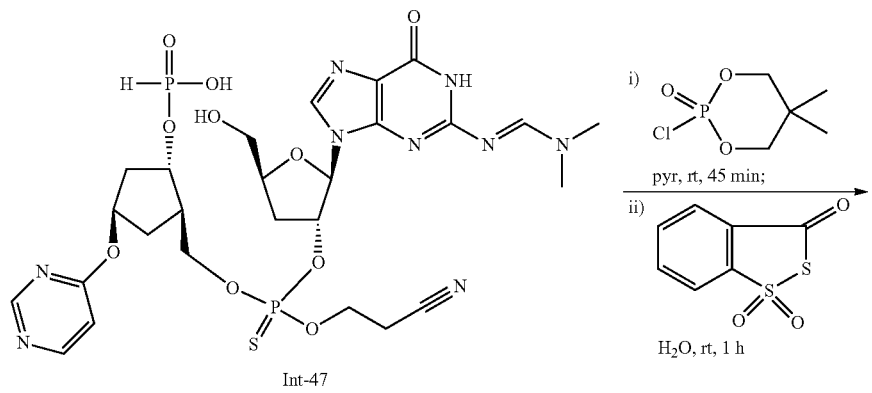

-continued

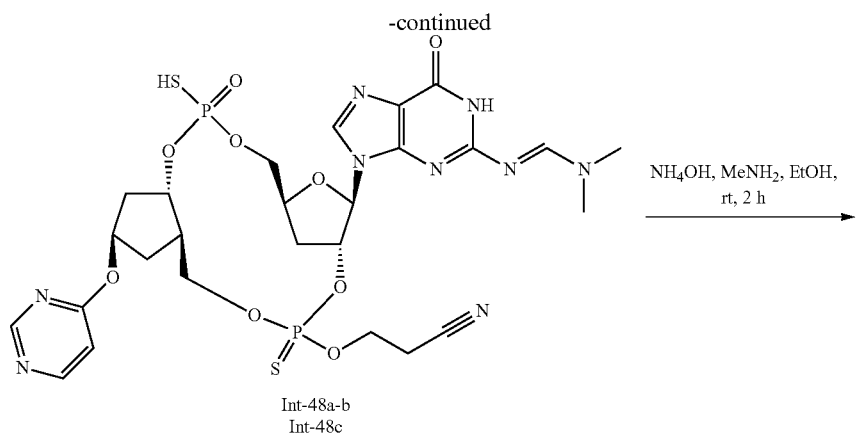

Int-48a-b
Int-48c

NH$_4$OH, MeNH$_2$, EtOH, rt, 2 h
→

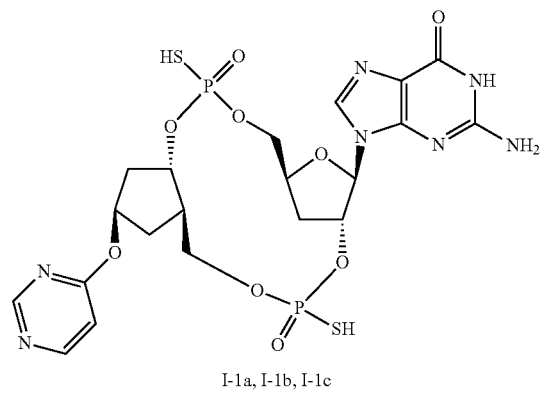

I-1a, I-1b, I-1c

Step 1: (1S,2R,4R)-2-({[(R)-(2-cyanoethoxy){[(2R, 3R,5S)-2-(2-{[(dimethylamino) methylene]amino}-6-oxo-1,6-dihydro-9H-purin-9-yl)-5-(hydroxymethyl) tetrahydrofuran-3-yl]oxy}phosphorothioyl] oxy}methyl)-4-(pyrimidin-4-yloxy) cyclopentyl hydrogen phosphonate, and (1S,2R,4R)-2-({[(S)-(2-cyanoethoxy){[(2R,3R,5S)-2-(2-{[(dimethylamino)methylene]amino}-6-oxo-1,6-dihydro-9H-purin-9-yl)-5-(hydroxymethyl)tetrahydrofuran-3-yl]oxy}phosphorothioyl]oxy}methyl)-4-(pyrimidin-4-yloxy)cyclopentyl hydrogen phosphonate, Intermediate 47

A mixture of Intermediate 6 (250 mg, 0.912 mmol) and N-[9-[(2R,3R,5S)-5-[[bis(4-methoxyphenyl)-phenylmethoxy]methyl]-3-[2-cyanoethoxy-(diisopropylamino) phosphanyl]oxy-tetrahydrofuran-2-yl]-6-oxo-1H-purin-2-yl]-N,N-dimethyl-formamidine (1.00 g, 1.21 mmol) was dissolved in dry acetonitrile and concentrated to dryness (3×15 mL). The residue was dissolved in ACN (3.42 mL) under an atmosphere of argon. In a separate flask 5-(ethylthio)-1H-tetrazole (364 mg, 2.80 mmol) was dissolved in dry acetonitrile and concentrated to dryness (3×15 mL), dissolved in ACN (1.55 mL), and added to the reaction mixture. The reaction mixture was allowed to stir at rt for 40 min. ((Dimethylamino-methylidene)amino)-3H-1,2,4-dithiazoline-3-thione (229 mg, 1.12 mmol) was added and stirring was continued at rt for 45 min. The reaction mixture was concentrated, and then dried on vacuum for 10 min. The residue was dissolved in a mixture of acetic acid (3.70 mL) and water (0.925 mL). The reaction mixture was sonicated for 2 minutes, and then allowed to stir at rt for 30 min. Toluene (15 mL) was added and the reaction mixture was concentrated, then concentrated from toluene (2×15 mL). The crude compound was purified by silica gel chromatography (0-100% MeOH in DCM) to provide Intermediate 47 as a mixture of diastereomers (420 mg, 63%). LCMS (FA): m/z=728.2 (M+H).

Step 2: N'-{9-[(2R,5S,7R,8R,10R,12aR,14R,15aS)-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-N,N-dimethylimidoformamide, or N'-{9-[(2S,5S,7R,8R,10R,12aR,14R,15aS)-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-N,N-dimethylimidoformamide, or N'-{9-[(2R,5S,7R,8R,10S,12aR,14R,15aS)-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-N,N-dimethylimidoformamide, or N'-{9-[(2S,5S,7R,8R,10S,12aR,14R,15aS)-10-(2-cyanoethoxy)-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-N,N-dimethylimidoformamide, Intermediates 48a-c Intermediate 47 (410 mg, 0.563 mmol) was dissolved in dry acetonitrile and concentrated to dryness (3×10 mL), dried on vacuum for 10 min. and dissolved in pyridine (11.3 mL) under a nitrogen atmosphere. 2-Chloro-5,5-dimethyl-1,3,2-dioxaphosphorinane 2-oxide (364 mg, 1.97 mmol) was added, and the reaction mixture was allowed to stir at rt for 45 min. Water (0.355 mL) was added followed by 3H-1,2-benzodithiol-3-one 1,1-dioxide (137 mg, 0.676 mmol). The reaction mixture was allowed to stir at rt for 1 h. An additional portion of 3H-1,2-benzodithiol-3-one 1,1-dioxide (40 mg, 0.197 mmol) was added and stirring was continued for 10 min. Toluene (10 mL) was added and the reaction mixture was concentrated. The residue was concentrated from toluene (3×10 mL). The crude compound was purified by silica gel chromatography (0-50% MeOH in DCM) to provide an impure mixture of Intermediates 48a-b (290 mg, 69%) and Intermediate 48c (40 mg, 10%). The mixture of Intermediates 48a-b was further purified by silica gel chromatography (0-50% MeOH in DCM) to provide a pure mixture of Intermediates 48a-b (160 mg). LCMS (AA): m/z=742.3 (M+H).

Step 3: 2-amino-9-[(2R,5S,7R,8R,10S,12aR,14R,15aS)-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5S,7R,8R,10S,12aR,14R,15aS)-2,10-dioxido-14-(pyrimidin-4-yloxy)-2,10-disulfanyl-decahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5S,7R,8R,10R,12aR,14R,15aS)-2,10-dioxido-14-(pyrimidin-4-yloxy)-2,10-disulfanyl-decahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5S,7R,8R,10R,12aR,14R,15aS)-2,10-dioxido-14-(pyrimidin-4-yloxy)-2,10-disulfanyl-decahydro-5,8-methanocyclopenta[l][1,3,6,9,11,2,10]pentaoxadiphosphacyclotetradecin-7-yl]-1,9-dihydro-6H-purin-6-one, I-1a-b The mixture of Intermediates 48a-b (150 mg, 0.202 mmol) was taken up in ammonium hydroxide (30%, 1.00 mL) and methylamine (33% in EtOH, 1.00 mL). The reaction mixture was allowed to stir at rt for 2 h, then concentrated. The crude mixture was purified by reverse phase flash column chromatography (0-20% ACN in aqueous triethylammonium acetate (10 mM)) to provide I-1a (29 mg, 17%) as an N,N-diethylethanamine salt. LCMS (AA): m/z=634.1 (M+H); $^1$H NMR (D$_2$O) δ 8.64 (s, 1H), 8.40 (d, J=6.0 Hz, 1H), 8.07 (s, 1H), 6.87 (d, J=6.0 Hz, 1H), 5.86 (d, J=6.5 Hz, 1H), 5.37-5.48 (m, 2H), 4.96-5.06 (m, 1H), 4.56-4.64 (m, 1H), 4.25 (td, J=11.3, 2.1 Hz, 1H), 3.97-4.08 (m, 2H), 3.85-3.94 (m, 1H), 3.15 (q, J=7.3 Hz, 12H), 2.35-2.67 (m, 6H), 1.55-1.72 (m, 1H), 1.23 (t, J=7.3 Hz, 18H); $^{31}$P NMR (D$_2$O) δ 57.15 (s, 1P), 54.61 (s, 1P) and I-1b (28 mg, 16%) as the N,N-diethylethanamine salt. LCMS (AA): m/z=634.1 (M+H); $^1$H NMR (D$_2$O) δ 8.64 (br s, 1H), 8.40 (br d, J=6.0 Hz, 1H), 7.97 (br s, 1H), 6.82 (br d, J=5.7 Hz, 1H), 5.84-5.91 (m, 1H), 5.34-5.45 (m, 2H), 4.85-4.97 (m, 1H), 4.53-4.64 (m, 1H), 4.29-4.42 (m, 1H), 3.96-4.10 (m, 2H), 3.83-3.95 (m, 1H), 3.15 (q, J=7.1 Hz, 12H), 2.65 (br d, J=4.4 Hz, 1H), 2.25-2.59 (m, 5H), 1.69 (br s, 1H), 1.23 (t, J=7.2 Hz, 18H); $^{31}$P NMR (D$_2$O) δ 54.89 (s, 1P), 53.29 (s, 1P).

Example 26A

The compound listed below (I-1c) was prepared as described in Example 26 starting with Step 3, substituting the starting material shown in the table (Intermediate 48c) for Intermediates 48a-b.

| Compound | Salt form | Starting material | LCMS data | NMR data |
|---|---|---|---|---|
| I-1c | 2•Et$_3$N | Intermediate 48c | LCMS (AA): m/z = 634.2 (M + H) | $^1$H NMR (D$_2$O) δ 8.64 (s, 1H), 8.44 (s, 1H), 8.40 (br d, J = 5.7 Hz, 1H), 6.87 (d, J = 6.1 Hz, 1H), 5.86 (d, J = 7.2 Hz, 1H), 5.34-5.47 (m, 2H), 4.96-5.07 (m, 1H), 4.52-4.62 (m, 1H), 4.06 (br d, J = 9.0 Hz, 3H), 3.84-3.95 (m, 1H), 3.15 (q, J = 7.2 Hz, 12H), 2.41-2.65 (m, 6H), 1.52-1.68 (m, 1H), 1.23 (t, J = 7.3 Hz, 18H); $^{31}$P NMR (D$_2$O) δ 57.75 (s, 1P), 53.77 (s, 1P). |

Example 27

2-cyanoethyl (6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl diisopropylphosphoramidite, Intermediate 52

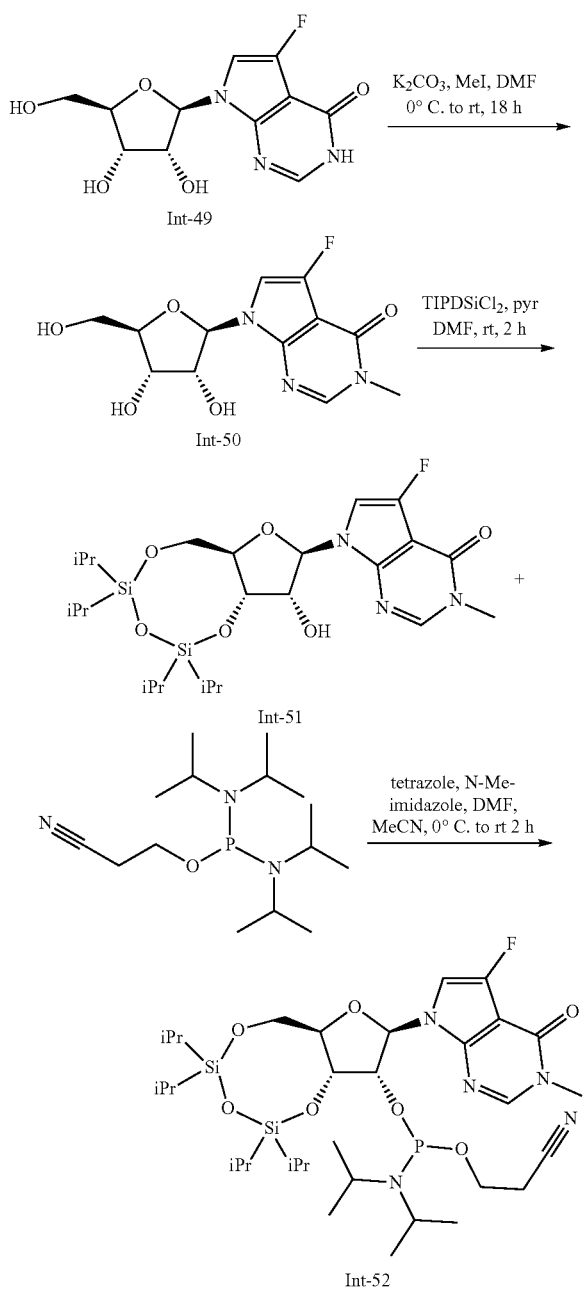

Step 1: 7-[(2R,3R,4S,5R)-3,4-dihydroxy-5-(hydroxymethyl)tetrahydrofuran-2-yl]-5-fluoro-3-methyl-3,7-dihydro-4H-pyrrolo[2,3-d]pyrimidin-4-one, Intermediate 50

7-((2R,3R,4S,5R)-3,4-dihydroxy-5-(hydroxymethyl)tetrahydrofuran-2-yl)-5-fluoro-3,7-dihydro-4H-pyrrolo[2,3-d]pyrimidin-4-one (1.54 g, 5.40 mmol) was taken up in DMF (16.9 mL) and potassium carbonate (1.12 g, 8.10 mmol) was added. The suspension was cooled to 0° C. and iodomethane (0.471 mL, 7.56 mmol) was added. The reaction mixture was allowed to stir at 0° C. for 5 min., then warmed to rt and allowed to stir overnight. The reaction mixture was concentrated by half, then water (10 mL) was added. 1 M HCl was added to adjust the reaction mixture to pH 5. The reaction mixture was concentrated and adsorbed onto Celite. The crude mixture was purified by reverse phase flash column chromatography (0-10% ACN in aqueous ammonium acetate (10 mM)) to provide 7-[(2R,3R,4S,5R)-3,4-dihydroxy-5-(hydroxymethyl)tetrahydrofuran-2-yl]-5-fluoro-3-methyl-3,7-dihydro-4H-pyrrolo[2,3-d]pyrimidin-4-one (Intermediate 50) (1.44 g, 89%). LCMS (FA): m/z=300.1 (M+H).

Step 2: 5-fluoro-7-[(6aR,8R,9R,9aS)-9-hydroxy-2,2,4,4-tetraisopropyltetrahydro-6H-furo[3,2-f][1,3,5,2,4]trioxadisilocin-8-yl]-3-methyl-3,7-dihydro-4H-pyrrolo[2,3-d]pyrimidin-4-one, Intermediate 51

7-[(2R,3R,4S,5R)-3,4-dihydroxy-5-(hydroxymethyl)tetrahydrofuran-2-yl]-5-fluoro-3-methyl-3,7-dihydro-4H-pyrrolo[2,3-d]pyrimidin-4-one was dissolved in dry acetonitrile and concentrated to dryness (3×25 mL) and taken up in pyridine (15.8 mL) and DMF (7.80 mL) under an atmosphere of nitrogen. TIPDSiCl$_2$ (1.65 mL, 5.16 mmol) was added dropwise, and the reaction mixture was allowed to stir at rt for 2 h. The reaction mixture was concentrated from toluene (2×30 mL), and the residue was partitioned between EtOAc (180 mL) and water (70 mL). The phases were separated, and the organic phase was washed with water (70 mL) and brine (70 mL), dried over Na$_2$SO$_4$ and concentrated. The residue was adsorbed onto Celite. The crude compound was purified by silica gel chromatography (0-70% EtOAc in hexanes) to provide 5-fluoro-7-[(6aR,8R,9R,9aS)-9-hydroxy-2,2,4,4-tetraisopropyltetrahydro-6H-furo[3,2-f][1,3,5,2,4]trioxadisilocin-8-yl]-3-methyl-3,7-dihydro-4H-pyrrolo[2,3-d]pyrimidin-4-one (Intermediate 51) (2.25 g, 86%). LCMS (FA): m/z=542.3 (M+H).

Step 3: 2-cyanoethyl (6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl diisopropylphosphoramidite, Intermediate 52

Intermediate 51 (2.91 g, 5.37 mmol) was concentrated from toluene (3×20 mL) and dissolved in DMF (8.31 mL) under an atmosphere of argon. 2-Cyanoethyl N,N,N',N'-tetraisopropylphosphoramidite (3.84 mL, 12.1 mmol), 1-methylimidazole (0.257 mL, 3.22 mmol) and 1H-tetrazole (0.45M in ACN, 14.6 mL, 6.50 mmol) were added. The reaction mixture was allowed to stir at rt for 2 h. EtOAc (25 mL) was added followed by saturated aqueous Na$_2$CO$_3$. The phases were separated, and the aqueous phase was extracted with EtOAc. The combined organic phases were washed with water, brine, dried with Na$_2$SO$_4$ and concentrated. The crude compound was purified by diol column chromatography (10-40% EtOAc in hexanes) to provide Intermediate 52 (3.7 g, 93%) as a mixture of diastereomers. $^1$H NMR (DMSO-d$_6$) δ 8.24-8.18 (m, 1H), 7.26-7.14 (m, 1H), 6.11-5.97 (m, 1H), 4.49-4.63 (m, 2H), 4.07-4.16 (m, 1H), 3.92-4.04 (m, 2H), 3.54-3.92 (m, 4H), 3.44-3.48 (m, 3H), 2.71-2.81 (m, 2H), 1.12-1.23 (m, 11H), 1.00-1.09 (m, 29H); $^{31}$P NMR (DMSO-d$_6$) δ 151.04 (s, 0.5P), 149.78 (s, 0.5P).

Example 28

The compounds listed below were prepared as described in Example 27 starting with Step 2, substituting the starting material shown in the table for Intermediate 50.

| Starting material | Intermediate | NMR data |
|---|---|---|
| 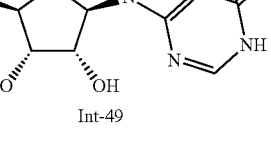<br>Int-49 | 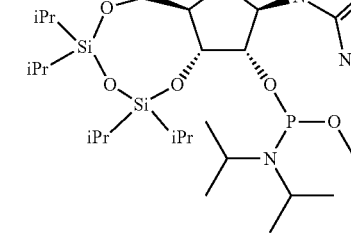<br>Int-53 | $^1$H NMR (DMSO-d$_6$) δ 12.15 (br s, 1H), 7.91 (s, 0.5H), 7.85 (s, 0.5H), 7.23 (d, J = 1.8 Hz, 0.5H), 7.15 (d, J = 2.0 Hz, 0.5H), 6.13 (s, 0.5H), 6.03 (s, 0.5H), 4.49-4.62 (m, 2H), 3.91-4.17 (m, 3H), 3.52-3.91 (m, 4H), 2.70-2.80 (m, 2H), 1.11-1.24 (m, 11H), 0.98-1.08 (m, 29 H); $^{31}$P NMR (DMSO-d$_6$) δ 151.10 (s, 0.5P), 149.66 (s, 0.5P). |
| <br>Int-115 | 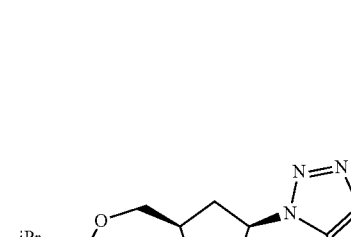<br>Int-116 | $^1$H NMR (DMSO-d$_6$) δ 12.61 (br s, 1H), 8.16-8.19 (m, 1H), 5.19-5.03 (m, 1H), 4.61-4.36 (m, 2H), 3.99-3.91 (m, 1H), 3.90-3.75 (m, 2H), 3.59-3.47 (m, 3H), 2.79-2.54 (m, 2H), 2.43-2.24 (m, 2H), 1.96-1.77 (m, 1H), 1.11-1.01 (m, 36H), 0.90-0.84 (m, 4H); $^{31}$P NMR (DMSO-d$_6$) δ 150.11 (s, 0.3P), 149.25 (s, 0.7P). |
| 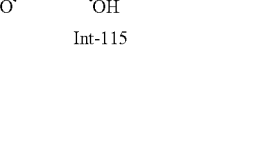<br>Int-113 | 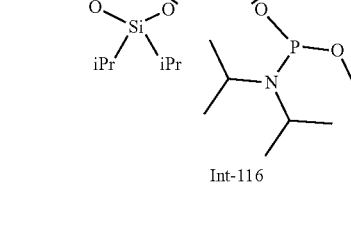<br>Int-114 | $^1$H NMR (DMSO-d$_6$) δ 11.86 (br s, 1H), 11.49-11.38 (m, 1H), 7.10-7.05 (m, 1H), 6.55 (d, J = 3.7 Hz, 0.5H), 6.52 (d, J = 3.3 Hz, 0.5H), 6.14-6.12 (m, 0.5H), 6.09-6.06 (m, 0.5H), 4.55-4.42 (m, 2H), 4.09-4.00 (m, 1H), 3.98-3.90 (m, 2H), 3.89-3.78 (m, 1H), 3.74-3.41 (m, 3H), 2.83-2.76 (m, 2H), 2.70-2.58 (m, 1H), 1.16-0.82 (m, 46H); $^{31}$P NMR (DMSO-d$_6$) δ 150.53 (s, 0.5P), 149.27 (s, 0.5P). |

-continued
| Starting material | Intermediate | NMR data |
|---|---|---|
| 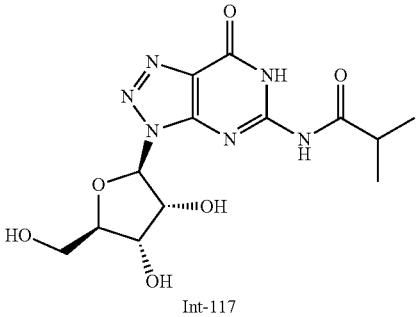<br>Int-117 | 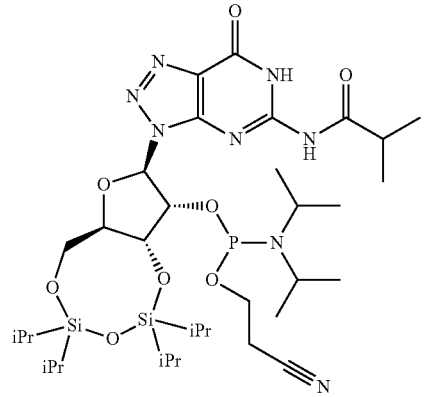 [SMILES: CC(C)C(=O)Nc1nc2c(nnn2[C@@H]2O[C@@H]3CO[Si](C(C)C)(C(C)C)O[Si](C(C)C)(C(C)C)O[C@H]3[C@H]2OP(OCCC#N)N(C(C)C)C(C)C)c(=O)[nH]1]<br>Int-118 | $^1$H NMR (DMSO-$d_6$) δ 12.47-11.75 (m, 2H), 6.13 (s, 0.3H), 6.01 (s, 0.7H), 5.08 (dd, J = 4.6, 8.7 Hz, 0.3H), 5.00 (dd, J = 4.8, 8.8 Hz, 0.7H), 4.89 (dd, J = 4.7, 13.0 Hz, 0.7H), 4.75 (dd, J = 4.7, 9.4 Hz, 0.3H), 4.15-4.03 (m, 1H), 4.02-3.80 (m, 3H), 3.76 3.36 (m, 3H), 2.91-2.59 (m, 3H), 1.23-0.96 (m, 46H); $^{31}$P NMR (DMSO-$d_6$) δ 152.20 (s, 0.3P), 149.62 (s, 0.7P) |
| 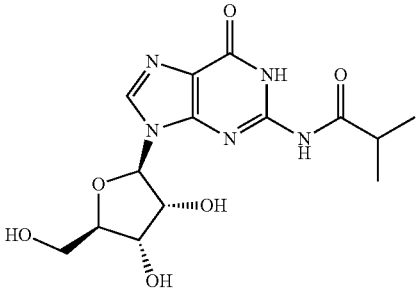 [SMILES: CC(C)C(=O)Nc1nc2c(ncn2[C@@H]2O[C@H](CO)[C@@H](O)[C@H]2O)c(=O)[nH]1] | 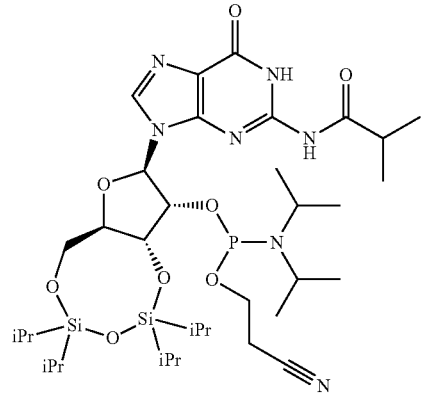 [SMILES: CC(C)C(=O)Nc1nc2c(ncn2[C@@H]2O[C@@H]3CO[Si](C(C)C)(C(C)C)O[Si](C(C)C)(C(C)C)O[C@H]3[C@H]2OP(OCCC#N)N(C(C)C)C(C)C)c(=O)[nH]1]<br>Int-90 | $^1$H NMR (DMSO-$d_6$) δ 12.12 (br s, 1H), 11.55 (br d, J = 11.1 Hz, 1H), 8.23 (s, 0.5H), 8.09 (s, 0.5H), 5.95 (s, 0.5H), 5.89 (d, J = 2.1 Hz, 0.5H), 4.78-4.66 (m, 1H), 4.58-4.49 (m, 1H), 4.11-3.49 (m, 9H), 2.84-2.76 (m, 2H), 2.72-2.57 (m, 1H), 1.19-0.90 (m, 46H; $^{31}$P NMR (DMSO-$d_6$) δ 150.84 (s, 0.5P), 148.98 (s, 0.5P) |

Example 29

5-fluoro-7-[(2S,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3,7-dihydro-4H-pyrrolo[2,3-d]pyrimidin-4-one, or 5-fluoro-7-[(2R,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3,7-dihydro-4H-pyrrolo[2,3-d]pyrimidin-4-one, or 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, or 5-fluoro-7-[(2R,5R,7R,8R,10S,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3,7-dihydro-4H-pyrrolo[2,3-d]pyrimidin-4-one, I-3a, I-3b

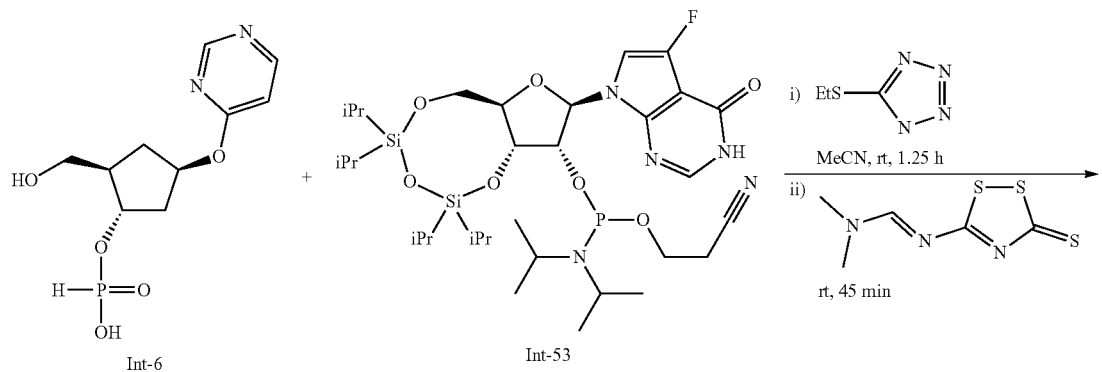

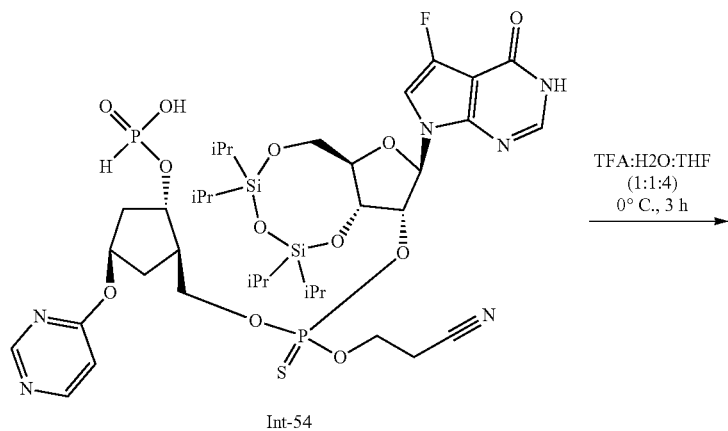

-continued
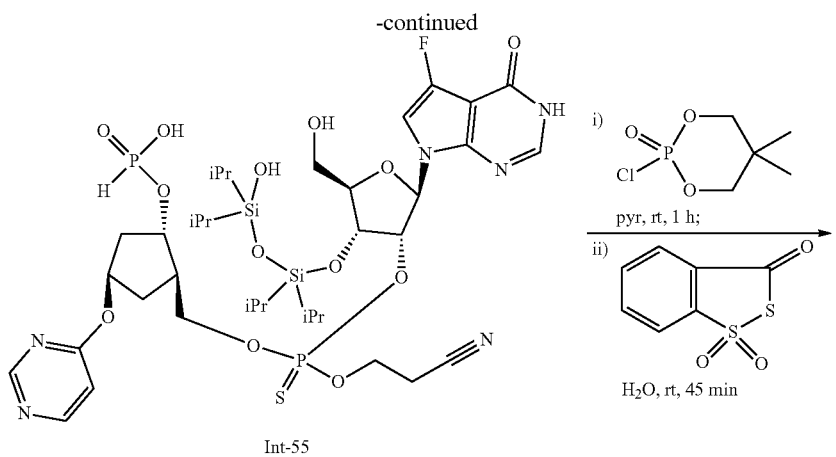
Int-55
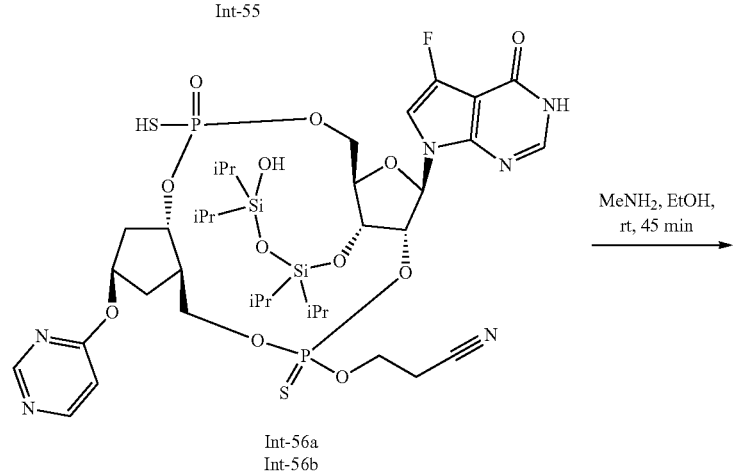
Int-56a
Int-56b
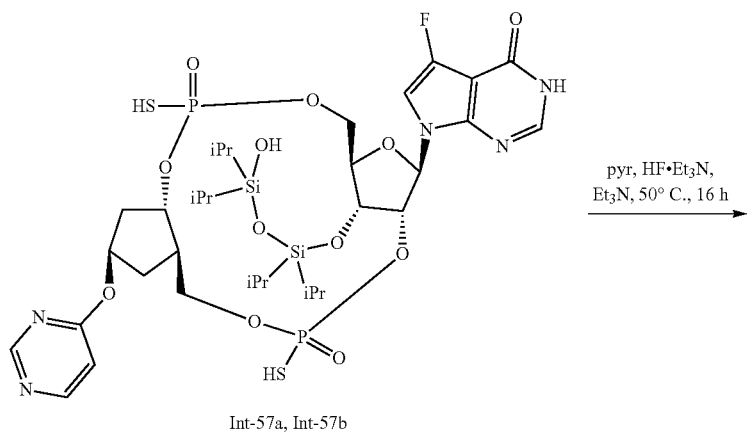
Int-57a, Int-57b
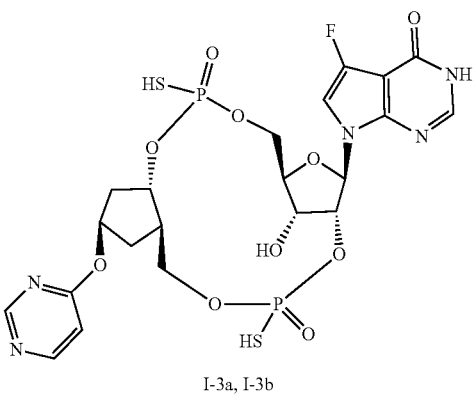
I-3a, I-3b Step 1: (1S,2R,4R)-2-({[(R)-(2-cyanoethoxy){[(6aR,8R,9R,9aR)-8-(5-fluoro-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphorothioyl]oxy}methyl)-4-(pyrimidin-4-yloxy)cyclopentyl hydrogen phosphonate, and (1S,2R,4R)-2-({[(S)-(2-cyanoethoxy){[(6aR,8R,9R,9aR)-8-(5-fluoro-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphorothioyl]oxy}methyl)-4-(pyrimidin-4-yloxy) cyclopentyl hydrogen phosphonate, Intermediate 54

A mixture of Intermediate 6 (660 mg, 2.41 mmol) and Intermediate 53 (2.28 g, 3.13 mmol) was dissolved in dry acetonitrile and concentrated to dryness (4×25 mL) and then dried under vacuum for 1 h. The residue was then dissolved in ACN (8.82 mL) under an atmosphere of argon. In a separate flask 5-(ethylthio)-1H-tetrazole (940 mg, 7.22 mmol) was dissolved in dry acetonitrile and concentrated to dryness (3×25 mL), dissolved in ACN (4.01 mL), and added to the reaction mixture. The reaction mixture was allowed to stir at rt for 1.25 h. ((Dimethylamino-methylidene)amino)-3H-1,2,4-dithiazoline-3-thione (593 mg, 2.89 mmol) was added and stirring was continued at rt for 90 min. The reaction mixture was adsorbed onto silica gel. The crude compound was purified by silica gel chromatography (0-50% MeOH in DCM) to provide Intermediate 54 (720 mg, 32%) as a mixture of diastereomers. LCMS (FA): m/z=933.3 (M+H).

Step 2: (1S,2R,4R)-2-({[(R)-(2-cyanoethoxy)({(2R,3R,4R,5R)-2-(5-fluoro-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphorothioyl]oxy}methyl)-4-(pyrimidin-4-yloxy)cyclopentyl hydrogen phosphonate, and (1S,2R,4R)-2-({[(S)-(2-cyanoethoxy)({(2R,3R,4R,5R)-2-(5-fluoro-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphorothioyl]oxy}methyl)-4-(pyrimidin-4-yloxy)cyclopentyl hydrogen phosphonate, Intermediate 55

Intermediate 54 (720 mg, 0.772 mmol) was dissolved in THF (8.00 mL,) and water (2.00 mL). The solution was cooled to 0° C. and TFA (2.00 mL, 26.0 mmol) was added dropwise. The reaction mixture was allowed to stir at 0° C. for 3 h. Sodium bicarbonate (5.00 mL) was added portionwise, followed by water and EtOAc. The reaction mixture was warmed to rt and extracted into EtOAc. The combined organic phases were washed with brine, dried with $Na_2SO_4$ and concentrated. The crude compound was purified by silica gel chromatography (10-80% MeOH in DCM) to provide Intermediate 55 (380 mg, 52%) as a mixture of diastereomers. LCMS (FA): m/z=952.3 (M+H).

Step 3: 3-{[(2S,5R,7R,8R,10R,12aR,14R,15aS,16R)-7-(5-fluoro-4-oxo-3,4-dihydro-7H-pyrrolo[2,3-d]pyrimidin-7-yl)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-10-yl]oxy}propanenitrile, or 3-{[(2R,5R,7R,8R,10R,12aR,14R,15aS,16R)-7-(5-fluoro-4-oxo-3,4-dihydro-7H-pyrrolo[2,3-d]pyrimidin-7-yl)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-10-yl]oxy}propanenitrile, or 3-{[(2S,5R,7R,8R,10S,12aR,14R,15aS,16R)-7-(5-fluoro-4-oxo-3,4-dihydro-7H-pyrrolo[2,3-d]pyrimidin-7-yl)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-10-yl]oxy}propanenitrile, or 3-{[(2R,5R,7R,8R,10S,12aR,14R,15aS,16R)-7-(5-fluoro-4-oxo-3,4-dihydro-7H-pyrrolo[2,3-d]pyrimidin-7-yl)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-10-yl]oxy}propanenitrile, Intermediate 56a and Intermediate 56b Intermediate 55 (400 mg, 0.421 mmol) was dissolved in dry acetonitrile and concentrated to dryness (3×15 mL), dried under vacuum for 15 min and then taken up in pyridine (8.41 mL) under an atmosphere of argon. 2-Chloro-5,5-dimethyl-1,3,2-dioxaphosphorinane 2-oxide (272 mg, 1.47 mmol) was added. The reaction mixture was allowed to stir at rt for 1 h. Water (0.265 mL, 14.72 mmol) was added followed by 3H-1,2-benzodithiol-3-one 1,1-dioxide (102 mg, 0.505 mmol), and the reaction mixture was allowed to stir at rt for 1 h. An additional portion of 3H-1,2-benzodithiol-3-one 1,1-dioxide (135 mg, 0.668 mmol) was added and stirring was continued for 15 min. The reaction mixture was diluted with toluene and concentrated to give the crude compound as a mixture of two major and two minor diastereomers. The crude mixture was purified by silica gel chromatography (5-50% MeOH in DCM) to provide the two major diastereomers, Intermediate 56a and Intermediate 56b, each requiring further purification. Intermediate 56a was combined with additional impure material and purified by silica gel chromatography (5-15% MeOH in DCM) to provide Intermediate 56a (118 mg, 20%). Intermediate 56b was combined with additional impure material and purified by silica gel chromatography (5-15% MeOH in DCM) to provide Intermediate 56b (250 mg, 58%). LCMS (FA): m/z=965.3 (M+H).

Step 4: 5-fluoro-7-[(2S,5R,7R,8R,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, or 5-fluoro-7-[(2R,5R,7R,8R,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, or 5-fluoro-7-[(2S,5R,7R,8R,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, or 5-fluoro-7-[(2R,5R,7R,8R,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one Intermediate 56b (250 mg, 0.259 mmol) was taken up in methylamine (33% in EtOH, 7.77 mL, 62.4 mmol) under an atmosphere of nitrogen. The reaction mixture was allowed to stir at rt for 90 min. The reaction mixture was concentrated and adsorbed onto silica. The crude compound was purified by reverse phase flash column chromatography (10-40% ACN in aqueous ammonium acetate (10 mM)) to provide Intermediate 57b ((75 mg, 32%). LCMS (AA): m/z=912.2 (M+H).

Intermediate 56a was treated in an analogous fashion to the above procedure to provide Intermediate 57a (46 mg, 41%). LCMS (AA): m/z=912.2 (M+H).

Step 5: 5-fluoro-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, or 5-fluoro-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, or 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3,7-dihydro-4H-pyrrolo[2,3-d]pyrimidin-4-one, or 5-fluoro-7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, I-3b To a polypropylene vial was added Intermediate 57b (75.0 mg, 0.0822 mmol), pyridine (0.411 mL, 5.08 mmol), triethylamine trihydrofluoride (0.109 mL, 0.658 mmol) and TEA (1.03 mL, 7.30 mmol). The vial was sealed and the reaction mixture was heated at 50° C. overnight with vigorous stirring. The reaction mixture was cooled to rt and water (1.54 mL) was added followed by dropwise addition of a solution of $CaCl_2$ (190 mg, 1.65 mmol) in water (1.54 mL). The reaction mixture was allowed to stir at rt for 1 h, then filtered through Celite, rinsing with water (5 mL). An additional portion of $CaCl_2$ (190 mg, 1.65 mmol) was added to the filtrate and it was allowed to stir for 15 min. at rt. The mixture was filtered again through Celite, and the Celite was rinsed with water (5×5 mL). The filtrate was concentrated. No HF was observed by $^{19}F$ NMR. The crude mixture was purified by reverse phase flash column chromatography (0-12% ACN in aqueous triethylammonium acetate (10 mM)) to provide I-3b (21 mg, 30%) as an N,N-diethylethanamine salt. LCMS (AA): m/z=652.2 (M+H). $^1H$ NMR (DMSO-$d_6$) δ 12.06 (br d, J=2.9 Hz, 1H), 9.36 (br s, 2H), 8.76 (s, 1H), 8.46 (d, J=5.9 Hz, 1H), 7.89 (d, J=3.7 Hz, 1H), 7.64 (d, J=1.0 Hz, 1H), 6.87 (dd, J=5.9, 1.0 Hz, 1H), 6.25 (dd, J=8.1, 1.0 Hz, 1H), 5.47 (quin, J=6.1 Hz, 1H), 4.99 (dt, J=8.3, 4.4 Hz, 1H), 4.88 (d, J=2.4 Hz, 1H), 4.80-4.87 (m, 1H), 4.58 (t, J=2.9 Hz, 1H), 4.08 (br s, 1H), 4.05 (dd, J=11.0, 3.4 Hz, 1H), 3.89 (t, J=10.8 Hz, 1H), 3.58-3.67 (m, 1H), 3.49 (q, J=10.0 Hz, 1H), 3.04 (br q, J=7.1 Hz, 12H), 2.25-2.42 (m, 3H), 2.12 (dt, J=13.7, 5.6 Hz, 1H), 1.23-1.33 (m, 1H), 1.14 (t, J=7.3 Hz, 18H). $^{31}P$ NMR (DMSO-$d_6$) δ 53.08 (s, 1P), 47.24 (s, 1P).

Example 29A

The compound listed below (I-3a) was prepared as described in Example 29 starting with Step 5, substituting the starting material shown in the table (Intermediate 57a) for Intermediate 57b.

| Compound | Salt form | Starting material | LCMS data | NMR data |
|---|---|---|---|---|
| I-3a | Et3N | Intermediate 57a | LCMS (AA): m/z = 652.1 (M + H) | $^1$H NMR (DMSO-$d_6$) δ 12.05 (br d, J = 3.3 Hz, 1H), 9.42 (br s, 2H), 8.76 (s, 1H), 8.47 (d, J = 5.7 Hz, 1H), 7.88 (d, J = 3.7 Hz, 1H), 7.48 (d, J = 1.5 Hz, 1H), 6.88 (dd, J = 5.9, 1.1 Hz, 1H), 6.24 (dd, J = 8.1, 1.3 Hz, 1H), 5.41-5.52 (m, 2H), 4.97 (dt, J = 8.8, 4.7 Hz, 1H), 4.86-4.93 (m, 1H), 4.39 (br d, J = 2.7 Hz, 1H), 3.95 (t, J = 11.5 Hz, 1H), 3.70-3.80 (m, 1H), 3.51-3.64 (m, 2H), 3.06 (q, J = 7.1 Hz, 12H), 2.33-2.45 (m, 2H), 2.22-2.30 (m, 1H), 2.14 (dt, J = 13.8, 5.9 Hz, 1H), 1.25 (dt, J = 14.1, 5.0 Hz, 1H), 1.16 (t, J = 7.3 Hz, 18H); $^{31}$P NMR (DMSO-$d_6$) δ 56.28 (s, 1P), 53.32 (s, 1P) |

Example 30

5-fluoro-7-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one, or 5-fluoro-7-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one, or 5-fluoro-7-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one, or 5-fluoro-7-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3-methyl-3,7-dihydro-4H-pyrrolo[2,3-d]pyrimidin-4-one, I-12a, I-12b

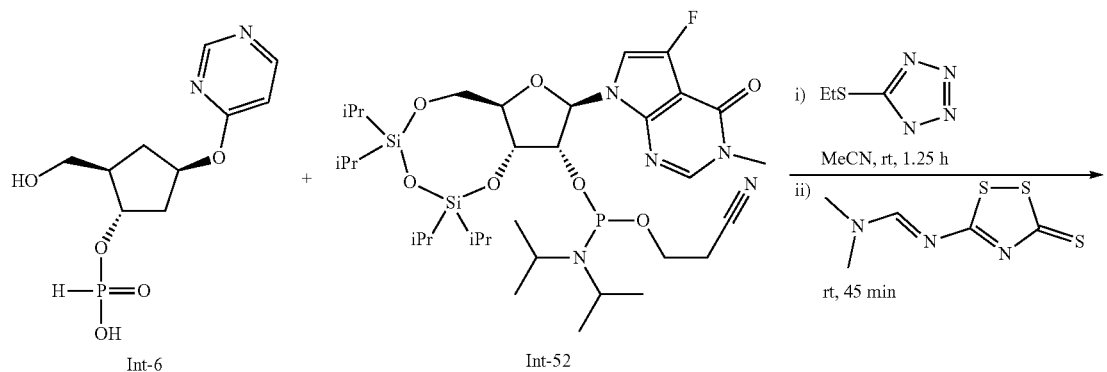

-continued
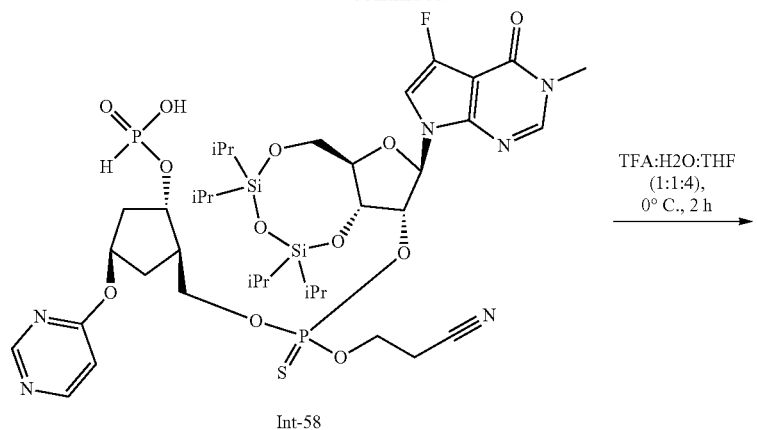
Int-58
TFA:H2O:THF
(1:1:4),
0° C., 2 h
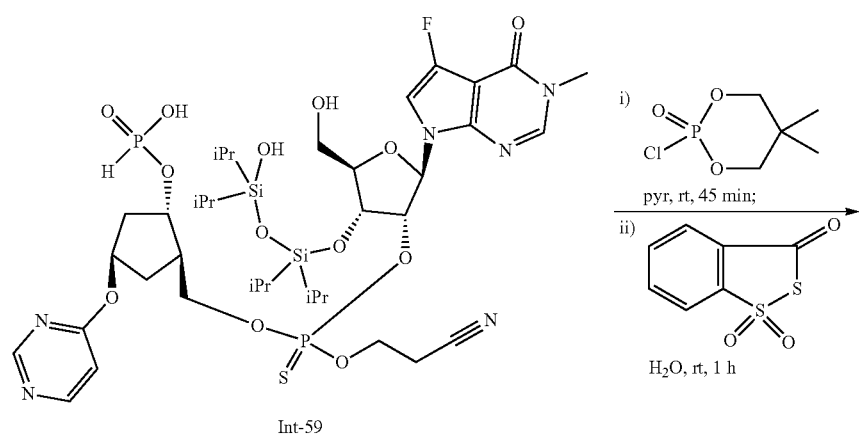
Int-59
i) 
pyr, rt, 45 min;
ii) 
H₂O, rt, 1 h
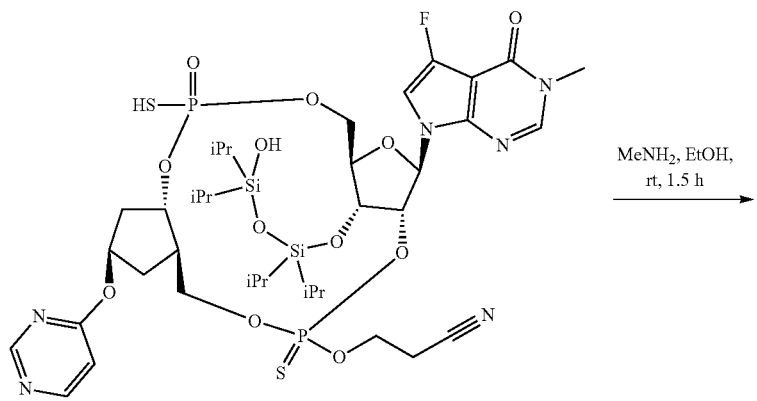
Int-60a, Int-60b
MeNH₂, EtOH,
rt, 1.5 h

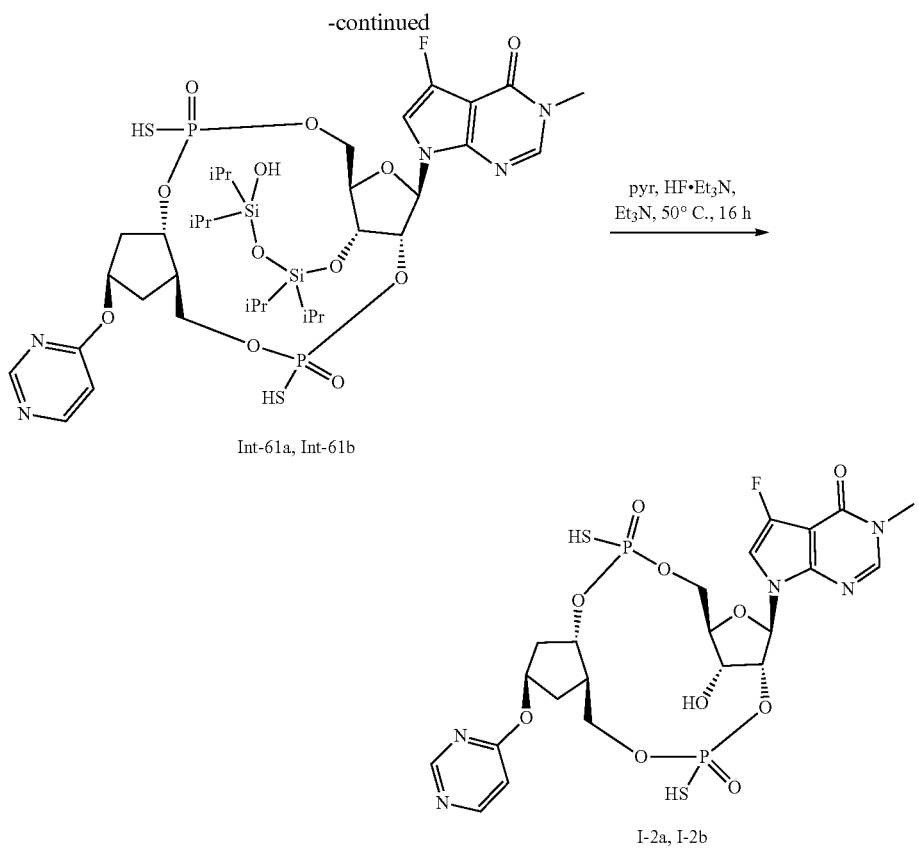

Int-61a, Int-61b

I-2a, I-2b

Step 1: (1S,2R,4R)-2-({[(R)-(2-cyanoethoxy) {[(6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphorothioyl] oxy}methyl)-4-(pyrimidin-4-yloxy)cyclopentyl hydrogen phosphonate, and (1S,2R,4R)-2-({[(S)-(2-cyanoethoxy){[(6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphorothioyl]oxy}methyl)-4-(pyrimidin-4-yloxy)cyclopentyl hydrogen phosphonate, Intermediate 58

A mixture of Intermediate 6 (654 mg, 2.39 mmol) and Intermediate 52 (2.30 g, 3.10 mmol) were combined and dissolved in dry acetonitrile and concentrated to dryness (3×50 mL). The residue was then dissolved in ACN (8.74 mL) under an atmosphere of argon. In a separate flask 5-(ethylthio)-1H-tetrazole (932 mg, 7.16 mmol) was dissolved in dry acetonitrile and concentrated to dryness (3×20 mL), the residue was dissolved in ACN (3.98 mL) and added to the reaction mixture under an atmosphere of nitrogen. The reaction mixture was allowed to stir at rt for 1 h. ((Dimethylamino-methylidene)amino)-3H-1,2,4-dithiazoline-3-thione (587 mg, 2.86 mmol) was added to the reaction mixture and stirring was continued for 45 min at rt. The reaction mixture was concentrated and dried on vacuum for 10 min. The crude compound was purified by silica gel chromatography (0-70% MeOH in DCM) to provide Intermediate 58 (1.10 g, 49%) as a mixture of diastereomers. LCMS (AA): m/z=948.4 (M+H).

Step 2: (1S,2R,4R)-2-({[(R)-(2-cyanoethoxy)({(2R,3R,4R,5R)-2-(5-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphorothioyl]oxy}methyl)-4-(pyrimidin-4-yloxy)cyclopentyl hydrogen phosphonate, and (1S,2R,4R)-2-({[(S)-(2-cyanoethoxy)({(2R,3R,4R,5R)-2-(5-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphorothioyl]oxy}methyl)-4-(pyrimidin-4-yloxy)cyclopentyl hydrogen phosphonate, Intermediate 59

Intermediate 58 (1.08 g, 1.14 mmol) was taken up in THF (12.0 mL) and water (3.0 mL) and cooled to 0° C. TFA (3.0 mL, 39.6 mmol) was added drop-wise and the reaction mixture was allowed to stir at 0° C. for 2 h. Sodium bicarbonate (5.20 g, 61.6 mmol) was added portion-wise, followed by water and EtOAc. The reaction mixture was allowed to warm to rt and extracted into EtOAc. The combined organic phases were washed with brine, dried with $Na_2SO_4$ and concentrated. The crude compound was purified by silica gel chromatography (0-80% MeOH in DCM) to provide Intermediate 59 (900 mg, 82%) as a mixture of diastereomers. LCMS (FA): m/z=965.3 (M+H).

Step 3: 3-{[(2S,5R,7R,8R,10R,12aR,14R,15aS, 16R)-7-(5-fluoro-3-methyl-4-oxo-3,4-dihydro-7H-pyrrolo[2,3-d]pyrimidin-7-yl)-16-[(3-hydroxy-1,1,3, 3-tetraisopropyldisiloxanyl)oxy]-2-oxido-14-(pyrimidin-4-yloxy)-2-sulfanyl-10-sulfidodecahydro-5,8-methanocyclopenta[1][1,3,6,9, 11,2,10]pentaoxadiphosphacyclotetradecin-10-yl] oxy}propanenitrile, or 3-{[(2R,5R,7R,8R,10R,12aR,14R,15aS,16R)-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl) oxy]-2-oxido-14-(pyrimidin-4-yloxy)-2-sulfanyl-10-sulfidodecahydro-5,8-methanocyclopenta[1][1,3,6,9,11,2,10]pentaoxadiphosphacyclotetradecin-10-yl]oxy}propane nitrile, or 3-{[(2S,5R,7R,8R,10S,12aR,14R,15aS,16R)-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl) oxy]-2-oxido-14-(pyrimidin-4-yloxy)-2-sulfanyl-10-sulfidodecahydro-5,8-methanocyclopenta[1][1,3,6,9,11,2,10]pentaoxadiphosphacyclotetradecin-10-yl]oxy}propane nitrile, or 3-{[(2R,5R,7R,8R,10S,12aR,14R,15aS,16R)-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl) oxy]-2-oxido-14-(pyrimidin-4-yloxy)-2-sulfanyl-10-sulfidodecahydro-5,8-methanocyclopenta[1][1,3,6,9,11,2,10]pentaoxadiphosphacyclotetradecin-10-yl]oxy}propane nitrile, Intermediates 60a and 60b Intermediate 59 (890 mg, 0.922 mmol) was azeoteotroped with ACN (3×20 mL), dried under vacuum for 10 min, and dissolved in pyridine (18.4 mL) under an atmosphere of nitrogen. 2-Chloro-5,5-dimethyl-1,3,2-dioxaphosphorinane 2-oxide (596 mg, 3.23 mmol) was added, and the reaction mixture was allowed to stir at rt for 45 min. Water (0.581 mL) was added followed by 3H-1,2-benzodithiol-3-one 1,1-dioxide (224 mg, 1.11 mmol), then stirring was continued at rt for 1 h. An additional portion of 3H-1,2-benzodithiol-3-one 1,1-dioxide (55.0 mg, 0.273 mmol) was added and stirring was continued for 10 min. The reaction mixture was concentrated and concentrated from toluene to provide a crude mixture of two major and two minor diastereomers. The crude compound was purified by silica gel chromatography (0-50% MeOH in DCM) to provide one of the major diastereomers Intermediate 60a (265 mg, 29%) LCMS (FA): m/z=979.3 (M+H) and the other major diastereomer mixed with the minor diastereomers Intermediate 60b (300 mg, 33%) LCMS (FA): m/z=979.2 (M+H).

Step 4: 5-fluoro-7-[(2S,5R,7R,8R,10R,12aR,14R, 15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[1][1,3,6,9,11,2,10] pentaoxadiphosphacyclotetradecin-7-yl]-3-methyl-3, 7-dihydro-4H-pyrrolo[2,3-d]pyrimidin-4-one, or 5-fluoro-7-[(2R,5R,7R,8R,10R,12aR,14R,15aS, 16R)-16-[(3-hydroxy-1,1,3,3-tetraisopropyldisiloxanyl)oxy]-2,10-dioxido-14-(pyrimidin-4-yloxy)-2, 10-disulfanyldecahydro-5,8-methanocyclopenta[1][1, 3,6,9,11,2,10]pentaoxadiphosphacyclotetradecin-7-yl-3-methyl-3,7-dihydro-4H-pyrrolo[2,3-d] pyrimidin-4-one, or 5-fluoro-7-[(2S,5R,7R,8R,10S,12aR,14R,15aS,16R)-16-[(3-hydroxy-1,1,3,3-tetraisopropyldisiloxanyl) oxy]-2,10-dioxido-14-(pyrimidin-4-yloxy)-2,10-disulfanyldecahydro-5,8-methanocyclopenta[1][1,3, 6,9,11,2,10]pentaoxadiphosphacyclotetradecin-7-yl]-3-methyl-3,7-dihydro-4H-pyrrolo[2,3-d]pyrimidin-4-one, or 5-fluoro-7-[(2R,5R,7R,8R,10S,12aR,14R,15aS, 16R)-16-[(3-hydroxy-1,1,3,3-tetraisopropyldisiloxanyl)oxy]-2,10-dioxido-14-(pyrimidin-4-yloxy)-2, 10-disulfanyldecahydro-5,8-methanocyclopenta[1][1, 3,6,9,11,2,10]pentaoxadiphosphacyclotetradecin-7-yl]-3-methyl-3,7-dihydro-4H-pyrrolo[2,3-d] pyrimidin-4-one, Intermediate 61b Intermediate 60b (293 mg, 0.299 mmol) was dissolved in methylamine (33% in EtOH, 8.98 mL, 72.1 mmol) and the reaction mixture was allowed to stir under an atmosphere of nitrogen at rt for 1.5 h. The reaction mixture was concentrated and dried on vacuum for 10 min. The crude compound was purified by reverse phase flash column chromatography (5-40% ACN in aqueous ammonium acetate (10 mM)) to provide Intermediate 61b (119 mg, 43%). LCMS (AA): m/z=926.1 (M+H).

Step 5: 5-fluoro-7-[(2S,5R,7R,8R,10R,12aR,14R, 15aS,16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3-methyl-3, 7-dihydro-4H-pyrrolo[2,3-d]pyrimidin-4-one, or 5-fluoro-7-[(2R,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3-methyl-3, 7-dihydro-4H-pyrrolo[2,3-d]pyrimidin-4-one, or 5-fluoro-7-[(2S,5R,7R,8R,10S,12aR,14R,15aS,16R)-16-hydroxy-2,10-dioxido-14-(pyrimidin-4-yloxy)-2, 10-disulfanyldecahydro-5,8-methanocyclopenta[l][1, 3,6,9,11,2,10]pentaoxadiphosphacyclotetradecin-7-yl]-3-methyl-3,7-dihydro-4H-pyrrolo[2,3-d] pyrimidin-4-one, or 5-fluoro-7-[(2R,5R,7R,8R,10S,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-3-methyl-3, 7-dihydro-4H-pyrrolo[2,3-d]pyrimidin-4-one, I-12b Intermediate 61b (119 mg, 0.128 mmol) was suspended in pyridine (0.642 mL) and TEA (1.61 mL) in a propylene tube. Triethylamine trihydrofluoride (0.107 mL, 0.642 mmol) was added, the tube was sealed, and the reaction mixture was allowed to stir at 50° C. overnight. The reaction mixture was cooled to rt, and water (1.62 mL) was added, followed by dropwise addition of a solution of calcium chloride (150 mg, 1.30 mmol) in water (1.62 mL). The reaction mixture was allowed to stir at rt for 30 min., then filtered through Celite and the Celite was rinsed with water (5×3 mL). The filtrate was concentrated to give a white solid. No HF was observed by $^{19}$F NMR. The crude mixture was purified by reverse phase flash column chromatography (0-20% ACN in aqueous triethylammonium acetate (10 mM)) to provide I-12b (87 mg, 74%) as an N,N-diethylethanamine salt. LCMS (AA): m/z=666.3 (M+H). $^1$H NMR (D$_2$O) δ 8.60 (s, 1H), 8.36 (d, J=6.1 Hz, 1H), 8.11 (s, 1H), 7.37 (d, J=1.6 Hz, 1H), 6.78 (dd, J=6.1, 0.6 Hz, 1H), 6.35 (dd, J=7.9, 0.6 Hz, 1H), 5.39 (spt, J=2.6 Hz, 1H), 5.05 (ddd, J=9.3, 8.5, 4.1 Hz, 1H), 4.83-4.93 (m, 1H), 4.66 (br d, J=4.1 Hz, 1H), 4.38 (br d, J=2.1 Hz, 1H), 4.30 (ddd, J=11.4, 10.4, 1.2 Hz, 1H), 3.93-4.05 (m, 2H), 3.77 (ddd, J=10.8, 7.2 Hz, 1H), 3.52 (s, 3H), 3.12 (q, J=7.3 Hz, 12H), 2.38-2.52 (m, 3H), 2.28-2.38 (m, 1H), 1.47-1.60 (m, 1H), 1.20 (t, J=7.3 Hz, 18H). $^{31}$P NMR (D$_2$O) δ 54.26 (s, 1P), 52.75 (s, 1P).

Example 30A

The compound listed below (I-12a) was prepared as described in Example 30 starting with Step 5, substituting the starting material shown in the table (Intermediate 60a) for Intermediate 60b.

| Compound | Salt form | Starting material | LCMS data | NMR data |
|---|---|---|---|---|
| I-12a | Et3N | Intermediate 60a | LCMS (AA): m/z = 666.1 (M + H). | $^1$H NMR (D$_2$O) δ 8.61 (s, 1H), 8.38 (d, J = 6.0 Hz, 1H), 8.11 (s, 1H), 7.40 (s, 1H), 6.86 (d, J = 5.9 Hz, 1H), 6.36 (br d, J = 7.8 Hz, 1H), 5.36-5.49 (m, 1H), 4.93-5.10 (m, 2H), 4.49 (br d, J = 4.1 Hz, 1H), 4.36 (br d, J = 1.4 Hz, 1H), 4.20-4.32 (m, 1H), 3.94-4.05 (m, 2H), 3.74-3.85 (m, 1H), 3.52 (s, 3H), 3.12 (q, J = 7.4 Hz, 12H), 2.39-2.51 (m, J = 5.3 Hz, 4H), 1.46-1.60 (m, 1H), 1.20 (t, J = 7.3 Hz, 18H); $^{31}$P NMR (D$_2$O) δ 58.56 (s, 1P), 54.42 (s, 1P) |

Example 31

2-amino-9-[(2R,5R,7R,8R,10S,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10S,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5R,7R,8R,10R,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10R,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, I-2a-b

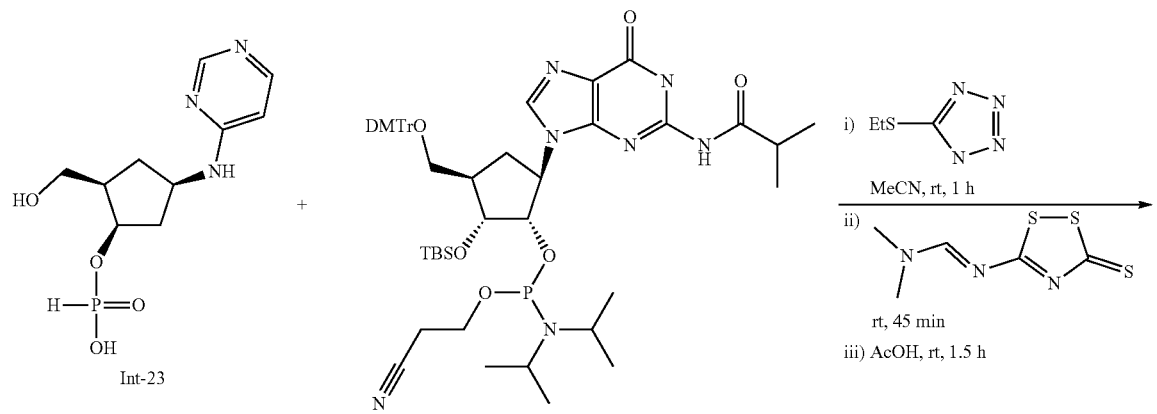

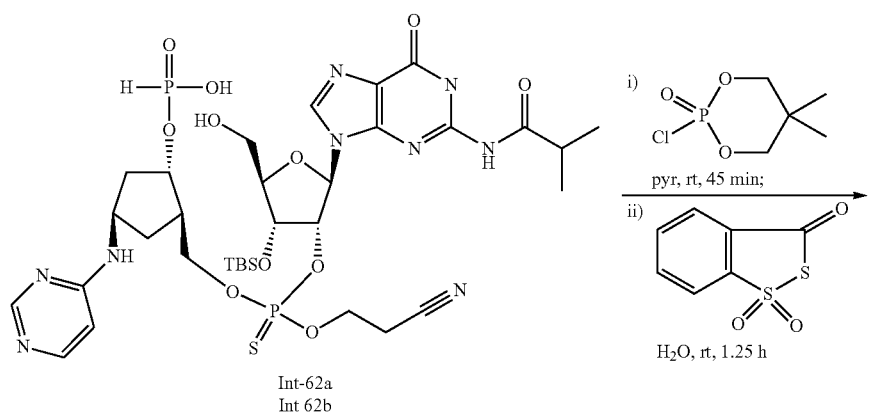

-continued
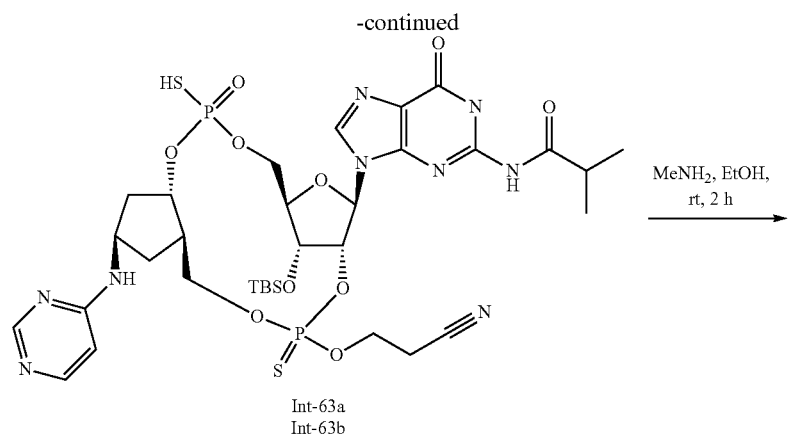
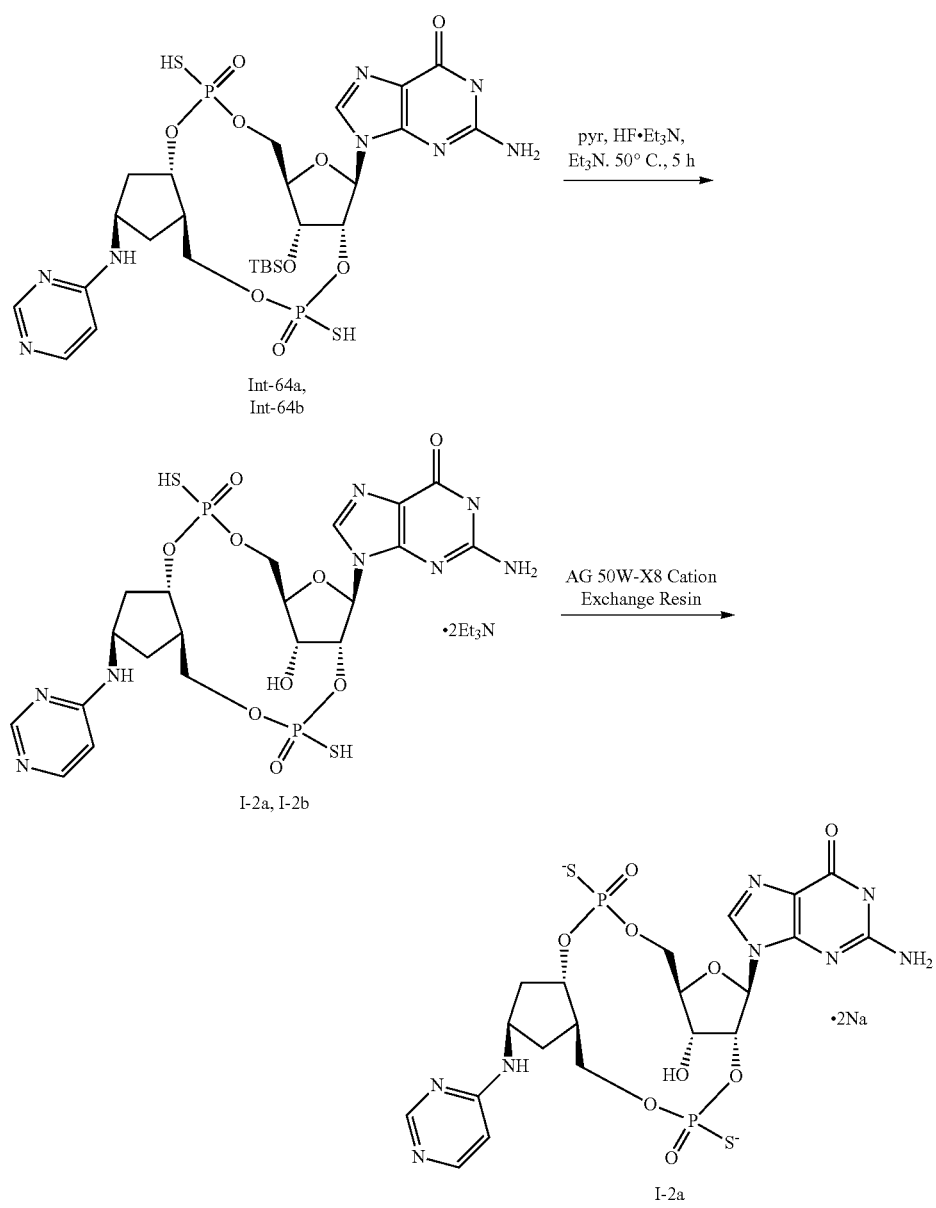

Step 1: (1S,2R,4R)-2-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-(pyrimidin-4-ylamino) cyclopentyl hydrogen phosphonate, or (1S,2R,4R)-2-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-(pyrimidin-4-ylamino)cyclopentyl hydrogen phosphonate Intermediate 23, N,N-diethylethanamine salt (804 mg, 2.15 mmol) and N-[9-[(2R,3R,4R,5R)-5-[[bis(4-methoxyphenyl)-phenyl-methoxy]methyl]-4-[tert-butyl(dimethyl)silyl]oxy-3-[2-cyanoethoxy-(diisopropylamino)phosphanyl]oxy-tetrahydrofuran-2-yl]-6-oxo-1H-purin-2-yl]-2-methylpropanamide (2.71 g, 2.79 mmol) were dissolved in dry acetonitrile and concentrated to dryness (3×100 mL). The residue was then dissolved in ACN (7.00 mL) under an atmosphere of argon. In a separate flask 5-(ethylthio)-1H-tetrazole (694 mg, 5.33 mmol) was dissolved in dry acetonitrile and concentrated to dryness (3×25 mL), dissolved in ACN (3.50 mL) and added to the reaction mixture. The reaction mixture was allowed to stir at rt for 1 h. ((Dimethylamino-methylidene)amino)-3H-1,2,4-dithiazoline-3-thione (529 mg, 2.58 mmol) was added and stirring was continued at rt for 45 min. The reaction mixture was concentrated and dried on vacuum for 10 min. Then the residue was dissolved in acetic acid (7.05 mL) and water (1.76 mL), sonicated for 2 min and allowed to stir at rt for 1.5 h. Toluene was added (15 mL) and the reaction mixture was concentrated, then concentrated from toluene (2×15 mL). The crude mixture was purified by silica gel chromatography (0-50% MeOH in DCM) to provide Intermediate 62a (490 mg, 26%) as the first eluting peak LCMS (AA): m/z=872.3 (M+H) and Intermediate 62b (490 mg, 26%) as the second eluting peak LCMS (AA): m/z=872.3 (M+H).

Step 2: N-{9-[(2R,5R,7R,8R,10R,12aR,14R,15aS,16R)-16-{[tert-butyl(dimethyl)silyl]oxy}-10-(2-cyanoethoxy)-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, or N-{9-[(2S,5R,7R,8R,10R,12aR,14R,15aS,16R)-16-{[tert-butyl(dimethyl)silyl]oxy}-10-(2-cyanoethoxy)-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, or N-{9-[(2R,5R,7R,8R,10S,12aR,14R,15aS,16R)-16-{[tert-butyl(dimethyl)silyl]oxy}-10-(2-cyanoethoxy)-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, or N-{9-[(2S,5R,7R,8R,10S,12aR,14R,15aS,16R)-16-{[tert-butyl(dimethyl)silyl]oxy}-10-(2-cyanoethoxy)-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 63a Intermediate 62a (470 mg, 0.539 mmol) was azeoteotroped with ACN (3×20 mL), dried on vacuum for 10 min and then dissolved in pyridine (10.0 mL) under an atmosphere of nitrogen. 2-Chloro-5,5-dimethyl-1,3,2-dioxaphosphorinane 2-oxide (348 mg, 1.89 mmol) was added and the reaction mixture was allowed to stir at rt for 45 min. Water (0.340 mL) was added, followed by 3H-1,2-benzodithiol-3-one 1,1-dioxide (131 mg, 0.647 mmol) then stirring was continued at rt for 30 min. An additional portion of 3H-1,2-benzodithiol-3-one 1,1-dioxide (32.0 mg, 0.158 mmol) was added and stirring was continued for an additional 30 min. Toluene was added (15 mL) and the reaction mixture was concentrated, then concentrated from toluene (2×15 mL) to provide a mixture of major and minor diastereomers. The crude mixture was purified by silica gel chromatography (0-50% MeOH in DCM) to provide the major diastereomer Intermediate 63a (430 mg, 90%) LCMS (AA): m/z=886.2 (M+H).

Step 3: 2-amino-9-[(2R,5R,7R,8R,10S,12aR,14R,15aS,16R)-16-{[tert-butyl(dimethyl) silyl]oxy}-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10S,12aR,14R,15aS,16R)-16-{[tert-butyl(dimethyl)silyl]oxy}-2,10-dioxido-14-(pyrimidin-4-ylamino)-2,10-disulfanyl-decahydro-5,8-methanocyclopenta[l][1,3,6,9,11,2,10]pentaoxadiphosphacyclotetradecin-7-yl]-1,9-dihydro-6H-purin- 6-one, or 2-amino-9-[(2R,5R,7R,8R,10R,12aR,14R,15aS,16R)-16-{[tert-butyl(dimethyl)silyl]oxy}-2,10-dioxido-14-(pyrimidin-4-ylamino)-2,10-disulfanyl-decahydro-5,8-methano cyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10R,12aR,14R,15aS,16R)-16-{[tert-butyl(dimethyl)silyl]oxy}-2,10-dioxido-14-(pyrimidin-4-ylamino)-2,10-disulfanyl-decahydro-5,8-methano cyclopenta[l][1,3,6,9,11,2,10]pentaoxadiphosphacyclotetradecin-7-yl]-1,9-dihydro-6H-purin-6-one, Intermediate 64a Intermediate 63a (430 mg, 0.485 mmol) was dissolved in methylamine (33% in EtOH, 14.6 mL) under an atmosphere of nitrogen and the reaction mixture was allowed to stir at rt for 1.5 h. The reaction mixture was concentrated and dried on vacuum for 10 min. The crude compound was purified by silica gel chromatography (0-60% MeOH in DCM) to provide Intermediate 64a (145 mg, 39%). LCMS (AA): m/z=763.2 (M+H).

Step 4: 2-amino-9-[(2R,5R,7R,8R,10S,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8R,10S,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10] pentaoxadiphosphacyclotetradecin-7-yl]-1,9-dihydro-6H-purin-6-one, or 2-amino-9-[(2R,5R,7R,8R,10R,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10] pentaoxadiphosphacyclotetradecin-7-yl]-1,9-dihydro-6H-purin-6-one, or 2-amino-9-[(2S,5R,7R,8R,10R,12aR,14R,15aS, 16R)-16-hydroxy-2,10-dioxido-14-(pyrimidin-4-ylamino)-2,10-disulfanyldecahydro-5,8-methanocyclopenta[l][1,3,6,9,11,2,10] pentaoxadiphosphacyclotetradecin-7-yl]-1,9-dihydro-6H-purin-6-one, I-2a In a polypropylene tube, Intermediate 64a (131 mg, 0.172 mmol) was suspended in pyridine (0.858 mL). Triethylamine trihydrofluoride (0.143 mL, 0.8587 mmol) was added, followed by TEA (2.14 mL). The reaction mixture was allowed to stir at 50° C. for 4 h. The reaction mixture was cooled to rt and water (3.21 mL) was added followed by dropwise addition of a solution of calcium chloride (199 mg, 1.72 mmol) in water (3.21 mL). The reaction mixture was allowed to stir at rt for 90 min, then filtered through Celite and the Celite was rinsed with water (5×5 mL). The filtrate was concentrated to give a white solid. No HF was observed by $^{19}$F NMR. The crude mixture was purified by reverse phase flash column chromatography (0-12% ACN in aqueous triethylammonium acetate (10 mM)) to provide I-2a (75 mg, 51%) as the N,N-diethylethanamine salt. LCMS (FA): m/z=649.1 (M+H). $^1$H NMR (D$_2$O) δ 8.50 (s, 1H), 8.02 (s, 1H), 7.94-8.01 (m, 1H), 6.55 (br s, 1H), 6.02 (d, J=8.4 Hz, 1H), 5.55 (ddd, J=10.5, 8.4, 4.2 Hz, 1H), 4.98 (quin, J=7.0 Hz, 1H), 4.68 (d, J=4.0 Hz, 1H), 4.43-4.52 (m, 2H), 4.40 (ddd, J=12.0, 7.9, 2.9 Hz, 1H), 4.13 (ddd, J=11.9, 3.2, 1.3 Hz, 1H), 4.00 (ddd, J=10.1, 3.7, 2.1 Hz, 1H), 3.85-3.94 (m, 1H), 3.20 (q, J=7.3 Hz, 10H), 2.40-2.54 (m, 2H), 2.23-2.35 (m, 2H), 1.44 (s, 1H), 1.28 (t, J=7.3 Hz, 15H). $^{31}$P NMR (D$_2$O) δ 51.83 (s, 1P), 50.55 (s, 1P).

Step 5: I-2a sodium salt (ML960450)

The title compound was prepared from I-2a following the procedure described in Example 16, Step 5. LCMS (AA): m/z=649.2. $^1$H NMR (D$_2$O) δ 8.46 (s, 1H), 8.03-7.95 (m, 2H), 6.50 (br s, 1H), 6.01 (d, J=8.4 Hz, 1H), 5.55 (ddd, J=4.1, 8.4, 10.5 Hz, 1H), 5.02-4.94 (m, 1H), 4.68 (d, J=4.0 Hz, 1H), 4.49-4.46 (m, 1H), 4.43-4.35 (m, 2H), 4.12 (ddd, J=1.3, 3.1, 11.9 Hz, 1H), 4.03-3.97 (m, 1H), 3.90 (td, J=5.3, 10.5 Hz, 1H), 2.53-2.41 (m, 2H), 2.36-2.21 (m, 2H), 1.48-1.37 (m, 1H); $^{31}$P NMR (D$_2$O) δ 53.93 (s, 1P), 52.65 (s, 1P).

Example 31A

The compound listed below (I-2b) was prepared as described in Example 31 starting with Step 2, substituting the starting material shown in the table (Intermediate 62b) for Intermediate 62a.

| Compound | Salt form | Starting material | LCMS data | NMR data |
| --- | --- | --- | --- | --- |
| I-2b | Et$_3$N | Intermediate 62b | LCMS (FA): m/z = 649.2 (M + H). | $^1$H NMR (D$_2$O) δ 8.43 (s, 1H), 8.00 (s, 1H), 7.91 (br d, J = 5.9 Hz, 1H), 6.57 (br d, J = 6.1 Hz, 1H), 5.98 (d, J = 8.4 Hz, 1H), 5.54 (ddd, J = 12.1, 8.2, 3.9 Hz, 1H), 4.97-5.09 (m, 1H), 4.57 (d, J = 4.2 Hz, 1H), 4.43 (br q, J = 1.2 Hz, 1H), 4.30-4.41 (m, 2H), 4.09 (dt, J = 11.6, 2.5 Hz, 1H), 3.85-3.98 (m, 2H), 3.16 (q, J = 7.3 Hz, 14H), 2.39-2.54 (m, 2H), 2.24 (br s, 2H), 1.34 (br d, J = 3.7 Hz, 1H), 1.23 (t, J = 7.3 Hz, 21H); $^{31}$P NMR (D$_2$O) δ 56.48 (s, 1P), 53.93 (s, 1P). |

Example 31B

Alternative synthesis of 2-amino-9-[(2R,5R,7R,8R,
10S,12aR,14R,15aS,16R)-16-hydroxy-2,10-dioxido-
14-(pyrimidin-4-ylamino)-2,10-disulfanyldecahydro-
5,8-methanocyclopenta[l][1,3,6,9,11,2,10]
pentaoxadiphosphacyclotetradecin-7-yl]-1,9-
dihydro-6H-purin-6-one, or 2-amino-9-[(2S,5R,7R,8R,10S,12aR,14R,15aS,
16R)-16-hydroxy-2,10-dioxido-14-(pyrimidin-4-
ylamino)-2,10-disulfanyldecahydro-5,8-methanocy-
clopenta[l][1,3,6,9,11,2,10]
pentaoxadiphosphacyclotetradecin-7-yl]-1,9-
dihydro-6H-purin-6-one, or 2-amino-9-[(2R,5R,7R,8R,10R,12aR,14R,15aS,
16R)-16-hydroxy-2,10-dioxido-14-(pyrimidin-4-
ylamino)-2,10-disulfanyldecahydro-5,8-methanocy-
clopenta[l][1,3,6,9,11,2,10]
pentaoxadiphosphacyclotetradecin-7-yl]-1,9-
dihydro-6H-purin-6-one, or 2-amino-9-[(2S,5R,7R,8R,10R,12aR,14R,15aS,
16R)-16-hydroxy-2,10-dioxido-14-(pyrimidin-4-
ylamino)-2,10-disulfanyldecahydro-5,8-methanocy-
clopenta[l][1,3,6,9,11,2,10]
pentaoxadiphosphacyclotetradecin-7-yl]-1,9-
dihydro-6H-purin-6-one, I-2a

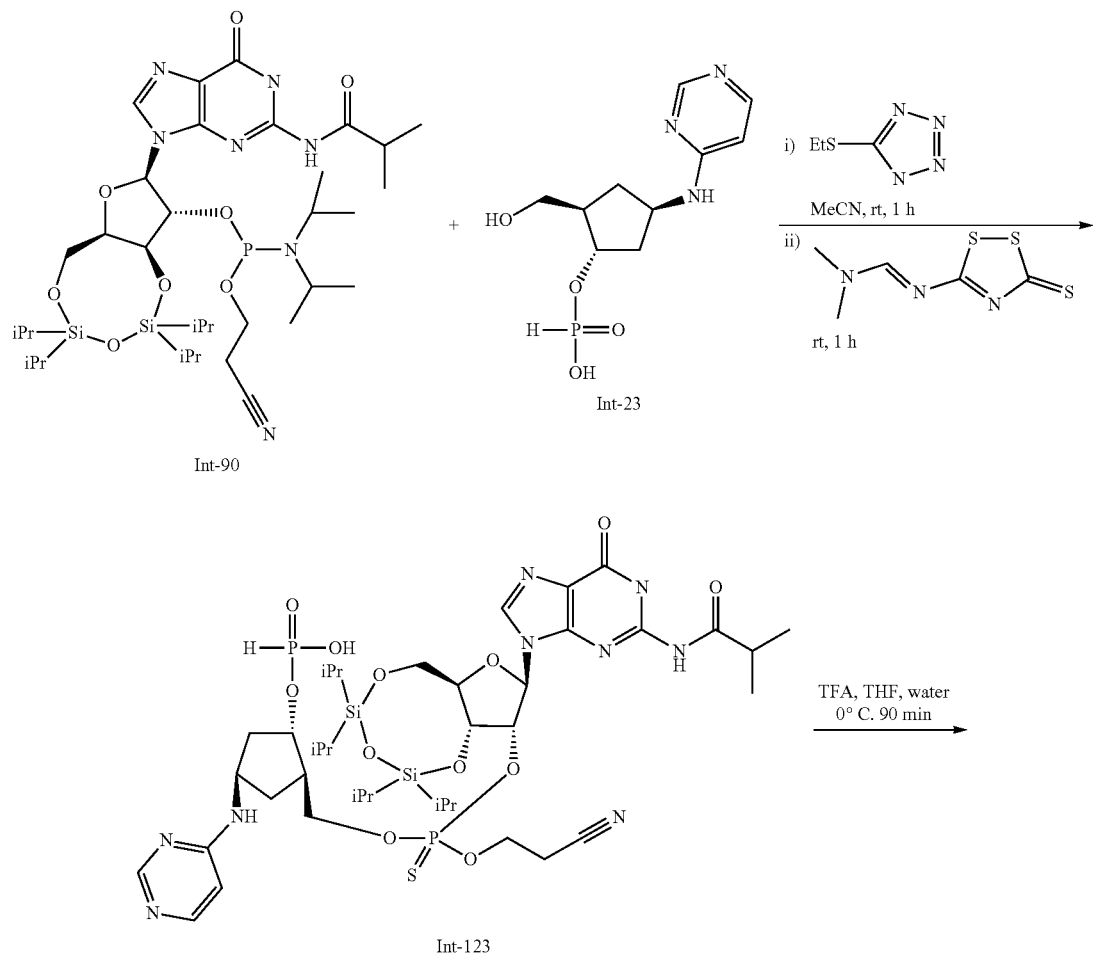

-continued
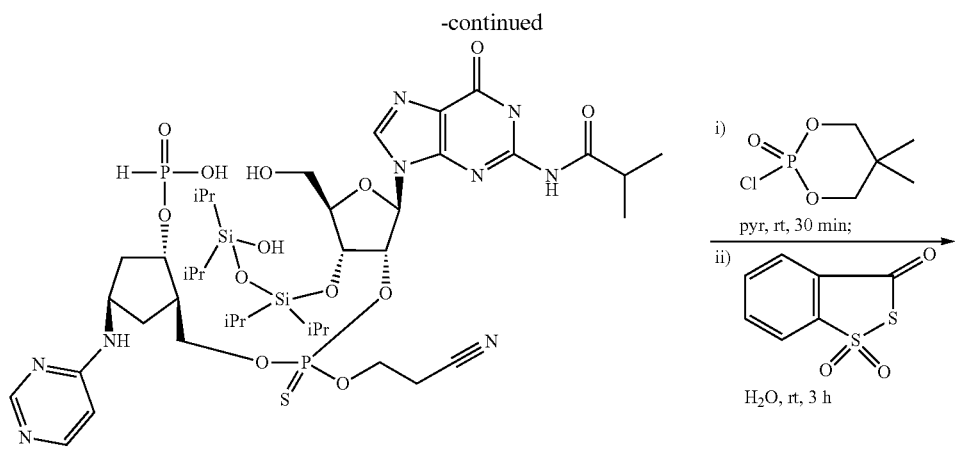
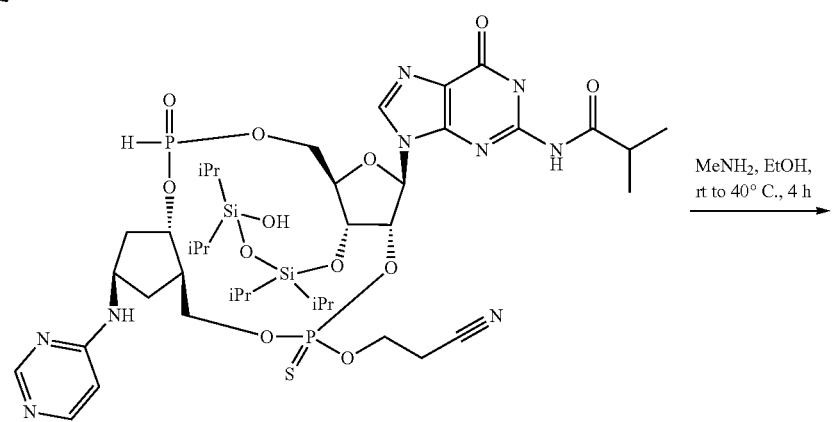
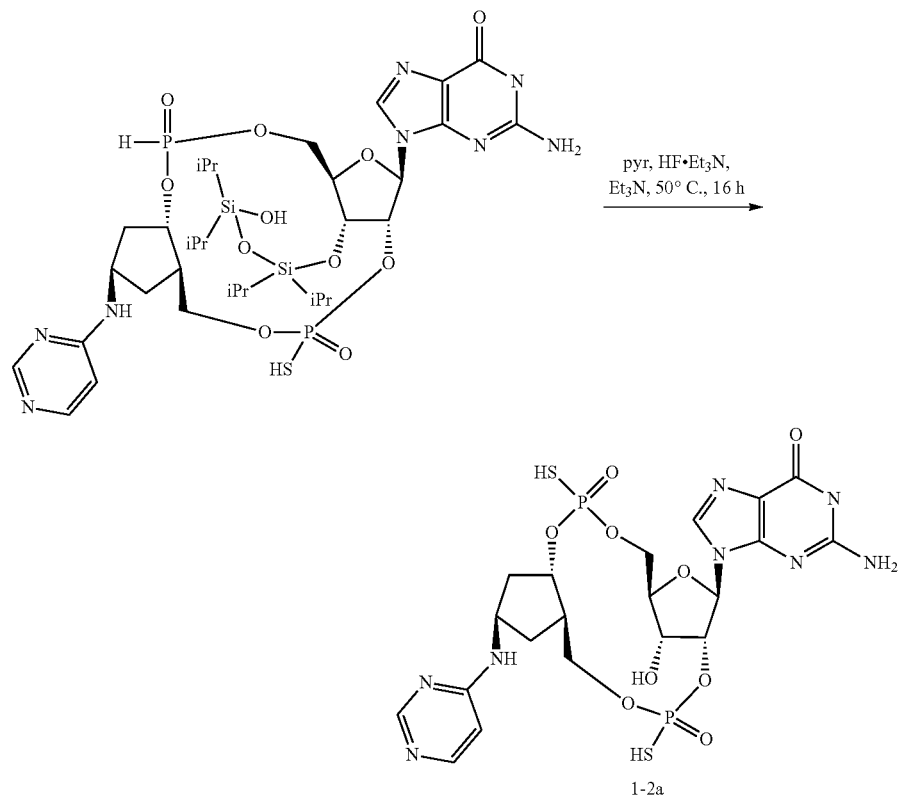

Step 1: (1S,2R,4R)-2-({[(R)-(2-cyanoethoxy) ({(6aR,8R,9R,9aR)-8-[2-(isobutyrylamino)-6-oxo-1, 6-dihydro-9H-purin-9-yl]-2,2,4,4-tetraisopropyltetra- hydro-6H-furo[3,2-f][1,3,5,2,4]trioxadisilocin-9-yl}oxy)phosphorothioyl]oxy}methyl)-4-(pyrimidin- 4-ylamino)cyclopentyl hydrogen phosphonate or (1S,2R,4R)-2-({[(S)-(2-cyanoethoxy)({(6aR,8R,9R, 9aR)-8-[2-(isobutyrylamino)-6-oxo-1,6-dihydro-9H- purin-9-yl]-2,2,4,4-tetraisopropyltetrahydro-6H-furo [3,2-f][1,3,5,2,4]trioxadisilocin-9-yl}oxy) phosphorothioyl]oxy}methyl)-4-(pyrimidin-4- ylamino)cyclopentyl hydrogen phosphonate, Intermediate 123

A mixture of Intermediate 23 (1.30 g (80% pure), 3.80 mmol) and Intermediate 90 (3.94 g, 4.95 mmol) was dissolved in dry acetonitrile and concentrated to dryness (3×6 mL). The residue was then dissolved in ACN (6.50 mL) under an atmosphere of argon. In a separate flask 5-(ethyl-thio)-1H-tetrazole (1.49 g, 11.4 mmol) was dissolved in dry acetonitrile and concentrated to dryness (3×3 mL), dissolved in ACN (3.00 mL) and added to the reaction mixture. The reaction mixture was allowed to stir at rt for 1 h.

((Dimethylamino-methylidene)amino)-3H-1,2,4-dithi- azoline-3-thione (938 mg, 4.57 mmol) was added and stirring was continued at rt for 1 h. The reaction mixture was concentrated and the residue was purified by silica gel chromatography (5-80% MeOH in DCM) to provide the title compound as a mixture of diasteromers. The mixture was further purified by silica gel chromatography (40% MeOH in DCM) to provide the desired compound as the first eluting diastereomer (2.08 g, 55%). LCMS (AA): m/z=1000.3 (M+H).

Steps 2-5: 2-amino-9-[(2R,5R,7R,8R,10S,12aR, 14R,15aS,16R)-16-hydroxy-2,10-dioxido-14-(py- rimidin-4-ylamino)-2,10-disulfanyldecahydro-5,8- methanocyclopenta[l][1,3,6,9,11,2,10] pentaoxadiphosphacyclotetradecin-7-yl]-1,9- dihydro-6H-purin-6-one, or 2-amino-9-[(2S,5R,7R,8R,10S,12aR,14R,15aS, 16R)-16-hydroxy-2,10-dioxido-14-(pyrimidin-4- ylamino)-2,10-disulfanyldecahydro-5,8-methanocy- clopenta[1][1,3,6,9,11,2,10] pentaoxadiphosphacyclotetradecin-7-yl]-1,9- dihydro-6H-purin-6-one, or 2-amino-9-[(2R,5R,7R,8R,10R,12aR,14R,15aS, 16R)-16-hydroxy-2,10-dioxido-14-(pyrimidin-4- ylamino)-2,10-disulfanyldecahydro-5,8-methanocy- clopenta[l][1,3,6,9,11,2,10] pentaoxadiphosphacyclotetradecin-7-yl]-1,9- dihydro-6H-purin-6-one, or 2-amino-9-[(2S,5R,7R,8R,10R,12aR,14R,15aS, 16R)-16-hydroxy-2,10-dioxido-14-(pyrimidin-4- ylamino)-2,10-disulfanyldecahydro-5,8-methanocy- clopenta[l][1,3,6,9,11,2,10] pentaoxadiphosphacyclotetradecin-7-yl]-1,9- dihydro-6H-purin-6-one, I-2a The title compound was prepared from Intermediate 123 following the procedures described in Example 60, steps 2-5 to provide the title compound as the N,N-diethylethanamine salt.

Example 32

(1S,2R,4R)-2-(hydroxymethyl)-4-(thiazolo[5,4-d] pyrimidin-7-ylamino)cyclopentanol, Intermediate 65

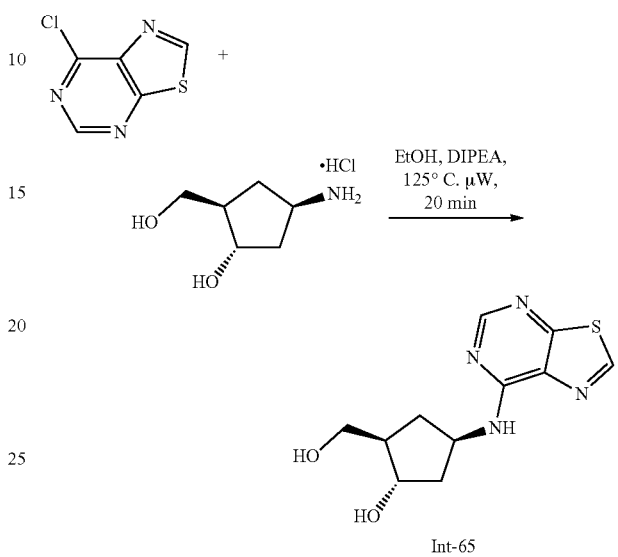

Int-65

7-Chlorothiazolo[5,4-d]pyrimidine (1.00 g, 5.54 mmol) was dissolved in EtOH (5.17 mL). DIPEA (2.30 mL, 13.2 mmol) was added, followed by (1S,2R,4R)-4-amino-2-(hy- droxymethyl)cyclopentanol hydrochloride (1.40 g, 8.40 mmol). The reaction mixture was heated under microwave irradiation at 125° C. for 20 min. The reaction mixture was concentrated and the crude compound was purified by silica gel chromatography (0-15% MeOH in DCM) to provide Intermediate 65 (1.10 g, 75%), LCMS (AA): m/z=267.0 (M+H).

Example 33

3-[[(1R,3S,4R)-3-hydroxy-4-(hydroxymethyl)cyclo- pentyl]amino]-1-methyl-pyrazin-2-one, Intermediate 67

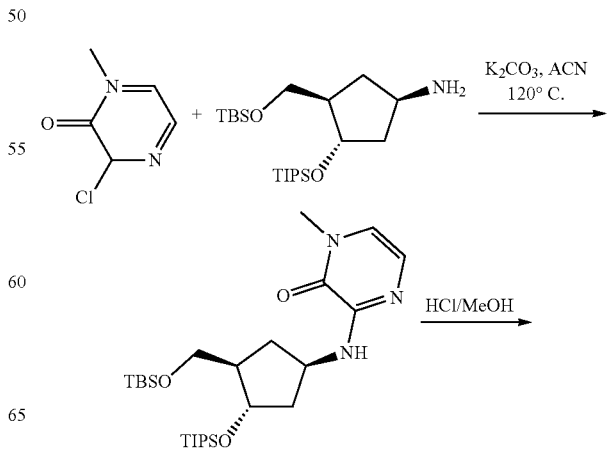

231

-continued

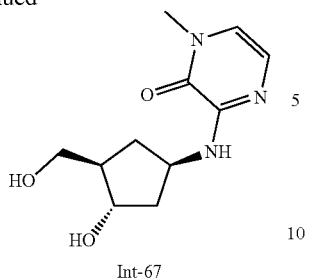

Int-67

Step 1: 3-(((1R,3R,4S)-3-((((tert-butyldimethylsilyl)oxy)methyl)-4-((triisopropylsilyl)oxy)cyclopentyl)amino)-1-methylpyrazin-2(1H)-one To a solution of (1R,3R,4S)-3-{[(tert-butyldimethylsilyl)oxy]methyl}-4-{[tris(propan-2-yl)silyl]oxy}cyclopentan-1-amine (9.60 g, 23.8 mmol) in ACN (100 mL) was added 3-chloro-1-methyl-1,2-dihydropyrazin-2-one (3.09 g, 21.4 mmol) and $K_2CO_3$ (9.86 g, 71.4 mmol) at rt. The mixture was heated at 120° C. and allowed to stir for 16 h. The reaction mixture was concentrated and the residue was purified by silica gel chromatography (10:1-5:1 PE/EtOAc) to provide the title compound (8.00 g, 66%) as colorless oil. $^1$H NMR (MeOD) δ 6.78 (d, J=4.4 Hz, 1H), 6.67 (d, J=4.4 Hz, 1H), 4.33-4.49 (m, 2H), 3.57-3.70 (m, 2H), 3.46 (s, 3H), 2.40 (dt, J=13.2, 8.1 Hz, 1H), 2.02-2.16 (m, 2H), 1.78-1.90 (m, 1H), 1.24-1.33 (m, 1H), 1.08 (s, 21H), 0.91 (s, 9H), 0.07 (s, 6H).

Step 2: 3-[[(1R,3S,4R)-3-hydroxy-4-(hydroxymethyl)cyclopentyl]amino]-1-methyl-pyrazin-2-one, Intermediate 67

To a solution of 3-(((1R,3R,4S)-3-((((tert-butyldimethylsilyl)oxy)methyl)-4-((triisopropylsilyl)oxy)cyclopentyl)amino)-1-methylpyrazin-2(1H)-one (8.00 g, 15.6 mmol) was added 4M HCl in MeOH (50 mL) at rt. The reaction mixture was concentrated and the residue was dissolved in MeOH (10 mL). The pH was adjusted to 8 by the addition of saturated $NaHCO_3$ solution. The solvents were evaporated and the residue was purified by silica gel chromatography (50:1-10:1 DCM/MeOH) to provide the title compound (3.60 g, 97%) as white solid. $^1$H NMR (MeOD) δ 6.77 (d, J=4.6 Hz, 1H), 6.67 (d, J=4.9 Hz, 1H), 4.38 (quin, J=7.4 Hz, 1H), 4.06-4.13 (m, 1H), 3.53-3.68 (m, 2H), 3.46 (s, 3H,) 2.40 (dt, J=13.2, 7.8 Hz, 1H), 1.98-2.07 (m, 2H), 1.87 (dt, J=13.6, 7.0 Hz, 1H), 1.30-1.39 (m, 1H).

Example 34

(1S,2R,4R)-2-[[bis(4-methoxyphenyl)-phenylmethoxy]methyl]-4-[(5-fluoropyrimidin-4-yl)amino]cyclopentanol, Intermediate 69

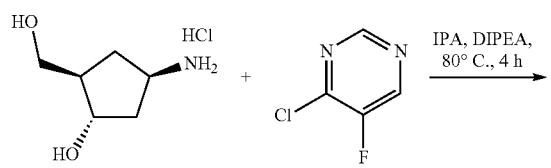

232

-continued

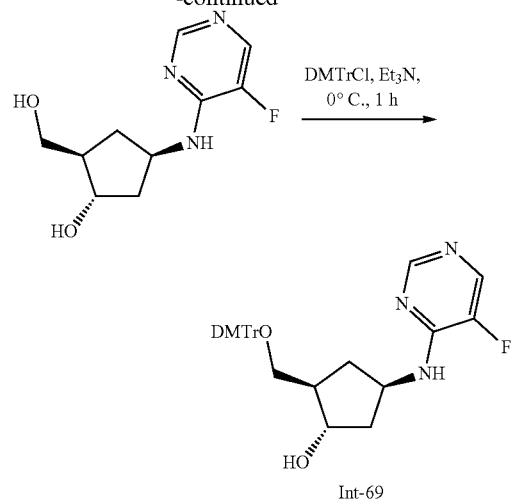

Int-69

Step 1: (1S,2R,4R)-4-[(5-fluoropyrimidin-4-yl)amino]-2-(hydroxymethyl)cyclopentanol A mixture of (1S,2R,4R)-4-amino-2-(hydroxymethyl)cyclopentanol hydrochloride (5.1 g, 24.0 mmol), 4-chloro-5-fluoropyrimidine (4.77 g, 36.0 mmol) and DIEA (9.30, 72.0 mmol) in IPA (100 mL) was heated at 80° C. for 4 h. The mixture was concentrated and the crude compound was purified by silica gel chromatography (4-10% MeOH in DCM) to provide (1S,2R,4R)-4-[(5-fluoropyrimidin-4-yl)amino]-2-(hydroxymethyl)cyclopentanol (2.55 g, 48%). $^1$H NMR (DMSO-$d_6$) δ 8.24 (d, J=3.1 Hz, 1H), 8.06 (d, J=4.2 Hz, 1H), 7.53 (br d, J=7.5 Hz, 1H), 4.44-4.66 (m, 3H), 3.84-3.97 (m, 1H), 3.37-3.47 (m, 1H), 3.28-3.33 (m, 1H), 2.15 (dt, J=13.1, 7.7 Hz, 1H), 1.65-1.89 (m, 3H) 1.23 (dt, J=12.84, 8.7 Hz, 1H).

Step 2: (1S,2R,4R)-2-[[bis(4-methoxyphenyl)-phenyl-methoxy]methyl]-4-[(5-fluoropyrimidin-4-yl)amino]cyclopentanol, Intermediate 69

A mixture of (1S,2R,4R)-4-[(5-fluoropyrimidin-4-yl)amino]-2-(hydroxymethyl)cyclopentanol (2.50 g, 11.0 mol) and TEA (1.82 mL, 13.1 mmol) in DCM (25 mL) was added DMTrCl (3.72 g, 11.0 mmol) in DCM (5 mL) at 0° C. and the reaction mixture was allowed to stir at 0° C. for 1 h. The mixture was concentrated and the crude compound was purified by silica gel chromatography (PE/EtOAc=2:1 to 1:1) to provide (1S,2R,4R)-2-[[bis(4-methoxyphenyl)-phenyl-methoxy]methyl]-4-[(5-fluoropyrimidin-4-yl)amino]cyclopentanol (Intermediate 69) as a white solid (2.0 g, 34%). $^1$H NMR (CDCl$_3$) δ 8.31-8.46 (m, 1H), 7.99 (d, J=3.1 Hz, 1H), 7.37-7.44 (m, 2H), 7.27-7.34 (m, 6H), 7.19-7.24 (m, 1H), 6.83 (d, J=8.3 Hz, 4H), 4.94 (br d, J=7.5 Hz, 1H), 4.55-4.70 (m, 1H), 4.14-4.21 (m, 1H), 3.79 (s, 6H), 3.36 (dd, J=9.2, 5.3 Hz, 1H,) 3.06 (t, J=8.8 Hz, 1H), 2.34-2.47 (m, 2H), 2.13-2.27 (m, 2H), 1.87 (dt, J=14.0, 7.0 Hz, 1H), 1.10-1.20 (m, 1H).

Example 35

(1S,2R,4R)-2-[[bis(4-methoxyphenyl)-phenyl-methoxy]methyl]-4-[(2-methylpyrimidin-4-yl)amino]cyclopentanol, Intermediate 71

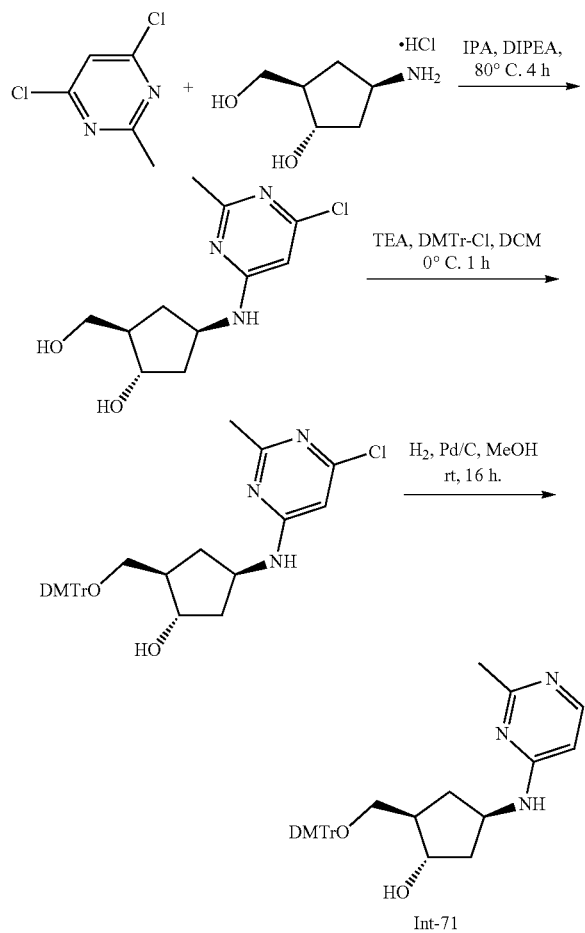

Int-71

Step 1: (1S,2R,4R)-4-((6-chloro-2-methylpyrimidin-4-yl)amino)-2-(hydroxymethyl)cyclopentan-1-ol 4,6-dichloro-2-methylpyrimidine (4.36 g, 26.8 mmol) was dissolved in IPA (100 mL). DIPEA (14.7 mL, 89.4 mmol) was added, followed by (1S,2R,4R)-4-amino-2-(hydroxymethyl)cyclopentanol hydrochloride (5.0 g, 29.8 mmol). The reaction mixture was heated at 80° C. for 4 h. The reaction mixture was concentrated and the crude compound was purified by silica gel chromatography (1:1 EtOAc/MeOH) to provide (1S,2R,4R)-4-((6-chloro-2-methylpyrimidin-4-yl)amino)-2-(hydroxymethyl)cyclopentan-1-ol (2.3 g, 30%). $^1$H NMR (MeOD) δ 6.27 (br s, 1H), 4.61 (br s, 1H), 4.00-4.12 (m, 1H), 3.45-3.67 (m, 2H), 2.28-2.46 (m, 4H), 1.93-2.10 (m, 2H), 1.67-1.84 (m, 1H), 1.14-1.34 (m, 1H).

Step 2: (1S,2R,4R)-2-((bis(4-methoxyphenyl)(phenyl)methoxy)methyl)-4-((6-chloro-2-methylpyrimidin-4-yl)amino)cyclopentan-1-ol A mixture of (1S,2R,4R)-4-((6-chloro-2-methylpyrimidin-4-yl)amino)-2-(hydroxymethyl)cyclopentan-1-ol (200 mg, 0.776 mmol) and TEA (0.129 mL, 0.931 mmol) in DCM (3 mL) was added DMTrCl (262 mg, 0.776 mmol) in DCM (1.0 mL) at 0° C. The reaction mixture was allowed to stir at 0° C. for 1 h. then the reaction mixture was combined with another reaction run on the same scale and concentrated. The residue was purified by silica gel chromatography (PE/EtOAc=2:1 to 1:1) to provide (1S,2R,4R)-2-((bis(4-methoxyphenyl)(phenyl)methoxy)methyl)-4-((6-chloro-2-methylpyrimidin-4-yl)amino)cyclopentan-1-ol (600 mg, 69%) as a white solid. $^1$H NMR (CDCl$_3$) δ 7.37-7.43 (m, 2H), 7.20-7.33 (m, 8H), 6.80-6.88 (m, 4H), 6.02 (br s, 1H), 5.07 (br s, 1H), 4.17 (br d, J=5.3 Hz, 1H), 3.79 (s, 6H), 3.36 (br dd, J=8.8, 4.82 Hz, 1H), 3.06 (t, J=8.3 Hz, 1H), 2.43 (s, 3H), 2.30-2.40 (m, 2H), 2.05-2.22 (m, 2H), 1.84 (dt, J=13.5, 6.6 Hz, 1H), 1.07-1.17 (m, 1H).

Step 3: (1S,2R,4R)-2-[[bis(4-methoxyphenyl)-phenyl-methoxy]methyl]-4-[(2-methylpyrimidin-4-yl)amino]cyclopentanol, Intermediate 71

(1S,2R,4R)-2-((bis(4-methoxyphenyl)(phenyl)methoxy)methyl)-4-((6-chloro-2-methylpyrimidin-4-yl)amino)cyclopentan-1-ol (3.00 g, 5.35 mmol) was dissolved a mixture of DIEA (1.76 g, 10.7 mmol) and EtOAc (50 mL). Pd/C (1.26 g) was added to the solution. A balloon of hydrogen was attached and the reaction mixture was allowed to stir at rt for 16 h. The reaction mixture was filtered and the filtrate was washed with water (50 mL×3), and concentrated. The residue was purified by silica gel chromatography (EtOAc) to provide (1S,2R,4R)-2-[[bis(4-methoxyphenyl)-phenyl-methoxy]methyl]-4-[(2-methylpyrimidin-4-yl)amino]cyclopentanol Intermediate 71 (2.2 g, 78%) as white foamy solid. $^1$H NMR (CDCl$_3$) δ 8.08 (br d, J=5.7 Hz, 1H), 7.40 (d, J=7.5 Hz, 2H), 7.27-7.33 (m, 6H), 7.19-7.25 (m, 1H), 6.78-6.90 (m, 4H), 6.05 (br d, J=5.7 Hz, 1H), 4.89 (br d, J=5.7 Hz, 1H), 4.08-4.27 (m, 2H), 3.79 (s, 6H), 3.34 (dd, J=9.0, 5.0 Hz, 1H), 3.05 (t, J=8.6 Hz, 1H), 2.33-2.45 (m, 1H), 2.45 (s, 3H), 2.28-2.40 (m, 1H), 2.06-2.23 (m, 2H), 1.83 (dt, J=13.6, 6.8 Hz, 1H), 1.07-1.17 (m, 1H).

Example 36

(1S,2S,4R)-2-[[bis(4-methoxyphenyl)-phenyl-methoxy]methyl]-4-(pyrazolo[1,5-a][1,3,5]triazin-4-ylamino)cyclopentanol, Intermediate 73

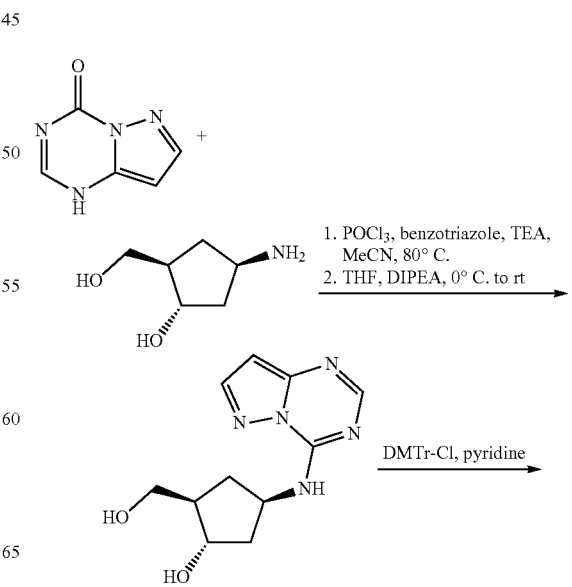

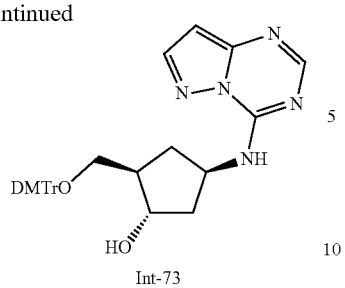

Int-73

Step 1: (1S,2R,4R)-2-(hydroxymethyl)-4-(pyrazolo [1,5-a][1,3,5]triazin-4-ylamino)cyclopentan-1-ol 1H, 4H-pyrazolo[1,5-a][1,3,5]triazin-4-one (1.30 g, 9.25 mmol) and benzotriazole (2.76 g, 23.1 mmol) were combined and suspended in ACN (13.0 mL). TEA (3.87 mL, 27.8 mmol) was then added followed by dropwise addition of phosphoryl chloride (1.29 mL, 13.9 mmol). The reaction mixture was heated at 80° C. for 6 h, cooled to rt and the solvents were evaporated. The residue was dissolved in THF (95 mL) and cooled to 0° C. (1S,2R,4R)-4-amino-2-(hydroxymethyl)cyclopentanol (1.21 g, 9.25 mmol) and DIPEA (10.8 mL, 62.0 mmol) were added and the reaction mixture was allowed to stir at rt overnight. The solvents were evaporated and the crude compound was purified by silica gel chromatography (0-15% MeOH in EtOAc) followed by further purification by silica gel chromatography (0-20% MeOH in DCM) to provide (1S,2R,4R)-2-(hydroxymethyl)-4-(pyrazolo[1,5-a][1,3,5]triazin-4-ylamino)cyclopentan-1-ol (375 mg, 16%). LCMS (FA): m/z=250.1 (M+H).

Step 2: (1S,2S,4R)-2-[[bis(4-methoxyphenyl)-phenyl-methoxy]methyl]-4-(pyrazolo[1,5-a][1,3,5]triazin-4-ylamino)cyclopentanol, Intermediate 73

(1S,2R,4R)-2-(hydroxymethyl)-4-(pyrazolo[1,5-a][1,3,5]triazin-4-ylamino)cyclopentan-1-ol (580 mg, 2.33 mmol) was concentrated from dry pyridine (3×20 mL). Pyridine (19.4 mL) was added and the reaction mixture was cooled to 0° C. DMTr-Cl (756 mg, 2.21 mmol) was added portionwise and the reaction mixture was allowed to stir at 0° C. for 20 min, then at rt overnight. Methanol (10 mL) was added and the reaction mixture was allowed to stir for 10 min. The solvents were evaporated and the crude compound was purified by silica gel chromatography (0-6% MeOH in DCM) to provide (1S,2S,4R)-2-[[bis(4-methoxyphenyl)-phenyl-methoxy]methyl]-4-(pyrazolo[1,5-a][1,3,5]triazin-4-ylamino)cyclopentanol, (827 mg, 64%). LCMS (FA): m/z=550.2 (M−H).

Example 37

(1S,2R,4R)-2-[[bis(4-methoxyphenyl)-phenyl-methoxy]methyl]-4-[methyl(1,3,5-triazin-2-yl)amino]cyclopentanol, Intermediate 76

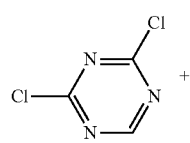

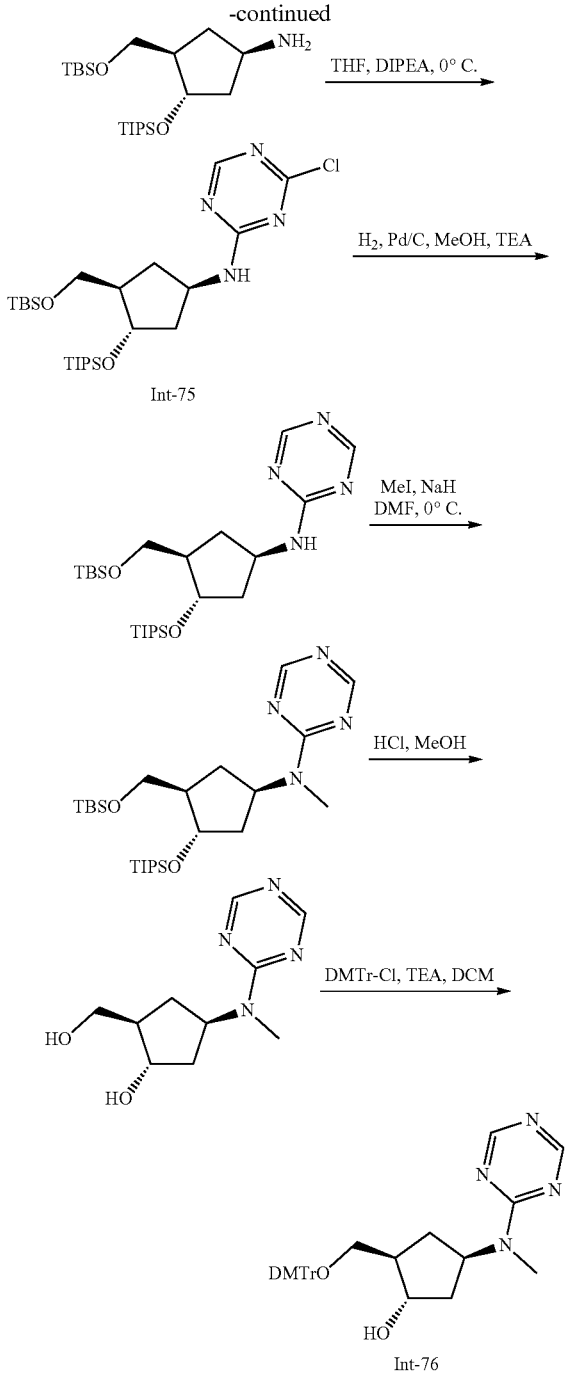

Step 1: N-((1R,3R,4S)-3-(((tert-butyldimethylsilyl)oxy)methyl)-4-((triisopropylsilyl)oxy)cyclopentyl)-4-chloro-1,3,5-triazin-2-amine, Intermediate 75

A solution of 2,4-dichloro-1,3,5-triazine (9.68 g, 64.6 mmol) and DIPEA (12.8 g, 99.4 mmol) in THF (200 mL) was cooled to 0° C. and (1R,3R,4S)-3-{[(tert-butyldimethylsilyl)oxy]methyl}-4-{[tris(propan-2-yl)silyl]oxy}cyclopentan-1-amine (20.0 g, 49.7 mmol) in THF (200 mL) was added slowly. The mixture was allowed to stir at 0° C. for 1 h. The reaction mixture was diluted with water (500 mL) and extracted with DCM (100 mL×3), then washed with brine, dried and evaporated. The residue was purified by silica gel chromatography (PE/EtOAc=20:1 to 15:1) to provide the title compound (11.7 g, 45.7%) as a yellow oil. $^1$H NMR (CDCl$_3$) δ 8.10-8.36 (m, 1H), 5.89-6.18 (m, 1H), 4.37-4.55 (m, 1H), 4.24 (quin, J=4.7 Hz, 1H), 3.46-3.71 (m, 2H), 2.24-2.39 (m, 1H), 2.00-2.10 (m, 1H), 1.89-2.00 (m, 1H), 1.70 (dq, J=12.6, 6.1 Hz, 1H), 1.21-1.31 (m, 1H), 0.96 (m, 21H), 0.82 (s, 9H), −0.02-0.03 (m, 6H).

Step 2: N-((1R,3R,4S)-3-(((tert-butyldimethylsilyl)oxy)methyl)-4-((triisopropylsilyl)oxy)cyclopentyl)-1,3,5-triazin-2-amine N-((1R,3R,4S)-3-(((tert-butyldimethylsilyl)oxy)methyl)-4-((triisopropylsilyl)oxy)cyclopentyl)-4-chloro-1,3,5-triazin-2-amine (11.7 g, 22.7 mmol) and TEA (4.59 g, 45.4 mmol) was dissolved in MeOH (120 mL) and 10 wt. % Pd/C (4.82 g, 4.54 mmol) was added. The mixture was stirred under H$_2$ (15 psi) at rt for 1 h. The reaction mixture was filtered, and the filtrate was concentrated. The residue was purified by silica gel chromatography (DCM:MeOH=100:1 to 50:1) to provide the title compound (8.0 g, 73.3%), as colorless oil. $^1$H NMR (CDCl$_3$) δ 8.56 (s, 1H), 8.45 (s, 1H), 5.82 (br d, J=7.5 Hz, 1H), 4.48-4.62 (m, 1H), 4.33 (q, J=4.7 Hz, 1H), 3.68-3.76 (m, 1H), 3.59 (dd, J=10.3, 4.5 Hz, 1H,) 2.41 (dt, J=13.2, 8.5 Hz, 1H), 2.01-2.20 (m, 2H), 1.78 (dt, J=12.9, 6.34 Hz, 1H), 1.33 (dt, J=13.3, 6.5 Hz, 1H), 1.02-1.08 (m, 21H), 0.90-0.95 (m, 9H), 0.09 (m, 6H).

Step 3: N-((1R,3R,4S)-3-(((tert-butyldimethylsilyl)oxy)methyl)-4-((triisopropylsilyl)oxy)cyclopentyl)-N-methyl-1,3,5-triazin-2-amine To a solution of N-((1R,3R,4S)-3-(((tert-butyldimethylsilyl)oxy)methyl)-4-((triisopropylsilyl)oxy)cyclopentyl)-1,3,5-triazin-2-amine (8.0 g, 16.6 mmol) in DMF (80 ml) was added 60% NaH (995 mg, 24.9 mmol) in portions at 0° C. The reaction mixture was allowed to stir at 0° C. for 30 min. MeI (0.925 mL, 14.9 mmol) was added at 0° C., then the reaction mixture was allowed to stir at 0° C. for 20 min. Ice-cooled water (100 mL) was added and the reaction mixture was extracted with EtOAc (3×100 mL). The combined organic phases were washed with brine (100 mL×4), dried over Na$_2$SO$_4$ and evaporated. The residue was purified by silica gel chromatography (0-10% EtOAc/PE) provide the title compound (7.0 g, 85%) as colorless oil. $^1$H NMR (CDCl$_3$) δ 8.50 (br d, J=3.5 Hz, 2H), 5.48 (quin, J=8.9 Hz, 1H), 4.25-4.35 (m, 1H), 3.54-3.74 (m, 2H), 3.00 (s, 3H), 1.97-2.13 (m, 2H), 1.79-1.94 (m, 2H), 1.47-1.57 (m, 1H), 1.04-1.09 (m, 21H), 0.88 (s, 9H), 0.04 (s, 6H).

Step 4: (1S,2R,4R)-2-(hydroxymethyl)-4-(methyl(1,3,5-triazin-2-yl)amino)cyclopentan-1-ol A solution of N-((1R,3R,4S)-3-(((tert-butyldimethylsilyl)oxy)methyl)-4-((triisopropylsilyl)oxy)cyclopentyl)-N-methyl-1,3,5-triazin-2-amine (7.0 g, 14.1 mmol) in 4 M HCl/methanol (100 ml) was stirred at rt for 16 h. under an atmosphere of nitrogen. The reaction mixture was concentrated and residue was purified by silica gel chromatography eluting with (EtOAc/MeOH=100/1 to 10:1) to provide the title compound (2.05 g, 64.8%) as colorless oil. $^1$H NMR (DMSO-d$_6$) δ 8.52 (s, 2H), 5.25-5.40 (m, 1H), 4.65 (d, J=4.2 Hz, 1H), 4.55 (t, J=5.2 Hz, 1H), 3.92 (dq, J=6.8, 3.4 Hz, 1H), 3.34-3.49 (m, 2H), 2.93 (s, 3H), 1.78-1.93 (m, 3H), 1.55-1.67 (m, 1H), 1.36 (m, 1H).

Step 5: (1S,2R,4R)-2-[[bis(4-methoxyphenyl)-phenyl-methoxy]methyl]-4-[methyl(1,3,5-triazin-2-yl)amino]cyclopentanol, Intermediate 76

To a solution of (1S,2R,4R)-2-(hydroxymethyl)-4-(methyl(1,3,5-triazin-2-yl)amino)cyclopentan-1-ol (2.0 g, 8.91 mmol) and TEA (1.34 g, 13.3 mmol) in DCM (100 mL) was added DMTr-Cl (3.89 g, 11.5 mmol). The reaction mixture was allowed to stir at rt for 16 h. The reaction mixture was concentrated. The crude residue was purified by flash column chromatography eluting with 20% to 60% EtOAc/PE to provide the title compound (combined with another batch of the same scale, 2.0 g, 21%) as yellow solid. $^1$H NMR (CDCl$_3$) δ 8.50 (br s, 2H), 7.37-7.44 (m, 2H), 7.27-7.34 (m, 6H), 7.19-7.25 (m, 1H), 6.84 (d, J=8.3 Hz, 4H), 5.41-5.52 (m, 1H), 4.09-4.17 (m, 1H), 3.80 (s, 6H), 3.38 (dd, J=9.00, 5.0 Hz, 1H), 3.09 (t, J=8.6 Hz, 1H), 2.96 (s, 3H), 2.55 (br d, J=4.0 Hz, 1H), 2.13-2.24 (m, 1H), 1.89-2.09 (m, 3H), 1.29-1.40 (m, 1H).

Example 38

(1S,2R,4R)-2-[[bis(4-methoxyphenyl)-phenyl-methoxy]methyl]-4-(1,3,5-triazin-2-ylamino)cyclopentanol, Intermediate 78

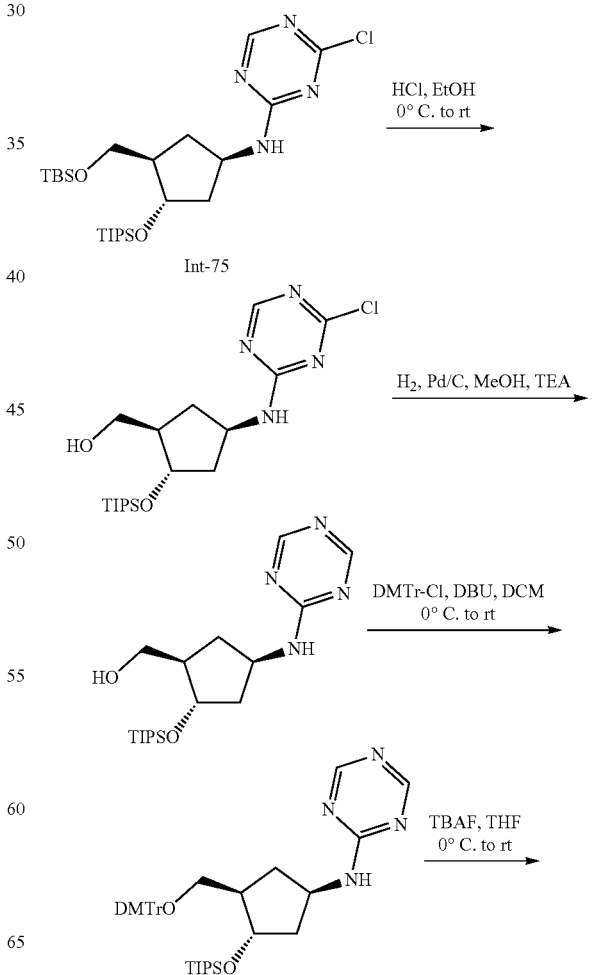

239

-continued

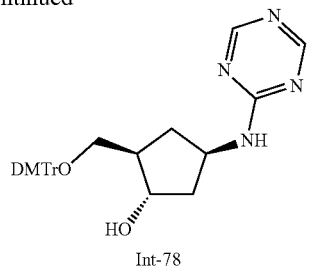

Int-78

Step 1: [(1R,2S,4R)-4-[(4-chloro-1,3,5-triazin-2-yl)amino]-2-triisopropylsilyloxy-cyclopentyl]methanol Intermediate 75 (4.50 g, 8.73 mmol) was dissolved in ethanol (45 mL) and the reaction mixture was cooled to 0° C. A solution of HCl (12 M, 1 mL) in ethanol (15 mL) was added and the reaction mixture was allowed to stir at rt for 1 h. TEA (6 mL) was added and the solvents were evaporated. The crude compound was purified by silica gel chromatography (10-50% EtOAc/PE to provide [(1R,2S,4R)-4-[(4-chloro-1,3,5-triazin-2-yl)amino]-2-triisopropylsilyloxy-cyclopentyl]methanol (3.30 g, 94%). $^1$H NMR CDCl$_3$) δ 8.44-8.25 (m, 1H), 6.22 (br d, J=7.1 Hz, 1H), 4.64-4.53 (m, 1H), 4.41-4.33 (m, 1H), 3.83-3.66 (m, 2H), 2.52-2.41 (m, 1H), 2.24-2.16 (m, 1H), 2.14-2.03 (m, 1H), 1.93-1.82 (m, 1H), 1.72 (br s, 1H), 1.44-1.35 (m, 1H), 1.30-1.23 (m, 1H), 1.12-1.02 (m, 18H).

Step 2: [(1R,2S,4R)-4-(1,3,5-triazin-2-ylamino)-2-triisopropylsilyloxy-cyclopentyl]methanol

[(1R,2S,4R)-4-[(4-chloro-1,3,5-triazin-2-yl)amino]-2-triisopropylsilyloxy-cyclopentyl]methanol (3.30 g, 8.22 mmol) was dissolved in methanol (15 mL) and TEA (997 mg, 9.86 mmol). 10% Palladium on carbon (84 mg, 0.822 mmol) was added and the reaction mixture was stirred under hydrogen (15 psi) at rt for 1 h. The reaction mixture was filtered and the filtrate was evaporated. The crude compound was purified by silica gel chromatography (20:1 to 2:1 EtOAc/PE) to provide [(1R,2S,4R)-4-(1,3,5-triazin-2-ylamino)-2-triisopropylsilyloxy-cyclopentyl]methanol (3.00 g, 95%). $^1$H NMR (CDCl$_3$) δ 8.58 (s, 1H), 8.46 (s, 1H), 5.93 (br d, J=7.7 Hz, 1H), 4.56 (qd, J=7.0, 14.0 Hz, 1H), 4.36 (q, J=5.5 Hz, 1H), 3.81-3.67 (m, 2H), 2.47 (td, J=8.5, 13.5 Hz, 1H), 2.23-2.14 (m, 1H), 2.14-2.05 (m, 1H), 1.92-1.84 (m, 1H), 1.79 (t, J=4.2 Hz, 1H), 1.59 (s, 2H), 1.36 (td, J=6.6, 13.4 Hz, 1H), 1.07 (s, 18H).

Step 3 and 4: (1S,2R,4R)-2-[[bis(4-methoxyphenyl)-phenyl-methoxy]methyl]-4-(1,3,5-triazin-2-ylamino)cyclopentanol, Intermediate 78

The title compound was prepared from [(1R,2S,4R)-4-(1,3,5-triazin-2-ylamino)-2-triisopropylsilyloxy-cyclopentyl]methanol following the procedures described in Example 6, steps 2 and 3. $^1$H NMR (CDCl$_3$) δ 8.56 (s, 1H), 8.45 (s, 1H), 7.35-7.45 (m, 2H), 7.27-7.33 (m, 6H), 7.18-7.25 (m, 1H), 6.83 (d, J 8.8 Hz, 4H), 5.40 (br d, J 7.5 Hz, 1H), 4.48-4.57 (m, 1H), 4.14 (q, J 6.4 Hz, 1H), 3.79 (s, 6H), 3.34 (dd, J 9.0, 5.0 Hz, 1H), 3.05 (t, J 8.6 Hz, 1H), 2.32-2.42 (m, 2H), 2.10-2.24 (m, 2H), 1.84 (dt, J=13.7, 7.0 Hz, 1H), 1.08-1.17 (m, 1H).

240

Example 38A

The compound listed below was prepared as described in Example 38 following Steps 1, 3, and 4, substituting the starting material shown in the table for Intermediate 75.

| Starting material | Intermediate |
|---|---|
| Int-156 | Int-157 |

Example 39

2-amino-9-[(5R,7R,8R,10S,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(5R,7R,8R,10R,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, I-19a, I-19b

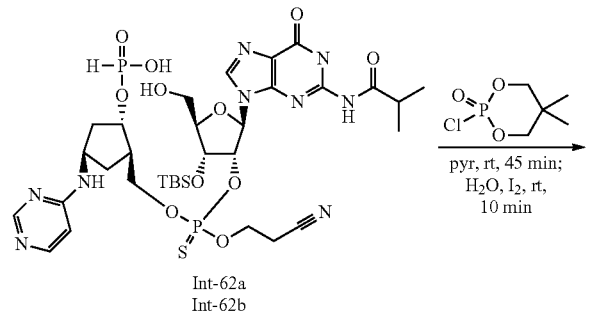

Int-62a
Int-62b

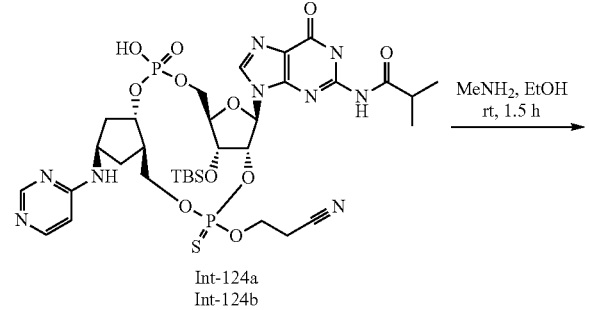

Int-124a
Int-124b

241

-continued

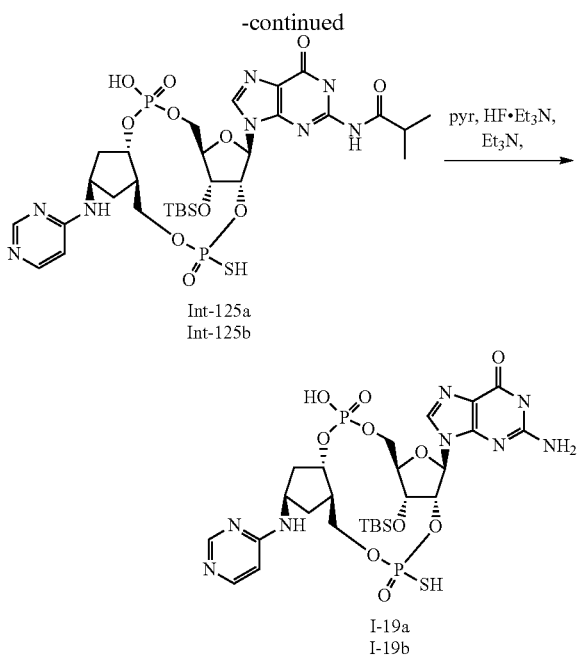

Int-125a
Int-125b

Step 1: N-{9-[(5R,7R,8R,10R,12aR,14R,15aS,16R)-16-{[tert-butyl(dimethyl)silyl]oxy}-10-(2-cyanoethoxy)-2-hydroxy-2-oxido-14-(pyrimidin-4-ylamino)-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, or N-{9-[(5R,7R,8R,10S,12aR,14R,15aS,16R)-16-{[tert-butyl(dimethyl)silyl]oxy}-10-(2-cyanoethoxy)-2-hydroxy-2-oxido-14-(pyrimidin-4-ylamino)-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 124a and Intermediate 124b Intermediate 62a (120 mg, 0.138 mmol) was dissolved in dry acetonitrile and concentrated to dryness (3×10 mL), dried under vacuum for 10 min and dissolved in pyridine (5.00 mL) under an atmosphere of argon. 2-Chloro-5,5-dimethyl-1,3,2-dioxaphosphorinane 2-oxide (92.6 mg, 0.482 mmol) was added and the reaction mixture was allowed to stir for 45 min. Water (0.087 mL, 4.82 mmol) and iodine (45.5 mg, 0.180 mmol) were added and stirring was continued at rt for 10 min. Sodium thiosulfate (29.2 mg, 0.179 mmol) in water (0.5 mL) was added and stirring was continued at rt for 15 min. Toluene (15 mL) was added and the reaction mixture was concentrated. The residue was concentrated from toluene (15 mL) and then dried under vacuum for 15 min. The crude compound was purified by silica gel chromatography (0-100% MeOH in DCM) to provide Intermediate 124a (90 mg, 75%). LCMS (AA): m/z=870.3 (M+H).

Intermediate 62b (125 mg, 0.143 mmol) was dissolved in dry acetonitrile and concentrated to dryness (3×10 mL), dried under vacuum for 10 min and dissolved in pyridine (5.00 mL) under an atmosphere of argon. 2-Chloro-5,5-dimethyl-1,3,2-dioxaphosphorinane 2-oxide (96.5 mg,

242

0.502 mmol) was added and the reaction mixture was allowed to stir for 45 min. Water (0.0904 mL, 5.02 mmol) and iodine (47.4 mg, 0.186 mmol) were added and stirring was continued at rt for 10 min. Sodium thiosulfate (30.4 mg, 0.186 mmol) in water (0.5 mL) was added and stirring was continued at rt for 15 min. Toluene (15 mL) was added and the reaction mixture was concentrated. The residue was concentrated from toluene (15 mL) and then dried on vacuum for 15 min. The crude compound was purified by silica gel chromatography (0-80% MeOH in DCM) to provide Intermediate 124b (82 mg, 66%). LCMS (AA): m/z=870.3 (M+H).

Step 2: 2-amino-9-[(5R,7R,8R,10S,12aR,14R,15aS,16R)-16-{[tert-butyl (dimethyl)silyl]oxy}-2-hydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(5R,7R,8R,10R,12aR,14R,15aS,16R)-16-{[tert-butyl(dimethyl)silyl]oxy}-2-hydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, Intermediate 125a or Intermediate 125b Intermediate 124a (90 mg, 0.1035 mmol) was dissolved in methylamine (33% in EtOH, 3.10 mL, 24.9 mmol) the reaction mixture was allowed to stir at rt for 1.5 h. The reaction mixture was concentrated and dried on vacuum for 10 min. The crude compound was purified by silica gel chromatography (0-60% MeOH in DCM) to provide Intermediate 125a (62 mg, 80%). LCMS (AA): m/z=747.2 (M+H).

Intermediate 124b (80 mg, 0.0920 mmol) was dissolved in methylamine (33% in EtOH, 2.76 mL, 22.2 mmol) the reaction mixture was allowed to stir at rt for 1.5 h. The reaction mixture was concentrated and dried on vacuum for 10 min. The crude compound was purified by silica gel chromatography (0-60% MeOH in DCM) to provide Intermediate 125b (60 mg, 87%). LCMS (AA): m/z=747.2 (M+H).

Step 3: 2-amino-9-[(5R,7R,8R,10S,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(5R,7R,8R,10R,12aR,14R,15aS,16R)-2,16-dihydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, I-19a or I-19b In a polypropylene tube Intermediate 125a (60 mg, 0.0804 mmol) was dissolved in pyridine (0.402 mL, 4.97 mmol) and triethylamine trihydrofluoride (0.0668 mL, 0.402 mmol) was added, followed by TEA (1.00 mL, 7.10 mmol). The reaction mixture was sealed and allowed to stir at rt overnight. Diluted the reaction mixture with water (2.0 mL). Then added CaCl$_2$ (111 mg, 0.964 mmol) in water (2.00 mL). The cloudy white mixture was allowed to stir at rt for 1.5 h. The suspension was filtered through celite and the celite was washed with water (5×5 mL). The clear aqueous filtrate was concentrated to a solid residue and dried on vacuum for 30 min. No HF was observed by $^{19}$F NMR. The crude mixture was purified by reverse phase flash column chromatography (0-10% ACN in aq. triethylammonium acetate (10 mM)) to provide I-19a as an N,N-diethylethanamine salt (38 mg, 57%). LCMS (AA): m/z=633.2 (M+H). $^1$H NMR (D$_2$O) δ 8.49 (br s, 1H), 8.05 (s, 1H), 8.00 (br s, 1H), 6.60 (br s, 1H), 6.04 (d, J=8.3 Hz, 1H), 5.57-5.47 (m, 1H), 4.70 (d, J=4.2 Hz, 2H), 4.43 (br d, J=2.4 Hz, 2H), 4.27-4.15 (m, 2H), 4.05-3.98 (m, 1H), 3.92-3.83 (m, 1H), 3.20 (q, J=7.3 Hz, 10H), 2.52-2.42 (m, 2H), 2.33-2.20 (m, 2H), 1.45-1.36 (m, 1H), 1.28 (t, J=7.3 Hz, 15H); $^{31}$P NMR (D$_2$O) δ 53.02 (s, 1P), −0.79 (s, 1P).

In a polypropylene tube Intermediate 125b (60 mg, 0.0804 mmol) was dissolved in pyridine (0.402 mL, 4.97 mmol) and triethylamine trihydrofluoride (0.0668 mL, 0.402 mmol) was added, followed by TEA (1.00 mL, 7.10 mmol). The reaction mixture was sealed and allowed to stir at 50° C. for 8 h. The reaction mixture was cooled to rt and diluted with water (2.0 mL). CaCl$_2$ (111 mg, 0.964 mmol) in water (2.00 mL) was added. The cloudy white mixture was allowed to stir at rt for 1.5 h. The suspension was filtered through celite and the celite was washed with water (5×5 mL). The clear aqueous filtrate was concentrated to a solid residue and dried on vacuum for 30 min. No HF was observed by $^{19}$F NMR. The crude mixture was purified by reverse phase flash column chromatography (0-10% ACN in aq. triethylammonium acetate (10 mM)) to provide I-19b as the N,Ndiethylethanamine salt (22 mg, 33%). LCMS (AA): m/z=633.2 (M+H). $^1$H NMR (D$_2$O) δ 8.45 (s, 1H), 8.05 (s, 1H), 7.93 (br d, J=5.7 Hz, 1H), 6.62 (br d, J=6.0 Hz, 1H), 5.99 (d, J=8.4 Hz, 1H), 5.48 (ddd, J=4.0, 8.3, 12.7 Hz, 1H), 4.86-4.80 (m, 1H), 4.57 (d, J=4.2 Hz, 1H), 4.47-4.36 (m, 2H), 4.20-4.11 (m, 2H), 3.97-3.85 (m, 2H), 3.15 (q, J=7.3 Hz, 10H), 2.52-2.38 (m, 2H), 2.32-2.10 (m, 2H), 1.34-1.26 (m, 1H), 1.23 (t, J=7.3 Hz, 15H) $^{31}$P NMR (D$_2$O) δ 57.47 (s, 1P), −0.86 (s, 1P).

Example 40

2-amino-9-[(2S,5R,7R,8R,12aR,14R,15aS,16R)-10,16-dihydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,12aR,14R,15aS,16R)-10,16-dihydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one, I-18

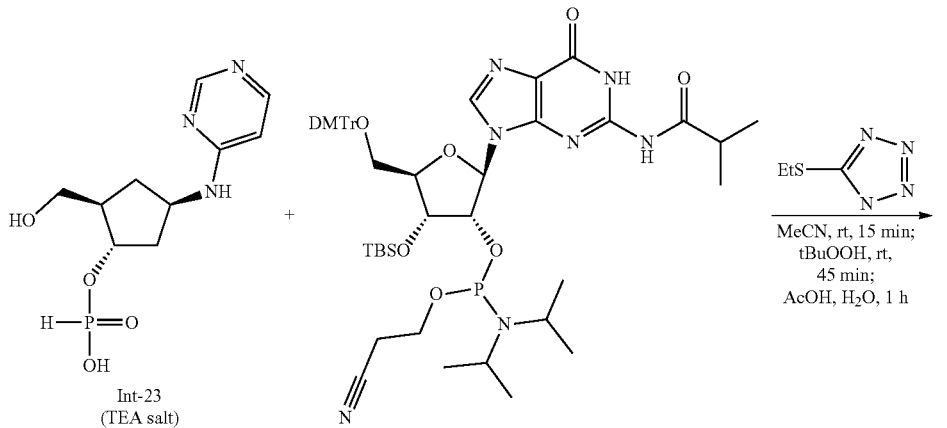

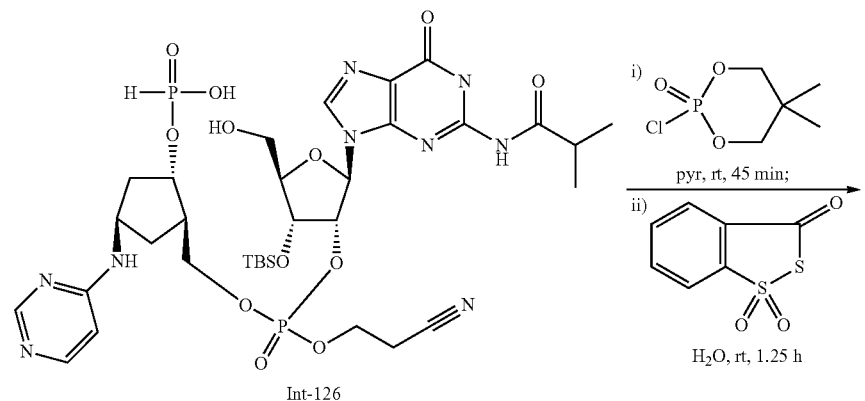

Int-126

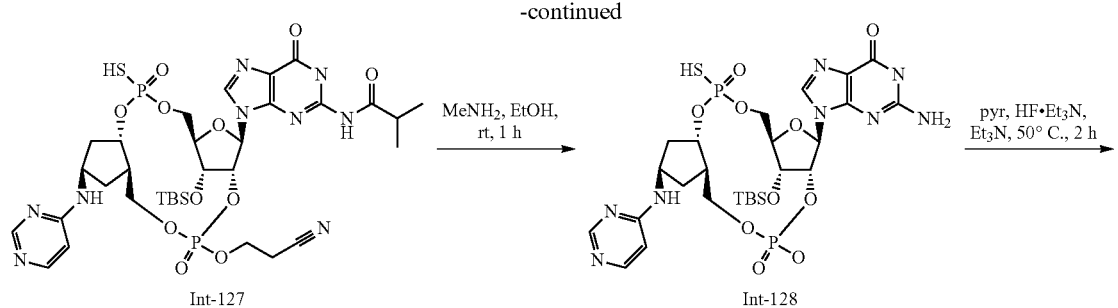

Int-127 → Int-128

Reagents: MeNH₂, EtOH, rt, 1 h; then pyr, HF·Et₃N, Et₃N, 50° C., 2 h

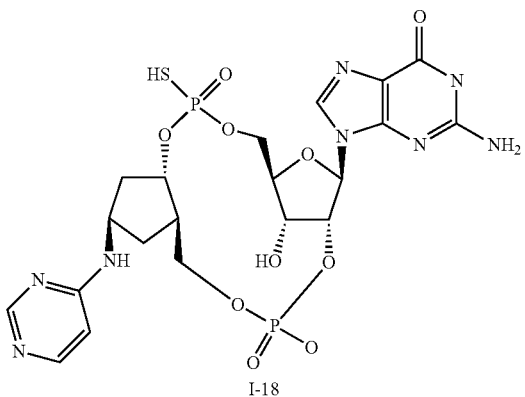

I-18

Step 1: [(1S,2R,4R)-2-[[[(2R,3R,4R,5R)-4-[tert-butyl(dimethyl)silyl]oxy-5-(hydroxymethyl)-2-[2-(2-methylpropanoylamino)-6-oxo-1H-purin-9-yl]tetrahydrofuran-3-yl]oxy-(2-cyanoethoxy)phosphoryl]oxymethyl]-4-(pyrimidin-4-ylamino)cyclopentoxy] phosphinic acid Intermediate 23 TEA salt was prepared from Intermediate 30 using steps 4 and 5 from Example 47.

[(1S,2R,4R)-2-[[[(2R,3R,4R,5R)-4-[tert-butyl(dimethyl)silyl]oxy-5-(hydroxymethyl)-2-[2-(2-methylpropanoylamino)-6-oxo-1H-purin-9-yl]tetrahydrofuran-3-yl]oxy-(2-cyanoethoxy)phosphoryl]oxymethyl]-4-(pyrimidin-4-ylamino)cyclopentoxy]phosphinic acid, Intermediate 126 was prepared from Intermediate 23-TEA salt and N-[9-[(2R,3R,4R,5R)-5-[[bis(4-methoxyphenyl)-phenyl-methoxy]methyl]-4-[tert-butyl(dimethyl) silyl]oxy-3-[2-cyanoethoxy-(diisopropylamino)phosphanyl]oxy-tetrahydrofuran-2-yl]-6-oxo-1H-purin-2-yl]-2-methyl-propanamide as described in Example 14, step 1. LCMS (AA): m/z=856.3 (M+H).

Step 2: 2-amino-9-[(2S,5R,7R,8R,12aR,14R,15aS,16R)-10,16-dihydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,12aR,14R,15aS,16R)-10,16-dihydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one, I-18

The title compound was prepared from [(1S,2R,4R)-2-[[[(2R,3R,4R,5R)-4-[tert-butyl(dimethyl)silyl]oxy-5-(hydroxymethyl)-2-[2-(2-methylpropanoylamino)-6-oxo-1H-purin-9-yl]tetrahydrofuran-3-yl]oxy-(2-cyanoethoxy)phosphoryl]oxymethyl]-4-(pyrimidin-4-ylamino)cyclopentoxy]phosphinic acid, Intermediate 126 using the procedures described in Example 31, steps 2-4. A single diastereomer was observed and isolated in step 2. LCMS (AA): m/z=633.2 (M+H); $^1$H NMR (D₂O) δ 8.48 (br s, 1H), 8.04-7.96 (m, 2H), 6.53 (br s, 1H), 6.01 (d, J=8.4 Hz, 1H), 5.45 (dt, J=4.2, 8.6 Hz, 1H), 4.98 (quin, J=6.7 Hz, 1H), 4.63 (d, J=3.9 Hz, 1H), 4.48 (br s, 1H), 4.45-4.36 (m, 2H), 4.17-4.10 (m, 1H), 3.99 (br d, J=10.3 Hz, 1H), 3.89-3.81 (m, 1H), 3.20 (q, J=7.3 Hz, 11H), 2.51-2.40 (m, 2H), 2.39-2.22 (m, 2H), 1.50-1.41 (m, 1H), 1.28 (t, J=7.3 Hz, 16H); $^{31}$P NMR (D₂O) δ=51.83 (s, 1P), −3.21 (s, 1P).

Example 41
2-amino-9-[(2S,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one, or
2-amino-9-[(2R,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one, I-21
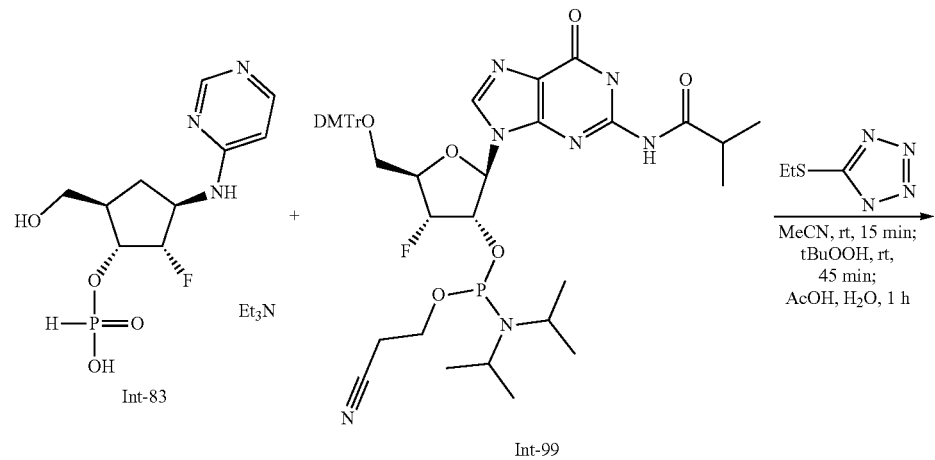
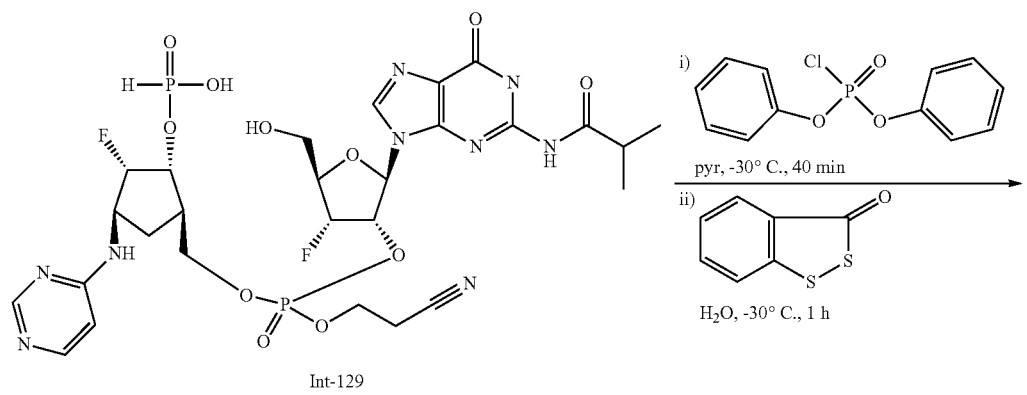
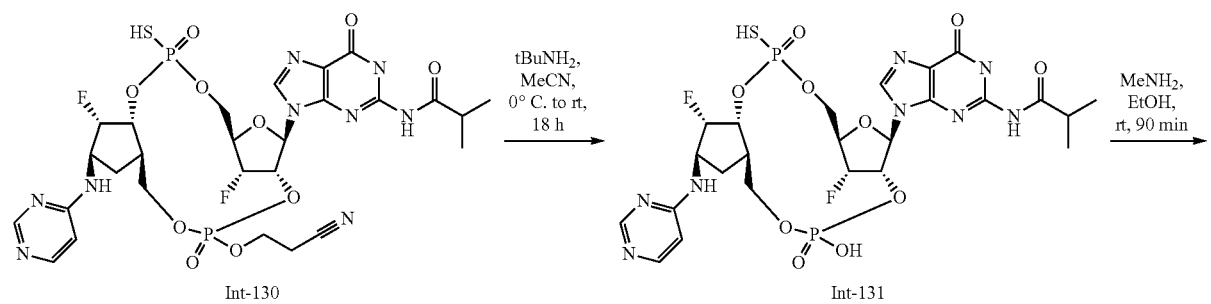

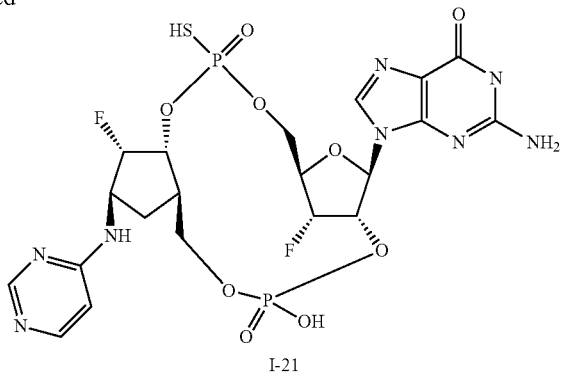

I-21

Step 1: (1R,2S,3R,5R)-5-({[(2-cyanoethoxy)({(2R,3S,4R,5R)-4-fluoro-5-(hydroxymethyl)-2-[2-(isobutyrylamino)-6-oxo-1,6-dihydro-9H-purin-9-yl]tetrahydrofuran-3-yl}oxy)phosphoryl]oxy}methyl)-2-fluoro-3-(pyrimidin-4-ylamino)cyclopentyl hydrogen phosphonate, Intermediate 129

The title compound was prepared from Intermediate 99 and Intermediate 83 following the procedure described in Example 14, step 1 to provide Intermediate 129 LCMS (AA): m/z=762.2 (M+H).

Step 2: N-{9-[(2S,5R,7R,8S,12aR,14R,15S,15aR,16R)-10-(2-cyanoethoxy)-15,16-difluoro-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, or N-{9-[(2R,5R,7R,8S,12aR,14R,15S,15aR,16R)-10-(2-cyanoethoxy)-15,16-difluoro-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 130

The title compound was prepared from Intermediate 129 following the procedure described in Example 52 step 2 to provide Intermediate 130. A single isomer was observed and isolated. LCMS (AA): m/z=776.2 (M+H).

Step 3: N-{9-[(2S,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, or N-{9-[(2R,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 131

A solution of Intermediate 130 (44.0 mg, 0.057 mmol) in ACN (0.50 mL) was cooled to 0° C. and t-butylamine (8.30 mg, 0.012 mmol) was added. The reaction mixture was allowed to stir at 0° C. for 2.5 h, and then allowed to warm to rt and stirred for 18 h. The reaction mixture was concentrated and was purified by reverse phase flash column chromatography (10-100% ACN in aq. ammonium bicarbonate (5 mM)) to provide Intermediate 131 as a white solid (5.4 mg, 13%). LCMS (AA): m/z=723.1 (M+H).

Step 4: 2-amino-9-[(2S,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5R,7R,8S,12aR,14R,15S,15aR,16R)-15,16-difluoro-10-hydroxy-2,10-dioxido-14-(pyrimidin-4-ylamino)-2-sulfanyldecahydro-5,8-methanocyclopenta[l][1,3,6,9,11,2,10]pentaoxadiphosphacyclotetradecin-7-yl]-1,9-dihydro-6H-purin-6-one I-21

Intermediate 131 (5.40 mg, 0.007 mmol) was dissolved in methylamine (33% in ethanol, 0.093 mL, 0.747 mmol) under an atmosphere of nitrogen. The reaction mixture was allowed to stir at rt for 90 min. The reaction mixture was concentrated and then dissolved in triethylammonium buffer and concentrated (3×5 mL). The crude compound was purified by reverse phase flash column chromatography (0-15% ACN in aqueous ammonium acetate (10 mM)) to provide I-21 as the N,N-diethylethanamine salt (3.3 mg, 59%). LCMS (AA): m/z=653.1 (M+H). $^1$H NMR (D$_2$O) δ 8.61-8.73 (m, 1H), 8.05-8.17 (m, 1H), 7.96 (s, 1H), 6.57-6.72 (m, 1H), 6.07 (d, J=8.6 Hz, 1H), 5.62 (dtd, J=27.0, 9.1, 3.3 Hz, 1H), 5.45 (dd, J=53.6, 3.3 Hz, 1H), 5.19 (dd, J=51.6, 3.2 Hz, 1H), 4.76-4.96 (m, 2H), 4.53 (ddd, J=11.5, 6.6, 3.2 Hz, 2H), 4.09-4.18 (m, 1H), 3.95-4.08 (m, 2H), 3.20 (d, J=7.3 Hz, 6H), 2.53-2.67 (m, 2H), 1.62-1.74 (m, 1H), 1.28 (t, I=7.3 Hz, 9H). $^{31}$P NMR (D$_2$O) δ: 54.62 (s, 1P), −1.59 (s, 1P).

Example 42

2-amino-9-[(2S,5R,7R,8R,10S,12aR,14R,15S,15aR, 16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15S,15aR, 16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15S,15aR, 16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15S,15aR, 16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, I-20a and I-20b

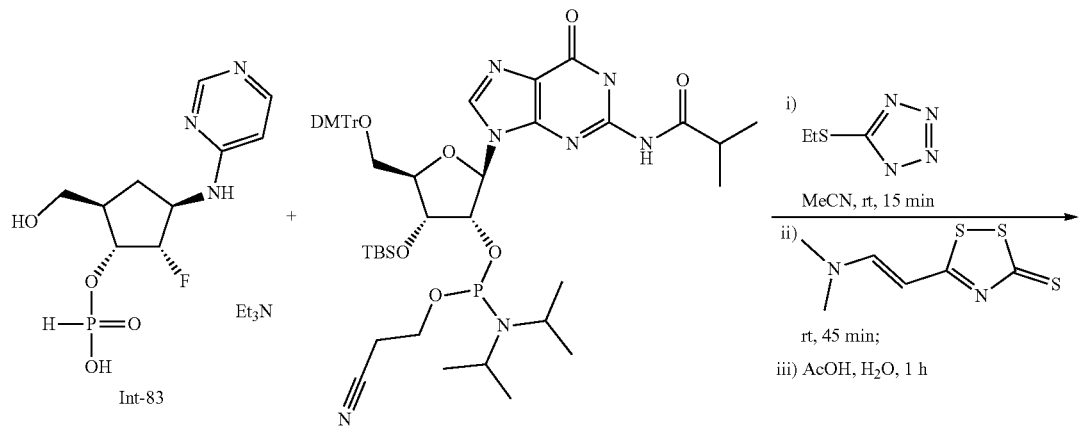

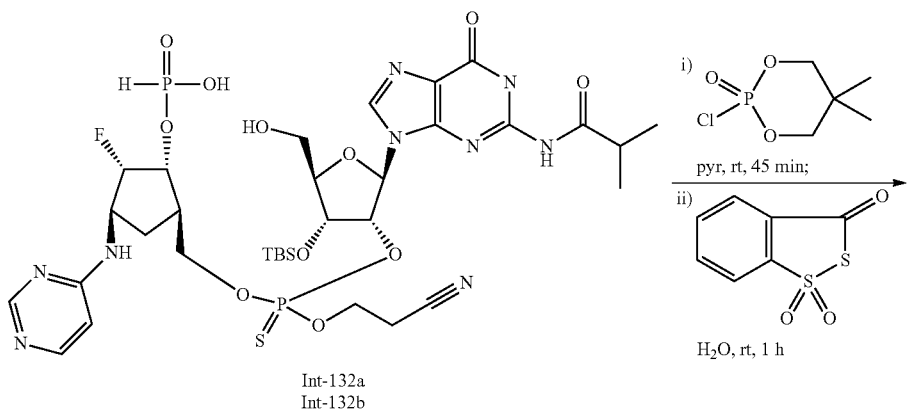

-continued

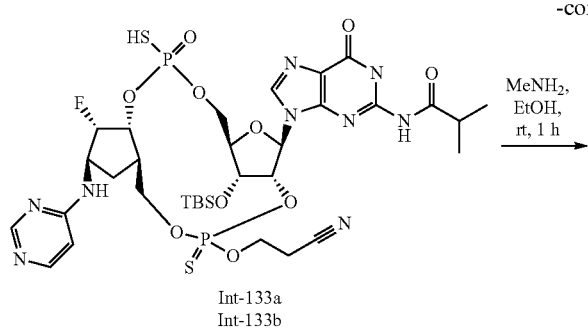

Int-133a
Int-133b

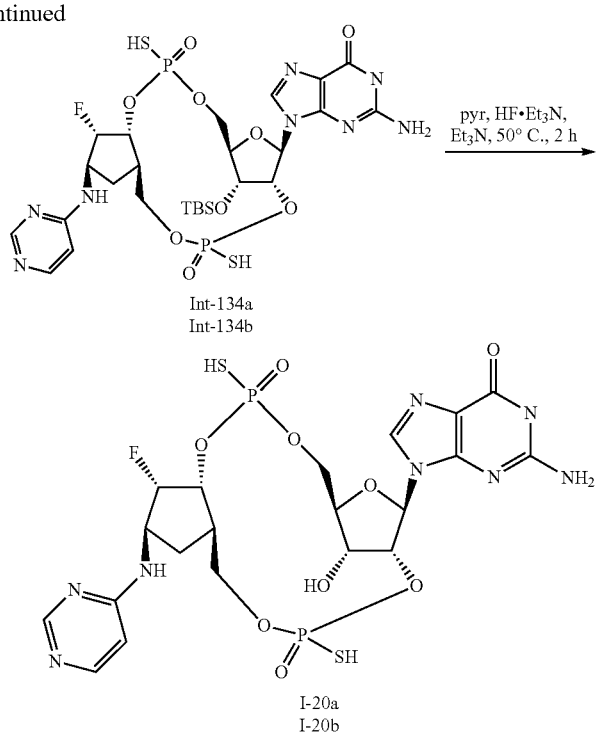

Int-134a
Int-134b

I-20a
I-20b

Step 1: (1R,2S,3R,5R)-5-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-2-fluoro-3-(pyrimidin-4-ylamino)cyclopentyl hydrogen phosphonate or (1R,2S,3R,5R)-5-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-2-fluoro-3-(pyrimidin-4-ylamino)cyclopentyl hydrogen phosphonate, Intermediate 132a and Intermediate 132b The title compounds were prepared following the procedure described in Example 31, step 1, substituting Intermediate 83 for Intermediate 23 to provide Intermediate 132a as the first eluting peak, LCMS (AA): m/z=890.3 (M+H) and Intermediate 132b as the second eluting peak LCMS (AA): m/z=890.3 (M+H).

Steps 2-4: 2-amino-9-[(2S,5R,7R,8R,10S,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, I-20a The title compound was prepared from Intermediate 132a following the procedures described in Example 31, steps 2-4. LCMS (AA): m/z=667.0 (M+H). $^1$H NMR (D$_2$O) δ 8.41 (s, 1H), 7.99 (br d, J=6.4 Hz, 1H), 7.85 (s, 1H), 6.34 (br s, 1H), 5.91 (d, J=8.4 Hz, 1H), 5.58 (ddd, J=4.2, 8.5, 10.4 Hz, 1H), 5.19-5.03 (m, 1H), 4.96-4.81 (m, 1H), 4.60 (d, J=3.9 Hz, 1H), 4.44-4.37 (m, 2H), 4.32-4.23 (m, 1H), 4.10-3.99 (m, 2H), 3.94-3.88 (m, 1H), 3.14 (q, J=7.3 Hz, 12H), 2.62-2.49 (m, 2H), 1.60-1.51 (m, 1H), 1.22 (t, J=7.3 Hz, 18H); $^{31}$P NMR (D$_2$O) δ=54.45 (s, 1P), 52.40 (s, 1P).

Steps 2-4: 2-amino-9-[(2S,5R,7R,8R,10S,12aR,14R, 15S,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15S,15aR, 16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15S,15aR, 16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15S,15aR, 16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, I-20b The title compound was prepared from Intermediate 132b following the procedures described in Example 31, steps 2-4. LCMS (AA): m/z=667.0 (M+H). $^1$H NMR (D$_2$O) δ 8.47 (s, 1H), 7.92 (br d, J=6.2 Hz, 1H), 7.86 (s, 1H), 6.54 (br d, J=6.4 Hz, 1H), 5.93 (d, J=8.2 Hz, 1H), 5.62 (ddd, J=4.0, 8.4, 12.3 Hz, 1H), 5.19 (d, J=52.7 Hz, 1H), 5.04-4.89 (m, 1H), 4.57 (d, J=3.9 Hz, 1H), 4.45-4.33 (m, 3H), 4.12-4.06 (m, 1H), 4.03-3.89 (m, 2H), 3.13 (q, J=7.3 Hz, 12H), 2.70-2.50 (m, 2H), 1.57 (br d, J=15.2 Hz, 1H), 1.21 (t, J=7.3 Hz, 18H); $^{31}$P NMR (D$_2$O) δ 54.51 (s, 1P).

Example 43

2-amino-7-[(2S,5R,7R,8R,10S,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2S,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10S,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, I-31a and I-31b

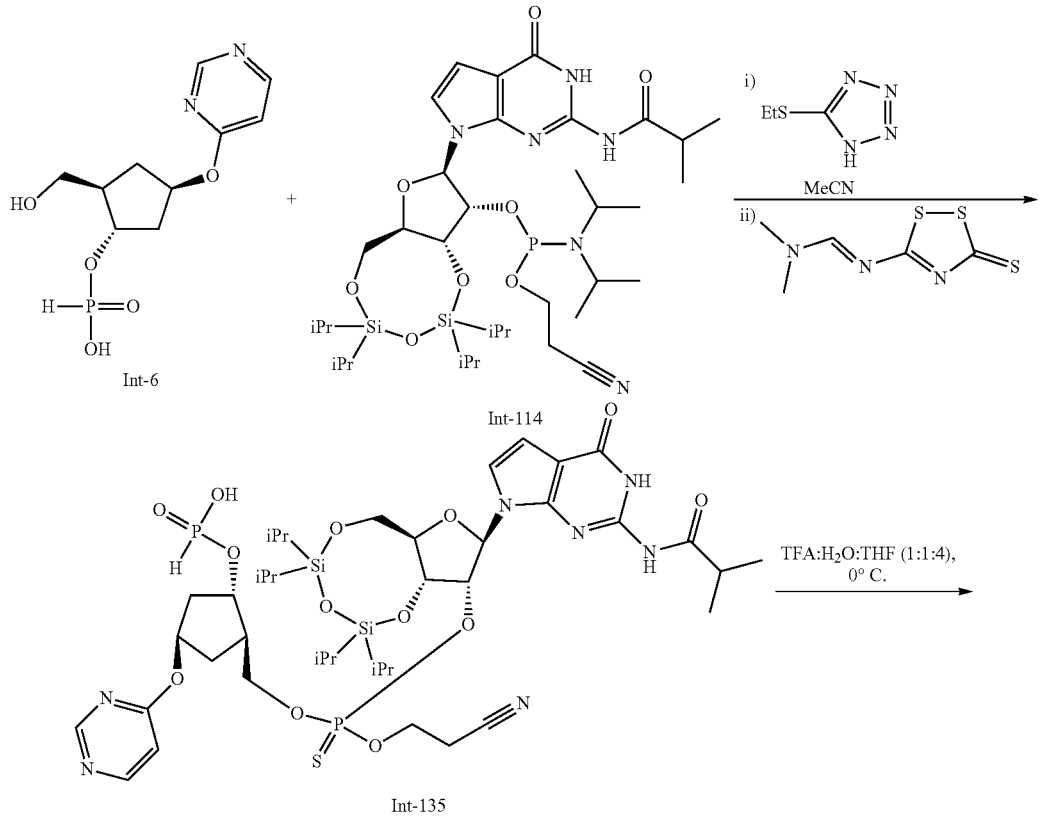

-continued
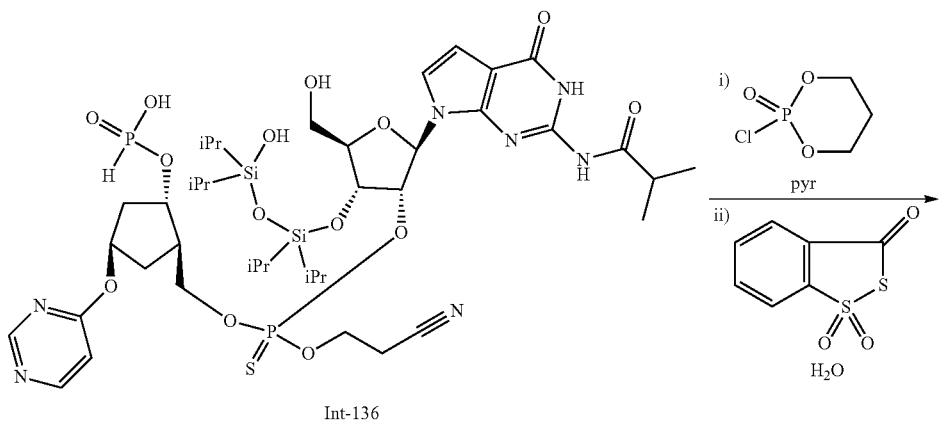
Int-136
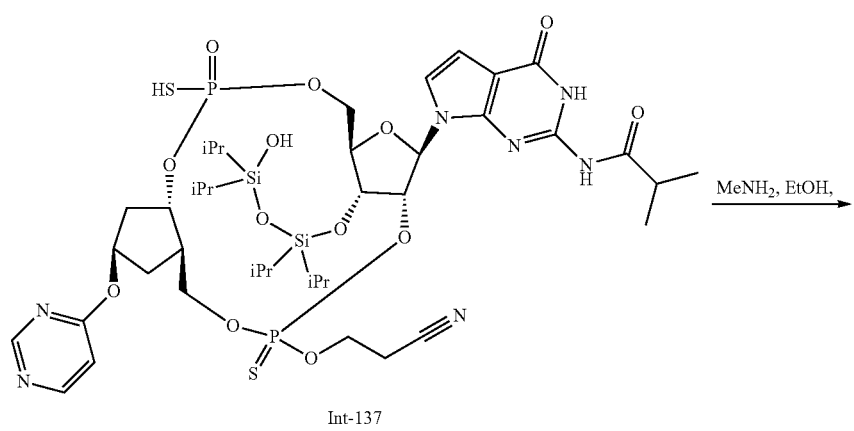
Int-137
MeNH₂, EtOH,
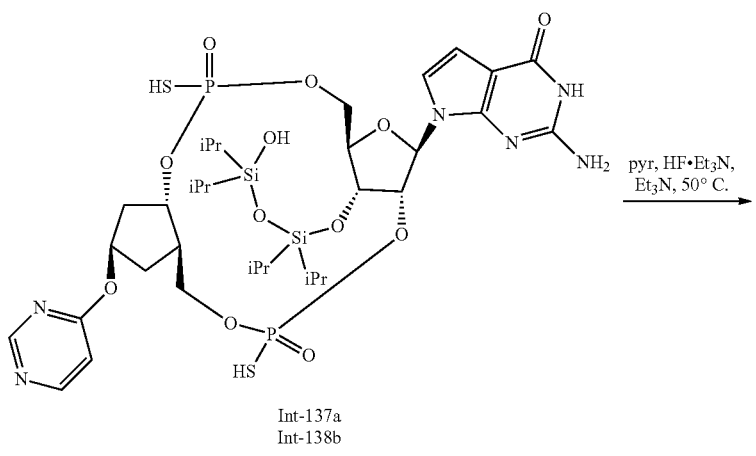
Int-137a
Int-138b
pyr, HF·Et₃N,
Et₃N, 50° C.

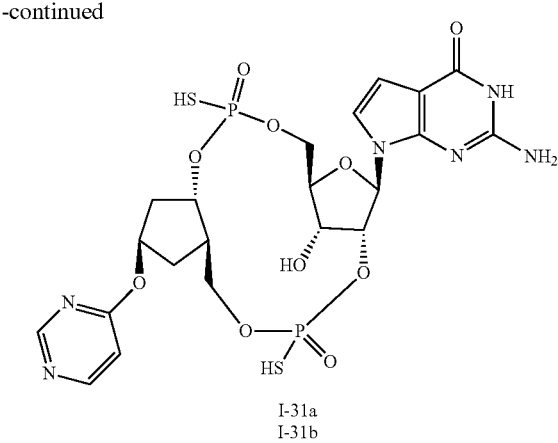

I-31a
I-31b

Step 1: (1S,2R,4R)-2-({[(R)-(2-cyanoethoxy)({(6aR,8R,9R,9aR)-8-[2-(isobutyrylamino)-4-oxo-3,4-dihydro-7H-pyrrolo[2,3-d]pyrimidin-7-yl]-2,2,4,4-tetraisopropyltetrahydro-6H-furo[3,2-f][1,3,5,2,4]trioxadisilocin-9-yl}oxy)phosphorothioyl]oxy}methyl)-4-(pyrimidin-4-yloxy)cyclopentyl hydrogen phosphonate and (1S,2R,4R)-2-({[(S)-(2-cyanoethoxy)({(6aR,8R,9R,9aR)-8-[2-(isobutyrylamino)-4-oxo-3,4-dihydro-7H-pyrrolo[2,3-d]pyrimidin-7-yl]-2,2,4,4-tetraisopropyltetrahydro-6H-furo[3,2-f][1,3,5,2,4]trioxadisilocin-9-yl}oxy)phosphorothioyl]oxy}methyl)-4-(pyrimidin-4-yloxy)cyclopentyl hydrogen phosphonate, Intermediate 135

A mixture of Intermediate 6 (598 mg, 2.06 mmol) and Intermediate 114 (1.83 g, 2.30 mmol) was dissolved in dry acetonitrile and concentrated to dryness (3×10 mL). The residue was then dissolved in ACN (7.52 mL) under an atmosphere of argon. In a separate flask 5-(ethylthio)-1H-tetrazole (801 mg, 6.15 mmol) was dissolved in dry acetonitrile and concentrated to dryness (3×6 mL), the residue was dissolved in ACN (3.42 mL) and added to the reaction mixture under an atmosphere of argon. The reaction mixture was allowed to stir at rt for 1 h. ((Dimethylamino-methylidene)amino)-3H-1,2,4-dithiazoline-3-thione (505 mg, 2.46 mmol) was added to the reaction mixture and stirring was continued for 45 min at rt. The reaction mixture was concentrated and dried on vacuum for 10 min. The crude compound was purified by silica gel chromatography (0-80% MeOH in DCM) to provide Intermediate 135 (206 mg, 10%) as a mixture of diastereomers. LCMS (FA): m/z=1000.4 (M+H).

Step 2: (1S,2R,4R)-2-({[(R)-(2-cyanoethoxy)({(2R,3R,4R,5R)-5-(hydroxymethyl)-4-[(3-hydroxy-1,1,3,3-tetraisopropyldisiloxanyl)oxy]-2-[2-(isobutyrylamino)-4-oxo-3,4-dihydro-7H-pyrrolo[2,3-d]pyrimidin-7-yl]tetrahydrofuran-3-yl}oxy)phosphorothioyl]oxy}methyl)-4-(pyrimidin-4-yloxy)cyclopentyl hydrogen phosphonate and (1S,2R,4R)-2-({[(S)-(2-cyanoethoxy)({(2R,3R,4R,5R)-5-(hydroxymethyl)-4-[(3-hydroxy-1,1,3,3-tetraisopropyldisiloxanyl)oxy]-2-[2-(isobutyrylamino)-4-oxo-3,4-dihydro-7H-pyrrolo[2,3-d]pyrimidin-7-yl]tetrahydrofuran-3-yl}oxy)phosphorothioyl]oxy}methyl)-4-(pyrimidin-4-yloxy)cyclopentyl hydrogen phosphonate, Intermediate 136

Intermediate 135 (204 mg, 0.20 mmol) was taken up in THF (2.3 mL) and water (0.57 mL) and cooled to 0° C. TFA (0.57 mL, 7.50 mmol) was added drop-wise and the reaction mixture was allowed to stir at 0° C. for 2 h. Sodium bicarbonate (930 mg, 11.0 mmol) was added portion-wise, followed by water and EtOAc. The reaction mixture was allowed to warm to rt and extracted into EtOAc. The combined organic phases were washed with brine, dried with Na$_2$SO$_4$ and concentrated. The crude compound was purified by silica gel chromatography (0-60% MeOH in DCM) to provide Intermediate 136 (155 mg, 75%) as a mixture of diastereomers. LCMS (FA): m/z=1018.4 (M+H).

Step 3: N-{7-[(2S,5R,7R,8R,10R,12aR,14R,15aS, 16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-4-oxo-4,7-dihydro-3H-pyrrolo[2,3-d]pyrimidin-2-yl}-2-methylpropanamide or N-{7-[(2S,5R,7R,8R,10S,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-4-oxo-4,7-dihydro-3H-pyrrolo[2,3-d]pyrimidin-2-yl}-2-methylpropanamide or N-{7-[(2R,5R,7R,8R,10R,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-4-oxo-4,7-dihydro-3H-pyrrolo[2,3-d]pyrimidin-2-yl}-2-methylpropanamide or N-{7-[(2R,5R,7R,8R,10S,12aR,14R,15aS,16R)-10-(2-cyanoethoxy)-16-[(3-hydroxy-1,1,3,3-tetraisopropyldisiloxanyl)oxy]-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-4-oxo-4,7-dihydro-3H-pyrrolo[2,3-d]pyrimidin-2-yl}-2-methylpropanamide, Intermediate 137

Intermediate 136 (154 mg, 0.15 mmol) was concentrated from dry pyridine (3×5 mL), dried under vacuum for 10 min and dissolved in pyridine (3.03 mL) under an atmosphere of argon. 2-Chloro-5,5-dimethyl-1,3,2-dioxaphosphorinane 2-oxide (97.7 mg, 0.53 mmol) was added and the reaction mixture was allowed to stir at rt for 45 min. Water (0.10 mL) was added followed by 3H-1,2-benzodithiol-3-one 1,1-dioxide (37.7 mg, 0.18 mmol) then stirring was continued at rt for 1 h. An additional portion of 3H-1,2-benzodithiol-3-one 1,1-dioxide (36.3 mg, 36.0 µmol) was added and stirring was continued for 10 min. The reaction mixture was concentrated and concentrated from toluene. The crude compound was purified by silica gel chromatography (0-40% MeOH in DCM) to provide slightly impure Intermediate 137 (204 mg) as a mixture of diastereomers. LCMS (FA): m/z=1032.3 (M+H).

Step 4: 2-amino-7-[(2S,5R,7R,8R,10S,12aR,14R, 15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2S,5R,7R,8R,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,7-dihydro-4H-pyrrolo[2,3-d]pyrimidin-4-one, Intermediate 138a and 138b Intermediate 137 (216 mg, 0.21 mmol) was dissolved in methylamine (33% in EtOH, 10.4 mL, 83.7 mmol) and the reaction mixture was allowed to stir under an atmosphere of nitrogen at rt overnight. The reaction mixture was concentrated and dried on vacuum for 10 min. The crude compound was purified by reverse phase flash column chromatography (10-100% ACN in aqueous ammonium acetate (10 mM)) to provide Intermediate 138a as the second eluting peak (67 mg, 34%). LCMS (AA): m/z=909.4 (M+H) and Intermediate 138b as the third eluting peak (22 mg, 11%). LCMS (AA): m/z=909.4 (M+H).

Step 5: 2-amino-7-[(2S,5R,7R,8R,10S,12aR,14R, 15aS,16R)-16-hydroxy-2,10-dioxido-14-(pyrimidin-4-yloxy)-2,10-disulfanyldecahydro-5,8-methanocyclopenta [l][1,3,6,9,11,2,10] pentaoxadiphosphacyclotetradecin-7-yl]-3,7-dihydro-4H-pyrrolo[2,3-d]pyrimidin-4-one or 2-amino-7-[(2S,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta [l][1,3,6,9,11,2,10] pentaoxadiphosphacyclotetradecin-7-yl]-3,7-dihydro-4H-pyrrolo[2,3-d]pyrimidin-4-one or 2-amino-7-[(2R,5R,7R,8R,10S,12aR,14R,15aS, 16R)-16-hydroxy-2,10-dioxido-14-(pyrimidin-4-yloxy)-2,10-disulfanyldecahydro-5,8-methanocyclopenta [l][1,3,6,9,11,2,10] pentaoxadiphosphacyclotetradecin-7-yl]-3,7-dihydro-4H-pyrrolo[2,3-d]pyrimidin-4-one or 2-amino-7-[(2R,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta [l][1,3,6,9,11,2,10] pentaoxadiphosphacyclotetradecin-7-yl]-3,7-dihydro-4H-pyrrolo[2,3-d]pyrimidin-4-one I-31a Intermediate 138a (67.0 mg, 0.07 mmol) was suspended in pyridine (0.37 mL) and TEA (0.92 mL) in a propylene tube. Triethylamine trihydrofluoride (0.06 mL, 0.37 mmol) was added and the tube was sealed and the reaction mixture was allowed to stir at 50° C. overnight. The reaction mixture was cooled to rt and water (1.38 mL) was added followed by dropwise addition of a solution of calcium chloride (170 mg, 1.47 mmol) in water (1.38 mL). The reaction mixture was allowed to stir at rt for 30 min, then filtered through Celite and the Celite was rinsed with water (5×3 mL). The filtrate was concentrated to give a white solid. No HF was observed by $^{19}$F NMR. The crude mixture was purified by reverse phase flash column chromatography (0-15% ACN in aqueous triethylammonium acetate (10 mM)) to provide I-31a (37 mg, 56%) as the N, N-diethylethanamine salt. LCMS (AA): m/z=648.9 (M+H); $^1$H NMR (D$_2$O) δ 8.69 (s, 1H), 8.46 (d, J=6.0 Hz, 1H), 7.31 (d, J=3.8 Hz, 1H), 6.94 (dd, J=1.0, 6.0 Hz, 1H), 6.55 (d, J=3.7 Hz, 1H), 6.20 (d, J=8.6 Hz, 1H), 5.53-5.47 (m, 1H), 5.33-5.25 (m, 1H), 5.13-5.06 (m, 1H), 4.59 (d, J=4.4 Hz, 1H), 4.40 (br s, 1H), 4.36-4.27 (m, 1H), 4.14-4.01 (m, 2H), 3.93-3.86 (m, 1H), 3.20 (q, J=7.3 Hz, 12H), 2.58-2.48 (m, 4H), 1.67-1.57 (m, 1H), 1.28 (t, J=7.3 Hz, 18H); $^{31}$P NMR (D$_2$O) δ 58.48 (s, 1P), 54.33 (s, 1P).

Example 43A

The compound listed below (I-31b) was prepared as described in Example 43 starting with Step 5, substituting the starting material shown in the table for Intermediate 138a.

| Compound | Salt form | Starting material | LCMS data | NMR data |
|---|---|---|---|---|
| I-31b | Et$_3$N | Intermediate 138b | LCMS (AA): m/z = 648.9 (M + H). | $^1$H NMR (D$_2$O) δ 8.69 (s, 1H), 8.44 (d, J = 6.0 Hz, 1H), 7.26 (d, J = 3.8 Hz, 1H), 6.85 (d, J = 6.1 Hz, 1H), 6.56 (d, J = 3.7 Hz, 1H), 6.19 (d, J = 8.4 Hz, 1H), 5.51-5.43 (m, 1H), 5.28 (dt, J = 4.2, 8.9 Hz, 1H), 4.99 (quin, J = 6.3 Hz, 1H), 4.58-4.57 (m, 1H), 4.42 (d, J = 2.1 Hz, 1H), 4.39-4.31 (m, 1H), 4.12-4.02 (m, 2H), 3.92-3.82 (m, 1H), 3.19 (q, J = 7.3 Hz, 12H), 2.60-2.47 (m, 3H), 2.46-2.36 (m, 1H), 1.68-1.57 (m, 1H), 1.27 (t, J = 7.3 Hz, 18H); $^{31}$P NMR (D$_2$O) δ 54.13 (s, 1P), 52.70 (s, 1P). |

Example 44

3-[(2S,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo [4,5-d]pyrimidin-7-one or 3-[(2S,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo [4,5-d]pyrimidin-7-one or 3-[(2R,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo [4,5-d]pyrimidin-7-one or 3-[(2R,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo [4,5-d]pyrimidin-7-one I-37a, I-37b and I-37c

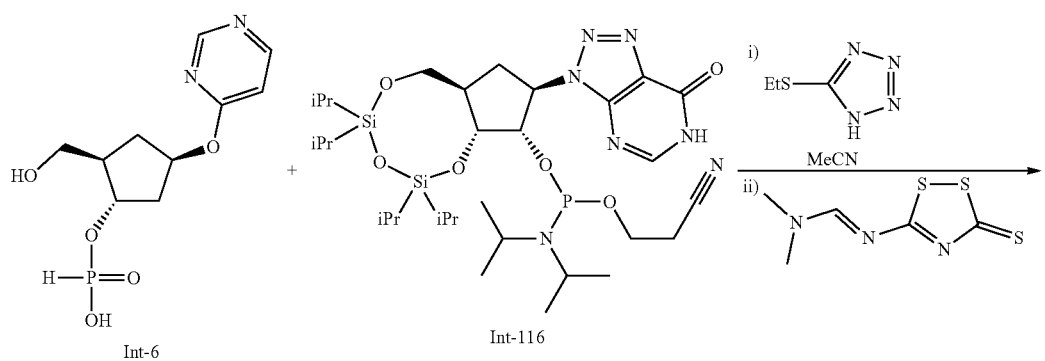

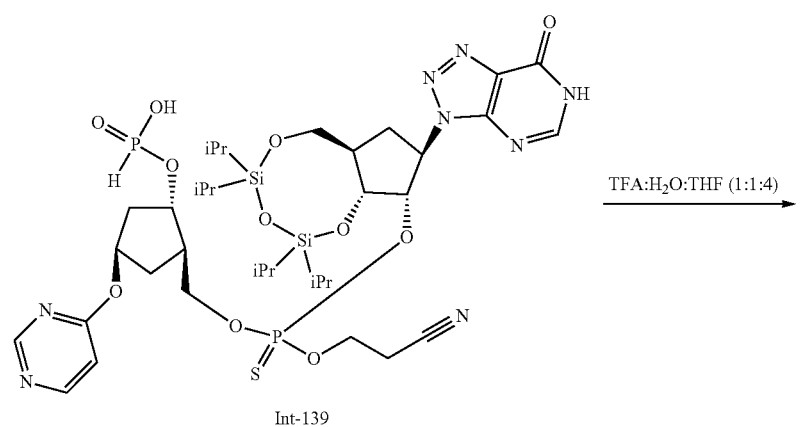

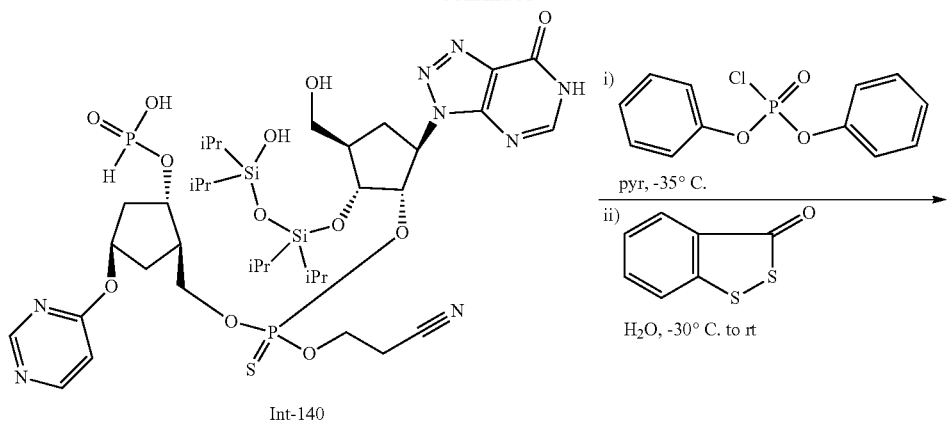
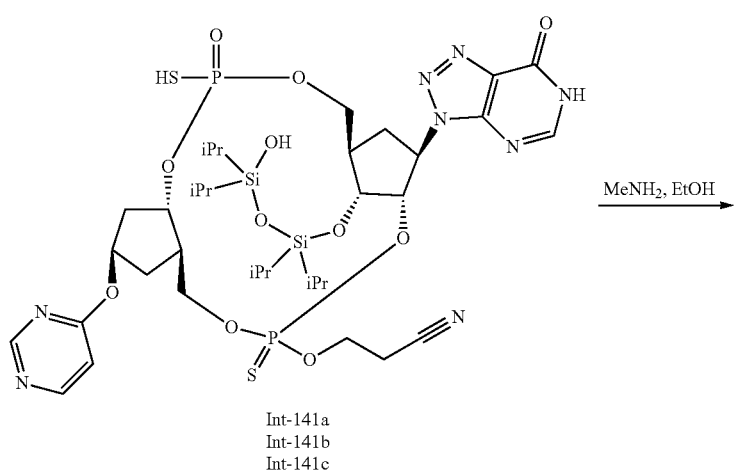
Int-141a
Int-141b
Int-141c
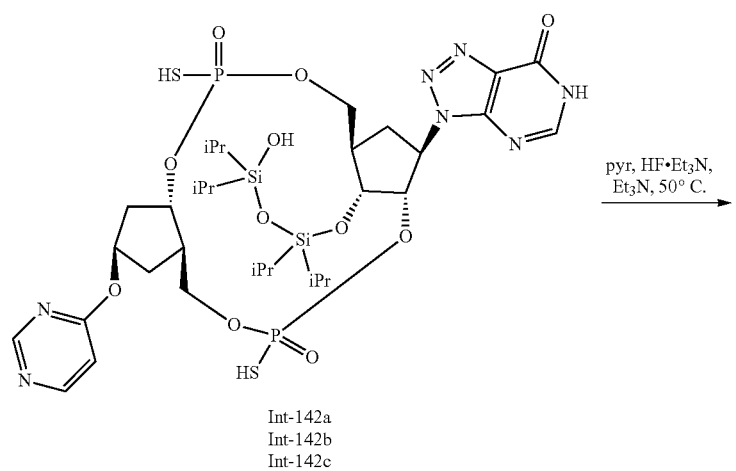
Int-142a
Int-142b
Int-142c

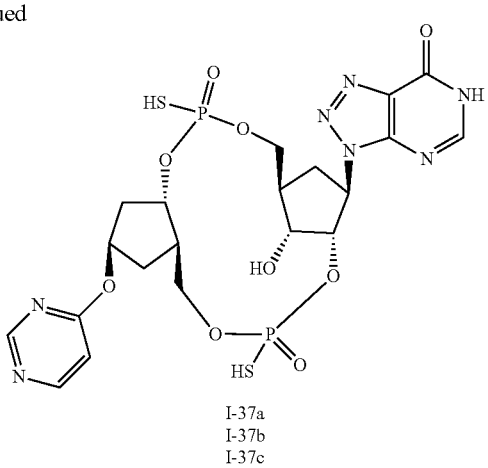

I-37a
I-37b
I-37c

Step 1: (1S,2R,4R)-2-({[(R)-(2-cyanoethoxy) {[(6aR,8R,9S,9aR)-2,2,4,4-tetraisopropyl-8-(7-oxo-6,7-dihydro-3H-[1,2,3]triazolo[4,5-d]pyrimidin-3-yl) hexahydrocyclopenta [f][1,3,5,2,4]trioxadisilocin-9-yl]oxy}phosphorothioyl]oxy}methyl)-4-(pyrimidin-4-yloxy)cyclopentyl hydrogen phosphonate and (1S,2R,4R)-2-({[(S)-(2-cyanoethoxy){[(6aR,8R,9S, 9aR)-2,2,4,4-tetraisopropyl-8-(7-oxo-6,7-dihydro-3H-[1,2,3]triazolo[4,5-d]pyrimidin-3-yl)hexahydro-cyclopenta [f][1,3,5,2,4]trioxadisilocin-9-yl] oxy}phosphorothioyl]oxy}methyl)-4-(pyrimidin-4-yloxy)cyclopentyl hydrogen phosphonate,
Intermediate 139

A mixture of Intermediate 6 (350 mg, 1.28 mmol) and Intermediate 116 (1.10 g, 1.55 mmol) was dissolved in dry acetonitrile and concentrated to dryness (3×10 mL). The residue was then dissolved in ACN (4.78 mL) under an atmosphere of argon. In a separate flask 5-(ethylthio)-1H-tetrazole (510 mg, 3.92 mmol) was dissolved in dry acetonitrile and concentrated to dryness (3×5 mL), the residue was dissolved in ACN (2.18 mL) and added to the reaction mixture under an atmosphere of argon. The reaction mixture was allowed to stir at rt for 40 min. ((Dimethylamino-methylidene)amino)-3H-1,2,4-dithiazoline-3-thione (321 mg, 1.56 mmol) was added to the reaction mixture and stirring was continued for 1.5 h at rt. The reaction mixture was concentrated and dried on vacuum for 10 min. The crude compound was purified by silica gel chromatography (0-75% MeOH in DCM) to provide Intermediate 139 (904 mg, 77%) as a mixture of diastereomers. LCMS (FA): m/z=915.4 (M+H).

Step 2: (1S,2R,4R)-2-({[(R)-(2-cyanoethoxy){[(1S, 2R,3R,5R)-3-(hydroxymethyl)-2-[(3-hydroxy-1,1,3, 3-tetraisopropyldisiloxanyl)oxy]-5-(7-oxo-6,7-dihydro-3H-[1,2,3]triazolo[4,5-d]pyrimidin-3-yl) cyclopentyl]oxy}phosphorothioyl]oxy}methyl)-4-(pyrimidin-4-yloxy)cyclopentyl hydrogen phosphonate and (1S,2R,4R)-2-({[(S)-(2-cyanoethoxy){[(1S,2R,3R, 5R)-3-(hydroxymethyl)-2-[(3-hydroxy-1,1,3,3-tetraisopropyldisiloxanyl)oxy]-5-(7-oxo-6,7-dihydro-3H-[1,2,3]triazolo[4,5-d]pyrimidin-3-yl)cyclopentyl] oxy}phosphorothioyl]oxy}methyl)-4-(pyrimidin-4-yloxy)cyclopentyl hydrogen phosphonate,
Intermediate 140

Intermediate 139 (903 mg, 0.99 mmol) was taken up in THF (9.03 mL) and water (2.05 mL) and cooled to 0° C. TFA (2.05 mL, 27.1 mmol) was added drop-wise and the reaction mixture was allowed to stir at 0° C. for 2.5 h. Sodium bicarbonate (3.12 g, 37.1 mmol) was added portion-wise, followed by water. The mixture was allowed to stir for 5 min then allowed to warm to rt and extracted into EtOAc. The combined organic phases were washed with brine, dried with Na₂SO₄ and concentrated. The crude compound was purified by silica gel chromatography to provide Intermediate 140 (580 mg, 63%) as a mixture of diastereomers. LCMS (FA): m/z=933.3 (M+H).

Step 3: 3-{[(2S,5R,7R,8S,10R,12aR,14R,15aS, 16R)-16-[(3-hydroxy-1,1,3,3-tetraisopropyldisiloxanyl)oxy]-2-oxido-7-(7-oxo-6,7-dihydro-3H-[1,2,3]triazolo[4,5-d]pyrimidin-3-yl)-14-(pyrimidin-4-yloxy)-2-sulfanyl-10-sulfidodecahydro-4H-5,8-methanocyclopenta[d][1,3,7,9,2,8]tetraoxadiphosphacyclotetradecin-10-yl]oxy}propanenitrile or 3-{[(2S,5R,7R,8S,10S,12aR,14R,15aS,16R)-16-[(3-hydroxy-1,1,3,3-tetraisopropyldisiloxanyl)oxy]-2-oxido-7-(7-oxo-6,7-dihydro-3H-[1,2,3]triazolo[4,5-d]pyrimidin-3-yl)-14-(pyrimidin-4-yloxy)-2-sulfanyl-10-sulfidodecahydro-4H-5,8-methanocyclopenta[d][1,3,7,9,2,8]tetraoxadiphosphacyclotetradecin-10-yl]oxy}propanenitrile or 3-{[(2R,5R,7R,8S,10R,12aR,14R,15aS,16R)-16-[(3-hydroxy-1,1,3,3-tetraisopropyldisiloxanyl)oxy]-2-oxido-7-(7-oxo-6,7-dihydro-3H-[1,2,3]triazolo[4,5-d]pyrimidin-3-yl)-14-(pyrimidin-4-yloxy)-2-sulfanyl-10-sulfidodecahydro-4H-5,8-methanocyclopenta[d][1,3,7,9,2,8]tetraoxadiphosphacyclotetradecin-10-yl]oxy}propanenitrile or 3-{[(2R,5R,7R,8S,10S,12aR,14R,15aS,16R)-16-[(3-hydroxy-1,1,3,3-tetraisopropyldisiloxanyl)oxy]-2-oxido-7-(7-oxo-6,7-dihydro-3H-[1,2,3]triazolo[4,5-d]pyrimidin-3-yl)-14-(pyrimidin-4-yloxy)-2-sulfanyl-10-sulfidodecahydro-4H-5,8-methanocyclopenta[d][1,3,7,9,2,8]tetraoxadiphosphacyclotetradecin-10-yl]oxy}propanenitrile, Intermediate 141a, 141b and 141c Diphenyl chlorophosphate (2.77 mL, 13.3 mmol) was added to pyridine (36.7 mL,) at −35° C. Intermediate 140 (550 mg, 0.59 mmol) was concentrated from dry pyridine (2×5 mL), taken up in DCM (14.7 mL) and pyridine (7.33 mL) and added to the reaction mixture over 20 min. The reaction mixture was allowed to stir at −35° C. for 40 min. 3H-1,2-Benzodithiol-3-one (220 mg, 1.31 mmol) and water (0.29 mL) were added at −30° C. The reaction mixture was allowed to stir at rt for 1 h. Sodium thiosulfate (2.93 mg, 18.0 mmol) in water was added at 0° C. and the reaction mixture was allowed to stir at rt for 5 min. The volatile solvents were removed by evaporation and the crude compound was purified by reverse phase flash column chromatography (10-100% ACN in aq. ammonium bicarbonate (5 mM)) to provide Intermediate 141a as the first eluting slightly impure product (90 mg, 16%), Intermediate 141b as the second eluting mixture of diastereomers (one major and one minor, 60 mg, 11%) and Intermediate 141c as the third eluting slightly impure product (181 mg, 32%). LCMS (FA): m/z=947.3 (M+H).

Step 4: 3-[(2S,5R,7R,8S,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one, Intermediate 142a Intermediate 141a (110 mg, 0.12 mmol) was dissolved in methylamine (33% in EtOH, 1.31 mL, 10.5 mmol) under an atmosphere of nitrogen and the reaction mixture was allowed to stir at rt for 3 h. The reaction mixture was concentrated and dried on vacuum for 10 min. The crude compound was purified by reverse phase flash column chromatography (10-100% ACN in aq. ammonium bicarbonate (5 mM)) to provide Intermediate 142a (42 mg, 40%). LCMS (AA): m/z=894.2 (M+H).

Step 5: 3-[(2S,5R,7R,8S,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyl-decahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyl-decahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyl-decahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one
Intermediate 142b Intermediate 142a was treated in the same manner as Intermediate 141a. Purification by reverse phase flash column chromatography (10-100% ACN in aq. ammonium bicarbonate (5 mM)) to provided Intermediate 142b as the second eluting peak. LCMS (AA): m/z=894.2 (M+H).

Step 6: 3-[(2S,5R,7R,8S,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyl-decahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyl-decahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-[(3-hydroxy-1,1,3,3-tetraisopropyldisiloxanyl)oxy]-2,10-dioxido-14-(pyrimidin-4-yloxy)-2,10-disulfanyl-decahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one
Intermediate 142c Intermediate 141c was treated in the same manner as Intermediate 141a. Purification by reverse phase flash column chromatography (10-100% ACN in aq. ammonium bicarbonate (5 mM)) to provided Intermediate 142c as the second eluting peak. LCMS (AA): m/z=894.2 (M+H).

Step 7: 3-[(2S,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2S,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10S,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 3-[(2R,5R,7R,8S,10R,12aR,14R,15aS,16R)-16-hydroxy-2,10-dioxido-14-(pyrimidin-4-yloxy)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one I-37a, I-37b and I-37c The compounds listed below were prepared as described in Example 43 starting with Step 5, substituting the starting material shown in the table for Intermediate 138a.

| Compound | Salt form | Starting material | LCMS data | NMR data |
| --- | --- | --- | --- | --- |
| I-37a | Et$_3$N | Intermediate 142a | LCMS (AA): m/z = 634.1 (M + H). | $^1$H NMR (MeOD) δ 8.70 (s, 1H), 8.39 (d, J = 5.9 Hz, 1H), 8.13 (s, 1H), 6.87 (dd, J = 0.9, 6.0 Hz, 1H), 5.63-5.57 (m, 1H), 5.49 (q, J = 9.6 Hz, 1H), 5.42-5.34 (m, 1H), 4.92-4.88 (m, 1H), 4.62 (br d, J = 3.0 Hz, 1H), 4.41-4.30 (m, 1H), 4.08-3.96 (m, 2H), 3.79-3.72 (m, 1H), 3.19 (q, J = 7.3 Hz, 12H), 2.79-2.71 (m, 1H), 2.66-2.49 (m, 3H), 2.48-2.35 (m, 2H), 2.26 (ddd, J = 4.0, 8.8, 13.3 Hz, 1H), 1.50-1.42 (m, 1H), 1.31 (t, J = 7.3 Hz, 18H); $^{31}$P NMR (MeOD) δ 59.83 (s, 1P), 54.96 (s, 1P). |
| I-37b | Et$_3$N | Intermediate 142b | LCMS (AA): m/z = 634.1 (M + H). | $^1$H NMR (D$_2$O) δ 8.68 (s, 1H), 8.45 (d, J = 6.0 Hz, 1H), 8.30 (s, 1H), 6.95 (d, J = 6.0 Hz, 1H), 5.52-5.41 (m, 2H), 5.13-5.04 (m, 1H), 5.01-4.94 (m, 1H), 4.38 (d, J = 4.2 Hz, 1H), 4.29-4.21 (m, 1H), 4.02-3.90 (m, 2H), 3.83-3.77 (m, 1H), 3.19 (q, J = 7.3 Hz, 13H), 2.72-2.41 (m, 7H), 1.63-1.53 (m, 1H), 1.27 (t, J = 7.3 Hz, 20H); $^{31}$P NMR (MeOD) δ 60.45 (s, 1P), 54.70 (s, 1P). |
| I-37c | Et$_3$N | Intermediate 142c | LCMS (AA): m/z = 634.1 (M + H). | $^1$H NMR (D$_2$O) δ 8.69 (s, 1H), 8.47 (d, J = 6.1 Hz, 1H), 8.30 (s, 1H), 6.98 (dd, J = 0.9, 6.0 Hz, 1H), 5.52-5.40 (m, 2H), 5.26 (dt, J = 4.0, 10.0 Hz, 1H), 5.10-5.01 (m, 1H), 4.54 (d, J = 4.0 Hz, 1H), 4.28 (ddd, J = 2.8, 7.4, 10.2 Hz, 1H), 4.03-3.92 (m, 2H), 3.82-3.72 (m, 1H), 3.19 (q, J = 7.4 Hz, 12H), 2.76-2.66 (m, 1H), 2.56-2.39 (m, 6H), 1.65-1.54 (m, 1H), 1.27 (t, J = 7.3 Hz, 18H); $^{31}$P NMR (D$_2$O) δ 53.45 (s, 1P), 52.04 (s, 1P). |

Example 45

2-amino-9-[(2S,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15R,15aR,16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15R,15aR,16R)-15-fluoro-16-hydroxy-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, I-35a, I-35b, I-35c and I-35d

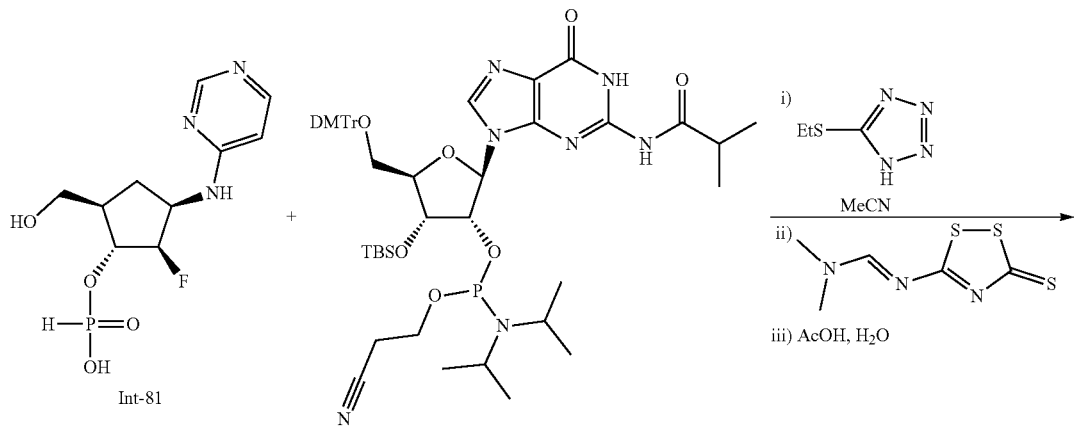

-continued
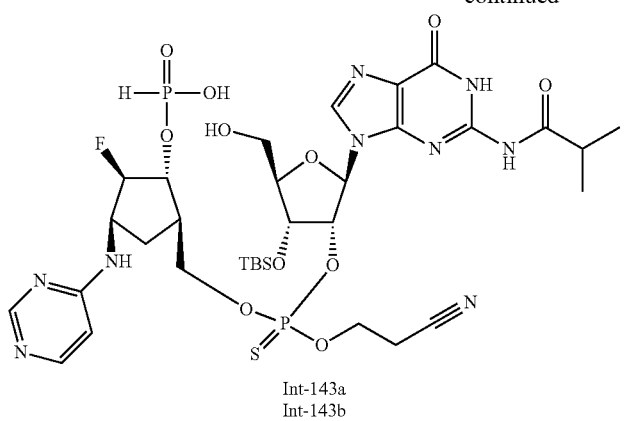 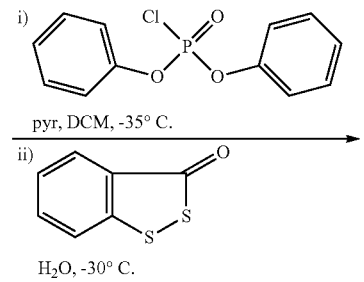
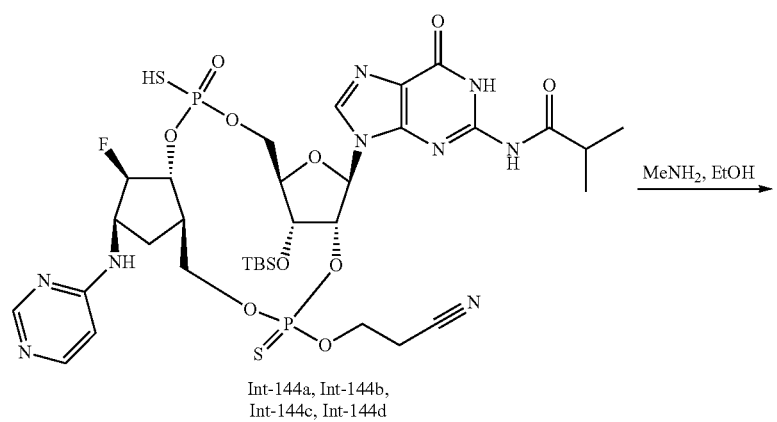
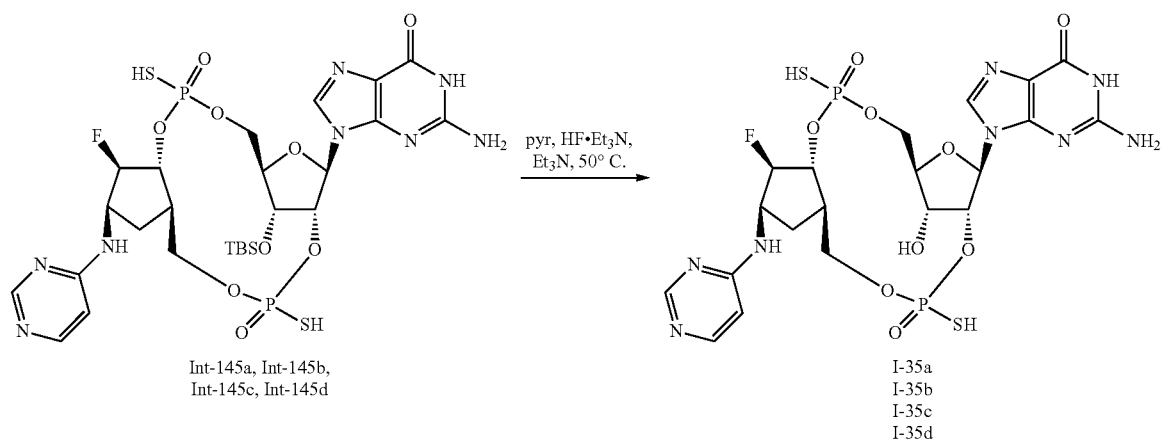

Step 1: (1R,2R,3R,5R)-5-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-2-fluoro-3-(pyrimidin-4-ylamino)cyclopentyl hydrogen phosphonate and (1R,2R,3R,5R)-5-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-2-fluoro-3-(pyrimidin-4-ylamino)cyclopentyl hydrogen phosphonate, Intermediate 143a and 143b (1R,2R,3R,5R)-2-Fluoro-5-(hydroxymethyl)-3-(pyrimidin-4-ylamino)cyclopentyl hydrogen phosphonate (Intermediate 81) (447 mg, 1.53 mmol) and N-[9-[(2R,3R,4R,5R)-5-[[bis(4-methoxyphenyl)-phenyl-methoxy]methyl]-4-[tert-butyl(dimethyl) silyl]oxy-3-[2-cyanoethoxy-(diisopropylamino)phosphanyl]oxy-tetrahydrofuran-2-yl]-6-oxo-1H-purin-2-yl]-2-methyl-propanamide (1.79 g, 1.84 mmol) were combined and dissolved in dry acetonitrile and concentrated to dryness (3×20 mL). The residue was then dissolved in ACN (6.11 mL) under an atmosphere of argon. In a separate flask 5-(ethylthio)-1H-tetrazole (652 mg, 5.01 mmol) was dissolved in dry acetonitrile and concentrated to dryness (3×10 mL) then dissolved in ACN (2.78 mL) and added to the reaction mixture under an atmosphere of argon. The reaction mixture was allowed to stir at rt for 40 min. ((Dimethylamino-methylidene)amino)-3H-1,2,4-dithiazoline-3-thione (410 mg, 2.00 mmol) was added and stirring was continued at rt for 45 min. The reaction mixture was concentrated and dried on vacuum for 10 min. The residue was dissolved in acetic acid (6.62 mL, 115 mmol) and water (1.65 mL), and allowed to stir at rt for 30 min. Toluene (15 mL) was added and the reaction mixture was concentrated. The residue was concentrated from toluene (2×15 mL) and then dried on vacuum for 10 min. The crude compound was purified by silica gel chromatography 3 times (25-45% MeOH in DCM, 0-40% MeOH in DCM and 25-40% MeOH in DCM) to provide Intermediate 143a (310 mg, 39%) in the first eluting peak and Intermediate 143b (350 mg, 44%) in the second eluting peak. LCMS (AA): m/z=890.3 (M+H).

Step 2: N-{9-[(2S,5R,7R,8R,10R,12aR,14R,15R,15aR,16R)-16-{[tert-butyl(dimethyl)silyl]oxy}-10-(2-cyanoethoxy)-15-fluoro-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2S,5R,7R,8R,10S,12aR,14R,15R,15aR,16R)-16-{[tert-butyl(dimethyl)silyl]oxy}-10-(2-cyanoethoxy)-15-fluoro-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10R,12aR,14R,15R,15aR,16R)-16-{[tert-butyl(dimethyl)silyl]oxy}-10-(2-cyanoethoxy)-15-fluoro-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10S,12aR,14R,15R,15aR,16R)-16-{[tert-butyl(dimethyl)silyl]oxy}-10-(2-cyanoethoxy)-15-fluoro-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediates 144a, 144b, 144c and 144d Diphenyl chlorophosphate 0.70 mL, 3.37 mmol) was added to pyridine (12.0 mL) at −30° C. A solution of Intermediate 143a (150 mg, 0.17 mmol) in DCM (8.00 mL) and pyridine (2.00 mL) was added to the reaction mixture. The reaction mixture was allowed to stir at −35° C. for 40 min. 3H-1,2-Benzodithiol-3-one (56.7 mg, 0.34 mmol) and water (0.12 mL) were added at −30° C. The reaction mixture was allowed to stir at rt for 1 h. Sodium thiosulfate (675 mg, 0.41 mmol) in water was added at 0° C. and the reaction mixture was allowed to stir at rt for 5 min. The volatile solvents were removed by evaporation and the residue was purified twice by silica gel chromatography (0-90% MeOH in DCM and 0-25% MeOH in DCM), followed by reverse phase flash column chromatography (10-65% ACN in aqueous triethylammonium acetate (10 mM)) to provide Intermediate 144a (50 mg, 33%) as an impure mixture in the first eluting peak, and Intermediate 144b (103 mg, 68%) as the second eluting peak. LCMS (AA): m/z=904.2 (M+H).

Intermediate 143b (343 mg, 0.39 mmol) from Step 1 was treated in an analogous fashion to the above procedure to provide Intermediate 144c (180 mg, 52%) as the first eluting peak and Intermediate 144d (10 mg, 2.9%) as the second eluting peak.

Step 3: 2-amino-9-[(2S,5R,7R,8R,10R,12aR,14R,15R,15aR,16R)-16-{[tert-butyl(dimethyl)silyl]oxy}-15-fluoro-10-hydroxy-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10S,12aR,14R,15R,15aR,16R)-16-{[tert-butyl(dimethyl)silyl]oxy}-15-fluoro-10-hydroxy-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15R,15aR,16R)-16-{[tert-butyl(dimethyl)silyl]oxy}-15-fluoro-10-hydroxy-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15R,15aR,16R)-16-{[tert-butyl(dimethyl)silyl]oxy}-15-fluoro-10-hydroxy-2-oxido-14-(pyrimidin-4-ylamino)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one, Intermediate 145a Intermediate 144a (100 mg, 0.11 mmol) was dissolved in methylamine (33% in EtOH, 3.32 mL, 26.7 mmol) under an atmosphere of nitrogen and the reaction mixture was allowed to stir at rt for 1 h. The reaction mixture was concentrated and dried on vacuum for 10 min. The crude compound was purified by reverse phase flash column chromatography (10-45% ACN in aqueous triethylammonium acetate (10 mM)) to provide Intermediate 145a (48 mg, 67%). LCMS (AA): m/z=781.2 (M+H).

Step 4: 2-amino-9-[(2S,5R,7R,8R,10S,12aR,14R, 15R,15aR,16R)-15-fluoro-16-hydroxy-2,10-dioxido-14-(pyrimidin-4-ylamino)-2,10-disulfanyldecahydro-5,8-methanocyclopenta[l][1,3,6,9,11,2,10] pentaoxadiphosphacyclotetradecin-7-yl]-1,9-dihydro-6H-purin-6-one or 2-amino-9-[(2S,5R,7R,8R,10R,12aR,14R,15R,15aR, 16R)-15-fluoro-16-hydroxy-2,10-dioxido-14-(pyrimidin-4-ylamino)-2,10-disulfanyldecahydro-5,8-methanocyclopenta [l][1,3,6,9,11,2,10] pentaoxadiphosphacyclotetradecin-7-yl]-1,9-dihydro-6H-purin-6-one or 2-amino-9-[(2R,5R,7R,8R,10S,12aR,14R,15R,15aR, 16R)-15-fluoro-16-hydroxy-2,10-dioxido-14-(pyrimidin-4-ylamino)-2,10-disulfanyldecahydro-5,8-methanocyclopenta [l][1,3,6,9,11,2,10] pentaoxadiphosphacyclotetradecin-7-yl]-1,9-dihydro-6H-purin-6-one or 2-amino-9-[(2R,5R,7R,8R,10R,12aR,14R,15R,15aR, 16R)-15-fluoro-16-hydroxy-2,10-dioxido-14-(pyrimidin-4-ylamino)-2,10-disulfanyldecahydro-5,8-methanocyclopenta [l][1,3,6,9,11,2,10] pentaoxadiphosphacyclotetradecin-7-yl]-1,9-dihydro-6H-purin-6-one, I-35a In a polypropylene tube, Intermediate 145a (58 mg, 0.07 mmol) was suspended in pyridine (0.45 mL). Triethylamine trihydrofluoride (45.0 µL, 0.27 mmol) was added, followed by TEA (0.67 mL). The reaction mixture was allowed to stir at 50° C. overnight. The reaction mixture was cooled to rt and water (1.30 mL) was added followed by dropwise addition of a solution of calcium chloride (238 mg, 2.06 mmol) in water (1.00 mL). The reaction mixture was allowed to stir at rt for 30 min, then filtered through Celite and the Celite was rinsed with water (5×5 mL). The filtrate was concentrated to give a white solid. No HF was observed by $^{19}$F NMR. The crude mixture was purified by reverse phase flash column chromatography (0-10% ACN in aqueous triethylammonium acetate (10 mM)) to provide I-35a (6.48 mg, 10%) as the N,N-diethylethanamine salt. LCMS (AA): m/z=667.2 (M+H); $^{1}$H NMR (D$_2$O) δ 8.61 (s, 1H), 8.40 (s, 1H), 8.06-7.97 (m, 1H), 6.85-6.73 (m, 1H), 6.05 (d, J=8.4 Hz, 1H), 5.42-5.25 (m, 2H), 4.87-4.79 (m, 1H), 4.71 (d, J=4.0 Hz, 2H), 4.46-4.42 (m, 1H), 4.27-4.06 (m, 3H), 3.85 (q, J=9.3 Hz, 1H), 3.17 (q, J=7.3 Hz, 12H), 2.65-2.53 (m, 1H), 2.44-2.33 (m, 1H), 1.61-1.55 (m, 1H) 1.24 (t, J=7.3 Hz, 18H); $^{31}$P NMR (D$_2$O) δ 54.63 (s, 1P), 52.99 (s, 1P).

Example 45A

The compounds listed below were prepared as described in Example 45 starting with Step 3, substituting the starting material shown in the table for Intermediate 144a.

| Compound | Salt form | Starting material | LCMS data | NMR data |
| --- | --- | --- | --- | --- |
| I-35b | Et$_3$N | Intermediate 144b | LCMS (AA): m/z = 667.1 (M + H). | $^{1}$H NMR (D$_2$O) δ 8.48 (s, 1H), 8.07-8.01 (m, 2H), 6.68-6.63 (m, 1H), 6.02 (d, J = 8.4 Hz, 1H), 5.49-5.41 (m, 1H), 5.25 (d, J = 51.6 Hz, 1H), 4.89-4.81 (m, 1H), 4.80-4.55 (m, 2H), 4.47-4.43 (m, 1H), 4.42-4.34 (m, 1H), 4.13-4.02 (m, 2H), 3.88-3.79 (m, 1H), 3.17 (q, J = 7.3 Hz, 12H), 2.55-2.42 (m, 1H), 2.42-2.30 (m, 1H), 1.59-1.47 (m, 1H), 1.25 (t, J = 7.3 Hz, 18H); $^{31}$P NMR (D$_2$O) δ 54.26 (s, 1P), 53.06 (s, 1P). |
| I-35c | Et$_3$N | Intermediate 144c | LCMS (AA): m/z = 667.1 (M + H). | $^{1}$H NMR (D$_2$O) δ 8.45 (s, 1H), 8.13 (s, 1H), 8.03 (d, J = 6.3 Hz, 1H), 6.66 (d, J = 6.3 Hz, 1H), 6.02 (d, J = 8.4 Hz, 1H), 5.45 (ddd, J = 4.3, 8.5, 12.7 Hz, 1H), 5.23 (d, J = 50.4 Hz, 1H), 5.00-4.89 (m, 1H), 4.80-4.65 (m, 1H), 4.54 (d, J = 4.3 Hz, 1H), 4.44 (br d, J = 2.1 Hz, 1H), 4.40-4.32 (m, 1H), 4.13-4.06 (m, 1H), 4.05-3.96 (m, 1H), 3.95-3.88 (m, 1H), 3.16 (q, J = 7.3 Hz, 12H), 2.53-2.36 (m, 2H), 1.48-1.38 (m, 1H), 1.24 (t, J = 7.3 Hz, 18H); $^{31}$P NMR (D$_2$O) δ = 58.99 (s, 1P), 54.31 (s, 1P). |
| I-35d | Et$_3$N | Intermediate 144d | LCMS (AA): m/z = 667.1 (M + H). | $^{1}$H NMR (D$_2$O) δ = 8.47-8.45 (m, 1H), 8.10-8.05 (m, 2H), 6.65-6.60 (m, 1H), 6.02 (d, J = 8.6 Hz, 1H), 5.50-5.40 (m, 1H), 5.24 (d, J = 53.3 Hz, 1H), 4.91-4.64 (m, 3H), 4.48-4.43 (m, 1H), 4.42-4.34 (m, 1H), 4.13-4.00 (m, 2H), 3.87-3.79 (m, 1H), 3.17 (q, J = 7.3 Hz, 24H), 2.54-2.43 (m, 1H), 2.41-2.31 (m, 1H), 1.68-1.46 (m, 1H), 1.25 (t, J = 7.3 Hz, 36H); $^{31}$P NMR (D$_2$O) δ 54.30 (s, 1P), 53.09 (s, 1P) |

Example 46

5-amino-3-[(2S,5S,7R,8R,10S,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 5-amino-3-[(2S,5S,7R,8R,10R,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 5-amino-3-[(2R,5S,7R,8R,10S,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one or 5-amino-3-[(2R,5S,7R,8R,10R,12aR,14R,15S,15aR)-15-fluoro-2,10-dioxido-14-(pyrimidin-4-ylamino)-2,10-disulfanyldecahydro-4H-5,8-methanocyclopenta[d][1,3,7,9,2,8]tetraoxadiphosphacyclotetradecin-7-yl]-3,6-dihydro-7H-[1,2,3]triazolo[4,5-d]pyrimidin-7-one, I-25a and I-25b

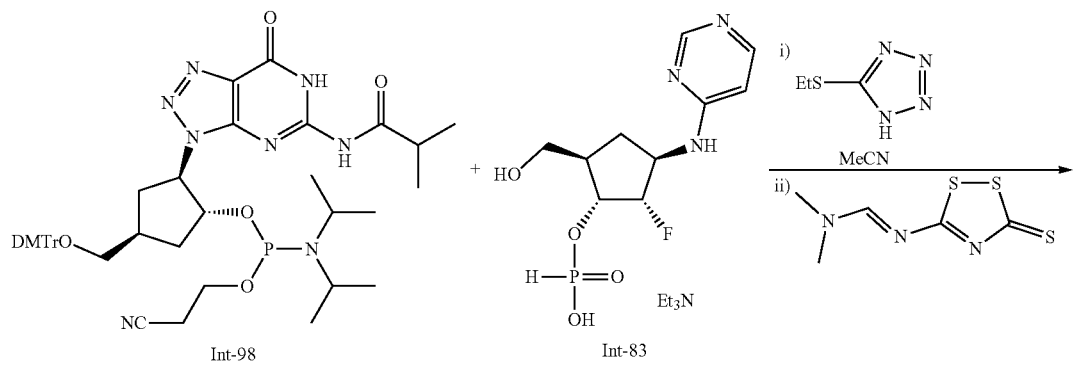

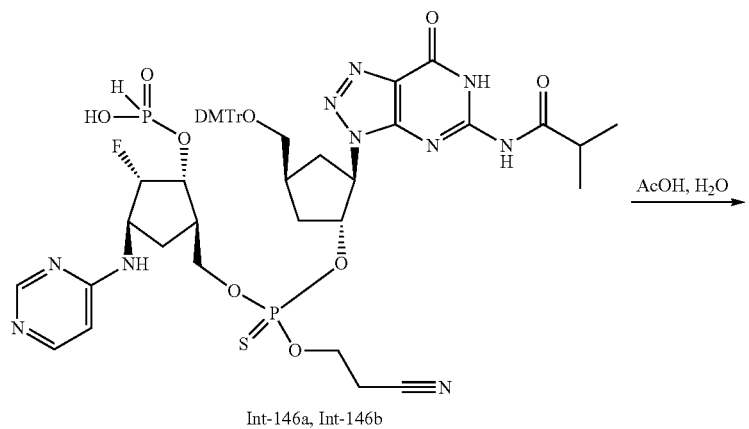

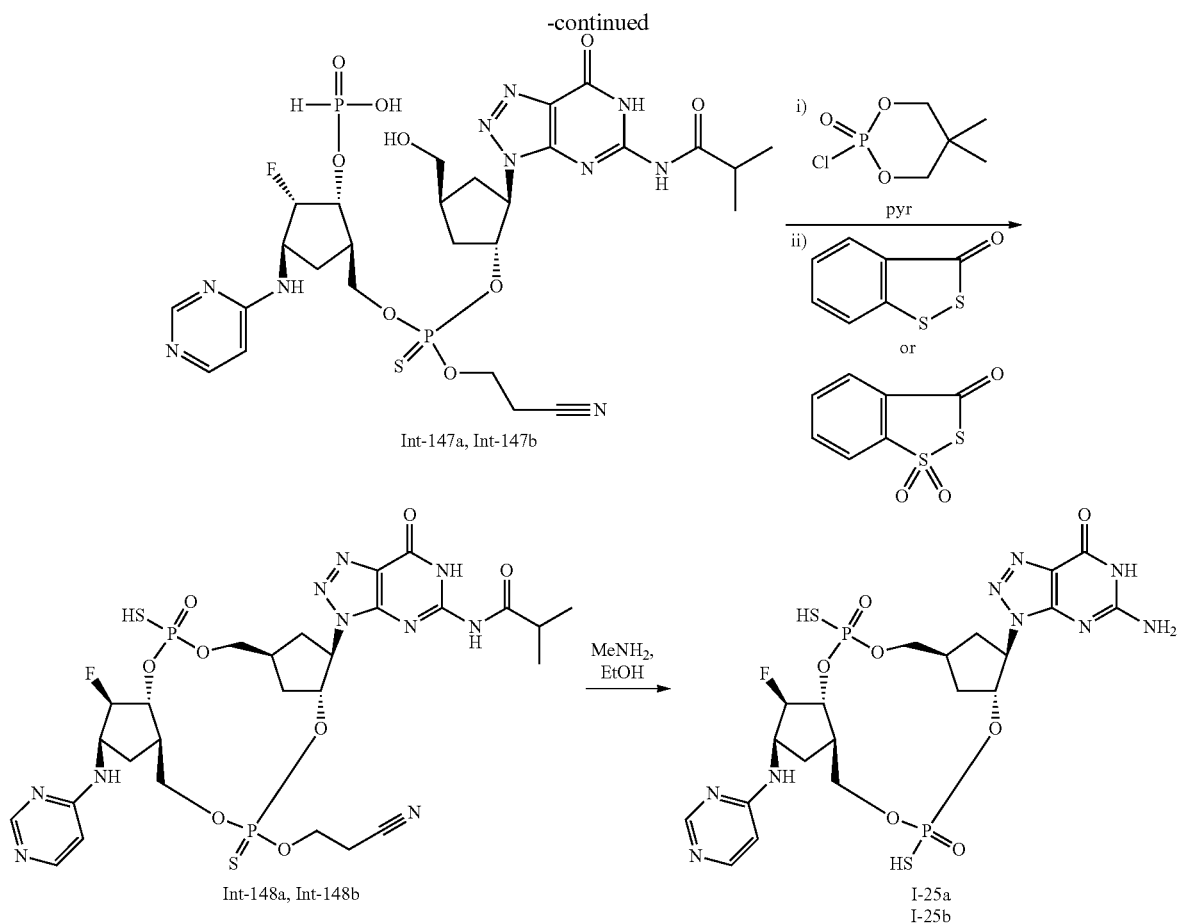

Step 1: (1R,2S,3R,5R)-5-({[(S)-({(1R,2R,4S)-4-{[bis(4-methoxyphenyl)(phenyl) methoxy]methyl}-2-[5-(isobutyrylamino)-7-oxo-6,7-dihydro-3H-[1,2,3]triazolo[4,5-d]pyrimidin-3-yl]cyclopentyl}oxy)(2-cyanoethoxy)phosphorothioyl]oxy}methyl)-2-fluoro-3-(pyrimidin-4-ylamino)cyclopentyl hydrogen phosphonate and (1R,2S,3R,5R)-5-({[(R)-({(1R,2R,4S)-4-{[bis(4-methoxyphenyl)(phenyl)methoxy]methyl}-2-[5-(isobutyrylamino)-7-oxo-6,7-dihydro-3H-[1,2,3]triazolo[4,5-d]pyrimidin-3-yl]cyclopentyl}oxy)(2-cyanoethoxy)phosphorothioyl]oxy}methyl)-2-fluoro-3-(pyrimidin-4-ylamino)cyclopentyl hydrogen phosphonate, Intermediate 146a and 146b

[(1R,2S,3R,5R)-2-Fluoro-5-(hydroxymethyl)-3-(pyrimidin-4-ylamino)cyclopentoxy]phosphinic acid, N,N-diethylethanamine salt (Intermediate 83) (420 mg, 1.07 mmol) and Intermediate 98 (1.20 g, 1.40 mmol) were combined, dissolved in dry acetonitrile and concentrated to dryness (3×20 mL). The residue was then dissolved in ACN (3.70 mL) under an atmosphere of argon. In a separate flask 5-(ethylthio)-1H-tetrazole (348 mg, 2.68 mmol) was dissolved in dry acetonitrile and concentrated to dryness (3×10 mL) then dissolved in ACN (1.80 mL) and added to the reaction mixture under an atmosphere of nitrogen. The reaction mixture was allowed to stir at rt for 1 h. ((Dimethylamino-methylidene)amino)-3H-1,2,4-dithiazoline-3-thione (264 mg, 1.28 mmol) was added and stirring was continued at rt for 45 min. The reaction mixture was evaporated. The crude compound was purified by reverse phase flash column chromatography (0-100% ACN in aqueous ammonium acetate (10 mM)) to Intermediate 146a as the first eluting peak (260 mg, 23%) and Intermediate 146b as the second eluting peak (250 mg, 22%). LCMS (AA): m/z=1061.1 (M−H).

Step 2: (1R,2S,3R,5R)-5-({[(R)-(2-cyanoethoxy)({(1R,2R,4S)-4-(hydroxymethyl)-2-[5-(isobutyrylamino)-7-oxo-6,7-dihydro-3H-[1,2,3]triazolo[4,5-d]pyrimidin-3-yl]cyclopentyl}oxy)phosphorothioyl]oxy}methyl)-2-fluoro-3-(pyrimidin-4-ylamino) cyclopentyl hydrogen phosphonate or (1R,2S,3R,5R)-5-({[(S)-(2-cyanoethoxy)({(1R,2R,4S)-4-(hydroxymethyl)-2-[5-(isobutyrylamino)-7-oxo-6,7-dihydro-3H-[1,2,3]triazolo[4,5-d]pyrimidin-3-yl]cyclopentyl}oxy)phosphorothioyl]oxy}methyl)-2-fluoro-3-(pyrimidin-4-ylamino)cyclopentyl hydrogen phosphonate (Intermediate 147a and 147b)

Intermediate 146a (260 mg, 0.25 mmol) was dissolved in acetic acid (4.46 mL) and water (1.12 mL) and allowed to stir at rt for 1 h. The solvents were evaporated and the residue was concentrated from toluene (3×). The crude compound was purified by reverse phase flash column chromatography (0-45% ACN in aqueous ammonium acetate (10 mM)) to provide Intermediate 147a (140 mg, 75%) LCMS (AA): m/z=759.0 (M+H).

Intermediate 146b was treated in the same manner as above to provide Intermediate 147b LCMS (AA): m/z=759.0 (M+H).

Step 3: N-{3-[(2S,5S,7R,8R,10R,12aR,14R,15S, 15aR)-10-(2-cyanoethoxy)-15-fluoro-2-oxido-14-(pyrimidin-4-ylamino)-2-sulfanyl-10-sulfidodecahydro-4H-5,8-methanocyclopenta[d][1,3,7,9,2,8]tetraoxadiphosphacyclotetradecin-7-yl]-7-oxo-6,7-dihydro-3H-[1,2,3]triazolo[4,5-d]pyrimidin-5-yl}-2-methylpropanamide or N-{3-[(2S,5S,7R,8R,10S,12aR,14R,15S,15aR)-10-(2-cyanoethoxy)-15-fluoro-2-oxido-14-(pyrimidin-4-ylamino)-2-sulfanyl-10-sulfidodecahydro-4H-5,8-methanocyclopenta[d][1,3,7,9,2,8]tetraoxadiphosphacyclotetradecin-7-yl]-7-oxo-6,7-dihydro-3H-[1,2,3]triazolo[4,5-d]pyrimidin-5-yl}-2-methylpropanamide or N-{3-[(2R,5S,7R,8R,10R,12aR,14R,15S,15aR)-10-(2-cyanoethoxy)-15-fluoro-2-oxido-14-(pyrimidin-4-ylamino)-2-sulfanyl-10-sulfidodecahydro-4H-5,8-methanocyclopenta[d][1,3,7,9,2,8]tetraoxadiphosphacyclotetradecin-7-yl]-7-oxo-6,7-dihydro-3H-[1,2,3]triazolo[4,5-d]pyrimidin-5-yl}-2-methylpropanamide or N-{3-[(2R,5S,7R,8R,10S,12aR,14R,15S,15aR)-10-(2-cyanoethoxy)-15-fluoro-2-oxido-14-(pyrimidin-4-ylamino)-2-sulfanyl-10-sulfidodecahydro-4H-5,8-methanocyclopenta[d][1,3,7,9,2,8]tetraoxadiphosphacyclotetradecin-7-yl]-7-oxo-6,7-dihydro-3H-[1,2,3]triazolo[4,5-d]pyrimidin-5-yl}-2-methylpropanamide (Intermediate 148a and 148b)

Intermediate 147a (140 mg, 0.19 mmol) was dissolved in dry acetonitrile and concentrated to dryness (3×~5 mL), dried under vacuum for 10 min, and then dissolved in pyridine (2.66 mL) under a nitrogen atmosphere. 2-Chloro-5,5-dimethyl-1,3,2-dioxaphosphorinane 2-oxide (124 mg, 0.65 mmol) was added. The reaction mixture was allowed to stir at rt for 1 h. Water was added 0.12 mL,) followed by 3H-1,2-benzodithiol-3-one (47.0 mg, 0.28 mmol), and the reaction mixture was allowed to stir at rt under nitrogen for 2.5 h. Toluene was added and the mixture was concentrated, then concentrated from toluene (3×25 mL). The crude compound was purified by reverse phase flash column chromatography (0-50% ACN in aqueous ammonium acetate (10 mM)) to provide Intermediate 148a (40 mg, 28%). LCMS (AA): m/z=773.0 (M+H).

Intermediate 147b (100 mg, 0.13 mmol) was dissolved in dry acetonitrile and concentrated to dryness (3×~2 mL), dried under vacuum for 10 min, and then dissolved in pyridine (1.90 mL) under a nitrogen atmosphere. 2-Chloro-5,5-dimethyl-1,3,2-dioxaphosphorinane 2-oxide (88.7 mg, 0.46 mmol) was added. The reaction mixture was allowed to stir at rt for 1 h. Water was added (83.0 μL, 4.61 mmol) followed by 3H-1,2-benzodithiol-3-one 1,1-dioxide (40.0 mg, 0.20 mmol), and the reaction mixture was allowed to stir at rt under nitrogen for 2.5 h. Toluene was added and the mixture was concentrated, then concentrated from toluene (3×25 mL). The crude compound was purified by reverse phase flash column chromatography (0-50% ACN in aqueous ammonium acetate (10 mM)) to provide Intermediate 148b (90 mg, 88%). LCMS (AA): m/z=773.0 (M+H).

Step 4: 5-amino-3-[(2S,5S,7R,8R,10S,12aR,14R, 15S,15aR)-15-fluoro-2,10-dioxido-14-(pyrimidin-4-ylamino)-2,10-disulfanyldecahydro-4H-5,8-methanocyclopenta [d][1,3,7,9,2,8]tetraoxadiphosphacyclotetradecin-7-yl]-3,6-dihydro-7H-[1,2,3]triazolo[4,5-d]pyrimidin-7-one or 5-amino-3-[(2S,5S,7R,8R,10R,12aR,14R,15S, 15aR)-15-fluoro-2,10-dioxido-14-(pyrimidin-4-ylamino)-2,10-disulfanyldecahydro-4H-5,8-methanocyclopenta [d][1,3,7,9,2,8]tetraoxadiphosphacyclotetradecin-7-yl]-3,6-dihydro-7H-[1,2,3]triazolo[4,5-d]pyrimidin-7-one or 5-amino-3-[(2R,5S,7R,8R,10S,12aR,14R,15S, 15aR)-15-fluoro-2,10-dioxido-14-(pyrimidin-4-ylamino)-2,10-disulfanyldecahydro-4H-5,8-methanocyclopenta [d][1,3,7,9,2,8]tetraoxadiphosphacyclotetradecin-7-yl]-3,6-dihydro-7H-[1,2,3]triazolo[4,5-d]pyrimidin-7-one or 5-amino-3-[(2R,5S,7R,8R,10R,12aR,14R,15S, 15aR)-15-fluoro-2,10-dioxido-14-(pyrimidin-4-ylamino)-2,10-disulfanyldecahydro-4H-5,8-methanocyclopenta [d][1,3,7,9,2,8]tetraoxadiphosphacyclotetradecin-7-yl]-3,6-dihydro-7H-[1,2,3]triazolo[4,5-d]pyrimidin-7-one, I-25a and I-25b Intermediate 148a (30 mg, 39.0 μmol) was dissolved in methylamine (33% in EtOH, 1.16 mL, 9.32 mmol) and the reaction mixture was allowed to stir at rt for 90 min. The reaction mixture was concentrated and 10 mM triethylammonium acetate with 1% ACN (50 mL) was added and evaporated (2×). The crude compound was purified by reverse phase flash column chromatography (0-12% ACN in aqueous triethylammonium acetate (10 mM)) to provide I-25a as an N,N-diethylethanamine salt (12 mg, 35%). LCMS (AA): m/z=650.0 (M+H); $^1$H NMR (D$_2$O) δ 8.37 (s, 1H), 7.92 (br d, J=5.7 Hz, 1H), 6.44 (br d, J=6.6 Hz, 1H), 5.29-5.19 (m, 1H), 5.04 (dd, J=3.9, 49.5 Hz, 1H), 4.95-4.88 (m, 1H), 4.81-4.69 (m, 2H), 4.34-4.22 (m, 1H), 4.14 (ddd, J=3.4, 7.4, 10.3 Hz, 1H), 3.92 (br s, 2H), 3.80 (dt, J=4.6, 9.7 Hz, 1H), 3.05 (q, J=7.3 Hz, 10H), 2.45-2.34 (m, 3H), 2.21-1.98 (m, 3H), 1.56-1.45 (m, 1H), 1.13 (t, J=7.3 Hz, 15H); $^{31}$P NMR (D$_2$O) δ 54.62 (s, 1P), 51.97 (s, 1P).

Intermediate 148b was treated in an analogous fashion to the above procedure to provide I-25b as the N,N-diethylethanamine salt. LCMS (AA): m/z=650.0 (M+H); $^1$H NMR (D$_2$O) δ 8.44 (s, 1H), 7.92 (br d, J=7.3 Hz, 1H), 6.58 (d, J=6.1 Hz, 1H), 5.44 (td, J=8.3, 16.4 Hz, 1H), 5.21-4.85 (m, 4H), 4.40-4.31 (m, 1H), 4.15-4.01 (m, 3H), 3.99-3.90 (m, 2H), 3.13 (q, J=7.3 Hz, 12H), 2.68-2.56 (m, 1H), 2.50-2.39 (m, 1H), 2.32-2.08 (m, 3H), 1.60-1.51 (m, 1H), 1.20 (t, J=7.3 Hz, 18H); $^{31}$P NMR (D$_2$O) δ 54.56 (s, 1P), 53.85 (s, 1P).

Example 47

[(1R,2R,3R,5R)-2-fluoro-5-(hydroxymethyl)-3-(pyrimidin-4-ylamino)cyclopentoxy]phosphinic acid, Intermediate 81

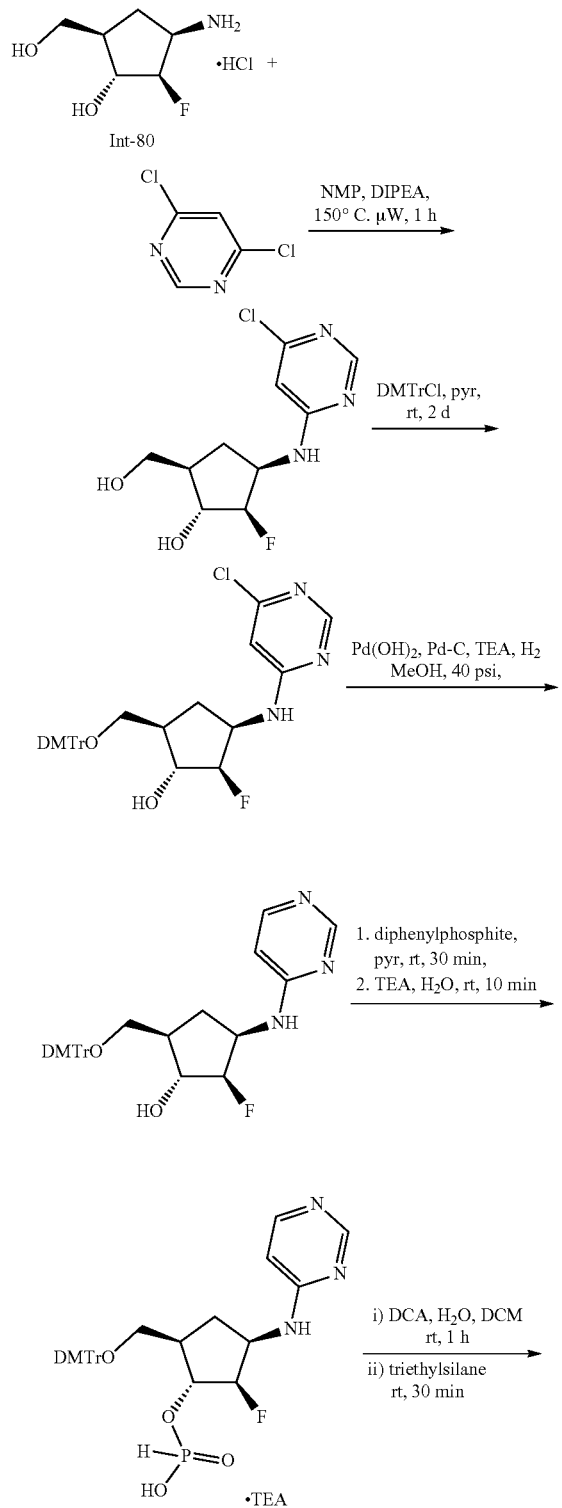

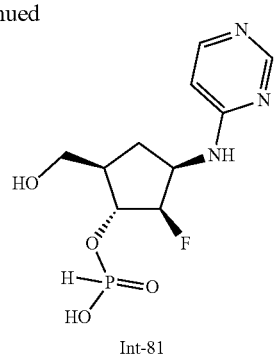

Int-81

Step 1: (1R,2R,3R,5R)-3-((6-chloropyrimidin-4-yl)amino)-2-fluoro-5-(hydroxymethyl)cyclopentan-1-ol 4,6-Dichloropyrimidine (1.13 g, 7.56 mmol) was dissolved in NMP (7.77 mL) and DIPEA (3.30 mL, 18.9 mmol). (1R,2R,3R,5R)-3-Amino-2-fluoro-5-(hydroxymethyl)cyclopentan-1-ol hydrochloride (Intermediate 80, 1.17 g, 6.30 mmol) was added. The reaction mixture was heated at 150° C. under microwave irradiation for 1 h. The reaction mixture was diluted with EtOAc and concentrated to provide (1R,2R,3R,5R)-3-((6-chloropyrimidin-4-yl)amino)-2-fluoro-5-(hydroxymethyl)cyclopentan-1-ol which was used without further purification.

Step 2: (1R,2R,3R,5R)-5-((bis(4-methoxyphenyl)(phenyl)methoxy)methyl)-3-((6-chloropyrimidin-4-yl)amino)-2-fluorocyclopentan-1-ol (1R,2R,3R,5R)-3-((6-Chloropyrimidin-4-yl)amino)-2-fluoro-5-(hydroxymethyl)cyclopentan-1-ol (1.60 g, 6.11 mmol) was concentrated from dry toluene (3×~15 mL). Pyridine (16 mL) was added and DMTr-Cl (2.97 g, 8.78 mmol) was added portion-wise and the reaction mixture was allowed to stir at rt for 2 days. The solvent was evaporated and the residue was partitioned between sat. NaHCO₃ and EtOAc. The organic phase was separated, washed with brine, dried (Na₂SO₄) and evaporated. The crude compound was purified by silica gel chromatography (0-5% MeOH in DCM) to provide (1R,2R,3R,5R)-3-((6-chloropyrimidin-4-yl)amino)-2-fluoro-5-(hydroxymethyl)cyclopentan-1-ol (3.72 g, 92%) as a yellow oil. LCMS (FA): m/z=564.2 (M+H).

Step 3: (1R,2R,3R,5R)-5-((bis(4-methoxyphenyl)(phenyl)methoxy)methyl)-2-fluoro-3-(pyrimidin-4-ylamino)cyclopentan-1-ol (1R,2R,3R,5R)-3-((6-Chloropyrimidin-4-yl)amino)-2-fluoro-5-(hydroxymethyl)cyclopentan-1-ol (3.70 g, 6.56 mmol) was dissolved in methanol (50 mL). Palladium hydroxide (20% on carbon, 138 mg, 0.20 mmol) was added, followed by TEA (2.74 mL, 19.7 mmol). The mixture stirred under 40 psi of hydrogen for 2 h. Palladium (10% on carbon, 500 mg) was added and the mixture was stirred under 40 psi of hydrogen for another hour. The reaction mixture was filtered and the filtrate was evaporated to provide crude (1R,2R,3R,5R)-5-((bis(4-methoxyphenyl)(phenyl)methoxy)methyl)-2-fluoro-3-(pyrimidin-4-ylamino)cyclopentan-1-ol which was used without further purification. LCMS (FA): m/z=530.2 (M+H).

Step 4: [(1R,2R,3R,5R)-5-[[bis(4-methoxyphenyl)-phenyl-methoxy]methyl]-2-fluoro-3-(pyrimidin-4-ylamino)cyclopentoxy]phosphinic acid To a solution of (1R,2R,3R,5R)-5-((bis(4-methoxyphenyl)(phenyl)methoxy) methyl)-2-fluoro-3-(pyrimidin-4-ylamino)cyclopentan-1-ol (3.50 g, 6.61 mmol) in pyridine (23.0 mL) was added diphenyl phosphite (2.55 mL, 13.3 mmol). The reaction mixture was stirred at rt under argon for 30 min. TEA (4.6 mL, 33.1 mmol) was added and the reaction mixture was allowed to stir for 5 min before water (79.7 mL) was added. Stirring was allowed to continue for 10 min. The reaction mixture was diluted with EtOAc and brine and extracted. The aqueous phase was then extracted with EtOAc (2×). The combined organic phases were washed with water, brine, dried using $Na_2SO_4$, filtered and concentrated to dryness. The crude compound was purified by silica gel chromatography (0-50% MeOH in DCM) to provide [(1R,2R,3R,5R)-5-[[bis(4-methoxyphenyl)-phenyl-methoxy]methyl]-2-fluoro-3-(pyrimidin-4-ylamino)cyclopentoxy]phosphinic acid as the N,N-diethylethanamine salt (1.36 g, 35%). LCMS (FA): m/z=594.2 (M+H).

Step 5: [(1R,2R,3R,5R)-2-fluoro-5-(hydroxymethyl)-3-(pyrimidin-4-ylamino)cyclopentoxy]phosphinic acid, Intermediate 81

To a solution of [(1R,2R,3R,5R)-5-[[bis(4-methoxyphenyl)-phenyl-methoxy]methyl]-2-fluoro-3-(pyrimidin-4-ylamino)cyclopentoxy]phosphinic acid, N,N-diethylethanamine salt (1.30 g, 1.87 mmol) in DCM (10.0 mL) was added water (0.17 mL) and a solution of DCA (0.72 mL, 8.78 mmol) in DCM (10.0 mL). The reaction mixture was allowed to stir at rt for 1 h. Triethylsilane (15.0 mL, 91.1 mmol) was added. The reaction mixture was allowed to stir at rt for 30 min and then the solvents were evaporated. The crude compound was purified by silica gel chromatography (0-90% MeOH in DCM) to provide [(1R,2R,3R,5R)-2-fluoro-5-(hydroxymethyl)-3-(pyrimidin-4-ylamino)cyclopentoxy]phosphinic acid (485 mg, 82%). LCMS (FA): m/z=292.1 (M+H); $^1$H NMR (DMSO-$d_6$ with $D_2O$) δ 8.72 (s, 1H), 8.09 (br d, J=6.6 Hz, 1H), 7.39 (s, 0.5H), 6.79 (br d, J=6.72 Hz, 1H), 5.88 (s, 0.5H), 4.82-5.06 (m, 1H), 4.48-4.69 (m, 1H), 4.22-4.41 (m, 1H), 3.39-3.50 (m, 2H), 2.09-2.19 (m, 1H), 2.01-2.09 (m, 1H), 1.51 (br d, J=11.0 Hz, 1H); $^{31}$P NMR (DMSO-$d_6$) δ 2.64 (s, 1P).

Example 47A

The compound listed below was prepared as described in Example 47 starting with Step 1, substituting the starting material shown in the table for Intermediate 80.

| Starting material | Intermediate | NMR data |
|---|---|---|
| 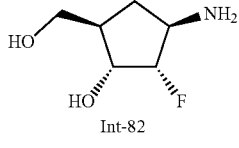 Int-82 | 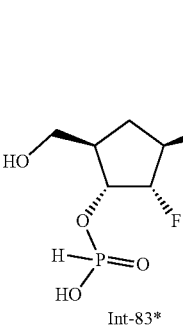 Int-83* | $^1$H NMR (DMSO-$d_6$) δ 9.91 (br s, 1H), 8.46 (s, 1H), 8.06 (br d, J = 5.7 Hz, 1H), 7.57 (br d, J = 6.8 Hz, 1H), 7.39 (s, 0.5H), 6.50 (dd, J = 0.9, 6.0 Hz, 1H), 5.91 (s, 0.5H), 4.68-4.51 (m, 1H), 4.27-4.13 (m, 2H), 3.57-3.41 (m, 2H), 3.31 (br s, 1 H), 3.06 (q, J = 7.3 Hz, 6H), 2.21 (td, J = 8.6, 13.2 Hz, 1H), 2.15-2.03 (m, 1H), 1.37-1.26 (m, 1H), 1.18 (t, J = 7.3 Hz, 9H); $^{31}$P NMR (DMSO-$d_6$) δ 1.44 (s, 1P). |

*DMTr deprotection as described in Example 47 step 5 substituting AcOH for DCA.

Example 47B

[(1R,2S,3R,5R)-2-fluoro-5-(hydroxymethyl)-3-(1,3,5-triazin-2-ylamino)cyclopentoxy]phosphinic acid, N,N-diethylethanamine salt, Intermediate 155

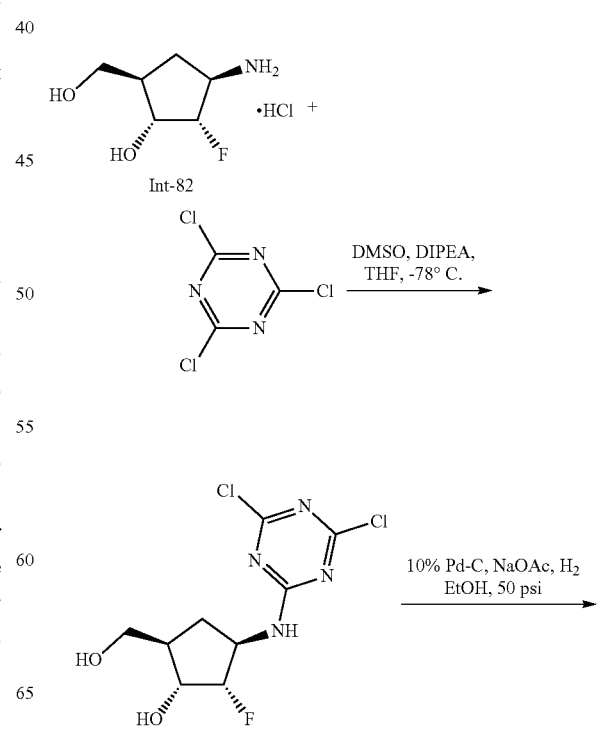

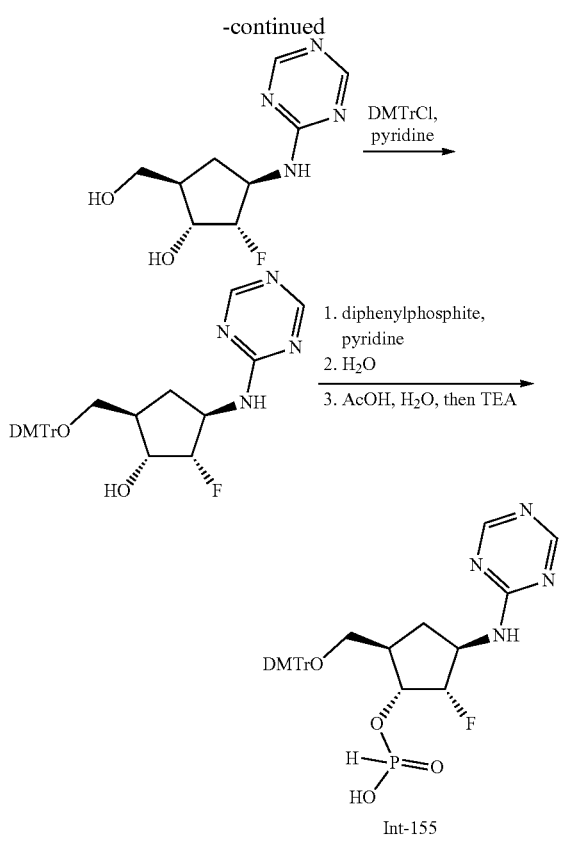

Step 1: (1R,2S,3R,5R)-3-[(4,6-Dichloro-1,3,5-triazin-2-yl)amino]-2-fluoro-5-(hydroxymethyl)cyclopentanol Cyanuric chloride (6.45 g, 35.0 mmol) was dissolved in THF (2.0 L) and cooled to −78° C. To this solution was added dropwise a solution of [(1R,2S,3R,4R)-2-fluoro-3-hydroxy-4-(hydroxymethyl)cyclopentyl]ammonium chloride (Intermediate 82, 3.25 g, 17.5 mmol) dissolved DMSO (12 mL) and DIPEA (9.15 mL, 52.5 mmol). The reaction mixture was stirred at −78° C. for 4 h. The reaction mixture was quenched by the addition of 4M HCl in dioxane (17.5 mL, 70 mmol) and slowly warmed to rt. The reaction mixture was concentrated to dryness and the residue was purified by reverse phase flash column chromatography (0-100% ACN in aqueous ammonium acetate (10 mM)) to provide (1R,2S,3R,5R)-3-[(4,6-dichloro-1,3,5-triazin-2-yl)amino]-2-fluoro-5-(hydroxymethyl)cyclopentanol (3.87 g, 75%). LCMS (AA): m/z=297.0 (M+H).

Step 2: (1R,2S,3R,5R)-2-Fluoro-5-(hydroxymethyl)-3-(1,3,5-triazin-2-ylamino)cyclopentanol (1R,2S,3R,5R)-3-[(4,6-Dichloro-1,3,5-triazin-2-yl)amino]-2-fluoro-5-(hydroxymethyl)cyclopentanol (3.87 g, 13.0 mmol) and sodium acetate (3.21 g, 39.0 mmol) was dissolved in ethanol (80 mL). Palladium (10% on carbon, 690 mg, 0.65 mmol) was added and the mixture was stirred under 50 psi of hydrogen for 3 h. The reaction mixture was filtered and the filtrate was evaporated to dryness. The crude product was purified by silica gel chromatography (0-50% MeOH in EtOAc) to provide (1R,2S,3R,5R)-2-fluoro-5-(hydroxymethyl)-3-(1,3,5-triazin-2-ylamino)cyclopentanol (2.63 g, 89%). LCMS (AA): m/z=229.1 (M+H).

Step 3: (1R,2S,3R,5R)-5-[[Bis(4-methoxyphenyl)-phenyl-methoxy]methyl]-2-fluoro-3-(1,3,5-triazin-2-ylamino)cyclopentanol The title compound was prepared from (1R,2S,3R,5R)-2-fluoro-5-(hydroxymethyl)-3-(1,3,5-triazin-2-ylamino)cyclopentanol (2.62 g, 11.5 mmol) following the procedure described in Example 47, step 2 stirring at rt for 2 h. Purification by silica gel chromatography (0-100% EtOAc in hexanes) provided (1R,2S,3R,5R)-5-[[bis(4-methoxyphenyl)-phenyl-methoxy]methyl]-2-fluoro-3-(1,3,5-triazin-2-ylamino)cyclopentanol (4.79 g, 79%). LCMS (AA): m/z=531.2 (M+H).

Step 4: [(1R,2S,3R,5R)-2-Fluoro-5-(hydroxymethyl)-3-(1,3,5-triazin-2-ylamino)cyclopentoxy]phosphinic acid To a solution of (1R,2S,3R,5R)-5-[[bis(4-methoxyphenyl)-phenyl-methoxy]methyl]-2-fluoro-3-(1,3,5-triazin-2-ylamino)cyclopentanol (4.78 g, 9.0 mmol) in pyridine (80.0 mL) cooled to 0° C. was added diphenyl phosphite (3.46 mL, 18.0 mmol). The reaction mixture was warmed to rt and stirred under argon for 2 h. The solution was then cooled to 0° C. and water (5.0 mL) was added. The reaction mixture was allowed to stir for 1 h at rt. The mixture was concentrated to dryness and the residue was concentrated from dry toluene (2×15 mL). The resulting residue was then dissolved in water (5.5 mL) and AcOH (21 mL) and stirred at rt for 2 h. The solution was then concentrated to dryness and the crude product was re-dissolved in methanol (10 mL) and TEA (2 mL) and stirred for 5 min. The solution was then concentrated and the crude compound was purified by silica gel chromatography (0-100% MeOH in DCM) to provide [(1R,2S,3R,5R)-2-fluoro-5-(hydroxymethyl)-3-(1,3,5-triazin-2-ylamino)cyclopentoxy]phosphinic acid as the N,N-diethylethanamine salt (2.22 g, 63%). LCMS (AA): m/z=293.1 (M+H); $^1$H NMR (MeOD) δ 8.53 (s, 1H), 8.43 (s, 1H), 7.62 (s, 0.5H), 6.06 (s, 0.5H), 4.83 (dt, J=51.4, 4.0 Hz, 1H), 4.58-4.39 (m, 2H), 3.72-3.65 (m, 2H), 3.15 (q, J=7.3 Hz, 6H), 2.46-2.29 (m, 2H), 1.51-1.44 (m, 1H), 1.29 (t, J=7.3 Hz, 9H); $^{31}$P NMR (MeOD) δ 3.44 (s, 1P).

Example 48
2-amino-9-[(5R,7R,8R,10S,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]pentaoxadiphosphacyclotetradecin-7-yl]-1,9-dihydro-6H-purin-6-one or
2-amino-9-[(5R,7R,8R,10R,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]pentaoxadiphosphacyclotetradecin-7-yl]-1,9-dihydro-6H-purin-6-one, I-23a and I-23b
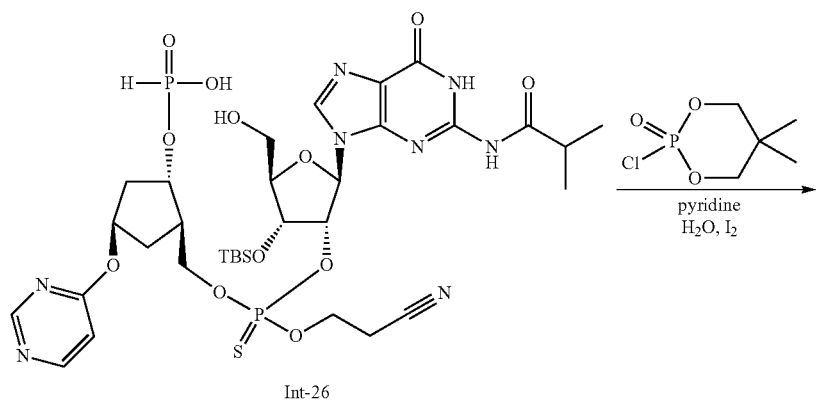
Int-26
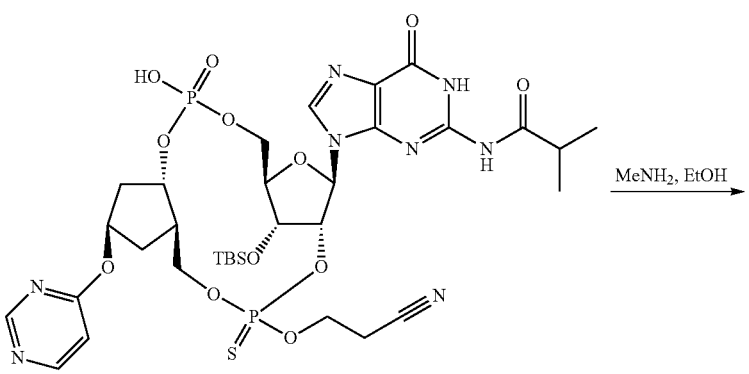
Int-88a, Int-88b
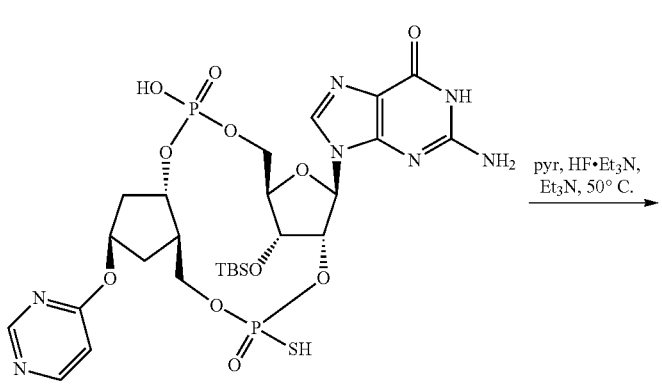
Int-89a, Int-89b

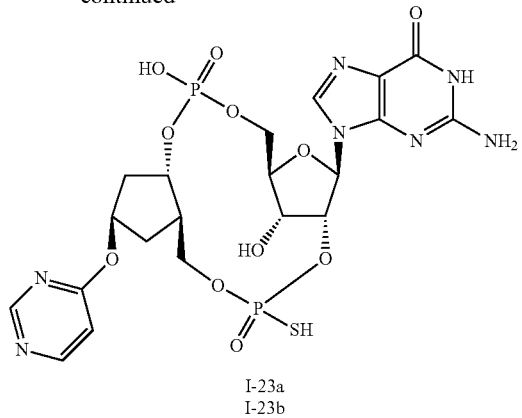

I-23a
I-23b

Step 1: N-{9-[(5R,7R,8R,10R,12aR,14R,15aS,16R)-16-{[tert-butyl(dimethyl)silyl]oxy}-10-(2-cyanoethoxy)-2-hydroxy-2-oxido-14-(pyrimidin-4-yloxy)-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(5R,7R,8R,10S,12aR,14R,15aS,16R)-16-{[tert-butyl(dimethyl)silyl]oxy}-10-(2-cyanoethoxy)-2-hydroxy-2-oxido-14-(pyrimidin-4-yloxy)-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 88a, Intermediate 88b Intermediate 26 (730 mg, 0.84 mmol) was dissolved in dry acetonitrile and concentrated to dryness (3×10 mL) and then placed under vacuum for 15 min. The residue was dissolved in pyridine (30 mL) under argon atmosphere. 2-Chloro-5,5-dimethyl-1,3,2-dioxaphosphorinane 2-oxide (563 mg, 2.93 mmol) was then added and the reaction mixture was allowed to stir at rt for 45 min. Water (0.53 mL) was added followed by iodine (276 mg, 1.09 mmol). The reaction mixture was allowed to stir at rt under argon atmosphere for 8 min. Sodium thiosulfate (177 mg, 1.09 mmol) in water (0.5 mL) was added. The reaction mixture was allowed to stir at rt for 15 min. Dry toluene was added (15 mL) and concentrated. The residue was concentrated from dry toluene (2×15 mL). The crude mixture was purified by reverse phase flash column chromatography (0-50% ACN in aqueous ammonium acetate (10 mM)). to provide Intermediate 88a as the first eluting peak (81 mg, 11%) and Intermediate 88b as the second eluting peak (111 mg, 15%). LCMS (AA): m/z=871.2 (M+H).

Step 2 and 3: 2-amino-9-[(5R,7R,8R,10S,12aR,14R,15aS,16R)-2,16-dihydroxy-2,10-dioxido-14-(pyrimidin-4-yloxy)-10-sulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(5R,7R,8R,10R,12aR,14R,15aS,16R)-2,16-dihydroxy-2,10-dioxido-14-(pyrimidin-4-yloxy)-10-sulfanyldecahydro-5,8-methanocyclopenta [l][1,3,6,9,11,2,10]pentaoxadiphosphacyclotetradecin-7-yl]-1,9-dihydro-6H-purin-6-one, I-23a I-23a was prepared from Intermediate 88a following the procedures described in Example 14 Steps 3 and 4. LCMS (AA): m/z=634.1 (M+H); $^1$H NMR (D$_2$O) δ 8.65 (s, 1H), 8.41 (d, J=6.0 Hz, 1H), 8.13 (s, 1H), 6.89 (dd, J=1.0, 6.1 Hz, 1H), 6.01 (d, J=8.3 Hz, 1H), 5.47-5.39 (m, 2H), 4.94-4.86 (m, 1H), 4.58 (d, J=4.4 Hz, 1H), 4.39-4.36 (m, 1H), 4.18-4.13 (m, 2H), 4.06 (q, J=9.7 Hz, 1H), 3.88-3.82 (m, 1H), 3.16 (q, J=7.3 Hz, 12H), 2.54-2.43 (m, 3H), 2.42-2.32 (m, 1H), 1.63-1.54 (m, 1H), 1.23 (t, J=7.3 Hz, 18H); $^{31}$P NMR (D$_2$O) δ 58.91 (s, 1P), −0.65 (s, 1P).

Step 2 and 3: 2-amino-9-[(5R,7R,8R,10S,12aR,14R,15aS,16R)-2,16-dihydroxy-2,10-dioxido-14-(pyrimidin-4-yloxy)-10-sulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(5R,7R,8R,10R,12aR,14R,15aS,16R)-2,16-dihydroxy-2,10-dioxido-14-(pyrimidin-4-yloxy)-10-sulfanyldecahydro-5,8-methanocyclopenta [l][1,3,6,9,11,2,10]pentaoxadiphosphacyclotetradecin-7-yl]-1,9-dihydro-6H-purin-6-one, I-23b I-23b was prepared from Intermediate 88b following the procedures described in Example 14 Steps 3 and 4. LCMS (AA): m/z=634.1 (M+H); $^1$H NMR (D$_2$O) δ 8.69 (s, 1H), 8.45 (d, J=5.7 Hz, 1H), 8.08 (s, 1H), 6.86 (dd, J=6.1, 1.1 Hz, 1H), 6.05 (d, J=8.4 Hz, 1H), 5.53-5.41 (m, 2H), 4.88-4.82 (m, 2H), 4.44-4.41 (m, 1H), 4.26-4.14 (m, 2H), 4.08-4.01 (m, 1H), 3.95-3.87 (m, CH), 3.19 (q, J=7.3 Hz, 12H), 2.58-2.44 (m, 3H), 2.35-2.27 (i, 2H), 1.70-1.63 (m, 1H), 1.28 (t, J=7.3 Hz, 18H); $^{31}$P NMR (D$_2$O) δ 52.93 (s, 1P), −0.62 (s, 1P).

Example 48A

The compound listed below was prepared as described in Example 48 starting with Step 1, substituting the intermediate shown in the table for Intermediate 26.

| Compound | Salt Form | Intermediate | Final compound/ LCMS data | NMR data |
|---|---|---|---|---|
| I-42* | Et$_3$N | 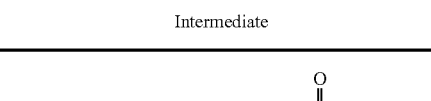<br>Int-159 | 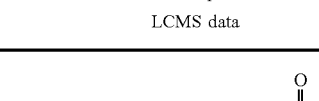<br>LCMS (AA): m/z = 652.4 (M + H) | $^1$H NMR (D$_2$O) δ 8.65 (s, 1H), 8.53 (s, 1H), 8.02 (s, 1H), 6.05 (d, J = 8.4 Hz, 1H), 5.67-5.61 (m, 1H), 5.17 (d, J = 51.5 Hz, 1H), 4.85-4.81 (m, 1H), 4.73 (d, J = 4.0 Hz, 1H), 4.53-4.41 (m, 2H), 4.35-4.23 (m, 2H), 4.12-3.99 (m, 2H), 3.24 (q, J = 7.3 Hz, 12H), 2.69-2.53 (m, 2H), 1.72-1.49 (m, 1H), 1.32 (t, J = 7.3 Hz, 18H) $^{31}$P NMR (D$_2$O) δ 52.92 (s, 1P), −1.30 (s, 1P). |

*In Step 2, 28% aqueous ammonium hydroxide was used instead of MeNH$_2$.

Example 49

2-amino-9-[(2S,5R,7R,8R,12aR,14R,15aS,16R)-10,16-dihydroxy-2,10-dioxido-14-(pyrimidin-4-yloxy)-2-sulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,12aR,14R,15aS,16R)-10,16-dihydroxy-2,10-dioxido-14-(pyrimidin-4-yloxy)-2-sulfanyldecahydro-5,8-methanocyclopenta[l][1,3,6,9,11,2,10]pentaoxadiphosphacyclotetradecin-7-yl]-1,9-dihydro-6H-purin-6-one, I-17

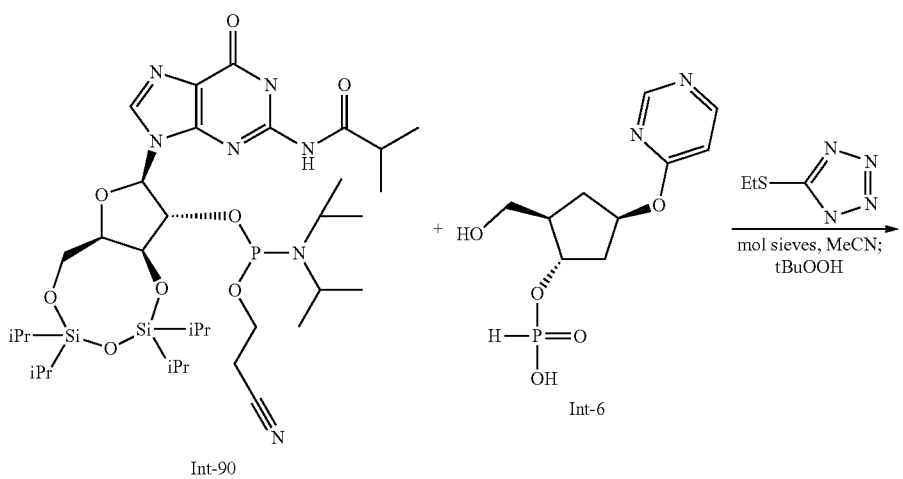

-continued
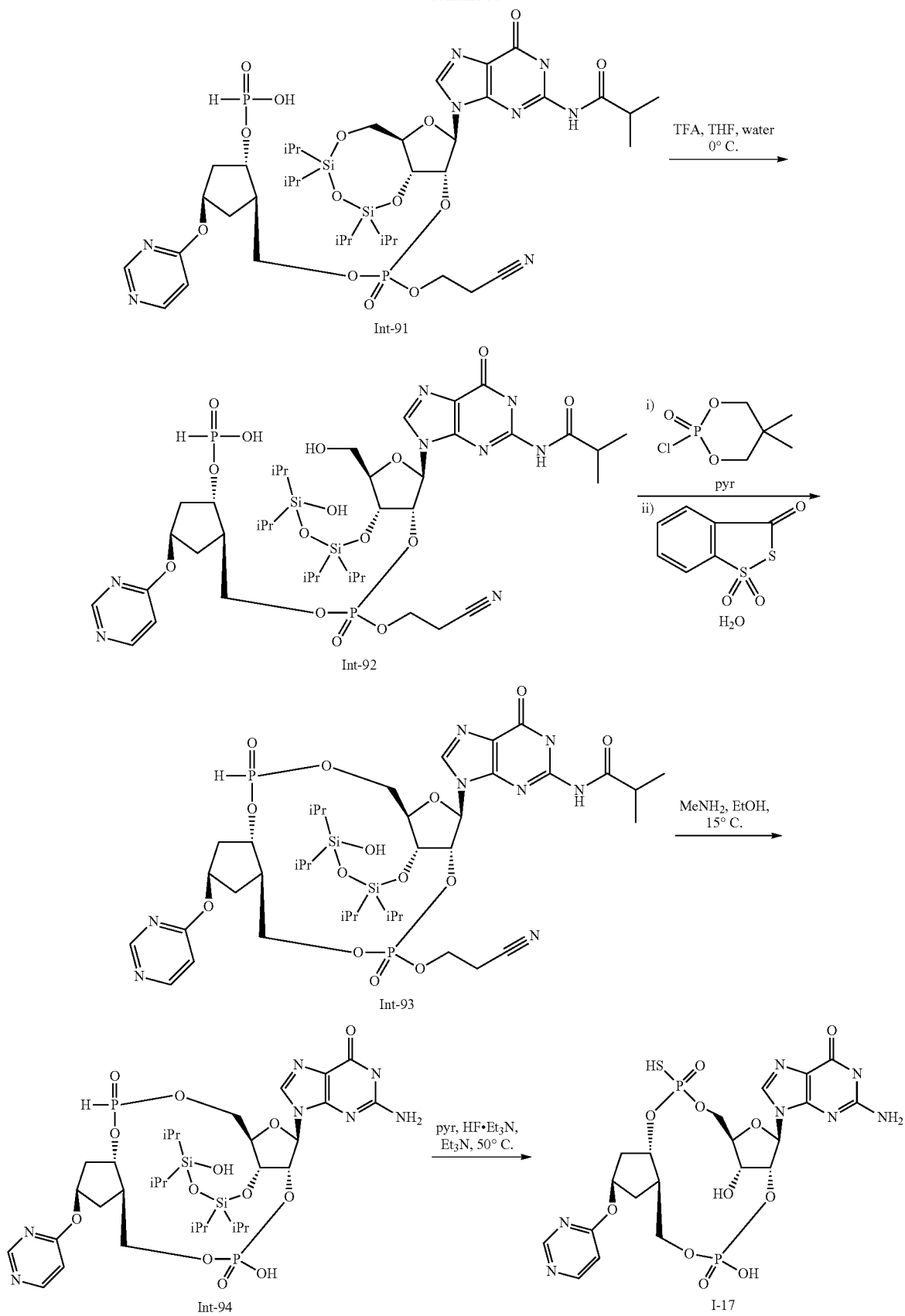

Step 1: (1R,2S,4S)-2-({[(2-cyanoethoxy)({(6aS,8S, 9S,9aS)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy) phosphoryl]oxy}methyl)-4-(pyrimidin-4-yloxy) cyclopentyl hydrogen phosphonate, Intermediate 91

A mixture of Intermediate 6 (500 mg, 1.82 mmol) and Intermediate 90 (1.87 g, 2.36 mmol) were dissolved in dry acetonitrile and concentrated to dryness (3×30 mL), molecular sieves (1.50 g) were added, and the mixture was then suspended in ACN (10 mL) under an atmosphere of nitrogen. In a separate flask, 5-(ethylthio)-1H-tetrazole (709 mg, 5.45 mmol) was dissolved in dry acetonitrile and concentrated to dryness (3×10 mL), dissolved in ACN (5.00 mL), and added to the reaction mixture under an atmosphere of nitrogen. The reaction mixture was allowed to stir at rt for 50 min. tert-butyl hydroperoxide (0.99 mL, 5.45 mmol)) was added and the reaction mixture was allowed to stir at rt for 1 h. The solvent was evaporated and the residue was purified by silica gel chromatography (0-40% MeOH in DCM) to give (1R,2S,4S)-2-({[(2-cyanoethoxy)({(6aS,8S,9S,9aS)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy)phosphoryl]oxy}methyl)-4-(pyrimidin-4-yloxy)cyclopentyl hydrogen phosphonate, Intermediate 91(1.40 g, 70%) as a white solid. HRMS: m/z=985.4592 (M+H).

Step 2: (1R,2S,4S)-2-({[(2-cyanoethoxy)({(2S,3S, 4S,5S)-5-(hydroxymethyl)-4-[(3-hydroxy-1,1,3,3-tetraisopropyldisiloxanyl)oxy]-2-[2-(isobutyrylamino)-6-oxo-1,6-dihydro-9H-purin-9-yl] tetrahydrofuran-3-yl}oxy)phosphoryl]oxy}methyl)-4-(pyrimidin-4-yloxy)cyclopentyl hydrogen phosphonate, Intermediate 92

A solution of Intermediate 91 (1.00 g, 1.01 mmol) in THF/water (4/1, 16.6 mL) was cooled to 0° C. and TFA (2.18 mL, 33.3 mmol) was added dropwise. The reaction mixture was allowed to stir at 0° C. for 2 h. Sodium carbonate was added portionwise until the pH was 7, then the reaction mixture was allowed to warm to rt. Water (20 mL) and EtOAc (20 mL) were added. After the phases were separated, the aqueous layer was washed with additional portions of EtOAc (2×). The combined organic layers were dried (Na$_2$SO$_4$) and evaporated. The crude material was combined with that obtained from another reaction carried out on a 400 mg scale and the mixture was purified by silica gel chromatography (0-50% MeOH in DCM) to provide Intermediate 92 (770 mg, 54%). HRMS: m/z=1003.3994 (M+H).

Step 3: N-{9-[(2S,5R,7R,8R,12aR,14R,15aS,16R)-10-(2-cyanoethoxy)-16-[(3-hydroxy-1,1,3,3-tetraisopropyldisiloxanyl)oxy]-2,10-dioxido-14-(pyrimidin-4-yloxy)-2-sulfanyldecahydro-5,8-methanocyclopenta[l][1,3,6,9,11,2,10] pentaoxadiphosphacyclotetradecin-7-yl]-6-oxo-6,9-dihydro-1H-purin-2-yl}-2-methylpropanamide, or N-{9-[(2R,5R,7R,8R,12aR,14R,15aS,16R)-10-(2-cyanoethoxy)-16-[(3-hydroxy-1,1,3,3-tetraisopropyldisiloxanyl)oxy]-2,10-dioxido-14-(pyrimidin-4-yloxy)-2-sulfanyldecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 93

Intermediate 92 (530 mg, 0.528 mmol) was concentrated from dry pyridine (3×10 mL), dried under vacuum for 10 min, and then dissolved in pyridine (13.2 mL) under a nitrogen atmosphere. 2-Chloro-5,5-dimethyl-1,3,2-dioxaphosphorinane 2-oxide (339 mg, 1.84 mmol) was added. The reaction mixture was allowed to stir at rt for 2 h. Water was added (0.331 mL, 18.4 mmol) followed by 3H-1,2-benzodithiol-3-one 1,1-dioxide (126 mg, 0.633 mmol), and the reaction mixture was allowed to stir at rt under nitrogen for 30 min. The mixture was concentrated to give the crude product as a single major diastereomer which was purified by reverse phase flash column chromatography (0-100% ACN with 0.1% TEA/water then lyophilized to give Intermediate 93 as a white solid (310 mg, 52%). $^1$H NMR (DMSO-d$_6$) δ 13.65-13.28 (m, 1H), 12.34-12.18 (m, 1H), 8.77-8.73 (m, 1H), 8.48-8.44 (m, 1H), 8.20 (s, 1H), 6.81-6.67 (m, 1H), 6.09-5.92 (m, 2H), 5.51-5.39 (m, 1H), 4.91-4.76 (m, 1H), 4.75-4.66 (m, 1H), 4.38-4.20 (m, 2H), 4.17-3.75 (m, 5H), 3.73-3.60 (m, 1H), 3.44-3.36 (m, 1H), 3.03-2.94 (m, 1H), 2.86-2.79 (m, 1H), 2.44-2.25 (m, 4H), 2.21-2.05 (m, 1H), 1.52-1.37 (m, 1H), 1.10-0.98 (m, 34H).

Step 4: 2-amino-9-[(2S,5R,7R,8R,12aR,14R,15aS, 16R)-10-hydroxy-16-[(3-hydroxy-1,1,3,3-tetraisopropyldisiloxanyl)oxy]-2,10-dioxido-14-(pyrimidin-4-yloxy)-2-sulfanyldecahydro-5,8-methanocyclopenta[l][1,3,6,9,11,2,10] pentaoxadiphosphacyclotetradecin-7-yl]-1,9-dihydro-6H-purin-6-one, or 2-amino-9-[(2R,5R,7R,8R,12aR,14R,15aS,16R)-10-hydroxy-16-[(3-hydroxy-1,1,3,3-tetraisopropyldisiloxanyl)oxy]-2,10-dioxido-14-(pyrimidin-4-yloxy)-2-sulfanyldecahydro-5,8-methanocyclopenta[l][1,3, 6,9,11,2,10]pentaoxadiphosphacyclotetradecin-7-yl]-1,9-dihydro-6H-purin-6-one, Intermediate 94

Intermediate 93 (310 mg, 0.304 mmol) was dissolved in methylamine (33% in EtOH, 10.0 mL, 20.0 mmol) and the reaction mixture was allowed to stir under an atmosphere of nitrogen at 15° C. for 1 h. The reaction mixture was concentrated and combined with a reaction run on a 120 mg scale. The crude mixture was adsorbed onto silica gel and purified by preparative HPLC (ACN/water with 0.1% NH$_4$OH/0.1% NH$_4$HCO$_3$ to give Intermediate 94 as the ammonium salt (253 mg, 65%), $^1$H NMR (400 MHz, DMSO-d$_6$) δ 10.70-10.62 (m, 1H), 8.78 (s, 1H), 8.49 (d, J=6.0 Hz, 1H), 8.18 (s, 1H), 7.40-7.06 (m, 5H), 6.93 (dd, J=0.9, 5.9 Hz, 1H), 6.66-6.53 (m, 1H), 5.89 (d, J=8.3 Hz, 1H), 5.52-5.44 (m, 1H), 5.40-5.31 (m, 1H), 4.86-4.78 (m, 1H), 4.72 (d, J=3.8 Hz, 1H), 4.22-4.17 (m, 1H), 4.02 (br t, J=9.9 Hz, 1H), 3.85-3.75 (m, 3H), 2.42-2.14 (m, 5H), 1.42-1.30 (m, 1H), 1.09-0.98 (m, 28H), 0.91-0.82 (m, 2H).

Step 5: 2-amino-9-[(2S,5R,7R,8R,12aR,14R,15aS, 16R)-10,16-dihydroxy-2,10-dioxido-14-(pyrimidin-4-yloxy)-2-sulfanyldecahydro-5,8-methanocyclopenta [l][1,3,6,9,11,2,10] pentaoxadiphosphacyclotetradecin-7-yl]-1,9-dihydro-6H-purin-6-one, or 2-amino-9-[(2R,5R,7R,8R,12aR,14R,15aS,16R)-10, 16-dihydroxy-2,10-dioxido-14-(pyrimidin-4-yloxy)-2-sulfanyldecahydro-5,8-methanocyclopenta [l][1,3, 6,9,11,2,10]pentaoxadiphosphacyclotetradecin-7-yl]-1,9-dihydro-6H-purin-6-one I-17

Intermediate 94 (117 mg, 0.128 mmol) was taken up in pyridine (0.644 mL) to give a suspension. Triethylamine trihydrofluoride (0.171 mL, 1.03 mmol) was added, followed by TEA (1.64 mL, 11.6 mmol). The reaction mixture was sealed in a propylene tube and allowed to stir at 50° C. overnight. The reaction mixture was diluted with water (2.46 mL), and a solution of $CaCl_2$ (297 mg, 2.57 mmol) in water (2.46 mL) was added. The cloudy white mixture was allowed to stir at rt for 60 min. The suspension was filtered through Celite, and the Celite was washed with water (5×5 mL). The clear aqueous filtrate was concentrated to a solid residue. No HF was observed by $^{19}F$ NMR. The crude compound was adsorbed onto Celite and purified by reverse phase flash column chromatography (0-10% ACN in aqueous triethylammonium acetate (10 mM)) to provide clean I-17 as the N,N-diethylethanamine salt (50 mg, 47%). LCMS (AA): m/z=634.0 (M+H). $^1H$ NMR ($D_2O$) δ 8.59 (s, 1H), 8.35 (d, J=6.0 Hz, 1H), 8.00 (s, 1H), 6.70 (d, J=6.0 Hz, 1H), 5.95 (d, J=8.4 Hz, 1H), 5.38-5.29 (m, 2H), 4.95 (quin, J=6.8 Hz, 1H), 4.56 (d, J=4.1 Hz, 1H), 4.42-4.37 (m, 1H), 4.35-4.27 (m, 1H), 4.06 (br dd, J=2.8, 12.0 Hz, 1H), 3.95-3.89 (m, 1H), 3.78 (td, J=5.5, 10.7 Hz, 1H), 3.14-3.07 (m, 16H), 2.55-2.30 (m, 3H), 2.25 (td, J=7.0, 14.2 Hz, 1H), 1.64-1.56 (m, 1H), 1.19 (t, J=7.3 Hz, 24H). $^{31}P$ NMR ($D_2O$) δ 54.13 (s, 1P), −0.80 (s, 1P).

Example 49A

The compound listed below was prepared as described in Example 49 following Steps 3, 4, and 5, substituting the intermediate shown in the table for Intermediate 92.

Example 50

(1S,2R,4R)-2-[[bis(4-methoxyphenyl)-phenyl-methoxy]methyl]-4-(1,2,5-thiadiazol-3-yloxy)cyclopentanol, Intermediate 95

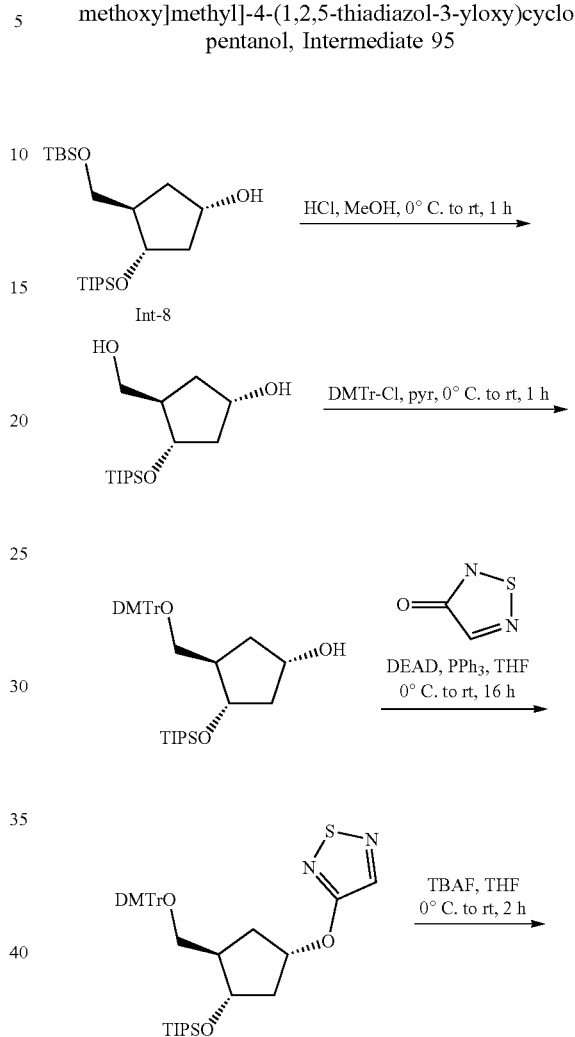

| Compound | Salt Form | Intermediate | Final compound/ LCMS data | NMR data |
|---|---|---|---|---|
| I-43 | $Et_3N$ | Int-160 | LCMS (AA): m/z = 652.1 (M + H) | $^1H$ NMR ($D_2O$) δ 8.62 (s, 1H), 8.47 (s, 1H), 7.95 (s, 1H), 5.99 (d, J = 8.4 Hz, 1H), 5.56-5.48 (m, 1H), 5.25 (br d, J = 2.2 Hz, 0.5H), 5.12 (d, J = 2.0 Hz, 0.5H), 4.98-4.84 (m, 1H), 4.62 (d, J = 3.9 Hz, 1H), 4.51-4.43 (m, 2H), 4.43-4.34 (m, 1H), 4.17-4.10 (m, 1H), 4.03-3.94 (m, 2H), 3.20 (q, J = 7.3 Hz, 12H), 2.64-2.53 (m, 2H), 1.71-1.59 (m, 1H), 1.28 (t, J = 7.3 Hz, 18H); $^{31}P$ NMR ($D_2O$) δ 54.62 (s, 1P), −1.12 (s, 1P). |

-continued

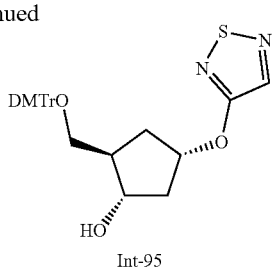

Int-95

Step 1: (1S,3R,4S)-3-(hydroxymethyl)-4-((triisopropylsilyl)oxy)cyclopentan-1-ol A solution of Intermediate 8 (16.1 g, 40.0 mmol) in methanol (650 mL) was added slowly to a mixture of concentrated hydrochloric acid (6.7 mL, 80 mmol) and methanol (650 mL) at 0° C. The reaction mixture was allowed to warm to rt and stirred for 1 h. Water (50 mL) and sodium bicarbonate (15.0 g, 178 mmol) were added and the reaction mixture was allowed to stir at rt for 10 min. The solvents were evaporated and the crude compound was purified by silica gel chromatography (0-5% MeOH in DCM) to provide the title compound (2.6 g, 23%). LCMS (AA): m/z=289.2 (M+H).

Step 2: (1S,3R,4S)-3-((bis(4-methoxyphenyl)(phenyl)methoxy)methyl)-4-((triisopropylsilyl)oxy)cyclopentan-1-ol A solution of (1S,3R,4S)-3-(hydroxymethyl)-4-((triisopropylsilyl)oxy) cyclopentan-1-ol (2.60 g, 9.01 mmol) in pyridine (30 mL) was cooled to 0° C. and a solution of DMTrCl (4.02 g, 11.3 mmol) in pyridine (15.0 mL) was added. The reaction mixture was allowed to stir at 0° C. for 15 min, then allowed to warm to rt and stir for 1 h. MeOH (20 mL) was added and the solvent was evaporated, then concentrated from toluene (2×50 mL). The crude residue was diluted with DCM (100 mL) and sat. NaHCO₃ solution (30 mL). After the phases were separated, the aqueous phase was extracted with DCM (2×100 mL). The combined organic phases were washed with brine (20 mL), dried over MgSO₄, filtered, and concentrated. The crude compound was purified by silica gel chromatography (0:1 to 1:1 EtOAc:hexane with 0.5% TEA) to give the title compound (4.3 g, 81%) as a foamy solid. LCMS (AA): m/z=589.3 (M–H).

Step 3: 3-((((1R,3R,4S)-3-((bis(4-methoxyphenyl)(phenyl)methoxy)methyl)-4-((triisopropylsilyl)oxy)cyclopentyl)oxy)-1,2,5-thiadiazole (1S,3R,4S)-3-((bis(4-methoxyphenyl)(phenyl)methoxy)methyl)-4-((triisopropylsilyl)oxy)cyclopentan-1-ol (1.50 g, 2.54 mmol), 1,2,5-thiadiazol-3(2H)-one (311 mg, 3.05 mmol), and triphenylphosphine (766 mg, 2.92 mmol) were dissolved in THF (30 mL) and the reaction mixture was cooled to 0° C. DEAD (0.440 mL, 2.79 mmol) was added dropwise and the reaction mixture was allowed to warm to rt and stirred overnight. The solvents were evaporated and the crude compound was purified by silica gel chromatography (0% to 15% EtOAc/hexane) to provide the title compound (1.38 g, 81%) as a pale yellow oil. LCMS (FA): m/z=673.3 (M–H).

Step 4: (1S,2R,4R)-2-[[bis(4-methoxyphenyl)-phenyl-methoxy]methyl]-4-(1,2,5-thiadiazol-3-yloxy)cyclopentanol, Intermediate 95

To a solution of 3-((((1R,3R,4S)-3-((bis(4-methoxyphenyl)(phenyl)methoxy) methyl)-4-((triisopropylsilyl)oxy)cyclopentyl)oxy)-1,2,5-thiadiazole (1.26 g, 1.87 mmol) in THF (9.0 mL) at 0° C. was added tetrabutylammonium fluoride hydrate (626 mg, 2.24 mmol). The reaction mixture was allowed to warm to rt and stirred for 2 h. Brine was added and the reaction mixture was extracted into EtOAc (2×), washed with water and brine, dried (Na₂SO₄) and evaporated. The residue was purified by silica gel chromatography (10% to 50% EtOAc/hexane) to provide the title compound (866 mg, 90%) as a white solid. LCMS (AA): m/z=517.1 (M–H).

Example 51

N-[3-[(1R,2R,4S)-2-hydroxy-4-(hydroxymethyl)cyclopentyl]-7-oxo-6H-triazolo[4,5-d]pyrimidin-5-yl]-2-methyl-propanamide, Intermediate 97

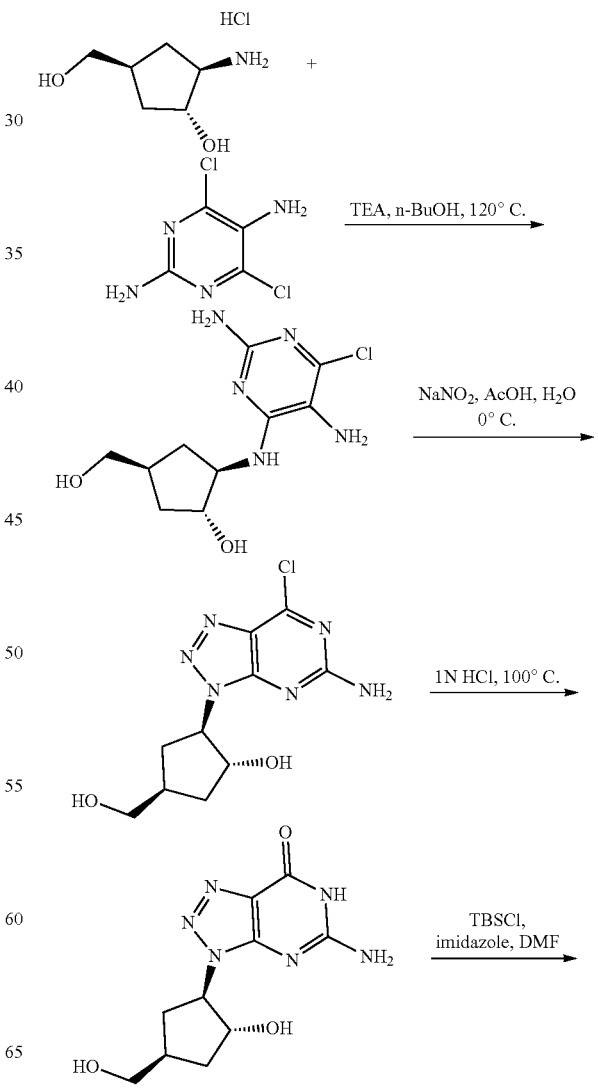

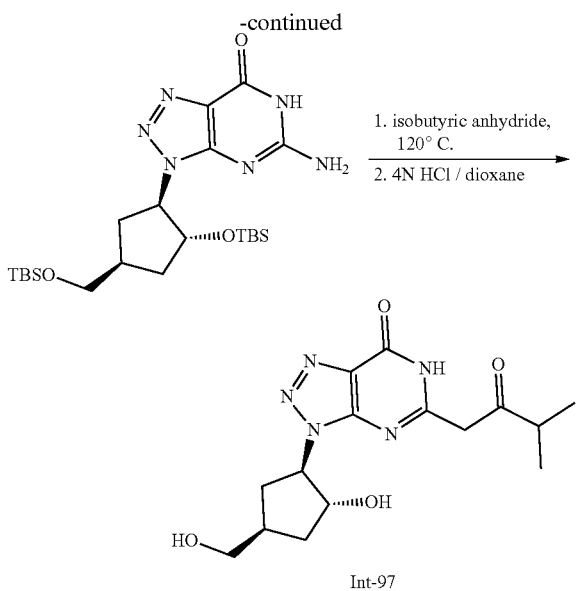

Int-97

Step 1: (1R,2R,4S)-2-[(2,5-diamino-6-methyl-pyrimidin-4-yl)amino]-4-(hydroxymethyl)cyclopentanol To a solution of (1R,2R,4S)-2-amino-4-(hydroxymethyl) cyclopentanol hydrochloride (30.0 g, 228 mmol) in n-BuOH (250 mL) was added 4,6-dichloropyrimidine-2,5-diamine (61.2 g, 342 mmol) and TEA (50 mL). The resulting suspension was heated to reflux under a nitrogen atmosphere for 48 h. The solvent was evaporated in vacuo and the dark residue was partitioned between 250 mL each of DCM and water. The aqueous phase was washed twice with 200 mL portions of DCM. The aqueous solution was then mixed with Dowex SBR (OH—) ion-exchange resin until pH=7. The resin was removed by filtration and the basic filtrate was evaporated. The residue was purified by chromatography on silica (EtOAc:MeOH 10:1) to provide (1R,2R,4S)-2-[(2,5-diamino-6-methyl-pyrimidin-4-yl)amino]-4-(hydroxymethyl)cyclopentanol as yellow oil (48.0 g, 77%). $^1$H NMR (DMSO-d$_6$) δ 6.36 (d, J=6.6 Hz, 1H,) 5.62 (br s, 2H), 4.77 (br s, 1H), 4.54 (t, J=5.1 Hz, 1H), 3.96-4.10 (m, 1H), 3.78-3.92 (m, 2H), 3.20-3.35 (m, 3H), 2.14 (quin, J=7.3 Hz, 2H), 1.59-1.68 (m, 1H), 1.43-1.56 (m, 1H), 1.03-1.18 (m, 1H).

Step 2: (1R,2R,4S)-2-(5-amino-7-chloro-triazolo[4,5-d]pyrimidin-3-yl)-4-(hydroxymethyl)cyclopentanol A solution of (1R,2R,4S)-2-[(2,5-diamino-6-methyl-pyrimidin-4-yl)amino]-4-(hydroxymethyl)cyclopentanol (48.0 g, 175 mmol) in water (500 mL) and glacial acetic acid (110 mL) was cooled to 0° C. under nitrogen. To this was added a solution of sodium nitrite (15.6 g, 227 mmol) in water (50 mL) dropwise over 10 min. The mixture was stirred at 0° C. for 2 h. The reaction mixture was concentrated under vacuum and the residue was purified by chromatography on silica (EtOAc:MeOH=10:1) to provide (1R,2R,4S)-2-(5-amino-7-chloro-triazolo[4,5-d]pyrimidin-3-yl)-4-(hydroxymethyl)cyclopentanol as yellow solid (42.0 g, 84%). $^1$H NMR (DMSO-d$_6$) δ 7.59 (br s, 2H), 5.14 (d, J=5.0 Hz, 1H), 4.68-4.78 (m, 1H), 4.61 (t, J=5.3 Hz, 1H), 4.43-4.54 (m, 1H), 3.38 (t, J=5.8 Hz, 2H), 2.29-2.39 (m, 1H), 2.14-2.26 (m, 1H), 1.79-1.94 (m, 2H), 1.63-1.75 (m, 1H).

Step 3: 5-amino-3-[(1R,2R,4S)-2-hydroxy-4-(hydroxymethyl)cyclopentyl]-6H-triazolo[4,5-d]pyrimidin-7-one A solution of (1R,2R,4S)-2-(5-amino-7-chloro-triazolo[4,5-d]pyrimidin-3-yl)-4-(hydroxymethyl)cyclopentanol (42.0 g, 147 mmol) in 1 N HCl (200 mL) was heated to reflux for 5 h. The solvent was concentrated in vacuum to provide 5-amino-3-[(1R,2R,4S)-2-hydroxy-4-(hydroxymethyl)cyclopentyl]-6H-triazolo[4,5-d]pyrimidin-7-one as yellow solid. (35 g, 90%). $^1$H NMR (DMSO-d$_6$) δ 10.91 (s, 1H), 6.90 (s, 2H), 4.58 (dt, J=9.9, 7.6 Hz, 1H), 4.45 (q, J=7.0 Hz, 1H), 3.36 (d, J=6.1 Hz, 2H), 3.23-3.60 (br s, 2H), 2.24-2.34 (m, 1H), 2.11-2.23 (m, 1H), 1.74-1.90 (m, 2H), 1.59-1.71 (m, 1H).

Step 4: 5-amino-3-[(1R,2R,4S)-2-[tert-butyl(dimethyl)silyl]oxy-4-[[tert-butyl(dimethyl)silyl]oxymethyl]cyclopentyl]-6H-triazolo[4,5-d]pyrimidin-7-one To a suspension of 5-amino-3-[(1R,2R,4S)-2-hydroxy-4-(hydroxymethyl)cyclopentyl]-6H-triazolo[4,5-d]pyrimidin-7-one (23 g, 86.3 mmol) in DMF (200 mL) was added TBSCl (38.8 g, 258 mmol) and imidazole (17.5 g, 258 mmol). The reaction mixture was allowed to stir at rt for 4 h. The mixture was poured into water (600 mL), extracted with EtOAc (200 mL×2), dried over anhydrous Na$_2$SO$_4$, filtered and concentrated. The crude product was purified by column chromatography on silica gel (PE:EtOAc=1:1) to provide 5-amino-3-[(1R,2R,4S)-2-[tert-butyl(dimethyl)silyl]oxy-4-[[tert-butyl(dimethyl)silyl]oxymethyl]cyclopentyl]-6H-triazolo[4,5-d]pyrimidin-7-one as white solid (38 g, 89%). $^1$H NMR (CDCl$_3$) δ 11.83 (br s, 1H), 6.70 (br s, 2H), 4.81 (dt, J=10.5, 7.7 Hz, 1H), 4.63 (q, J=7.0 Hz, 1H), 3.62 (br d, J=5.7 Hz, 2H), 2.48 (m, 1H), 2.31 (m, 1H), 2.18 (m, 1H), 1.97 (m, 1H), 1.82 (m, 1H), 0.92 (s, 9H), 0.74 (s, 9H), 0.09 (s, 6H), −0.14 (s, 3H), −0.22 (s, 3H).

Step 5: N-[3-[(1R,2R,4S)-2-[tert-butyl(dimethyl)silyl]oxy-4-[[tert-butyl(dimethyl)silyl]oxymethyl]cyclopentyl]-7-oxo-6H-triazolo[4,5-d]pyrimidin-5-yl]-2-methyl-propanamide A suspension of 5-amino-3-[(1R,2R,4S)-2-[tert-butyl(dimethyl)silyl]oxy-4-[[tert-butyl(dimethyl)silyl]oxymethyl]cyclopentyl]-6H-triazolo[4,5-d]pyrimidin-7-one (38.0 g, 76.8 mmol) in isobutyric anhydride (150 mL) was heated at 120° C. for 3 h then allowed to cool to rt. PE (300 mL) was added and the mixture was stirred for 0.5 h, then filtered. The solid was triturated with EtOAc (100 mL) and dried under reduced pressure to provide N-[3-[(1R,2R,4S)-2-[tert-butyl(dimethyl)silyl]oxy-4-[[tert-butyl(dimethyl)silyl]oxymethyl]cyclopentyl]-7-oxo-6H-triazolo[4,5-d]pyrimidin-5-yl]-2-methyl-propanamide as white solid (37 g, 85%). $^1$H NMR (CDCl$_3$) δ 12.29 (br s, 1H), 8.39 (s, 1H), 5.07 (dt, J=10.8, 7.6 Hz, 1H), 4.92 (q, J=7.3 Hz, 1H), 3.91 (m, 2H), 2.93 (m, 1H), 2.77 (m, 1H), 2.54 (m, 2H), 2.29 (dt, J=13.4, 6.7 Hz, 1H), 2.10 (ddd, J=13.3, 9.4, 7.3 Hz, 1H), 1.60 (d, J=6.8 Hz, 6H), 1.21 (s, 9H), 1.02 (s, 9H), 0.37 (s, 6H), 0.15 (s, 3H), 0.00 (s, 3H).

Step 6: N-[3-[(1R,2R,4S)-2-hydroxy-4-(hydroxymethyl)cyclopentyl]-7-oxo-6H-triazolo[4,5-d]pyrimidin-5-yl]-2-methyl-propanamide, Intermediate 97

A solution of N-[3-[(1R,2R,4S)-2-[tert-butyl(dimethyl)silyl]oxy-4-[[tert-butyl(dimethyl)silyl]oxymethyl]cyclopentyl]-7-oxo-6H-triazolo[4,5-d]pyrimidin-5-yl]-2-methyl-propanamide (42.0 g, 74.3 mmol) and 4N HCl/dioxane (20 mL) was stirred at rt for 2 h. The reaction mixture was combined with the same reaction carried out on a 1 g scale. The combined mixtures were concentrated, triturated with EtOAc (100 mL) and filtered? to provide N-[3-[(1R,2R,4S)-2-hydroxy-4-(hydroxymethyl)cyclopentyl]-7-oxo-6H-triazolo[4,5-d]pyrimidin-5-yl]-2-methyl-propanamide, Intermediate 97, as white solid (23 g, 92%). $^1$H NMR (500 MHz, DMSO-$d_6$) δ 12.27 (s, 1H), 11.95 (s, 1H), 5.28 (m, 1H), 4.76 (dt, J=10.2, 7.5 Hz, 1H), 4.56 (q, J=7.1 Hz, 1H), 3.45 (m, 2H), 2.85 (m, 1H), 2.35 (m, 2H), 1.95 (m, 2H), 1.76 (m, 1H), 1.17 (d, J=6.7 Hz, 6H).

Example 52

2-amino-9-[(2S,5R,7R,8S,10S,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5R,7R,8S,10R,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2R,5R,7R,8S,10S,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, or 2-amino-9-[(2S,5R,7R,8S,10R,12aR,14R,15aS,16R)-16-fluoro-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-1,9-dihydro-6H-purin-6-one, I-22a and I-22b

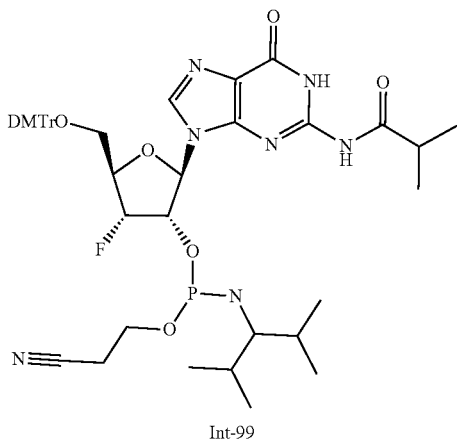

Int-99

Int-6

Int-100

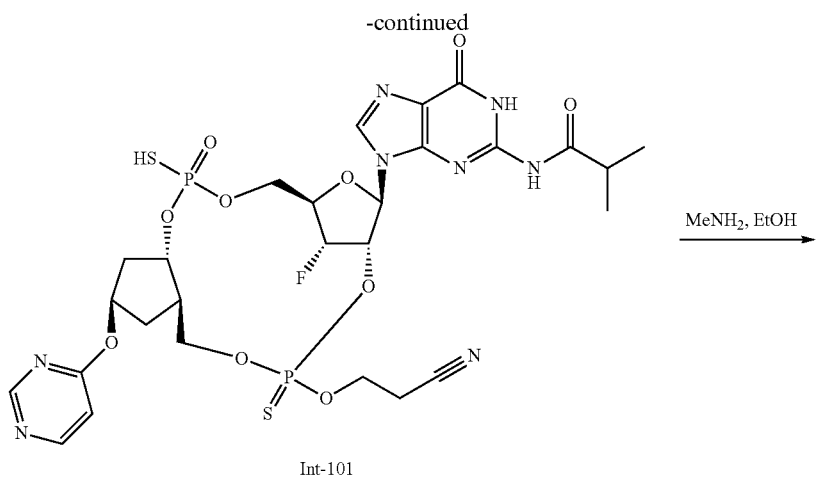

Int-101

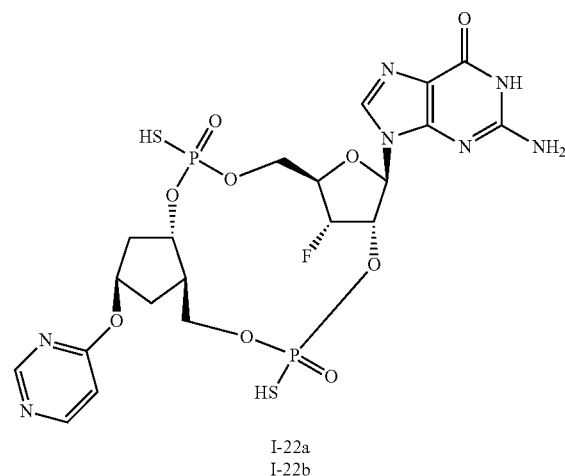

I-22a
I-22b

Step 1: (1S,2R,4R)-2-({[(R)-(2-cyanoethoxy)({(2R, 3S,4R,5R)-4-fluoro-5-(hydroxymethyl)-2-[2-(isobu- tyrylamino)-6-oxo-1,6-dihydro-9H-purin-9-yl]tetra- hydrofuran-3-yl}oxy)phosphorothioyl]oxy}methyl)- 4-(pyrimidin-4-yloxy)cyclopentyl hydrogen phosphonate, and (1S,2R,4R)-2-({[(S)-(2-cyanoethoxy)({(2R,3S,4R, 5R)-4-fluoro-5-(hydroxymethyl)-2-[2-(isobutyry- lamino)-6-oxo-1,6-dihydro-9H-purin-9-yl]tetrahy- drofuran-3-yl}oxy)phosphorothioyl]oxy}methyl)-4- (pyrimidin-4-yloxy)cyclopentyl hydrogen phosphonate, Intermediate 100

A mixture of [(1S,2R,4R)-2-(hydroxymethyl)-4-pyrimi- din-4-yloxy-cyclopentoxy]phosphinic acid (Intermediate 6, 56.0 mg, 0.204 mmol) and N-[9-[(2R,3S,4R,5R)-5-[[bis(4- methoxyphenyl)-phenyl-methoxy]methyl]-3-[2-cyanoeth- oxy-(diisopropylamino)phosphanyl]oxy-4-fluoro-tetrahy- drofuran-2-yl]-6-oxo-1H-purin-2-yl]-2-methyl- propanamide (Intermediate 99, 224 mg, 0.261 mmol) was dissolved in dry acetonitrile and concentrated to dryness (3×20 mL). The residue was then dissolved in ACN (0.765 mL) under an atmosphere of argon. In a separate flask 5-(ethylthio)-1H-tetrazole (81.6 mg, 0.627 mmol) was dis- solved in dry acetonitrile and concentrated to dryness (3×10 mL) then dissolved in ACN (0.348 mL) and added to the reaction mixture under an atmosphere of nitrogen. The reaction mixture was allowed to stir at rt for 40 min. ((Dimethylamino-methylidene)amino)-3H-1,2,4-dithiazo- line-3-thione (51.4 mg, 0.250 mmol) was added to the reaction mixture, and stirring was continued at rt for 45 min. The reaction mixture was concentrated and dried under? vacuum for 10 min. The residue was dissolved in acetic acid (0.829 mL, 14.5 mmol) and water (0.207 mL, 11.5 mmol), sonicated for 2 min, then allowed to stir at rt for 30 min. Toluene (15 mL) was added and the reaction mixture was concentrated. The residue was concentrated from toluene (2×15 mL) and then dried on vacuum for 10 minutes. The crude compound was purified by silica gel chromatography (0-100% MeOH in DCM) to provide Intermediate 100 (120 mg, 77%) as a mixture of diastereomers. LCMS (AA): m/z=761.1 (M+H).

Step 2: N-{9-[(2S,5R,7R,8S,10R,12aR,14R,15aS, 16R)-10-(2-cyanoethoxy)-16-fluoro-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, and N-{9-[(2R,5R,7R,8S,10S,12aR,14R,15aS,16R)-10-(2-cyanoethoxy)-16-fluoro-2-oxido-14-(pyrimidin-4-yloxy)-2-sulfanyl-10-sulfidodecahydro-5,8-methanocyclopenta [l][1,3,6,9,11,2,10]pentaoxadiphosphacyclotetradecin-7-yl]-6-oxo-6,9-dihydro-1H-purin-2-yl}-2-methylpropanamide, and N-{9-[(2R,5R,7R,8S,10R,12aR,14R,15aS,16R)-10-(2-cyanoethoxy)-16-fluoro-2-oxido-14-(pyrimidin-4-yloxy)-2-sulfanyl-10-sulfidodecahydro-5,8-methanocyclopenta [l][1,3,6,9,11,2,10]pentaoxadiphosphacyclotetradecin-7-yl]-6-oxo-6,9-dihydro-1H-purin-2-yl}-2-methylpropanamide, and N-{9-[(2S,5R,7R,8S,10S,12aR,14R,15aS,16R)-10-(2-cyanoethoxy)-16-fluoro-2-oxido-14-(pyrimidin-4-yloxy)-2-sulfanyl-10-sulfidodecahydro-5,8-methanocyclopenta [l][1,3,6,9,11,2,10]pentaoxadiphosphacyclotetradecin-7-yl]-6-oxo-6,9-dihydro-1H-purin-2-yl}-2-methylpropanamide, Intermediate 101

Diphenyl chlorophosphate (0.546 mL, 2.63 mmol) was added to pyridine (8.00 mL, 98.9 mmol) at −35° C. Intermediate 100 (100 mg, 0.131 mmol) was concentrated from pyridine (2×5 mL), taken up in DCM (5.33 mL) and added to the reaction mixture. Pyridine (1.33 mL, 16.5 mmol) was added to the reaction mixture and stirring was continued at −35° C. for 40 min. 3H-1,2-Benzodithiol-3-one (44.2 mg, 0.263 mmol) and water (0.0947 mL, 5.26 mmol) were added at −35° C. The reaction mixture was allowed to warm to rt and stir for 1 h. Sodium thiosulfate (107 mg, 0.657 mmol) in water (0.500 mL) was added at 0° C. and the reaction mixture was allowed to stir at rt for 5 min. The volatile solvent was removed by evaporation and the residue was purified by silica gel chromatography (0-50% MeOH in DCM) to provide Intermediate 101 as an impure mixture of diastereomers that was taken on without further purification.

Step 3: 2-amino-9-[(2S,5R,7R,8S,10S,12aR,14R, 15aS,16R)-16-fluoro-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, or 2-amino-9-[(2R,5R,7R,8S,10R,12aR,14R,15aS, 16R)-16-fluoro-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, or 2-amino-9-[(2R,5R,7R,8S,10S,12aR,14R,15aS, 16R)-16-fluoro-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, or 2-amino-9-[(2S,5R,7R,8S,10R,12aR,14R,15aS, 16R)-16-fluoro-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, I-22a and I-22b To Intermediate 101 (100 mg, 0.1291 mmol) was added methylamine (33% in EtOH, 0.643 mL, 5.16 mmol), and the reaction mixture was allowed to stir at rt overnight. The reaction mixture was purified by reverse phase flash column chromatography (0%-100% ACN in aq. ammonium acetate (10 mM)) to provide an impure product that was further purified by reverse phase flash column chromatography 10-100% ACN in aq. triethylammonium acetate (10 mM)) to provide the N,N-diethylethanamine salt of I-22a as the first eluting major product (3.5 mg, 3%), LCMS (FA): m/z=652.1 (M+H), $^{1}$H NMR (D$_2$O) δ 8.54 (s, 1H), 8.29 (d, J=6.0 Hz, 1H), 7.97 (s, 1H), 6.75 (d, J=5.9 Hz, 1H), 5.95 (d, J=8.5 Hz, 1H), 5.27-5.38 (m, 2H), 4.87-5.01 (m, 1H), 4.28 (t, J=12.1 Hz, 1H), 3.86-4.06 (m, 2H), 3.75 (m, 1H), 3.05 (q, J=7.3 Hz, 12H), 2.25-2.48 (m, 5H), 1.42-1.55 (m, 1H), 1.13 (t, J=7.3 Hz, 18H), $^{31}$P NMR (D$_2$O) δ 58.59 (s, 1P), 54.01 (s, 1P); and the N,N-diethylethanamine of I-22b as the second eluting major product (6.8 mg, 5%), LCMS (FA): m/z=652.1 (M+H), $^{1}$H NMR (D$_2$O) δ 8.52 (s, 1H), 8.28 (d, J=6.0 Hz, 1H), 7.88 (s, 1H), 6.65 (d, J=5.9 Hz, 1H), 5.91 (d, J=8.5 Hz, 1H), 5.20-5.34 (m, 2H), 4.86 (quin, J=6.8 Hz, 1H), 4.28 (ddd, J=11.2, 8.7, 2.3 Hz, 1H), 3.96 (br d, J=12.3 Hz, 1H), 3.85 (br s, 1H), 3.69-3.80 (m, 1H), 3.02 (q, J=7.3 Hz, 12H), 2.24-2.47 (m, 4H), 2.10-2.22 (m, 1H), 1.42-1.60 (m, 1H), 1.10 (t, J=7.3 Hz, 18H), $^{31}$P NMR (D$_2$O) δ 54.08 (s, 1P), 53.20 (s, 1P).

Example 53
2-amino-9-[(5R,7R,8S,10S,12aR,14R,15S,15aR,16R)-15,16-difluoro-2-hydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one, or
2-amino-9-[(5R,7R,8S,10R,12aR,14R,15S,15aR,16R)-15,16-difluoro-2-hydroxy-2,10-dioxido-14-(pyrimidin-4-ylamino)-10-sulfanyldecahydro-5,8-methanocyclopenta[l][1,3,6,9,11,2,10]pentaoxadiphosphacyclotetradecin-7-yl]-1,9-dihydro-6H-purin-6-one I-24a and I-24b
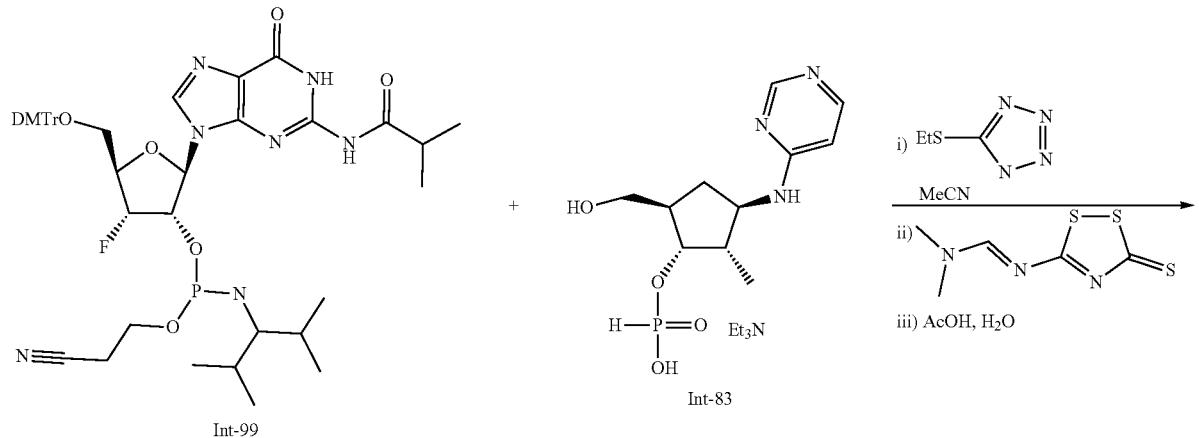
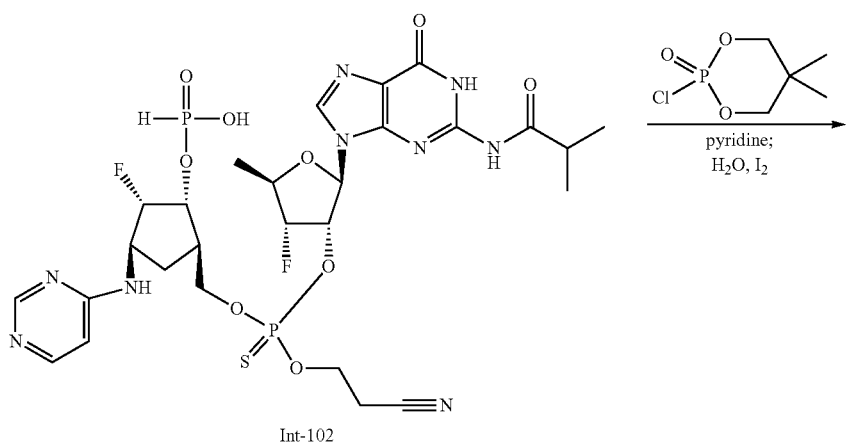

-continued

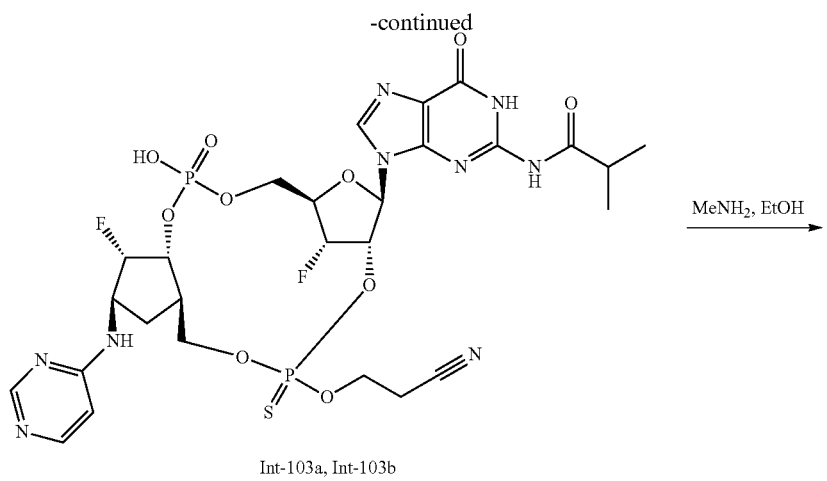

Int-103a, Int-103b

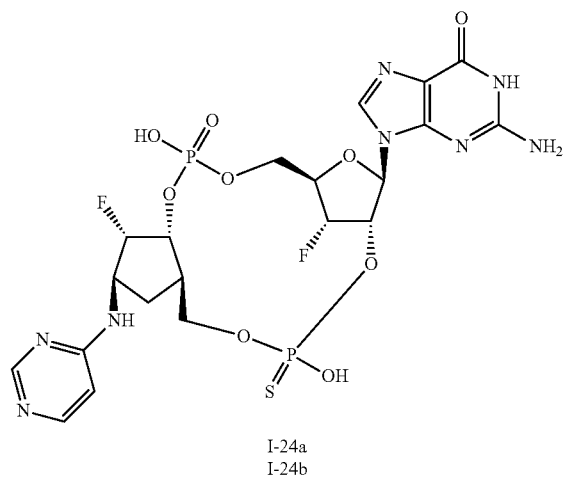

I-24a
I-24b

Step 1: (1R,2S,3R,5R)-5-({[(R)-(2-cyanoethoxy)({(2R,3S,4R,5R)-4-fluoro-5-(hydroxymethyl)-2-[2-(isobutyrylamino)-6-oxo-1,6-dihydro-9H-purin-9-yl]tetrahydrofuran-3-yl}oxy)phosphorothioyl]oxy}methyl)-2-fluoro-3-(pyrimidin-4-ylamino)cyclopentyl hydrogen phosphonate and (1R,2S,3R,5R)-5-({[(S)-(2-cyanoethoxy)({(2R,3S,4R,5R)-4-fluoro-5-(hydroxymethyl)-2-[2-(isobutyrylamino)-6-oxo-1,6-dihydro-9H-purin-9-yl]tetrahydrofuran-3-yl}oxy)phosphorothioyl]oxy}methyl)-2-fluoro-3-(pyrimidin-4-ylamino)cyclopentyl hydrogen phosphonate, Intermediate 102

[(1R,2S,3R,5R)-2-Fluoro-5-(hydroxymethyl)-3-(pyrimidin-4-ylamino)cyclopentoxy]phosphinic acid (Intermediate 83, 330 mg, 0.841 mmol) and N-[9-[(2R,3S,4R,5R)-5-[[bis(4-methoxyphenyl)-phenyl-methoxy]methyl]-3-[2-cyanoethoxy-(diisopropylamino)phosphanyl]oxy-4-fluoro-tetrahydrofuran-2-yl]-6-oxo-1H-purin-2-yl]-2-methylpropanamide (Intermediate 99, 950 mg, 1.11 mmol) were dissolved in dry acetonitrile and concentrated to dryness (3×20 mL). The residue was then dissolved in ACN (2.90 mL) under an atmosphere of argon. In a separate flask 5-(ethylthio)-1H-tetrazole (274 mg, 2.10 mmol) was dissolved in dry acetonitrile and concentrated to dryness (3×10 mL) then dissolved in ACN (1.40 mL) and added to the reaction mixture under an atmosphere of nitrogen. The reaction mixture was allowed to stir at rt for 1 h. ((Dimethylamino-methylidene)amino)-3H-1,2,4-dithiazoline-3-thione (207 mg, 1.01 mmol) was added and stirring was continued at rt for 45 min. The reaction mixture was concentrated and dried on vacuum for 10 min. The residue was dissolved in acetic acid (3.50 mL, 60.0 mmol) and water (0.860 mL, 48.0 mmol), sonicated for 2 min, then allowed to stir at rt for 1.5 h. Toluene (15 mL) was added and the reaction mixture was concentrated. The residue was concentrated from toluene (2×15 mL) and then dried on vacuum for 10 minutes. The crude compound was purified by silica gel chromatography (0-50% MeOH in DCM) to provide Intermediate 102 (620 mg, 95%) as a mixture of diastereomers. LCMS (AA): m/z=778.2 (M+H).

Step 2: N-{9-[(5R,7R,8S,10R,12aR,14R,15S,15aR, 16R)-10-(2-cyanoethoxy)-15,16-difluoro-2-hydroxy-2-oxido-14-(pyrimidin-4-ylamino)-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(5R,7R,8S,10S,12aR,14R,15S,15aR,16R)-10-(2-cyanoethoxy)-15,16-difluoro-2-hydroxy-2-oxido-14-(pyrimidin-4-ylamino)-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide Intermediate 102 (100 mg, 0.129 mmol) was dissolved in dry acetonitrile and concentrated to dryness (3×10 mL), dried under vacuum for 10 min and dissolved in pyridine (4.17 mL) under an atmosphere of argon. 2-Chloro-5,5-dimethyl-1,3,2-dioxaphosphorinane 2-oxide (86.5 mg, 0.450 mmol) was added and the reaction mixture was allowed to stir for 45 min. Water (0.081 mL, 4.50 mmol) and iodine (42.5 mg, 0.167 mmol) were added and stirring was continued at rt for 10 min. Sodium thiosulfate (27.2 mg, 0.167 mmol) in water (0.5 mL) was added and stirring was continued at rt for 15 min. Toluene (15 mL) was added and the reaction mixture was concentrated. The residue was concentrated from toluene (15 mL) and then dried on vacuum for 15 min. The crude compound was purified by reverse phase flash column chromatography (0-30% ACN in aqueous ammonium acetate (10 mM)) to provide Intermediate 103a as the first eluting diastereomer (30 mg, 30%) and intermediate 103b (40 mg, 40%) as the second eluting diastereomer LCMS (AA): m/z=776.2 (M+H).

Step 3: 2-amino-9-[(5R,7R,8S,10S,12aR,14R,15S, 15aR,16R)-15,16-difluoro-2-hydroxy-2,10-dioxido-14-(pyrimidin-4-ylamino)-10-sulfanyldecahydro-5, 8-methanocyclopenta[l][1,3,6,9,11,2,10]pentaoxadiphosphacyclotetradecin-7-yl]-1,9-dihydro-6H-purin-6-one or 2-amino-9-[(5R,7R,8S,10R,12aR,14R,15S,15aR, 16R)-15,16-difluoro-2-hydroxy-2,10-dioxido-14-(pyrimidin-4-ylamino)-10-sulfanyldecahydro-5,8-methanocyclopenta [l][1,3,6,9,11,2,10]pentaoxadiphosphacyclotetradecin-7-yl]-1,9-dihydro-6H-purin-6-one I-24a Intermediate 103a (30 mg, 0.039 mmol) was dissolved in a solution of methylamine (33% in EtOH, 1.16 mL, 9.32 mmol) and the reaction mixture was allowed to stir at rt for 16 h. The reaction mixture was concentrated and 10 mM triethylammonium acetate with 1% ACN (10 mL) was added and evaporated (2×). The residue was adsorbed onto Celite. The crude compound was purified by reverse phase flash column chromatography (0-10% ACN in aqueous triethylammonium acetate (10 mM)) to I-24a as the TEA salt (8 mg, 28%) LCMS (AA): m/z=653.1 (M+H). $^1$H NMR (D$_2$O) δ 8.36 (br d, J=3.3 Hz, 1H), 7.83 (br d, J=5.7 Hz, 1H), 7.76 (s, 1H), 6.47-6.38 (m, 1H), 5.91 (d, J=8.4 Hz, 1H), 5.70-5.54 (m, 1H), 5.32 (dd, J=3.1, 53.8 Hz, 1H), 4.99 (dd, J=1.0, 51.8 Hz, 1H), 4.74-4.65 (m, 1H), 4.32-4.21 (m, 1H), 4.21-4.13 (m, 1H), 4.10-4.02 (m, 1H), 3.94-3.82 (m, 2H), 3.03 (q, J=7.3 Hz, 6H), 2.57-2.39 (m, 3H), 1.47-1.39 (m, 1H), 1.10 (t, J=7.3 Hz, 9H). $^{31}$P NMR (D$_2$O) δ=55.13 (s, 1P), −1.50 (s, 1P).

Step 4: 2-amino-9-[(5R,7R,8S,10S,12aR,14R,15S, 15aR,16R)-15,16-difluoro-2-hydroxy-2,10-dioxido-14-(pyrimidin-4-ylamino)-10-sulfanyldecahydro-5, 8-methanocyclopenta[l][1,3,6,9,11,2,10]pentaoxadiphosphacyclotetradecin-7-yl]-1,9-dihydro-6H-purin-6-one or 2-amino-9-[(5R,7R,8S,10R,12aR,14R,15S,15aR, 16R)-15,16-difluoro-2-hydroxy-2,10-dioxido-14-(pyrimidin-4-ylamino)-10-sulfanyldecahydro-5,8-methanocyclopenta [l][1,3,6,9,11,2,10]pentaoxadiphosphacyclotetradecin-7-yl]-1,9-dihydro-6H-purin-6-one, I-24b Intermediate 103b was treated in an analogous fashion to the above procedure to provide I-24b as the N,Ndiethylethanamine salt (4 mg, 12%). LCMS (AA): m/z=653.1 (M+H). $^1$H NMR (D$_2$O) δ 8.45 (s, 1H), 8.08 (br d, J=4.5 Hz, 1H), 7.92 (s, 1H), 6.48-6.40 (m, 1H), 6.05 (d, J=8.7 Hz, 1H), 5.85-5.70 (m, 1H), 5.50 (dd, J=53.8, 3.3 Hz, 1H), 5.13 (d, J=52.0 Hz, 1H), 4.82-4.68 (m, 1H), 4.38-4.29 (m, 2H), 4.26-4.19 (m, 1H), 4.12-4.06 (m, 1H), 4.01-3.96 (m, 1H), 3.25-3.15 (m, 4H), 2.67-2.55 (m, 3H), 1.64-1.54 (m, 1H), 1.33-1.23 (m, 6H); $^{31}$P NMR (D$_2$O) δ 53.14 (s, 1P), −1.49 (s, 1P).

Example 54

2-amino-9-[(2S,5R,7R,8S,10S,12aR,14R,15S,15aR, 16R)-15,16-difluoro-2,10-dioxido-14-(pyrimidin-4-ylamino)-2,10-disulfanyldecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8S,10S,12aR,14R,15S,15aR, 16R)-15,16-difluoro-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2S,5R,7R,8S,10R,12aR,14R,15S,15aR, 16R)-15,16-difluoro-2,10-dioxido-14-(pyrimidin-4-ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one or 2-amino-9-[(2R,5R,7R,8S,10R,12aR,14R,15S,15aR, 16R)-15,16-difluoro-2,10-dioxido-14-(pyrimidin-4- ylamino)-2,10-disulfanyldecahydro-5,8-methanocyclopenta [l][1,3,6,9,11,2,10]pentaoxadiphosphacyclotetradecin-7-yl]-1,9-dihydro-6H-purin-6-one, I-38a and I-38b
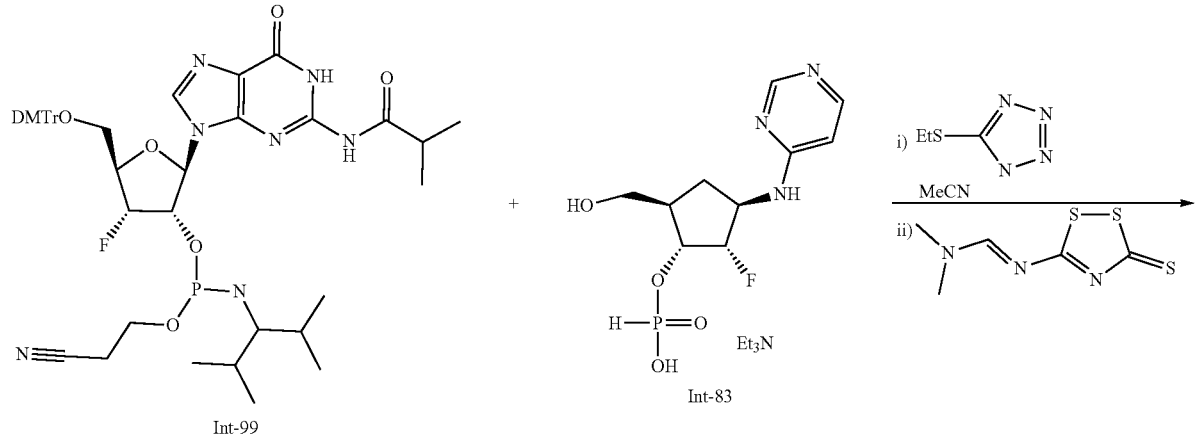
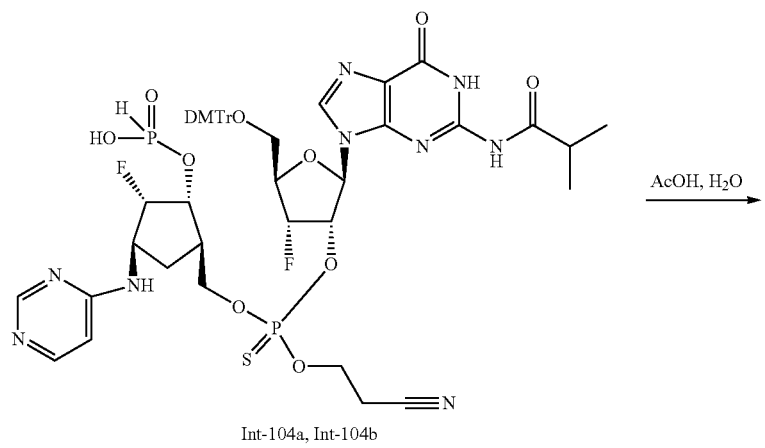
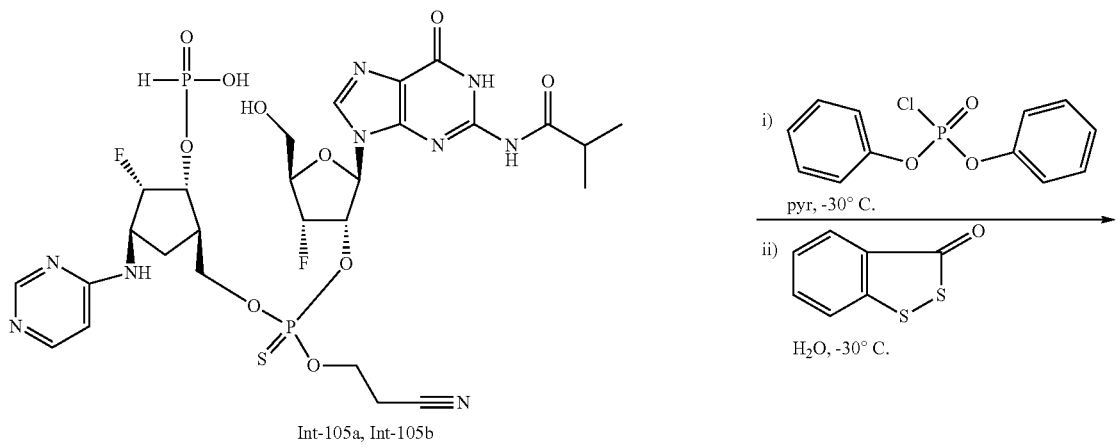

-continued

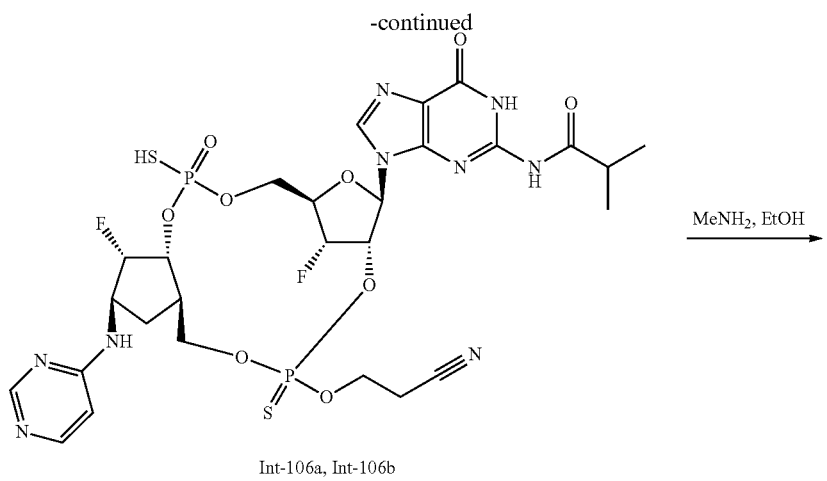

Int-106a, Int-106b

MeNH₂, EtOH →

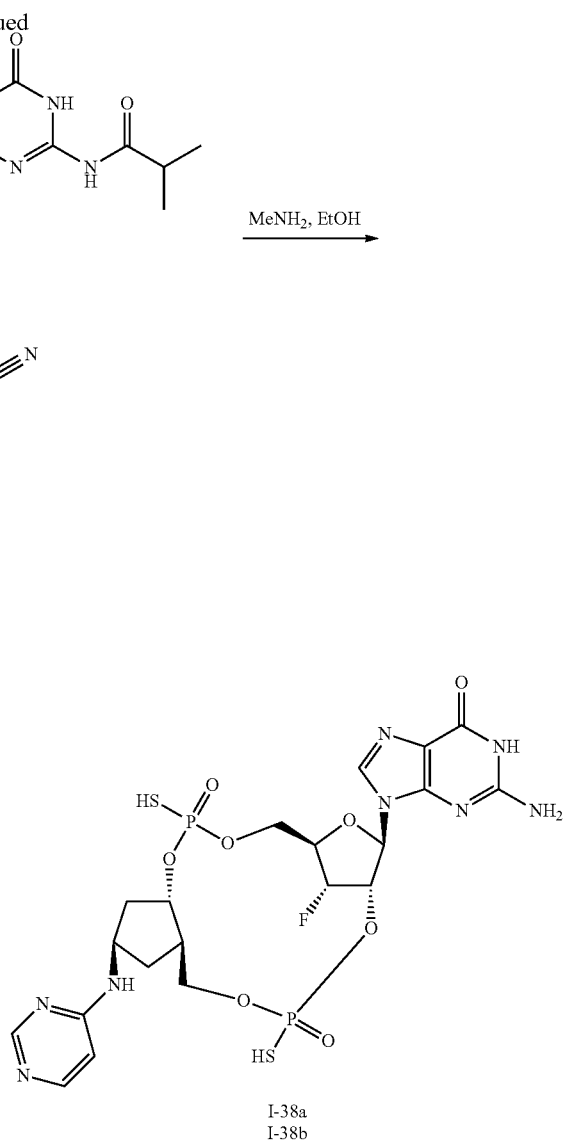

I-38a
I-38b

Step 1: (1R,2S,3R,5R)-5-({[(R)-({(2R,3S,4R,5R)-5-{[bis(4-methoxyphenyl)(phenyl) methoxy]methyl}-4-fluoro-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-2-fluoro-3-(pyrimidin-4-ylamino)cyclopentyl hydrogen phosphonate and (1R,2S,3R,5R)-5-({[(S)-({(2R,3S,4R,5R)-5-{[bis(4-methoxyphenyl)(phenyl)methoxy]methyl}-4-fluoro-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-2-fluoro-3-(pyrimidin-4-ylamino)cyclopentyl hydrogen phosphonate Intermediate 104a and Intermediate 104b

[(1R,2S,3R,5R)-2-Fluoro-5-(hydroxymethyl)-3-(pyrimidin-4-ylamino)cyclopentoxy]phosphinic acid (Intermediate 83, 383 mg, 0.976 mmol) and N-[9-[(2R,3S,4R,5R)-5-[[bis(4-methoxyphenyl)-phenyl-methoxy]methyl]-3-[2-cyanoethoxy-(diisopropylamino)phosphanyl]oxy-4-fluoro-tetrahydrofuran-2-yl]-6-oxo-1H-purin-2-yl]-2-methyl-propanamide (Intermediate 99, 1.08 g, 1.26 mmol) were dissolved in dry acetonitrile and concentrated to dryness (3×20 mL). The residue was then dissolved in ACN (3.35 mL) under an atmosphere of argon. In a separate flask 5-(ethylthio)-1H-tetrazole (318 mg, 2.44 mmol) was dissolved in dry acetonitrile and concentrated to dryness (3×10 mL) then dissolved in ACN (1.67 mL) and added to the reaction mixture under an atmosphere of nitrogen. The reaction mixture was allowed to stir at rt for 1 h. ((Dimethylamino-methylidene)amino)-3H-1,2,4-dithiazoline-3-thione (241 mg, 1.17 mmol) was added, and stirring was continued at rt for 45 min. The reaction mixture was partitioned between 15% n-Butanol/water (250 mL) and water (100 mL). The organic phase was separated, dried (Na₂SO₄) and evaporated. The crude compound was purified by reverse phase flash column chromatography (0-50% ACN in aqueous ammonium acetate (10 mM)) to provide Intermediate 104a as the first eluting peak (233 mg, 22%) and Intermediate 104b as the second eluting peak (277 mg, 26%). LCMS (FA): m/z=1078.3 (M−H).

Step 2: (1R,2S,3R,5R)-5-({[(R)-(2-cyanoethoxy)
({(2R,3S,4R,5R)-4-fluoro-5-(hydroxymethyl)-2-[2-
(isobutyrylamino)-6-oxo-1,6-dihydro-9H-purin-9-yl]
tetrahydrofuran-3-yl}oxy)phosphorothioyl]
oxy}methyl)-2-fluoro-3-(pyrimidin-4-ylamino)
cyclopentyl hydrogen phosphonate or (1R,2S,3R,5R)-5-({[(S)-(2-cyanoethoxy)({(2R,3S,
4R,5R)-4-fluoro-5-(hydroxymethyl)-2-[2-(isobutyry-
lamino)-6-oxo-1,6-dihydro-9H-purin-9-yl]tetrahy-
drofuran-3-yl}oxy)phosphorothioyl]oxy}methyl)-2-
fluoro-3-(pyrimidin-4-ylamino)cyclopentyl
hydrogen phosphonate, Intermediate 105a Intermediate 104a (233 mg, 0.216 mmol) was dissolved in acetic acid (4.00 mL) and water (1.00 mL) and allowed to stir at rt for 1 h. The solvents were evaporated and the residue was concentrated from toluene (3×). The crude compound was purified by reverse phase flash column chromatography (0-30% ACN in aqueous ammonium acetate (10 mM)) to provide Intermediate 105a (81 mg, 48%) LCMS (FA): m/z=778.2 (M+H).

Steps 3 and 4: 2-amino-9-[(2S,5R,7R,8S,10S,12aR,
14R,15S,15aR,16R)-15,16-difluoro-2,10-dioxido-
14-(pyrimidin-4-ylamino)-2,10-disulfanyldecahydro-
5,8-methanocyclopenta[l][1,3,6,9,11,2,10]
pentaoxadiphosphacyclotetradecin-7-yl]-1,9-
dihydro-6H-purin-6-one or 2-amino-9-[(2R,5R,7R,8S,10S,12aR,14R,15S,15aR,
16R)-15,16-difluoro-2,10-dioxido-14-(pyrimidin-4-
ylamino)-2,10-disulfanyldecahydro-5,8-methanocy-
clopenta [l][1,3,6,9,11,2,10]
pentaoxadiphosphacyclotetradecin-7-yl]-1,9-di-
hydro-6H-purin-6-one or 2-amino-9-[(2S,5R,7R,8S,10R,12aR,14R,15S,15aR,
16R)-15,16-difluoro-2,10-dioxido-14-(pyrimidin-4-
ylamino)-2,10-disulfanyldecahydro-5,8-methanocy-
clopenta [l][1,3,6,9,11,2,10]
pentaoxadiphosphacyclotetradecin-7-yl]-1,9-
dihydro-6H-purin-6-one or 2-amino-9-[(2R,5R,7R,8S,10R,12aR,14R,15S,15aR,
16R)-15,16-difluoro-2,10-dioxido-14-(pyrimidin-4-
ylamino)-2,10-disulfanyldecahydro-5,8-methanocy-
clopenta [l][1,3,6,9,11,2,10]
pentaoxadiphosphacyclotetradecin-7-yl]-1,9-
dihydro-6H-purin-6-one, I-38a The title compound was prepared from Intermediate 105a following the procedures described in Example 52, steps 2 and 3. LCMS (AA): m/z=669.1 (M+H). $^1$H NMR (MeOD) δ 8.57 (br s, 1H), 7.94-7.78 (m, 2H), 6.78 (d, J=6.8 Hz, 1H), 5.92-5.72 (m, 2H), 5.28 (d, J=55.8 Hz, 1H), 5.09 (d, J=52.5 Hz, 1H), 4.57-4.38 (m, 3H), 4.09 (br d, J=11.1 Hz, 1H), 4.00 (br d, J=9.3 Hz, 1H), 3.89 (br d, J=9.0 Hz, 1H), 2.58-2.41 (m, 3H), 1.58-1.48 (m, 1H). $^{31}$P NMR (MeOD) δ=55.86 (s, 1P), 55.44 (s, 1P).

Example 54A

The compound listed below (I-38b) was prepared as described in Example 54 starting with Step 2, substituting the starting material shown in the table for Intermediate 104a

| Compound | Salt Form | Starting Material | Final compound/ LCMS data | NMR data |
|---|---|---|---|---|
| I-38b | parent | Intermediate 104b | LCMS (AA): m/z = 669.1 (M + H) | $^1$H NMR (MeOD) δ 8.43 (s, 1H), 8.07-7.95 (m, 2H), 6.52 (br d, J = 5.9 Hz, 1H), 5.99 (d, J = 8.4 Hz, 1H), 5.81-5.66 (m, 1H), 0.00 (dd, J = 3.1, 54.3 Hz, 1H), 4.89-4.73 (m, 2H), 4.60-4.41 (m, 3H), 4.15-3.95 (m, 3H), 2.61-2.51 (m, 1H), 2.50-2.39 (m, 1H), 1.51 (ddd, J = 4.6, 8.5, 13.6 Hz, 1H); $^{31}$P NMR (MeOD) δ = 55.71 (s, 1P), 55.11 (s, 1P). |

Example 55

2-amino-9-[(2S,5R,7R,8R,10S,12aR,14R,15S,15aR,16R)-15-fluoro-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]pentaoxadiphosphacyclotetradecin-7-yl]-1,9-dihydro-6SH-purin-6-one or 2-amino-9-[(2S,5R,7R,8R,10R,12aR,14R,15S,15aR,16R)-15-fluoro-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]pentaoxadiphosphacyclotetradecin-7-yl]-1,9-dihydro-6SH-purin-6-one or 2-amino-9-[(2R,5R,7R,8R,10S,12aR,14R,15S,15aR,16R)-15-fluoro-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]pentaoxadiphosphacyclotetradecin-7-yl]-1,9-dihydro-6SH-purin-6-one or 2-amino-9-[(2R,5R,7R,8R,10R,12aR,14R,15S,15aR,16R)-15-fluoro-2,10-dioxido-14-(pyrimidin-4-yloxy)-2,10-disulfanyl-16-(2,2,2-trifluoroethoxy)decahydro-5,8-methanocyclopenta[l][1,3,6,9,11,2,10]pentaoxadiphosphacyclotetradecin-7-yl]-1,9-dihydro-6SH-purin-6-one, I-32a and I-32b

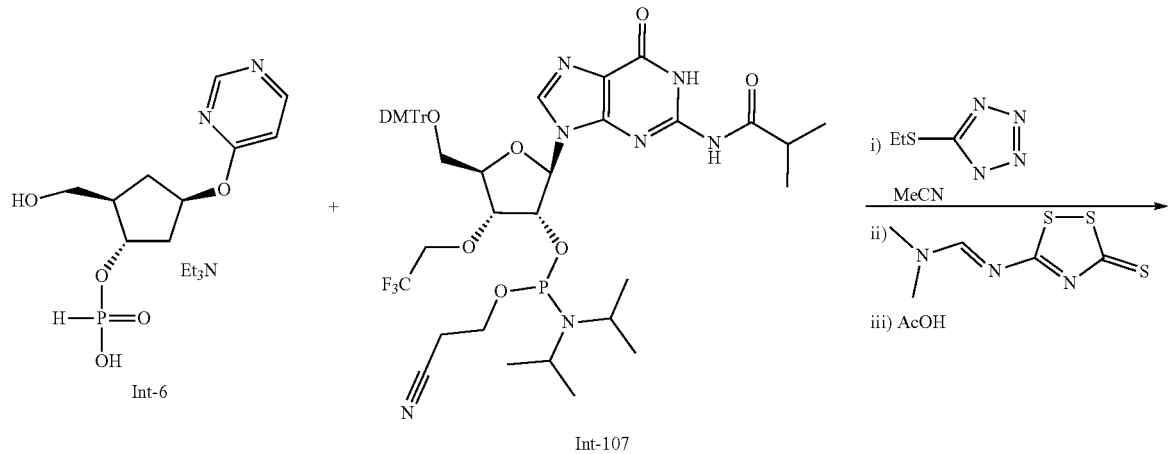

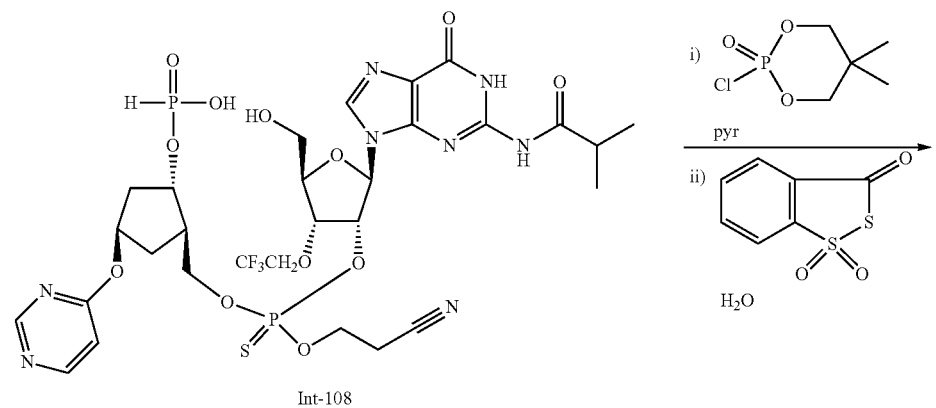

-continued

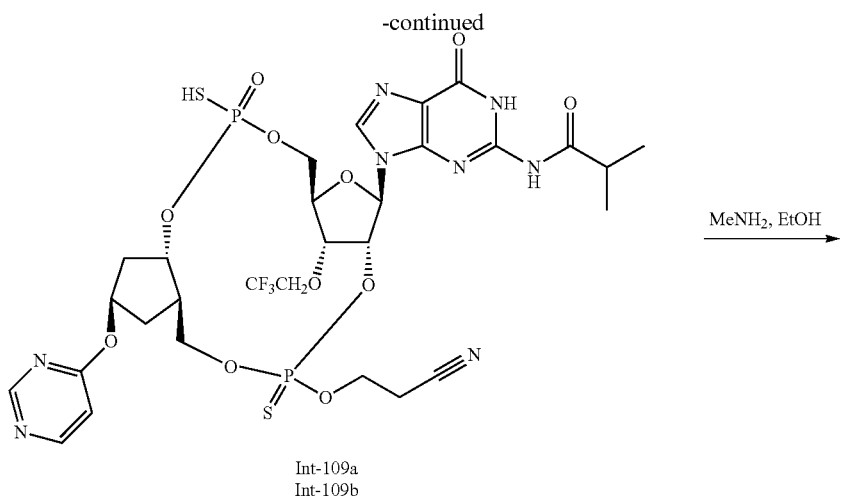

Int-109a
Int-109b

→ MeNH₂, EtOH

I-32a
I-32b

Step 1: (1S,2R,4R)-2-({[(R)-(2-cyanoethoxy){[(2R, 3R,4R,5R)-5-(hydroxymethyl)-2-[2-(isobutyrylamino)-6-oxo-1,6-dihydro-9H-purin-9-yl]-4-(2,2,2-trifluoroethoxy)tetrahydrofuran-3-yl]oxy}phosphorothioyl]oxy}methyl)-4-(pyrimidin-4-yloxy)cyclopentyl hydrogen phosphonate and (1S,2R,4R)-2-({[(S)-(2-cyanoethoxy){[(2R,3R,4R, 5R)-5-(hydroxymethyl)-2-[2-(isobutyrylamino)-6-oxo-1,6-dihydro-9H-purin-9-yl]-4-(2,2,2-trifluoroethoxy)tetrahydrofuran-3-yl]oxy}phosphorothioyl]oxy}methyl)-4-(pyrimidin-4-yloxy)cyclopentyl hydrogen phosphonate, Intermediate 108

The title compound was prepared following the procedure described in Example 31, step 1, substituting Intermediate 6 for Intermediate 23 and Intermediate 107 for N-[9-[(2R,3R,4R,5R)-5-[[bis(4-methoxyphenyl)-phenyl-methoxy]methyl]-4-[tert-butyl(dimethyl) silyl]oxy-3-[2-cyanoethoxy-(diisopropylamino)phosphanyl]oxy-tetrahydrofuran-2-yl]-6-oxo-1H-purin-2-yl]-2-methyl-propanamide to provide Intermediate 108 as a mixture of diastereomers. LCMS (AA): m/z=841.2 (M+H).

333

Step 2: N-{9-[(2S,5R,7R,8R,10R,12aR,14R,15aS, 16R)-10-(2-cyanoethoxy)-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10R,12aR,14R,15aS,16R)-10-(2-cyanoethoxy)-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2S,5R,7R,8R,10S,12aR,14R,15aS,16R)-10-(2-cyanoethoxy)-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10S,12aR,14R,15aS,16R)-10-(2-cyanoethoxy)-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 109a, Intermediate 109b The title compounds were prepared from Intermediate 108 following the procedure described in Example 31, step 2. Purification by silica gel chromatography (0-80% MeOH in EtOAc) provided Intermediate 109a as the first eluting product and Intermediate 109b as the second eluting product. LCMS (AA): m/z=855.2 (M+H).

Step 3: 2-amino-9-[(2R,5R,7R,8R,10S,12aR,14R, 15aS,16R)-10-hydroxy-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10R,12aR,14R,15aS, 16R)-10-hydroxy-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15aS, 16R)-10-hydroxy-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10S,12aR,14R,15aS, 16R)-10-hydroxy-2-oxido-14-(pyrimidin-4-yloxy)-2-sulfanyl-10-sulfido-16-(2,2,2-trifluoroethoxy)decahydro-5,8-methanocyclopenta[l][1,3,6,9,11,2,10]pentaoxadiphosphacyclotetradecin-7-yl]-1,9-dihydro-6H-purin-6-one I-32a and I-32b Intermediate 109a (63 mg, 0.074 mmol) was taken up in methylamine (33% in EtOH, 0.734 mL, 5.90 mmol) and the reaction mixture was allowed to stir at rt overnight. The reaction mixture was concentrated and purified by reverse phase flash column chromatography (0%-55% ACN in aq. ammonium acetate (10 mM)) to provide an impure product that was further purified by reverse phase flash column chromatography 10-100% ACN in aq. triethylammonium acetate (10 mM)) to provide I-32a as an N,Ndiethylethanamine salt (45 mg, 62%), LCMS (AA): m/z=732.1 (M+H). $^1$H NMR (D$_2$O) δ 8.69 (s, 1H), 8.45 (d, J=6.0 Hz, 1H), 8.15 (s, 1H), 6.93 (dd, J=1.1, 6.1 Hz, 1H), 6.05 (d, J=8.7 Hz, 1H), 5.59-5.47 (m, 2H), 5.14-5.07 (m, 1H), 4.63-4.57 (m, 1H), 4.54 (d, J=4.4 Hz, 1H), 4.52-4.23 (m, 3H), 4.18-4.08 (m, 2H), 3.89 (td, J=2.9, 10.5 Hz, 1H), 3.20 (q, J=7.3 Hz, 12H), 2.60-2.46 (m, 4H), 1.69-1.59 (m, 1H), 1.28 (t, J=7.3 Hz, 18H). $^{31}$P NMR (D$_2$O) δ 59.19 (s, 1P), 54.12 (s, 1P).

Intermediate 109b was treated in an analogous fashion to the above procedure to provide I-32b as an N,Ndiethylethanamine salt. LCMS (AA): m/z=732.1 (M+H). $^1$H NMR (D$_2$O) δ 8.69 (s, 1H), 8.46 (d, J=5.9 Hz, 1H), 8.07 (s, 1H), 6.87 (dd, J=1.0, 6.1 Hz, 1H), 6.04 (d, J=8.6 Hz, 1H), 5.61-5.51 (m, 1H), 5.46 (td, J=3.0, 6.1 Hz, 1H), 5.05-4.95 (m, 1H), 4.66 (d, J=4.3 Hz, 1H), 4.63-4.58 (m, 1H), 4.55-4.25 (m, 3H), 4.13 (ddd, J=1.7, 4.3, 12.2 Hz, 1H), 4.06-3.98 (m, 1H), 3.90 (td, J=7.1, 10.4 Hz, 1H), 3.20 (q, J=7.3 Hz, 12H), 2.61-2.46 (m, 3H), 2.43-2.34 (m, 1H), 1.70-1.59 (m, 1H), 1.28 (t, J=7.3 Hz, 18H). $^{31}$P NMR (D$_2$O) δ 54.18 (s, 1P), 53.39 (s, 1P).

Example 56

2-amino-9-{(2S,5R,7R,8R,10S,12aR,14R,15aS, 16R)-14-[(5-fluoropyrimidin-4-yl)amino]-16-hydroxy-2,10-dioxido-2,10-disulfanyldecahydro-5,8-methanocyclopenta [l][1,3,6,9,11,2,10] pentaoxadiphosphacyclotetradecin-7-yl}-1,9-dihydro-6H-purin-6-one or 2-amino-9-{(2S,5R,7R,8R,10R,12aR,14R,15aS, 16R)-14-[(5-fluoropyrimidin-4-yl)amino]-16-hydroxy-2,10-dioxido-2,10-disulfanyldecahydro-5,8-methanocyclopenta [l][1,3,6,9,11,2,10] pentaoxadiphosphacyclotetradecin-7-yl}-1,9-dihydro-6H-purin-6-one or 2-amino-9-{(2R,5R,7R,8R,10S,12aR,14R,15aS, 16R)-14-[(5-fluoropyrimidin-4-yl)amino]-16-hydroxy-2,10-dioxido-2,10-disulfanyldecahydro-5,8-methanocyclopenta [l][1,3,6,9,11,2,10] pentaoxadiphosphacyclotetradecin-7-yl}-1,9-dihydro-6H-purin-6-one or 2-amino-9-{(2R,5R,7R,8R,10R,12aR,14R,15aS, 16R)-14-[(5-fluoropyrimidin-4-yl)amino]-16-hydroxy-2,10-dioxido-2,10-disulfanyldecahydro-5,8-methanocyclopenta [l][1,3,6,9,11,2,10]pentaoxadiphosphacyclotetradecin-7-yl}-1,9-dihydro-6H-purin-6-one, I-34a and I-34b
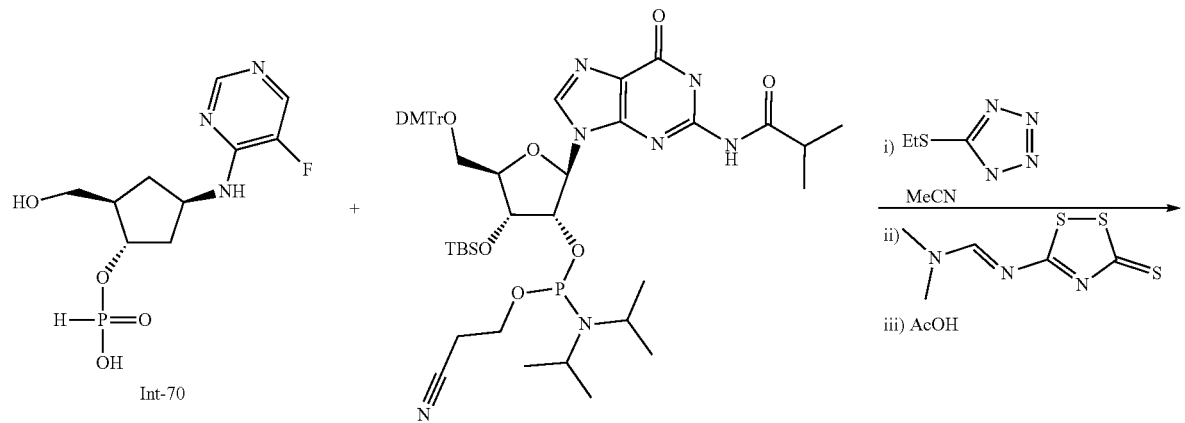
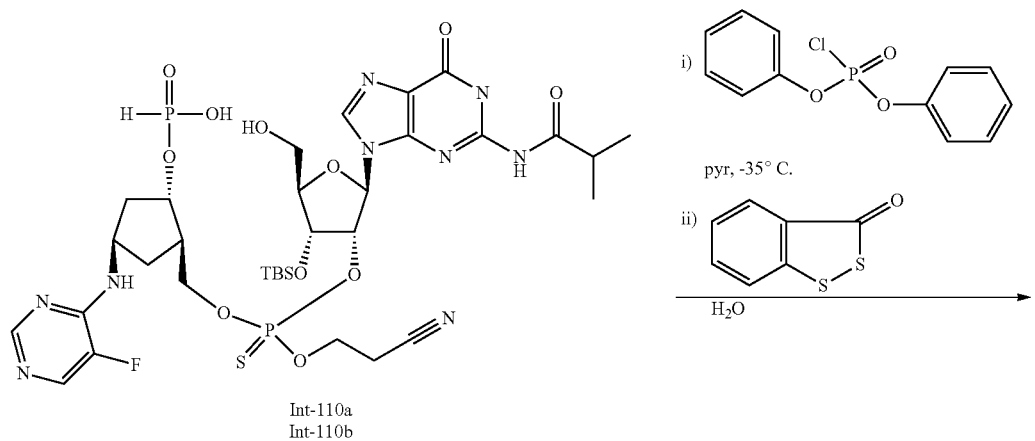
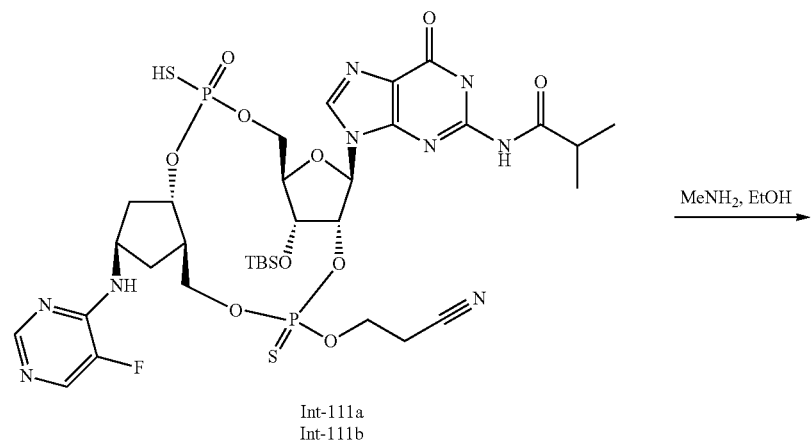

-continued

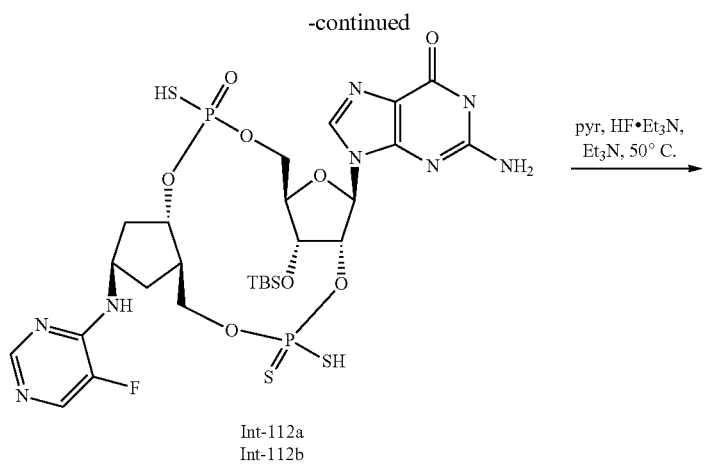

Int-112a
Int-112b

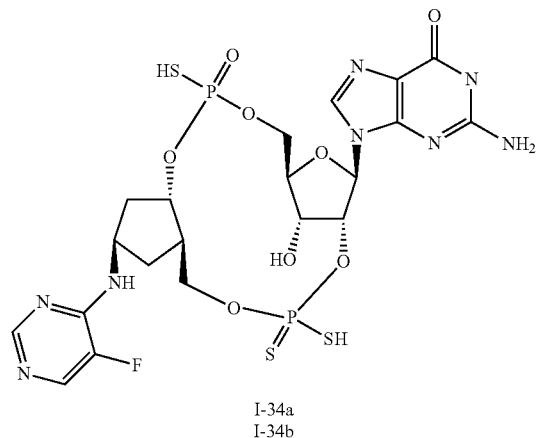

I-34a
I-34b

Step 1: (1S,2R,4R)-2-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl]oxy)(2-cyanoethoxy)phosphorothioyl]oxy}methyl)-4-[(5-fluoropyrimidin-4-yl)amino]cyclopentyl hydrogen phosphonate or (1S,2R,4R)-2-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-[(5-fluoropyrimidin-4-yl)amino]cyclopentyl hydrogen phosphonate, Intermediates 110a and 110b N-[9-[(2R,3R,4R,5R)-5-[[bis(4-methoxyphenyl)-phenyl-methyl]-4-[tert-butyl(dimethyl)silyl]oxy-3-[2-cyanoethoxy-(diisopropylamino)phosphanyl]oxy-tetrahydrofuran-2-yl]-6-oxo-1H-purin-2-yl]-2-methyl-propanamide (1.35 g, 1.39 mmol) and Intermediate 70 (350 mg, 1.20 mmol) were dissolved in dry acetonitrile and concentrated to dryness (3×50 mL) and dried under vacuum for 1 h, then suspended in ACN (4.78 mL) under an atmosphere of argon. Separately, 5-(ethylthio)-1H-tetrazole (510 mg, 3.92 mmol) was dissolved in dry acetonitrile and concentrated to dryness (3×20 mL), dried under vacuum for 1 h, dissolved in ACN (2.18 mL) and added to the reaction mixture. The reaction mixture was allowed to stir at rt for 40 min. ((Dimethyl-amino-methylidene)amino)-3H-1,2,4-dithiazoline-3-thione (321 mg, 1.56 mmol) was added and the reaction mixture was allowed to stir at rt for 45 min. The reaction mixture was concentrated and the residue was dried under vacuum for 10 min. To the residue was added acetic acid (5.18 mL) and water (1.3 mL) and the reaction mixture was allowed to stir at rt for 30 min. The reaction mixture was concentrated and the residue was concentrated from toluene and dried under vacuum. The crude compound was purified by silica gel chromatography (25-50% MeOH in DCM) to provide a mixture of Intermediate 110a and Intermediate 110b which was further purified by silica gel chromatography (0-85% MeOH in DCM) to provide Intermediate 110a (340 mg, 32%) as the first eluting peak and Intermediate 110b (161 mg, 15%) as the second eluting peak. LCMS (FA): m/z=890.3 (M+H).

Step 2: N-(9-{(2S,5R,7R,8R,10R,12aR,14R,15aS,16R)-16-{[tert-butyl(dimethyl)silyl]oxy}-10-(2-cyanoethoxy)-14-[(5-fluoropyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide or N-(9-{(2S,5R,7R,8R,10S,12aR,14R,15aS,16R)-16-{[tert-butyl(dimethyl)silyl]oxy}-10-(2-cyanoethoxy)-14-[(5-fluoropyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide or N-(9-{(2R,5R,7R,8R,10R,12aR,14R,15aS,16R)-16-{[tert-butyl(dimethyl)silyl]oxy}-10-(2-cyanoethoxy)-14-[(5-fluoropyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide or N-(9-{(2R,5R,7R,8R,10S,12aR,14R,15aS,16R)-16-{[tert-butyl(dimethyl)silyl]oxy}-10-(2-cyanoethoxy)-14-[(5-fluoropyrimidin-4-yl)amino]-2-oxido-2-sulfanyl-10-sulfidodecahydro-5,8-methanocyclopenta[l][1,3,6,9,11,2,10]pentaoxadiphosphacyclotetradecin-7-yl}-6-oxo-6,9-dihydro-1H-purin-2-yl)-2-methylpropanamide, Intermediate 111a A solution of diphenyl chlorophosphate (2.15 g, 8.00 mmol) in pyridine (22 mL) at −30° C. was added to a solution of Intermediate 110a (330 mg, 0.37 mmol) in DCM (8.8 mL) and pyridine (4.4 mL) at −30° C. dropwise over 20 min. The resulting mixture was stirred at −35° C. for 40 min. 3H-1,2-benzodithiol-3-one (132 mg, 0.78 mmol) and water (0.176 mL) were added at −30° C. The mixture was allowed to stir at rt for 1 h. Sodium thiosulfate (1.76 g, 10.8 mmol) in water was added at 0° C. and the reaction mixture was allowed to stir for 5 min at rt. The solvents were evaporated and the crude residue was purified by reverse phase flash column chromatography (10-100% ACN in aqueous ammonium acetate (10 mM)) to provide Intermediate 111a (179 mg, 53%). LCMS (FA): m/z=904.3 (M+H).

Step 3: 2-amino-9-{(2S,5R,7R,8R,10S,12aR,14R,15aS,16R)-16-{[tert-butyl (dimethyl)silyl]oxy}-14-[(5-fluoropyrimidin-4-yl)amino]-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one or 2-amino-9-{(2R,5R,7R,8R,10S,12aR,14R,15aS,16R)-16-{[tert-butyl(dimethyl)silyl]oxy}-14-[(5-fluoropyrimidin-4-yl)amino]-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one or 2-amino-9-{(2S,5R,7R,8R,10R,12aR,14R,15aS,16R)-16-{[tert-butyl(dimethyl)silyl]oxy}-14-[(5-fluoropyrimidin-4-yl)amino]-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one or 2-amino-9-{(2R,5R,7R,8R,10R,12aR,14R,15aS,16R)-16-{[tert-butyl(dimethyl)silyl]oxy}-14-[(5-fluoropyrimidin-4-yl)amino]-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one, Intermediate 112a The title compound was prepared from Intermediate 111a using the conditions described for Example 23, step 3. LCMS (FA): m/z=781.3 (M+H).

Step 4: 2-amino-9-{(2S,5R,7R,8R,10S,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one or 2-amino-9-{(2S,5R,7R,8R,10R,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one or 2-amino-9-{(2R,5R,7R,8R,10S,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one or 2-amino-9-{(2R,5R,7R,8R,10R,12aR,14R,15aS,16R)-14-[(5-fluoropyrimidin-4-yl)amino]-16-hydroxy-2,10-dioxido-2,10-disulfanyldecahydro-5,8-methanocyclopenta[l][1,3,6,9,11,2,10]pentaoxadiphosphacyclotetradecin-7-yl}-1,9-dihydro-6H-purin-6-one, I-34a The title compound was prepared from Intermediate 112a using the conditions described for Example 23, step 4. LCMS (AA): m/z=667.1 (M+H). $^1$H NMR (D$_2$O) δ 8.24 (d, J=2.0 Hz, 1H), 8.04 (s, 1H), 7.95 (d, J=3.8 Hz, 1H), 6.01 (d, J=8.4 Hz, 1H), 5.52 (dt, J=4.1, 8.9 Hz, 1H), 5.00 (td, J=6.4, 12.9 Hz, H), 4.54-4.43 (m, 3H), 4.43-4.35 (m, 1H), 4.16-4.10 (m, 1H), 4.09-4.03 (m, 1H), 3.95-3.88 (m, 1H), 3.20 (q, J=7.3 Hz, 12H), 2.54-2.41 (m, 2H), 2.30 (t, J=6.2 Hz, 2H), 1.51-1.40 (m, 1H), 1.28 (t, J=7.3 Hz, 18H). $^{31}$P NMR (0.20) δ 53.95 (s, 1P), 52.55 (s, 1P).

Example 56A

The compound listed below (I-34b) was prepared as described in Example 56 starting with Step 2, substituting the starting material shown in the table for Intermediate 110a

| Compound | Salt Form | Starting Material | Final compound/ LCMS data | NMR data |
|---|---|---|---|---|
| I-34b | Et₃N | Intermediate 110b | 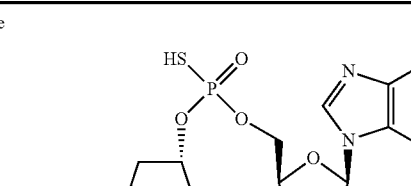<br>LCMS (AA): m/z = 667.2 (M + H) | $^1$H NMR (MeOD) δ 8.36 (s, 1H), 8.24 (d, J = 2.0 Hz, 1H), 7.97 (d, J = 3.9 Hz, 1H), 6.06 (d, J = 8.6 Hz, 1H), 5.43 (ddd, J = 4.3, 8.4, 12.2 Hz, 1H), 5.21-5.14 (m, 2H), 4.87-4.76 (m, 1H), 4.54 (d, J = 4.2 Hz, 1H), 4.34-4.23 (m, 2H), 4.13 (q, J = 10.8 Hz, 1H), 4.02-3.95 (m, 1H), 3.78-3.71 (m, 1H), 3.23-3.14 (q J = 7.2 Hz, 12H), 2.65-2.58 (m, 1H), 2.54-2.44 (m, 2H), 1.29 (t, J = 7.3 Hz, 18H), 1.10-1.01 (m, 1H); $^{31}$P NMR (MeOD) δ 61.41 (s, 1P), 55.22 (s, 1P). |

Example 57

N-[7-[(2R,3R,4S,5R)-3,4-dihydroxy-5-(hydroxymethyl)tetrahydrofuran-2-yl]-4-oxo-3H-pyrrolo[2,3-d]pyrimidin-2-yl]-2-methyl-propanamide, Intermediate 113

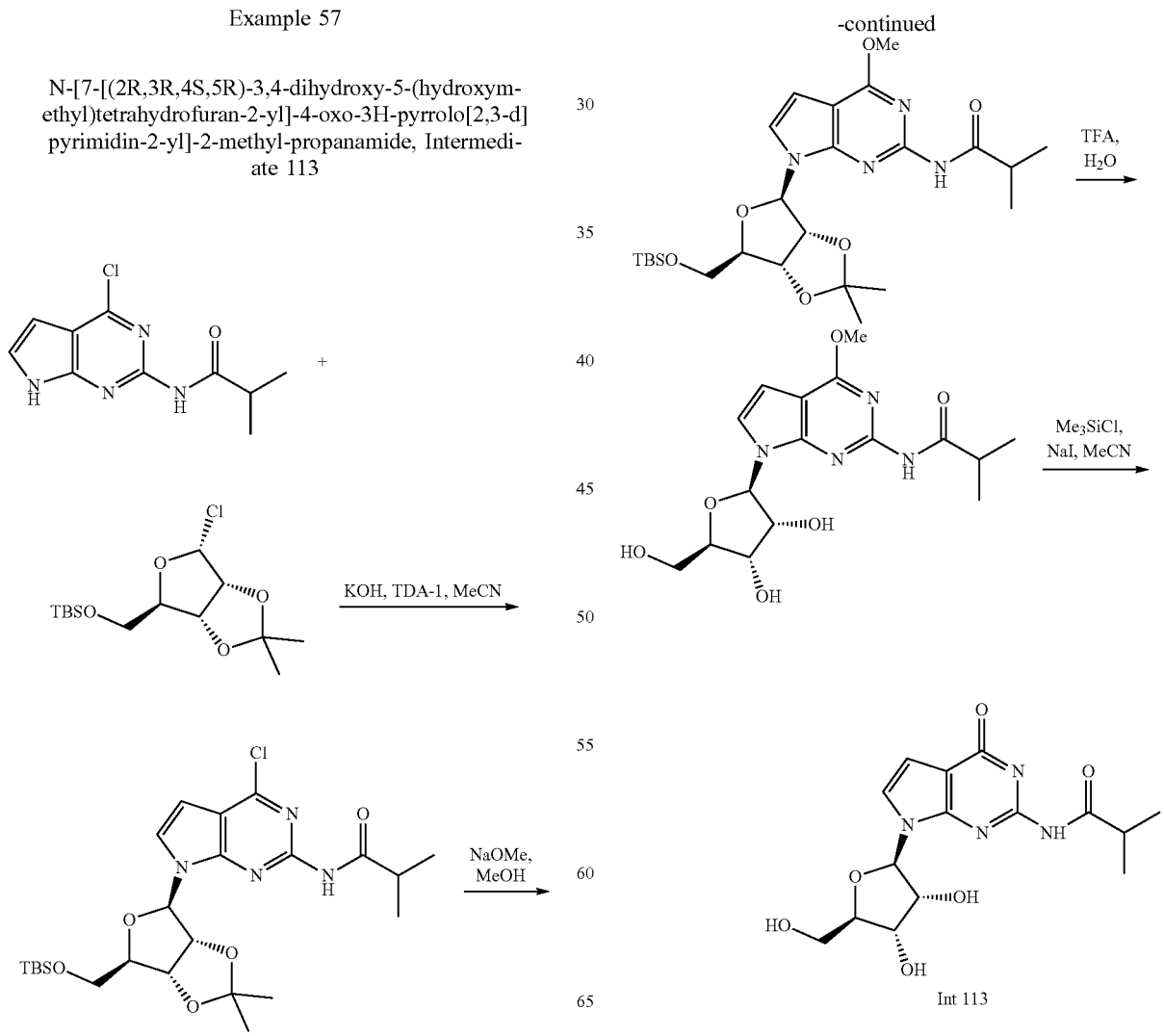

Step 1: N-[7-[(3aR,4R,6R,6aR)-6-[[tert-butyl(dimethyl)silyl]oxymethyl]-2,2-dimethyl-3a,4,6,6a-tetrahydrofuro[3,4-d][1,3]dioxol-4-yl]-4-chloro-pyrrolo[2,3-d]pyrimidin-2-yl]-2-methyl-propanamide A solution of [(3aR,4R,6R,6aR)-4-chloro-2,2-dimethyl-3a,4,6,6a tetrahydrofuro[3,4-d][1,3]dioxol-6-yl]methoxy-tert-butyl-dimethyl-silane (53.9 g, 167 mmol) in ACN (500 mL) was added to a vigorously stirred suspension of N-(4-chloro-7H-pyrrolo[2,3-d]pyrimidin-2-yl)isobutyramide (20.0 g, 83.7 mmol), Powdered KOH (9.37 g, 167 mmol), and TDA-1 (13.3 mL, 41.8 mmol) in ACN (100 mL). The mixture was stirred for 16 h. at rt. The reaction mixture was combined with another reaction carried out on the same scale and was filtered. The organic phase was quenched with sat. NH$_4$C$_1$ solution (500 mL), and extracted with DCM (1 L×3). The combined organic extracts were dried over Na$_2$SO$_4$, filtered, evaporated, and the crude residue was purified by silica gel chromatography (20:1 to 7:1 PE:EtOAc) to provide the title compound as a yellow oil (37.5 g, 38.4%). $^1$H NMR (DMSO-d$_6$) δ 10.72-10.77 (m, 1H), 7.66-7.76 (m, 1H), 6.57-6.69 (m, 1H), 6.21-6.26 (m, 1H), 5.42-5.48 (m, 1H), 5.25-5.31 (m, 1H), 4.73-4.76 (m, 1H), 4.37-4.41 (m, 1H), 4.16-4.20 (m, 1H), 4.08-4.14 (m, 1H), 3.62-3.71 (m, 2H), 2.75-2.85 (m, 1H), 1.51-1.57 (m, 3H), 1.35 (s, 3H), 1.09-1.14 (m, 6H).

Step 2: N-[7-[(3aR,4R,6R,6aR)-6-[[tert-butyl(dimethyl)silyl]oxymethyl]-2,2-dimethyl-3a,4,6,6a-tetrahydrofuro[3,4-d][1,3]dioxol-4-yl]-4-methoxy-pyrrolo[2,3-d]pyrimidin-2-yl]-2-methyl-propanamide To a mixture of N-[7-[(3aR,4R,6R,6aR)-6-[[tert-butyl(dimethyl)silyl]oxymethyl]-2,2-dimethyl-3a,4,6,6a-tetrahydrofuro[3,4-d][1,3]dioxol-4-yl]-4-chloro-pyrrolo[2,3-d]pyrimidin-2-yl]-2-methyl-propanamide (47.5 g, 90.4 mmol) in MeOH (80 mL) was added NaOMe (24.3 g, 135 mmol, 30% in MeOH) and the reaction mixture was allowed to stir at rt for 3 h. The reaction mixture was adjusted to pH7 by the addition of 1N HCl. Water (60 mL) was added and the mixture was extracted with DCM (600 mL×3). The combined organic phases were dried over Na$_2$SO$_4$, filtered and concentrated. The crude residue was purified by silica gel chromatography (20:1 to 4:1 PE:EtOAc) to provide the title compound as colorless oil (37.0 g, 55%). The product was used directly in the next step without purification.

Step 3: N-[7-[(2R,3R,4S,5R)-3,4-dihydroxy-5-(hydroxymethyl)tetrahydrofuran-2-yl]-4-methoxy-pyrrolo[2,3-d]pyrimidin-2-yl]-2-methyl-propanamide N-[7-[(3aR,4R,6R,6aR)-6-[[tert-butyl(dimethyl)silyl]oxymethyl]-2,2-dimethyl-3a,4,6,6a-tetrahydrofuro[3,4-d][1,3]dioxol-4-yl]-4-methoxy-pyrrolo[2,3-d]pyrimidin-2-yl]-2-methyl-propanamide (37.0 g, 49.7 mmol) was added to TFA/H$_2$O (9:1, 150 mL) at rt. The solution was allowed to stir for 30 min. The volatiles were removed in vacuo, and the residue co-evaporated several times with MeOH. The residue was purified by silica gel chromatography (DCM/MeOH 20:1-5:1) to provide the title compound as sticky solid (18.0 g, 72.5%), $^1$H NMR (DMSO-d$_6$) δ 10.22 (s, 1H), 7.48 (d, J=3.5 Hz, 1H), 6.49 (d, J=3.5 Hz, 1H), 6.07 (d, J=6.4 Hz, 1H), 4.40 (t, J=5.7 Hz, 1H), 4.10 (dd, J=4.9, 3.0 Hz, 1H), 4.03 (s, 3H), 3.87 (br d, J=3.1 Hz, 1H), 3.55 (m 2H), 2.80-2.92 (m, 1H), 1.06-1.12 (m, 6H).

Step 4: N-[7-[(2R,3R,4S,5R)-3,4-dihydroxy-5-(hydroxymethyl)tetrahydrofuran-2-yl]-4-oxo-3H-pyrrolo[2,3-d]pyrimidin-2-yl]-2-methyl-propanamide, Intermediate 113

To a solution of N-[7-[(2R,3R,4S,5R)-3,4-dihydroxy-5-(hydroxymethyl)tetrahydrofuran-2-yl]-4-methoxy-pyrrolo[2,3-d]pyrimidin-2-yl]-2-methyl-propanamide (18.0 g, 36.0 mmol) in ACN (180 mL) was added NaI (8.09 g, 54.0 mmol) and Me$_3$SiCl (6.06 g, 55.8 mmol). The mixture was allowed to stir at rt for 16 h. The reaction mixture was concentrated and purified by prep-HPLC to provide the title compound as a yellow solid (5.34 g, 40.9%). $^1$H NMR (MeOD) δ 7.29 (d, J=3.8 Hz, 1H), 6.62 (d, J=3.8 Hz, 1H), 6.16 (d, J=5.5 Hz, 1H), 4.41 (t, J=5.4 Hz, 1H), 4.28 (dd, J=5.1, 4.1 Hz, 1H), 4.03 (q, J=3.7 Hz, 1H), 3.80-3.86 (m, 1H), 3.71-3.78 (m, 1H), 2.67-2.78 (m, 1H), 1.24 (d, J=6.8 Hz, 6H).

Example 58

3-[(1R,2S,3R,4R)-2,3-dihydroxy-4-(hydroxymethyl)cyclopentyl]-6H-triazolo[4,5-d]pyrimidin-7-one, Intermediate 115

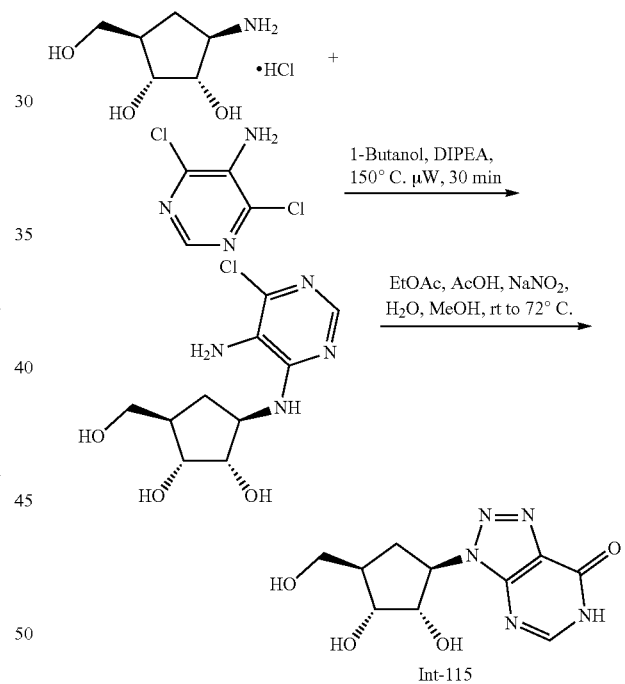

Int-115

Step 1: (1R,2S,3R,5R)-3-((5-amino-6-chloropyrimidin-4-yl)amino)-5-(hydroxymethyl)cyclopentane-1,2-diol To a 20-mL microwave vial was added (1R,2S,3R,4R)-2,3-Dihydroxy-4-(hydroxymethyl)-1-aminocyclopentane hydrochloride (1.66 g, 9.04 mmol), 5-amino-4,6-dichloropyrimidine (1.78 g, 10.9 mmol), 1-butanol (8.0 mL), and DIPEA (3.15 mL, 22.6 mmol). The reaction mixture was heated at 150° C. under microwave irradiation for 30 min. The reaction mixture was combined with two more batches on the same scale and the solvents were evaporated, then concentrated from toluene (3×150 mL) to provide the title compound which was used without further purification. LCMS (FA): m/z=275.1 (M+H).

Step 2: 3-[(1R,2S,3R,4R)-2,3-dihydroxy-4-(hydroxymethyl)cyclopentyl]-6H-triazolo[4,5-d]pyrimidin-7-one (1R,2S,3R,5R)-3-((5-amino-6-chloropyrimidin-4-yl)amino)-5-(hydroxymethyl)cyclopentane-1,2-diol (7.45 g, 27.1 mmol) was suspended in EtOAc (100 mL), methanol (100 mL), acetic acid (20.0 mL) and water (40 mL). Sodium nitrite (2.80 g, 41.0 mmol) was added. The reaction mixture was allowed to stir at rt for 7 h and then then heated at 72° C. for 16 h. The solvents were evaporated, and the residue was concentrated from toluene (2×100 mL). The crude compound was purified by silica gel chromatography (1:0 to 4:1 DCM: MeOH) to provide the title compound (Intermediate 115, 5.40 g, 75%). LCMS (FA): m/z=268.2 (M+H).

Example 59

N-[3-[(2R,3R,4S,5R)-3,4-dihydroxy-5-(hydroxymethyl)tetrahydrofuran-2-yl]-7-oxo-6H-triazolo[4,5-d]pyrimidin-5-yl]-2-methyl-propanamide, Intermediate 117

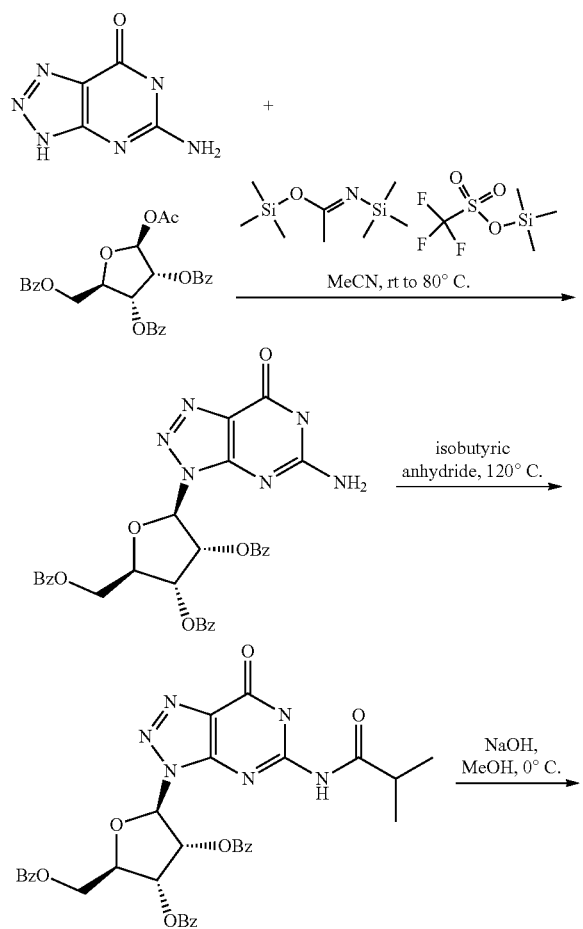

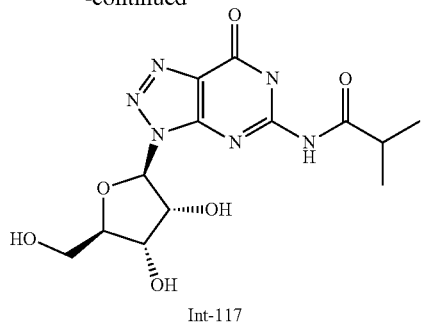

Int-117

Step 1: [(2R,3R,4R,5R)-5-(5-amino-7-oxo-6H-triazolo[4,5-d]pyrimidin-3-yl)-3,4-dibenzoyloxy-tetrahydrofuran-2-yl]methyl benzoate To a suspension of 8-azaguanine (980 mg, 6.44 mmol) in dry ACN (27.0 mL) under argon was added sequentially N,O-bis(trimethylsilyl)acetamide (3.93 g, 19.3 mmol), [(2R,3R,4R,5S)-5-acetoxy-3,4-dibenzoyloxy-tetrahydrofuran-2-yl]methyl benzoate (3.56 g, 7.06 mmol) and trimethylsilyl trifluoromethanesulfonate (2.86 g, 12.9 mmol). The reaction mixture was allowed to stir at rt for 15 min and then heated at 80° C. for 1 h. The reaction mixture was allowed to cool to rt and the solvents were evaporated. The residue was partitioned between EtOAc and sat. NaHCO$_3$ solution and the phases were separated. The organic phase was washed with water and brine, dried over Na$_2$SO$_4$, filtered and concentrated. The residue was adsorbed onto Celite. The crude mixture was purified by silica gel chromatography (0-7% MeOH/DCM) to provide [(2R,3R,4R,5R)-5-(5-amino-7-oxo-6H-triazolo[4,5-d]pyrimidin-3-yl)-3,4-dibenzoyloxy-tetrahydrofuran-2-yl]methyl benzoate as a yellow solid (2.30 g, 57%). LCMS (AA): m/z=597.2 (M+H).

Step 2: [(2R,3R,4R,5R)-3,4-dibenzoyloxy-5-[5-(2-methylpropanoylamino)-7-oxo-6H-triazolo[4,5-d]pyrimidin-3-yl]tetrahydrofuran-2-yl]methyl benzoate

[(2R,3R,4R,5R)-5-(5-amino-7-oxo-6H-triazolo[4,5-d]pyrimidin-3-yl)-3,4-dibenzoyloxy-tetrahydrofuran-2-yl]methyl benzoate (2.30 g, 3.70 mmol) was concentrated from dry toluene (3×20 mL), then isobutyric anhydride (1.02 mL, 73 mmol) was added and the reaction mixture was heated at 120° C. for 16 h. Additional isobutyric anhydride (6.10 mL, 37 mmol) was added and heating continued for 4 h, mixture was then allowed to cool to rt. EtOAc was added and the mixture was washed with 1:1 water/brine, sat. NaHCO$_3$ and brine. Organic extract was dried over Na$_2$SO$_4$, filtered and concentrated. The crude mixture was purified by silica gel chromatography (0-60% EtOAc/hexane) to provide [(2R,3R,4R,5R)-3,4-dibenzoyloxy-5-[5-(2-methylpropanoylamino)-7-oxo-6H-triazolo[4,5-d]pyrimidin-3-yl]tetrahydrofuran-2-yl]methyl benzoate as a yellow foam (2.29 g, 89%). LCMS (AA): m/z=667.2 (M+H).

Step 3: N-[3-[(2R,3R,4S,5R)-3,4-dihydroxy-5-(hydroxymethyl)tetrahydrofuran-2-yl]-7-oxo-6H-triazolo[4,5-d]pyrimidin-5-yl]-2-methyl-propanamide, Intermediate 117

[(2R,3R,4R,5R)-3,4-dibenzoyloxy-5-[5-(2-methylpropanoylamino)-7-oxo-6H-triazolo[4,5-d]pyrimidin-3-yl]tetrahydrofuran-2-yl]methyl benzoate (4.70 g, 7.0 mmol) was dissolved in THF (32 mL) and MeOH (25 mL) and the reaction mixture was cooled to 0° C. NaOH solution (1.0 N, 25 mL, 25 mmol) was added and the reaction mixture was allowed to stir at 0° C. for 30 min. The reaction mixture was concentrated, concentrated from toluene (3×) and adsorbed onto Celite. The crude mixture was purified by reverse phase flash column chromatography (0-100% ACN in aqueous ammonium acetate (10 mM)) to provide N-[3-[(2R,3R,4S,5R)-3,4-dihydroxy-5-(hydroxymethyl)tetrahydrofuran-2-yl]-7-oxo-6H-triazolo[4,5-d]pyrimidin-5-yl]-2-methyl-propanamide, Intermediate 117 as a white solid (2,14 g, 86%). LCMS (AA): m/z=355.1 (M+H).

Example 60

5-amino-3-[(2S,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2S,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d] pyrimidin-7-one or 5-amino-3-[(2R,5R,7R,8R,10S,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS,16R)-16-hydroxy-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one, I-30a I-30b I-30c I-30d

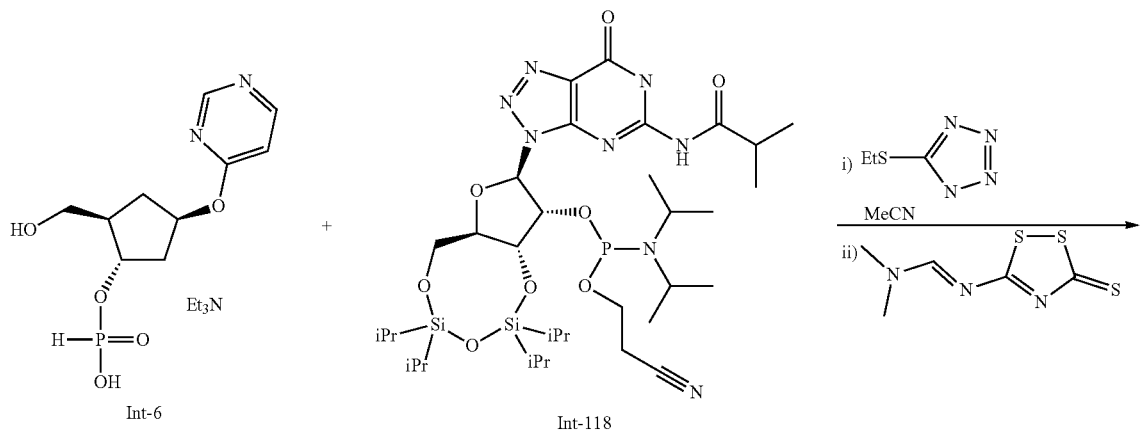

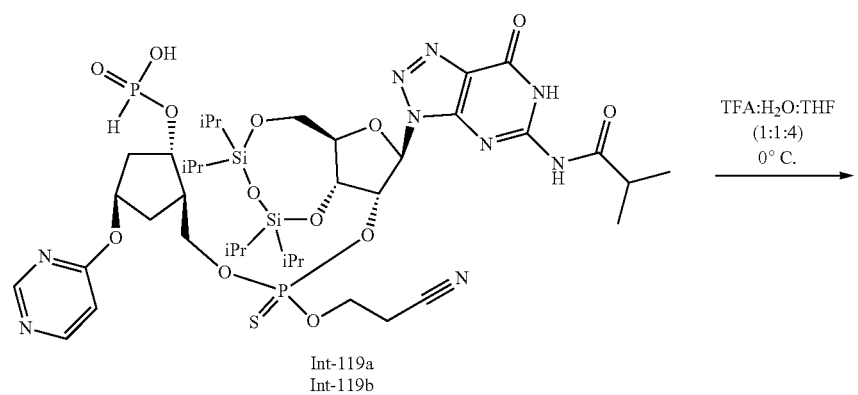

-continued
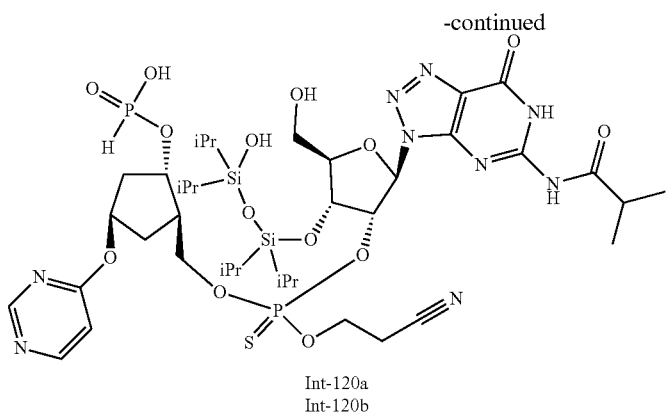
Int-120a
Int-120b
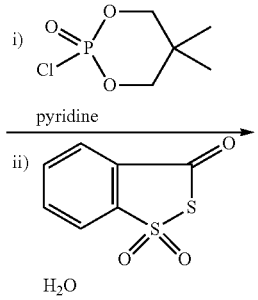
i) pyridine
ii) H₂O
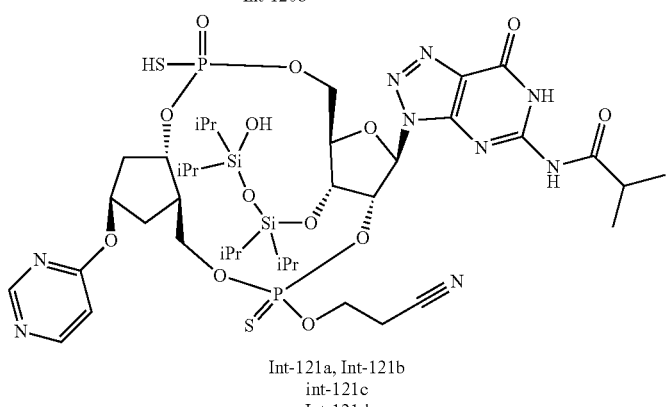
Int-121a, Int-121b
int-121c
Int-121d
MeNH₂, EtOH
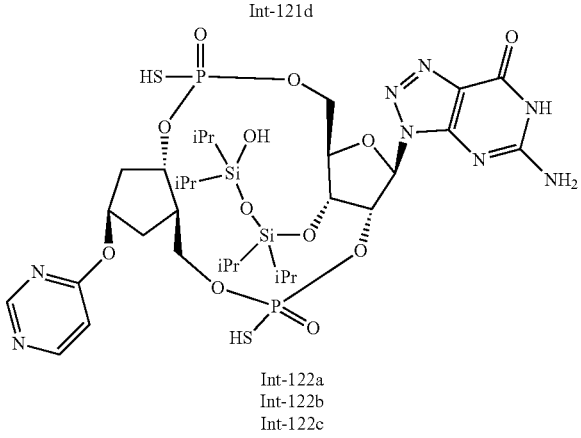
Int-122a
Int-122b
Int-122c
Int-122d
pyr, HF-Et₃N,
Et₃N, 50° C.
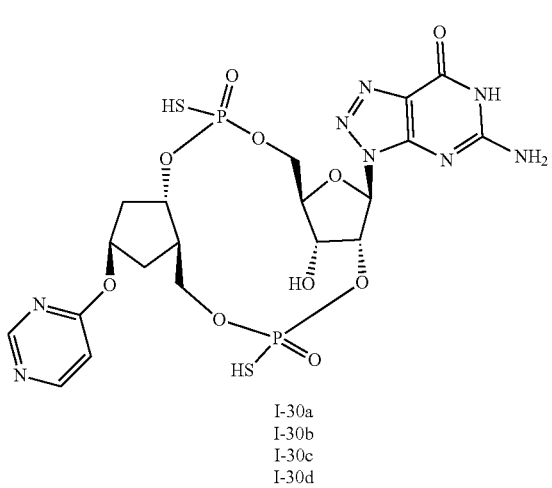
I-30a
I-30b
I-30c
I-30d Step 1: (1S,2R,4R)-2-({[(R)-(2-cyanoethoxy)
({(6aR,8R,9R,9aR)-8-[5-(isobutyrylamino)-7-oxo-6,
7-dihydro-3H-[1,2,3]triazolo[4,5-d]pyrimidin-3-yl]-
2,2,4,4-tetraisopropyltetrahydro-6H-furo[3,2-f][1,3,
5,2,4]trioxadisilocin-9-yl}oxy)phosphorothioyl]
oxy}methyl)-4-(pyrimidin-4-yloxy)cyclopentyl
hydrogen phosphonate and (1S,2R,4R)-2-({[(S)-(2-cyanoethoxy)({(6aR,8R,9R,
9aR)-8-[5-(isobutyrylamino)-7-oxo-6,7-dihydro-3H-
[1,2,3]triazolo[4,5-d]pyrimidin-3-yl]-2,2,4,4-tet-
raisopropyltetrahydro-6H-furo[3,2-f][1,3,5,2,4]
trioxadisilocin-9-yl}oxy)phosphorothioyl]
oxy}methyl)-4-(pyrimidin-4-yloxy)cyclopentyl
hydrogen phosphonate, Intermediate 119a and 119b A mixture of Intermediate 6 TEA salt (345 mg, 0.919 mmol) and Intermediate 118 (947 mg, 1.19 mmol) was dissolved in dry acetonitrile and concentrated to dryness (3×~5 mL). The residue was then dissolved in ACN (3.37 mL) under an atmosphere of argon. In a separate flask, 5-(ethylthio)-1H-tetrazole (359 mg, 2.76 mmol) was dissolved in dry acetonitrile and concentrated to dryness (3×~2 mL), dissolved in ACN (1.69 mL) and added to the reaction mixture. The reaction mixture was allowed to stir at rt for 1 h.
((Dimethylamino-methylidene)amino)-3H-1,2,4-dithiazoline-3-thione (226 mg, 1.10 mmol) was added and stirring was continued at rt for 1 h. The reaction mixture was concentrated and the residue was dissolved in DCM and washed with sat. NaHCO$_3$. The aqueous phase was separated and further extracted with DCM (3×). The combined organic phases were dried over Na$_2$SO$_4$, filtered and concentrated. The crude material was purified by silica gel chromatography (5-50% MeOH in EtOAc) to provide the first eluting diastereomer Intermediate 119a as a slightly impure pale yellow solid (267 mg, 29%) and the second eluting diastereomer Intermediate 119b as a while solid (269 mg, 29%). LCMS (AA): m/z=1002.3 (M+H).

Step 2: (1S,2R,4R)-2-({[(R)-(2-cyanoethoxy)({(2R,
3R,4R,5R)-5-(hydroxymethyl)-4-[(3-hydroxy-1,1,3,
3-tetraisopropyldisiloxanyl)oxy]-2-[5-(isobutyry-
lamino)-7-oxo-6,7-dihydro-3H-[1,2,3]triazolo[4,5-d]
pyrimidin-3-yl]tetrahydrofuran-3-yl}oxy)
phosphorothioyl]oxy}methyl)-4-(pyrimidin-4-yloxy)
cyclopentyl hydrogen phosphonate and (1S,2R,4R)-2-({[(S)-(2-cyanoethoxy)({(2R,3R,4R,
5R)-5-(hydroxymethyl)-4-[(3-hydroxy-1,1,3,3-tet-
raisopropyldisiloxanyl)oxy]-2-[5-(isobutyrylamino)-
7-oxo-6,7-dihydro-3H-[1,2,3]triazolo[4,5-d]
pyrimidin-3-yl]tetrahydrofuran-3-yl}oxy)
phosphorothioyl]oxy}methyl)-4-(pyrimidin-4-yloxy)
cyclopentyl hydrogen phosphonate Intermediate
120a and 120b Intermediate 119a (412 mg, 0.411 mmol) was taken up in THF (4.60 mL) and water (1.20 mL). The solution was cooled to 0° C. and TFA (1.20 mL, 15.0 mmol) was added dropwise. The reaction mixture was allowed to stir at 0° C. for 90 min. Sodium bicarbonate (1.87 g, 22.2 mmol) was added portion-wise, followed by water and EtOAc. The reaction mixture was allowed to warm to rt and extracted into EtOAc (3×). The combined organic phases were washed with brine, dried with Na$_2$SO$_4$, filtered and concentrated. The crude material was adsorbed onto Celite and purified by silica gel chromatography (0-20% MeOH in EtOAc) to provide Intermediate 120a (243 mg, 58%). LCMS (AA): m/z=1020.3 (M+H).
Intermediate 120b was prepared from Intermediate 119b following the procedure described above for Intermediate 120a LCMS (AA): m/z=1020.3 (M+H).

Step 3: N-{3-[(2S,5R,7R,8R,10R,12aR,14R,15aS,
16R)-10-(2-cyanoethoxy)-16-[(3-hydroxy-1,1,3,3-
tetraisopropyldisiloxanyl)oxy]-2-oxido-14-(pyrimi-
din-4-yloxy)-2-sulfanyl-10-sulfidodecahydro-5,8-
methanocyclopenta[l][1,3,6,9,11,2,10]
pentaoxadiphosphacyclotetradecin-7-yl]-7-oxo-6,7-
dihydro-3H-[1,2,3]triazolo[4,5-d]pyrimidin-5-yl}-2-
methylpropanamide or N-{3-[(2S,5R,7R,8R,10S,12aR,14R,15aS,16R)-10-
(2-cyanoethoxy)-16-[(3-hydroxy-1,1,3,3-tetraisopro-
pyldisiloxanyl)oxy]-2-oxido-14-(pyrimidin-4-
yloxy)-2-sulfanyl-10-sulfidodecahydro-5,8-
methanocyclopenta[l][1,3,6,9,11,2,10]
pentaoxadiphosphacyclotetradecin-7-yl]-7-oxo-6,7-
dihydro-3H-[1,2,3]triazolo[4,5-d]pyrimidin-5-yl}-2-
methylpropanamide or N-{3-[(2R,5R,7R,8R,10R,12aR,14R,15aS,16R)-10-
(2-cyanoethoxy)-16-[(3-hydroxy-1,1,3,3-tetraisopro-
pyldisiloxanyl)oxy]-2-oxido-14-(pyrimidin-4-
yloxy)-2-sulfanyl-10-sulfidodecahydro-5,8-
methanocyclopenta[l][1,3,6,9,11,2,10]
pentaoxadiphosphacyclotetradecin-7-yl]-7-oxo-6,7-
dihydro-3H-[1,2,3]triazolo[4,5-d]pyrimidin-5-yl}-2-
methylpropanamide or N-{3-[(2R,5R,7R,8R,10S,12aR,14R,15aS,16R)-10-
(2-cyanoethoxy)-16-[(3-hydroxy-1,1,3,3-tetraisopro-
pyldisiloxanyl)oxy]-2-oxido-14-(pyrimidin-4-
yloxy)-2-sulfanyl-10-sulfidodecahydro-5,8-
methanocyclopenta[l][1,3,6,9,11,2,10]
pentaoxadiphosphacyclotetradecin-7-yl]-7-oxo-6,7-
dihydro-3H-[1,2,3]triazolo[4,5-d]pyrimidin-5-yl}-2-
methylpropanamide, Intermediates 121a, 121b,
121c and 121d Intermediate 120a (240 mg, 0.224 mmol) was dissolved in dry acetonitrile and concentrated to dryness (3×15 mL), dried under vacuum for 15 min and then taken up in pyridine (4.56 mL) under an atmosphere of argon. 2-Chloro-5,5-dimethyl-1,3,2-dioxaphosphorinane 2-oxide (158 mg, 0.823 mmol) was added. The reaction mixture was allowed to stir at rt for 45 min. Water (0.15 mL, 8.23 mmol) was added followed by 3H-1,2-benzodithiol-3-one 1,1-dioxide (71.4 mg, 0.353 mmol) and the reaction mixture was allowed to stir at rt for 3 h. The reaction mixture was diluted with toluene and concentrated to give a crude mixture of one major and one minor diastereomer. The residue was dissolved in EtOAc and 5% NaHCO$_3$ solution was added. The phases were separated and the aqueous phase was extracted with EtOAc (3×). The combined organic phases were washed with brine, dried over Na$_2$SO$_4$, filtered and concentrated. The crude mixture was adsorbed onto Celite and purified by silica gel chromatography (0-10% MeOH in EtOAc) to provide the Intermediates 121a and 121b as a mixture of diastereomers (181 mg, 74%). LCMS (AA): m/z=1034.3 (M+H).
Intermediates 121c and 121d were prepared from Intermediate 120b following the procedure described above for Intermediates 121a and 121b. Purification by silica gel chromatography (0-10% MeOH in EtOAc) provided Intermediate 121c as the first eluting diastereomer, and Intermediate 121d as the second eluting diastereomer LCMS (AA): m/z=1034.3 (M+H).

Step 4: 5-amino-3-[(2S,5R,7R,8R,10S,12aR,14R, 15aS,16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2S,5R,7R,8R,10R,12aR,14R,15aS, 16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10S,12aR,14R,15aS, 16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS, 16R)-16-[(3-hydroxy-1,1,3,3-tetraisopropyldisiloxanyl)oxy]-2,10-dioxido-14-(pyrimidin-4-yloxy)-2,10-disulfanyldecahydro-5,8-methanocyclopenta[l][1,3,6,9,11,2,10]pentaoxadiphosphacyclotetradecin-7-yl]-3,6-dihydro-7H-[1,2,3]triazolo[4,5-d]pyrimidin-7-one, Intermediates 122a, 122b, 122c and 122d A mixture of Intermediates 121a and 121b (180 mg, 0.174 mmol) was taken up in methylamine (33% in EtOH, 1.73 mL, 13.9 mmol) under an atmosphere of nitrogen. The reaction mixture was allowed to stir at rt for 2.5 h. The reaction mixture was concentrated and adsorbed onto Celite. The crude material was purified by reverse phase flash column chromatography (20-55% ACN in aqueous ammonium acetate (10 mM)) to provide Intermediate 122a as the first eluting diastereomer (14 mg, 9%) and Intermediate 122b as the second eluting diastereomer (105 mg, 66%) LCMS (AA): m/z=911.3 (M+H).

Intermediate 121c was treated in an analogous fashion to the above procedure to provide Intermediate 122c LCMS (AA): m/z=911.3 (M+H).

Intermediate 121d was treated in an analogous fashion to the above procedure to provide Intermediate 122d LCMS (AA): m/z=911.3 (M+H).

Step 5: 5-amino-3-[(2S,5R,7R,8R,10S,12aR,14R, 15aS,16R)-16-hydroxy-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2S,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10S,12aR,14R,15aS, 16R)-16-hydroxy-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-3,6-dihydro-7H-[1,2,3]triazolo[4,5-d]pyrimidin-7-one or 5-amino-3-[(2R,5R,7R,8R,10R,12aR,14R,15aS, 16R)-16-hydroxy-2,10-dioxido-14-(pyrimidin-4-yloxy)-2,10-disulfanyldecahydro-5,8-methanocyclopenta [l][1,3,6,9,11,2,10]pentaoxadiphosphacyclotetradecin-7-yl]-3,6-dihydro-7H-[1,2,3]triazolo[4,5-d]pyrimidin-7-one, I-30a To a polypropylene vial was added Intermediate 122a (14 mg, 0.016 mmol), pyridine (0.078 mL, 0.963 mmol), triethylamine trihydrofluoride (0.013 mL, 0.078 mmol) and TEA (0.195 mL, 1.38 mmol). The vial was sealed and the reaction mixture was heated at 50° C. overnight with vigorous stirring. The reaction mixture was cooled to rt and water (0.292 mL) was added followed by dropwise addition of a solution of $CaCl_2$) (27 mg, 0.234 mmol) in water (0.292 mL). The reaction mixture was allowed to stir at rt for 1 h, then filtered through Celite, and finally rinsed with water (7×2 mL). The filtrate was concentrated, and removal of fluoride was confirmed by $^{19}F$ NMR. The crude mixture was purified by reverse phase flash column chromatography (0-30% ACN in aqueous triethylammonium acetate (10 mM)) to provide I-30a (0.97 mg, 7%) as an N,N-diethylethanamine salt. LCMS (AA): m/z=651.2 (M+H). $^1H$ NMR (MeOD) δ 8.60 (s, 1H), 8.30 (d, J=5.6 Hz, 1H), 6.74 (d, J=5.7 Hz, 1H), 6.16 (d, J=8.3 Hz, 1H), 5.98-5.87 (m, 1H), 5.52-5.41 (m, 1H), 4.98-4.87 (m, 2H), 4.27-4.18 (m, 1H), 4.13-4.04 (m, 1H), 3.91-3.81 (m, 1H), 3.80-3.68 (m, 1H), 3.02 (q, J=7.2 Hz, 10H), 2.54-2.30 (m, 5H), 1.52-1.40 (m, 1H), 1.17 (t, J=7.5 Hz, 15H). $^{31}P$ NMR (MeOD) δ 54.50 (s, 1P), 53.72 (s, 1P).

Example 60A

The compounds listed below were prepared as described in Example 60 starting with Step 5, substituting the starting material shown in the table for Intermediate 122a.

| Compound | Salt form | Starting material | LCMS data | NMR data |
| --- | --- | --- | --- | --- |
| I-30b | Et$_3$N | Intermediate 122b | LCMS (AA): m/z = 651.1 (M + H) | $^1H$ NMR (D$_2$O) δ 8.52 (s, 1H), 8.29 (d, J = 6.5 Hz, 1H), 6.69 (dd, J = 1.1, 6.0 Hz, 1H), 6.15 (d, J = 8.6 Hz, 1H), 5.70 (ddd, J = 4.1, 8.5, 9.8 Hz, 1H), 5.29-5.23 (m, 1H), 5.05 (quin, J = 7.1 Hz, 1H), 4.56 (br s, 1H), 4.36-4.34 |

| Compound | Salt form | Starting material | LCMS data | NMR data |
|---|---|---|---|---|
| | | | | (m, 1H), 4.29-4.22 (m, 1H), 3.97-3.92 (m, 1H), 3.86-3.81 (m, 1H), 3.79-3.73 (m, 1H), 3.03 (q, J = 7.3 Hz, 12H), 2.46-2.38 (m, 1H), 2.38-2.26 (m, 2H), 2.19-2.10 (m, 1H), 1.62-1.54 (m, 1H), 1.10 (t, J = 7.3 Hz, 18H). $^{31}$P NMR (D$_2$O) δ 53.86 (s, 1P), 52.23 (s, 1P). |
| I-30c | Et$_3$N | Intermediate 122c | LCMS (AA): m/z = 651.1 (M + H) | $^1$H NMR (D$_2$O) δ 8.62 (s, 1H), 8.37 (d, J = 6.0 Hz, 1H), 6.83 (dd, J = 1.0, 6.0 Hz, 1H), 6.26 (d, J = 8.5 Hz, 1H), 5.77 (ddd, J = 4.1, 8.3, 12.4 Hz, 1H), 5.43-5.37 (m, 1H), 5.15-5.08 (m, 1H), 4.56 (d, J = 4.3 Hz, 1H), 4.47-4.43 (m, 1H), 4.35 (ddd, J = 3.2, 8.4, 11.8 Hz, 1H), 4.14-4.08 (m, 1H), 4.01-3.93 (m, 1H), 3.85-3.79 (m, 1H), 3.13 (q, J = 7.3 Hz, 14H), 2.54-2.41 (m, 3H), 2.40-2.30 (m, 1H), 1.68-1.58 (m, 1H), 1.21 (t, J = 7.3 Hz, 20H). $^{31}$P NMR (D$_2$O) δ 57.34 (s, 1P), 53.77 (s, 1P). |
| I-30d | Et$_3$N | Intermediate 122d | LCMS (AA): m/z = 651.1 (M + H) | $^1$H NMR (MeOD) δ 8.51 (s, 1H), 8.21 (d, J = 5.9 Hz, 1H), 6.68 (d, J = 5.9 Hz, 1H), 6.07 (d, J = 8.2 Hz, 1H), 5.91-5.79 (m, 1H), 5.43-5.35 (m, 1H), 4.84-4.70 (m, 2H), 4.17-4.10 (m, 1H), 3.96-3.85 (m, 1H), 3.78-3.70 (m, 1H), 3.68-3.60 (m, 1H), 2.97 (q, J = 7.6 Hz, 8H), 2.60-2.49 (m, 1H), 2.39-2.24 (m, 4H), 1.35-1.23 (m, 1H), 1.10 (t, J = 7.3 Hz, 11H). $^{31}$P NMR (MeOD) δ 59.66 (br s, 1P), 54.32 (br s, 1P). |

Example 60B

The compounds listed below were prepared as described in Example 60 starting with Step 1, substituting the H-phosphonate shown for Intermediate 6, the phosphoramidite shown for Intermediate 118, and the compounds in the intermediate column for Intermediates 120a and 120b.

| Compound | Salt Form | H-phosphonate | Phosphoramidite | Intermediate | Final compound/ LCMS data | NMR data |
|---|---|---|---|---|---|---|
| I-44a* | NH₃ | Int-79 | Int-90 | Int-161a | LCMS (AA): m/z = 650.0 (M+H) | ¹H NMR (D₂O) δ 8.54 (s, 1H), 8.42 (s, 1H), 8.18 (br s, 1H), 6.05 (d, J = 8.4 Hz, 1H), 5.04-5.50-5.44 (m, 1H), 4.99 (m, 1H), 4.57 (d, J = 4.3 Hz, 1H), 4.53-4.45 (m, 2H), 4.39-4.33 (m, 1H), 4.15-4.10 (m, 1H), 3.99-3.86 (m, 2H), 2.52-2.43 (m, 3H), 2.13-2.05 (m, 1H), 1.30-1.22 (m, 1H); ³¹P NMR (D₂O) δ 58.46 (s, 1P), 53.99 (s, 1P). |
| I-44b* | NH₃ | Int-79 | Int-90 | Int-161b | LCMS (AA): m/z = 650.0 (M+H) | ¹H NMR (D₂O) δ 8.55 (s, 1H), 8.41 (s, 1H), 8.06 (s, 1H), 6.03 (d, J = 8.6 Hz, 1H), 5.56-5.51 (m, 1H), 4.99-4.93 (m, 1H), 4.68 (d, J = 4.0 Hz, 1H), 4.50-4.36 (m, 3H), 4.14-4.09 (m, 1H), 4.03-3.98 (m, 1H), 3.91-3.84 (m, 1H), 2.50-2.22 (m, 4H), 1.44-1.37 (m, 1H); ³¹P NMR (D₂O) δ 53.97 (s, 1P), 53.09 (s, 1P). |
| I-45 | Et₃N | Int-155 | Int-90 | Int-159 | LCMS (AA): m/z = 668.3 (M+H) | ¹H NMR (D₂O) δ 8.65 (br s, 1H), 8.52 (br s, 1H), 8.00 (s, 1H), 6.03 (br d, J = 8.2 Hz, 1H), 5.67-5.59 (m, 1H), 5.23 (d, J = 52.3 Hz, 1H), 4.97-4.84 (m, 1H), 4.71 (br d, J = 3.8 Hz, 1H), 4.57-4.40 (m, 3H), 4.20-3.99 (m, 3H), 3.23 (q, J = 7.3 Hz, 12H), 2.72-2.55 (m, 2H), 1.72-1.48 (m, 2H), 1.31 (t, J = 7.3 Hz, 18H); ³¹P NMR (D₂O) δ 54.59 (s, 1P), 52.82 (s, 1P). |

*The Step 3 cyclization was performed under the conditions described in Example 44 Step 3.

Example 61

(1R,2R,3R,5R)-5-{[bis(4-methoxyphenyl)(phenyl)methoxy]methyl}-2-fluoro-3-(pyrimidin-4-yloxy)cyclopentanol, Intermediate 150

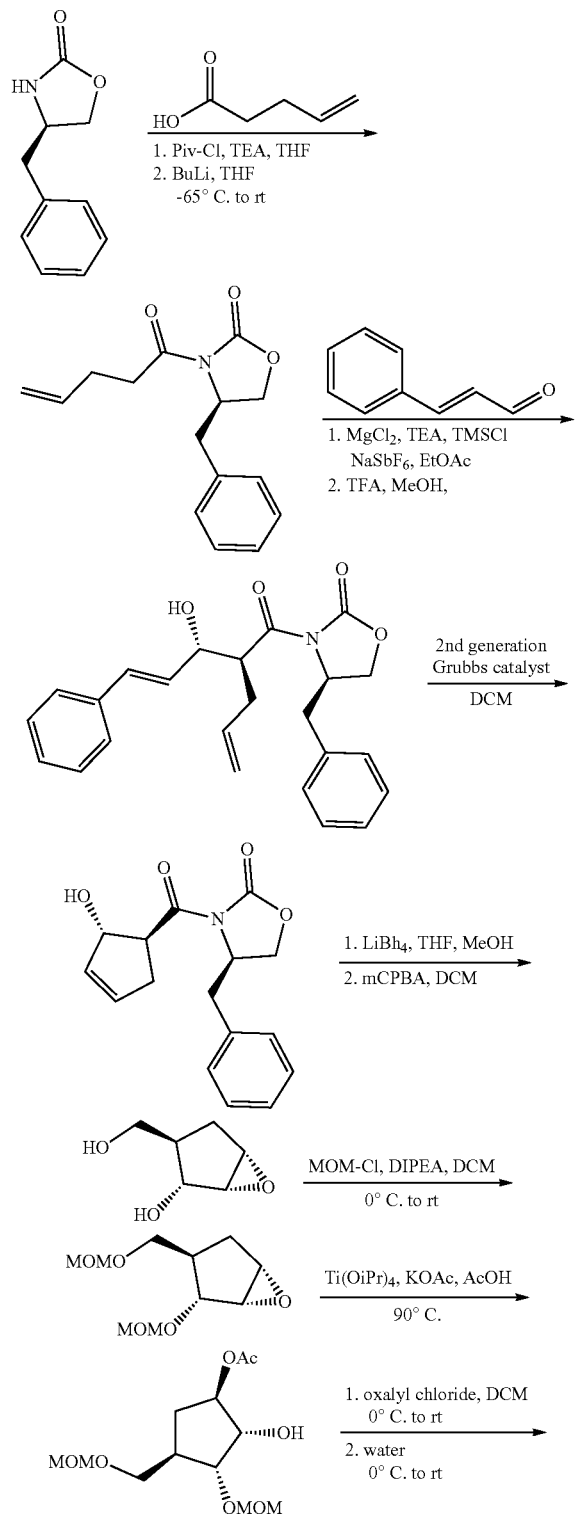

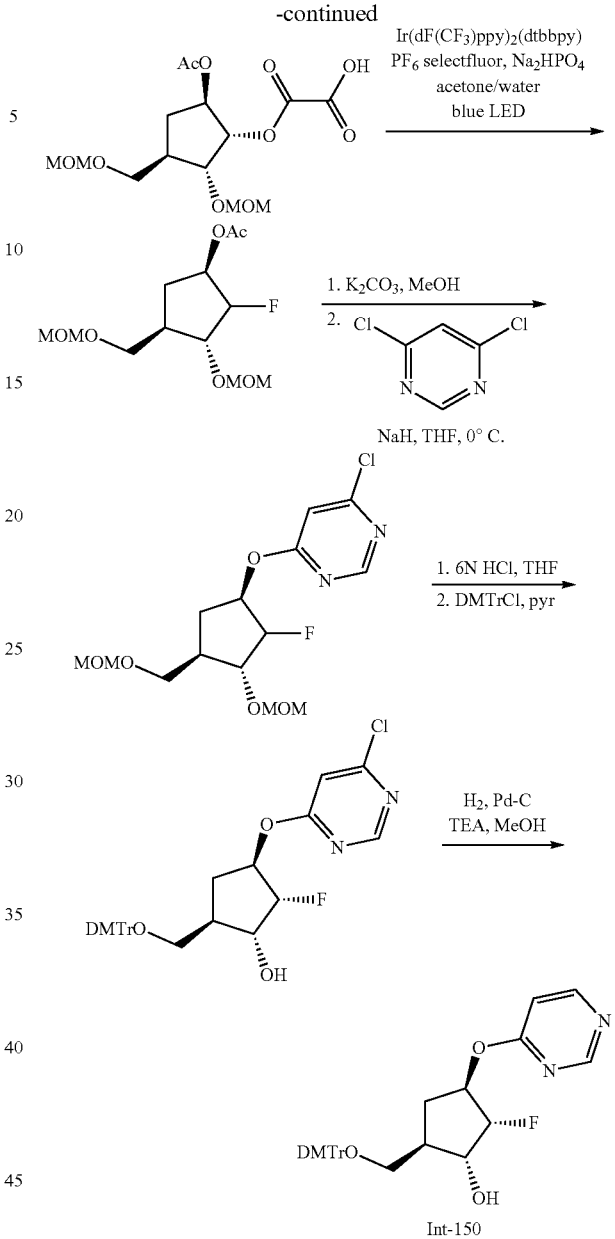

Int-150

Step 1: (R)-4-benzyl-3-(pent-4-enoyl)oxazolidin-2-one

To a solution of (R)-4-benzyloxazolidin-2-one (125 g, 705 mmol) in dry THF (1.25 L) was added dropwise n-BuLi (296 mL, 740 mmol) at −40° C. under nitrogen atmosphere. The reaction mixture was allowed to stir at −40° C. for 30 min, and then cooled to −65° C. In a separate flask, pivaloyl chloride (118 g, 986 mmol) was added to a solution of 4-pentenoic acid (91.7 g, 916 mmol) and TEA (127 g, 1.26 mol) in dry THF (1.80 L) at −65° C. under nitrogen atmosphere. The reaction mixture was allowed to stir at 0° C. for 1 h, and then cooled to −65° C. To this reaction mixture was added the (R)-4-benzyloxazolidin-2-one reaction mixture, and the resulting mixture was allowed to stir at −65° C. for 30 min and then to warm to rt and to stir for 16 h. The reaction mixture was poured into saturated aqueous NH₄Cl solution (2.00 L), extracted with EtOAc (3×1.00 L). The combined organic phases were washed with brine (2.00 L), dried over anhydrous Na₂SO₄, filtered and concentrated. The residue was combined with another reaction carried out on the same scale and purified by silica gel chromatography (1:20 to 1:5 EtOAc in PE) to provide (R)-4-benzyl-3-(pent-4-enoyl)oxazolidin-2-one as a yellow oil (250 g, 67%). $^1$H NMR (CDCl₃) δ 7.28-7.38 (m, 3H), 7.22 (br d, J=7.1 Hz, 2H), 5.90 (ddt, J=16.9, 10.3, 6.5, 6.5 Hz, 1H), 5.00-5.18 (m, 2H,) 4.63-4.74 (m, 1H), 4.13-4.27 (m, 2H), 3.31 (dd, J=13.4, 2.9 Hz, 1H), 2.96-3.19 (m, 2H), 2.77 (dd, J=13.2, 9.8 Hz, 1H), 2.47 (q, J=7.0 Hz, 2H).

Step 2: (4R)-3-[(2S,3S,4E)-2-allyl-3-hydroxy-5-phenylpent-4-enoyl]-4-benzyl-1,3-oxazolidin-2-one To a solution of (R)-4-benzyl-3-(pent-4-enoyl)oxazolidin-2-one (126.5 g, 485 mmol), MgCl₂ (4.61 g, 48.5 mmol), Et₃N (98.1 g, 970 mmol), TMSCl (78.9 g, 727 mmol), and NaSbF₆ (37.5 g, 145 mmol) in EtOAc (2.53 L) was added (2E)-3-phenylprop-2-enal (83.2 g, 630 mmol) at rt under an atmosphere of nitrogen. The reaction mixture was allowed to stir at rt for 16 h. The reaction mixture was combined with another reaction carried out on the same scale and filtered through a pad of Celite. The filter cake was washed with EtOAc (1.00 L×3). The combined filtrates were concentrated to dryness. MeOH (5.00 L) and TFA (20 mL) were added and the reaction mixture was allowed to stir at rt for 1 h. The reaction mixture was adjusted to pH=8 with TEA and then concentrated. The residue was purified by silica gel chromatography (1:20 to 1:5 EtOAc in PE) to provide (4R)-3-[(2S,3S,4E)-2-allyl-3-hydroxy-5-phenylpent-4-enoyl]-4-benzyl-1,3-oxazolidin-2-one (311 g, 81%) as a yellow oil. $^1$H NMR (CDCl₃) δ 7.37-7.43 (m, 2H), 7.33 (br t, J=7.3 Hz, 2H), 7.27 (br s, 4H,) 7.16 (br d, J=7.3 Hz, 2H), 6.69 (br d, J=15.9 Hz, 1H), 6.33 (dd, J=15.9, 6.1 Hz, 1H), 5.75-5.90 (m, 1H), 5.00-5.19 (m, 2H), 4.63-4.73 (m, 1H), 4.54 (q, J=6.3 Hz, 1H), 4.30-4.39 (m, 1H), 4.13-4.20 (m, 2H), 3.26 (br dd, J=13.4, 2.4 Hz, 1H), 2.93 (br d, J=8.1 Hz, 1H), 2.42-2.68 (m, 3H).

Step 3: (4R)-4-benzyl-3-{[(1S,2S)-2-hydroxycyclopent-3-en-1-yl]carbonyl}-1,3-oxazolidin-2-one To a solution of (4R)-3-[(2S,3S,4E)-2-allyl-3-hydroxy-5-phenylpent-4-enoyl]-4-benzyl-1,3-oxazolidin-2-one (156 g, 395 mmol) in DCM (3.11 L) was added (1,3-Bis(2,4,6-trimethylphenyl)-2-imidazolidinylidene)dichloro(phenylmethylene)(tricyclohexylphosphine) ruthenium (3.35 g, 3.95 mmol, Grubb's 2$^{nd}$ generation catalyst) at rt under a nitrogen atmosphere. The reaction mixture was allowed to stir at rt for 4 h. The reaction mixture was combined with another reaction carried out on the same scale and concentrated. The residue was purified by silica gel chromatography (1:20 to 1:2 EtOAc in PE) to provide (4R)-4-benzyl-3-{[(1S,2S)-2-hydroxycyclopent-3-en-1-yl]carbonyl}-1,3-oxazolidin-2-one (180 g, 79%) as a light yellow solid, H NMR (MeOD) δ 7.21-7.37 (m, 5H), 5.83-5.90 (m, 1H), 5.76 (dd, J=5.6, 2.2 Hz, 1H), 5.27 (br s, 1H), 4.71-4.80 (m, 1H), 4.22-4.35 (m, 2H), 4.09 (ddd, J=9.2, 5.9, 4.8 Hz, 1H), 3.17 (dd, J=13.6, 3.1 Hz, 1H), 2.85-3.02 (m, 2H), 2.34-2.46 (m, 1H).

Step 4: (1R,5S)-5-(hydroxymethyl)cyclopent-2-en-1-ol

To a solution of (4R)-4-benzyl-3-{[(1S,2S)-2-hydroxycyclopent-3-en-1-yl]carbonyl}-1,3-oxazolidin-2-one (90.0 g, 313 mmol) in THF (1.35 L) was added MeOH (22.0 g, 688 mmol) and LiBH₄ (14.9 g, 688 mmol) at 0° C. under an atmosphere of nitrogen. The reaction mixture was allowed to stir at 0° C. for 1 h. The reaction mixture was quenched with aqueous NaOH (10%, 500 mL). The reaction mixture was extracted with EtOAc (5×1.0 L). The combined organic phases were washed with brine (1.0 L×2), dried over anhydrous Na₂SO₄, filtered and concentrated in vacuum. The residue was combined with another reaction carried out on the same scale and purified by silica gel chromatography (5-50% EtOAc in PE). The combined aqueous phases were concentrated and purified by silica gel chromatography eluted with (1:5 to 1:2 EtOAc in PE) The products from the columns were combined to provide (1R,5S)-5-(hydroxymethyl)cyclopent-2-en-1-ol (58 g, 81%) as a yellow oil. $^1$H NMR (CDCl₃) δ 5.91 (td, J=2.3, 1.1 Hz, 1H), 5.78 (dd, J=4.9, 2.0 Hz, 1H), 4.73 (br s, 1H) 3.62-3.82 (m, 2H) 2.55-2.68 (m, 1H) 2.21-2.34 (m, 1H) 1.95-2.04 (m, 1H).

Step 5: (1R,2R,3R,5S)-3-(hydroxymethyl)-6-oxabicyclo[3.1.0]hexan-2-ol

To a solution of (1R,5S)-5-(hydroxymethyl)cyclopent-2-en-1-ol (36.0 g, 315 mmol) in DCM (520 mL) was added mCPBA (101 g, 472 mmol) at 0° C. under an atmosphere of nitrogen. The reaction mixture was allowed to stir at 0° C. for 2 h. The suspension was filtered through a pad of Celite and the filter cake was washed with DCM (30 mL×3). The filtrates were combined and Celite (100 g) was added, then concentrated to dryness. The residue was purified by silica gel chromatography (1:2 EtOAc:PE to EtOAc to 1:10 MeOH:EtOAc) to provide (1R,2R,3R,5S)-3-(hydroxymethyl)-6-oxabicyclo[3.1.0]hexan-2-ol (15.0 g, 36.6%) as a yellow solid. $^1$H NMR (DMSO-d₆) δ 4.82 (d, J=6.1 Hz, 1H), 4.44 (t, J=5.0 Hz, 1H), 3.81 (t, J=6.4 Hz, 1H), 3.49-3.43 (m, 1H), 3.33 (s, 3H), 1.97-1.90 (m, 1H), 1.56-1.41 (m, 2H).

Step 6: (1R,2S,3S,5R)-2-(methoxymethoxy)-3-[(methoxymethoxy)methyl]-6-oxabicyclo[3.1.0]hexane To a solution of (1R,2R,3R,5S)-3-(hydroxymethyl)-6-oxabicyclo[3.1.0]hexan-2-ol (17.8 g, 136 mmol) in anhydrous DCM (500 mL) at 0° C. was added DIEA (105 g, 816 mmol), followed by MOM-Cl (65.6 g, 816 mmol). The reaction mixture was allowed to stir at rt for 15 h. Water (100 mL) was added, and the mixture was extracted with DCM (100 mL×2), washed with water then brine, dried over anhydrous Na₂SO₄, and concentrated. The residue was purified by silica gel chromatography (1:10 to 1:3 EtOAc in PE) and then further purified by silica gel chromatography (1:10 to 1:3 EtOAc in PE) to provide (1R,2S,3S,5R)-2-(methoxymethoxy)-3-[(methoxymethoxy)methyl]-6-oxabicyclo[3.1.0]hexane (14.0 g, 38%) as a yellow oil. $^1$H NMR (CDCl₃) δ 4.80-4.77 (m, 1H), 4.74-4.69 (m, 1H), 4.59 (s, 2H), 3.95 (dd, J=1.2, 7.8 Hz, 1H), 3.57 (dd, J=1.4, 2.8 Hz, 1H), 3.54 (d, J=4.4 Hz, 2H), 3.44-3.42 (m, 1H), 3.41 (s, 3H), 3.32 (s, 3H), 2.16 (dd, J=7.9, 13.9 Hz, 1H), 2.00-1.90 (m, 1H), 1.70-1.61 (m, 1H).

Step 7: (1R,2S,3R,4R)-2-hydroxy-3-(methoxymethoxy)-4-[(methoxymethoxy) methyl] cyclopentyl acetate To a solution of (1R,2S,3S,5R)-2-(methoxymethoxy)-3-[(methoxymethoxy) methyl]-6-oxabicyclo[3.1.0]hexane (14 g, 64.1 mmol) in AcOH (300 mL) was added KOAc (31.3 g, 320 mmol) and Ti(OiPr)$_4$ (18.2 g, 64.1 mmol). The reaction mixture was allowed to stir at 90° C. for 3 h. The mixture was diluted with EtOAc, filtered through Celite and washed with water (500 mL×2). Sat. solution of NaHCO$_3$ was added to adjust the pH to 7. The mixture was extracted with EtOAc (500 mL×2), washed by brine, dried over anhydrous Na$_2$SO$_4$ and concentrated. The residue was purified by silica gel chromatography (1:5 to 1:2 EtOAc in PE) then combined with additional reactions carried out on 1 g and 2 g scale and re-purified by silica gel chromatography (1:10 to 1:2 EtOAc in PE) to provide (1R,2S,3R,4R)-2-hydroxy-3-(methoxymethoxy)-4-[(methoxymethoxy) methyl]cyclopentyl acetate as a colorless oil (7.4 g, 34%). $^1$H NMR (CDCl$_3$) δ 4.97-4.91 (m, 1H), 4.71-4.64 (m, 2H), 4.58 (s, 2H), 4.01-3.95 (m, 1H), 3.88 (t, J=5.3 Hz, 1H), 3.50 (d, J=5.4 Hz, 2H), 3.37 (s, 3H), 3.32 (s, 3H), 2.83 (br d, J=4.2 Hz, 1H), 2.42-2.26 (m, 2H), 2.02 (s, 3H), 1.39-1.29 (m, 1H).

Step 8: ({(1R,2S,3S,5S)-5-acetoxy-2-(methoxymethoxy)-3-[(methoxymethoxy) methyl] cyclopentyl}oxy)(oxo)acetic acid A solution of (1R,2S,3R,4R)-2-hydroxy-3-(methoxymethoxy)-4-[(methoxymethoxy)methyl]cyclopentyl acetate (992 mg, 3.56 mmol) in Et$_2$O (35.7 mL) under an atmosphere of nitrogen was cooled to 0° C. and oxalyl chloride (2.0M in DCM, 3.56 mL, 7.12 mmol) was added dropwise. The reaction mixture was allowed to warm to rt and stirred overnight. The reaction mixture was cooled to 0° C. and water (6.40 mL, 355 mmol) was added dropwise, then was allowed to warm to rt and stirred for 1 h. The mixture was partitioned between water and EtOAc, extracted into Et$_2$O (2×), washed with brine, dried (Na$_2$SO$_4$) and evaporated to provide crude ({(1R,2S,3S,5S)-5-acetoxy-2-(methoxymethoxy)-3-[(methoxymethoxy)methyl] cyclopentyl}oxy)(oxo)acetic acid (1.42 g) as a clear oil which was used without purification.

Step 9: (1R,2R,3R,4R)-2-fluoro-3-(methoxymethoxy)-4-[(methoxymethoxy)methyl] cyclopentyl acetate and (1R,2S,3R,4R)-2-fluoro-3-(methoxymethoxy)-4-[(methoxymethoxy)methyl]cyclopentyl acetate To a 100 mL round bottom flask fitted with a rubber septa was added ({(1R,2S,3S,5S)-5-acetoxy-2-(methoxymethoxy)-3-[(methoxymethoxy)methyl] cyclopentyl}oxy)(oxo)acetic acid (1.25 g, 3.57 mmol), [4,4'-bis(1,1-dimethylethyl)-2,2'-bipyridine-N1,N1']bis[3,5-difluoro-2-[5-(trifluoromethyl)-2-pyridinyl-N]phenyl-C] iridium(III) hexafluorophosphate (40.0 mg, 0.036 mmol), disodium hydrogen phosphate (1.01 g, 7.14 mmol), N-fluoro-N'-chloromethyl-triethylenediamine-bis(tetrafluoroborate) (5.69 g, 16.1 mmol), acetone (27.5 mL) and water (7.0 mL). The reaction mixture was degassed with nitrogen and a balloon of argon was attached. The flask was placed between two Kessil® LED illuminators (model H150 blue) and the reaction mixture was allowed to stir for 2 h. Water was added and the mixture was extracted into Et$_2$O (3×). The organic phase was washed with water, sat. NaHCO$_3$ and brine, dried (Na$_2$SO$_4$) and evaporated. The residue was purified by silica gel chromatography (10% to 50% EtOAc in hexane) to provide (1R,2R,3R,4R)-2-fluoro-3-(methoxymethoxy)-4-[(methoxymethoxy)methyl]cyclopentyl acetate and (1R,2S,3R,4R)-2-fluoro-3-(methoxymethoxy)-4-[(methoxymethoxy)methyl] cyclopentyl acetate as a mixture of diastereomers (578 mg, 58%). $^1$H NMR (MeOD) δ 5.17-5.04 (m, 1H), 4.98-4.89 (m, 0.5H), 4.84-4.76 (m, 0.5H), 4.74-4.66 (m, 2H), 4.65-4.60 (m, 2H), 4.13-3.99 (m, 0.5H), 3.95-3.86 (m, 0.5H), 3.63-3.51 (m, 2H), 3.40-3.34 (m, 6H), 2.46-2.11 (m, 2H), 2.08-2.06 (m, 1.5H), 2.06-2.03 (m, 1.5H), 1.71-1.62 (m, 0.5H), 1.56-1.44 (m, 0.5H).

Step 10: (1R,2R,3R,4R)-2-fluoro-3-(methoxymethoxy)-4-[(methoxymethoxy)methyl] cyclopentanol and (1R,2S,3R,4R)-2-fluoro-3-(methoxymethoxy)-4-[(methoxymethoxy)methyl]cyclopentanol To a solution of (1R,2R,3R,4R)-2-fluoro-3-(methoxymethoxy)-4-[(methoxymethoxy)methyl]cyclopentyl acetate and (1R,2S,3R,4R)-2-fluoro-3-(methoxymethoxy)-4-[(methoxymethoxy)methyl] cyclopentyl acetate (1.42 g, 5.07 mmol) in methanol (35.0 mL) was added potassium carbonate (135 mg, 0.977 mmol). The reaction mixture was allowed to stir at rt for 2.5 h, after which time further potassium carbonate (233 mg, 1.69 mmol) was added and the reaction mixture was allowed to stir at rt for 2 h. The methanol was evaporated and the residue was partitioned between EtOAc and water and extracted into EtOAc. The combined organic phases were washed with water and brine, dried over Na$_2$SO$_4$ and evaporated. The residue was purified by silica gel chromatography (10% to 90% EtOAc/hexane) to provide (1R,2R,3R,4R)-2-fluoro-3-(methoxymethoxy)-4-[(methoxymethoxy)methyl] cyclopentanol and (1R,2S,3R,4R)-2-fluoro-3-(methoxymethoxy)-4-[(methoxymethoxy)methyl] cyclopentanol as a mixture of diastereomers (475 mg, 39%). $^1$H NMR (DMSO-d$_6$) δ 5.13 (d, J=4.2 Hz, 0.5H), 5.02 (d, J=5.0 Hz, 0.5H), 4.75-4.67 (m, 1H), 4.67-4.58 (m, 2H), 4.57-4.55 (m, 2H), 4.10-3.93 (m, 1H), 3.92-3.76 (m, 1H), 3.56-3.47 (m, 1H), 3.46-3.38 (m, 1H), 3.29-3.26 (m, 3H), 3.26-3.25 (m, 3H), 2.22-2.10 (m, 1H), 2.05-1.94 (m, 1H), 1.43-1.32 (m, 0.5H), 1.32-1.20 (m, 0.5H).

Step 11: 4-chloro-6-({(1R,2S,3R,4R)-2-fluoro-3-(methoxymethoxy)-4-[(methoxymethoxy)methyl] cyclopentyl}oxy)pyrimidine (1R,2R,3R,4R)-2-fluoro-3-(methoxymethoxy)-4-[(methoxymethoxy)methyl]cyclopentanol and (1R,2S,3R,4R)-2-fluoro-3-(methoxymethoxy)-4-[(methoxymethoxy) methyl]cyclopentanol (1.19 g, 4.99 mmol) in THF (14.5 mL) was added to a suspension of sodium hydride (392 mg, 15.5 mmol) in THF (43.5 mL) at 0° C. The reaction mixture was allowed to stir at 0° C. for 30 min. A solution of 4,6-dichloropyrimidine (1.02 g, 6.85 mmol) in THF (23 mL) was added and the reaction mixture was allowed to stir at 0° C. for 4 h. The reaction mixture was quenched with a saturated NH$_4$C$_1$ solution and extracted with EtOAc (3×). The combined organic phases were washed with brine, dried over anhydrous MgSO$_4$, filtered and concentrated. The residue was purified by silica gel chromatography (0% to 40% EtOAc/hexane) to provide 4-chloro-6-({(1R,2S,3R, 4R)-2-fluoro-3-(methoxymethoxy)-4-[(methoxymethoxy) methyl]cyclopentyl}oxy)pyrimidine as the first eluting diastereomer (584 mg, 33%). LCMS (FA): m/z=351.1 (M+H).

Step 12: (1R,2R,3R,5R)-3-[(6-chloropyrimidin-4-yl) oxy]-2-fluoro-5-(hydroxymethyl)cyclopentanol To a solution of 4-chloro-6-({(1R,2S,3R,4R)-2-fluoro-3-(methoxymethoxy)-4-[(methoxymethoxy)methyl] cyclopentyl}oxy)pyrimidine (270.5 mg, 0.771 mmol) in THF (10.0 mL) was added an HCl solution (6 N, 2.0 mL). The reaction mixture was heated at 60° C. for 2 h. The mixture was concentrated and the crude compound was purified by reverse phase flash column chromatography (10-100% ACN in aq. ammonium bicarbonate (5 mM)) to provide (1R,2R,3R,5R)-3-[(6-chloropyrimidin-4-yl)oxy]-2-fluoro-5-(hydroxymethyl)cyclopentanol (185 mg, 91%). LCMS (AA): m/z=263.1 (M+H).

Step 13: (1R,2R,3R,5R)-5-{[bis(4-methoxyphenyl) (phenyl)methoxy]methyl}-3-[(6-chloropyrimidin-4-yl)oxy]-2-fluorocyclopentanol 4,4'-Dimethoxytrityl chloride (543 mg, 1.59 mmol) was added to a solution of (1R,2R,3R,5R)-3-[(6-chloropyrimidin-4-yl)oxy]-2-fluoro-5-(hydroxymethyl)cyclopentanol (379 mg, 1.44 mmol) in pyridine (12 mL). The reaction mixture was allowed to stir at rt for 1 h. The solvents were evaporated and the residue was purified by silica gel chromatography (0% to 100% EtOAx in hexane) to provide (1R,2R,3R,5R)-5-{[bis(4-methoxyphenyl)(phenyl) methoxy]methyl}-3-[(6-chloropyrimidin-4-yl)oxy]-2-fluorocyclopentanol (550 mg, 68%) as a white powder. $^1$H NMR (MeOD) δ 8.58-8.54 (m, 1H), 7.43-7.38 (m, 2H), 7.30-7.20 (m, 6H), 7.19-7.13 (m, 1H), 6.91-6.86 (m, 1H), 6.83-6.77 (m, 4H), 5.52-5.40 (m, 1H), 4.86 (td, J=3.5, 52.0 Hz, 1H), 4.17-4.11 (m, 1H), 3.75-3.71 (m, 6H), 3.22 (d, J=4.9 Hz, 2H), 2.59-2.48 (m, 1H), 2.35-2.24 (m, 1H), 1.59-1.50 (m, 1H).

Step 14: (1R,2R,3R,5R)-5-{[bis(4-methoxyphenyl) (phenyl)methoxy]methyl}-2-fluoro-3-(pyrimidin-4-yloxy)cyclopentanol, Intermediate 150

(1R,2R,3R,5R)-5-{[bis(4-methoxyphenyl)(phenyl) methoxy]methyl}-3-[(6-chloropyrimidin-4-yl)oxy]-2-fluorocyclopentanol (548 mg, 0.973 mmol) and triethylamine (0.41 mL, 2.91 mmol) were dissolved in methanol (40 mL). Palladium (10% on carbon, 6.0 mg) was added to the solution and the reaction mixture was allowed to under an atmosphere of hydrogen at rt for 2 h. The reaction mixture was filtered through Celite and washed with methanol. The filtrate was evaporated and the residue was dissolved in DCM (50 mL) and then washed with water (2×10 mL) dried over Na$_2$SO$_4$ and concentrated to provide (1R,2R,3R,5R)-5-{[bis(4-methoxyphenyl)(phenyl)methoxy]methyl}-2-fluoro-3-(pyrimidin-4-yloxy)cyclopentanol, Intermediate 150 (494 mg, 96%) as a white solid. LCMS (AA): m/z=531.2 (M+H).

Example 62

2-amino-9-[(2S,5R,7R,8R,10S,12aR,14R,15S,15aR, 16R)-15-fluoro-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-1,9-dihydro-6H-purin-6-one or 2-amino-9-[(2S,5R,7R,8R,10R,12aR,14R,15S,15aR, 16R)-15-fluoro-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-1,9-dihydro-6H-purin-6-one or 2-amino-9-[(2R,5R,7R,8R,10S,12aR,14R,15S,15aR, 16R)-15-fluoro-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-1,9-dihydro-6H-purin-6-one or 2-amino-9-[(2R,5R,7R,8R,10R,12aR,14R,15S,15aR, 16R)-15-fluoro-16-hydroxy-2,10-dioxido-14-(pyrimidin-4-yloxy)-2,10-disulfanyldecahydro-5,8-methanocyclopenta[l][1,3,6,9,11,2,10] pentaoxadiphosphacyclotetradecin-7-yl]-1,9-dihydro-6H-purin-6-one, I-39a (ML01168516) and I-39b (ML01168514)

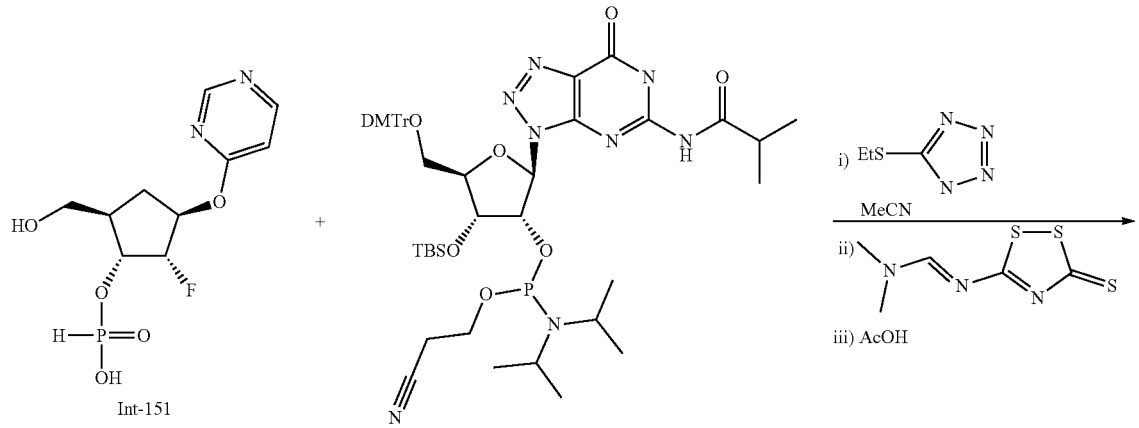

-continued
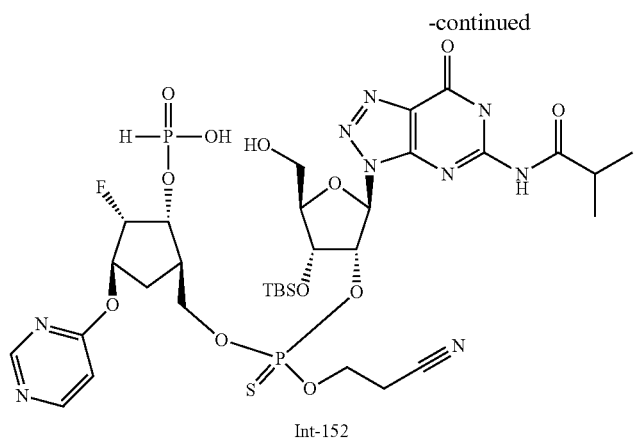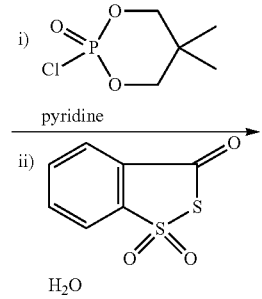
Int-152
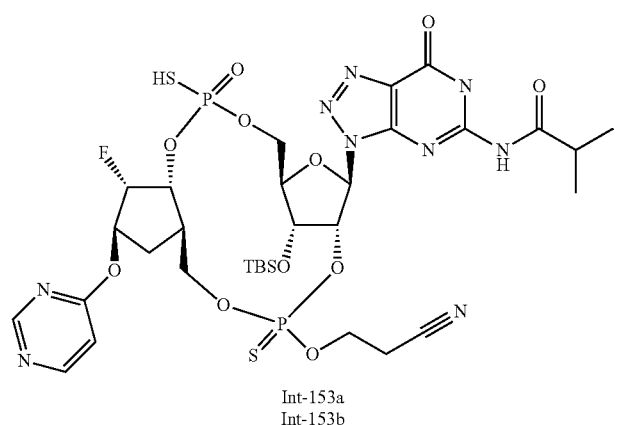
Int-153a
Int-153b
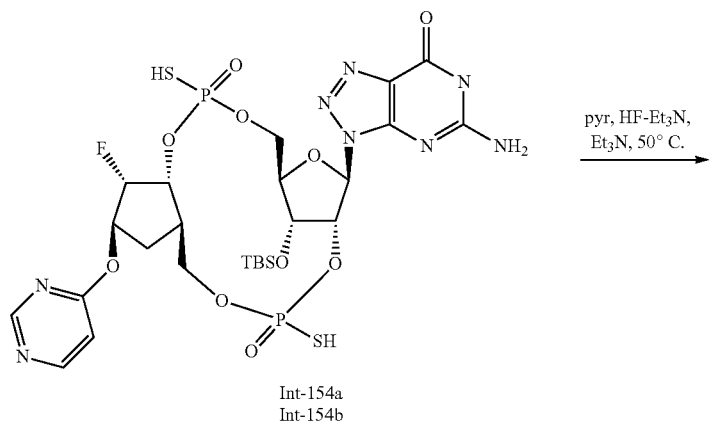
Int-154a
Int-154b
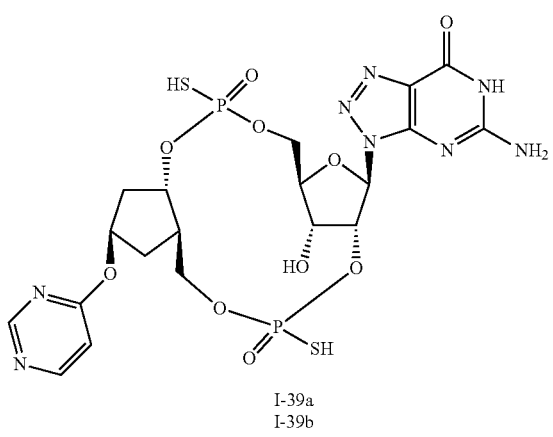
I-39a
I-39b Step 1: (1S,2R,4R)-2-({[(R)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-(pyrimidin-4-ylamino) cyclopentyl hydrogen phosphonate, or (1S,2R,4R)-2-({[(S)-({(2R,3R,4R,5R)-4-{[tert-butyl(dimethyl)silyl]oxy}-5-(hydroxymethyl)-2-[2-(isobutyrylamino)-6-oxo-1,6-dihydro-9H-purin-9-yl]tetrahydrofuran-3-yl}oxy)(2-cyanoethoxy)phosphorothioyl]oxy}methyl)-4-(pyrimidin-4-ylamino)cyclopentyl hydrogen phosphonate Intermediate 151 as the N,N-diethylethanamine salt (265 mg, 0.67 mmol) and N-[9-[(2R,3R,4R,5R)-5-[[bis(4-methoxyphenyl)-phenyl-methoxy]methyl]-4-[tert-butyl(dimethyl) silyl]oxy-3-[2-cyanoethoxy-(diisopropylamino)phosphanyl]oxy-tetrahydrofuran-2-yl]-6-oxo-1H-purin-2-yl]-2-methyl-propanamide (850 mg, 0.88 mmol) were combined and concentrated from ACN (3×10 mL). The residue was then dissolved in ACN (2.46 mL) under an atmosphere of argon. In a separate flask, 5-(ethylthio)-1H-tetrazole (263 mg, 2.02 mmol) was dissolved in ACN and then concentrated (3×5 mL), dissolved in ACN again (1.13 mL) and added to the reaction mixture. The reaction mixture was allowed to stir at rt for 50 min. ((Dimethylaminomethylidene)amino)-3H-1,2,4-dithiazoline-3-thione (166 mg, 0.81 mmol) was added and stirring was continued at rt for 45 min. The reaction mixture was concentrated and dried under vacuum for 10 min. Then the residue was dissolved in acetic acid (2.70 mL) and water (0.67 mL), sonicated for 2 min and allowed to stir at rt for 1 h. Toluene was added (15 mL) and the reaction mixture was concentrated, then azeotroped with toluene (2×15 mL). The crude mixture was purified by silica gel chromatography (0-50% MeOH in DCM) to provide Intermediate 152 as a mixture of diastereomers (490 mg, 65%) LCMS (AA): m/z=891.2 (M+H).

Step 2: N-{9-[(2S,5R,7R,8R,10R,12aR,14R,15S,15aR,16R)-16-{[tert-butyl (dimethyl)silyl]oxy}-10-(2-cyanoethoxy)-15-fluoro-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10S,12aR,14R,15S,15aR,16R)-16-{[tert-butyl(dimethyl) silyl]oxy}-10-(2-cyanoethoxy)-15-fluoro-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2S,5R,7R,8R,10S,12aR,14R,15S,15aR,16R)-16-{[tert-butyl(dimethyl) silyl]oxy}-10-(2-cyanoethoxy)-15-fluoro-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10R,12aR,14R,15S,15aR,16R)-16-{[tert-butyl(dimethyl) silyl]oxy}-10-(2-cyanoethoxy)-15-fluoro-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediates 153a and 153b Intermediate 152 (490 mg, 0.44 mmol) was concentrated from ACN (3×20 mL), dried under vacuum for 10 min and then dissolved in pyridine (8.90 mL) under an atmosphere of nitrogen. 2-Chloro-5,5-dimethyl-1,3,2-dioxaphosphorinane 2-oxide (284 mg, 1.54 mmol) was added and the reaction mixture was allowed to stir at rt for 45 min. Water (0.28 mL) was added, followed by 3H-1,2-benzodithiol-3-one 1,1-dioxide (131 mg, 0.647 mmol) then stirring was continued at rt for 30 min. An additional portion of 3H-1,2-benzodithiol-3-one 1,1-dioxide (134 mg, 0.66 mmol) was added and stirring was continued for an additional 1 h. Toluene was added (15 mL) and the reaction mixture was concentrated, then concentrated from toluene (2×15 mL). The crude mixture was purified by reverse phase flash column chromatography (0-100% ACN in aqueous ammonium acetate (10 mM)) to provide Intermediate 153a (100 mg, 25%) as the first eluting peak (LCMS (AA): m/z=905.2 (M+H)) and Intermediate 153b (120 mg, 30%) as the second eluting peak (LCMS (AA): m/z=905.2 (M+H)).

Step 3: N-{9-[(2S,5R,7R,8R,10R,12aR,14R,15S,15aR,16R)-16-{[tert-butyl(dimethyl) silyl]oxy}-15-fluoro-10-hydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10S,12aR,14R,15S,15aR,16R)-16-{[tert-butyl(dimethyl) silyl]oxy}-15-fluoro-10-hydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2S,5R,7R,8R,10S,12aR,14R,15S,15aR,16R)-16-{[tert-butyl(dimethyl) silyl]oxy}-15-fluoro-10-hydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide or N-{9-[(2R,5R,7R,8R,10R,12aR,14R,15S,15aR,16R)-16-{[tert-butyl(dimethyl) silyl]oxy}-15-fluoro-10-hydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide, Intermediate 154a Intermediate 153a (100 mg, 0.11 mmol) was dissolved in methylamine (33% in EtOH, 3.3 mL) under an atmosphere of nitrogen and the reaction mixture was allowed to stir at rt for 2.5 h. The reaction mixture was concentrated and dried under vacuum for 10 min. The crude compound was purified by reverse phase flash column chromatography (0-60% ACN in aqueous ammonium acetate (10 mM)) to provide Intermediate 154a (53 mg, 61%). LCMS (AA): m/z=782.1 (M+H).

Step 4: 2-amino-9-[(2S,5R,7R,8R,10R,12aR,14R,15S,15aR,16R)-15-fluoro-10,16-dihydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10S,12aR,14R,15S,15aR,16R)-15-fluoro-10,16-dihydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one or 2-amino-9-[(2S,5R,7R,8R,10S,12aR,14R,15S,15aR,16R)-15-fluoro-10,16-dihydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one or 2-amino-9-[(2R,5R,7R,8R,10R,12aR,14R,15S,15aR,16R)-15-fluoro-10,16-dihydroxy-2-oxido-14-(pyrimidin-4-yloxy)-2-sulfanyl-10-sulfidodecahydro-5,8-methanocyclopenta[l][1,3,6,9,11,2,10]pentaoxadiphosphacyclotetradecin-7-yl]-1,9-dihydro-6H-purin-6-one, I-39a In a polypropylene tube, Intermediate 154a (55 mg, 0.07 mmol) was suspended in pyridine (0.35 mL). Triethylamine trihydrofluoride (0.059 mL, 0.35 mmol) was added, followed by TEA (0.88 mL). The reaction mixture was allowed to stir at 50° C. for 20 h. The reaction mixture was cooled to rt, and water (1.32 mL) was added, followed by dropwise addition of a solution of calcium chloride (122 mg, 1.06 mmol) in water (1.32 mL). The reaction mixture was allowed to stir at rt for 60 min then filtered through Celite, and the Celite was rinsed with water (5×5 mL). The filtrate was concentrated to give a white solid. No HF was observed by $^{19}$F NMR. The crude mixture was purified by reverse phase flash column chromatography (0-15% ACN in aqueous triethylammonium acetate (10 mM)) to provide I-39a (35 mg, 57%) as the N,N-diethylethanamine salt. LCMS (FA): m/z=668.1 (M+H). $^1$H NMR (D$_2$O) δ 8.73 (s, 1H), 8.46 (d, J=5.9 Hz, 1H), 8.09 (s, 1H), 6.87 (dd, J=1.0, 6.0 Hz, 1H), 6.03 (d, J=8.3 Hz, 1H), 5.56-5.29 (m, 3H), 5.01-4.90 (m, 1H), 4.63 (d, J=4.3 Hz, 1H), 4.51-4.43 (m, 2H), 4.18-4.13 (m, 1H), 4.08-3.94 (m, 2H), 3.20 (q, J=7.3 Hz, 12H), 2.68-2.58 (m, 2H), 1.72-1.62 (m, 1H), 1.28 (t, J=7.3 Hz, 18H); $^{31}$P NMR (D$_2$O) δ 57.04 (s, 1P), 54.39 (s, 1P).

Example 62A

The compound listed below (I-39b) was prepared as described in Example 62 starting with Step 3, substituting the starting material shown in the table (Intermediate 153b) for Intermediate 153a.

| Compound | Salt form | Starting material | LCMS data | NMR data |
|---|---|---|---|---|
| I-39b | Et$_3$N | Intermediate 153b | LCMS (FA): m/z = 668.1 (M + H). | $^1$H NMR (D$_2$O) δ 8.73 (s, 1H), 8.48 (d, J = 6.0 Hz, 1H), 8.03 (s, 1H), 6.79 (d, J = 6.0 Hz, 1H), 6.01 (d, J = 8.4 Hz, 1H), 5.55-5.29 (m, 3H), 4.96-4.83 (m, 1H), 4.75-4.73 (m, 1H), 4.51-4.44 (m, 2H), 4.17-4.12 (m, 1H), 4.07-3.98 (m, 2H), 3.20 (q, J = 7.3 Hz, 12H), 2.67-2.56 (m, 2H), 1.77-1.68 (m, 1H), 1.28 (t, J = 7.3 Hz, 18H); $^{31}$P NMR (D$_2$O) δ 54.57 (s, 1P), 52.26 (s, 1P). |

Example 63

2-amino-9-[(5R,7R,8R,12aR,14R,15S,15aR,16R)-15-fluoro-2,10,16-trihydroxy-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one

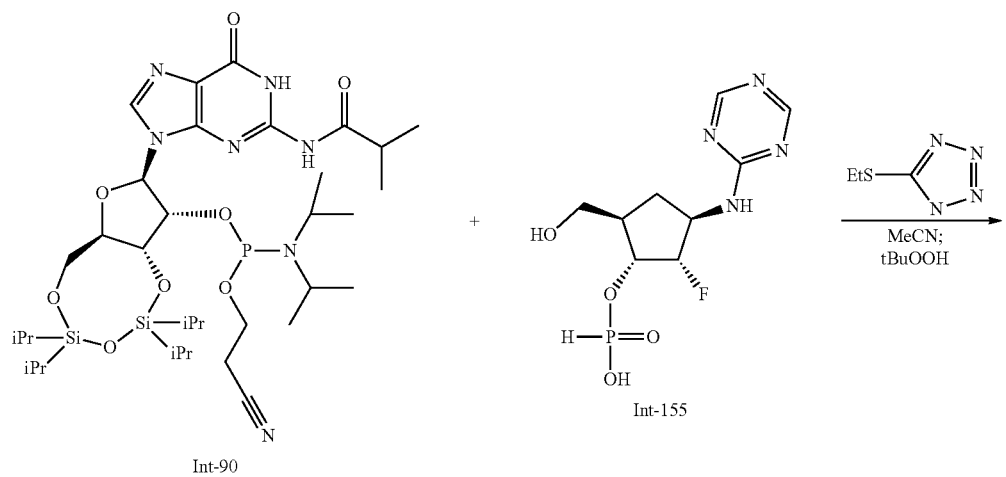

-continued
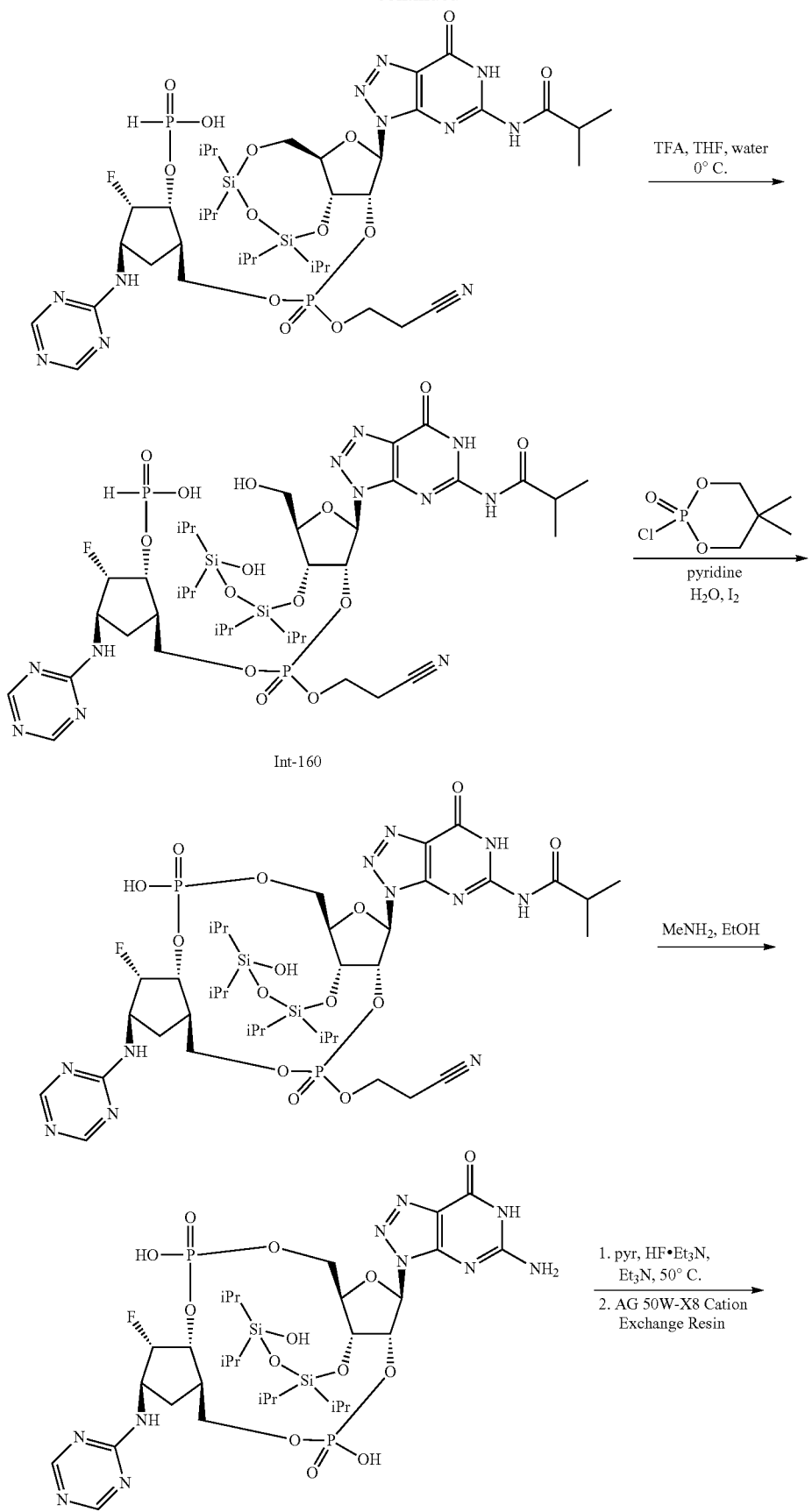
Int-160

-continued

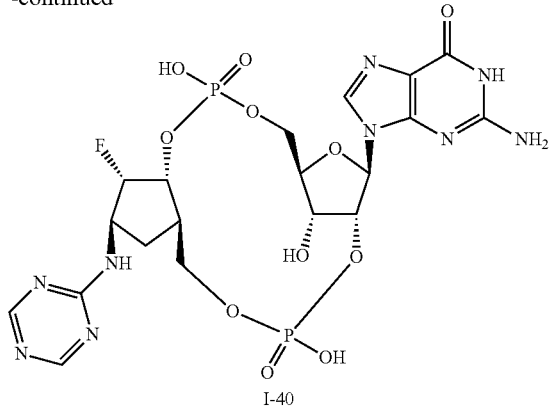

I-40

Step 1: (1R,2S,3R,5R)-5-({[(S)-(2-cyanoethoxy)({(6aR,8R,9R,9aR)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy)phosphoryl]oxy}methyl)-2-fluoro-3-(1,3,5-triazin-2-ylamino)cyclopentyl hydrogen phosphonate and (1R,2S,3R,5R)-5-({[(R)-(2-cyanoethoxy)({(6aR,8R,9R,9aR)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy)phosphoryl]oxy}methyl)-2-fluoro-3-(1,3,5-triazin-2-ylamino)cyclopentyl hydrogen phosphonate The title compound was prepared from (1R,2S,3R,5R)-2-fluoro-5-(hydroxymethyl)-3-(1,3,5-triazin-2-ylamino)cyclopentyl hydrogen phosphonate (Intermediate 155, 440 mg, 1.12 mmol) and Intermediate 90 (1.16 g, 1.45 mmol) following the procedure described in Example 49, step 1 without the addition of molecular sieves. Purification by silica gel chromatography (0-50% MeOH in DCM) provided the desired product as a mixture of diastereomers (1.01 g, 81%). LCMS (AA): m/z=1003.3 (M+H).

Step 2: (1R,2S,3R,5R)-5-({[(S)-(2-cyanoethoxy)({(2R,3R,4R,5R)-5-(hydroxymethyl)-4-[(3-hydroxy-1,1,3,3-tetraisopropyldisiloxanyl)oxy]-2-[2-(isobutyrylamino)-6-oxo-1,6-dihydro-9H-purin-9-yl]tetrahydrofuran-3-yl}oxy)phosphoryl]oxy}methyl)-2-fluoro-3-(1,3,5-triazin-2-ylamino)cyclopentyl hydrogen phosphonate and (1R,2S,3R,5R)-5-({[(R)-(2-cyanoethoxy)({(2R,3R,4R,5R)-5-(hydroxymethyl)-4-[(3-hydroxy-1,1,3,3-tetraisopropyldisiloxanyl)oxy]-2-[2-(isobutyrylamino)-6-oxo-1,6-dihydro-9H-purin-9-yl]tetrahydrofuran-3-yl}oxy)phosphoryl]oxy}methyl)-2-fluoro-3-(1,3,5-triazin-2-ylamino)cyclopentyl hydrogen phosphonate Intermediate 160 was prepared from (1R,2S,3R,5R)-5-({[(S)-(2-cyanoethoxy)({(6aR,8R,9R,9aR)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy)phosphoryl]oxy}methyl)-2-fluoro-3-(1,3,5-triazin-2-ylamino)cyclopentyl hydrogen phosphonate and (1R,2S,3R,5R)-5-({[(R)-(2-cyanoethoxy)({(6aR,8R,9R,9aR)-8-[2-(isobutyrylamino)-6-oxo-1,6-dihydro-9H-purin-9-yl]-2,2,4,4-tetraisopropyltetrahydro-6H-furo[3,2-f][1,3,5,2,4]trioxadisilocin-9-yl}oxy)phosphoryl]oxy}methyl)-2-fluoro-3-(1,3,5-triazin-2-ylamino)cyclopentyl hydrogen phosphonate (1.00 g, 1.0 mmol) following the procedure described in Example 49, step 2 stirring at rt for 2.5 h. Purification by silica gel chromatography (0-80% MeOH in DCM) provided the desired product as a mixture of diastereomers (0.74 g, 73%). LCMS (AA): m/z=1021.4 (M+H).

Step 3: N-{9-[(5R,7R,8R,10S,12aR,14R,15S,15aR,16R)-10-(2-cyanoethoxy)-15-fluoro-2-hydroxy-16-[(3-hydroxy-1,1,3,3-tetraisopropyldisiloxanyl)oxy]-2,10-dioxido-14-(1,3,5-triazin-2-ylamino)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide and N-{9-[(5R,7R,8R,10R,12aR,14R,15S,15aR,16R)-10-(2-cyanoethoxy)-15-fluoro-2-hydroxy-16-[(3-hydroxy-1,1,3,3-tetraisopropyldisiloxanyl)oxy]-2,10-dioxido-14-(1,3,5-triazin-2-ylamino)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide The title compound was prepared from Intermediate 160 (578 mg, 0.57 mmol) following the procedure described in Example 48, step 1. Purification by reverse phase flash column chromatography (0-100% ACN in aqueous ammonium acetate (10 mM)) provided the desired product as a mixture of diastereomers (387 mg, 67%). LCMS (AA): m/z=1019.3 (M+H).

Step 4: 2-amino-9-[(5R,7R,8R,12aR,14R,15S,15aR,16R)-15-fluoro-2,10-dihydroxy-16-[(3-hydroxy-1,1,3,3-tetraisopropyldisiloxanyl)oxy]-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one The title compound was prepared from N-{9-[(5R,7R,8R,10S,12aR,14R,15S,15aR,16R)-10-(2-cyanoethoxy)-15-fluoro-2-hydroxy-16-[(3-hydroxy-1,1,3,3-tetraisopropyldisiloxanyl)oxy]-2,10-dioxido-14-(1,3,5-triazin-2-ylamino)decahydro-5,8-methanocyclopenta[l][1,3,6,9,11,2,10]pentaoxadiphosphacyclotetradecin-7-yl]-6-oxo-6,9- dihydro-1H-purin-2-yl}-2-methylpropanamide and N-{9-[(5R,7R,8R,10R,12aR,14R,15S,15aR,16R)-10-(2-cyanoethoxy)-15-fluoro-2-hydroxy-16-[(3-hydroxy-1,1,3,3-tetraisopropyldisiloxanyl)oxy]-2,10-dioxido-14-(1,3,5-triazin-2-ylamino)decahydro-5,8-methanocyclopenta[l][1,3,6,9,11,2,10]pentaoxadiphosphacyclotetradecin-7-yl]-6-oxo-6,9-dihydro-1H-purin-2-yl}-2-methylpropanamide (385 mg, 0.38 mmol) following the procedure described in Example 14, step 3 stirring at rt for 3 h. Purification by reverse phase flash column chromatography (0-100% ACN in aqueous ammonium acetate (10 mM)) provided the desired compound (239 mg, 71%). LCMS (AA): m/z=896.3 (M+H).

Step 5: 2-amino-9-[(5R,7R,8R,12aR,14R,15S,15aR,16R)-15-fluoro-2,10,16-trihydroxy-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one N,N-diethylethanamine The title compound was prepared from 2-amino-9-[(5R,7R,8R,12aR,14R,15S,15aR,16R)-15-fluoro-2,10-dihydroxy-16-[(3-hydroxy-1,1,3,3-tetraisopropyldisiloxanyl)oxy]-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one (223 mg, 0.25 mmol) following the procedure described in Example 14, step 4 stirring at 50° C. overnight. Purification by reverse phase flash column chromatography (0-20% ACN in aqueous triethylammonium acetate (10 mM)) provided 2-amino-9-[(5R,7R,8R,12aR,14R,15S,15aR,16R)-15-fluoro-2,10,16-trihydroxy-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one as the N,N-diethylethanamine salt (35 mg, 17%). LCMS (AA): m/z=636.2 (M+H).

Step 6: 2-amino-9-[(5R,7R,8R,12aR,14R,15S,15aR,16R)-15-fluoro-2,10,16-trihydroxy-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one, I-40

The bis-sodium salt of the title compound was prepared from the N,N-diethylethanamine salt of 2-amino-9-[(5R,7R,8R,12aR,14R,15S,15aR,16R)-15-fluoro-2,10,16-trihydroxy-2,10-dioxido-14-(1,3,5-triazin-2-ylamino)decahydro-5,8-methanocyclopenta[l][1,3,6,9,11,2,10]pentaoxadiphosphacyclotetradecin-7-yl]-1,9-dihydro-6H-purin-6-one (32 mg, 0.038 mmol) following the procedure described in Example 16, step 5. Lyophilization of the collected material overnight provided I-40 as the disodium salt (25 mg, 98%). LCMS (FA): m/z=636.3 (M+H). $^1$H NMR (D$_2$O) δ 8.58 (s, 1H), 8.45 (s, 1H), 7.94 (s, 1H), 5.98 (d, J=8.4 Hz, 1H), 5.53-5.46 (m, 1H), 5.13 (d, J=52.3 Hz, 1H), 4.75-4.65 (m, 1H), 4.62 (d, J=4.1 Hz, 1H), 4.42-4.34 (m, 2H), 4.28-4.18 (m, 2H), 4.01-3.91 (m, 2H), 2.59-2.48 (m, 2H), 1.66-1.57 (m, 1H). $^{31}$P NMR (D$_2$O) δ −0.95 (s, 1P), −1.30 (s, 1P).

Example 63A

The compound listed below was prepared as described in Example 63 starting with Step 1, substituting the H-phosphonate shown in the table for Intermediate 155.

| Compound | Salt Form | H-phosphonate | Final compound/ LCMS data | NMR data |
|---|---|---|---|---|
| I-46 | Et$_3$N | 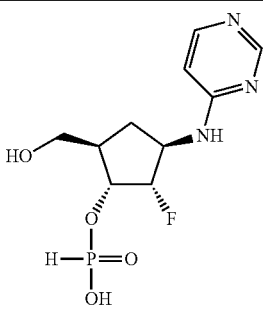 Int-83 | 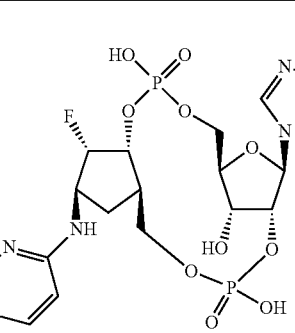 LCMS (AA): m/z = 635.4 (M + H) | $^1$H NMR (D$_2$O) δ 8.54 (s, 1H), 8.11 (br s, 1H), 7.98 (s, 1H), 6.55 (br s, 1H), 6.03 (d, J = 8.4 Hz, 1H), 5.60-5.51 (m, 1H), 5.18 (d, J = 51.8 Hz, 1H), 4.84-4.80 (m, 1H), 4.68 (d, J = 4.2 Hz, 1H), 4.53-4.36 (m, 2H), 4.36-4.21 (m, 2H), 4.10-3.94 (m, 2H), 3.23 (q, J = 7.3 Hz, 12H), 2.68-2.53 (m, 2H), 1.72-1.58 (m, 1H), 1.31 (t, J = 7.3 Hz, 18H). $^{31}$P NMR (D$_2$O) δ −1.14 (s, 1P), −1.36 (s, 1P). |

Example 64

6-(((1R,3R,4S)-3-(((tert-Butyldimethylsilyl)oxy)methyl)-4-((triisopropylsilyl)oxy)cyclopentyl)amino)pyrimidin-4(3H)-one, Intermediate 156

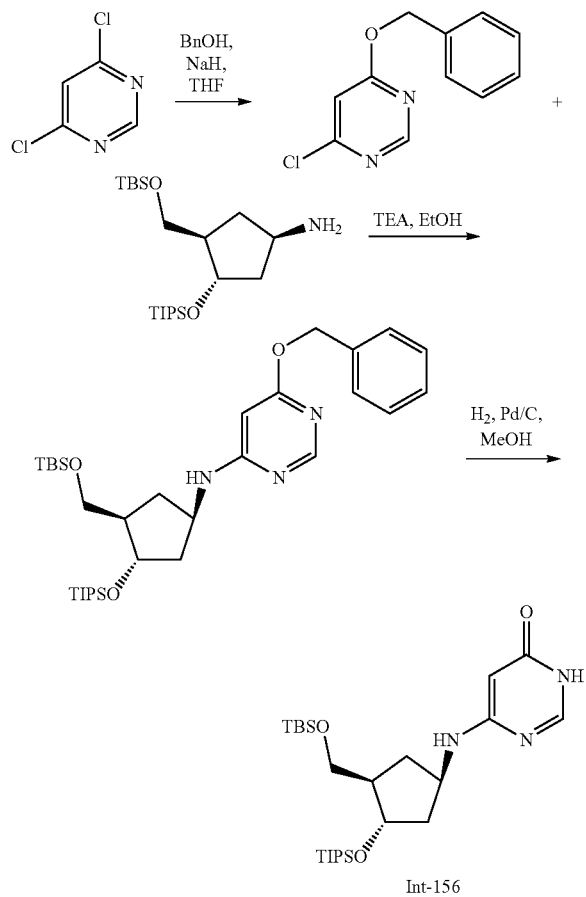

Int-156

Step 1: 4-(Benzyloxy)-6-chloropyrimidine

To a stirred solution of phenylmethanol (20.2 g, 187 mmol) in THF (300 mL) was added 60% NaH (11.0 g, 276 mmol) in portions under a $N_2$ atmosphere. The resulting suspension was stirred at 15° C. for 20 min. A solution of 4,6-dichloropyrimidine (28.0 g, 134 mmol) in THF (40 mL) was added dropwise at 0° C. and the mixture was allowed to stir at 0° C. for 1.5 h and then at 15° C. for 12 h. The reaction mixture was quenched with sat.aq. $NH_4Cl$ (300 mL) and extracted with EtOAc (300 mL×2). The combined organic phases were washed with brine (300 mL), dried over $Na_2SO_4$ and evaporated. The crude residue was purified by silica gel chromatography (PE to PE/EtOAc=50/1) to provide the title compound (29.4 g, 71%) as a yellow oil. $^1$H NMR (CDCl$_3$) δ 8.60 (s, 1H), 7.49-7.32 (m, 5H), 6.82 (s, 1H), 5.45 (s, 2H).

Step 2: 6-(Benzyloxy)-N-((1R,3R,4S)-3-(((tert-butyldimethylsilyl)oxy)methyl)-4-((triisopropylsilyl)oxy)cyclopentyl)pyrimidin-4-amine To a solution of 4-(benzyloxy)-6-chloropyrimidine (15.0 g, 67.9 mmol) in EtOH (300 mL) was added (1R,3R,4S)-3-{[(tert-butyldimethylsilyl)oxy]methyl}-4-{[tris(propan-2-yl)silyl]oxy}cyclopentan-1-amine (28.6 g, 71.2 mmol) and TEA (15 mL, 108 mmol). The reaction mixture was heated to 100° C. and stirred for 60 h. The solvents were evaporated and the residue was purified by silica gel chromatography (PE to PE/EtOAc=10/1) to provide the title compound (25.0 g, 63%) as a yellow oil.

Step 3: 6-(((1R,3R,4S)-3-(((tert-Butyldimethylsilyl)oxy)methyl)-4-((triisopropylsilyl)oxy)cyclopentyl)amino)pyrimidin-4(3H)-one, Intermediate 156

6-(Benzyloxy)-N-((1R,3R,4S)-3-(((tert-butyldimethylsilyl)oxy)methyl)-4-((triisopropylsilyl)oxy)cyclopentyl)pyrimidin-4-amine (25 g, 42.6 mmol) was dissolved in MeOH (426 mL) and Pd/C (5% by weight, 1.00 g, 0.469 mmol) was added under an Ar atmosphere. The mixture was purged and flushed with $H_2$ (3 times) and then stirred at 15° C. under $H_2$ (40 psi) for 4 h. The reaction mixture was filtered through celite, rinsed with MeOH, and the filtrate was concentrated to provide the title compound (20.4 g, 97%). LCMS (FA): m/z=496.3 (M+H).

Example 65

Biological Protocols and Sting Binding Assay Data

Cloning, Expression, and Purification of STING

Human STING (accession number GB:BC047779) DNA encoding residues 140-379 (H232R) was cloned into pET28 as N-terminal HIS and C-terminal Avi tagged fusion protein, and a rTEV cleavage site between HIS tag and STING. The sequence was verified before recombinant protein expression using E. coli expression system.

For expression, STING expression vector was transformed into BL21(DE3) cells. The expression was induced by adding IPTG and expressing in 16° C. for 20 hours.

For purification, STING was purified by Nickel affinity resin (Thermo Scientific #25215), followed by TEV enzyme cleavage and Superdex 200 column (GE Healthcare #28-9893-35) purification. For site directed in vitro biotinylation, purified Avi-tagged STING protein was incubated with Biotin (SUPELCO #47868), ATP (SIGMA #A-7699) and BirA enzyme, followed by further purification through a Superdex 200 column (GE Healthcare #28-9893-35). Biotinylation was confirmed by Mass Spectrometry analysis.

Human STING TR-FRET Assay 40 nL of test compounds in DMSO were added to wells in a white, 384 well microtitre plate (Greiner 784075). 2 uL STING assay buffer (PBS and 0.01% BSA) containing fluorescein labeled ligand (c[G(2',5')p-2'-Fluo-AHC-A(3',5')p]-Biolog C 195, 100 nM final) and Tb labeled Streptavidin (Streptavidin-Tb cryptate-CisBio 610SATLB) were added. Then 2 uL STING assay buffer containing STING protein (100 nM final) was added and the mixture was incubated at rt for 60 minutes. The plates were then read on a BMG PheraStar Plus reader (LanthaScreen module).

For the assay method described above, test compound percent inhibition, at various concentrations, was calculated relative to untreated and DMSO only treated samples. Compound concentration versus percent inhibition curves were fitted to generate $IC_{50}$ values. One skilled in the art will appreciate that the values generated either as percentage inhibition at a single concentration or $IC_{50}$ values are subject to experimental variation.

THP-1 Dual Lucia Reporter Gene Assay Conditions

THP1-Dual™ cells (InvivoGen #thpd-nfis) were derived from the human THP-1 monocyte cell line by stable integration of the Lucia luciferase gene, a secreted luciferase reporter gene, under the control of an ISG54 (interferon-stimulated gene) minimal promoter in conjunction with five interferon (IFN)-stimulated response elements. On the day of experiment, the cells were plated to a black, 384-well plate (Corning 356697) at 7500 cells/25 µl per well density in growth media (RPMI 1640, 2 mM L-glutamine, 25 mM HEPES, 10% heat-inactivated fetal bovine serum, 100 µg/mL Normocin™, 100 U/mL-100 µg/mL Pen-Strep, 10 µg/mL of blasticidin, and 100 µg/mL of Zeocin). The cell plates were dosed with 62.5 nL of the testing compounds, and then incubated at 37° C. for 20 hours. At the end of the incubation, 15 µL/well of the QUANTI-Luc™ (InvivoGen #rep-qlc1) were added, and luminescence was measured immediately using the LeadSeeker.

For the assay method described above, test compound percent luminescence signal induction, at various concentrations, was calculated relative to untreated and DMSO only treated samples. Compound concentration versus percent signal induction curves were fitted to generate $EC_{50}$ values. One skilled in the art will appreciate that the values generated as $EC_{50}$ values are subject to experimental variation.

As detailed above, compounds of this disclosure modulates STING. In certain embodiments, compounds of this disclosure are STING agonists with the $IC_{50}$ and $EC_{50}$ values shown in the table below.

| Compound | Enz-TR-Fret $IC_{50}$ (µM) | Cellular THP1 $EC_{50}$ (µM) |
|---|---|---|
| I-1a | B | C |
| I-1b | A | B |
| I-1c | C | D |
| I-2a | A | B |
| I-2b | B | C |
| I-3a | C | D |
| I-3b | C | C |
| I-4a | B | D |
| I-4b | B | D |
| I-5a | C | D |
| I-5b | B | B |
| I-5c | A | B |
| I-5d | B | C |
| I-6 | B | C |
| I-7 | B | D |
| I-8 | B | D |
| I-9a | B | C |
| I-9b | A | B |
| I-9c | D | D |
| I-9d | B | C |
| I-10 | A | B |
| I-11 | C | D |
| I-12a | C | D |
| I-12b | B | A |
| I-13 | B | C |
| I-14 | C | D |
| I-15 | C | D |
| I-16 | C | C |
| I-17 | A | B |
| I-18 | A | B |
| I-19a | A | B |
| I-19b | B | D |
| I-20a | A | B |
| I-20b | A | B |
| I-21 | A | B |
| I-22a | B | B |
| I-22b | A | A |
| I-23a | B | D |
| I-23b | A | B |
| I-24a | A | B |
| I-24b | A | B |
| I-25a | A | B |
| I-25b | B | D |
| I-26 | B | D |
| I-27 | A | C |
| I-28 | C | C |
| I-29 | C | D |
| I-30a | A | B |
| I-30b | A | A |
| I-30c | B | B |
| I-30d | C | D |
| I-31a | C | D |
| I-31b | B | B |
| I-32a | B | B |
| I-32b | A | A |
| I-33 | C | D |
| I-34a | A | A |
| I-34b | A | B |
| I-35a | A | C |
| I-35b | A | B |
| I-35c | C | D |
| I-35d | B | C |
| I-36 | B | C |
| I-37a | D | D |
| I-37b | C | D |
| I-37c | B | B |
| I-38a | A | B |
| I-38b | A | B |
| I-39a | A | B |
| I-39b | A | A |
| I-40 | A | C |
| I-41a | B | D |
| I-41b | B | C |
| I-42 | A | B |
| I-43 | A | B |
| I-44a | B | C |
| I-44b | A | B |
| I-45 | A | B |
| I-46 | A | C |

$IC_{50}$: A) less than 1.0 µM; B) 1.0 µM-10 µM; C) 10 µM-100 µM; D) greater than 100 µM.
$EC_{50}$: A) less than 1.0 µM; B) 1.0 µM-10 µM; C) 10 µM-25 µM; D) greater than 25 µM.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was

What is claimed is:

1. A compound of Formula I:

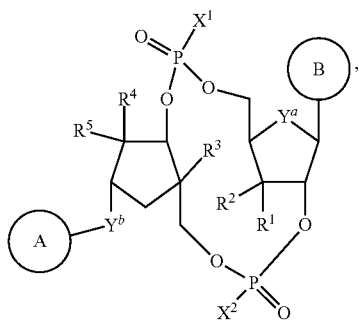

or a pharmaceutically acceptable salt thereof, wherein:
one of $X^1$ and $X^2$ is —OH and the other is selected from —SH and —OH;
$Y^a$ is —O—, —S—, or —CH$_2$—;
$Y^b$ is —O—, —S—, —NH—, or —NR$^a$—, wherein R$^a$ is $C_1$-$C_4$alkyl;
$R^1$ is hydrogen, fluoro, —OH, —NH$_2$, —OR$^b$, or —NHR$^b$;
$R^2$ is hydrogen or fluoro;
$R^3$ is hydrogen; $R^4$ is hydrogen, fluoro, —OH, —NH$_2$, —OR$^b$, or —NHR$^b$; or $R^3$ and $R^4$ are taken together to form —CH$_2$O—;
$R^5$ is hydrogen or fluoro;
$R^b$ is $C_1$-$C_6$alkyl, halo($C_1$-$C_6$)alkyl, or $C_3$-$C_6$cycloalkyl;
Ring A is an optionally substituted 5- or 6-membered monocyclic heteroaryl ring containing 1-4 heteroatoms selected from N, O, or S, or an optionally substituted 9- or 10-membered bicyclic heteroaryl ring containing 1-5 heteroatoms selected from N, O, or S; wherein Ring A comprises at least one N atom in the ring, and wherein $Y^b$ is attached to a carbon atom of Ring A; and
Ring B is an optionally substituted 9- or 10-membered bicyclic heteroaryl ring containing 2-5 heteroatoms selected from N, O, or S; wherein Ring B comprises at least two N atoms in the ring.

2. The compound of claim 1 or a pharmaceutically acceptable salt thereof, wherein: $X^1$ and $X^2$ are —OH.

3. The compound of claim 1 or a pharmaceutically acceptable salt thereof, wherein:
one of $X^1$ and $X^2$ is —OH, and the other is —SH; and
the phosphorous atom of the phosphorothioate linkage is chiral and is $R_p$ or $S_p$.

4. The compound of claim 1, having Formula (IV-A):

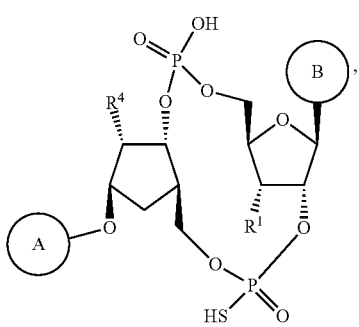

or a pharmaceutically acceptable salt thereof, wherein $R^1$ and $R^4$ are each independently hydrogen, fluoro, —OH, or —OCH$_2$CF$_3$.

5. The compound of claim 1, having Formula (IV-B):

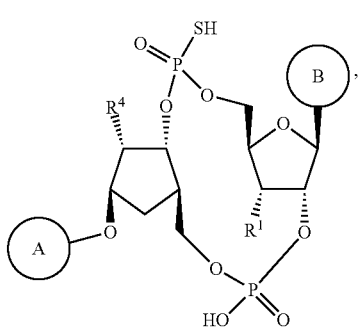

or a pharmaceutically acceptable salt thereof, wherein $R^1$ and $R^4$ are each independently hydrogen, fluoro, —OH, or —OCH$_2$CF$_3$.

6. The compound of claim 1, having Formula (IV-C):

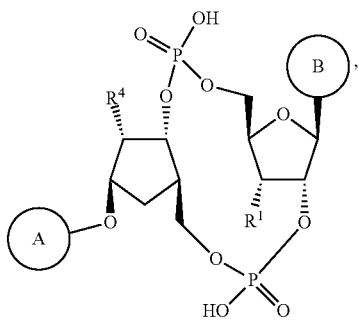

or a pharmaceutically acceptable salt thereof, wherein $R^1$ and $R^4$ are each independently hydrogen, fluoro, —OH, or —OCH$_2$CF$_3$.

7. The compound of claim 1, having Formula (V-A):

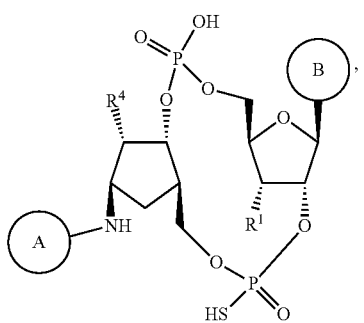

(V-A)

or a pharmaceutically acceptable salt thereof, wherein $R^1$ and $R^4$ are each independently hydrogen, fluoro, —OH, or —OCH$_2$CF$_3$.

8. The compound of claim 1, having Formula (V-B):

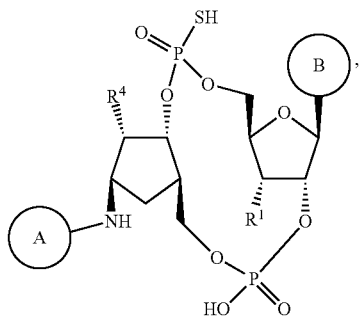

(V-B)

or a pharmaceutically acceptable salt thereof, wherein $R^1$ and $R^4$ are each independently hydrogen, fluoro, —OH, or —OCH$_2$CF$_3$.

9. The compound of claim 1, having Formula (V-C:

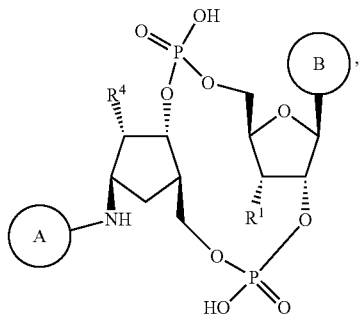

(V-C)

or a pharmaceutically acceptable salt thereof, wherein $R^1$ and $R^4$ are each independently hydrogen, fluoro, —OH, or —OCH$_2$CF$_3$.

10. The compound of claim 1, or a pharmaceutically acceptable salt thereof, wherein Ring A is

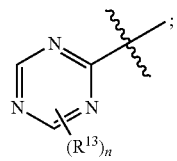

$(R^{13})_n$ wherein:
each $R^{13}$ is independently hydrogen, halogen, —OH, —NH$_2$, C$_1$-C$_6$alkyl, halo(C$_1$-C$_6$)alkyl, C$_3$-C$_6$cycloalkyl, —OR$^{11}$, —NHR$^{11}$, —CN, —NO$_2$, or —C(O)NHR$^{12}$;
$R^{11}$ is C$_1$-C$_6$alkyl, halo(C$_1$-C$_6$)alkyl, or C$_3$-C$_6$cycloalkyl;
$R^{12}$ is hydrogen, C$_1$-C$_6$alkyl, halo(C$_1$-C$_6$)alkyl, or C$_3$-C$_6$cycloalkyl; and
n is 0, 1, or 2.

11. The compound of claim 10 or a pharmaceutically acceptable salt thereof, wherein each $R^{13}$ is independently hydrogen, fluoro, chloro, —OH, —NH$_2$, —CH$_3$, —CF$_3$, —OCH$_3$, —CN, —NO$_2$, or —C(O)NH$_2$.

12. The compound of claim 11, or a pharmaceutically acceptable salt thereof, wherein Ring A is:

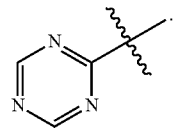

13. The compound of claim 1 or a pharmaceutically acceptable salt thereof, wherein Ring A is an optionally substituted 5-membered monocyclic heteroaryl ring.

14. The compound of claim 1, or a pharmaceutically acceptable salt thereof, wherein:
Ring B is an optionally substituted 9-membered bicyclic heteroaryl ring containing 3-5 N atoms; and
the $Y^a$-containing 5-membered ring is attached to a nitrogen atom of Ring B.

15. The compound of claim 14, or a pharmaceutically acceptable salt thereof, wherein Ring B is:

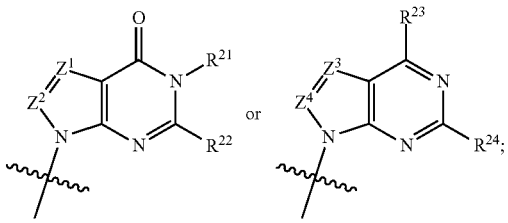

$Z^1$, $Z^2$, $Z^3$, and $Z^4$ are each independently N or CR$^{20}$;
$R^{21}$ is hydrogen or C$_1$-C$_6$alkyl, halo(C$_1$-C$_6$)alkyl, or C$_3$-C$_6$cycloalkyl;
$R^{23}$ is hydrogen or —NH$_2$; and
$R^{20}$, $R^{22}$, and $R^{24}$ are each independently hydrogen, halogen, —OH, —NH$_2$, —CN, C$_1$-C$_6$alkyl, halo(C$_1$-C$_6$)alkyl, or C$_3$-C$_6$cycloalkyl.

16. The compound of claim 15, or a pharmaceutically acceptable salt thereof, wherein:
$Z^1$, $Z^2$, $Z^3$, and $Z^4$ are each independently N, CH, or CF;
$R^{21}$ is hydrogen or —CH$_3$; and $R^{22}$ and $R^{24}$ are each independently hydrogen, —$NH_2$, or —$CH_3$.

17. The compound of claim 16, or a pharmaceutically acceptable salt thereof, wherein Ring B is selected from:

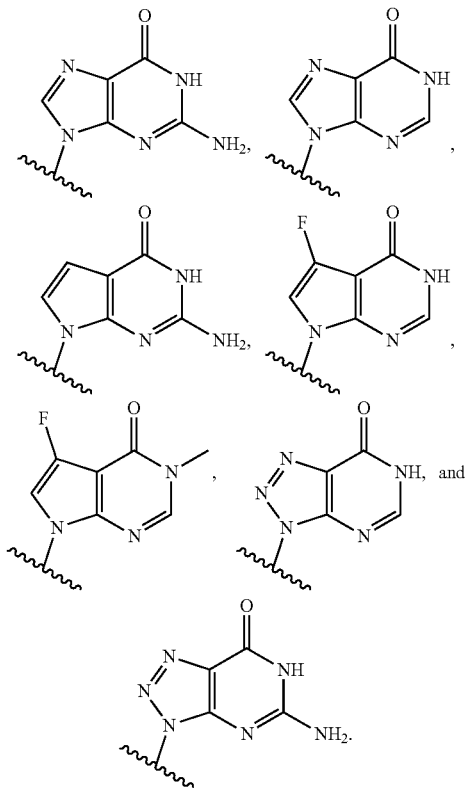

18. A pharmaceutical composition comprising (a) the compound of claim 1, or a pharmaceutically acceptable salt thereof, and (b) a pharmaceutically acceptable carrier.

19. A method of treating a cell proliferation disorder in a subject, comprising administering to the subject in need thereof a therapeutically effective amount of the compound of claim 1, or a pharmaceutically acceptable salt thereof.

20. The method of claim 19, wherein the cell proliferation disorder is cancer.

21. A compound which is

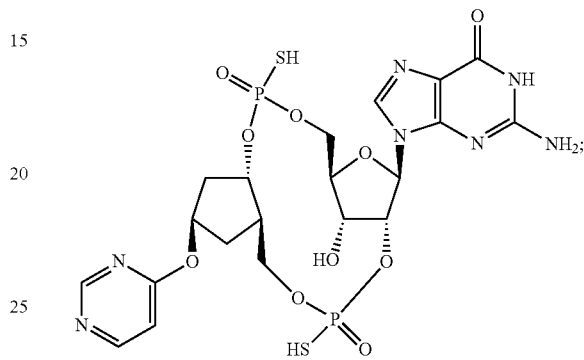

or a pharmaceutically acceptable salt thereof.

22. A method of treating a cell proliferation disorder in a subject, comprising administering to the subject in need thereof a therapeutically effective amount of the compound of claim 21, or a pharmaceutically acceptable salt thereof.

23. The method of claim 22, wherein the cell proliferation disorder is cancer.

* * * * *